US012692276B2

(12) United States Patent
Hummel et al.

(10) Patent No.: US 12,692,276 B2
(45) Date of Patent: Jul. 28, 2026

(54) TRICYCLIC TRIAZOLO COMPOUNDS AS DGK INHIBITORS

(71) Applicant: Incyte Corporation, Wilmington, DE (US)

(72) Inventors: Joshua Hummel, Hockessin, DE (US); Liana Hie, Wilmington, DE (US); Jacob J. Lacharity, Chesterbrook, PA (US); Sharada Manns, Wilmington, DE (US); Ding-Quan Qian, Newark, DE (US); Xiaozhao Wang, Moorestown, NJ (US)

(73) Assignee: Incyte Corporation, Wilmington, DE (US)

( * ) Notice: Subject to any disclaimer, the term of this patent is extended or adjusted under 35 U.S.C. 154(b) by 453 days.

(21) Appl. No.: 18/330,623

(22) Filed: Jun. 7, 2023

(65) Prior Publication Data

US 2023/0399342 A1 Dec. 14, 2023

Related U.S. Application Data

(60) Provisional application No. 63/436,248, filed on Dec. 30, 2022, provisional application No. 63/350,244, filed on Jun. 8, 2022.

(51) Int. Cl.
*C07D 513/14* (2006.01)
*C07D 487/14* (2006.01)

(52) U.S. Cl.
CPC ......... *C07D 513/14* (2013.01); *C07D 487/14* (2013.01); *C07B 2200/05* (2013.01)

(58) Field of Classification Search
CPC .. C07D 513/14; C07D 487/14; C07B 2200/05
See application file for complete search history.

(56) References Cited

U.S. PATENT DOCUMENTS 6,833,454 B1 12/2004 Koppes et al.
7,381,401 B2 6/2008 Gajewski et al.
7,488,802 B2 2/2009 Collins et al.
7,943,743 B2 5/2011 Korman et al.
8,008,449 B2 8/2011 Korman et al.
8,168,757 B2 5/2012 Finnefrock et al.
8,217,149 B2 7/2012 Irving et al.
8,618,288 B2 12/2013 Dvorak et al.
10,087,180 B2 10/2018 Ford et al.
10,308,644 B2 6/2019 Wu et al.
2007/0161072 A1 7/2007 Prescott et al.
2017/0145025 A1 5/2017 Li et al.
2017/0174671 A1 6/2017 Wu et al.
2017/0174679 A1 6/2017 Lajkiewicz et al.
2017/0320875 A1 11/2017 Li et al.
2017/0342060 A1 11/2017 Lu et al.
2017/0362253 A1 12/2017 Xiao et al.
2018/0016260 A1 1/2018 Yu et al.
2018/0028501 A1 2/2018 Lindsley et al.
2018/0057486 A1 3/2018 Wu et al.
2018/0177784 A1 6/2018 Wu et al.
2018/0177870 A1 6/2018 Liu et al.
2018/0179179 A1 6/2018 Wu et al.
2018/0179197 A1 6/2018 Wu et al.
2018/0179201 A1 6/2018 Wu et al.
2018/0179202 A1 6/2018 Wu et al.
2018/0273519 A1 9/2018 Wu et al.
2019/0040082 A1 2/2019 Xiao et al.
2019/0062345 A1 2/2019 Xiao et al.
2019/0071439 A1 3/2019 Li et al.
2019/0127467 A1 5/2019 Shah et al.
2019/0144439 A1 5/2019 Wu et al.
2019/0202824 A1 7/2019 Wu et al.
2019/0225601 A1 7/2019 Wu et al.
2019/0300524 A1 10/2019 Wu et al.
2019/0345170 A1 11/2019 Wu et al.
2024/0025900 A1 1/2024 Hummel et al.
2024/0034734 A1 2/2024 Hummel et al.
2024/0083898 A1 3/2024 Hummel et al.
2024/0217989 A1 7/2024 Xiang et al.
2024/0270739 A1 8/2024 Xiang et al.
2024/0374497 A1* 11/2024 Joyal ........................ A61Q 7/00
2025/0066363 A1 2/2025 Hummel et al.
2025/0179083 A1* 6/2025 Hummel .............. A61K 31/519
2025/0186450 A1 6/2025 Ren et al.
2026/0001880 A1 1/2026 Hummel et al.

FOREIGN PATENT DOCUMENTS

CN 105315293 A 2/2016
CN 109180686 A 1/2019
CN 110643705 A 1/2020
CN 111097048 A 5/2020
CN 112300194 A 2/2021
CN 113061132 A 7/2021
CN 115463214 A 12/2022
(Continued)

OTHER PUBLICATIONS

Wichroski, Cancer Immunol Res vol. 13(9), Sep. 2025, 1342-1362. (Year: 2025).*
Offringa, J Immunotherapy Cancer 2023, 11(suppl 1):A1-A1731, A1079. (Year: 2023).*
Ikeda, Mol Cancer Ther, 24(6), Jun. 2025, 884-895. (Year: 2025).*
Arranz-Nicolás et al., "Diacylglycerol kinase α inactivation is an integral component of the costimulatory pathway that amplifies TCR signals," Cancer Immunology Immunotherapy, Jun. 2018, 67(6):965-980.
Atzrodt et al., "The renaissance of H/D exchange," Angewandte Chemie International Edition English, Oct. 2007, 46(41):7744-7765.
Bennett et al., "Proposals for the classification of the myelodysplastic syndromes," British Journal of Haematology, Jun. 1982, 51(2):189-199.
Blom et al., "Optimizing preparative LC/MS configurations and methods for parallel synthesis purification," Journal of Combinatorial Chemistry, Sep. 2003, 5(5):670-683.
(Continued)

*Primary Examiner* — D Margaret M Seaman
(74) *Attorney, Agent, or Firm* — Fish & Richardson P.C.

(57) ABSTRACT

The present application provides tricyclic triazolo compounds that modulate the activity of diacylglycerol kinase (DGK), which are useful in the treatment of various diseases, including cancer.

40 Claims, No Drawings

(56) References Cited

FOREIGN PATENT DOCUMENTS

| | | | |
|---|---|---|---|
| CN | 116969943 | A | 10/2023 |
| EP | 4083038 | A1 | 11/2022 |
| WO | WO 2001/002398 | A1 | 1/2001 |
| WO | WO 2002/000196 | A2 | 1/2002 |
| WO | WO 2002/077177 | A2 | 10/2002 |
| WO | WO 2003/042402 | A2 | 5/2003 |
| WO | WO 2004/021984 | A2 | 3/2004 |
| WO | WO 2005/121138 | A2 | 12/2005 |
| WO | WO 2007/019083 | A1 | 2/2007 |
| WO | WO 2007/109251 | A2 | 9/2007 |
| WO | WO 2008/017161 | A1 | 2/2008 |
| WO | WO 2008/148926 | A2 | 12/2008 |
| WO | WO 2008/156712 | A1 | 12/2008 |
| WO | WO 2009/017863 | A2 | 2/2009 |
| WO | WO 2007/114239 | A1 | 8/2009 |
| WO | WO 2010/036959 | A2 | 4/2010 |
| WO | WO 2010/089411 | A2 | 8/2010 |
| WO | WO 2011/066342 | A2 | 6/2011 |
| WO | WO 2011/082400 | A2 | 7/2011 |
| WO | WO 2011/143423 | A2 | 11/2011 |
| WO | WO 2011/159877 | A2 | 12/2011 |
| WO | WO 2011/161699 | A2 | 12/2011 |
| WO | WO 2012/080727 | A2 | 6/2012 |
| WO | WO 2012/080729 | A2 | 6/2012 |
| WO | WO 2012/130780 | A1 | 10/2012 |
| WO | WO 2014/096423 | A1 | 6/2014 |
| WO | WO 2015/054572 | A1 | 4/2015 |
| WO | WO 2015/095492 | A1 | 6/2015 |
| WO | WO 2015/193167 | A1 | 12/2015 |
| WO | WO 2016/044772 | A1 | 3/2016 |
| WO | WO 2018/062954 | A1 | 4/2018 |
| WO | WO 2019/005883 | A1 | 1/2019 |
| WO | WO 2019/046795 | A1 | 3/2019 |
| WO | WO 2020/006016 | A1 | 1/2020 |
| WO | WO 2020/006018 | A1 | 1/2020 |
| WO | WO 2020/110127 | A1 | 6/2020 |
| WO | WO 2020/239123 | A1 | 12/2020 |
| WO | WO 2021/013561 | A1 | 1/2021 |
| WO | WO 2021/041588 | A1 | 3/2021 |
| WO | WO 2021/052499 | A1 | 3/2021 |
| WO | WO 2021/083167 | A1 | 5/2021 |
| WO | WO 2021/105115 | A1 | 6/2021 |
| WO | WO 2021/105116 | A1 | 6/2021 |
| WO | WO 2021/105117 | A1 | 6/2021 |
| WO | WO 2021/127554 | A1 | 6/2021 |
| WO | WO 2021/130638 | A1 | 7/2021 |
| WO | WO 2021/133748 | A1 | 7/2021 |
| WO | WO 2021/133749 | A1 | 7/2021 |
| WO | WO 2021/133750 | A1 | 7/2021 |
| WO | WO 2021/133751 | A1 | 7/2021 |
| WO | WO 2021/133752 | A1 | 7/2021 |
| WO | WO 2021/219513 | A1 | 11/2021 |
| WO | WO 2021/234607 | A1 | 11/2021 |
| WO | WO 2021/132422 | A1 | 12/2021 |
| WO | WO 2021/243421 | A1 | 12/2021 |
| WO | WO 2021/258010 | A1 | 12/2021 |
| WO | WO 2022/037630 | A1 | 2/2022 |
| WO | WO 2022/076446 | A1 | 4/2022 |
| WO | WO 2022/108980 | A1 | 5/2022 |
| WO | WO 2022/114164 | A1 | 6/2022 |
| WO | WO 2022/114812 | A1 | 6/2022 |
| WO | WO 2022/133083 | A1 | 6/2022 |
| WO | WO 2022/171745 | A1 | 8/2022 |
| WO | WO 2022/187406 | A1 | 9/2022 |
| WO | WO 2022/271650 | A1 | 12/2022 |
| WO | WO 2022/271659 | A1 | 12/2022 |
| WO | WO 2022/271677 | A1 | 12/2022 |
| WO | WO 2022/271684 | A1 | 12/2022 |
| WO | WO 2023/011456 | A1 | 2/2023 |
| WO | WO 2023/125681 | A1 | 7/2023 |
| WO | WO 2023/150186 | A1 | 8/2023 |
| WO | WO 2023/165525 | A1 | 9/2023 |
| WO | WO 2023/165528 | A1 | 9/2023 |
| WO | WO 2023/184327 | A1 | 10/2023 |
| WO | WO 2024/160277 | A1 | 8/2024 |

OTHER PUBLICATIONS

Blom et al., "Preparative LC-MS Purification: Improved Compound-Specific Method Optimization," Journal of Combinatorial Chemistry, Nov. 2004, 6(6):874-883.

Blom, "Two-Pump at-Column-Dilution Configuration for Preparative Liquid Chromatography—Mass Spectrometry," Journal of Combinatorial Chemistry, Jul. 2002, 4(4):295-301.

Cai et al., "Increased diacylglycerol kinase ζ expression in human metastatic colon cancer cells augments Rho GTPase activity and contributes to enhanced invasion," BMC cancer, Mar. 19, 2014, 14:208.

Chen et al., "Diacylglycerol Kinases in T Cell Tolerance and Effector Function," Frontiers in Cell and Development Biology, Nov. 10, 2016, 4:130.

Chen et al., "The diacylglycerol kinase α (DGKα)/Akt/NF-κB feedforward loop promotes esophageal squamous cell carcinoma (ESCC) progression via FAK-dependent and FAK-independent manner," Oncogene, Apr. 2019, 38(14):2533-2550.

Chinchilla et al., "Recent advances in Sonogashira reactions," Chemical Society Reviews, Oct. 2011, 40(10):5084-5121.

Cooke et al., "Overarching roles of diacylglycerol signaling in cancer development and antitumor immunity," Science Signaling, Apr. 2022, 15(729):eabo0264.

Cordovilla et al., "The Stille reaction, 38 years later," ACS Catalysis, May 2015, 5(5):3040-3053.

Eurasian Office Action in Eurasia Application No. 202493158, dated Apr. 15, 2025, 6 pages (with English translation).

Fu et al., "DGKA interacts with SRC/FAK to promote the metastasis of non-small cell lung cancer," Cancer Letters, Apr. 2022, 532:215585.

Gonzalez et al., "Roles of the immune system in cancer: from tumor initiation to metastatic progression," Genes & Development, Oct. 2018, 32(19-20):1267-1284.

Gu et al., "DGKζ exerts greater control than DGKα over CD8+ T cell activity and tumor inhibition," Oncoimmunology, Jan. 2021, 10(1):1941566.

Haas et al., "Recent developments in Negishi cross-coupling reactions," ACS Catalysis, Mar. 2016, 6(3):1540-1552.

Harabuchi et al. "Manipulation of diacylglycerol and ERK-mediated signaling differentially controls CD8+ T cell responses during chronic viral infection," Frontiers in Immunology, Nov. 2022, 13:1032113.

Harris et al., "World Health Organization classification of neoplastic diseases of the hematopoietic and lymphoid tissues: report of the Clinical Advisory Committee meeting—Airlie House, Virginia, Nov. 1997," Journal of Clinical Oncology, Dec. 1999, 17(12):3835-3849.

International Preliminary Report on Patentability in International Application No. PCT/US2023/024679, dated Dec. 10, 2024, 7 pages.

International Search Report and Written Opinion in International Appln. No. PCT/US2023/024679, mailed on Aug. 7, 2023, 13 pages.

Joshi et al., "Diacylglycerol kinases: regulated controllers of T cell activation, function, and development," International Journal of Molecular Sciences, Mar. 2013, 14(4):6649-6673.

Jung et al., "CRISPR/Cas9-mediated knockout of DGK improves antitumor activities of human T cells," Cancer Research, Aug. 2018, 78(16):4692-4703.

Kerekes et al., "Aurora kinase inhibitors based on the imidazo [1, 2-a] pyrazine core: fluorine and deuterium incorporation improve oral absorption and exposure," Journal of Medicinal Chemistry, Jan. 2011, 54(1):201-210.

Kotha et al., "Recent applications of the Suzuki-Miyaura cross-coupling reaction in organic synthesis," Tetrahedron, Nov. 2002, 58(48):9633-9695.

(56) References Cited

OTHER PUBLICATIONS

Krishna et al., "Regulation of lipid signaling by diacylglycerol kinases during T cell development and function," Frontiers in Immunology, Jul. 2013, 4:178.
Mérida et al., "Diacylglycerol kinases in cancer," Advances in Biological Regulation, Jan. 2017, 63:22-31.
Panama Office Action in Panama Application No. PI/2024/95245-01, dated Feb. 17, 2025, 2 pages (with English translation).
Prinz et al., "High DGK-α and disabled MAPK pathways cause dysfunction of human tumor-infiltrating CD8+ T cells that is reversible by pharmacologic intervention," The Journal of Immunology, Jun. 15, 2012, 188(12):5990-6000.
Rainero et al., "The diacylglycerol kinase α/atypical PKC/α1 integrin pathway in SDF-lα mammary carcinoma invasiveness," PloS One, Jun. 2014, 9(6):e97144.
Remington's Pharmaceutical Sciences, 17th ed., 1985, p. 1418.
Riese et al., "Diacylglycerol kinases (DGKs): novel targets for improving T cell activity in cancer," Frontiers in Cell and Developmental Biology, Oct. 2016, 4:108.
Riese et al., "Enhanced effector responses in activated CD8+ T cells deficient in diacylglycerol kinases," Cancer Research, Jun. 2013, 73(12):3566-3577.
Ruffo et al., "Inhibition of diacylglycerol kinase α restores restimulation-induced cell death and reduces immunopathology in XLP-1" Science Translational Medicine, Jan. 2016, 8(321):321ra7.
Sakane et al., "New era of diacylglycerol kinase, phosphatidic acid and phosphatidic acid-binding protein," International Journal of Molecular Sciences, Sep. 2020, 21(18):6794-6829.
Sharma et al., "Primary, adaptive, and acquired resistance to cancer immunotherapy," Cell, Feb. 2017, 168(4):707-723.
Sharma et al., "The next decade of immune checkpoint therapy," Cancer Discovery, Apr. 2021, 11(4):838-857.
Sitaram et al., "Beyond the cell surface: targeting intracellular negative regulators to enhance T cell anti-tumor activity," International Journal of Molecular Sciences, Nov. 2019, 20(23):5821-5848.
Speiser et al., "Regulatory circuits of T cell function in cancer," Nature Reviews Immunology, Oct. 2016, 16(10):599-611.
Surry et al., "Dialkylbiaryl Phosphines in Pd-Catalyzed Amination: A User's Guide," Royal Society of Chemistry, 2011, 2(1):27-50.
Swerdlow et al., WHO Classification of Tumours of Haematopoietic and Lymphoid Tissues, $4^{th}$ ed., 2008, pp. 88-103.
Takeishi et al., "Diacylglycerol kinase alpha enhances hepatocellular carcinoma progression by activation of Ras-Raf-MEK-ERK pathway" Journal of Hepatology, Jul. 2012, 57(1):77-83.
Torres-Ayuso et al., "Diacylglycerol kinase α promotes 3D cancer cell growth and limits drug sensitivity through functional interaction with Src," Oncotarget, Oct. 2014, 5(20):9710-9726.
Vardiman et al., "The 2008 revision of the World Health Organization (WHO) classification of myeloid neoplasms and acute leukemia: rationale and important changes," Blood, Jul. 2009, 114(5):937-951.
Vardiman et al., "The World Health Organization (WHO) classification of the myeloid neoplasms," Blood, Oct. 2002, 100(7):2292-2302.
Velnati et al., "Identification of a novel DGKα inhibitor for XLP-1 therapy by virtual screening," European Journal of Medicinal Chemistry, Feb. 2019, 164:378-390.
Wesley et al., "Diacylglycerol Kinase ζ (DGKζ) and Casitas b-Lineage Proto-Oncogene b-deficient mice have similar functional outcomes in T Cells but DGKζ-deficient mice have increased T cell activation and tumor clearance," Immunohorizons, Apr. 2018, 2(4):107-118.
Xu et al., "Design, synthesis and biological evaluation of deuterated nintedanib for improving pharmacokinetic properties," Journal of Labelled Compounds and Radiopharmaceuticals, Jun. 2015, 58(7):308-312.
Yu et al., "DGKZ acts as a potential oncogene in osteosarcoma proliferation through its possible interaction with ERK1/2 and MYC pathway," Frontiers in Oncology, Jan. 4, 2019, 8:655.
Eurasian Office Action in Eurasia Application No. 202493158, dated Nov. 13, 2025, 4 pages (with English translation).
European Office Action in Europe Application No. 23738298.1, dated Nov. 14, 2025, 6 pages.
Georgian Office Action in Georgia Application No. AP 2023 16670, dated Oct. 8, 2025, 8 pages (with English translation).
Noessner, "DGK-α: A Checkpoint in Cancer-Mediated Immuno-Inhibition and Target for Immunotherapy," Frontiers in Cell and Developmental Biology, Mar. 3, 2017, 5(Article 16):7 pages.
Sadreddini et al., "Immune checkpoint blockade opens a new way to cancer immunotherapy," Cellular Physiology, Jun. 2019, 234:8541-8549.

* cited by examiner

TRICYCLIC TRIAZOLO COMPOUNDS AS DGK INHIBITORS

TECHNICAL FIELD

The present invention provides tricyclic triazolo compounds that modulate the activity of diacylglycerol kinase (DGK) and are useful in the treatment of diseases related to diacylglycerol kinase, including cancer.

BACKGROUND

Diacylglycerol kinases (DGKS) are a family of enzymes that regulate many biological processes, including cellular proliferation, migration, immunity and pathogenesis of diseases such as cancer. In mammalian systems, there are ten DGK family members classified into five subtypes based on shared common domains (Sakane F. et al., *Int. J. Mol. Sci.,* 2020. 21: p 6794-6829). The diverse and specific cellular function of individual DGK isoforms is regulated through their tissue restricted expression, localization within cells and interactions with regulatory proteins (Joshi, R. P. and Koretzky, G. A., *Int. J Mol. Sci.,* 2013. 14: p 6649-6673).

In T lymphocytes, DGKα and ξ are the dominant DGK isoforms expressed (Krishna, S. and Zhong, X.-P., *Front Immunol.,* 2013. 4:178). Specifically, in response to T cell receptor (TCR) activation, phospholipase Cγ1 (PLCγ1) hydrolyzes membrane phospholipid PIP2 to produce diacylglycerol (DAG) (Krishna, S. and Zhong, X.-P., *Front Immunol.,* 2013. 4:178; Riese, M. J. et al., *Front Cell Dev Biol.,* 2016. 4:108). In turn, DAG functions as a second messenger to recruit RasGRP1 and PKC⊕ to the cell membrane and thereby initiates multiple downstream signaling events resulting in T cell activation. To prevent hyperactivation of T cells, DGKα and ξ tightly regulate the levels of intracellular DAG by phosphorylating DAG to produce phosphatidic acid (PA). Both mouse and human cell line genetic studies support the important regulatory role of DGKα and ξ in T cell activation. Knockout or depletion of DGKα and ξ has been reported to enhance T cell activation, cytokine production and proliferation. Furthermore, knockout of both DGKα and ξ show even greater T-cell activation over individual knockouts, indicating a non-redundant role of these two isoforms (Riese, M. J. et al., *Cancer Res.,* 2013. 73:p 3566-3577; Jung, I.-Y. et al., *Cancer Res.,* 2018. 78: p 4692-4703). Thus, DGKα and ξ, by regulating cellular DAG levels link lipid metabolism and intracellular signaling cascades and function as key regulators of T cell activation.

Cytotoxic T lymphocytes (CTLs) are a major component of the adaptive immune system that recognize and kill cells with bacterial or viral infections, or cells displaying abnormal proteins, such as tumor antigens. However, cancer cells can evolve to utilize multiple mechanisms that mimic peripheral immune tolerance to avoid immune surveillance and killing by CTLs. Such mechanisms include downregulation of antigen presentation, suppression of T cell function through increased expression of inhibitory molecules, as well as increased production of immunosuppressive proteins in the tumor microenvironment (Speiser, D. E. et al., *Nat. Rev. Immunol.,* 2016. 16: p. 599-611, Gonzalez H. et al., *Genes & Dev.,* 2018. 32:p 1267-1284). Immune checkpoint therapy (ICT) by blocking inhibitory molecules such as PD(L)-1 and CTLA4, can restore T cell activity and have been clinically useful in treating many different types of cancers. However, only subsets of patients respond to ICT due to primary or acquired resistance (Sharma, P. et al., *Cell.* 2017. 168: p 707-723). Thus, despite the significant recent clinical successes of immunotherapies to treat cancer, resistance remains a challenge (Sharma, P., et al., *Cancer Discov.,* 2021. 11: p 838-857).

Overexpression of DGKα and ξ has been observed in tumor infiltrating lymphocytes (TILs) from human tumors and proposed to suppress T cell function. Importantly, significant immune-mediated antitumor activity has been shown in DGKα and DGKξ deficient mouse models (Merida, I. et al., Adv. Biol. Regul., 2017. 63:p 22-31, Prinz, P. U. et al., J. Immunol., 2012. 188:p 5990-6000). Furthermore, DGKα and DGKξ deficient T cells are resistant to several immunosuppressive factors within the tumor microenvironment such as TGFβ, PGE2 and adenosine, and to other T cell inhibitory pathways such as PD(L)-1 mediated immune suppression (Riese, M. J. et al., *Cancer Res.,* 2013. 73:p 3566-77; Jung, I.-Y. et al. (2018) *Cancer Res.,* 2018. 78:p 4692-4703; Arranz-Nicolas, J. et al., *Cancer-Immunol. Immunother.,* 2018. 67:p 965-980; Riese, M. J. et al., *Front. Cell Dev. Biol.,* 2016. 4:108). Thus DGKα and DGKξ are attractive targets as immunotherapies alone or in combination with current ICT therapies such as PD(L)-1 and CTLA4. By targeting T cell lipid metabolism, DGKα and DGKξ inhibition can potentially restore antitumor immunity in subsets of patient who have primary or acquired immune resistance and are consequently refractory to current ICTs. In addition to its function in T lymphocytes, DGKα and DGKξ, by regulating DAG level in cancer cells, have also been reported to directly contribute to cancer proliferation, migration, invasion and survival. Thus, DGK inhibition may have direct antitumor effect by interfering with tumor intrinsic oncogenic survival pathways (Cooke, M. and Kazanietz, M. G., *Sci. Signal.,* 2022. 15:eabo0264).

Compounds in this application may have selective activities towards one or both DGKα and DGKξ. These DGK inhibitors alone or in combination with other therapeutic agent(s) can be used in treatment of cancer.

SUMMARY

The present invention relates to, inter alia, compounds of Formula I:

I

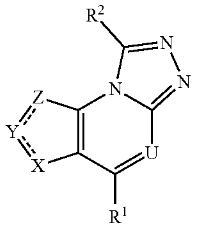

or pharmaceutically acceptable salts thereof, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of diacylglycerol kinase (DGK), comprising contacting the kinase with a compound of Formula I, or a pharmaceutically acceptable salt thereof.

The present invention further provides methods of treating a disease or a disorder associated with expression or activity of a diacylglycerol kinase (DGK) in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present application provides a compound of Formula I:

I

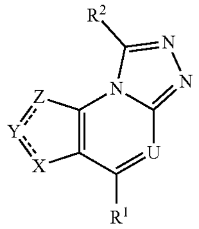

or a pharmaceutically acceptable salt thereof, wherein:

each ═ ═ ═ is a single or double bond, wherein at least one ═ ═ ═ is a double bond;

U is $CR^3$ or N;

X is $CR^4$, N, $NR^4$, S, or O;

Y is $CR^5$, N, or $NR^5$;

Z is $CR^6$, N, NR, S, or O;

$R^1$ is $Cy^1$ or L-$Cy^1$;

L is $NR^{c7}$, O, $C_{1-3}$ alkyl, $C_{2-3}$ alkenyl, or $C_{2-3}$ alkynyl;

$Cy^1$ is a $C_{3-10}$ cycloalkyl, 5-15 membered heteroaryl, or 4-15 membered heterocycloalkyl, wherein the $C_{3-10}$ cycloalkyl, 5-15 membered heteroaryl or 4-15 membered heterocycloalkyl are each optionally substituted with 1, 2, 3, 4, 5, 6, 7, or 8 independently selected $R^{1A}$ substituents;

each $R^{1A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{d11}C(O)NR^{c11}R^{d11}$, $C(=NR^{e11})R^{b11}$, $C(=NR^{e11})NR^{c11}R^{d11}$, $C(=NOR^{a11})R^{b11}$, $C(=NOR^{a11})OR^{a11}$, $NR^{c11}C(=NR^{e11})NR^{a11}R^{11}$, $NR^{c11}C(=NR^{e11})R^{b11}$, $NR^{d11}$ $S(O)R^{b11}$, $NR^{d11}$ $S(O)NR^{c11}R^{d11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, and $OS(O)_2R^{b11}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, 4, 5, 6, 7, or 8 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a11}$, $R^{c11}$ and $R^{d11}$ are each optionally substituted with 1, 2, 3, 4, 5, 6, 7, or 8 independently selected $R^{1B}$ substituents;

or, any $R^{c11}$ and $R^{d11}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{1B}$ substituents;

each $R^{b11}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b11}$ are each optionally substituted with 1, 2, 3, 4, 5, 6, 7, or 8 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{1B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a12}$, $SR^{a12}$, $NHOR^{a12}$, $C(O)R^{b12}$, $C(O)NR^{c12}R^{d12}$, $C(O)NR^{c12}(OR^{d12})$, $C(O)OR^{d12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{d12}$, $NR^{c12}C(O)NR^{c12}R^{d12}$, $C(=NR^{e12})R^{b12}$, $C(=NR^{e12})NR^{c12}R^{d12}$, $C(=NOR^{d12})R^{b12}$, $C(=NOR^{d12})OR^{d12}$, $NR^{c12}C(=NR^{e12})NR^{c12}R^{a12}$, $NR^{e12}C(=NR^{e12})R^{b12}$, $NR^{c12}S(O)R^{b12}$, $NR^{c12}S(O)NR^{e12}R^{a12}$, $NR^{c12}S(O)_2R^{b12}$, $NR^{c12}S(O)(=NR^{e12})R^{b12}$, $NR^{e12}S(O)_2NR^{e12}R^{a12}$, $S(O)R^{b12}$, $S(O)NR^{c12}R^{d12}$, $S(O)_2R^{b12}$, $S(O)_2NR^{c12}R^{c12}$, $OS(O)(=NR^{e12})R^{b12}$, and $OS(O)_2R^{b12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, 4, 5, 6, 7, or 8 independently selected $R^{1C}$ substituents;

each $R^{d12}$, $R^{e12}$, and $R^{a12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a12}$, $R^{c12}$ and $R^{d12}$ are each optionally substituted with 1, 2, 3, 4, 5, 6, 7, or 8 independently selected $R^{1C}$ substituents;

or, any $R^{c12}$ and $R^{d12}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{1C}$ substituents;

each $R^{b12}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b1}2$ are each optionally substituted with 1, 2, 3, 4, 5, 6, 7, or 8 independently selected $R^{1C}$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{1C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a13}$, $SR^{a13}$, $NHOR^{a13}$, $C(O)R^{b13}$, $C(O)NR^{c13}R^{d13}$, $C(O)NR^{c13}(OR^{a13})$, $C(O)OR^{a13}$, $OC(O)R^{b13}$, $OC(O)NR^{c13}R^{d13}$, $NR^{c13}R^{d13}$, $NR^{c13}NR^{c13}R^{d13}$, $NR^{c13}C(O)R^{b13}$, $NR^{c13}C(O)OR^{d13}$, $NR^{c13}C(O)NR^{c13}R^{d13}$, $C(=NR^{e13})R^{b13}$, $C(=NR^{e13})NR^{c13}R^{d13}$, $C(=NOR^{a12})R^{b12}$, $C(=NOR^{a12})OR^{a12}$, $NR^{c13}C(=NR^{e13})NR^{c13}R^{d13}$, $NR^{c13}C(=NR^{e13})R^{b13}$, $NR^{c13}S(O)R^{b13}$, $NR^{c13}S(O)NR^{c13}R^{d13}$, $NR^{c13}S(O)_2R^{b13}$, $NR^{c13}S(O)(=NR^{e13})R^{b13}$, $NR^{c13}S(O)_2NR^{c13}R^{c13}$, $S(O)R^{b13}$, $S(O)NR^{c13}R^{d13}$, $S(O)_2R^{b13}$, $S(O)_2NR^{c13}R^{d13}$, $OS(O)(=NR^{e13})R^{b13}$, and $OS(O)_2R^{b13}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{1C}$ are each optionally substituted with 1, 2, 3, or 4 independently selected RD substituents;

each $R^{a13}$, $R^{c13}$, and $R^{d13}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a13}$, $R^{c13}$ and $R^{d13}$ are each optionally substituted with 1, 2, 3, or 4 independently selected RD substituents;

or, any $R^{c13}$ and $R^{d13}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected RD substituents;

each $R^{b13}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b13}$ are each optionally substituted with 1, 2, 3, or 4 independently selected RD substituents;

each $R^{e13}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{1D}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a14}$, $SR^{a14}$, $NHOR^{a14}$, $C(O)R^{b14}$, $C(O)NR^{c14}R^{a14}$, $C(O)NR^{c14}(OR^{d14})$, $C(O)OR^{d14}$, $OC(O)R^{b14}$, $OC(O)NR^{c14}R^{a14}$, $NR^{c14}R^{a14}$, $NR^{c14}NR^{c14}R^{a14}$, $NR^{c14}C(O)R^{b14}$, $NR^{c14}C(O)OR^{d14}$, $NR^{c14}C(O)NR^{c14}R^{a14}$, $C(=NR^{e14})R^{b14}$, $C(=NR^{e14})NR^{c14}R^{a14}$, $NR^{c14}C(=NR^{e14})NR^{c14}R^{a14}$, $NR^{c14}C(=NR^{e14})R^{b14}$, $NR^{c14}S(O)R^{b14}$, $NR^{c14}S(O)NR^{e14}R^{a14}$, $NR^{c14}S(O)_2R^{b14}$, $NR^{c14}S(O)(=NR^{e14})R^{b14}$, $NR^{c14}S(O)_2NR^{c14}R^{d14}$, $S(O)R^{b14}$, $S(O)NR^{c14}R^{a14}$, $S(O)_2R^{b14}$, $S(O)_2NR^{c14}R^{a14}$, $OS(O)(=NR^{e14})R^{b14}$, and $OS(O)_2R^{b14}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of RD are each optionally substituted with 1, 2, 3, or 4 independently selected $R^M$ substituents;

each $R^{a14}$, $R^{c14}$, and $R^{d14}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a14}$, $R^{c14}$ and $R^{d14}$ are each optionally substituted with 1, 2, 3, or 4 independently selected $R^M$ substituents;

or, any $R^{c14}$ and $R^{d14}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b14}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b14}$ are each optionally substituted with 1, 2, 3, or 4 independently selected $R^M$ substituents;

each $R^{e14}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a2}$, $NHOR^{a2}$, $C(O)R^{b2}$, $C(O)NR^{c2}R^{c2}$, $C(O)NR^{c2}(OR^{a2})$, $C(O)OR^{a2}$, $OC(O)R^{b2}$, $OC(O)NR^{e2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{e2}R^{d2}$, $C({=}NR^{e2})R^{b2}$, $C({=}NR^{e2})NR^{e2}R^{d2}$, $NR^{e2}C({=}NR^{e2})NR^{e2}R^{d2}$, $NR^{e2}C({=}NR^{e2})R^{b2}$, $NR^{c2}S(O)R^{b2}$, $NR^{c2}S(O)NR^{c2}R^{d2}$, $NR^{e2}S(O)_2R^{b2}$, $NR^{e2}S(O)({=}NR^{e2})R^{b2}$, $NR^{e2}S(O)_2NR^{c2}R^{d2}$, $S(O)R^{b2}$, $S(O)NR^{c2}R^{d2}$, $S(O)_2R^{b2}$, $S(O)_2NR^{e2}R^{d2}$, $OS(O)({=}NR^{e2})R^{b2}$, and $OS(O)_2R^{b2}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a2}$, $R^{c2}$ and $R^{d2}$ are each optionally substituted with 1, 2, 3, 4, 5, 6, 7, or 8 independently selected $R^{2A}$ substituents;

or, any $R^{c2}$ and $R^{d2}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{2A}$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b2}$ are each optionally substituted with 1, 2, 3, 4, 5, 6, 7, or 8 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{2A}$ is selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$ $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{21}$, $C({=}NR^{e21})R^{b21}$, $C({=}NR^{e21})NR^{c21}R^{21}$, $NR^{c21}C({=}NR^{e21})NR^{c21}R^{d21}$, $NR^{c21}C({=}NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)({=}NR^{e21})R^{b21}$, $NR^{c21}S(O)_2NR^{b21}R^{a21}$, $S(O)R^{b21}$, $S(O)NR^{c21}R^{21}$, $S(O)_2R^{b21}$, $S(O)_2NR^{e21}R^{c21}$, $OS(O)({=}NR^{e21})R^{b21}$, and $OS(O)_2R^{b21}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{2A}$ are each optionally substituted with 1, 2, 3, or 4 independently selected $R^M$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a21}$, $R^{c21}$ and $R^{d21}$ are each optionally substituted with 1, 2, 3, or 4 independently selected $R^M$ substituents;

or, any $R^{c21}$ and $R^{d21}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b21}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b21}$ are each optionally substituted with 1, 2, 3, or 4 independently selected $R^M$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{e3}R^{d3}$, $C(O)NR^{c3}(OR^{a3})$, $C(O)OR^{d3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^3C(=NR^{e3})NR^{c3}R^{d3}$, $NR^3C(=NR^{e3})R^{b3}$, $NR^{c3}S(O)R^{b3}$, $NR^{c3}S(O)NR^{c3}R^{d3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{e3}R^{d3}$, $S(O)_2R^{b3}$, $S(O)_2NR^{c3}R^{d3}$, $OS(O)(=NR^3)R^{b3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{3A}$ is selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$ $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{3A}$ are each optionally substituted with 1, 2, 3, or 4 independently selected $R^M$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a31}$, $R^{c31}$ and $R^{d31}$ are each optionally substituted with 1, 2, 3, or 4 independently selected $R^{M}$ substituents;

or, any $R^{c31}$ and $R^{d31}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^{M}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b3}$ are each optionally substituted with 1, 2, 3, or 4 independently selected $R^{M}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{a4}$, $OS(O)(=NR^{e4})R^{b4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, 6, 7, or 8 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, 4, 5, 6, 7, or 8 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b4}$ are each optionally substituted with 1, 2, 3, 4, 5, 6, 7, or 8 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{4A}$ is selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)R^{b41}$, $NR^{c41}S(O)NR^{c41}R^{d41}$, $NR^{c41}S(O)_2R^{b41}$, $NR^{c41}S(O)(=NR^{c41})R^{b41}$, $NR^{c41}S(O)_2NR^{c41}R^{a41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{b41}$, and $OS(O)_2R^{b41}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{4A}$ are each optionally substituted with 1, 2, 3, or 4 independently selected $R^{M}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a41}$, $R^{c41}$ and $R^{d41}$ are each optionally substituted with 1, 2, 3, or 4 independently selected $R^{M}$ substituents;

or, any $R^{c41}$ and $R^{d41}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b41}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b41}$ are each optionally substituted with 1, 2, 3, or 4 independently selected $R^M$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{c5}$, $SR^a$, $NHOR^{a5}$, $C(O)R^{b5}$, $C(O)NR^{c5}R^{d5}$, $C(O)NR^{c5}(OR^{a5})$, $C(O)OR^{d5}$, $OC(O)R^{b5}$, $OC(O)NR^{c5}R^{d5}$, $NR^{c5}R^{d5}$, $NR^5NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{c5})R^{b5}$, $C(=NR^{c5})NR^{c5}R^{d5}$, $NR^5C(=NR^{c5})NR^{c5}R^{d5}$, $NR^5C(=NR^{c5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{c5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{c5})R^{b5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, 4, 5, 6, 7, or 8 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, 4, 5, 6, 7, or 8 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, 4, 5, 6, 7, or 8 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{5A}$ is selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a51}$, $SR^{a51}$, $NHOR^{a51}$, $C(O)R^{b51}$, $C(O)NR^{c51}R^{d51}$, $C(O)NR^{c51}(OR^aS)$, $C(O)OR^{d51}$, $OC(O)R^{b5}$, $OC(O)NR^{c51}R^{d51}$, $NR^{c5}1R^{d51}$, $NR^{c51}NR^{c51}R^{d51}$, $NR^{c51}C(O)R^{b51}$, $NR^{c51}C(O)OR^{a5}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{b51}R^{a51}$, $NR^{c51}C(=NR^{e51})R^{b51}$, $NR^{c51}S(O)R^{b51}$, $NR^{c51}S(O)NR^{c51}R^{a51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, and $OS(O)_2R^{b51}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^A$ are each optionally substituted with 1, 2, 3, or 4 independently selected $R^M$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a51}$, $R^{c51}$ and $R^{d51}$ are each optionally substituted with 1, 2, 3, or 4 independently selected $R^M$ substituents;

or, any $R^{c51}$ and $R^{d51}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b51}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b51}$ are each optionally substituted with 1, 2, 3, or 4 independently selected $R^M$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^6$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, and $OS(O)_2R^{b6}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, 4, 5, 6, 7, or 8 independently selected $R^{6A}$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a6}$, $R^{c6}$ and $R^{d6}$ are each optionally substituted with 1, 2, 3, 4, 5, 6, 7, or 8 independently selected $R^{6A}$ substituents;

or, any $R^{c6}$ and $R^{d6}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{6A}$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b6}$ are each optionally substituted with 1, 2, 3, 4, 5, 6, 7, or 8 independently selected $R^{6A}$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^{6A}$ is selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a61}$, $SR^{a61}$, $NHOR^{a61}$, $C(O)R^{b61}$, $C(O)NR^{c61}R^{d61}$, $C(O)NR^{c61}(OR^{a61})$ $C(O)OR^{a61}$, $OC(O)R^{b61}$, $OC(O)NR^{c61}R^{d61}$, $NR^{c61}R^{d61}$, $NR^{c61}NR^{c61}R^{d61}$, $NR^{c61}C(O)R^{b61}$, $NR^{c61}C(O)OR^{a61}$, $NR^{c61}C(O)NR^{c61}R^{d61}$, $C(=NR^{e61})R^{b61}$, $C(=NR^{e61})NR^{c61}R^{d61}$, $NR^{c61}C(=NR^{e61})NR^{c61}R^{d61}$, $NR^{c61}C(=NR^{e61})R^{b61}$, $NR^{c61}S(O)R^{b61}$, $NR^{c61}S(O)NR^{c61}R^{d61}$, $NR^{c61}S(O)_2R^{b61}$, $NR^{c61}S(O)(=NR^{e61})R^{b61}$, $NR^{c61}S(O)_2NR^{b61}R^{a61}$, $S(O)R^{b61}$, $S(O)NR^{e61}R^{d61}$, $S(O)_2R^{b61}$, $S(O)_2NR^{b61}R^{c61}$, $OS(O)(=NR^{e61})R^{b61}$, and $OS(O)_2R^{b61}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{6A}$ are each optionally substituted with 1, 2, 3, or 4 independently selected $R^M$ substituents;

each $R^{a61}$, $R^{c61}$, and $R^{d61}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a61}$, $R^{c61}$ and $R^{d61}$ are each optionally substituted with 1, 2, 3, or 4 independently selected $R^M$ substituents;

or, any $R^{e61}$ and $R^{d61}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b61}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b61}$ are each optionally substituted with 1, 2, 3, or 4 independently selected $R^{M}$ substituents;

each $R^{e61}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^{c7}$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{c7}$ is optionally substituted with 1, 2, 3, 4, 5, 6, 7, or 8 independently selected $R^{7A}$ substituents;

each $R^{7A}$ is independently selected from halo, oxo, $C_{1-6}$ alkyl, $C_{1-6}$ haloalkyl, $C_{2-6}$ alkenyl, $C_{2-6}$ alkynyl, $C_{6-15}$ aryl, $C_{3-15}$ cycloalkyl, 5-15 membered heteroaryl, 4-15 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a71}$, $SR^{a71}$, $NHOR^{a7}$, $C(O)R^{b71}$, $C(O)NR^{c71}R^{d71}$, $C(O)NR^{c71}(OR^{a71})$, $C(O)OR^{a71}$, $OC(O)R^{b71}$, $OC(O)NR^{c71}R^{d71}$, $NR^{c71}R^{d71}$, $NR^{c71}NR^{c71}R^{d71}$, $NR^{c7}C(O)R^{b71}$, $NR^{c71}C(O)OR^{a71}$, $NR^{c7}C(O)NR^{c71}R^{d71}$, $C(=NR^{e71})R^{b71}$, $C(=NR^{e71})NR^{c71}R^{d71}$, $C(=NOR^{a71})R^{b71}$, $C(=NOR^{a71})OR^{a71}$, $NR^{c71}C(=NR^{e71})NR^{c71}R^{d71}$, $NR^{c71}C(=NR^{e71})R^{b71}$, $NR^{c71}S(O)R^{b71}$, $NR^{c7}S(O)NR^{c71}R^{d71}$, $NR^{c71}S(O)_2R^{b71}$, $NR^{c71}S(O)(=NR^{e71})R^{b71}$, $NR^{c71}S(O)_2NR^{71}R^{71}$, $S(O)R^{b7}$, $S(O)NR^{c71}R^{d71}$, $S(O)_2R^{b71}$, $S(O)_2NR^{c71}R^{d71}$, $OS(O)(=NR^{e71})R^{b71}$, and $OS(O)_2R^{b71}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{7A}$ are each optionally substituted with 1, 2, 3, 4, 5, 6, 7, or 8 independently selected $R^{7B}$ substituents;

each $R^{a71}$, $R^{c71}$, and $R^{d71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a71}$, $R^{c71}$ and $R^{d11}$ are each optionally substituted with 1, 2, 3, 4, 5, 6, 7, or 8 independently selected $R^{7B}$ substituents;

or, any $R^{c71}$ and $R^{d71}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, 4, 5, 6, 7, or 8 independently selected $R^{7B}$ substituents;

each $R^{b71}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b7}$ are each optionally substituted with 1, 2, 3, 4, 5, 6, 7, or 8 independently selected $R^{7B}$ substituents;

each $R^{e71}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-membered heteroaryl)-$C_{1-6}$ alkyl-, and (4-10 membered heterocycloalkyl)-$C_{1-6}$ alkyl-;

each $R^{7B}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a72}$, $SR^{a72}$, $NHOR^{a72}$, $C(O)R^{b72}$, $C(O)NR^{c72}R^{d72}$, $C(O)NR^{c72}(OR^{a72})$, $C(O)OR^{a72}$, $OC(O)R^{b72}$, $OC(O)NR^{c72}R^{d72}$, $NR^{c72}R^{d72}$, $NR^{c72}NR^{c72}R^{d72}$, $NR^{c72}C(O)R^{b72}$, $NR^{c72}C(O)OR^{a72}$, $NR^{c72}C(O)NR^{c72}R^{d72}$, $C(=NR^{e72})R^{b72}$, $C(=NR^{e72})NR^{c72}R^{d72}$, $NR^{c72}C(=NR^{e72})NR^{c72}R^{d72}$, $NR^{c72}C(=NR^{e72})R^{b72}$, $NR^{c72}S(O)R^{b72}$, $NR^{c72}S(O)NR^{e72}R^{a72}$, $NR^{c72}S(O)_2R^{b72}$, $NR^{c72}S(O)(=NR^{e72})R^{b72}$, $NR^{c72}S(O)_2NR^{c72}R^{d72}$, $S(O)R^{b72}$, $S(O)NR^{c72}R^{d72}$, $S(O)_2R^{b72}$, $S(O)_2NR^{c72}R^{d72}$, $OS(O)(=NR^{e72})R^{b72}$, and $OS(O)_2R^{b72}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{7B}$ are each optionally substituted with 1, 2, 3, or 4 independently selected $R^{M}$ substituents;

each $R^{a72}$, $R^{c72}$, and $R^{d72}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a72}$, $R^{c72}$ and $R^{d72}$ are each optionally substituted with 1, 2, 3, or 4 independently selected $R^M$ substituents;

or, any $R^{c72}$ and $R^{d72}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b72}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b72}$ are each optionally substituted with 1, 2, 3, or 4 independently selected $R^M$ substituents;

each $R^{e72}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-; and each $R^M$ is independently selected from H, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments, U is $CR^3$.

In some embodiments, $R^3$ is selected from H, halo, $C_{1-6}$ alkyl, $C_{1-6}$ haloalkyl, $C_{2-6}$ alkenyl, and $C_{2-6}$ alkynyl.

In some embodiments, $R^3$ is selected from H and $C_{1-6}$ alkyl.

In some embodiments, U is CH or N.

In some embodiments, U is CH.

In some embodiments, U is N.

In some embodiments, X is $CR^4$ or $NR^4$.

In some embodiments, X is $CR^4$.

In some embodiments, X is $NR^4$.

In some embodiments, $R^4$ is selected from H, halo, $C_{1-6}$ alkyl, $C_{1-6}$ haloalkyl, $C_{2-6}$ alkenyl, and $C_{2-6}$ alkynyl.

In some embodiments, $R^4$ is H or $C_{1-6}$ alkyl.

In some embodiments, $R^4$ is H or $C_{1-3}$ alkyl.

In some embodiments, $R^4$ is H, methyl, or ethyl.

In some embodiments, X is CH, $CCH_3$, N, or $—NCH_2CH_3$.

In some embodiments, X is N.

In some embodiments, X is S.

In some embodiments, X is O.

In some embodiments, X is CH, $CCH_3$, N, $—NCH_2CH_3$, S, or 0.

In some embodiments, Y is $CR^5$ or N.

In some embodiments, Y is N.

In some embodiments, Y is $CR^5$.

In some embodiments, $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^a$s, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^5)NR^{c5}R^{d5}$, $NR^{c5}C(=NR^{c5})NR^{c5}R^{d5}$, $NR^5C(=NR^{c5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, 4, 5, 6, 7, or 8 independently selected $R^{5A}$ substituents.

In some embodiments, $R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments, $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments, $R^5$ is selected from H, D, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^{5A}$ substituents.

In some embodiments, $R^5$ is selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^{5A}$ substituents.

In some embodiments, $R^5$ is selected from H, D, $C_{1-6}$ alkyl, $C_{1-6}$ haloalkyl, and 5-6 membered heteroaryl, wherein the $C_{1-6}$ alkyl and 5-6 membered heteroaryl of $R^5$ are each optionally substituted with 1, 2, 3, or 4 independently selected $R^{5A}$ substituents.

In some embodiments, $R^5$ is selected from H, $C_{1-6}$ alkyl, $C_{1-6}$ haloalkyl, and 5-6 membered heteroaryl, wherein the $C_{1-6}$ alkyl and 5-6 membered heteroaryl of $R^5$ are each optionally substituted with 1, 2, 3, or 4 independently selected $R^{5A}$ substituents.

In some embodiments, $R^5$ is selected from H, D, methyl, ethyl, difluoromethyl, and pyrazolyl, wherein the methyl, ethyl, and pyrazolyl of R are each optionally substituted with 1, 2, 3, or 4 independently selected $R^{5A}$ substituents.

In some embodiments, $R^5$ is selected from H, methyl, ethyl, difluoromethyl, and pyrazolyl, wherein the methyl, ethyl, and pyrazolyl of R are each optionally substituted with 1, 2, 3, or 4 independently selected $R^{5A}$ substituents.

In some embodiments, $R^5$ is selected from H, D, ethyl, difluoromethyl, and pyrazolyl, wherein the ethyl and pyrazolyl of $R^5$ are each optionally substituted with 1, 2, 3, or 4 independently selected $R^{5A}$ substituents.

In some embodiments, $R^5$ is selected from H, ethyl, difluoromethyl, and pyrazolyl, wherein the ethyl and pyrazolyl of $R^5$ are each optionally substituted with 1, 2, 3, or 4 independently selected $R^{5A}$ substituents.

In some embodiments, each $R^{5A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, (4-7 membered heterocycloalkyl)-$C_{1-6}$alkyl-, and CN, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{5A}$ are each optionally substituted with 1, 2, 3, or 4 independently selected $R^M$ substituents.

In some embodiments, each $R^{5A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, and CN.

In some embodiments, each $R^{5A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, and CN.

In some embodiments, each $R^{5A}$ is independently selected from halo, $C_{1-6}$ alkyl, $C_{1-6}$ haloalkyl, $C_{2-6}$ alkenyl, $C_{2-6}$ alkynyl, and CN.

In some embodiments, each $R^{5A}$ is CN.

In some embodiments, $R^5$ is selected from H, D, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^{5A}$ substituents; and each $R^{5A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, and CN.

In some embodiments, $R^5$ is selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^{5A}$ substituents; and each $R^{5A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, and CN.

In some embodiments, $R^5$ is selected from H, D, $C_{1-6}$ alkyl, $C_{1-6}$ haloalkyl, and 5-6 membered heteroaryl, wherein the $C_{1-6}$ alkyl and 5-6 membered heteroaryl of $R^5$ are each optionally substituted with 1, 2, 3, or 4 independently selected $R^{5A}$ substituents; and each $R^{5A}$ is independently selected from halo, $C_{1-6}$ alkyl, $C_{1-6}$ haloalkyl, $C_{2-6}$ alkenyl, $C_{2-6}$ alkynyl, and CN.

In some embodiments, $R^5$ is selected from H, $C_{1-6}$ alkyl, $C_{1-6}$ haloalkyl, and 5-6 membered heteroaryl, wherein the $C_{1-6}$ alkyl and 5-6 membered heteroaryl of $R^5$ are each optionally substituted with 1, 2, 3, or 4 independently selected $R^{5A}$ substituents; and each $R^{5A}$ is independently selected from halo, $C_{1-6}$ alkyl, $C_{1-6}$ haloalkyl, $C_{2-6}$ alkenyl, $C_{2-6}$ alkynyl, and CN.

In some embodiments, $R^5$ is selected from H, D, $C_{1-6}$ alkyl, $C_{1-6}$ haloalkyl, and 5-6 membered heteroaryl, wherein the $C_{1-6}$ alkyl of $R^5$ is optionally substituted with cyano.

In some embodiments, $R^5$ is selected from H, $C_{1-6}$ alkyl, $C_{1-6}$ haloalkyl, and 5-6 membered heteroaryl, wherein the $C_{1-6}$ alkyl of $R^5$ is optionally substituted with cyano.

In some embodiments, $R^5$ is selected from H, D, methyl, cyanoethyl, difluoromethyl, and pyrazolyl.

In some embodiments, $R^5$ is selected from H, methyl, cyanoethyl, difluoromethyl, and pyrazolyl.

In some embodiments, $R^5$ is selected from H, cyanoethyl, difluoromethyl, and pyrazolyl.

In some embodiments, Z is $CR^6$, NR, or S.

In some embodiments, Z is $CR^6$.

In some embodiments, Z is NR.

In some embodiments, Z is S.

In some embodiments, $R^6$ is H, halo, $C_{1-6}$ alkyl, $C_{1-6}$ haloalkyl, $C_{2-6}$ alkenyl, $C_{2-6}$ alkynyl, $C_{3-10}$ cycloalkyl-$C_{1-6}$ alkyl-, or (4-10 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-10}$ cycloalkyl-$C_{1-6}$ alkyl-, and (4-10 membered heterocycloalkyl)-$C_{1-6}$ alkyl- are each optionally substituted by 1, 2, 3, or 4 independently selected $R^{6A}$ substitutents.

In some embodiments, $R^6$ is H, halo, $C_{1-6}$ alkyl, $C_{1-6}$ haloalkyl, $C_{2-6}$ alkenyl, $C_{2-6}$ alkynyl, $C_{3-7}$ cycloalkyl-$C_{1-6}$ alkyl-, or (4-7 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-7}$ cycloalkyl-$C_{1-6}$ alkyl-, and (4-7 membered heterocycloalkyl)-$C_{1-6}$ alkyl- are each optionally substituted by 1, 2, 3, or 4 independently selected $R^{6A}$ substitutents.

In some embodiments, $R^6$ is H, halo, $C_{1-6}$ alkyl, $C_{1-6}$ haloalkyl, $C_{2-6}$ alkenyl, $C_{2-6}$ alkynyl, $C_{3-7}$ cycloalkyl-$C_{1-6}$ alkyl-, or (4-7 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-7}$ cycloalkyl-$C_{1-6}$ alkyl-, and (4-7 membered heterocycloalkyl)-$C_{1-6}$ alkyl- are each optionally substituted by 1 or 2 independently selected $R^{6A}$ substitutents.

In some embodiments, $R^6$ is H, $C_{1-6}$ alkyl, $C_{3-7}$ cycloalkyl-$C_{1-6}$ alkyl-, or (4-7 membered heterocycloalkyl)-$C_{1-6}$ alkyl-, wherein the $C_{1-6}$ alkyl, $C_{3-7}$ cycloalkyl-$C_{1-6}$ alkyl-, or (4-7 membered heterocycloalkyl)-$C_{1-6}$ alkyl- are each optionally substituted by 1, 2, 3, or 4 independently selected $R^{6A}$ substitutents.

In some embodiments, $R^6$ is H, $C_{1-6}$ alkyl, $C_{3-7}$ cycloalkyl-$C_{1-6}$ alkyl-, or (4-7 membered heterocycloalkyl)-$C_{1-6}$ alkyl-, wherein the $C_{1-6}$ alkyl, $C_{3-7}$ cycloalkyl-$C_{1-6}$ alkyl-, or (4-7 membered heterocycloalkyl)-$C_{1-6}$ alkyl- are each optionally substituted by 1 or 2 independently selected $R^{6A}$ substitutents.

In some embodiments, each $R^{6A}$ is independently selected from halo, $C_{1-6}$ alkyl, $C_{1-6}$ haloalkyl, $C_{2-6}$ alkenyl, $C_{2-6}$ alkynyl, CN, and $NR^{c61}R^{d61}$.

In some embodiments, each $R^{6A}$ is independently selected from $NR^{c61}R^{d61}$.

In some embodiments, each $R^{a61}$, $R^{b61}$, $R^{c61}$, and $R^{d61}$ is independently selected from H, $C_{1-6}$ alkyl, and $C_{1-6}$ haloalkyl.

In some embodiments, each $R^{a61}$, $R^{b61}$, $R^{c61}$, and $R^{d61}$ is independently selected from H and $C_{1-6}$ alkyl.

In some embodiments, each $R^{c61}$ and $R^{d61}$ is independently selected from H, $C_{1-6}$ alkyl, and $C_{1-6}$ haloalkyl.

In some embodiments, each $R^{c61}$ and $R^{d61}$ is independently selected from H and $C_{1-6}$ alkyl.

In some embodiments, each $R^{6A}$ is independently selected from $NR^{c61}R^{d61}$, wherein each $R^{c61}$ and $R^{d61}$ is independently selected from H and $C_{1-6}$ alkyl.

In some embodiments, each $R^{6A}$ is independently selected from $NR^{c61}R^{d61}$, wherein each $R^{c61}$ and $R^{d61}$ is an independently selected $C_{1-6}$ alkyl.

In some embodiments, $R^6$ is H, $C_{1-6}$ alkyl, $C_{3-7}$ cycloalkyl-$C_{1-6}$ alkyl-, or (4-7 membered heterocycloalkyl)-$C_{1-6}$ alkyl-, wherein the $C_{1-6}$ alkyl is optionally substituted by $NR^{c61}R^{d61}$, wherein the $R^{c61}$ and $R^{d61}$ are each independently selected from H and $C_{1-6}$ alkyl.

In some embodiments, $R^6$ is H, $C_{1-6}$ alkyl, $C_{3-7}$ cycloalkyl-$C_{1-6}$ alkyl-, or (4-7 membered heterocycloalkyl)-$C_{1-6}$ alkyl-, wherein the $C_{1-6}$ alkyl is optionally substituted by $NR^{c61}R^{d61}$, wherein the $R^{c61}$ and $R^{d61}$ are each an independently selected $C_{1-6}$ alkyl.

In some embodiments, $R^6$ is H, halo, $C_{1-6}$ alkyl, $C_{1-6}$ haloalkyl, $C_{2-6}$ alkenyl, and $C_{2-6}$ alkynyl.

In some embodiments, $R^6$ is H or $C_{1-6}$ alkyl.

In some embodiments, $R^6$ is H or $C_{1-3}$ alkyl.

In some embodiments, $R^6$ is H, methyl, cyclopropylmethyl, tetrahydrofuranylmethyl, and dimethylaminoethyl.

In some embodiments, $R^6$ is H or methyl.

In some embodiments, $R^6$ is H.

In some embodiments, $R^6$ is methyl.

In some embodiments, $R^6$ is cyclopropylmethyl.

In some embodiments, $R^6$ is tetrahydrofuranylmethyl.

In some embodiments, R is dimethylaminoethyl.

In some embodiments, Z is CH, $NCH_3$, $NCH_2CH_2N(CH_3)_2$, $NCH_2$-cyclopropyl, $NCH_2$-tetrahydrofuranyl, or S.

In some embodiments, Z is CH, $NCH_3$, or S.

In some embodiments, Z is CH.

In some embodiments, Z is $NCH_3$.

In some embodiments, Z is $NCH_2CH_2N(CH_3)_2$.

In some embodiments, Z is $NCH_2$-cyclopropyl.

In some embodiments, Z is $NCH_2$-tetrahydrofuranyl.

In some embodiments, Z is S.

In some embodiments, $R^1$ is $Cy^1$.

In some embodiments, $R^1$ is L-$Cy^1$.

In some embodiments, $Cy^1$ is a $C_{3-10}$ cycloalkyl, 5-10 membered heteroaryl, or 4-10 membered heterocycloalkyl, wherein the $C_{3-10}$ cycloalkyl, 5-10 membered heteroaryl or 4-10 membered heterocycloalkyl are each optionally substituted with 1, 2, 3, 4, 5, 6, 7, or 8 independently selected $R^{1A}$ substituents.

In some embodiments, $Cy^1$ is a $C_{3-10}$ cycloalkyl, 5-10 membered heteroaryl, or 4-10 membered heterocycloalkyl, wherein the $C_{3-10}$ cycloalkyl, 5-10 membered heteroaryl or 4-10 membered heterocycloalkyl are each optionally substituted with 1, 2, 3, or 4 independently selected $R^{1A}$ substituents.

In some embodiments, $Cy^1$ is a $C_{3-7}$ cycloalkyl, 5-6 membered heteroaryl, or 4-7 membered heterocycloalkyl, wherein the $C_{3-7}$ cycloalkyl, 5-6 membered heteroaryl, and 4-7 membered heterocycloalkyl are each optionally substituted with 1, 2, 3, or 4 independently selected $R^{1A}$ substituents.

In some embodiments, $Cy^1$ is a 4-7 membered heterocycloalkyl which is optionally substituted with 1, 2, 3, or 4 independently selected $R^{1A}$ substituents.

In some embodiments, $Cy^1$ is a 4-7 membered heterocycloalkyl which is substituted with 1, 2, 3, or 4 independently selected $R^{1A}$ substituents.

In some embodiments, $Cy^1$ is a 4-7 membered heterocycloalkyl which is substituted with 2 or 3 independently selected $R^{1A}$ substituents.

In some embodiments, $Cy^1$ is piperazinyl, which is optionally substituted with 1, 2, 3, or 4 independently selected $R^{1A}$ substituents.

In some embodiments, $Cy^1$ is piperazinyl, which is optionally substituted with 2 or 3 independently selected $R^{1A}$ substituents.

In some embodiments, $Cy^1$ is piperazinyl, which is substituted with 1, 2, 3, or 4 independently selected $R^{1A}$ substituents.

In some embodiments, $Cy^1$ is piperazinyl, which is substituted with 2 or 3 independently selected $R^{1A}$ substituents.

In some embodiments, $Cy^1$ is:

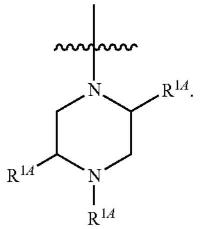

In some embodiments, $Cy^1$ is:

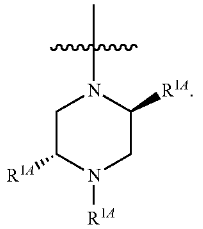

In some embodiments, $Cy^1$ is:

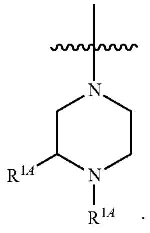

In some embodiments, $Cy^1$ is:

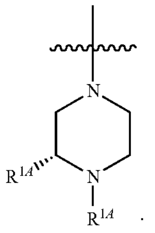

In some embodiments, each $R^{1A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, or 4 independently selected $R^{1B}$ substituents.

In some embodiments, each $R^{1A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{1A}$ are each optionally substituted with 1, 2, 3, or 4 independently selected $R^{1B}$ substituents.

In some embodiments, each $R^{1A}$ is independently selected from halo, oxo, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{1A}$ are each optionally substituted with 1, 2, 3, or 4 independently selected $R^{1B}$ substituents.

In some embodiments, each $R^{1A}$ is independently selected from $C_{1-6}$ alkyl and $C_{1-6}$ haloalkyl, wherein the $C_{1-6}$ alkyl of $R^{1A}$ are each optionally substituted with 1, 2, 3, or 4 independently selected $R^{1B}$ substituents.

In some embodiments, each $R^{1A}$ is independently selected from $C_{1-6}$ alkyl, each of which are optionally substituted with 1, 2, 3, or 4 independently selected $R^{1B}$ substituents.

In some embodiments, $Cy^1$ is:

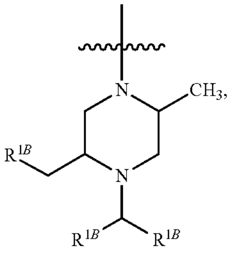

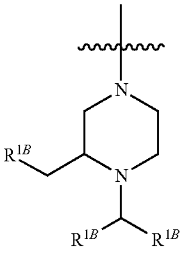
,

-continued

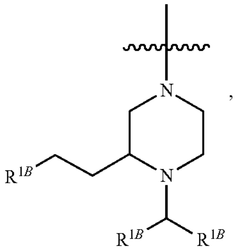
,

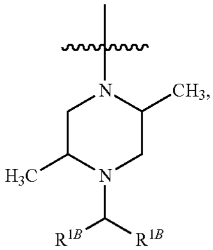

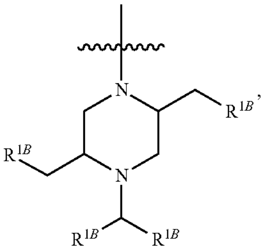

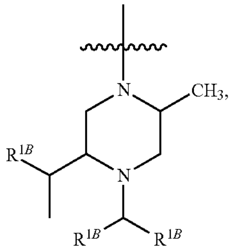
or

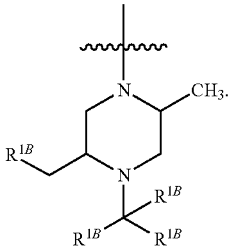

In some embodiments, $Cy^1$ is:

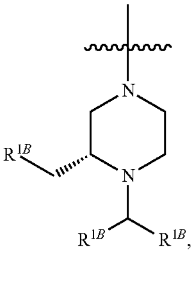

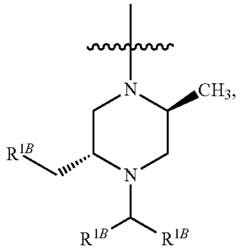

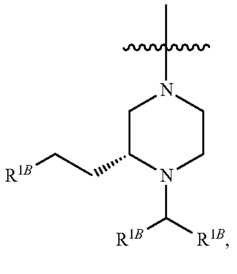

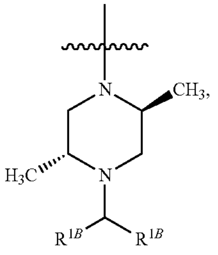

-continued
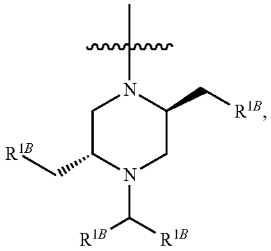
,
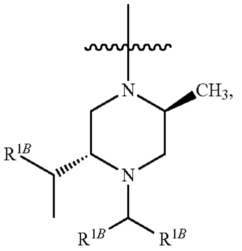
or
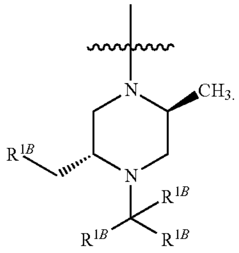
.
In some embodiments, $Cy^1$ is:
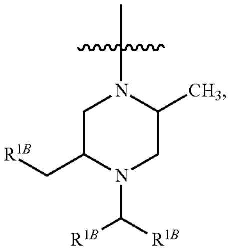
,
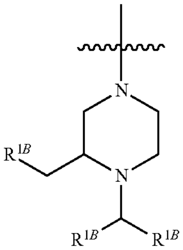
,
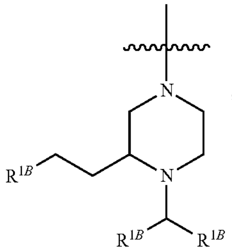
,
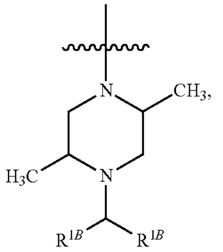
or
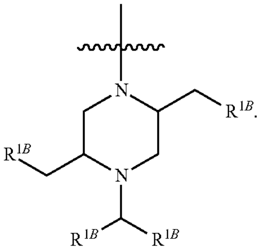
.
In some embodiments, $Cy^1$ is:
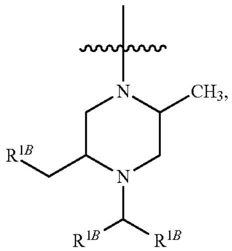
,
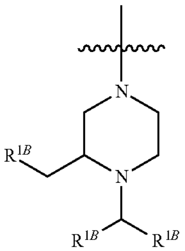
, or
-continued
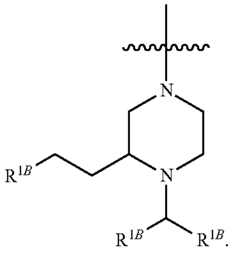
.
In some embodiments, $Cy^1$ is:
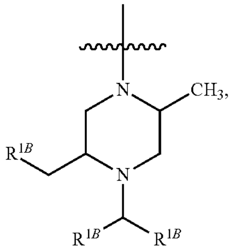
,
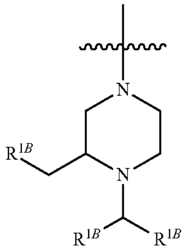
,
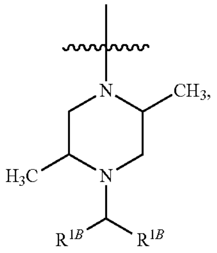
or
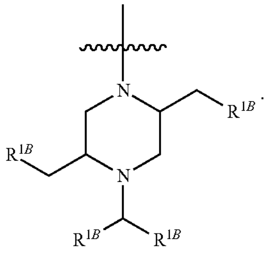
.
In some embodiments, $Cy^1$ is:
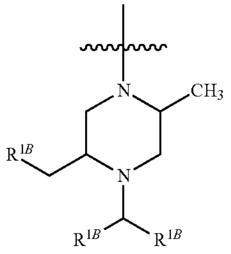
or
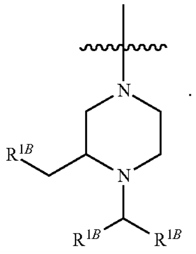
.
In some embodiments, $Cy^1$ is:
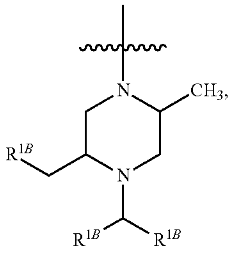
,
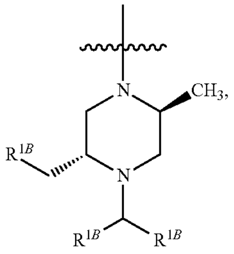
, -continued
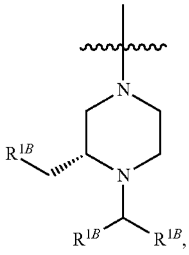
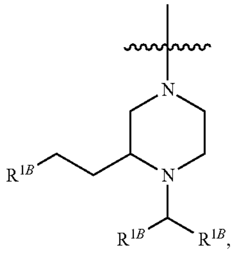
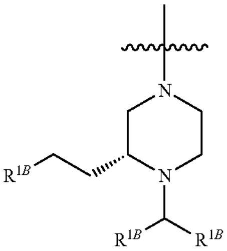
,
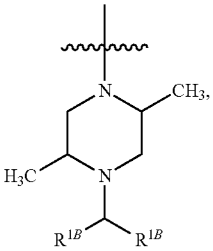
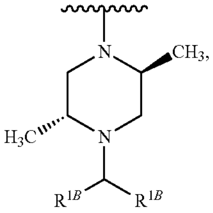
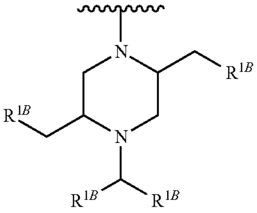
or
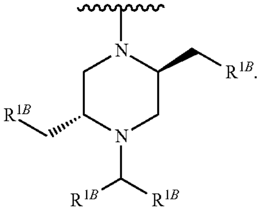
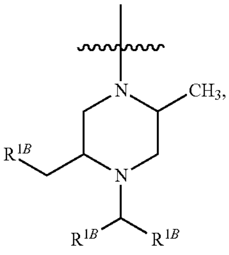
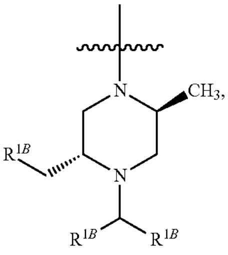
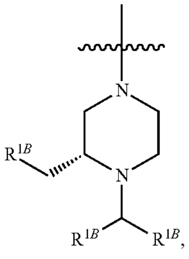
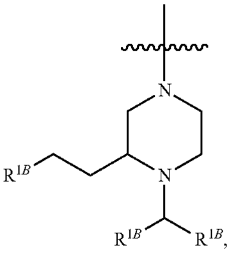
or
-continued
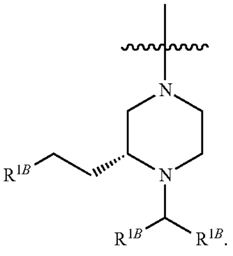
In some embodiments, $Cy^1$ is:
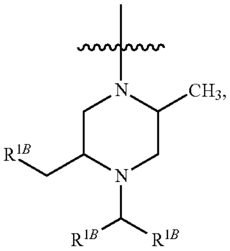
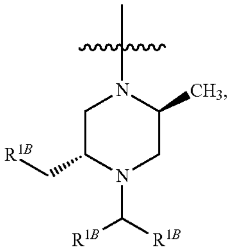
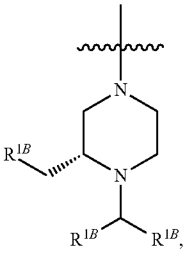
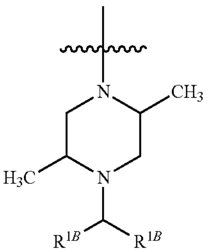
,
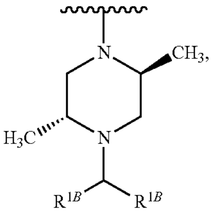
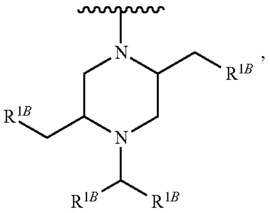
or
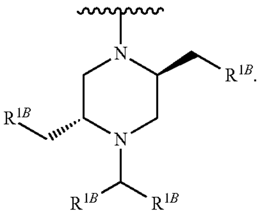
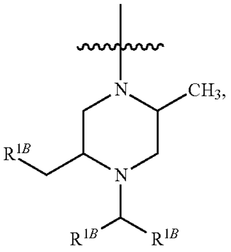
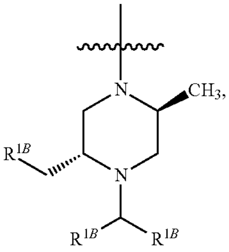
or -continued
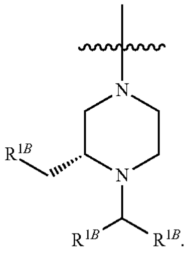
In some embodiments, $Cy^1$ is:
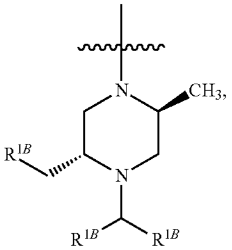
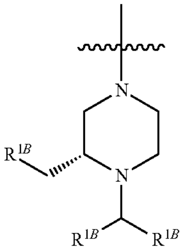
,
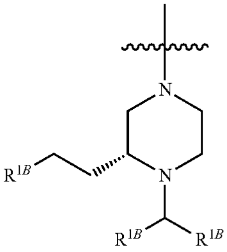
,
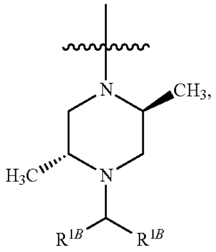
or
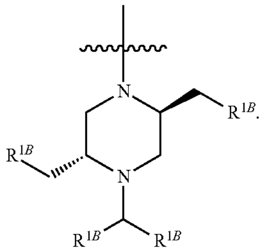
In some embodiments, $Cy^1$ is:
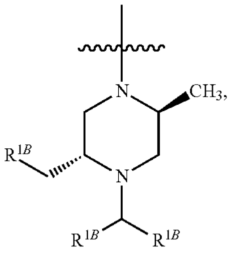
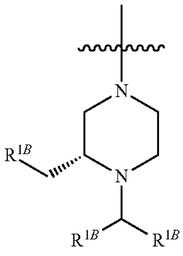
, or
-continued
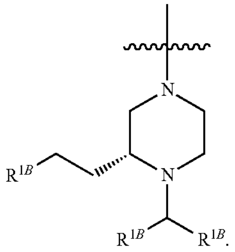
In some embodiments, $Cy^1$ is:
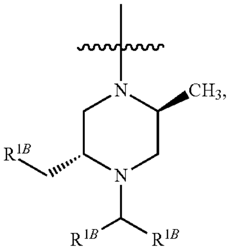
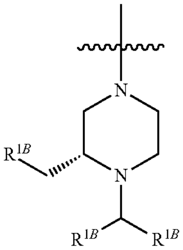
,
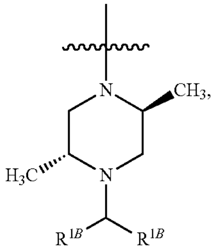
or
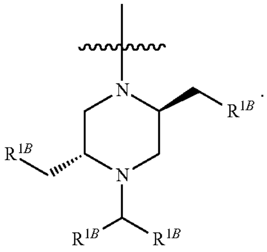
In some embodiments, $Cy^1$ is:
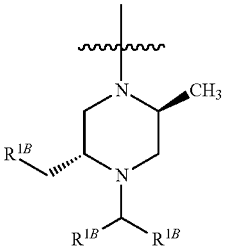
or
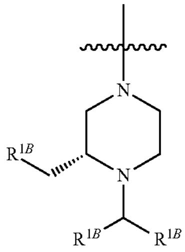
.
In some embodiments, $Cy^1$ is:
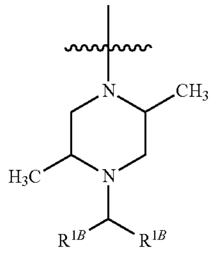

In some embodiments, $Cy^1$ is:

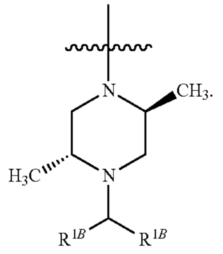

In some embodiments, each $R^{1B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, and $OR^{a12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents.

In some embodiments, each $R^{1B}$ is independently selected from $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a12}$, wherein the $C_{1-6}$ alkyl, $C_{6-10}$ aryl, $C_{3-10}$ cycloalkyl, 5-membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents.

In some embodiments, each $R^{1B}$ is independently selected from $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a12}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents.

In some embodiments, each $R^{1B}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a12}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents.

In some embodiments, each $R^{1B}$ is independently selected from $C_{1-6}$ alkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, and $OR^{a12}$, wherein the $C_{1-6}$ alkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{1B}$ are each optionally substituted with 1, 2, 3, or 4 independently selected $R^{1C}$ substituents.

In some embodiments, each $R^{1B}$ is independently selected from $C_{1-6}$ alkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, and $OR^{a12}$, wherein the phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{1B}$ are each optionally substituted with 1, 2, 3, or 4 independently selected $R^{1C}$ substituents.

In some embodiments, each $R^{1B}$ is independently selected from phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, and $OR^{a12}$, wherein the phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{1B}$ are each optionally substituted with 1, 2, 3, or 4 independently selected $R^{1C}$ substituents.

In some embodiments, each $R^{1B}$ is independently selected from $C_{1-6}$ alkyl, phenyl, $C_{3-7}$ cycloalkyl, 5-6 membered heteroaryl, 4-7 membered heterocycloalkyl, CN, and $OR^{a12}$, wherein the $C_{1-6}$ alkyl, phenyl, $C_{3-7}$ cycloalkyl, 5-6 membered heteroaryl, and 4-7 membered heterocycloalkyl of $R^{1B}$ are each optionally substituted with 1, 2, 3, or 4 independently selected $R^{1C}$ substituents.

In some embodiments, each $R^{1B}$ is independently selected from $C_{1-6}$ alkyl, phenyl, $C_{3-7}$ cycloalkyl, 5-6 membered heteroaryl, 4-7 membered heterocycloalkyl, CN, and $OR^{a12}$, wherein the phenyl, $C_{3-7}$ cycloalkyl, 5-6 membered heteroaryl, and 4-7 membered heterocycloalkyl of RB are each optionally substituted with 1, 2, 3, or 4 independently selected $R^{1C}$ substituents.

In some embodiments, each $R^{1B}$ is independently selected from phenyl, $C_{3-7}$ cycloalkyl, 5-6 membered heteroaryl, 4-7 membered heterocycloalkyl, CN, and $OR^{a12}$, wherein the phenyl, $C_{3-7}$ cycloalkyl, 5-6 membered heteroaryl, and 4-7 membered heterocycloalkyl of $R^{1B}$ are each optionally substituted with 1, 2, 3, or 4 independently selected $R^{1C}$ substituents.

In some embodiments, each $R^{1B}$ is independently selected from $C_{1-6}$ alkyl, phenyl, $C_{3-7}$ cycloalkyl, 5-6 membered heteroaryl, CN, and $OR^{a12}$, wherein the $C_{1-6}$ alkyl, phenyl, $C_{3-7}$ cycloalkyl, and 5-6 membered heteroaryl of $R^{1B}$ are each optionally substituted with 1, 2, 3, or 4 independently selected $R^{1C}$ substituents.

In some embodiments, each $R^{1B}$ is independently selected from $C_{1-6}$ alkyl, phenyl, 5-6 membered heteroaryl, CN, and $OR^{a12}$, wherein the phenyl of $R^{1B}$ are each optionally substituted with 1, 2, 3, or 4 independently selected $R^{1C}$ substituents.

In some embodiments, each $R^{1B}$ is independently selected from methyl, isopropyl, cyclobutyl, cyclohexyl, phenyl, pyridinyl, CN, and methoxy, wherein each methyl, isopropyl, cyclobutyl, cyclohexyl, phenyl, and pyridinyl of $R^{1B}$ are each optionally substituted with 1, 2, 3, or 4 independently selected $R^{1C}$ substituents.

In some embodiments, each $R^{1C}$ is independently selected from halo, $C_{1-6}$ alkyl, $C_{1-6}$ haloalkyl, $C_{2-6}$ alkenyl, $C_{2-6}$ alkynyl, CN, and $OR^{d13}$, wherein the $C_{1-6}$ alkyl, $C_{1-6}$ haloalkyl, $C_{2-6}$ alkenyl, and $C_{2-6}$ alkynyl of $R^{1C}$ are each optionally substituted with 1, 2, 3, or 4 independently selected RD substituents.

In some embodiments, each $R^{1C}$ is independently selected from halo, $C_{1-6}$ alkyl, $C_{1-6}$ haloalkyl, $C_{2-6}$ alkenyl, $C_{2-6}$ alkynyl, CN, and $OR^{d13}$ In some embodiments, each $R^{1C}$ is independently selected from halo, $C_{1-6}$ alkyl, $C_{1-6}$ haloalkyl, CN, and $OR^{a13}$ In some embodiments, each $R^{1C}$ is independently selected from halo, $C_{1-6}$ alkyl, $C_{1-6}$ haloalkyl, $C_{2-6}$ alkenyl, $C_{2-6}$ alkynyl, CN, and $OR^{d13}$; and each $R^{a13}$ is independently selected from H, $C_{1-6}$ alkyl, $C_{2-6}$ alkenyl, $C_{2-6}$ alkynyl, and $C_{1-6}$ haloalkyl.

In some embodiments, each $R^{1C}$ is independently selected from halo, $C_{1-6}$ alkyl, $C_{1-6}$ haloalkyl, CN, and $OR^{a13}$; and each $R^{a13}$ independently selected from H, $C_{1-6}$ alkyl, and $C_{1-6}$ haloalkyl.

In some embodiments, each $R^{1C}$ is independently selected from chloro, fluoro, bromo, methyl, difluoromethyl, trifluoromethyl, CN, methoxy, difluoromethoxy, trifluoromethoxy, and hydroxy.

In some embodiments, each $R^{1B}$ is independently selected from $C_{1-6}$ alkyl, phenyl, $C_{3-7}$ cycloalkyl, pyridinyl, CN, and $OR^{a12}$, wherein the $C_{1-6}$ alkyl, phenyl, $C_{3-7}$ cycloalkyl, and pyridinyl of $R^{1B}$ are each optionally substituted with 1, 2, 3, or 4 $R^{1C}$ substituents independently selected from halo, $C_{1-6}$ alkyl, $C_{1-6}$ haloalkyl, CN, and $OR^{a13}$In some embodiments, each $R^{1B}$ is independently selected from $C_{1-6}$ alkyl, phenyl, pyridinyl, CN, and $OR^{a12}$, wherein the phenyl and pyridinyl of $R^{1B}$ are each optionally substituted with 1, 2, 3, or 4 independently selected halo or $OR^{a13}$ groups.

In some embodiments, each $R^{1B}$ is independently selected from methyl, isopropyl, cyclobutyl, cyclohexyl, phenyl, pyridinyl, CN, and methoxy, wherein each methyl, isopropyl, cyclobutyl, cyclohexyl, phenyl, and pyridinyl of $R^{1B}$ are each optionally substituted with 1, 2, 3, or 4 independently selected $R^{1C}$ substituents independently selected from halo, $C_{1-6}$ alkyl, $C_{1-6}$ haloalkyl, CN, and $OR^{a13}$ In some embodiments, each $R^{a12}$, $R^{b12}$, $R^{c12}$, and $R^{d12}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a12}$, $R^{b12}$, $R^{c12}$, and $R^{d12}$ is independently selected from H and $C_{1-6}$ alkyl.

In some embodiments, each $R^{a13}$, $R^{b13}$, $R^{c13}$, and $R^{d13}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a13}$, $R^{b13}$, $R^{c13}$, and $R^{d13}$ is independently selected from H, $C_{1-6}$ alkyl, and $C_{1-6}$ haloalkyl.

In some embodiments, each $R^{d13}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a13}$ is independently selected from H, $C_{1-6}$ alkyl, and $C_{1-6}$ haloalkyl.

In some embodiments, each $R^{a13}$ is independently selected from H, $C_{1-3}$ alkyl, and $C_{1-3}$ haloalkyl.

In some embodiments, each $R^{a13}$ is $C_{1-6}$ haloalkyl.

In some embodiments, each $R^{a13}$ is $C_{1-3}$ haloalkyl.

In some embodiments, each $R^{a13}$ is trifluoromethyl.

In some embodiments, each $R^{1B}$ is independently selected from $C_{1-6}$ alkyl, phenyl, $C_{3-7}$ cycloalkyl, pyridinyl, CN, and $OR^{a12}$, wherein the $C_{1-6}$ alkyl, phenyl, $C_{3-7}$ cycloalkyl, and pyridinyl, of $R^{1B}$ are each optionally substituted with 1, 2, 3, or 4 independently selected $R^{1C}$ substituents;

each $R^{1C}$ is independently selected from halo, $C_{1-6}$ alkyl, $C_{1-6}$ haloalkyl, $C_{2-6}$ alkenyl, $C_{2-6}$ alkynyl, CN, and $OR^{a13}$;

each $R^{a12}$ is independently selected from H, $C_{1-6}$ alkyl, $C_{1-6}$ haloalkyl, $C_{2-6}$ alkenyl, and $C_{2-6}$ alkynyl; and each $R^{a13}$ is independently selected from H, $C_{1-6}$ alkyl, and $C_{1-6}$ haloalkyl.

In some embodiments, each $R^{1B}$ is independently selected from $C_{1-6}$ alkyl, phenyl, 5-6 membered heteroaryl, CN, and $OR^{a12}$, wherein the phenyl of $R^{1B}$ are each optionally substituted with 1, 2, 3, or 4 independently selected $R^{1C}$ substituents; and each $R^{a12}$ is independently selected from H, $C_{1-6}$ alkyl, $C_{1-6}$ haloalkyl, $C_{2-6}$ alkenyl, and $C_{2-6}$ alkynyl.

In some embodiments, each $R^{1B}$ is independently selected from $C_{1-6}$ alkyl, phenyl, $C_{3-7}$ cycloalkyl, pyridinyl, CN, and $OR^{a12}$, wherein the $C_{1-6}$ alkyl, $C_{3-7}$ cycloalkyl, phenyl and pyridinyl of $R^{1B}$ are each optionally substituted with 1, 2, 3, or 4 independently selected $R^{1C}$ substituents;

each $R^{1C}$ is independently selected from halo, $C_{1-6}$ alkyl, $C_{1-6}$ haloalkyl, CN, and $OR^{a13}$;

each $R^{a12}$ is independently selected from H and $C_{1-6}$ alkyl; and each $R^{a13}$ is independently H, $C_{1-6}$ alkyl, or $C_{1-6}$ haloalkyl.

In some embodiments, each $R^{1B}$ is independently selected from $C_{1-6}$ alkyl, phenyl, pyridinyl, CN, and $OR^{a12}$, wherein the phenyl and pyridinyl of $R^{1B}$ are each optionally substituted with 1, 2, 3, or 4 independently selected halo or $OR^{a13}$ groups;

each $R^{a12}$ is independently selected from H and $C_{1-6}$ alkyl; and each $R^{a13}$ is independently H, $C_{1-6}$ alkyl, or $C_{1-6}$ haloalkyl.

In some embodiments, each $R^{1B}$ is independently selected from phenyl, CN, and $OR^{a12}$, wherein the phenyl of $R^{1B}$ are each optionally substituted with 1, 2, 3, or 4 independently selected $R^{1C}$ substituents; and each $R^{a12}$ is independently selected from H, $C_{1-6}$ alkyl, $C_{1-6}$ haloalkyl, $C_{2-6}$ alkenyl, and $C_2$-6 alkynyl.

In some embodiments, $R^{1B}$ is independently selected from phenyl, CN, and $OR^{a12}$, wherein the phenyl of $R^{1B}$ are each optionally substituted with 1, 2, 3, or 4 independently selected $R^{1C}$ substituents; and each $R^{a12}$ is independently selected from H, $C_{1-6}$ alkyl, $C_{1-6}$ haloalkyl, $C_{2-6}$ alkenyl, and $C_2$-6 alkynyl.

In some embodiments, each $R^{1B}$ is independently selected from phenyl, CN, and $OR^{a12}$, wherein the phenyl of $R^{1B}$ are each optionally substituted with 1, 2, 3, or 4 independently selected halo groups; and each $R^{a12}$ is independently selected from H and $C_{1-6}$ alkyl.

In some embodiments, each $R^{1B}$ is independently selected from methyl, isopropyl, cyclobutyl, cyclohexyl, phenyl, pyridinyl, CN, hydroxy, and methoxy, wherein each methyl, isopropyl, cyclobutyl, cyclohexyl, phenyl, and pyridinyl of $R^{1B}$ are each optionally substituted with 1, 2, 3, or 4 independently selected $R^{1C}$ substituents independently selected from halo, $C_{1-6}$ alkyl, $C_{1-6}$ haloalkyl, CN, and $OR^{a13}$; and each $R^{a13}$ is independently selected from H, $C_{1-6}$ alkyl, and $C_{1-6}$ haloalkyl.

In some embodiments, each $R^{1B}$ is independently selected from methyl, isopropyl, cyclobutyl, cyclohexyl, phenyl, pyridinyl, CN, and methoxy, wherein each methyl, isopropyl, cyclobutyl, cyclohexyl, phenyl, and pyridinyl of $R^{1B}$ are each optionally substituted with 1, 2, 3, or 4 independently selected $R^{1C}$ substituents independently selected from halo, $C_{1-6}$ alkyl, $C_{1-6}$ haloalkyl, CN, and $OR^{a13}$; and each $R^{a13}$ is independently selected from H, $C_{1-6}$ alkyl, and $C_{1-6}$ haloalkyl.

In some embodiments, each $R^{1B}$ is independently selected from methyl, isopropyl, cyclobutyl, cyclohexyl, phenyl, pyridinyl, CN, hydroxy, and methoxy, wherein each methyl, isopropyl, cyclobutyl, cyclohexyl, phenyl, and pyridinyl of $R^{1B}$ are each optionally substituted with 1, 2, 3, or 4 independently selected $R^{1C}$ substituents independently selected from chloro, fluoro, bromo, methyl, difluoromethyl, trifluoromethyl, CN, methoxy, difluoromethoxy, trifluoromethoxy, and hydroxy.

In some embodiments, each $R^{1B}$ is independently selected from methyl, isopropyl, cyclobutyl, cyclohexyl, phenyl, pyridinyl, CN, and methoxy, wherein each methyl, isopropyl, cyclobutyl, cyclohexyl, phenyl, and pyridinyl of $R^{1B}$ are each optionally substituted with 1, 2, 3, or 4 independently selected $R^{1C}$ substituents independently selected from chloro, fluoro, bromo, methyl, difluoromethyl, trifluoromethyl, CN, methoxy, difluoromethoxy, trifluoromethoxy, and hydroxy.

In some embodiments, each $R^{1B}$ is independently selected from isopropyl, hydroxymethyl, difluorocyclobutyl, trifluoromethylcyclobutyl, difluorocyclohexyl, fluorophenyl, difluorophenyl, chlorophenyl, dichlorophenyl, bromophenyl, bromofluorophenyl, chlorofluorophenyl, (fluoro)(difluoromethyl)phenyl, (fluoro)(trifluoromethyl)phenyl, (chloro)(methyl)phenyl, difluoromethylphenyl, trifluoromethylphenyl, (trifluoromethyl)(methyl)phenyl, (trifluoromethyl)(difluoro)phenyl, (chloro)(trifluoromethyl)phenyl, (chloro)(difluoro)phenyl, (trifluoromethoxy)(fluoro)phenyl, trifluoromethoxyphenyl, methoxyphenyl, cyanophenyl, trifluoromethylpyridinyl, (trifluoromethyl)(fluoro)pyridinyl, trifluoromethoxypyridinyl, CN, hydroxy, and methoxy.

In some embodiments, each $R^{1B}$ is independently selected from isopropyl, hydroxymethyl, difluorocyclobutyl, trifluoromethylcyclobutyl, difluorocyclohexyl, fluorophenyl, difluorophenyl, chlorophenyl, dichlorophenyl, bromophenyl, bromofluorophenyl, chlorofluorophenyl, (fluoro)(difluoromethyl)phenyl, (fluoro)(trifluoromethyl)phenyl, (chloro)(methyl)phenyl, difluoromethylphenyl, trifluoromethylphenyl, (trifluoromethyl)(methyl)phenyl, (trifluoromethyl)(difluoro)phenyl, (chloro)(trifluoromethyl)phenyl, (chloro)(difluoro)phenyl, (trifluoromethoxy)(fluoro)phenyl, trifluoromethoxyphenyl, methoxyphenyl, cyanophenyl, trifluoromethylpyridinyl, (trifluoromethyl)(fluoro)pyridinyl, trifluoromethoxypyridinyl, CN, and methoxy.

In some embodiments, each $R^{1B}$ is independently selected from isopropyl, CN, methoxy, hydroxy, hydroxymethyl,

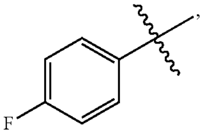,
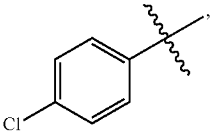,
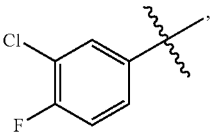,
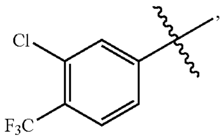,

-continued

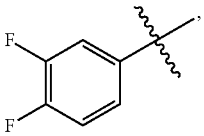,
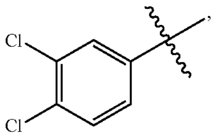,
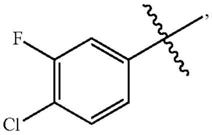,
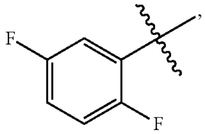,
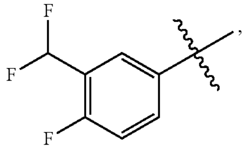,
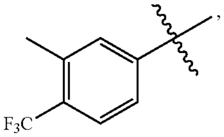,
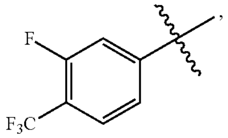,
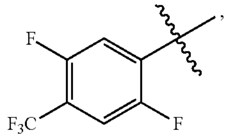,
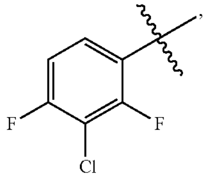,
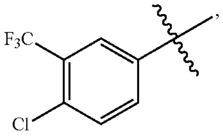,
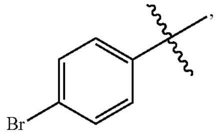,
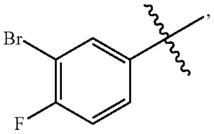,
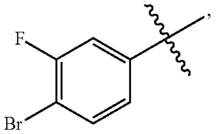,
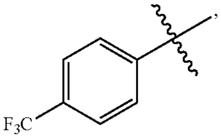,
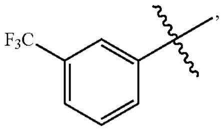,
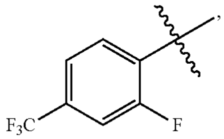,
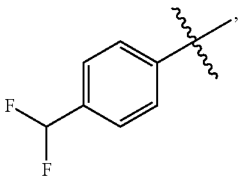,
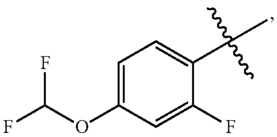,
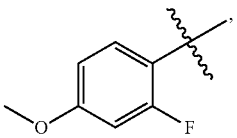,
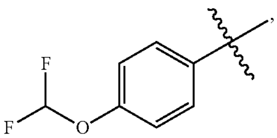,
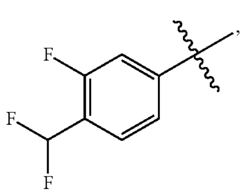,
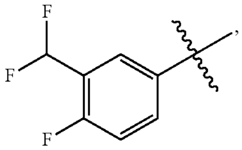, -continued
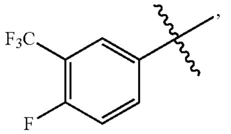
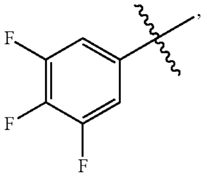
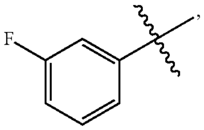
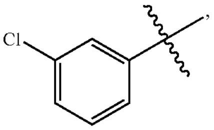
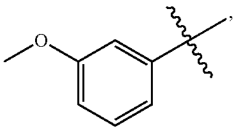
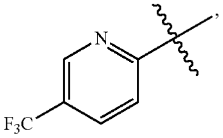
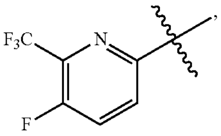
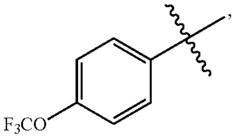
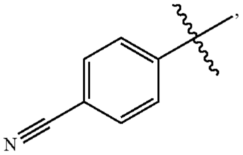
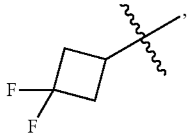
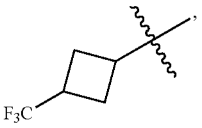
and
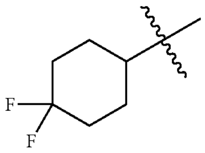
In some embodiments, each $R^{1B}$ is independently selected from CN, methoxy, hydroxy,
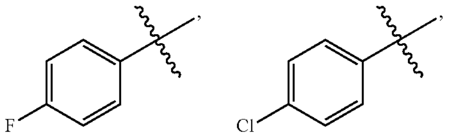
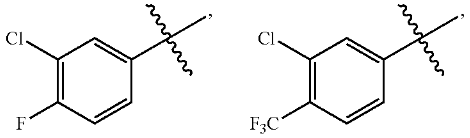
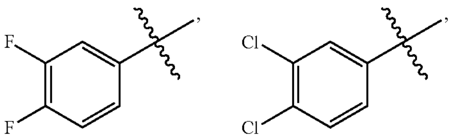
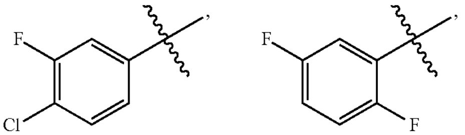
-continued
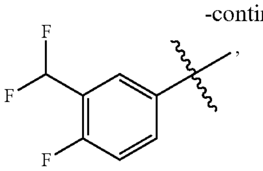
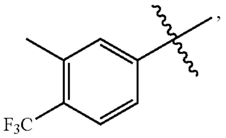
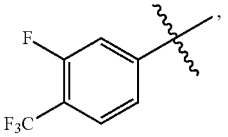
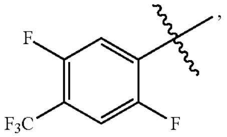
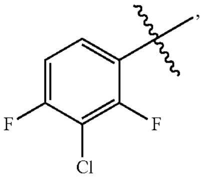
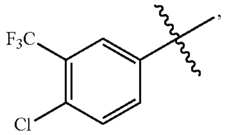
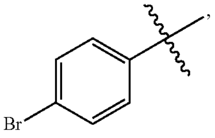
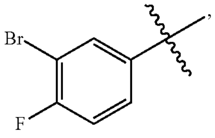
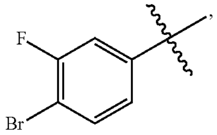
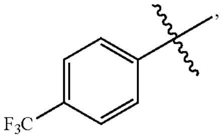
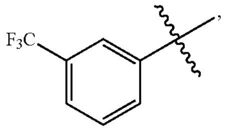
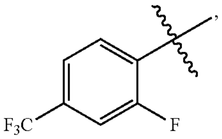
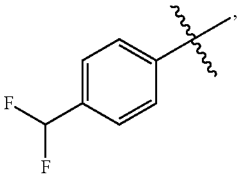
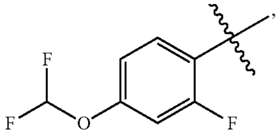
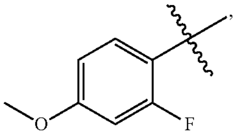
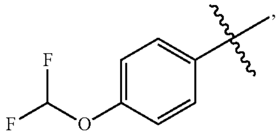
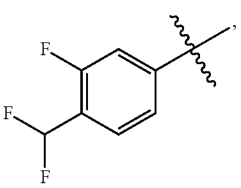
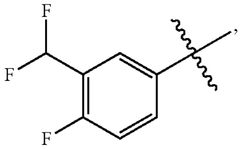
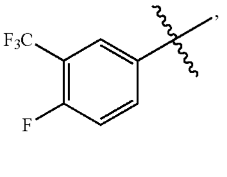
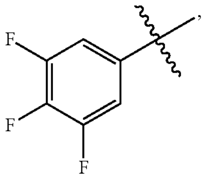
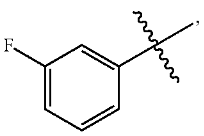
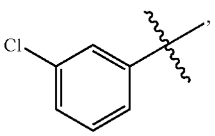

-continued

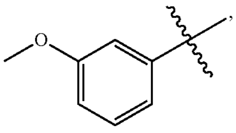,
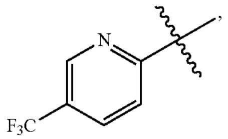,
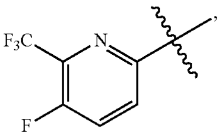,
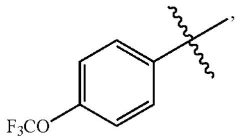,
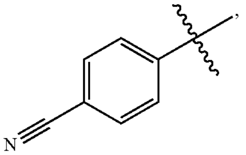,
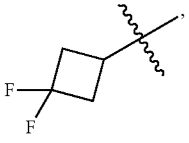,
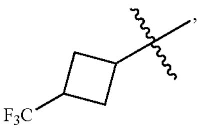, and
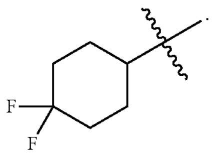.

In some embodiments, each $R^{1B}$ is independently selected from isopropyl, fluorophenyl, trifluoromethoxypyridinyl, CN, and methoxy.

In some embodiments, each $R^{1B}$ is independently selected from fluorophenyl, CN, and methoxy.

In some embodiments, $R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-membered heteroaryl, and 4-10 membered heterocycloalkyl of $R^2$ are each optionally substituted with 1, 2, 3, or 4 independently selected $R^{2A}$ substituents.

In some embodiments, $R^2$ is selected from H, $C_{1-6}$ alkyl, $C_{1-6}$ haloalkyl, phenyl, $C_{3-7}$ cycloalkyl, 5-6 membered heteroaryl, and 4-7 membered heterocycloalkyl, wherein the $C_{1-6}$ alkyl, phenyl, $C_{3-7}$ cycloalkyl, 5-6 membered heteroaryl, and 4-7 membered heterocycloalkyl of $R^2$ are each optionally substituted with 1, 2, 3, or 4 independently selected $R^{2A}$ substituents.

In some embodiments, $R^2$ is selected from H, $C_{1-6}$ alkyl, and $C_{3-7}$ cycloalkyl.

In some embodiments, $R^2$ is selected from H, methyl, and cyclopropyl.

In some embodiments, $R^2$ is H.

In some embodiments, $R^2$ is methyl.

In some embodiments, $R^2$ is cyclopropyl.

In some embodiments:

each $\overset{---}{---}$ is a single or double bond, wherein at least one $\overset{---}{---}$ is a double bond;

U is CH or N;

X is $CR^4$, N, $NR^4$, S, or O;

Y is $CR^5$ or N;

Z is $CR^6$, NR, or S;

$R^1$ is $Cy^1$ or L-$Cy^1$;

L is $NR^{c7}$, O, $C_{1-3}$ alkyl, $C_{2-3}$ alkenyl, or $C_{2-3}$ alkynyl;

$Cy^1$ is a $C_{3-10}$ cycloalkyl, 5-15 membered heteroaryl, or 4-15 membered heterocycloalkyl, wherein the $C_{3-10}$ cycloalkyl, 5-15 membered heteroaryl or 4-15 membered heterocycloalkyl are each optionally substituted with 1, 2, 3, or 4 independently selected $R^{1A}$ substituents;

each $R^{1A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, or 4 independently selected $R^{1B}$ substituents;

each $R^{1B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, and $OR^{a12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents;

each $R^{1C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, and $OR^{a13}$;

each $R^{a13}$ is independently selected from H, $C_{1-6}$ alkyl, and $C_{1-6}$ haloalkyl;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, halo, $C_{1-6}$ alkyl, $C_{1-6}$ haloalkyl, $C_{2-6}$ alkenyl, and $C_{2-6}$ alkynyl;

$R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R are each optionally substituted with 1, 2, 3, or 4 independently selected $R^{5A}$ substituents;

each $R^{5A}$ is independently selected from halo, $C_{1-6}$ alkyl, $C_{1-6}$ haloalkyl, $C_{2-6}$ alkenyl, $C_{2-6}$ alkynyl, and CN;

$R^6$ is H, halo, $C_{1-6}$ alkyl, $C_{1-6}$ haloalkyl, $C_{2-6}$ alkenyl, $C_{2-6}$ alkynyl, $C_{3-10}$ cycloalkyl-$C_{1-6}$ alkyl-, or (4-10 membered heterocycloalkyl)-$C_{1-6}$ alkyl-, wherein the $C_{1-6}$ alkyl, $C_{1-6}$ haloalkyl, $C_{2-6}$ alkenyl, $C_{2-6}$ alkynyl, $C_{3-10}$ cycloalkyl-$C_{1-6}$ alkyl-, and (4-10 membered heterocycloalkyl)-$C_{1-6}$ alkyl- are each optionally substituted by 1, 2, 3, or 4 independently selected $R^{6A}$ substitutents;

each $R^{6A}$ is independently selected from halo, $C_{1-6}$ alkyl, $C_{1-6}$ haloalkyl, $C_{2-6}$ alkenyl, $C_{2-6}$ alkynyl, CN, and $NR^{c61}R^{d61}$;

each $R^{c61}$ and $R^{d61}$ is independently selected from H and $C_{1-6}$ alkyl; and $R^{c7}$ is selected from H, $C_{1-6}$ alkyl, $C_{1-6}$ haloalkyl, $C_{2-6}$ alkenyl, $C_{2-6}$ alkynyl, $C_{6-10}$ aryl, $C_3$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments of the previous embodiment, $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments:

each ═══ is a single or double bond, wherein at least one ═══ is a double bond;

U is CH or N;

X is $CR^4$, N, $NR^4$, S, or O;

Y is $CR^5$ or N;

Z is $CR^6$, $NR^6$, or S;

$R^1$ is $Cy^1$ or L-$Cy^1$;

L is $NR^{c7}$, O, $C_{1-3}$ alkyl, $C_{2-3}$ alkenyl, or $C_{2-3}$ alkynyl;

$Cy^1$ is a $C_{3-10}$ cycloalkyl, 5-15 membered heteroaryl, or 4-15 membered heterocycloalkyl, wherein the $C_{3-10}$ cycloalkyl, 5-15 membered heteroaryl or 4-15 membered heterocycloalkyl are each optionally substituted with 1, 2, 3, or 4 independently selected $R^{1A}$ substituents;

each $R^{1A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, or 4 independently selected $R^{1B}$ substituents;

each $R^{1B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, and $OR^{a12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents;

each $R^{1C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, and CN;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, halo, $C_{1-6}$ alkyl, $C_{1-6}$ haloalkyl, $C_{2-6}$ alkenyl, and $C_{2-6}$ alkynyl;

$R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R are each optionally substituted with 1, 2, 3, or 4 independently selected $R^{5A}$ substituents;

each $R^{5A}$ is independently selected from halo, $C_{1-6}$ alkyl, $C_{1-6}$ haloalkyl, $C_{2-6}$ alkenyl, $C_{2-6}$ alkynyl, and CN;

$R^6$ is H, halo, $C_{1-6}$ alkyl, $C_{1-6}$ haloalkyl, $C_{2-6}$ alkenyl, and $C_{2-6}$ alkynyl; and $R^{c7}$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments of the previous embodiment, $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments:

U is CH or N;

X is $CR^4$, N, $NR^4$, S, or O;

Y is $CR^5$ or N;

Z is $CR^6$, $NR^6$, or S;

$R^1$ is $Cy^1$;

$Cy^1$ is a $C_{3-7}$ cycloalkyl, 5-6 membered heteroaryl, or 4-7 membered heterocycloalkyl, wherein the $C_{3-7}$ cycloalkyl, 5-6 membered heteroaryl, and 4-7 membered heterocycloalkyl are each optionally substituted with 1, 2, 3, or 4 independently selected $R^{1A}$ substituents;

each $R^{1A}$ is independently selected from halo, oxo, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{1A}$ are each optionally substituted with 1, 2, 3, or 4 independently selected $R^{1B}$ substituents;

each $R^{1B}$ is independently selected from $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, and $OR^{a12}$, wherein the $C_{1-6}$ alkyl, $C_{6-10}$ aryl, $C_{3-10}$ cycloalkyl, 5-10 membered heteroaryl, 4-membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents;

each $R^{1C}$ is independently selected from halo, $C_{1-6}$ alkyl, $C_{1-6}$ haloalkyl, $C_{2-6}$ alkenyl, $C_{2-6}$ alkynyl, CN, and $OR^{a13}$;

each $R^{a12}$ is independently selected from H, $C_{1-6}$ alkyl, $C_{1-6}$ haloalkyl, $C_{2-6}$ alkenyl, and $C_{2-6}$ alkynyl;

each $R^{a13}$ is independently selected from H, $C_{1-6}$ alkyl, and $C_{1-6}$ haloalkyl;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-membered heterocycloalkyl of $R^2$ are each optionally substituted with 1, 2, 3, or 4 independently selected $R^{2A}$ substituents;

$R^4$ is H or $C_{1-6}$ alkyl;

$R^5$ is selected from H, D, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^{5A}$ substituents;

each $R^{5A}$ is independently selected from halo, $C_{1-6}$ alkyl, $C_{1-6}$ haloalkyl, $C_{2-6}$ alkenyl, $C_{2-6}$ alkynyl, and CN;

$R^6$ is H, halo, $C_{1-6}$ alkyl, $C_{1-6}$ haloalkyl, $C_{2-6}$ alkenyl, $C_{2-6}$ alkynyl, $C_{3-7}$ cycloalkyl-$C_{1-6}$ alkyl-, or (4-7 membered heterocycloalkyl)-$C_{1-6}$ alkyl-, wherein the $C_{1-6}$ alkyl, $C_{3-7}$ cycloalkyl-$C_{1-6}$ alkyl-, and (4-7 membered heterocycloalkyl)-$C_{1-6}$ alkyl- are each optionally substituted by $NR^{c61}R^{d61}$; and each $R^{c61}$ and $R^{d61}$ is independently selected from H and $C_{1-6}$ alkyl.

In some embodiments of the previous embodiment, $R^5$ is selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^{5A}$ substituents.

In some embodiments:

each ═ ═ ═ is a single or double bond, wherein at least one ═ ═ ═ is a double bond;

U is CH or N;

X is $CR^4$, N, $NR^4$, S, or O;

Y is $CR^5$ or N;

Z is $CR^6$, NR, or S;

$R^1$ is $Cy^1$ or L-$Cy^1$;

L is $NR^{c7}$, O, $C_{1-3}$ alkyl, $C_{2-3}$ alkenyl, or $C_{2-3}$ alkynyl;

$Cy^1$ is a $C_{3-10}$ cycloalkyl, 5-10 membered heteroaryl, or 4-10 membered heterocycloalkyl, wherein the $C_{3-10}$ cycloalkyl, 5-10 membered heteroaryl, or 4-10 membered heterocycloalkyl are each optionally substituted with 1, 2, 3, or 4 independently selected $R^{1A}$ substituents;

each $R^{1A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1A}$ are each optionally substituted with 1, 2, 3, or 4 independently selected $R^{1B}$ substituents;

each $R^{1B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, and $OR^{a12}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents;

each $R^{1C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, and CN;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, halo, $C_{1-6}$ alkyl, $C_{1-6}$ haloalkyl, $C_{2-6}$ alkenyl, and $C_{2-6}$ alkynyl;

$R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of R are each optionally substituted with 1, 2, 3, or 4 independently selected $R^{5A}$ substituents;

each $R^{5A}$ is independently selected from halo, $C_{1-6}$ alkyl, $C_{1-6}$ haloalkyl, $C_{2-6}$ alkenyl, $C_{2-6}$ alkynyl, and CN;

$R^6$ is H, halo, $C_{1-6}$ alkyl, $C_{1-6}$ haloalkyl, $C_{2-6}$ alkenyl, and $C_{2-6}$ alkynyl; and $R^{c7}$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments of the previous embodiment, $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments:

U is CH or N;

X is CH, $CCH_3$, N, $—NCH_2CH_3$, S, or O;

Y is $CR^5$ or N;

Z is CH, $NCH_3$, $NCH_2CH_2N(CH_3)_2$, $NCH_2$-cyclopropyl, $NCH_2$-tetrahydrofuranyl, or S;

$R^1$ is $Cy^1$;

$Cy^1$ is a 4-7 membered heterocycloalkyl which is optionally substituted with 1, 2, 3, or 4 independently selected $R^{1A}$ substituents;

each $R^{1A}$ is independently selected from $C_{1-6}$ alkyl, each of which are optionally substituted with 1, 2, 3, or 4 independently selected $R^{1B}$ substituents;

each $R^{1B}$ is independently selected from $C_{1-6}$ alkyl, phenyl, $C_{3-7}$ cycloalkyl, 5-6 membered heteroaryl, 4-7 membered heterocycloalkyl, CN, and $OR^{a12}$, wherein the $C_{1-6}$ alkyl, phenyl, $C_{3-7}$ cycloalkyl, 5-6 membered heteroaryl, and 4-7 membered heterocycloalkyl of $R^{1B}$ are each optionally substituted with 1, 2, 3, or 4 independently selected $R^{1C}$ substituents;

each $R^{1C}$ is independently selected from halo, $C_{1-6}$ alkyl, $C_{1-6}$ haloalkyl, $C_{2-6}$ alkenyl, $C_{2-6}$ alkynyl, CN, and $OR^{a13}$;

each $R^{a12}$ is independently selected from H, $C_{1-6}$ alkyl, $C_{1-6}$ haloalkyl, $C_{2-6}$ alkenyl, and $C_2$-6 alkynyl;

each $R^{a13}$ is independently H, $C_{1-6}$ alkyl, or $C_{1-6}$ haloalkyl;

$R^5$ is selected from H, D, $C_{1-6}$ alkyl, $C_{1-6}$ haloalkyl, and 5-6 membered heteroaryl, wherein the $C_{1-6}$ alkyl and 5-6 membered heteroaryl of $R^5$ are each optionally substituted with 1, 2, 3, or 4 independently selected $R^{5A}$ substituents; and each $R^{5A}$ is independently selected from halo, $C_{1-6}$ alkyl, $C_{1-6}$ haloalkyl, $C_{2-6}$ alkenyl, $C_{2-6}$ alkynyl, and CN.

In some embodiments:

U is CH or N;

X is CH, $CCH_3$, N, $—NCH_2CH_3$, S, or O;

Y is $CR^5$ or N;

Z is CH, $NCH_3$, $NCH_2CH_2N(CH_3)_2$, $NCH_2$-cyclopropyl, $NCH_2$-tetrahydrofuranyl, or S;

$R^1$ is $Cy^1$;

$Cy^1$ is a 4-7 membered heterocycloalkyl which is optionally substituted with 1, 2, 3, or 4 independently selected $R^{1A}$ substituents;

each $R^{1A}$ is independently selected from $C_{1-6}$ alkyl, each of which are optionally substituted with 1, 2, 3, or 4 independently selected $R^{1B}$ substituents;

each $R^{1B}$ is independently selected from $C_{1-6}$ alkyl, phenyl, $C_{3-7}$ cycloalkyl, 5-6 membered heteroaryl, 4-7 membered heterocycloalkyl, CN, and $OR^{a12}$, wherein the phenyl, $C_{3-7}$ cycloalkyl, 5-6 membered heteroaryl, and 4-7 membered heterocycloalkyl of $R^{1B}$ are each optionally substituted with 1, 2, 3, or 4 independently selected $R^{1C}$ substituents;

each $R^{1C}$ is independently selected from halo, $C_{1-6}$ alkyl, $C_{1-6}$ haloalkyl, $C_{2-6}$ alkenyl, $C_{2-6}$ alkynyl, CN, and $OR^{a13}$;

each $R^{a12}$ is independently selected from H, $C_{1-6}$ alkyl, $C_{1-6}$ haloalkyl, $C_{2-6}$ alkenyl, and $C_{2-6}$ alkynyl;

each $R^{a13}$ is independently H, $C_{1-6}$ alkyl, or $C_{1-6}$ haloalkyl;

$R^5$ is selected from H, $C_{1-6}$ alkyl, $C_{1-6}$ haloalkyl, and 5-6 membered heteroaryl, wherein the $C_{1-6}$ alkyl and 5-6 membered heteroaryl of $R^5$ are each optionally substituted with 1, 2, 3, or 4 independently selected $R^{5A}$ substituents; and each $R^{5A}$ is independently selected from halo, $C_{1-6}$ alkyl, $C_{1-6}$ haloalkyl, $C_{2-6}$ alkenyl, $C_{2-6}$ alkynyl, and CN.

In some embodiments:

U is CH or N;

X is $CR^4$, N, $NR^4$, S, or O;

Y is $CR^5$ or N;

Z is $CR^6$, $NR^6$, or S;

$R^1$ is $Cy^1$;

$Cy^1$ is a $C_{3-7}$ cycloalkyl, 5-6 membered heteroaryl, or 4-7 membered heterocycloalkyl, wherein the $C_{3-7}$ cycloalkyl, 5-6 membered heteroaryl, and 4-7 membered heterocycloalkyl are each optionally substituted with 1, 2, 3, or 4 independently selected $R^{1A}$ substituents;

each $R^{1A}$ is independently selected from halo, oxo, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{1A}$ are each optionally substituted with 1, 2, 3, or 4 independently selected $R^{1B}$ substituents;

each $R^{1B}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-membered heteroaryl)-$C_{1-6}$ alkyl-, (4-10 membered heterocycloalkyl)-$C_{1-6}$ alkyl-, CN, and $OR^{a12}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{1B}$ are each optionally substituted with 1, 2, 3, or 4 independently selected $R^{1C}$ substituents;

each $R^{1C}$ is independently selected from halo, $C_{1-6}$ alkyl, $C_{1-6}$ haloalkyl, $C_{2-6}$ alkenyl, $C_{2-6}$ alkynyl, and CN;

each $R^{a12}$ is independently selected from H, $C_{1-6}$ alkyl, $C_{1-6}$ haloalkyl, $C_{2-6}$ alkenyl, and $C_2$-6 alkynyl;

$R^2$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-membered heterocycloalkyl of $R^2$ are each optionally substituted with 1, 2, 3, or 4 independently selected $R^{2A}$ substituents;

$R^4$ is H or $C_{1-6}$ alkyl;

$R^5$ is selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, wherein the $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl of $R^5$ are each optionally substituted with 1, 2, 3, or 4 independently selected $R^{5A}$ substituents;

each $R^{5A}$ is independently selected from halo, $C_{1-6}$ alkyl, $C_{1-6}$ haloalkyl, $C_{2-6}$ alkenyl, $C_{2-6}$ alkynyl, and CN;

$R^6$ is H, halo, $C_{1-6}$ alkyl, $C_{1-6}$ haloalkyl, $C_{2-6}$ alkenyl, and $C_{2-6}$ alkynyl.

In some embodiments:

U is CH or N;

X is CH, $CCH_3$, N, $—NCH_2CH_3$, S, or O;

Y is $CR^5$ or N;

Z is CH, $NCH_3$, or S;

$R^1$ is $Cy^1$;

$Cy^1$ is a 4-7 membered heterocycloalkyl which is optionally substituted with 1, 2, 3, or 4 independently selected $R^{1A}$ substituents;

each $R^{1A}$ is independently selected from $C_{1-6}$ alkyl, each of which are optionally substituted with 1, 2, 3, or 4 independently selected $R^{1B}$ substituents;

each $R^{1B}$ is independently selected from phenyl, $C_{3-7}$ cycloalkyl, 5-6 membered heteroaryl, 4-7 membered heterocycloalkyl, CN, and $OR^{a12}$, wherein the phenyl, $C_{3-7}$ cycloalkyl, 5-6 membered heteroaryl, and 4-7 membered heterocycloalkyl of $R^{1B}$ are each optionally substituted with 1, 2, 3, or 4 independently selected $R^{1C}$ substituents;

each $R^{1C}$ is independently selected from halo, $C_{1-6}$ alkyl, $C_{1-6}$ haloalkyl, $C_{2-6}$ alkenyl, $C_{2-6}$ alkynyl, and CN;

each $R^{a12}$ is independently selected from H, $C_{1-6}$ alkyl, $C_{1-6}$ haloalkyl, $C_{2-6}$ alkenyl, and $C_2$-6 alkynyl;

$R^5$ is selected from H, $C_{1-6}$ alkyl, $C_{1-6}$ haloalkyl, and 5-6 membered heteroaryl, wherein the $C_{1-6}$ alkyl and 5-6 membered heteroaryl of $R^5$ are each optionally substituted with 1, 2, 3, or 4 independently selected $R^{5A}$ substituents; and each $R^{5A}$ is independently selected from halo, $C_{1-6}$ alkyl, $C_{1-6}$ haloalkyl, $C_{2-6}$ alkenyl, $C_{2-6}$ alkynyl, and CN.

In some embodiments the compound of Formula I is a compound of Formula II:

II

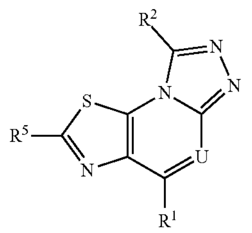

or a pharmaceutically acceptable salt thereof.

In some embodiments the compound of Formula I is a compound of Formula IIa:

IIa

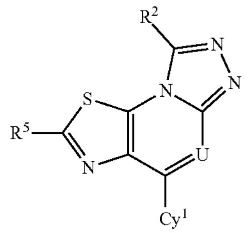

or a pharmaceutically acceptable salt thereof.

In some embodiments the compound of Formula I is a compound of Formula IIb:

IIb

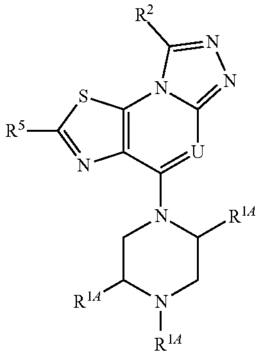

or a pharmaceutically acceptable salt thereof.

In some embodiments, the compound of Formula I is a compound of Formula III:

III

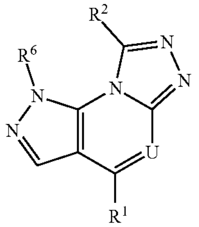

or a pharmaceutically acceptable salt thereof.

In some embodiments, the compound of Formula I is a compound of Formula IIIa:

IIIa

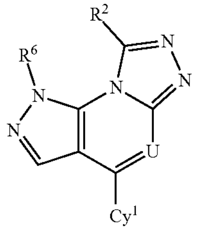

or a pharmaceutically acceptable salt thereof.

In some embodiments, the compound of Formula I is a compound of Formula IIIb:

IIIb

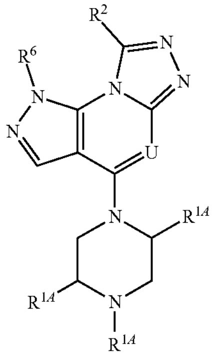

or a pharmaceutically acceptable salt thereof.

In some embodiments, the compound of Formula I is a compound of Formula IV:

IV

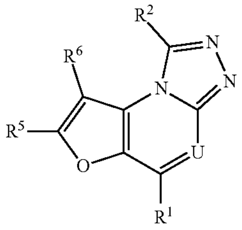

or a pharmaceutically acceptable salt thereof.

In some embodiments, the compound of Formula I is a compound of Formula IVa:

IVa

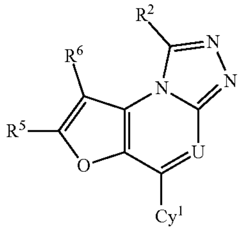

or a pharmaceutically acceptable salt thereof.

In some embodiments, the compound of Formula I is a compound of Formula IVb:

IVb

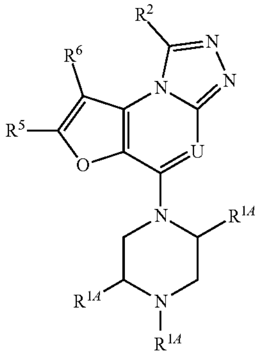

or a pharmaceutically acceptable salt thereof.

In some embodiments, the compound of Formula I is a compound of Formula V:

V

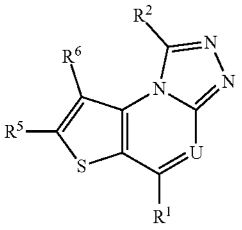

or a pharmaceutically acceptable salt thereof.

In some embodiments, the compound of Formula I is a compound of Formula Va:

Va

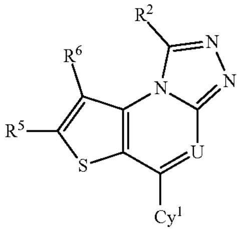

or a pharmaceutically acceptable salt thereof.

In some embodiments, the compound of Formula I is a compound of Formula Vb:

Vb

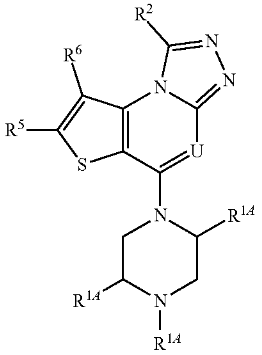

or a pharmaceutically acceptable salt thereof.

In some embodiments, the compound of Formula I is a compound of Formula VI:

VI

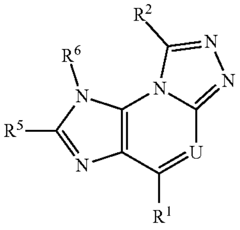

or a pharmaceutically acceptable salt thereof.

In some embodiments, the compound of Formula I is a compound of Formula VIa:

VIa

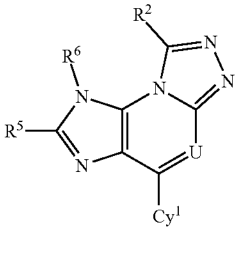

or a pharmaceutically acceptable salt thereof.

In some embodiments, the compound of Formula I is a compound of Formula VIb:

VIb

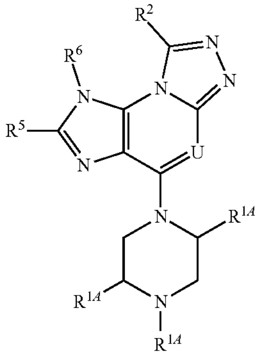

or a pharmaceutically acceptable salt thereof.

In some embodiments, the compound of Formula I is a compound of Formula VII:

VII

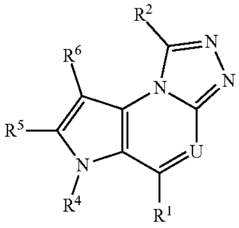

or a pharmaceutically acceptable salt thereof.

In some embodiments, the compound of Formula I is a compound of Formula VIIa:

VIIa

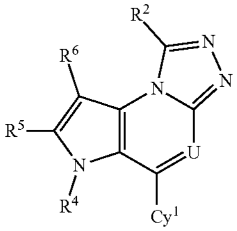

or a pharmaceutically acceptable salt thereof.

In some embodiments, the compound of Formula I is a compound of Formula VIIb:

VIIb

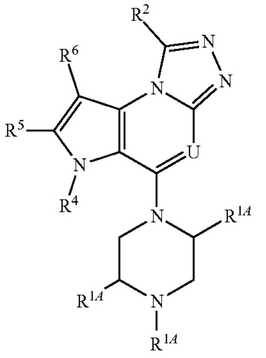

or a pharmaceutically acceptable salt thereof.

In some embodiments, the compound of Formula I is a compound of Formula VIII:

VIII

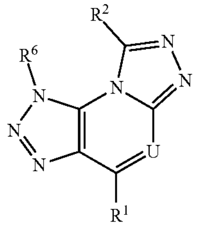

or a pharmaceutically acceptable salt thereof.

In some embodiments, the compound of Formula I is a compound of Formula VIIIa:

VIIIa

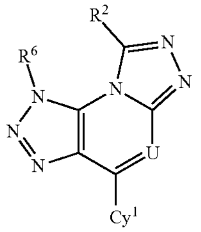

or a pharmaceutically acceptable salt thereof.

In some embodiments, the compound of Formula I is a compound of Formula VIIIb:

VIIIb

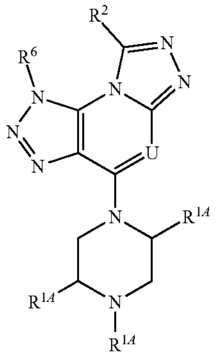

or a pharmaceutically acceptable salt thereof.

In some embodiments, the compound of Formula I is a compound of Formula IX:

IX

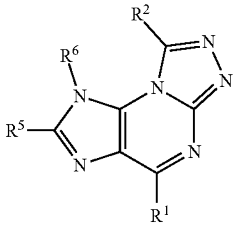

or a pharmaceutically acceptable salt thereof.

In some embodiments, the compound of Formula I is a compound of Formula IXa:

IXa

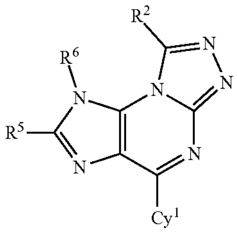

or a pharmaceutically acceptable salt thereof.

In some embodiments, the compound of Formula I is a compound of Formula IXb:

IXb

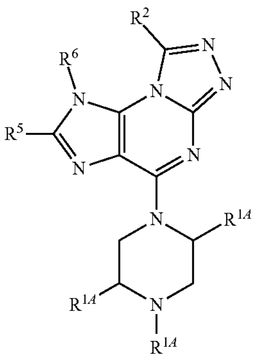

or a pharmaceutically acceptable salt thereof.

In some embodiments, the compound of Formula I is a compound of Formula X:

X

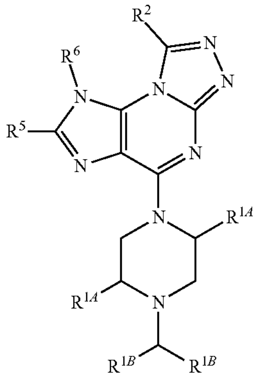

or a pharmaceutically acceptable salt thereof.

In some embodiments, the compound of Formula I is a compound of Formula Xa:

Xa

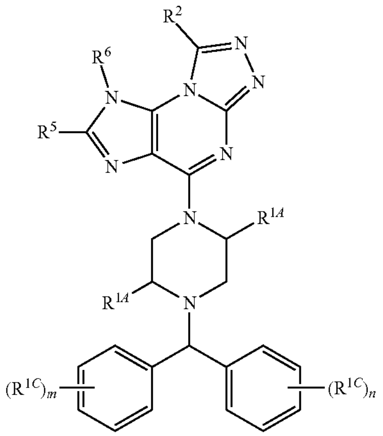

or a pharmaceutically acceptable salt thereof, wherein:

m is 0, 1, 2, 3, 4, or 5; and n is 0, 1, 2, 3, 4, or 5.

In some embodiments, the compound of Formula I is a compound of Formula Xb:

Xb

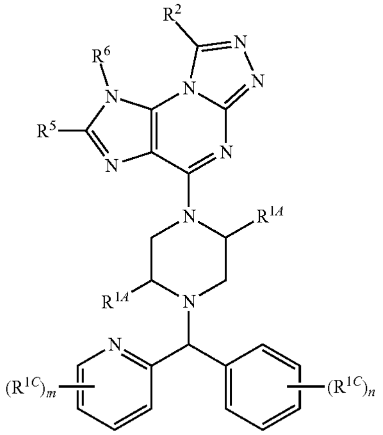

or a pharmaceutically acceptable salt thereof, wherein:

In some embodiments, the compound of Formula I is a compound of Formula Xc:

Xc

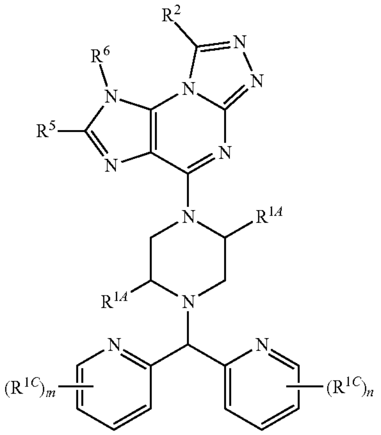

or a pharmaceutically acceptable salt thereof, wherein:

m is 0, 1, 2, 3, 4, or 5; and n is 0, 1, 2, 3, 4, or 5.

In some embodiments, the compound of Formula I is a compound of Formula Xd:

Xd

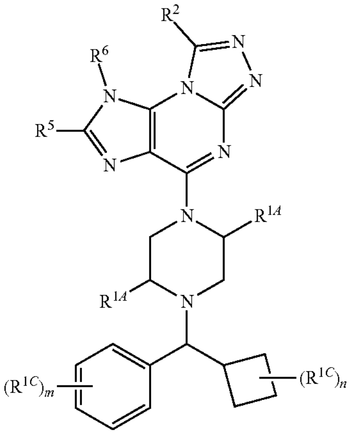

or a pharmaceutically acceptable salt thereof, wherein:

m is 0, 1, 2, 3, 4, or 5; and n is 0, 1, 2, or 3.

In some embodiments, the compound of Formula I is a compound of Formula Xe:

Xe

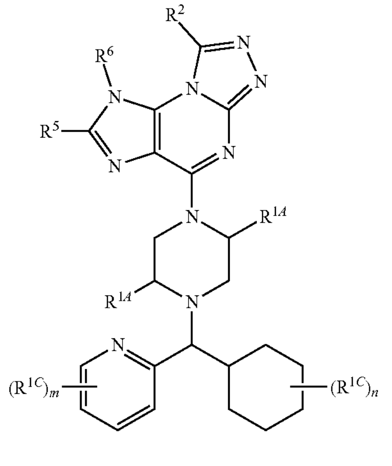

or a pharmaceutically acceptable salt thereof, wherein:

m is 0, 1, 2, 3, 4, or 5; and n is 0, 1, 2, 3, 4, or 5.

In some embodiments, the compound of Formula I is a compound of Formula XI:

XI

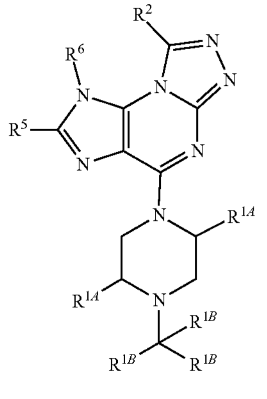

or a pharmaceutically acceptable salt thereof.

In some embodiments of Formulas X, Xa, Xb, Xc, Xd, Xe, and XI, each $R^{1A}$ is independently selected from $C_{1-6}$ alkyl and $C_{1-6}$ haloalkyl, wherein the $C_{1-6}$ alkyl of $R^{1A}$ are each optionally substituted with 1, 2, 3, or 4 independently selected $R^{1B}$ substituents.

In some embodiments of Formulas X, Xa, Xb, Xc, Xd, Xe, and XI, each $R^{1A}$ is independently selected from $C_{1-6}$ alkyl, wherein the $C_{1-6}$ alkyl of $R^{1A}$ are each optionally substituted with 1, 2, 3, or 4 independently selected $R^{1B}$ substituents.

In some embodiments, the compound provided herein is selected from:

4-((2S,5R)-4-(bis(4-fluorophenyl)methyl)-2,5-dimethylpiperazin-1-yl)thiazolo[4,5-e][1,2,4]triazolo[4,3-a]pyrimidine;

4-((2S,5R)-4-(bis(4-fluorophenyl)methyl)-2,5-dimethylpiperazin-1-yl)-8-methylthiazolo[4,5-e][1,2,4]triazolo[4,3-a]pyrimidine;

4-((2S,5R)-4-(bis(4-fluorophenyl)methyl)-2,5-dimethylpiperazin-1-yl)-2-(difluoromethyl)thiazolo[4,5-e][1,2,4]triazolo[4,3-a]pyrimidine;

3-(4-((2S,5R)-4-(bis(4-fluorophenyl)methyl)-2,5-dimethylpiperazin-1-yl)thiazolo[4,5-e][1,2,4]triazolo[4,3-a]pyrimidin-2-yl)propanenitrile;

4-((2S,5R)-4-(bis(4-fluorophenyl)methyl)-2,5-dimethylpiperazin-1-yl)-2-(1H-pyrazol-4-yl)thiazolo[4,5-e][1,2,4]triazolo[4,3-a]pyrimidine;

4-((2S,5R)-4-(bis(4-fluorophenyl)methyl)-2,5-dimethylpiperazin-1-yl)-1-methyl-1H-pyrazolo[4,3-e][1,2,4]triazolo[4,3-a]pyrimidine;

5-((2S,5R)-4-(bis(4-fluorophenyl)methyl)-2,5-dimethylpiperazin-1-yl)furo[2,3-e][1,2,4]triazolo[4,3-a]pyrimidine;

5-((2S,5R)-4-(bis(4-fluorophenyl)methyl)-2,5-dimethylpiperazin-1-yl)thieno[2,3-e][1,2,4]triazolo[4,3-a]pyrimidine;

4-((2S,5R)-4-(bis(4-fluorophenyl)methyl)-2,5-dimethylpiperazin-1-yl)-1-methyl-1H-[1,2,4]triazolo[3,4-b]purine;

5-((2S,5R)-4-(bis(4-fluorophenyl)methyl)-2,5-dimethylpiperazin-1-yl)-6-ethyl-6H-pyrrolo[2,3-e][1,2,4]triazolo[4,3-a]pyrimidine;

5-((2S,5R)-4-(bis(4-fluorophenyl)methyl)-2,5-dimethylpiperazin-1-yl)thieno[2,3-e][1,2,4]triazolo[4,3-a]pyridine;

4-((2S,5R)-4-(bis(4-fluorophenyl)methyl)-2,5-dimethylpiperazin-1-yl)-1,3-dimethyl-1H-pyrazolo[4,3-e][1,2,4]triazolo[4,3-a]pyridine;

4-((2S,5S)-4-(bis(4-fluorophenyl)methyl)-5-(methoxymethyl)-2-methylpiperazin-1-yl)thiazolo[4,5-e][1,2,4]triazolo[4,3-a]pyrimidine;

2-((2R,5S)-1-(bis(4-fluorophenyl)methyl)-5-methyl-4-(thiazolo[4,5-e][1,2,4]triazolo[4,3-a]pyrimidin-4-yl)piperazin-2-yl)acetonitrile;

2-((2R,5S)-1-(bis(4-fluorophenyl)methyl)-4-(8-cyclopropylthiazolo[4,5-e][1,2,4]triazolo[4,3-a]pyrimidin-4-yl)-5-methylpiperazin-2-yl)acetonitrile;

2-((2R,5S)-1-(bis(4-fluorophenyl)methyl)-5-methyl-4-(1-methyl-1H-[1,2,4]triazolo[3,4-b]purin-4-yl)piperazin-2-yl)acetonitrile;

(R)-3-(1-(bis(4-fluorophenyl)methyl)-4-(thiazolo[4,5-e][1,2,4]triazolo[4,3-a]pyrimidin-4-yl)piperazin-2-yl)propanenitrile;

4-((2S,5R)-4-(bis(4-fluorophenyl)methyl)-2,5-dimethylpiperazin-1-yl)-1-(cyclopropylmethyl)-1H-[1,2,4]triazolo[3,4-b]purine;

4-((2S,5R)-4-(bis(4-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(bis(4-fluorophenyl)methyl)-5-ethyl-2-methylpiperazin-1-yl)-2-methyl-1-(((S)-tetrahydrofuran-2-yl)methyl)-1H-[1,2,4]triazolo[3,4-b]purine;

4-((2S,5R)-4-(bis(4-fluorophenyl)methyl)-2,5-diethylpiperazin-1-yl)-1-(cyclopropylmethyl)-1H-[1,2,4]triazolo[3,4-b]purine;

1-(cyclopropylmethyl)-4-((2S,5R)-4-((S)-1-(4-fluorophenyl)-2-methylpropyl)-2,5-dimethylpiperazin-1-yl)-1H-[1,2,4]triazolo[3,4-b]purine;

1-(cyclopropylmethyl)-4-((2S,5R)-4-((R)-1-(4-fluorophenyl)-2-methylpropyl)-2,5-dimethylpiperazin-1-yl)-1H-[1,2,4]triazolo[3,4-b]purine;

1-(cyclopropylmethyl)-4-((2S,5R)-4-((S)-(4-fluorophenyl)(5-(trifluoromethoxy)pyridin-2-yl)methyl)-2,5-dimethylpiperazin-1-yl)-1H-[1,2,4]triazolo[3,4-b]purine;

1-(cyclopropylmethyl)-4-((2S,5R)-4-((R)-(4-fluorophenyl)(5-(trifluoromethoxy)pyridin-2-yl)methyl)-2,5-dimethylpiperazin-1-yl)-1H-[1,2,4]triazolo[3,4-b]purine;

4-((2S,5R)-4-((S)-(4-fluorophenyl)(5-(trifluoromethoxy)pyridin-2-yl)methyl)-2,5-dimethylpiperazin-1-yl)-1-(((S)-tetrahydrofuran-2-yl)methyl)-1H-[1,2,4]triazolo[3,4-b]purine;

4-((2S,5R)-4-((R)-(4-fluorophenyl)(5-(trifluoromethoxy)pyridin-2-yl)methyl)-2,5-dimethylpiperazin-1-yl)-1-(((S)-tetrahydrofuran-2-yl)methyl)-1H-[1,2,4]triazolo[3,4-b]purine;

2-(4-((2S,5R)-4-(bis(4-fluorophenyl)methyl)-2,5-dimethylpiperazin-1-yl)-1H-[1,2,4]triazolo[3,4-b]purin-1-yl)-N,N-dimethylethan-1-amine;

4-((2S,5R)-4-(bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine;

4-((2S,5R)-4-(bis(4-fluorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine;

4-((2S,5R)-4-(bis(4-fluorophenyl)methyl)-2,5-diethylpiperazin-1-yl)-1-(((S)-tetrahydrofuran-2-yl)methyl)-1H-[1,2,3]triazolo[4,5-e][1,2,4]triazolo[4,3-a]pyrimidine;

4-((2S,5R)-4-(bis(4-fluorophenyl)methyl)-5-ethyl-2-methylpiperazin-1-yl)-1-(((R)-tetrahydrofuran-2-yl)methyl)-1H-[1,2,3]triazolo[4,5-e][1,2,4]triazolo[4,3-a]pyrimidine;

4-((2S,5R)-4-(bis(4-fluorophenyl)methyl)-2,5-diethylpiperazin-1-yl)-1-(((R)-tetrahydrofuran-2-yl)methyl)-1H-[1,2,3]triazolo[4,5-e][1,2,4]triazolo[4,3-a]pyrimidine;

2-(4-((2S,5R)-4-(bis(4-fluorophenyl)methyl)-2,5-diethylpiperazin-1-yl)-1H-[1,2,4]triazolo[3,4-b]purin-1-yl)-N,N-dimethylethan-1-amine;

2-(4-((2S,5R)-4-(bis(4-fluorophenyl)methyl)-2,5-diethylpiperazin-1-yl)-1H-[1,2,4]triazolo[3,4-b]purin-1-yl-2-d)-N,N-dimethylethan-1-amine;

2-(4-((2S,5R)-4-(bis(4-fluorophenyl)methyl)-5-ethyl-2-methylpiperazin-1-yl)-1H-[1,2,4]triazolo[3,4-b]purin-1-yl)-N,N-dimethylethan-1-amine;

2-(4-((2S,5R)-4-(bis(4-fluorophenyl)methyl)-5-ethyl-2-methylpiperazin-1-yl)-1H-[1,2,4]triazolo[3,4-b]purin-1-yl-2-d)-N,N-dimethylethan-1-amine;

4-((2S,5R)-4-(bis(4-chlorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine;

4-((2S,5R)-4-(bis(4-chlorophenyl)methyl)-5-ethyl-2-methylpiperazin-1-yl)-1-(((R)-tetrahydrofuran-2-yl)methyl)-1H-[1,2,3]triazolo[4,5-e][1,2,4]triazolo[4,3-a]pyrimidine;

4-((2S,5R)-4-(bis(4-chlorophenyl)methyl)-5-ethyl-2-methylpiperazin-1-yl)-2-methyl-1-(((S)-tetrahydrofuran-2-yl)methyl)-1H-[1,2,4]triazolo[3,4-b]purine;

4-((2S,5R)-4-(bis(4-chlorophenyl)methyl)-5-ethyl-2-methylpiperazin-1-yl)-2-methyl-1-(((R)-tetrahydrofuran-2-yl)methyl)-1H-[1,2,4]triazolo[3,4-b]purine;

4-((2S,5R)-4-((3,3-difluorocyclobutyl)(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3-chloro-4-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3,3-difluorocyclobutyl)(3-fluoro-4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-(3,3-difluorocyclobutyl)(3,4-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-(3,3-difluorocyclobutyl)(3,4-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-(3,4-dichlorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-(3,4-dichlorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((4-chloro-3-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((4-chloro-3-methylphenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3,3-difluorocyclobutyl)(3,4,5-trifluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3,3-difluorocyclobutyl)(2,5-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3,3-difluorocyclobutyl)(3-(difluoromethyl)-4-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3,3-difluorocyclobutyl)(3-methyl-4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((2,5-difluoro-4-(trifluoromethyl)phenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3-chloro-2,4-difluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3-chloro-4-(trifluoromethyl)phenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((4-chloro-3-(trifluoromethyl)phenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((4-chlorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((4-bromophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3-bromo-4-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((4-bromo-3-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

2-(4-((2S,5R)-4-((4-chlorophenyl)(3,3-difluorocyclobutyl)methyl)-2,5-dimethylpiperazin-1-yl)-1H-[1,2,4]triazolo[3,4-b]purin-1-yl)-N,N-dimethylethan-1-amine;

2-(4-((2S,5R)-4-((4-bromophenyl)(3,3-difluorocyclobutyl)methyl)-2,5-dimethylpiperazin-1-yl)-1H-[1,2,4]triazolo[3,4-b]purin-1-yl)-N,N-dimethylethan-1-amine;

2-(4-((2S,5R)-4-((4-chlorophenyl)(3,3-difluorocyclobutyl)methyl)-5-ethyl-2-methylpiperazin-1-yl)-1H-[1,2,4]triazolo[3,4-b]purin-1-yl)-N,N-dimethylethan-1-amine;

4-((2S,5R)-2,5-dimethyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine;

4-((2S,5R)-2,5-dimethyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine;

4-((2S,5R)-2,5-dimethyl-4-((S)-2-methyl-1-(3-(trifluoromethyl)phenyl)propyl)piperazin-1-yl)-2-methyl-1-(((S)-tetrahydrofuran-2-yl)methyl)-1H-[1,2,4]triazolo[3,4-b]purine;

4-((2S,5R)-2,5-dimethyl-4-((R)-2-methyl-1-(3-(trifluoromethyl)phenyl)propyl)piperazin-1-yl)-2-methyl-1-(((S)-tetrahydrofuran-2-yl)methyl)-1H-[1,2,4]triazolo[3,4-b]purine;

4-((2S,5R)-4-((S)-1-(2-fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(2-fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(4-(difluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(4-(difluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(4-(difluoromethoxy)-2-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(4-(difluoromethoxy)-2-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(4-methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(4-methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(4-(difluoromethoxy)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(4-(difluoromethoxy)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(1-(4-(difluoromethyl)-3-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(1-(3-(difluoromethyl)-4-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(1-(3-fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(1-(4-fluoro-3-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(1-(3-chloro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(3-chloro-4-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(3-chloro-4-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(4-chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(4-chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

2-(4-((2S,5R)-4-((S)-1-(4-chlorophenyl)-2-methylpropyl)-2,5-dimethylpiperazin-1-yl)-1H-[1,2,4]triazolo[3,4-b]purin-1-yl)-N,N-dimethylethan-1-amine;

2-(4-((2S,5R)-4-((R)-1-(4-chlorophenyl)-2-methylpropyl)-2,5-dimethylpiperazin-1-yl)-1H-[1,2,4]triazolo[3,4-b]purin-1-yl)-N,N-dimethylethan-1-amine;

4-((2S,5R)-4-((4-(difluoromethyl)phenyl)(4-methoxyphenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(bis(4-chlorophenyl)methyl)-2,5-dimethylpiperazin-1-yl)-1-(((S)-tetrahydrofuran-2-yl)methyl)-1H-[1,2,4]triazolo[3,4-b]purine;

4-((2S,5R)-4-((S)-1-(3-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(3-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(3-chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(3-chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((S)-1-(3-methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(3-methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;

2-(4-((2S,5R)-4-(bis(4-(difluoromethyl)phenyl)methyl)-2,5-dimethylpiperazin-1-yl)-1H-[1,2,4]triazolo[3,4-b]purin-1-yl)-N,N-dimethylethan-1-amine;

2-(4-((2S,5R)-2,5-dimethyl-4-((S)-(4-(trifluoromethyl)phenyl)(5-(trifluoromethyl)pyridin-2-yl)methyl)piperazin-1-yl)-1H-[1,2,4]triazolo[3,4-b]purin-yl)-N,N-dimethylethan-1-amine;

2-(4-((2S,5R)-2,5-dimethyl-4-((R)-(4-(trifluoromethyl)phenyl)(5-(trifluoromethyl)pyridin-2-yl)methyl)piperazin-1-yl)-1H-[1,2,4]triazolo[3,4-b]purin-yl)-N,N-dimethylethan-1-amine;

4-((2S,5R)-4-((S)-(5-fluoro-6-(trifluoromethyl)pyridin-2-yl)(4-fluorophenyl)methyl)-2,5-dimethylpiperazin-1-yl)-1-(((S)-tetrahydrofuran-2-yl)methyl)-1H-[1,2,4]triazolo[3,4-b]purine;

4-((2S,5R)-4-((R)-(5-fluoro-6-(trifluoromethyl)pyridin-2-yl)(4-fluorophenyl)methyl)-2,5-dimethylpiperazin-1-yl)-1-(((S)-tetrahydrofuran-2-yl)methyl)-1H-[1,2,4]triazolo[3,4-b]purine;

4-((2S,5R)-4-(bis(4-chlorophenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-(bis(4-chlorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine;

2-(4-((2S,5R)-4-(bis(4-chlorophenyl)methyl)-2,5-dimethylpiperazin-1-yl)-1H-[1,2,4]triazolo[3,4-b]purin-1-yl)-N,N-dimethylethan-1-amine;

4-((2S,5R)-4-(bis(4-bromophenyl)methyl)-2,5-dimethylpiperazin-1-yl)-2-methyl-1-(((S)-tetrahydrofuran-2-yl)methyl)-1H-[1,2,4]triazolo[3,4-b]purine;

2-(4-((2S,5R)-4-(bis(4-bromophenyl)methyl)-2,5-dimethylpiperazin-1-yl)-1H-[1,2,4]triazolo[3,4-b]purin-1-yl)-N,N-dimethylethan-1-amine;

4-((2S,5R)-4-(bis(4-bromophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine;

4-((2S,5R)-4-(bis(4-bromophenyl)methyl)-2,5-dimethylpiperazin-1-yl)-1-(((S)-tetrahydrofuran-2-yl)methyl)-1H-[1,2,3]triazolo[4,5-e][1,2,4]triazolo[4,3-a]pyrimidine;

2-(4-((2S,5R)-4-(bis(5-(trifluoromethyl)pyridin-2-yl)methyl)-2,5-dimethylpiperazin-1-yl)-1H-[1,2,4]triazolo[3,4-b]purin-1-yl)-N,N-dimethylethan-1-amine;

4-((2S,5R)-4-((3-chloro-4-fluorophenyl)((trans)-3-(trifluoromethyl)cyclobutyl)methyl)-2,5-dimethylpiperazin-1-yl)-2-methyl-1-(((S)-tetrahydrofuran-2-yl)methyl)-1H-[1,2,4]triazolo[3,4-b]purine;

2-(4-((2S,5R)-4-((3-chloro-4-fluorophenyl)((trans)-3-(trifluoromethyl)cyclobutyl)methyl)-2,5-dimethylpiperazin-1-yl)-1H-[1,2,4]triazolo[3,4-b]purin-1-yl)-N,N-dimethylethan-1-amine;

4-((2S,5R)-2,5-dimethyl-4-(((trans)-3-(trifluoromethyl)cyclobutyl)(4-(trifluoromethyl)phenyl)methyl)piperazin-1-yl)-2-methyl-1-(((S)-tetrahydrofuran-2-yl)methyl)-1H-[1,2,4]triazolo[3,4-b]purine;

2-(4-((2S,5R)-2,5-dimethyl-4-(((trans)-3-(trifluoromethyl)cyclobutyl)(4-(trifluoromethyl)phenyl)methyl)piperazin-1-yl)-1H-[1,2,4]triazolo[3,4-b]purin-1-yl)-N,N-dimethylethan-1-amine;

4-((2S,5R)-4-((4,4-difluorocyclohexyl)(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-2,5-dimethyl-4-((S)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine;

4-((2S,5R)-2,5-dimethyl-4-((R)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine;

4-((2S,5R)-4-((3,3-difluorocyclobutyl)(4-fluorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine;

4-((2S,5R)-4-((4-chlorophenyl)(3,3-difluorocyclobutyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine; ((2S,5S)-1-((3,3-difluorocyclobutyl)(4-(trifluoromethyl)phenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)methanol;

(R)-1-((2S,5S)-1-(bis(4-fluorophenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)ethan-1-ol;

(S)-1-((2S,5S)-1-(bis(4-fluorophenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)ethan-1-ol;

2-((2R,5S)-2-ethyl-5-methyl-4-(2-methyl-1-(((S)-tetrahydrofuran-2-yl)methyl)-1H-[1,2,4]triazolo[3,4-b]purin-4-yl)piperazin-1-yl)-2,2-bis(4-fluorophenyl)ethan-1-ol;

4-((2S,5R)-4-((S)-1-(4-(difluoromethoxy)phenyl)-2-methylpropyl)-5-ethyl-2-methylpiperazin-1-yl)-2-methyl-1-(((S)-tetrahydrofuran-2-yl)methyl)-1H-[1,2,4]triazolo[3,4-b]purine;

4-((2S,5R)-4-((R)-1-(4-(difluoromethoxy)phenyl)-2-methylpropyl)-5-ethyl-2-methylpiperazin-1-yl)-2-methyl-1-(((S)-tetrahydrofuran-2-yl)methyl)-1H-[1,2,4]triazolo[3,4-b]purine;

4-((2S,5R)-5-ethyl-2-methyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine;

4-((2S,5R)-5-ethyl-2-methyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine;

4-((2S,5R)-5-ethyl-2-methyl-4-((S)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine;

4-((2S,5R)-5-ethyl-2-methyl-4-((R)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine;

4-(((2R,5S)-2-ethyl-5-methyl-4-(2-methyl-1-(((S)-tetrahydrofuran-2-yl)methyl)-1H-[1,2,4]triazolo[3,4-b]purin-4-yl)piperazin-1-yl)(4-fluorophenyl)methyl)benzonitrile;

4-(((2R,5S)-2-ethyl-5-methyl-4-(2-methyl-1-(((S)-tetrahydrofuran-2-yl)methyl)-1H-[1,2,4]triazolo[3,4-b]purin-4-yl)piperazin-1-yl)(4-fluorophenyl)methyl)benzonitrile;

4-((2S,5R)-4-(bis(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine;

4-((2S,5R)-4-((3,3-difluorocyclobutyl)(4-(difluoromethyl)-3-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

2-(4-((2S,5R)-4-((4-chloro-3-fluorophenyl)(3,3-difluorocyclobutyl)methyl)-2,5-dimethylpiperazin-1-yl)-1H-[1,2,4]triazolo[3,4-b]purin-1-yl)-N,N-dimethylethan-1-amine;

((2S,5S)-1-(bis(4-chlorophenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)methanol;
4-((2S,5R)-4-((S)-1-(4-bromophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-4-((R)-1-(4-bromophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-4-((3-chloro-4-fluorophenyl)(4-chlorophenyl)methyl)-2,5-dimethylpiperazin-1-yl)-2-methyl-1-(((S)-tetrahydrofuran-2-yl)methyl)-1H-[1,2,4]triazolo[3,4-b]purine; and
4-((2S,5R)-4-((3-chloro-4-fluorophenyl)(4-bromophenyl)methyl)-2,5-dimethylpiperazin-1-yl)-2-methyl-1-(((S)-tetrahydrofuran-2-yl)methyl)-1H-[1,2,4]triazolo[3,4-b]purine;

or a pharmaceutically acceptable salt thereof.

In some embodiments, the compound provided herein is selected from:

2-(4-((2S,5R)-4-(bis(4-fluorophenyl)methyl)-2,5-dimethylpiperazin-1-yl)-1H-[1,2,4]triazolo[3,4-b]purin-1-yl)-N,N-dimethylethan-1-amine;
4-((2S,5R)-4-(bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine;
2-(4-((2S,5R)-4-(bis(4-fluorophenyl)methyl)-2,5-dimethylpiperazin-1-yl)-1H-[1,2,4]triazolo[3,4-b]purin-1-yl-2-d)-N,N-dimethylethan-1-amine;
4-((2S,5R)-4-(bis(4-chlorophenyl)methyl)-5-ethyl-2-methylpiperazin-1-yl)-1-(((R)-tetrahydrofuran-2-yl)methyl)-1H-[1,2,3]triazolo[4,5-e][1,2,4]triazolo[4,3-a]pyrimidine;
4-((2S,5R)-4-(bis(4-chlorophenyl)methyl)-5-ethyl-2-methylpiperazin-1-yl)-2-methyl-1-(((S)-tetrahydrofuran-2-yl)methyl)-1H-[1,2,4]triazolo[3,4-b]purine;
4-((2S,5R)-4-((3,3-difluorocyclobutyl)(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-4-((3-chloro-4-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-4-((4-chloro-3-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-4-((4-bromo-3-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-2,5-dimethyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine;
4-((2S,5R)-2,5-dimethyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine 4-((2S,5R)-4-((S)-1-(2-fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-4-((R)-1-(2-fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine;
2-(4-((2S,5R)-2,5-dimethyl-4-((S)-(4-(trifluoromethyl)phenyl)(5-(trifluoromethyl)pyridin-2-yl)methyl)piperazin-1-yl)-1H-[1,2,4]triazolo[3,4-b]purin-1-yl)-N,N-dimethylethan-1-amine;
2-(4-((2S,5R)-2,5-dimethyl-4-((R)-(4-(trifluoromethyl)phenyl)(5-(trifluoromethyl)pyridin-2-yl)methyl)piperazin-1-yl)-1H-[1,2,4]triazolo[3,4-b]purin-1-yl)-N,N-dimethylethan-1-amine;
4-((2S,5R)-4-(bis(4-chlorophenyl)methyl)-2,5-dimethylpiperazin-1-yl)-2-methyl-1-(((S)-tetrahydrofuran-2-yl)methyl)-1H-[1,2,4]triazolo[3,4-b]purine;
4-((2S,5R)-4-(bis(4-chlorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine;
2-(4-((2S,5R)-4-(bis(4-chlorophenyl)methyl)-2,5-dimethylpiperazin-1-yl)-1H-[1,2,4]triazolo[3,4-b]purin-1-yl)-N,N-dimethylethan-1-amine;
2-(4-((2S,5R)-4-(bis(4-bromophenyl)methyl)-2,5-dimethylpiperazin-1-yl)-1H-[1,2,4]triazolo[3,4-b]purin-1-yl)-N,N-dimethylethan-1-amine;
4-((2S,5R)-4-(bis(4-bromophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine; and
4-((2S,5R)-4-((3,3-difluorocyclobutyl)(4-(difluoromethyl)-3-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine;

or a pharmaceutically acceptable salt thereof.

In some embodiments, the compound provided herein is 2-(4-((2S,5R)-4-(bis(4-fluorophenyl)methyl)-2,5-dimethylpiperazin-1-yl)-1H-[1,2,4]triazolo[3,4-b]purin-1-yl)-N,N-dimethylethan-1-amine, or a pharmaceutically acceptable salt thereof.

In some embodiments, the compound provided herein is 2-(4-((2S,5R)-4-(bis(4-fluorophenyl)methyl)-2,5-dimethylpiperazin-1-yl)-1H-[1,2,4]triazolo[3,4-b]purin-1-yl)-N,N-dimethylethan-1-amine.

In some embodiments, the compound provided herein is 4-((2S,5R)-4-(bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine, or a pharmaceutically acceptable salt thereof.

In some embodiments, the compound provided herein is 4-((2S,5R)-4-(bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine.

In some embodiments, the compound provided herein is 2-(4-((2S,5R)-4-(bis(4-fluorophenyl)methyl)-2,5-dimethylpiperazin-1-yl)-1H-[1,2,4]triazolo[3,4-b]purin-1-yl-2-d)-N,N-dimethylethan-1-amine, or a pharmaceutically acceptable salt thereof.

In some embodiments, the compound provided herein is 2-(4-((2S,5R)-4-(bis(4-fluorophenyl)methyl)-2,5-dimethylpiperazin-1-yl)-1H-[1,2,4]triazolo[3,4-b]purin-1-yl-2-d)-N,N-dimethylethan-1-amine.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, $—NR(CR'R'')_n—$ includes both $—NR(CR'R'')_n—$ and —$(CR'R'')_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the terms "$C_{n-m}$" and "$C_{m-n}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, from 2 to 6 carbon atoms, from 2 to 4 carbon atoms, from 2 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$aryl" refers to an aryl group having from n to m ring carbon atoms. Aryl groups include, e.g., phenyl, naphthyl, anthracenyl, phenanthrenyl, and the like. In some embodiments, aryl groups have from 5 to 10 carbon atoms. In some embodiments, the aryl group is phenyl or naphthyl. In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-, 7-, 8-, 9-, 10-, 11-, 12-, 13-, 14- or 15-membered monocyclic or bicyclic heteroaryl having 1, 2, 3, or 4 heteroatom ring members independently selected from N, O, S, and B. In some embodiments, the heteroaryl is a 5-10, or 5-15, membered monocyclic or bicyclic heteroaryl having 1, 2, 3, or 4 heteroatom ring members independently selected from N, O, and S. In some embodiments, the heteroaryl is a 5-, 7-, 8-, 9-, or 10-membered monocyclic or bicyclic heteroaryl having 1, 2, 3, or 4 heteroatom ring members independently selected from N, O, and S. In some embodiments, the heteroaryl is a 5-6 membered monocyclic heteroaryl having 1 or 2 heteroatom ring members independently selected from N, O, S, and B. In some embodiments, the heteroaryl is a 5 membered monocyclic heteroaryl having 1 or 2 heteroatom ring members independently selected from N, O, S, and B. In some embodiments, the heteroaryl is a 5 membered monocyclic heteroaryl having 1 or 2 heteroatom ring members independently selected from N, O, and S. In some embodiments, the heteroaryl group contains 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a]pyridinyl, 1H-pyrrolo[3,2-b]pyridinyl, 1H-pyrrolo[2,3-b]pyridinyl, pyrazolo[1,5-a]pyridinyl, indazolyl, thiazolo[4,5-e][1,2,4]triazolo[4,3-a]pyrimidinyl, 1H-pyrazolo[4,3-e][1,2,4]triazolo[4,3-a]pyrimidinyl, furo[2,3-e][1,2,4]triazolo[4,3-a]pyrimidinyl, thieno[2,3-e][1,2,4]triazolo[4,3-a]pyrimidinyl, 1H-[1,2,4]triazolo[3,4-b]purinyl, 6H-pyrrolo[2,3-e][1,2,4]triazolo[4,3-a]pyrimidinyl, thieno[2,3-e][1,2,4]triazolo[4,3-a]pyridinyl, 1H-pyrazolo[4,3-e][1,2,4]triazolo[4,3-a]pyridinyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or $S(O)_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 15, 3 to 10, 4 to 10, 4 to 15, 5 to 10, 4 to 7, 5 to 7, or 5 to 6 membered heterocycloalkyl groups. Heterocycloalkyl groups can also include spirocycles and bridged rings (e.g., a 5 to 10, or 4 to 15, membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring.

In some embodiments, the heterocycloalkyl group contains 3 to 10 ring-forming atoms, 4 to 15 ring-forming atoms, 4 to 10 ring-forming atoms, 4 to 8 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10, or 5-15, membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, tetrahydrothiopheneyl, tetrahydrothiopheneyl 1,1-dioxide, benzazapene, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2. 1]heptanyl, azabicyclo[3.1.1]heptanyl, diazabicyclo[3.1.1]heptanyl, azabicyclo[3.2.1]octanyl, diazabicyclo[3.2.1]octanyl, oxobicyclo[2.2.2]octanyl, azabicyclo[2.2.2]octanyl, azaadamantanyl, diazaadamantanyl, oxo-adamantanyl, azaspiro[3.3]heptanyl, 2-azaspiro[3.3]heptanyl, diazaspiro[3.3]heptanyl, azaspiro[3.5]nonanyl, 7-azaspiro[3.5]nonanyl, oxo-azaspiro[3.3]heptanyl, azaspiro[3.4]octanyl, diazaspiro[3.4]octanyl, oxo-azaspiro[3.4]octanyl, azaspiro[2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxo-hexahydropyrrolo[1,2-a]pyrazinyl, 3-oxopiperazinyl, oxo-pyrrolidinyl, oxo-pyridinyl, diazaspiro[5.5]undecanyl, diazaspiro[5.6]dodecanyl, diazaspiro[6.6]tridecanyl, and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" or "alkylene linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-diyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent (e.g., each $R^M$), are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula II, etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as R-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein.

Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula I can be synthesized using the process shown in Scheme 1. As depicted in Scheme 1, a number of methods (e.g., nucleophilic aromatic substitution or a suitable cross-coupling reaction) can be used to access compounds of the general Formula 1-2. For example, compounds of Formula 1-1 (i.e., each Hal can independently be F, Cl, Br, or I) can be reacted with an appropriate amine nucleophile in an appropriate solvent (e.g., 1-butanol) at an appropriate temperature (e.g., ranging from room temperature to 200° C.) for a suitable time (e.g., ranging from several minutes to several days) to generate compounds of Formula 1-2.

Alternatively, transition metal (e.g., Pd, Cu, Ni) catalyzed reactions (including, but not limited to, Buchwald, Ullman, Suzuki, Stille, Negishi couplings) of compounds 1-1 and appropriate coupling partners (e.g., primary or secondary amines, nitrogen heterocycles, or heteroaryl boronic acids/esters, trialkyl tin, or zinc reagents) affords compounds of Formula 1-2. Compounds of Formula 1-1 are commercially available, or can be readily synthesized according to methods known by persons skilled in the art. C—N bond forming reactions (e.g., transition metal catalyzed or nucleophilic aromatic substitution) between compounds of Formula 1-2 and hydrazine under appropriate conditions (e.g., in the presence of a palladium catalyst, such as methanesulfonato (2-(di-t-butylphosphino)-3,6-dimethoxy-2',4',6'-tri-1-propyl-1,1'-biphenyl)(2'-amino-1,1'-biphenyl-2-yl)palladium (II) ("tBuBrettPhos Pd G3"), and a base, such as $Cs_2CO_3$ or NaOt-Bu, in an appropriate solvent, such as THF or 1,4-dioxane) generates compounds of Formula 1-3. Reaction of compounds of Formula 1-3 with compounds of Formula 1-4 (e.g., trimethyl orthoformate or triethyl orthoacetate) under appropriate conditions (e.g., in the presence of AcOH) provides compounds of Formula I.

Scheme 1.

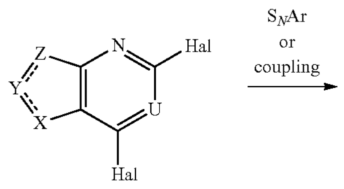

1-1

-continued

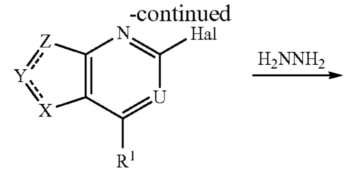

1-2

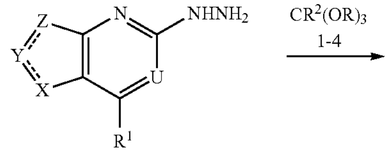

1-3

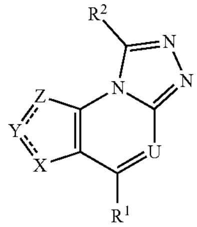

I

Compounds of Formula I can also be prepared using the process illustrated in Scheme 2. As depicted in Scheme 2, compounds of Formula 2-1 can be converted into compounds of Formula 2-2 by a number of methods. For example, halogenation of compounds of Formula 2-1 (e.g., via deprotonation with an appropriate base, such as 2,2,6,6-tetramethylpiperidinylmagnesium chloride lithium chloride ("TMPMgCl LiCl"), followed by addition of an appropriate electrophile, such as 1-chloro-2-10 doethane) followed by a suitable cross-coupling affords compounds of Formula 2-2. Examples of suitable cross-coupling reactions include, but are not limited to, Suzuki (see e.g., *Tetrahedron* 2002, 58, 9633-9695), Negishi (see e.g., *ACS Catalysis* 2016, 6, 1540-1552), Stille (see e.g., *ACS Catalysis* 2015, 5, 3040-3053), Sonogashira (see e.g., *Chem. Soc. Rev.* 2011, 40, 5084-5121), Buchwald-Hartwig amination (see e.g., *Chem. Sci.* 2011, 2, 27-50), Cu-catalyzed amination (see e.g., *Org. React.* 2014, 85, 1-688), among others. Alternatively, compounds of Formula 2-2 can be accessed by conversion of compounds of Formula 2-1 to a carbonyl intermediate (e.g., by deprotonation with an appropriate base, such as TMPMgCl LiCl, followed by addition of an appropriate electrophile, such as DMF) followed by reaction with a suitable fluorinating reagent (e.g., diethylaminosulfur trifluoride). C—N bond forming reactions (e.g., transition metal catalyzed or nucleophilic aromatic substitution) between compounds of Formula 2-2 and hydrazine under appropriate conditions (e.g., in the presence of a palladacycle precatalyst, such as tBuBrettPhos Pd G3, and a base, such as $Cs_2CO_3$) generates compounds of Formula 2-2. Reaction of compounds of Formula 2-2 with compounds of Formula 2-3 (e.g., triethyl orthoformate) under appropriate conditions (e.g., in the presence of AcOH) provides compounds of Formula I Scheme 2.

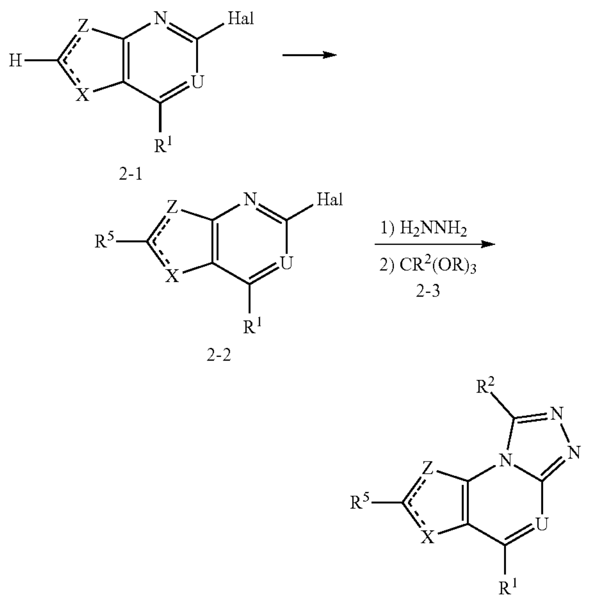

2-1

2-2

I

Compounds of Formula 3-8 can be synthesized, for example, according to the process shown in Scheme 3. As depicted in Scheme 3, protection of amino compounds of Formula 3-1 under appropriate conditions (e.g., including, but not limited to, reductive amination reactions with an appropriate aldehyde, such as benzaldehyde, in the presence of a reducing agent, such as sodium triacetoxyborohydride) generates compounds of Formula 3-2. Compounds of Formula 3-1 are commercially available, or can be readily synthesized according to methods known by persons skilled in the art. Amide coupling reactions of compounds of Formula 3-2 with compounds of Formula 3-3 under suitable conditions (e.g., in the presence of a coupling reagent, such as HATU, and a base, such as N-ethyl-N-isopropylpropan-2-amine, in an appropriate solvent, such as N,N-dimethylformamide) affords compounds of Formula 3-4. Deprotection of the tert-butyloxycarbonyl group in compounds of Formula 3-4 under appropriate conditions (e.g., using an acid, such as trifluoroacetic acid), followed by intramolecular cyclization under appropriate conditions (e.g., using a suitable solvent, such as MeOH) provides compounds of Formula 3-5. Reduction of compounds of Formula 3-5 under suitable conditions (e.g., using a reducing agent, such as borane, in a suitable solvent, such as THF) generates compounds of Formula 3-6. Protection of compounds of Formula 3-6 under appropriate conditions (e.g., via reaction with di-tert-butyl dicarbonate in the presence of a base, such as N-ethyl-N-isopropylpropan-2-amine) provides compounds of Formula 3-7. Selective deprotection of PG in compounds of Formula 3-7 (e.g., where PG is a protecting group such as benzyl) under appropriate conditions (e.g., using an appropriate catalyst, such as palladium on carbon, in the presence of hydrogen gas), affords compounds of Formula 3-8.

Scheme 3.

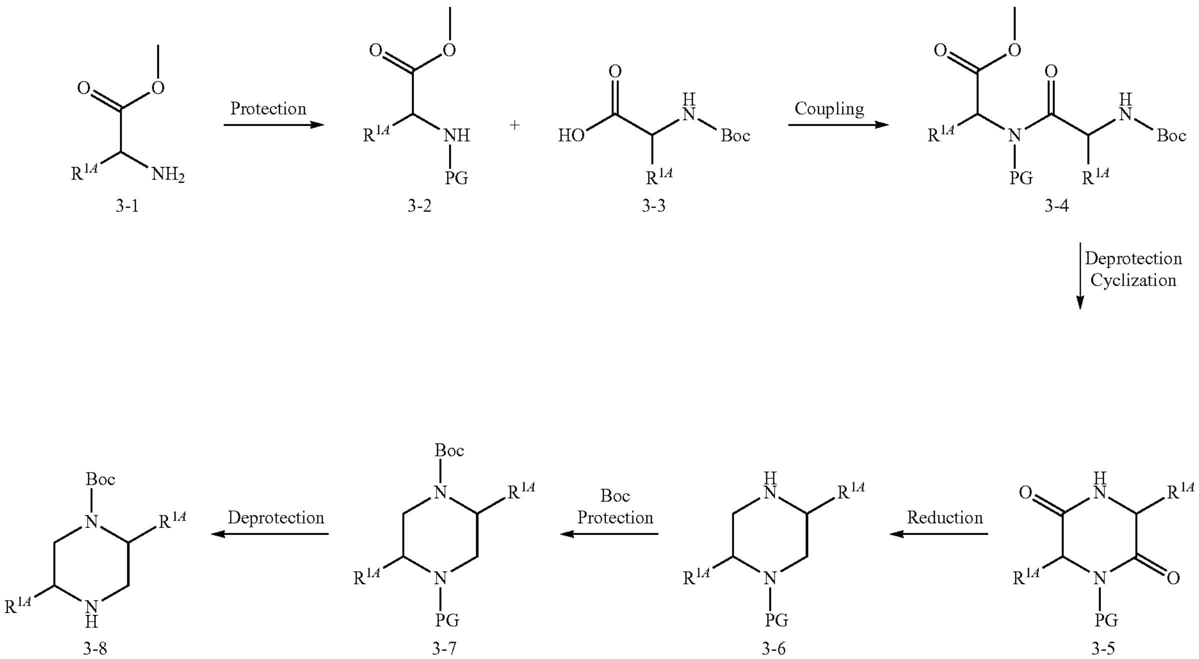

3-1 3-2 3-3 3-4 3-5 3-6 3-7 3-8

Compounds of Formula 4-4 can be prepared, for example, using the process illustrated in Scheme 4. In the process depicted in Scheme 4, nucleophilic substitution reactions between compounds of Formula 4-1 and compounds of Formula 4-2 under appropriate conditions (e.g., in the presence of a base, such as N-ethyl-N-isopropylpropan-2-amine, in an appropriate solvent, such as $CH_3CN$) generates compounds of Formula 4-3. Removal of an appropriate protecting group (e.g., wherein PG is a group such as tert-butoxycarbonyl) from compounds of Formula 4-3 under appropriate conditions (e.g., in the presence of an acid, such as HCl or trifluoroacetic acid, in a suitable solvent, such as tetrahydrofuran, 1-4-dioxane, or $CH_2Cl_2$) affords compounds of Formula 4-4.

Scheme 4.

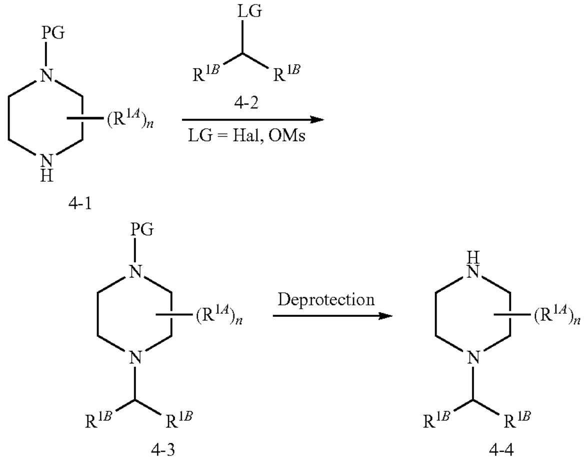

Alternatively, compounds of Formula 4-4 can be prepared, for example, using the process illustrated in Scheme 5. In the process depicted in Scheme 5, amide coupling reactions of compounds of Formula 5-1 with compounds of Formula 5-2 affords compounds of Formula 5-3. Subjection of compounds of Formula 5-3 to reductive alkylation conditions (e.g., through the use of an appropriate transition metal catalyst, such as $IrCl(CO)(PPh_3)_2$, in the presence of a silane, such as 1,1,3,3-tetramethyldisiloxane, followed by addition of a suitable organometallic reagent, such as a Grignard reagent) affords compounds of Formula 5-4. Removal of an appropriate protecting group (e.g., wherein PG is a group such as tert-butoxycarbonyl) from compounds of Formula 5-4 under appropriate conditions (e.g., in the presence of an acid, such as HCl or trifluoroacetic acid, in a suitable solvent, such as tetrahydrofuran, 1-4-dioxane, or $CH_2Cl_2$) affords compounds of Formula 4-4.

Scheme 5.

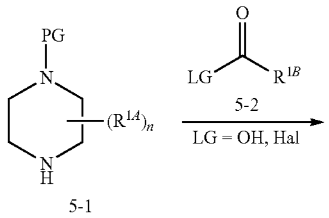

-continued

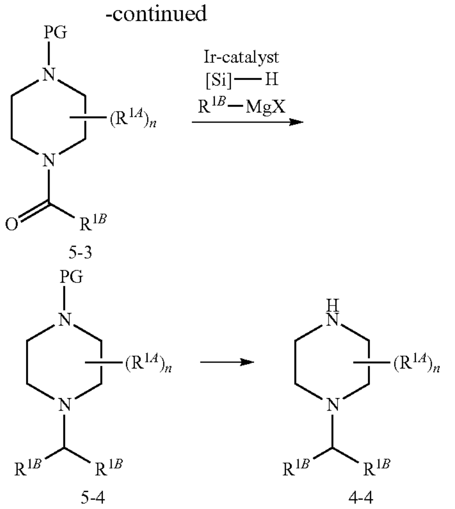

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds described herein can inhibit the activity of DGK. Compounds that inhibit DGK are useful in providing a means of preventing the growth or inducing apoptosis of cancer cells. Such compounds are also useful in treating cancer cells exhibiting alterations in diacylglycerol-regulating enzymes and effectors. It is therefore anticipated that the compounds of the disclosure are useful in treating or preventing cancer, such as solid tumors.

In certain embodiments, the disclosure provides a method for treating a DGK-related disorder in a patient in need thereof, comprising the step of administering to said patient a compound of the disclosure, or a pharmaceutically acceptable composition thereof.

The compounds or salts described herein can be selective. By "selective," it is meant that the compound binds to or inhibits DGKα or DGKξ with greater affinity or potency, respectively, compared to at least one other DGK isoforms, or kinase, etc. In some embodiments, selectivity can be at least about 2-fold, 5-fold, 10-fold, at least about 20-fold, at least about 50-fold, at least about 100-fold, at least about 200-fold, at least about 500-fold or at least about 1000-fold. The compounds of the present disclosure can also be dual antagonists (i.e., inhibitors), e.g. inhibit both DGKα and DGKξ kinases. In some embodiments, the compounds of the invention are selective inhibitors of DGKα (e.g., over one or more other DGK isoforms, or kinase, etc.). In some embodiments, the compounds of the invention are selective inhibitors of DGKξ (e.g., over one or more other DGK isoforms, or kinase, etc.). Selectivity can be measured by methods routine in the art. In some embodiments, selectivity can be tested at the $K_m$ ATP concentration of each enzyme. In some embodiments, the selectivity of compounds of the invention can be determined by cellular assays associated with particular DGK kinase activity.

Based on compelling evidence that DGKα and DGKξ negatively regulate signaling pathways downstream of the T cell receptor, developing DGK inhibitors can boost T cell effector function and inhibit tumor progression. DGK inhibitors can be used to treat, alone or in combination with other therapies, cancers including solid tumors and hematological malignancies, including renal cell carcinoma, mesothelioma, glioblastoma multiforme, colorectal cancer, melanoma, pancreatic cancer (Chen, S. S. et al., *Front. Cell Dev. Biol.,* 2016. 4:130; Gu, J. et al., *Oncoimmunol.,* 2021. 10, e1941566; Jung I.-Y. et al., *Cancer Res.,* 2018. 78:p 4692-4703; Sitaram, P., et al., *Int. J Mol. Sci.,* 2019. 20:p 5821-5848; Wesley, E. M., et al., *Immunohorizons,* 2018. 2:p 107-118). Furthermore, pharmacological inhibition of DGK provides benefit to control viral infections, and can be used to treatment such viral infections including Coronavirus infection, HIV infection, hepatitis virus infection in preclinical model (Harabuchi, S. et al., *Front. Immunol.,* 2022. 13:1032113).

In addition, DGKα has been shown to enhance esophageal squamous cell carcinoma (ESCC), and human hepatocellular carcinoma (HCC) progression (Chen, J. et al., *Oncogene,* 2019. 38: p 2533-2550; Takeishi, K. et al., *J. Hepatol.,* 2012. 57:p 77-83), to support colon and breast cancer growth in three-dimensional (3D) culture (Torres-Ayuso, P. et al., *Oncotarget,* 2014. 5:p 9710-9726), to enhance mammary carcinoma invasiveness (Rainero, E. et al., *PLOS ONE,* 2014. 9(6): e97144) and promote metastasis of non-small cell lung cancer (NSCLC) (Fu, L. et al., *Cancer letters,* 2022. 532: 215585) whereas DGKξ has been implicated as a potential oncogene in osteosarcoma proliferation (Yu, W. et al., *Front. Oncol.,* 2019. 8:655) and contributed to enhanced invasion of human metastatic colon cancer cells (Cai, K. et al., *BMC Cancer,* 2014. 14:208). It has also been reported DGK inhibition has the potential to reduce immunopathology in X-linked lymphoproliferative disease patient (Velnati, S. et al., *Eur. J. Med. Chem.,* 2019. 164: p 378-390; Ruffo, E. et al., *Sci. Transl. Med.* 2016. 8 (321):321ra7).

In some embodiments, the DGK-related disorder is a solid tumor. Example solid tumors include, but are not limited to, breast cancer, colorectal cancer, gastric cancer, and glioblastoma (see e.g., Cooke & Kazanietz, *Sci. Signal,* 2022, 15, eabo0264:1-26). Example cancers associated with alterations in DAG-regulating enzymes and effector include, but are not limited to, uveal melanoma, myelodysplastic syndrome (MDS), angiosarcoma, nodal peripheral T cell lymphoma, adult T-cell leukemia lymphoma (ATLL), cutaneous T-cell lymphoma (CTCL)/Sezary syndrome, chronic lymphocytic leukemia (CLL), breast cancer, gastric cancer, colorectal cancer, oral squamous cell carcinoma (SCC), esophageal SCC, chronic myeloid leukemia (CML), colon cancer, prostate cancer, hepatocellular carcinoma (HCC), blue nevi, NK/T cell lymphoma, glioma, ovarian cancer, liver cancer, melanoma, heptacarcinoma, ostersarcoma, chordiod glioma, pigmented epithelioid melanocytoma, papillary glioneuronal tumor, fibrous histiocytoma, pituitary tumor, thyroid cancer, head and neck SCC, lung cancer, pediatric T-cell acute lymphoblastic leukemia (T-ALL), endometrial cancer, angiolipoma, salivary gland cancer, acute myeloid leukemia (AML), Epstein-Barr virus-associated (EBV)-associated B cell lymphoma, diffuse large B cell lymphoma (DLBCL), and cervical cancer (see e.g., Cooke & Kazanietz, Sci. *Signal,* 2022, 15, eabo0264:1-26).

In some embodiments, the cancer is selected from lung cancer, bladder cancer, urothelial cancer, esophageal cancer, stomach cancer, mesothelioma, liver cancer, diffuse large B cell lymphoma, kidney cancer, head and neck cancer, cholangiocarcinoma, cervical cancer, endocervical cancer, melanoma, merkel cell carcinoma (MCC), cutaneous squamous cell carcinoma (CSCC), melanoma, MSI high tumors, ICI sensitive tumors, and viral infection related cancers such as HPV-associated anal cancer, vaginal cancer, vulvar cancer, cervical cancer and oropharyngeal cancer.

In some embodiments, the cancer is selected from lung cancer, bladder cancer, urothelial cancer, esophageal cancer, stomach cancer, mesothelioma, liver cancer, diffuse large B cell lymphoma, kidney cancer, head and neck cancer, cholangiocarcinoma, cervical cancer, endocervical cancer, and melanoma.

In some embodiments, the cancer is selected from non-small cell lung cancer (lung squamous cell carcinoma (LUSC), lung adenocarcinoma (LUAD)), bladder urothelial carcinoma, esophageal carcinoma, stomach adenocarcinoma, mesothelioma, liver hepatocellular carcinoma, diffuse large B cell lymphoma (DLBCL), kidney renal clear cell carcinoma, head and neck squamous cell carcinoma, cholangiocarcinoma, cervical squamous cell carcinoma, endocervical adenocarcinoma, and metastatic melanoma.

In some embodiments, the cancer is a myelodysplastic syndrome. As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br J Haematol.* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114: 937-951; Swerdlow, et al., *WHO Classification of Tumours of Haematopoietic and Lymphoid Tissues.* 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues.* (*ed.* 4th edition): Lyon, France: IARC Press; 2008:88-103).

TABLE 1

2008 WHO Classification for De Novo Myelodysplastic Syndrome

| Subtype | Blood | Bone Marrow |
|---|---|---|
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × $10^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × $10^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × $10^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory anemia with ring sideroblasts associated with thrombocytosis (RARS-T).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

In some embodiments, the compounds of the disclosure can be useful in the treatment of myeloproliferative disorder/myelodysplastic overlap syndrome (MPD/MDS overlap syndrome).

In some embodiments, provided herein is a method of increasing survival or progression-free survival in a patient, comprising administering a compound provided herein to the patient. In some embodiments, the patient has cancer. In some embodiments, the patient has a disease or disorder described herein. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a DGK with a compound described herein includes the administration of a compound described herein to an individual or patient, such as a human, having a DGK, as well as, for example, introducing a compound described herein into a sample containing a cellular or purified preparation containing the DGK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable cater or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005*; Handbook of Pharmaceutical Excipients,* 6th ed.; Rowe et al., Eds.; The Pharmaceutical Press and the American Pharmaceutical Association: 2009*; Handbook of Pharmaceutical Additives,* 3rd ed.; Ash and Ash Eds.; Gower Publishing Company: 2007*; Pharmaceutical Preformulation and Formulation,* 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapies

I. Immune-Checkpoint Therapies

In some embodiments, DGKα and DGKξ inhibitors provided herein can be used in combination with one or more immune checkpoint inhibitors for the treatment of cancer as described herein.

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1 BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal or bispecific antibody. In some embodiments, the anti-PD-1 or anti-PD-L1 antibody is nivolumab, pembrolizumab, atezolizumab, durvalumab, avelumab, cemiplimab, tislelizumab, spartalizumab (PDR001), cetrelimab (JNJ-63723283), toripalimab (JS001), camrelizumab (SHR-1210), sintilimab (IBI308), AB122 (GLS-010), AMP-224, AMP-514/MEDI-0680, BMS936559, JTX-4014, BGB-108, SHR-1210, MED14736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943, 743, 8,008,449, 8,168,757, 8,217, 149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008156712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550. In some embodiments, the inhibitor of PD-L1 is INCB099280.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX- 4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012 (INCMGA0012; retifanlimab). In some embodiments, the anti-PD-1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MEDI1873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MED19197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGF.beta. receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Examples of agents that may be combined with compounds of the present disclosure, or solid forms or salts thereof, include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pim kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure, or solid forms or salts thereof, can be used in combination with one or more other enzyme/protein/receptor inhibitors for the treatment of diseases, such as cancer. Examples of cancers include solid tumors and liquid tumors, such as blood cancers. For example, the compounds of the present disclosure, or solid forms or salts thereof, can be combined with one or more inhibitors of the following kinases for the treatment of cancer: Akt1, Akt2, Akt3, TGF-IR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure, or solid forms or salts thereof, can be combined with one or more of the following inhibitors for the treatment of cancer. Non-limiting examples of inhibitors that can be combined with the compounds of the present disclosure, or solid forms or salts thereof, for treatment of cancers include an FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a P13K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

Compounds of the present disclosure, or solid forms or salts thereof, can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure, or solid forms or salts thereof, can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, CAR (Chimeric antigen receptor) T cell treatment as a booster for T cell activation, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, amsacrine, anastrozole, aphidicolon, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vindesine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk, and SGK.

Other anti-cancer agents also include those that block immune cell migration such as antagonists to chemokine receptors, including CCR2 and CCR4.

The compounds of the present disclosure, or solid forms or salts thereof, can further be used in combination with one or more anti-inflammatory agents, steroids, immunosuppressants or therapeutic antibodies. The steroids include but are not limited to 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

The compounds of the present disclosure, or solid forms or salts thereof, can also be used in combination with lonafarnib (SCH6636), tipifarnib (R115777), L778123, BMS 214662, tezacitabine (MDL 101731), Sml1, triapine, didox, trimidox and amidox.

The compounds of the disclosure, or salts or solid forms thereof, can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure, or solid forms or salts thereof, can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure, or solid forms or salts thereof, can be used in combination with tumor specific antigen such as heat shock proteins isolated from tumor tissue itself. In some embodiments, the compounds of the present disclosure, or solid forms or salts thereof, can be combined with dendritic cells immunization to activate potent anti-tumor responses.

The compounds of the present disclosure, or solid forms or salts thereof, can be used in combination with bispecific macrocyclic peptides that target Fe alpha or Fe gamma receptor-expressing effectors cells to tumor cells. The compounds of the present disclosure, or solid forms or salts thereof, can also be combined with macrocyclic peptides that activate host immune responsiveness.

The compounds of the present disclosure, or solid forms or salts thereof, can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents).

In some embodiments, the compounds of the present disclosure, or solid forms or salts thereof, can be used in combination with INCB086550.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating DGK in tissue samples, including human, and for identifying DGK inhibitors by binding of a labeled compound. Substitution of one or more of the atoms of the compounds of the present disclosure can also be useful in generating differentiated ADME (Adsorption, Distribution, Metabolism and Excretion.) Accordingly, the present disclosure includes DGK assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$ $^{125}I$ and $^{131}I$. For example, one or more hydrogen atoms in a compound of the present disclosure can be replaced by deuterium atoms to allow the compound to be deuterated (e.g., one or more hydrogen atoms of a $C_{1-6}$ alkyl group of Formula I can be optionally substituted with deuterium atoms, such as —$CD_3$ being substituted for —$CH_3$). In some embodiments, alkyl groups of the disclosed Formulas (e.g., Formula I) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, 1-6, 1-8, 1-10, 1-12, 1-14, 1-16, 1-18, or 1-20 deuterium atoms. In some embodiments, all of the hydrogen atoms in a compound can be replaced or substituted by deuterium atoms.

In some embodiments, each hydrogen atom of the compounds provided herein, such as hydrogen atoms attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is optionally replaced by deuterium atoms.

In some embodiments, each hydrogen atom of the compounds provided herein, such as hydrogen atoms to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is replaced by deuterium atoms (i.e., the alkyl, alkenyl, alkynyl, aryl, phenyl, cycloalkyl, heterocycloalkyl, or heteroaryl substituents, or —$C_{1-4}$ alkyl-, alkylene, alkenylene, and alkynylene linking groups are perdeuterated).

In some embodiments, 1, 2, 3, 4, 5, 6, 7, 8, 9, 10, 11, or 12 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, the compound provided herein (e.g., the compound of any of Formulas I-XI), or a pharmaceutically acceptable salt thereof, comprises at least one deuterium atom.

In some embodiments, the compound provided herein (e.g., the compound of any of Formulas I-XI), or a pharmaceutically acceptable salt thereof, comprises two or more deuterium atoms.

In some embodiments, the compound provided herein (e.g., the compound of any of Formulas I-XI), or a pharmaceutically acceptable salt thereof, comprises three or more deuterium atoms.

In some embodiments, for a compound provided herein (e.g., the compound of any of Formulas I-XI), or a pharmaceutically acceptable salt thereof, all of the hydrogen atoms are replaced by deuterium atoms (i.e., the compound is "perdeuterated").

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro DGK labeling and competition assays, compounds that incorporate $^{3}H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind DGK by monitoring its concentration variation when contacting with DGK, through tracking of the labeling. For example, a test compound (labeled) can be evaluated for its ability to reduce binding of another compound which is known to bind to DGK (i.e., standard compound). Accordingly, the ability of a test compound to compete with the standard compound for binding to DGK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of DGK-associated diseases or disorders as described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Examples

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J Comb. Chem.*, 6, 874-883 (2004)). For purifications using a 30×100 mm column, the flow rate was 60 mL/minute.

pH=10 purifications: Waters XBridge™ $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)). For purifications using a 30×100 mm column, the flow rate was 60 mL/minute.

Intermediate 1. (2R,5S)-1-(Bis(4-fluorophenyl)methyl)-2,5-dimethylpiperazine hydrochloride

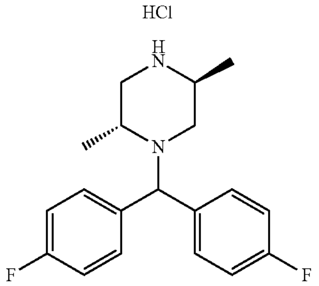 [SMILES: Cl ; C[C@@H]1CN[C@@H](C)CN1C(c1ccc(F)cc1)c1ccc(F)cc1]

Step 1. tert-Butyl (2S,5R)-4-(bis(4-fluorophenyl)methyl)-2,5-dimethylpiperazine-1-carboxylate

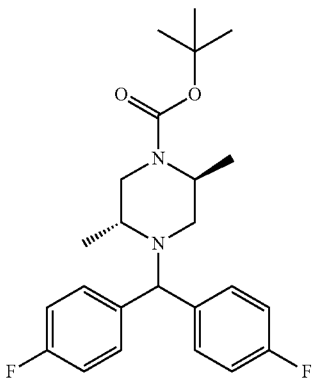 [SMILES: C[C@@H]1CN(C(=O)OC(C)(C)C)[C@@H](C)CN1C(c1ccc(F)cc1)c1ccc(F)cc1]

A mixture of tert-butyl (2S,5R)-2,5-dimethylpiperazine-1-carboxylate (15.0 g, 70 mmol, Combi-Blocks OR-8588), 4,4'-(chloromethylene)bis(fluorobenzene) (19.2 g, 80 mmol, Combi-Blocks QA-4728) and N-ethyl-N-isopropylpropan-2-amine (37 mL, 210 mmol) in $CH_3CN$ (175 mL) was stirred at 85° C. overnight. After cooling to rt, the reaction mixture was concentrated in vacuo and the residue was dissolved in EtOAc and washed with water and brine. The organic phase was dried over $MgSO_4$, filtered, and concentrated and the crude residue was purified using flash column chromatography (330 g $SiO_2$, EtOAc/hexanes) to afford tert-butyl (2S,5R)-4-(bis(4-fluorophenyl)methyl)-2,5-dimethylpiperazine-1-carboxylate (26.0 g, 89% yield) as a light yellow waxy solid. LC-MS calculated for $C_{24}H_{31}F_2N_2O_2$ $(M+H)^+$: m/z=417.2; found 417.1.

Step 2. (2R,5S)-1-(Bis(4-fluorophenyl)methyl)-2,5-dimethylpiperazine hydrochloride To a mixture of tert-butyl (2S,5R)-4-(bis(4-fluorophenyl)methyl)-2,5-dimethylpiperazine-1-carboxylate (1.86 g, 4.5 mmol) in THF (25 mL) was added a 4 molar solution of HCl in 1,4-dioxane (6.25 mL, 25.0 mmol) and the reaction mixture was purged with $N_2$ and stirred at 80° C. for 4 h. After cooling to rt, the reaction mixture was diluted with $Et_2O$ (25 mL) and hexanes (50 mL) and slurried for 30 mins. The solid precipitate was collected via filtration, washed with $Et_2O$ and hexanes, and dried under vacuum to afford the desired product (1.34 g, 85% yield) as a white solid. LC-MS calculated for $C_{19}H_{23}F_2N_2$ $(M+H)^+$: m/z=317.2; found 317.2.

Intermediate 2. 7-((2S,5R)-4-(Bis(4-fluorophenyl)methyl)-2,5-dimethylpiperazin-1-yl)-5-chlorothiazolo[5,4-d]pyrimidine

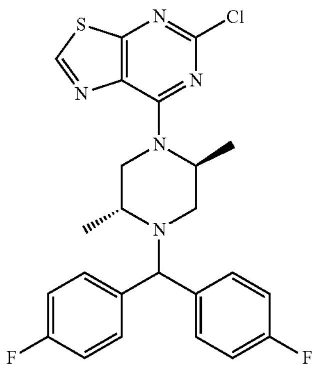 [SMILES: C[C@@H]1CN(c2nc(Cl)nc3scnc23)[C@@H](C)CN1C(c1ccc(F)cc1)c1ccc(F)cc1]

To a mixture of 5,7-dichlorothiazolo[5,4-d]pyrimidine (618 mg, 3.0 mmol, PharmaBlock PB03220) and (2R,5S)-1-(bis(4-fluorophenyl)methyl)-2,5-dimethylpiperazine hydrochloride (Intermediate 1, 1.06 g, 3.0 mmol) in 1-butanol (15.0 mL) was added N-ethyl-N-isopropylpropan-2-amine (1.57 mL, 9.0 mmol) and the mixture was stirred at rt overnight. The reaction mixture was diluted with $CH_2Cl_2$ and extracted with sat. aq. $NaHCO_3$. The combined organic layers were dried over $MgSO_4$, concentrated, and the crude residue was purified using flash column chromatography ($SiO_2$, EtOAc/hexanes) to afford the desired product (1.42 g, 97% yield) as a very light yellow waxy solid. LC-MS calculated for $C_{24}H_{23}ClF_2N_5S$ $(M+H)^+$: m/z=486.1; found 486.2.

Intermediate 3. 7-((2S,5R)-4-(Bis(4-fluorophenyl)methyl)-2,5-dimethylpiperazin-1-yl)-5-chloro-2-idothiazolo[5,4-d]pyrimidine

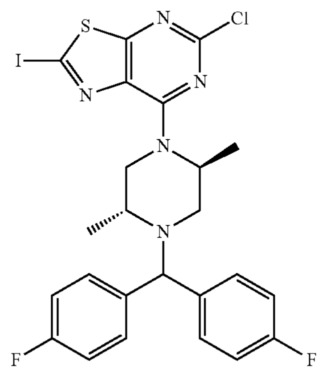 [SMILES: C[C@@H]1CN(c2nc(Cl)nc3sc(I)nc23)[C@@H](C)CN1C(c1ccc(F)cc1)c1ccc(F)cc1]

In an oven-dried vial with a stir bar, a mixture of 7-((2S,5R)-4-(bis(4-fluorophenyl)methyl)-2,5-dimethylpiperazin-1-yl)-5-chlorothiazolo[5,4-d]pyrimidine (Intermediate 2, 761 mg, 1.57 mmol) in anhydrous THF (7.8 mL) was cooled to −78° C. before a 1 molar solution of 2,2,6,6-tetramethylpiperidinylmagnesium chloride lithium chloride complex in THF/toluene (2.5 mL, 2.5 mmol, Aldrich 703540) was added dropwise and the mixture was stirred at −78° C. for 30 mins before 1-chloro-2-10 doethane (571 μL, 6.3 mmol) was added dropwise and the reaction mixture was stirred at −78° C. for an additional 30 mins. The reaction mixture was warmed to 0° C. and stirred for 30 mins before the mixture was quenched via the addition of sat. aq. $NH_4Cl$. After warming to rt, the mixture was extracted with $CH_2Cl_2$. The combined organic layers were dried over $MgSO_4$, concentrated, and the crude residue was purified by flash column chromatography (40 g $SiO_2$, EtOAc/hexanes) to afford the desired product (843 mg, 88% yield) as a very light yellow waxy solid. LC-MS calculated for $C_{24}H_{22}ClF_{21}N_5S$ $(M+H)^+$: m/z=612.0; found 612.1.

Intermediate 4. 7-((2S,5R)-4-(Bis(4-fluorophenyl)methyl)-2,5-dimethylpiperazin-1-yl)-5-chloro-2-(difluoromethyl)thiazolo[5,4-d]pyrimidine

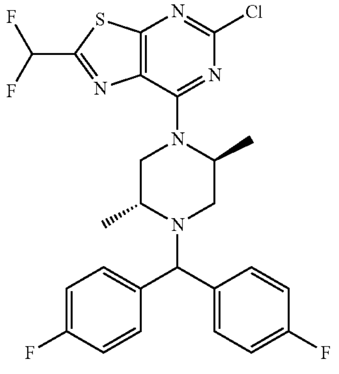 [SMILES: C[C@@H]1CN(c2nc(Cl)nc3sc(C(F)F)nc23)[C@@H](C)CN1C(c1ccc(F)cc1)c1ccc(F)cc1]

Step 1. 7-((2S,5R)-4-(Bis(4-fluorophenyl)methyl)-2,5-dimethylpiperazin-1-yl)-5-chlorothiazolo[5,4-d]pyrimidine-2-carbaldehyde

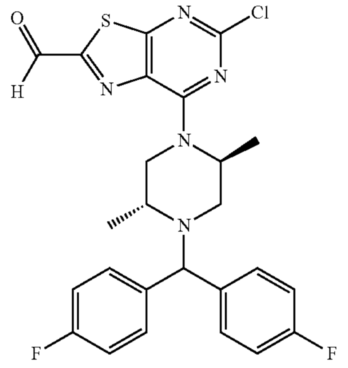

In an oven-dried vial with a stir bar, a mixture of 7-((2S,5R)-4-(bis(4-fluorophenyl)methyl)-2,5-dimethylpiperazin-1-yl)-5-chlorothiazolo[5,4-d]pyrimidine (Intermediate 2, 200.0 mg, 0.412 mmol) in THF (2.1 mL) was cooled to −78° C. before a 1 molar solution of 2,2,6,6-Tetramethylpiperidinylmagnesium chloride lithium chloride complex solution in THF/toluene (0.66 mL, 0.66 mmol, Aldrich 703540) was added dropwise and the reaction mixture was stirred at −78° C. for 30 mins before N,N-dimethylformamide (301 mg, 4.12 mmol) was added dropwise and the reaction mixture was stirred at −78° C. for an additional 30 mins. The reaction mixture was warmed to 0° C. and stirred for 30 mins before the mixture was quenched via the addition of sat. aq. $NH_4Cl$. After warming to rt, the mixture was extracted with $CH_2Cl_2$. The combined organic layers were dried over $MgSO_4$, concentrated, and the crude residue was purified by flash column chromatography (12 g $SiO_2$, EtOAc/hexanes) to afford the desired product as a very light yellow waxy solid. LC-MS calculated for $C_{25}H_{23}ClF_2N_5OS$ $(M+H)^+$: m/z=514.1; found 514.2.

Step 2: 7-((2S,5R)-4-(Bis(4-fluorophenyl)methyl)-2,5-dimethylpiperazin-1-yl)-5-chloro-2-(difluoromethyl)thiazolo[5,4-d]pyrimidine In an oven-dried vial with a stir bar, to a mixture of 7-((2S,5R)-4-(bis(4-fluorophenyl)methyl)-2,5-dimethylpiperazin-1-yl)-5-chlorothiazolo[5,4-d]pyrimidine-2-carbaldehyde (Step 1) in $CH_2Cl_2$ (2.1 mL) was added (diethylamino) sulfur trifluoride (163 μL, 1.2 mmol, Aldrich 235253) dropwise and the reaction mixture was stirred at rt for 4 h. The reaction mixture was slowly quenched via dropwise addition of sat. aq. $NaHCO_3$ and extracted with $CH_2Cl_2$. The combined organic phases were dried over $MgSO_4$, concentrated, and the crude residue was purified by flash column chromatography (12 g $SiO_2$, EtOAc/hexanes) to afford the desired product. LC-MS calculated for $C_{25}H_{23}ClF_4N_5S$ $(M+H)^+$: m/z=536.1; found 536.1.

Intermediate 5. 3-(7-((2S,5R)-4-(Bis(4-fluorophenyl)methyl)-2,5-dimethylpiperazin-1-yl)-5-chlorothiazolo[5,4-d]pyrimidin-2-yl)propanenitrile

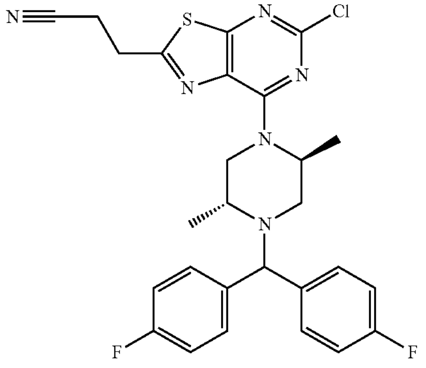 [SMILES: C[C@@H]1CN(c2nc(Cl)nc3sc(CCC#N)nc23)[C@@H](C)CN1C(c1ccc(F)cc1)c1ccc(F)cc1]

In an oven-dried vial with a stir bar, to a mixture of 7-((2S,5R)-4-(bis(4-fluorophenyl)methyl)-2,5-dimethylpiperazin-1-yl)-5-chloro-2-idothiazolo[5,4-d]pyrimidine (Intermediate 3, 122.4 mg, 0.200 mmol) and $Pd(PPh_3)_4$(46.2 mg, 0.040 mmol, Aldrich 216666) in DMF (1.0 mL) was added a 0.5 molar solution of (2-cyanoethyl)zinc(II) bromide in THF (0.48 mL, 0.24 mmol, Aldrich 497908) and the mixture was purged with $N_2$ and stirred at 85° C. for 4 h. After cooling to rt, the reaction mixture was concentrated in vacuo and the crude residue was purified by flash column chromatography (12 g $SiO_2$, EtOAc/hexanes) to afford the desired product (87.9 mg, 82% yield) as a yellow waxy solid. LC-MS calculated for $C_{27}H_{26}ClF_2N_6S$ $(M+H)^+$: m/z=539.2; found 539.2.

Intermediate 6. 4-((2S,5R)-4-(Bis(4-fluorophenyl)methyl)-2,5-dimethylpiperazin-1-yl)-6-chloro-1-methyl-1H-pyrazolo[3,4-d]pyrimidine

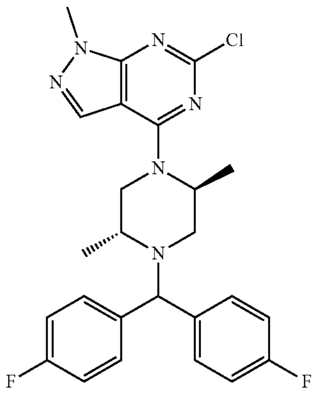

To a mixture of 4,6-dichloro-1-methyl-1H-pyrazolo[3,4-d]pyrimidine (102 mg, 0.50 mmol, Combi-Blocks QB-6771) and (2R,5S)-1-(bis(4-fluorophenyl)methyl)-2,5-dimethylpiperazine hydrochloride (Intermediate 1, 177 mg, 0.50 mmol) in 1-butanol (2.5 mL) was added N-ethyl-N-isopropylpropan-2-amine (0.26 mL, 1.5 mmol) and the reaction mixture was stirred at 60° C. for 2 h. After cooling to rt, the reaction mixture was concentrated in vacuo and the crude residue was purified by flash column chromatography (24 g $SiO_2$, EtOAc/hexanes) to afford the desired product (224 mg, 92% yield) as a colorless waxy solid. LC-MS calculated for $C_{25}H_{26}ClF_2N_6(M+H)^+$: m/z=483.2; found 483.2.

Intermediate 7. 4-((2S,5R)-4-(Bis(4-fluorophenyl) methyl)-2,5-dimethylpiperazin-1-yl)-2-chlorofuro[3, 2-d]pyrimidine

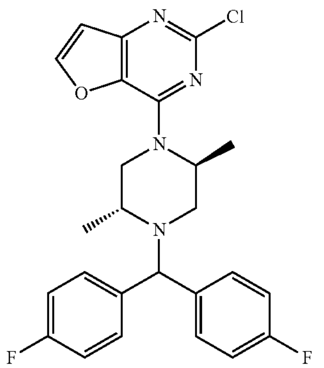 [SMILES: C[C@@H]1CN(c2nc(Cl)nc3ccoc23)[C@@H](C)CN1C(c1ccc(F)cc1)c1ccc(F)cc1]

This compound was prepared according to the procedures described in Intermediate 6, with 2,4-dichlorofuro[3,2-d] pyrimidine replacing 4,6-dichloro-1-methyl-1H-pyrazolo[3, 4-d]pyrimidine. LC-MS calculated for $C_{25}H_{24}ClF_2N_4O$ $(M+H)^+$: m/z=469.2; found 469.1.

Intermediate 8. 4-((2S,5R)-4-(Bis(4-fluorophenyl) methyl)-2,5-dimethylpiperazin-1-yl)-2-chlorothieno [3,2-d]pyrimidine

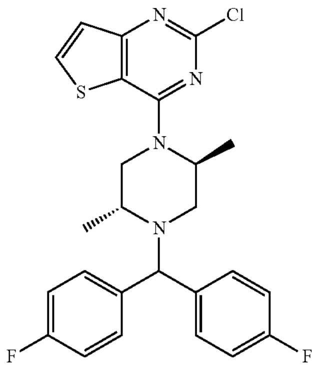 [SMILES: C[C@@H]1CN(c2nc(Cl)nc3ccsc23)[C@@H](C)CN1C(c1ccc(F)cc1)c1ccc(F)cc1]

This compound was prepared according to the procedures described in Intermediate 6, with 2,4-dichlorothieno[3,2-d] pyrimidine replacing 4,6-dichloro-1-methyl-1H-pyrazolo[3, 4-d]pyrimidine. LC-MS calculated for $C_{25}H_{24}ClF_2N_4S$ $(M+H)^+$: m/z=485.1; found 485.2.

Intermediate 9. 6-((2S,5R)-4-(Bis(4-fluorophenyl) methyl)-2,5-dimethylpiperazin-1-yl)-2-chloro-9-methyl-9H-purine

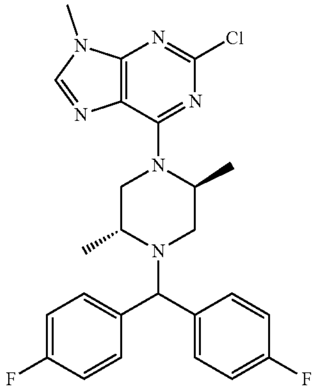 [SMILES: C[C@@H]1CN(c2nc(Cl)nc3c2ncn3C)[C@@H](C)CN1C(c1ccc(F)cc1)c1ccc(F)cc1]

To a mixture of 2,6-dichloro-9-methyl-9H-purine (203 mg, 1.00 mmol, Combi-Blocks ST-3696) and (2R,5S)-1-(bis (4-fluorophenyl)methyl)-2,5-dimethylpiperazine hydrochloride (Intermediate 1, 353 mg, 1.00 mmol) in 1-butanol (5.0 mL) was added N-ethyl-N-isopropylpropan-2-amine (0.52 mL, 3.0 mmol) and the mixture was stirred at 85° C. for 2 h. After cooling to rt, the reaction mixture was diluted with $CH_2Cl_2$ and extracted with sat. aq. $NaHCO_3$. The combined organic layers were dried over $MgSO_4$, concentrated, and purified by flash column chromatography (40 g $SiO_2$, EtOAc/hexanes). LC-MS calculated for $C_{25}H_{26}ClF_2N_6(M+H)^+$: m/z=483.2; found 483.2.

Intermediate 10. 4-((2S,5R)-4-(Bis(4-fluorophenyl) methyl)-2,5-dimethylpiperazin-1-yl)-2-chloro-5-ethyl-5H-pyrrolo[3,2-d]pyrimidine

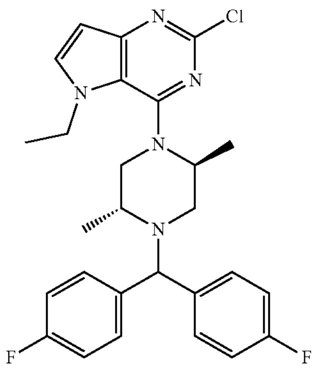 [SMILES: CCn1ccc2nc(Cl)nc(N3C[C@@H](C)N(C(c4ccc(F)cc4)c4ccc(F)cc4)C[C@@H]3C)c21]

To a mixture of 2,4-dichloro-5-ethyl-5H-pyrrolo[3,2-d] pyrimidine (54 mg, 0.25 mmol, Ambeed A478597) and (2R,5S)-1-(bis(4-fluorophenyl)methyl)-2,5-dimethylpiperazine hydrochloride (Intermediate 1, 88 mg, 0.25 mmol) in 1-butanol (1.25 mL) was added N-ethyl-N-isopropylpropan-2-amine (0.13 mL, 0.75 mmol) and the reaction mixture was stirred at 110° C. for 4 h. After cooling to rt, the reaction mixture was concentrated in vacuo and the crude residue was purified using flash column chromatography (12 g $SiO_2$, EtOAc/hexanes). LC-MS calculated for $C_{27}H_{29}ClF_2N_5(M+H)^+$: m/z=496.2; found 496.1.

Intermediate 11. 7-((2S,5R)-4-(Bis(4-fluorophenyl)methyl)-2,5-dimethylpiperazin-1-yl)-5-chlorothieno[3,2-b]pyridine

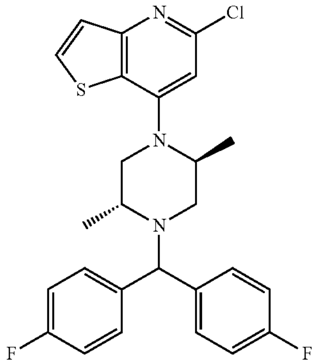 [SMILES: C[C@@H]1CN(c2cc(Cl)nc3ccsc23)[C@@H](C)CN1C(c1ccc(F)cc1)c1ccc(F)cc1]

To a mixture of 5,7-dichlorothieno[3,2-b]pyridine (103 mg, 0.50 mmol, AstaTech 26642) and (2R,5S)-1-(bis(4-fluorophenyl)methyl)-2,5-dimethylpiperazine hydrochloride (Intermediate 1, 177 mg, 0.50 mmol) in 1-butanol (2.5 mL) was added N-ethyl-N-isopropylpropan-2-amine (0.26 mL, 1.5 mmol) and the reaction mixture was stirred at 160° C. for 5 d. After cooling to rt, the reaction mixture was concentrated in vacuo and the crude residue was purified by flash column chromatography (12 g $SiO_2$, EtOAc/hexanes) to afford the desired product (31 mg, 13% yield) as a brown waxy solid. LC-MS calculated for $C_{26}H_{25}ClF_2N_3S$ $(M+H)^+$: m/z=484.1; found 484.1.

Intermediate 12. 4-((2S,5R)-4-(Bis(4-fluorophenyl)methyl)-2,5-dimethylpiperazin-1-yl)-6-chloro-1,3-dimethyl-1H-pyrazolo[3,4-b]pyridine

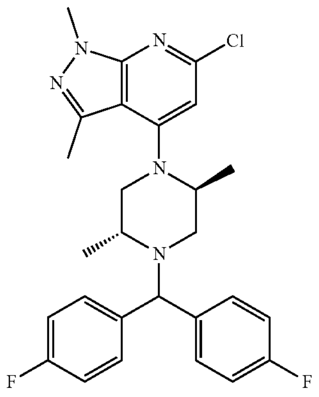 [SMILES: Cc1nn(C)c2nc(Cl)cc(N3C[C@@H](C)N(C(c4ccc(F)cc4)c4ccc(F)cc4)C[C@@H]3C)c12]

This compound was prepared according to the procedures described in Intermediate 11, with 4,6-dichloro-1,3-dimethyl-1H-pyrazolo[3,4-b]pyridine (Enamine EN300-295293) replacing 5,7-dichlorothieno[3,2-b]pyridine. LC-MS calculated for $C_{27}H_{29}ClF_2N_5(M+H)^+$: m/z=496.2; found 496.3.

Intermediate 13. tert-Butyl (2S,5S)-4-(bis(4-fluorophenyl)methyl)-5-(hydroxymethyl)-2-methylpiperazine-1-carboxylate

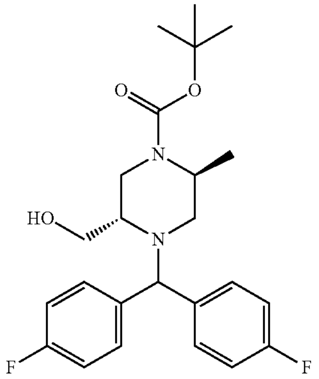 [SMILES: C[C@H]1CN(C(c2ccc(F)cc2)c2ccc(F)cc2)[C@H](CO)CN1C(=O)OC(C)(C)C]

A mixture of tert-butyl (2S,5S)-5-(hydroxymethyl)-2-methylpiperazine-1-carboxylate (921.2 mg, 4.00 mmol, AstaTech AT10033), 4,4'-(chloromethylene)bis(fluorobenzene) (955 mg, 4.00 mmol, Combi-Blocks QA-4728) and N-ethyl-N-isopropylpropan-2-amine (2.1 mL, 12 mmol) in $CH_3CN$ (10.0 mL) was stirred at 85° C. overnight. After cooling to rt, the reaction mixture was concentrated in vacuo and the crude residue was purified using flash column chromatography (40 g $SiO_2$, EtOAc/hexanes) to afford the desired product (854 mg, 49% yield) as a colorless waxy solid. LC-MS calculated for $C_{24}H_{31}F_2N_2O_3(M+H)^+$: m/z=433.2; found 433.2.

Intermediate 14. (2S,5S)-1-(Bis(4-fluorophenyl)methyl)-2-(methoxymethyl)-5-methylpiperazine hydrochloride

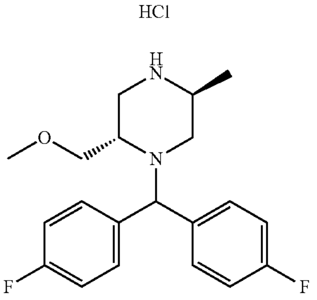 [SMILES: Cl ; COC[C@@H]1CN[C@@H](C)CN1C(c1ccc(F)cc1)c1ccc(F)cc1]

Step 1. tert-Butyl (2S,5S)-4-(bis(4-fluorophenyl)methyl)-5-(methoxymethyl)-2-methylpiperazine-1-carboxylate

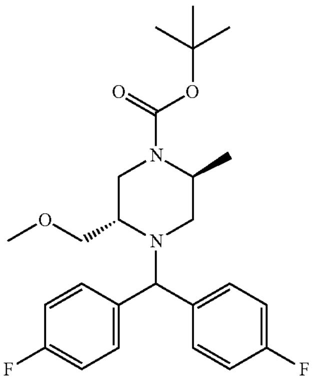 [SMILES: COC[C@@H]1CN(C(=O)OC(C)(C)C)[C@@H](C)CN1C(c1ccc(F)cc1)c1ccc(F)cc1]

In an oven-dried vial with a stir bar, to a mixture of tert-butyl (2S,5S)-4-(bis(4-fluorophenyl)methyl)-5-(hydroxymethyl)-2-methylpiperazine-1-carboxylate (Intermediate 13, 143 mg, 0.33 mmol) in a 1:1 mixture of THF/DMF (1.65 mL) was added sodium hydride (26.4 mg, 0.66 mmol) (60% dispersion in mineral oil, Aldrich 452912) and the mixture was purged with $N_2$ and stirred at rt for 15 mins before iodomethane (141 mg, 0.99 mmol) was added and the reaction mixture was stirred at rt overnight. The reaction mixture was diluted with $CH_2Cl_2$ and quenched via the dropwise addition of sat. aq. $NaHCO_3$. The organic layer was removed and the aqueous layer was extracted with $CH_2Cl_2$. The combined organic layers were dried over $MgSO_4$, concentrated, and purified by flash column chromatography (12 g $SiO_2$, EtOAc/hexanes) to afford the desired product (69 mg, 47% yield) as a colorless waxy solid. LC-MS calculated for $C_{25}H_{33}F_2N_2O_3(M+H)^+$: m/z=447.2; found 447.3.

Step 2. (2S,5S)-1-(Bis(4-fluorophenyl)methyl)-2-(methoxymethyl)-5-methylpiperazine hydrochloride To a mixture of tert-butyl (2S,5S)-4-(bis(4-fluorophenyl)methyl)-5-(methoxymethyl)-2-methylpiperazine-1-carboxylate (69 mg, 0.15 mmol) in THF (1.5 mL) was added a 4 molar solution of HCl in 1,4-dioxane (0.4 mL, 1.6 mmol) and the reaction mixture was purged with $N_2$ and stirred at 85° C. for 2 h. After cooling to rt, the reaction mixture was concentrated to ½ volume, diluted with $Et_2O$ (3 mL) and hexanes (5 mL), and slurried for 30 mins. The solid precipitate was allowed to settle, and the supernatant solvent was decanted off and the residual solid dried under vacuum to afford the desired product as a white solid. LC-MS calculated for $C_{20}H_{25}F_2N_2O$ $(M+H)^+$: m/z=347.2; found 347.1.

Intermediate 15. 2-((2R,5S)-1-(Bis(4-fluorophenyl)methyl)-5-methylpiperazin-2-yl)acetonitrile hydrochloride

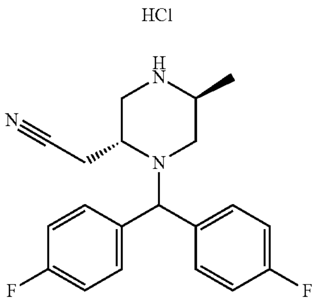 [SMILES: Cl ; C[C@H]1CN(C(c2ccc(F)cc2)c2ccc(F)cc2)[C@H](CC#N)CN1]

Step 1. tert-Butyl (2S,5S)-4-(bis(4-fluorophenyl)methyl)-2-methyl-5-(((methylsulfonyl)oxy)methyl)piperazine-1-carboxylate

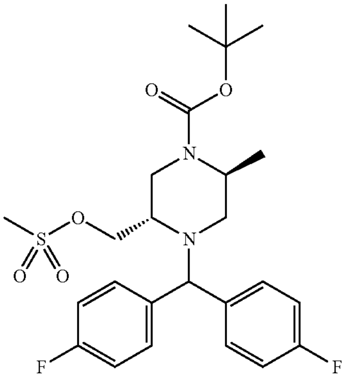 [SMILES: C[C@H]1CN(C(c2ccc(F)cc2)c2ccc(F)cc2)[C@H](COS(C)(=O)=O)CN1C(=O)OC(C)(C)C]

A mixture of tert-butyl (2S,5S)-4-(bis(4-fluorophenyl)methyl)-5-(hydroxymethyl)-2-methylpiperazine-1-carboxylate (Intermediate 13, 432.5 mg, 1.00 mmol) and N-ethyl-N-isopropylpropan-2-amine (524 μL, 3.00 mmol) in THF (5.0 mL) was cooled to in an ice-bath before methanesulfonyl chloride (156 μL, 2.0 mmol) was added dropwise. The ice bath was removed and the reaction mixture was stirred at ambient temperature for 4 h. The mixture was then concentrated in vacuo and the crude residue was purified using flash column chromatography (24 g $SiO_2$, EtOAc/hexanes) to afford the desired product (481 mg, 94% yield) as a colorless oil. LC-MS calculated for $C_{25}H_{33}F_2N_2O_5S$ $(M+H)^+$: m/z=511.2; found 511.2.

Step 2: tert-Butyl (2S,5R)-4-(bis(4-fluorophenyl)methyl)-5-(cyanomethyl)-2-methylpiperazine-1-carboxylate

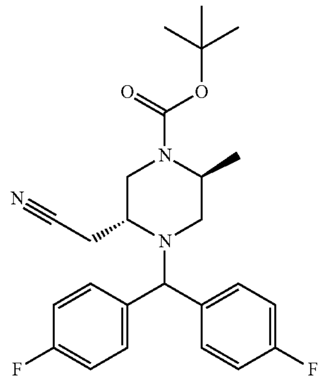 [SMILES: C[C@H]1CN(C(c2ccc(F)cc2)c2ccc(F)cc2)[C@H](CC#N)CN1C(=O)OC(C)(C)C]

To a mixture of tert-butyl (2S,5S)-4-(bis(4-fluorophenyl)methyl)-2-methyl-5-(((methylsulfonyl)oxy)methyl)piperazine-1-carboxylate (481 mg, 0.94 mmol) in dimethylacetamide (4.7 mL) was added potassium cyanide (307 mg, 4.7 mmol) and the reaction mixture was stirred at 55° C. overnight. After cooling to rt, the reaction mixture was diluted with a 5% aqueous LiCl solution and extracted with $CH_2Cl_2$. The combined organic phases were dried over $MgSO_4$ and concentrated. The crude residue was purified using flash column chromatography (40 g $SiO_2$, EtOAc/hexanes) to afford the desired product (370 mg, 89% yield) as a colorless waxy solid. LC-MS calculated for $C_{25}H_{29}F_2N_3O_2Na$ $(M+Na)^+$: m/z=464.2; found 464.1.

Step 3. 2-((2R,5S)-1-(Bis(4-fluorophenyl)methyl)-5-methylpiperazin-2-yl)acetonitrile hydrochloride

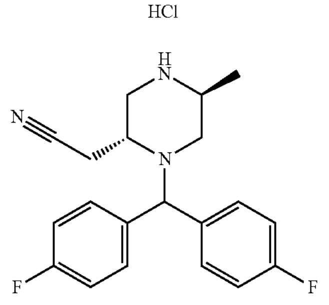 [SMILES: Cl ; C[C@H]1CN(C(c2ccc(F)cc2)c2ccc(F)cc2)[C@H](CC#N)CN1]

To a mixture of tert-butyl (2S,5R)-4-(bis(4-fluorophenyl)methyl)-5-(cyanomethyl)-2-methylpiperazine-1-carboxylate (370 mg, 0.84 mmol) in THF (4.2 mL) was added a 4 molar solution of HCl in 1,4-dioxane (1.05 mL, 4.2 mmol) and the reaction mixture was purged with $N_2$ and stirred at 60° C. for 30 min. After cooling to rt, the reaction mixture was diluted with $Et_2O$ (8 mL) and hexanes (16 mL) and slurried for 30 mins. The solid precipitate was allowed to settle, and the supernatant solvent was decanted off and the residual solid was dried under vacuum to afford the desired product (288 mg, 91% yield) as a white solid. LC-MS calculated for $C_{20}H_{22}F_2N_3$ $(M+H)^+$: m/z=342.2; found 342.1.

Intermediate 16. 2-((2R,5S)-1-(Bis(4-fluorophenyl)methyl)-4-(5-chlorothiazolo[5,4-d]pyrimidin-7-yl)-5-methylpiperazin-2-yl)acetonitrile

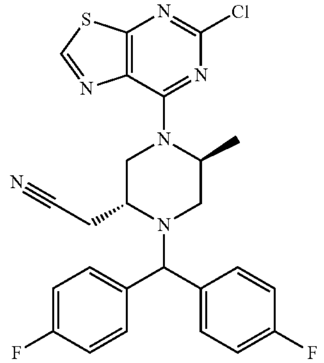 [SMILES: C[C@H]1CN(C(c2ccc(F)cc2)c2ccc(F)cc2)[C@H](CC#N)CN1c1nc(Cl)nc2scnc12]

To a mixture of 5,7-dichlorothiazolo[5,4-d]pyrimidine (52 mg, 0.25 mmol, PharmaBlock PB03220) and 2-((2R,5S)-1-(bis(4-fluorophenyl)methyl)-5-methylpiperazin-2-yl)acetonitrile hydrochloride (Intermediate 15, 95 mg, 0.25 mmol) in 1-butanol (1.3 mL) was added N-ethyl-N-isopropylpropan-2-amine (0.13 mL, 0.75 mmol) and the reaction mixture was stirred at 60° C. for 1 h. After cooling to rt, the reaction mixture was concentrated in vacuo and the crude residue was purified using flash column chromatography (24 g $SiO_2$, EtOAc/hexanes) to afford the desired product (85 mg, 66% yield) as a light yellow waxy solid. LC-MS calculated for $C_{25}H_{22}ClF_2N_6S$ $(M+H)^+$: m/z=511.1; found 511.0.

Intermediate 17. 2-((2R,5S)-1-(Bis(4-fluorophenyl)methyl)-4-(2-chloro-9-methyl-9H-purin-6-yl)-5-methylpiperazin-2-yl)acetonitrile

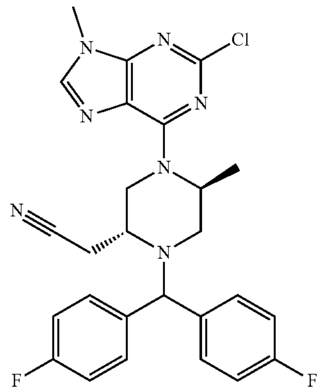 [SMILES: C[C@H]1CN(C(c2ccc(F)cc2)c2ccc(F)cc2)[C@H](CC#N)CN1c1nc(Cl)nc2c1ncn2C]

This compound was prepared according to the procedures described in Intermediate 16, with 2,6-dichloro-9-methyl-9H-purine (Combi-Blocks ST-3696) replacing 5,7-dichlorothiazolo[5,4-d]pyrimidine. LC-MS calculated for $C_{26}H_{25}ClF_2N_7(M+H)^+$: m/z=508.2; found 508.1.

Intermediate 18. tert-Butyl (R)-4-(bis(4-fluorophenyl)methyl)-3-(2-hydroxyethyl)piperazine-1-carboxylate

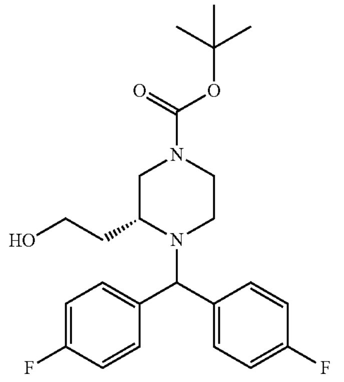 [SMILES: CC(C)(C)OC(=O)N1CCN(C(c2ccc(F)cc2)c2ccc(F)cc2)[C@H](CCO)C1]

This compound was prepared according to the procedures described in Intermediate 13, with tert-butyl (R)-3-(2-hydroxyethyl)piperazine-1-carboxylate (AstaTech 70239) replacing tert-butyl (2S,5S)-5-(hydroxymethyl)-2-methylpiperazine-1-carboxylate. LC-MS calculated for $C_{24}H_{31}F_2N_2O_3$(M+H)$^+$: m/z=433.2; found 433.3.

Intermediate 19. (R)-3-(1-(Bis(4-fluorophenyl)methyl)piperazin-2-yl)propanenitrile hydrochloride

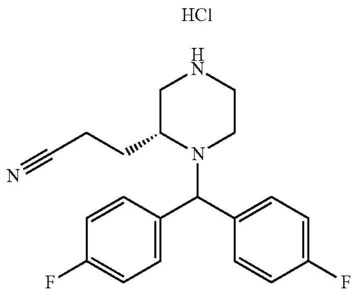 [SMILES: Cl ; N#CCC[C@@H]1CNCCN1C(c1ccc(F)cc1)c1ccc(F)cc1]

This compound was prepared according to the procedures described in Intermediate 15, with tert-butyl (R)-4-(bis(4-fluorophenyl)methyl)-3-(2-hydroxyethyl)piperazine-1-carboxylate (Intermediate 18) replacing tert-butyl (2S,5S)-4-(bis(4-fluorophenyl)methyl)-5-(hydroxymethyl)-2-methylpiperazine-1-carboxylate. LC-MS calculated for $C_{20}H_{22}F_2N_3$ (M+H)$^+$: m/z=342.2; found 342.2.

Intermediate 20. (R)-3-(1-(Bis(4-fluorophenyl)methyl)-4-(5-chlorothiazolo[5,4-d]pyrimidin-7-yl)piperazin-2-yl)propanenitrile

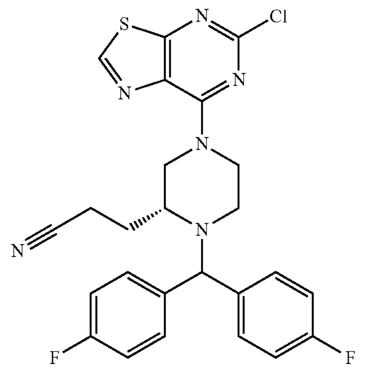 [SMILES: N#CCC[C@@H]1CN(c2nc(Cl)nc3scnc23)CCN1C(c1ccc(F)cc1)c1ccc(F)cc1]

This compound was prepared according to the procedures described in Intermediate 16, with (R)-3-(1-(bis(4-fluorophenyl)methyl)piperazin-2-yl)propanenitrile hydrochloride (Intermediate 19) replacing 2-((2R,5S)-1-(bis(4-fluorophenyl)methyl)-5-methylpiperazin-2-yl)acetonitrile hydrochloride. LC-MS calculated for $C_{25}H_{22}ClF_2N_6S$ (M+H)$^+$: m/z=511.1; found 511.2.

Intermediate 21. 6-((2S,5R)-4-(Bis(4-fluorophenyl)methyl)-2,5-dimethylpiperazin-1-yl)-2-chloro-9H-purine

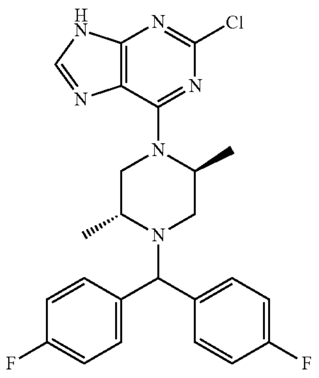 [SMILES: C[C@@H]1CN(c2nc(Cl)nc3[nH]cnc23)[C@@H](C)CN1C(c1ccc(F)cc1)c1ccc(F)cc1]

To a mixture of 2,6-dichloropurine (2.79 g, 14.7 mmol, Ambeed A101242) and (2R,5S)-1-(bis(4-fluorophenyl)methyl)-2,5-dimethylpiperazine hydrochloride (Intermediate 1, 5.20 g, 14.7 mmol) in 2-propanol (73.7 mL) was added N-ethyl-N-isopropylpropan-2-amine (7.72 mL, 44.2 mmol) and the mixture was stirred at 85° C. for 12 h. After cooling to rt, the reaction mixture was concentrated in vacuo, and the crude residue was diluted with $CH_2Cl_2$ and extracted with saturated aqueous $NaHCO_3$. The combined organic layers were dried over $MgSO_4$ and the filtrate was concentrated. The crude residue was triturated with cold MeOH (100 mL) and filtered to afford the desired product (5.40 g, 78% yield) as a light tan solid. LC-MS calculated for $C_{24}H_{24}ClF_2N_6$ (M+H)$^+$: m/z=469.2; found 469.2.

As one skilled in the art would understand, compounds of the present disclosure can exist as tautomers. For example, Intermediate 21 can exist as the 7H-purine or 9H-purine form (e.g., 6-((2S,5R)-4-(bis(4-fluorophenyl)methyl)-2,5-dimethylpiperazin-1-yl)-2-chloro-7H-purine).

Intermediate 22. (S)-(Tetrahydrofuran-2-yl)methyl methanesulfonate

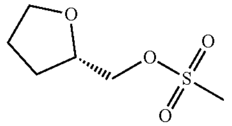

A mixture of (S)-(tetrahydrofuran-2-yl)methanol (2.00 g, 19.6 mmol, BLD Pharmatech BD48351) and N-ethyl-N-isopropylpropan-2-amine (5.12 mL, 29.4 mmol) in $CH_2Cl_2$ (15 mL) was purged with $N_2$ and cooled to 0° C. before methanesulfonyl chloride (1.97 mL, 25.5 mmol) was added dropwise. The reaction mixture was allowed to warm to rt and stirred for 30 mins. The mixture was quenched with saturated aqueous $NaHCO_3$, the organic layer was removed, and the aqueous layer was extracted with $CH_2Cl_2$. The combined organic layers were dried over $MgSO_4$, filtered, and concentrated under reduced pressure to afford the desired product (3.39 g, 96% yield) as a light orange oil that was used directly without further purification. $^1H$ NMR (400 MHz, $CDCl_3$) δ 4.28-4.20 (m, 1H), 4.20-4.13 (m, 2H), 3.88 (dt, J=8.4, 6.6 Hz, 1H), 3.80 (dt, J=8.2, 6.6 Hz, 1H), 3.05 (s, 3H), 2.08-1.97 (m, 1H), 1.97-1.87 (m, 2H), 1.73-1.63 (m, 1H).

Intermediate 23. 6-((2S,5R)-4-(Bis(4-fluorophenyl)methyl)-2,5-dimethylpiperazin-1-yl)-2-chloro-8-methyl-9H-purine

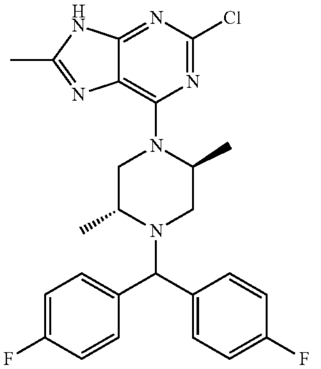 [SMILES: Cc1nc2c(N3C[C@@H](C)N(C(c4ccc(F)cc4)c4ccc(F)cc4)C[C@@H]3C)nc(Cl)nc2[nH]1]

A mixture of (2R,5S)-1-(bis(4-fluorophenyl)methyl)-2,5-dimethylpiperazine hydrochloride (Intermediate 1, 2.00 g, 5.67 mmol), 2,6-dichloro-8-methylpurine (1.24 g, 6.11 mmol, PharmaBlock PB02898), and N-ethyl-N-isopropylpropan-2-amine (2.97 mL, 17.00 mmol) in 1-butanol (14.2 mL) was stirred at 85° C. overnight. After cooling to rt, the reaction mixture was diluted with toluene and concentrated in vacuo. The crude residue was purified directly by flash column chromatography ($SiO_2$, EtOAc/hexanes) to afford the desired product (1.82 g, 66% yield) as a brown solid. LC-MS calculated for $C_{25}H_{26}ClF_2N_6(M+H)^+$: m/z=483.2; found 483.1.

Intermediate 24. Methyl (R)-2-(benzylamino)butanoate

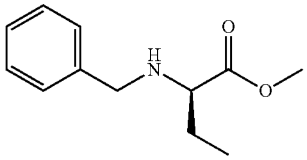

To a stirred solution of methyl (R)-2-aminobutanoate hydrochloride (30.0 g, 195 mmol, Combi-Blocks QA-7768) in $CH_2Cl_2$ (500 mL) was added benzaldehyde (20.7 g, 195 mmol) and the reaction mixture was stirred at rt for 6 h. The reaction mixture was cooled to 0° C. in an ice-bath before sodium triacetoxyborohydride (20.7 g, 98 mmol) was added portionwise over 20 min. The ice-bath was removed and the reaction mixture was stirred at ambient temperature overnight. The mixture was transferred to a separatory funnel and extracted with 1 M aqueous HCl (3×300 mL). The combined aqueous layers were made basic with solid KOH (pH>12) and extracted with EtOAc (3×300 mL). The combined organic layers were washed with saturated aqueous NaCl, dried over $MgSO_4$, and the filtrate was concentrated to afford the desired product (28.3 g, 70% yield) as a colorless oil. The crude material obtained was used directly without further purification. LC-MS calculated for $C_{12}H_{18}NO_2$ $(M+H)^+$: m/z=208.1; found 208.2.

Intermediate 25. tert-Butyl (2S,5R)-5-ethyl-2-methylpiperazine-1-carboxylate

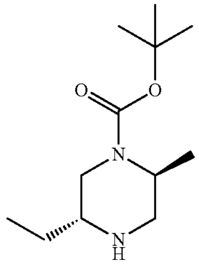 [SMILES: CC[C@@H]1CN(C(=O)OC(C)(C)C)[C@@H](C)CN1]

Step 1: Methyl (R)-2-((S)—N-benzyl-2-((tert-butoxycarbonyl)amino)propanamido)butanoate

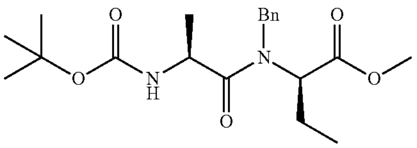 [SMILES: CC[C@H](C(=O)OC)N(Cc1ccccc1)C(=O)[C@H](C)NC(=O)OC(C)(C)C]

To a mixture of methyl (R)-2-(benzylamino)butanoate (Intermediate 24, 18.4 g, 89 mmol) and (tert-butoxycarbonyl)-L-alanine (21.8 g, 115 mmol, Combi-Blocks QA-6543) in N,N-dimethylformamide (100 mL) was added HATU (50.6 g, 133 mmol, Oakwood 023926) followed by N-ethyl-N-isopropylpropan-2-amine (41.9 mL, 240 mmol) and the reaction mixture was stirred at rt overnight. The mixture was diluted with $Et_2O$ (600 mL) and washed with water (200 mL). After phase separation the organic layer was removed and the aqueous layer was extracted with $Et_2O$ (2×200 mL). The combined organic layers were dried over $MgSO_4$, concentrated, and the crude residue was purified by flash column chromatography ($SiO_2$, EtOAc/hexanes) to afford the desired product (30 g, 89% yield). LC-MS calculated for $C_{20}H_{31}N_2O_5$ $(M+H)^+$: m/z=379.2; found 379.3.

Step 2: (3S,6R)-1-Benzyl-6-ethyl-3-methylpiperazine-2,5-dione

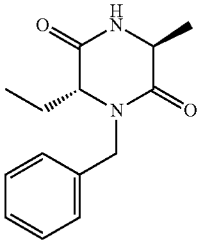 [SMILES: CC[C@@H]1C(=O)N[C@@H](C)C(=O)N1Cc1ccccc1]

To a mixture of methyl (R)-2-((S)—N-benzyl-2-((tert-butoxycarbonyl)amino)propanamido)butanoate (30 g, 79 mmol) in $CH_2Cl_2$ (200 mL) was added trifluoroacetic acid (50 mL, 649 mmol) and the reaction mixture was stirred at rt overnight. The reaction mixture was concentrated in vacuo. To the crude residue was added MeOH (200 mL) and the reaction mixture was sealed and stirred at 70° C. overnight. After cooling to rt, the reaction mixture was concentrated in vacuo to afford the desired product (27 g). The crude material obtained was used directly without further purification. LC-MS calculated for $C_{14}H_{19}N_2O_2$ $(M+H)^+$: m/z=247.1; found 247.2.

Step 3: (2R,5S)-1-Benzyl-2-ethyl-5-methylpiperazine

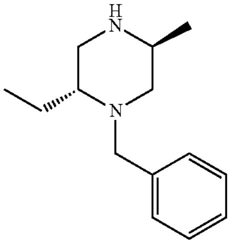 [SMILES: CC[C@@H]1CN[C@@H](C)CN1Cc1ccccc1]

A mixture of (3S,6R)-1-benzyl-6-ethyl-3-methylpiperazine-2,5-dione (Step 2) in THF (200 mL) was cooled to 0° C. in an ice-bath before borane tetrahydrofuran complex (1 M in THF, 375 mL, 375 mmol, Aldrich 176192) was added slowly. The ice-bath was removed and the reaction mixture was stirred at 70° C. for 20 h. After cooling to rt, the reaction mixture was quenched via the slow addition of MeOH (100 mL) followed by 1 M aqueous HCl (112 mL, 112 mmol). The mixture was stirred at 70° C. for an additional 2 h. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$, and concentrated. The crude material obtained was used directly without further purification. LC-MS calculated for $C_{14}H_{23}N_2$ $(M+H)^+$: m/z=219.2; found 219.1.

Step 4: tert-Butyl (2S,5R)-4-benzyl-5-ethyl-2-methylpiperazine-1-carboxylate

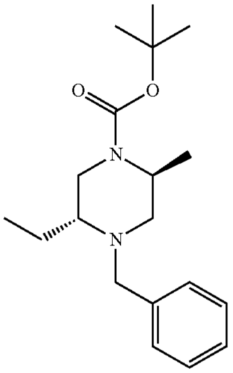 [SMILES: CC[C@@H]1CN(C(=O)OC(C)(C)C)[C@@H](C)CN1Cc1ccccc1]

To a mixture of (2R,5S)-1-benzyl-2,5-diethylpiperazine (Step 3) in $CH_2Cl_2$ (150 mL) was added triethylamine (31.3 mL, 225 mmol) and di-tert-butyl dicarbonate (26.1 mL, 112 mmol) and the reaction mixture was stirred at rt overnight. The mixture was diluted with $CH_2Cl_2$ and washed with water (150 mL) and saturated aqueous NaCl. The organic layer was dried over $MgSO_4$, concentrated, and the crude residue was purified by flash column chromatography ($SiO_2$, EtOAc/hexanes) to afford the desired product (22.2 g) as an off-white solid. LC-MS calculated for $C_{19}H_{31}N_2O_2$ $(M+H)^+$: m/z=319.2; found 319.3.

Step 5: tert-Butyl (2S,5R)-5-ethyl-2-methylpiperazine-1-carboxylate

To a mixture of tert-butyl (2S,5R)-4-benzyl-2,5-diethylpiperazine-1-carboxylate (22.2 g, 69.7 mmol) in MeOH (170 mL) was added palladium on carbon (10 wt %, 3.2 g, 3 mmol) and the reaction mixture was shaken in a Parr shaker under 50 psi of $H_2$ (g) for 20 h. The mixture was filtered over a pad of Celite®, and the filter cake was washed with MeOH (170 mL). The filtrate was concentrated and dried under vacuum to afford the desired product (12.5 g, 78% yield). The material obtained was used directly without further purification. LC-MS calculated for $C_{12}H_{25}N_2O_2$ $(M+H)^+$: m/z=229.2; found 229.3.

Intermediate 26. (2R,5S)-1-(Bis(4-fluorophenyl)methyl)-2-ethyl-5-methylpiperazine hydrochloride

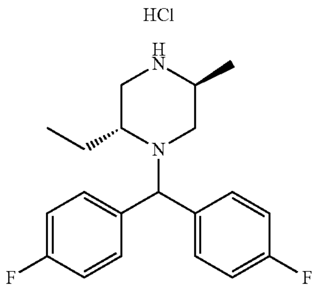 [SMILES: Cl ; CC[C@@H]1CN[C@@H](C)CN1C(c1ccc(F)cc1)c1ccc(F)cc1]

Step 1: tert-Butyl (2S,5R)-4-(bis(4-fluorophenyl)methyl)-5-ethyl-2-methylpiperazine-1-carboxylate

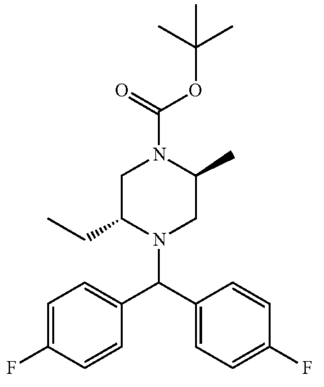 [SMILES: CC[C@@H]1CN(C(=O)OC(C)(C)C)[C@@H](C)CN1C(c1ccc(F)cc1)c1ccc(F)cc1]

A mixture of tert-butyl (2S,5R)-5-ethyl-2-methylpiperazine-1-carboxylate (Intermediate 25, 1.50 g, 6.57 mmol), 4,4'-(chloromethylene)bis(fluorobenzene) (1.35 mL, 7.23 mmol, Combi-Blocks QA-4728) and N-ethyl-N-isopropylpropan-2-amine (2.3 mL, 13 mmol) in $CH_3CN$ (12 mL) was sealed and stirred at 140° C. for 2.5 h. After cooling to rt, the reaction mixture was concentrated in vacuo and the crude residue was purified using flash column chromatography ($SiO_2$, EtOAc/hexanes) to afford the desired product (2.23 g, 79% yield). LC-MS calculated for $C_{25}H_{33}F_2N_2O_2(M+H)^+$: m/z=431.3; found 431.3.

Step 2: (2R,5S)-1-(Bis(4-fluorophenyl)methyl)-2-ethyl-5-methylpiperazine hydrochloride To a mixture of tert-butyl (2S,5R)-4-(bis(4-fluorophenyl)methyl)-5-ethyl-2-methylpiperazine-1-carboxylate (2.23 g, 5.18 mmol) in THF (40 mL) was added a 4 M solution of HCl in 1,4-dioxane (16.4 mL, 66 mmol) and the reaction mixture was purged with $N_2$ and stirred at 60° C. for 4 h. After cooling to rt, the reaction mixture was diluted with $Et_2O$ (100 mL) and hexanes (50 mL) and slurried for 30 min. The solid precipitate was collected via filtration, washed with $Et_2O$ and hexanes, and dried under vacuum to afford the desired product (1.17 g). LC-MS calculated for $C_{20}H_{25}F_2N_2$ $(M+H)^+$: m/z=331.2; found 331.3.

Intermediate 27. 6-((2S,5R)-4-(Bis(4-fluorophenyl)methyl)-5-ethyl-2-methylpiperazin-1-yl)-2-chloro-8-methyl-9H-purine

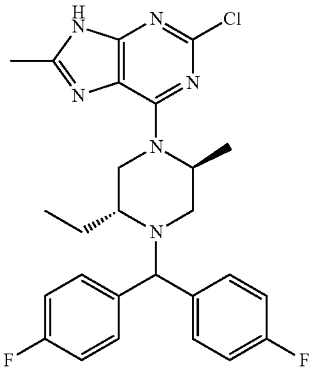 [SMILES: CC[C@@H]1CN(c2nc(Cl)nc3[nH]c(C)nc23)[C@@H](C)CN1C(c1ccc(F)cc1)c1ccc(F)cc1]

To a mixture of 2,6-dichloro-8-methylpurine (1.11 g, 5.45 mmol, PharmaBlock PB02898) and (2R,5S)-1-(bis(4-fluorophenyl)methyl)-2-ethyl-5-methylpiperazine hydrochloride (Intermediate 26, 2.00 g, 5.45 mmol) in 1-butanol (10 mL) was added N-ethyl-N-isopropylpropan-2-amine (2.86 mL, 16.4 mmol) and the mixture was stirred at 80° C. overnight before heating to 90° C. for 2 h. After cooling to rt, the reaction mixture was concentrated in vacuo, and the crude residue was purified directly by flash column chromatography (40 g $SiO_2$, EtOAc/hexanes) to afford the desired product (2.1 g, 78% yield) as a very light yellow waxy solid. LC-MS calculated for $C_{26}H_{28}ClF_2N_6(M+H)^+$: m/z=497.2; found 497.3.

Intermediate 28. tert-Butyl (2S,5R)-2,5-diethylpiperazine-1-carboxylate

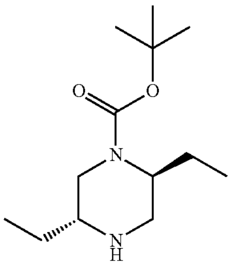 [SMILES: CC[C@@H]1CN(C(=O)OC(C)(C)C)[C@@H](CC)CN1]

Step 1: Methyl (R)-2-((S)—N-benzyl-2-((tert-butoxycarbonyl)amino)butanamido)butanoate

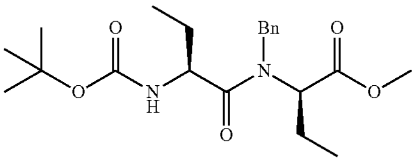 [SMILES: CC[C@H](NC(=O)OC(C)(C)C)C(=O)N(Cc1ccccc1)[C@H](CC)C(=O)OC]

To a mixture of methyl (R)-2-(benzylamino)butanoate (Intermediate 24, 9.4 g, 45 mmol) and (S)-2-((tert-butoxycarbonyl)amino)butanoic acid (11 g, 54 mmol, Combi-Blocks OR-1176) in N,N-dimethylformamide (60 mL) was added HATU (24 g, 63 mmol, Oakwood 023926) followed by N-ethyl-N-isopropylpropan-2-amine (21 mL, 121 mmol) and the reaction mixture was stirred at rt overnight. The mixture was diluted with $Et_2O$ (600 mL) and washed with water (200 mL). After phase separation the organic layer was removed and the aqueous layer was extracted with $Et_2O$ (2×200 mL). The combined organic layers were dried over $MgSO_4$, concentrated, and the crude residue was purified by flash column chromatography ($SiO_2$, EtOAc/hexanes) to afford the desired product (14.5 g, 81% yield). LC-MS calculated for $C_{21}H_{33}N_2O_5$ $(M+H)^+$: m/z=393.2; found 393.3.

Step 2: (3S,6R)-1-Benzyl-3,6-diethylpiperazine-2,5-dione

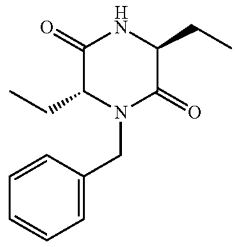 [SMILES: CC[C@@H]1NC(=O)[C@@H](CC)N(Cc2ccccc2)C1=O]

To a mixture of methyl (R)-2-((S)—N-benzyl-2-((tert-butoxycarbonyl)amino)butanamido)butanoate (Step 1) in $CH_2Cl_2$ (100 mL) was added trifluoroacetic acid (24.5 mL, 318 mmol) and the reaction mixture was stirred at rt overnight. The reaction mixture was concentrated in vacuo. To the crude residue was added MeOH (170 mL) and the reaction mixture was sealed and stirred at 70° C. overnight. After cooling to rt, the reaction mixture was concentrated in vacuo to afford the desired product (12.9 g). The crude material obtained was used directly without further purification. LC-MS calculated for $C_{15}H_{21}N_2O_2$ $(M+H)^+$: m/z=261.2; found 261.1.

Step 3: (2R,5S)-1-Benzyl-2,5-diethylpiperazine

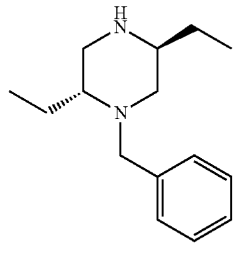 [SMILES: CC[C@H]1CN(Cc2ccccc2)[C@H](CC)CN1]

A mixture of (3S,6R)-1-benzyl-3,6-diethylpiperazine-2,5-dione (Step 2) in THF (200 mL) was cooled to 0° C. in an ice-bath before borane tetrahydrofuran complex (1 M in THF, 172 mL, 172 mmol, Aldrich 176192) was added slowly. The ice-bath was removed and the reaction mixture was stirred at 70° C. for 20 h. After cooling to rt, the reaction mixture was quenched via the slow addition of MeOH (100 mL) followed by 1 M aqueous HCl (103 mL, 103 mmol). The mixture was stirred at 70° C. for an additional 2 h. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$, and concentrated. The crude material obtained was used directly without further purification. LC-MS calculated for $C_{15}H_{25}N_2$ $(M+H)^+$: m/z=233.2; found 233.1.

Step 4: tert-Butyl (2S,5R)-4-benzyl-2,5-diethylpiperazine-1-carboxylate

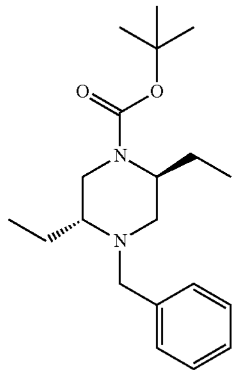 [SMILES: CC[C@@H]1CN(C(=O)OC(C)(C)C)[C@@H](CC)CN1Cc1ccccc1]

To a mixture of (2R,5S)-1-benzyl-2,5-diethylpiperazine (Step 3) in $CH_2Cl_2$ (150 mL) was added triethylamine (12 mL, 86 mmol) and di-tert-butyl dicarbonate (12 mL, 52 mmol) and the reaction mixture was stirred at rt overnight. The mixture was diluted with $CH_2Cl_2$ and washed with water (150 mL) and saturated aqueous NaCl. The organic layer was dried over $MgSO_4$, concentrated, and the crude residue was purified by flash column chromatography ($SiO_2$, EtOAc/hexanes) to afford the desired product (8.8 g). LC-MS calculated for $C_{20}H_{33}N_2O_2$ $(M+H)^+$: m/z=333.3; found 333.2.

Step 5: tert-Butyl (2S,5R)-2,5-diethylpiperazine-1-carboxylate

To a mixture of tert-butyl (2S,5R)-4-benzyl-2,5-diethylpiperazine-1-carboxylate (8.8 g, 26.5 mmol) in MeOH (170 mL) was added palladium on carbon (10 wt %, 2.1 g, 2 mmol) and the reaction mixture was shaken in a Parr shaker under 50 psi of $H_2$ (g) overnight. The mixture was filtered over a pad of Celite®, and the filter cake was washed with MeOH. The filtrate was concentrated and dried under vacuum to afford the desired product (6.5 g) in quantitative yield. The material obtained was used directly without further purification. LC-MS calculated for $C_{13}H_{27}N_2O_2$ $(M+H)^+$: m/z=243.2; found 243.2.

Intermediate 29. (2R,5S)-1-(Bis(4-fluorophenyl)methyl)-2,5-diethylpiperazine hydrochloride

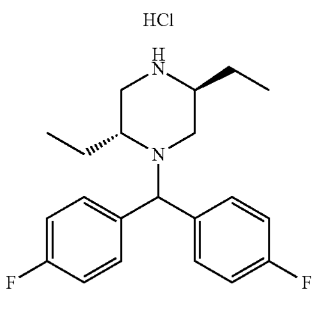 [SMILES: Cl ; CC[C@H]1CN(C(c2ccc(F)cc2)c2ccc(F)cc2)[C@H](CC)CN1]

Step 1: tert-Butyl (2S,5R)-4-(bis(4-fluorophenyl)methyl)-2,5-diethylpiperazine-1-carboxylate

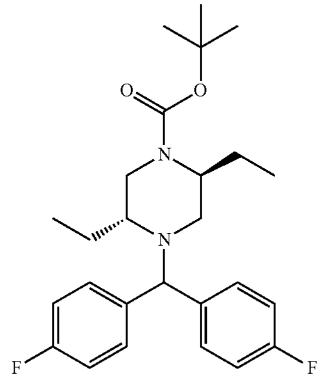 [SMILES: CC[C@H]1CN(C(c2ccc(F)cc2)c2ccc(F)cc2)[C@H](CC)CN1C(=O)OC(C)(C)C]

A mixture of tert-butyl (2S,5R)-2,5-diethylpiperazine-1-carboxylate (Intermediate 28, 2.00 g, 8.25 mmol), 4,4'-(chloromethylene)bis(fluorobenzene) (2.56 g, 10.7 mmol, Combi-Blocks QA-4728) and N-ethyl-N-isopropylpropan-2-amine (2.9 mL, 17 mmol) in $CH_3CN$ (12 mL) was sealed and stirred at 140° C. for 2.5 h. After cooling to rt, the reaction mixture was concentrated in vacuo and the crude residue was purified using flash column chromatography ($SiO_2$, EtOAc/hexanes) to afford the desired product (2.8 g, 76% yield). LC-MS calculated for $C_{26}H_{35}F_2N_2O_2(M+H)^+$: m/z=445.3; found 445.3.

Step 2: (2R,5S)-1-(Bis(4-fluorophenyl)methyl)-2,5-diethylpiperazine hydrochloride To a mixture of tert-butyl (2S,5R)-4-(bis(4-fluorophenyl)methyl)-2,5-diethylpiperazine-1-carboxylate (2.8 g, 6.3 mmol) in THF (30 mL) was added a 4 M solution of HCl in 1,4-dioxane (15 mL, 60 mmol) and the reaction mixture was purged with $N_2$ and stirred at 60° C. for 4 h. After cooling to rt, the reaction mixture was diluted with $Et_2O$ and hexanes and slurried for 30 min. The solid precipitate was collected via filtration, washed with $Et_2O$ and hexanes, and dried under vacuum to afford the desired product. LC-MS calculated for $C_{21}H_{27}F_2N_2$ $(M+H)^+$: m/z=345.2; found 345.3.

Intermediate 30. 6-((2S,5R)-4-(Bis(4-fluorophenyl)methyl)-2,5-diethylpiperazin-1-yl)-2-chloro-9H-purine

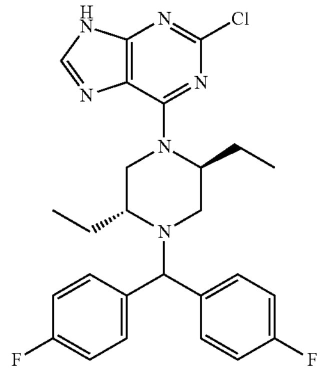 [SMILES: CC[C@H]1CN(C(c2ccc(F)cc2)c2ccc(F)cc2)[C@H](CC)CN1c1nc(Cl)nc2[nH]cnc12]

To a mixture of 2,6-dichloropurine (0.198 g, 1.05 mmol, Ambeed A101242) and (2R,5S)-1-(bis(4-fluorophenyl)methyl)-2,5-diethylpiperazine hydrochloride (Intermediate 29, 0.400 g, 1.05 mmol) in 1-butanol (5 mL) was added N-ethyl-N-isopropylpropan-2-amine (0.55 mL, 3.15 mmol) and the mixture was stirred at 60° C. for 12 h. After cooling to rt, the reaction mixture was concentrated in vacuo, and the crude residue was diluted with $CH_2Cl_2$ and extracted with saturated aqueous $NaHCO_3$. The combined organic layers were dried over $MgSO_4$ and the filtrate was concentrated. The crude residue was purified by flash column chromatography (12 g $SiO_2$, EtOAc/hexanes) to afford the desired product (0.467 g, 89% yield) as a white solid. LC-MS calculated for $C_{26}H_{28}ClF_2N_6(M+H)^+$: m/z=497.2; found 497.2.

Intermediate 31. tert-Butyl (2S,5R)-4-(4-fluorobenzoyl)-2,5-dimethylpiperazine-1-carboxylate

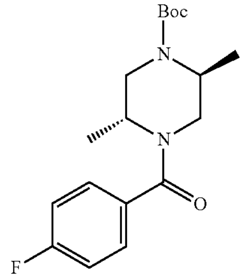 [SMILES: C[C@@H]1CN(C(=O)OC(C)(C)C)[C@@H](C)CN1C(=O)c1ccc(F)cc1]

To a mixture of tert-butyl (2S,5R)-2,5-dimethylpiperazine-1-carboxylate (3.00 g, 14.0 mmol, Combi-Blocks OR-8588) and N,N-diisopropylethylamine (2.69 mL, 15.4 mmol) in $CH_2Cl_2$ (70 mL) was added 4-fluorobenzoyl chloride (1.74 mL, 14.7 mmol, Sigma-Aldrich 119946) and the mixture was stirred at rt overnight. The reaction was quenched with saturated aqueous $NaHCO_3$. The layers were separated, and the organic layer was dried over $MgSO_4$ and concentrated in vacuo. The crude material was purified by flash column chromatography (40 g $SiO_2$, EtOAc/hexanes) to afford the desired product (4.33 g, 92% yield) as a clear oil that solidified to a white solid over several hours. LC-MS calculated for $C_{14}H_{18}FN_2O_3(M-C_4H8+H)^+$: m/z=281.1; found 281.1.

Intermediate 32. 2-Chloro-6-((2S,5R)-4-(1-(4-fluorophenyl)-2-methylpropyl)-2,5-dimethylpiperazin-1-yl)-9H-purine

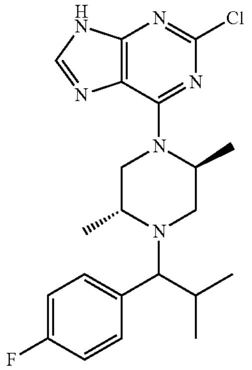 [SMILES: CC(C)C(c1ccc(F)cc1)N1C[C@H](C)N(c2nc(Cl)nc3[nH]cnc23)C[C@H]1C]

Step 1: tert-Butyl (2S,5R)-4-(1-(4-fluorophenyl)-2-methylpropyl)-2,5-dimethylpiperazine-1-carboxylate

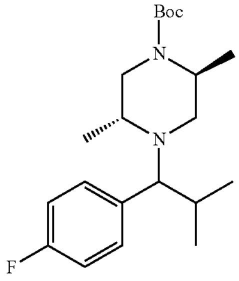 [SMILES: CC(C)C(c1ccc(F)cc1)N1C[C@H](C)N(C(=O)OC(C)(C)C)C[C@H]1C]

To a solution of tert-butyl (2S,5R)-4-(4-fluorobenzoyl)-2,5-dimethylpiperazine-1-carboxylate (Intermediate 31, 2.25 g, 6.69 mmol) and chlorocarbonylbis(triphenylphosphine)iridium(I) (0.157 g, 0.201 mmol, Strem 77-0300) in $CH_2Cl_2$ (67 mL) under a nitrogen atmosphere was added 1,1,3,3-tetramethyldisiloxane (2.36 mL, 13.4 mmol, Sigma-Aldrich 235733). The reaction mixture was stirred for 25 minutes at rt. Gas evolution was observed and over the course of 15 minutes the yellow color of the catalyst became bleached. Additional chlorocarbonylbis(triphenylphosphine)iridium(I) (0.157 g, 0.201 mmol) and 1,1,3,3-tetramethyldisiloxane (1.18 mL, 6.69 mmol) was added and stirring was continued at rt for another 25 minutes. The reaction mixture was cooled to −78° C. and stirred for 5 minutes before a 2.0 M solution of isopropylmagnesium chloride in THF (4.18 mL, 8.36 mmol, Sigma-Aldrich 230111) was added dropwise and the mixture was stirred at −78° C. for an additional 5 minutes. The reaction mixture was warmed to 0° C. and stirred for 1 h before being quenched with saturated aqueous $NH_4Cl$. The layers were separated and the aqueous layer was extracted with $CH_2Cl_2$. The combined organic layers were dried over $MgSO_4$ and concentrated under reduced pressure. The residue was purified by flash column chromatography (40 g $SiO_2$, EtOAc/hexanes) to afford a yellow oil containing the desired product as a mixture of diastereomers. LC-MS calculated for $C_{21}H_{34}FN_2O_2(M+H)^+$: m/z=365.3; found 365.3.

Step 2: (2R,5S)-1-(1-(4-Fluorophenyl)-2-methylpropyl)-2,5-dimethylpiperazine hydrochloride

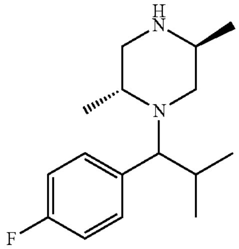

To a mixture of tert-butyl (2S,5R)-4-(1-(4-fluorophenyl)-2-methylpropyl)-2,5-dimethylpiperazine-1-carboxylate (Step 1) in THF (17.1 mL) was added a 4 molar solution of HCl in 1,4-dioxane (17.1 mL, 68.4 mmol) and the reaction mixture was stirred at 60° C. for 1 h. After cooling to rt, the mixture was concentrated in vacuo to give the desired product as a mixture of diastereomers in the form of a white solid, which was used directly without further purification. LC-MS calculated for $C_{16}H_{26}FN_2$ $(M+H)^+$: m/z=265.2; found 265.3.

Step 3: 2-Chloro-6-((2S,5R)-4-(1-(4-fluorophenyl)-2-methylpropyl)-2,5-dimethylpiperazin-1-yl)purine To a mixture of (2R,5S)-1-(1-(4-fluorophenyl)-2-methylpropyl)-2,5-dimethylpiperazine hydrochloride (Step 2) in n-BuOH (17 mL) was added 2,6-dichloropurine (1.41 g, 7.43 mmol, Ambeed A101242) followed by N,N-diisopropylethylamine (3.50 mL, 20.1 mmol) and the reaction mixture was stirred at 60° C. for 16 h. After cooling to rt the mixture was quenched with saturated aqueous $NaHCO_3$. The layers were separated, and the aqueous layer was extracted with $CH_2Cl_2$. The combined organic layers were dried over $MgSO_4$. Toluene (20 mL) was added, and the mixture was concentrated in vacuo. This process was repeated twice more. The crude material was purified by flash column chromatography (40 g $SiO_2$, EtOAc/hexanes) to afford the desired product (1.74 g, 62% yield) as mixture of diastereomers in the form of a white solid. LC-MS calculated for $C_{21}H_{27}ClFN_6$ $(M+H)^+$: m/z=417.2; found 417.2.

Intermediate 33. tert-Butyl (2S,5R)-4-((4-fluorophenyl)(5-(trifluoromethoxy)pyridin-2-yl)methyl)-2,5-dimethylpiperazine-1-carboxylate

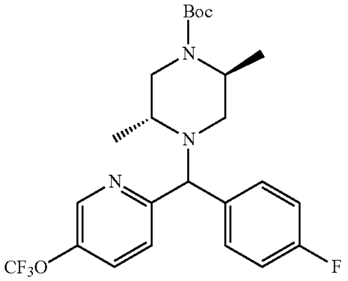

Step 1: (4-Fluorophenyl)(5-(trifluoromethoxy)pyridin-2-yl)methanol

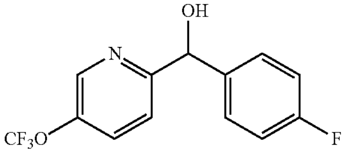

A 1.3 M solution of isopropylmagnesium chloride lithium chloride complex in THF (16.7 mL, 21.7 mmol, Sigma-Aldrich 656984) was cooled to 0° C. before 2-bromo-5-(trifluoromethoxy)pyridine (5.00 g, 20.7 mmol, Combi-Blocks QI-9136) was added. The reaction mixture was stirred at 0° C. for 30 min before 4-fluorobenzaldehyde (2.33 mL, 21.7 mmol, Sigma-Aldrich 128376) was added dropwise, and the mixture was stirred at 0° C. for an additional 20 minutes before being quenched with saturated aqueous $NH_4Cl$. The layers were separated and the aqueous layer was extracted with $CH_2Cl_2$. The combined organic layers were dried over $MgSO_4$ and concentrated in vacuo. The residue was purified by flash column chromatography (120 g $SiO_2$, EtOAc/hexanes) to give the desired product (4.44 g, 75% yield) as a deep orange oil. LC-MS calculated for $C_{13}H_{10}F_4NO_2$ $(M+H)^+$: m/z=288.1; found 288.1.

Step 2: 2-(Chloro(4-fluorophenyl)methyl)-5-(trifluoromethoxy)pyridine

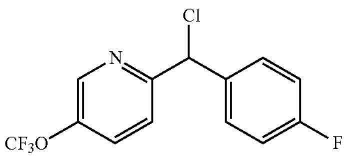

A solution of (4-fluorophenyl)(5-(trifluoromethoxy)pyridin-2-yl)methanol (Step 1, 4.44 g, 15.5 mmol) in $CH_2Cl_2$ (77 mL) was treated with thionyl chloride (22.6 mL, 309 mmol) and stirred at 45° C. overnight. After cooling to rt, the mixture was poured into ice-cold saturated aqueous $NaHCO_3$ and the layers were separated. The aqueous layer was extracted with $CH_2Cl_2$ and the combined organic layers were dried over $MgSO_4$ and concentrated in vacuo. The resulting orange oil was used directly without further purification. LC-MS calculated for $C_{13}H9ClF_4NO$ $(M+H)^+$: m/z=306.0; found 306.1.

Step 3: tert-Butyl (2S,5R)-4-((4-fluorophenyl)(5-(trifluoromethoxy)pyridin-2-yl)methyl)-2,5-dimethylpiperazine-1-carboxylate To a mixture of 2-(chloro(4-fluorophenyl)methyl)-5-(trifluoromethoxy)pyridine (Step 2) in MeCN (77 mL) was sequentially added tert-butyl (2S,5R)-2,5-dimethylpiperazine-1-carboxylate (3.31 g, 15.5 mmol, Combi-Blocks OR-8588), potassium iodide (0.257 g, 1.546 mmol), and N,N-diisopropylethylamine (5.40 mL, 30.9 mmol). The mixture was stirred at 90° C. for 5 h. Additional potassium iodide (0.257 g, 1.546 mmol) was added and the mixture was stirred at the 90° C. for an additional 16 h. The reaction was cooled to rt, filtered, and concentrated under in vacuo. The residue was purified by flash column chromatography (120 g $SiO_2$, EtOAc/hexanes) to give the desired product (4.09 g, 55% yield over 2 steps) as a mixture of diastereomers in the form of a sticky, orange-brown solid. LC-MS calculated for $C_{24}H30F_4N_3O_3$ $(M+H)^+$: m/z=484.2; found 484.3.

Intermediate 34. 2-Chloro-6-((2S,5R)-4-((4-fluorophenyl)(5-(trifluoromethoxy)pyridin-2-yl)methyl)-2,5-dimethylpiperazin-1-yl)-9H-purine

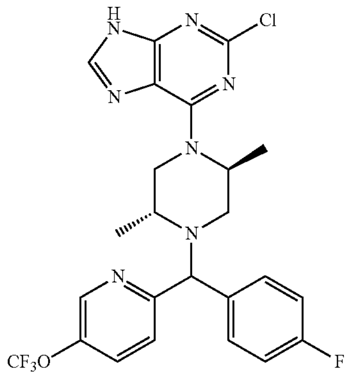

Step 1: (2R,5S)-1-((4-Fluorophenyl)(5-(trifluoromethoxy)pyridin-2-yl)methyl)-2,5-dimethylpiperazine hydrochloride

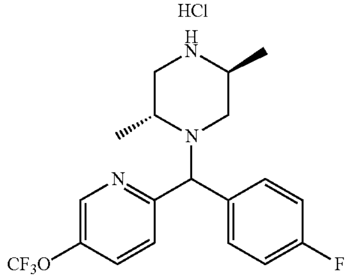

A solution of tert-butyl (2S,5R)-4-((4-fluorophenyl)(5-(trifluoromethoxy)pyridin-2-yl)methyl)-2,5-dimethylpiperazine-1-carboxylate (Intermediate 33, 1.50 g, 3.10 mmol) in THF (7.8 mL) was treated with HCl (4 M in 1,4-dioxane) (7.8 mL, 31.2 mmol) and stirred at 60° C. for 2 h. The mixture was carefully concentrated to give a crude, brown-orange solid containing the desired product as a mixture of diastereomers, which was used without further purification. LC-MS calculated for $C_{19}H_{22}F_4N_{30}$ $(M+H)^+$: m/z=384.2; found 384.2.

Step 2: 2-Chloro-6-((2S,5R)-4-((4-fluorophenyl)(5-(trifluoromethoxy)pyridin-2-yl)methyl)-2,5-dimethylpiperazin-1-yl)purine To a suspension of (2R,5S)-1-((4-fluorophenyl)(5-(trifluoromethoxy)pyridin-2-yl)methyl)-2,5-dimethylpiperazine hydrochloride (Step 1) in n-BuOH (7.8 mL) was added 2,6-dichloropurine (0.586 g, 3.10 mmol, Ambeed A101242) and N,N-diisopropylethylamine (1.626 mL, 9.31 mmol). The mixture was stirred at 85° C. for 16 h, cooled to rt, and quenched with saturated aqueous $NaHCO_3$. The layers were separated, and the aqueous layer was extracted with $CH_2Cl_2$. The combined organic layers were dried over magnesium sulfate and concentrated in vacuo. The residue was purified by flash column chromatography (40 g $SiO_2$, EtOAc/hexanes) to give the desired product (1.14 g, 69% yield over 2 steps) as a mixture of diastereomers in the form of a light orange solid. LC-MS calculated for $C_{24}H_{23}ClF_4N_7O$ $(M+H)^+$: m/z=536.2; found 536.1.

Intermediate 35. tert-Butyl (2-(6-((2S,5R)-4-(bis(4-fluorophenyl)methyl)-2,5-dimethylpiperazin-1-yl)-2-chloro-9H-purin-9-yl)ethyl)(methyl)carbamate

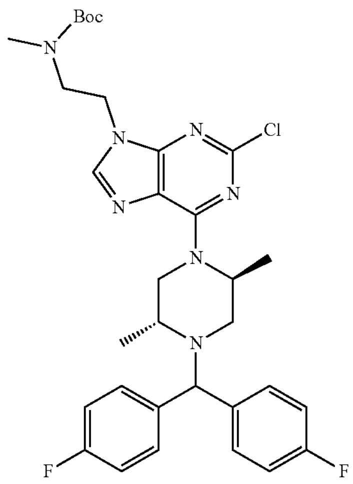 [SMILES: C[C@@H]1CN(c2nc(Cl)nc3c2ncn3CCN(C)C(=O)OC(C)(C)C)[C@@H](C)CN1C(c1ccc(F)cc1)c1ccc(F)cc1]

To a mixture of 6-((2S,5R)-4-(bis(4-fluorophenyl)methyl)-2,5-dimethylpiperazin-1-yl)-2-chloro-9H-purine (Intermediate 21, 7.00 g, 14.9 mmol), tert-butyl (2-hydroxyethyl)(methyl)carbamate (3.92 g, 22.4 mmol), and triphenylphosphine (7.83 g, 29.9 mmol) in THF (50 mL) was added a 40% solution of diethyl azodicarboxylate in toluene (13.0 g, 29.9 mmol, Aldrich 563110) and the reaction mixture was stirred at rt for 30 min. Hexanes (200 mL) was added and the reaction mixture was slurried for 30 min. The mixture was filtered and the filter cake was washed with a THF/hexanes (1:4, 20 mL). The filtrate was concentrated and purified by flash column chromatography ($SiO_2$, 0-50% EtOAc/hexanes) to afford the desired product (8.0 g, 86% yield). LC-MS calculated for $C_{32}H_{39}ClF_2N_7O_2$ $(M+H)^+$: m/z=626.3; found 626.3.

Intermediate 36. tert-Butyl (2-(6-((2S,5R)-4-(bis(4-fluorophenyl)methyl)-2,5-diethylpiperazin-1-yl)-2-chloro-9H-purin-9-yl)ethyl)(methyl)carbamate

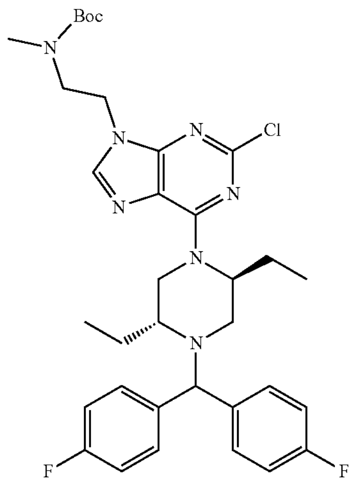 [SMILES: CC[C@H]1CN(C(c2ccc(F)cc2)c2ccc(F)cc2)[C@H](CC)CN1c1nc(Cl)nc2c1ncn2CCN(C)C(=O)OC(C)(C)C]

This compound was prepared according to the procedures described in Intermediate 35, with 6-((2S,5R)-4-(Bis(4-fluorophenyl)methyl)-2,5-diethylpiperazin-1-yl)-2-chloro-9H-purine (Intermediate 30) replacing 6-((2S,5R)-4-(bis(4-fluorophenyl)methyl)-2,5-dimethylpiperazin-1-yl)-2-chloro-9H-purine. LC-MS calculated for $C_{34}H4_3ClF_2N_7O_2$ $(M+H)^+$: m/z=654.3; found 654.3.

Intermediate 37. 6-((2S,5R)-4-(bis(4-fluorophenyl)methyl)-5-ethyl-2-methylpiperazin-1-yl)-2-chloro-9H-purine

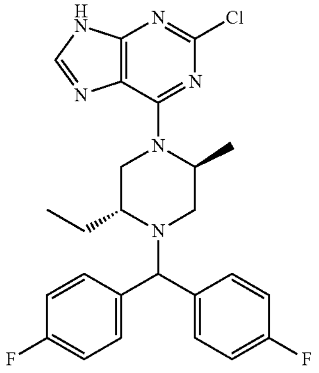 [SMILES: CC[C@@H]1CN(c2nc(Cl)nc3[nH]cnc23)[C@@H](C)CN1C(c1ccc(F)cc1)c1ccc(F)cc1]

To a mixture of (2R,5S)-1-(bis(4-fluorophenyl)methyl)-2-ethyl-5-methylpiperazine hydrochloride (Intermediate 26) (0.500 g, 1.36 mmol) in n-BuOH (3.41 mL) was added N,N-diisopropylethylamine (0.714 mL, 4.09 mmol) and 2,6-dichloro-9H-purine (0.258 g, 1.36 mmol) and the reaction was stirred at 90° C. overnight. After cooling to rt, the reaction mixture was concentrated in vacuo. The crude residue was purified by flash column chromatography ($SiO_2$, EtOAc/hexanes) to afford the desired product (0.53 g, 81% yield) as an off-white solid. LC-MS calculated for $C_{25}H_{26}ClF_2N_6$$(M+H)^+$: m/z=483.2; found 483.1.

Intermediate 38. (2R,5S)-1-(Bis(4-chlorophenyl)methyl)-2-ethyl-5-methylpiperazine hydrochloride

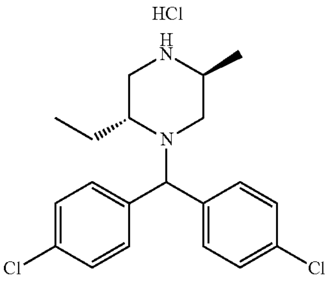 [SMILES: Cl ; CC[C@@H]1CN[C@@H](C)CN1C(c1ccc(Cl)cc1)c1ccc(Cl)cc1]

Step 1. tert-Butyl (2S,5R)-4-(bis(4-chlorophenyl)methyl)-5-ethyl-2-methylpiperazine-1-carboxylate

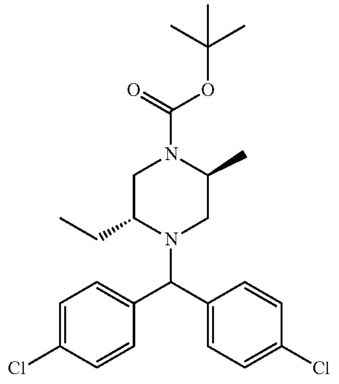 [SMILES: CC[C@@H]1CN(C(=O)OC(C)(C)C)[C@@H](C)CN1C(c1ccc(Cl)cc1)c1ccc(Cl)cc1]

A mixture of tert-butyl (2S,5R)-5-ethyl-2-methylpiperazine-1-carboxylate (Intermediate 25, 345 mg, 1.51 mmol), 4,4'-(chloromethylene)bis(chlorobenzene) (492 mg, 1.81 mmol, A2B Chem AC49945) and added N,N-diisopropylethylamine (0.79 mL, 4.5 mmol) in MeCN (20 mL) was stirred at 100° C. overnight. After cooling to rt, the reaction mixture was diluted with saturated aqueous $NaHCO_3$ and extracted with EtOAc (3x20 mL). The combined organic layers were dried over $MgSO_4$, filtered, and concentrated in vacuo. The crude residue was purified using flash column chromatography ($SiO_2$, 0-20% EtOAc in hexanes) to afford the desired product (580 mg, 83% yield). LC-MS calculated for $C_{25}H_{33}C_{12}N_2O_2$ $(M+H)^+$: m/z=463.2; found 463.2.

Step 2. (2R,5S)-1-(Bis(4-chlorophenyl)methyl)-2-ethyl-5-methylpiperazine hydrochloride To a mixture of tert-butyl (2S,5R)-4-(bis(4-chlorophenyl)methyl)-5-ethyl-2-methylpiperazine-1-carboxylate (580 mg, 1.25 mmol) in $CH_2Cl_2$/MeOH (4:1, 5 mL) was added a 4 molar solution of HCl in 1,4-dioxane (2 mL, 8 mmol) and the reaction mixture was stirred at rt for 1 h. The reaction mixture was slowly diluted with $Et_2O$ (10 mL) and slurried for 30 min. The solid precipitate was collected via filtration, washed with $Et_2O$, and dried under vacuum to afford the desired product as a white solid. LC-MS calculated for $C_{20}H_{25}Cl_2N_2(M+H)^+$: m/z=363.1; found 363.1.

Intermediate 39. 6-((2S,5R)-4-(Bis(4-chlorophenyl)methyl)-5-ethyl-2-methylpiperazin-1-yl)-2-chloro-$N^4$—(((S)-tetrahydrofuran-2-yl)methyl)pyrimidine-4,5-diamine

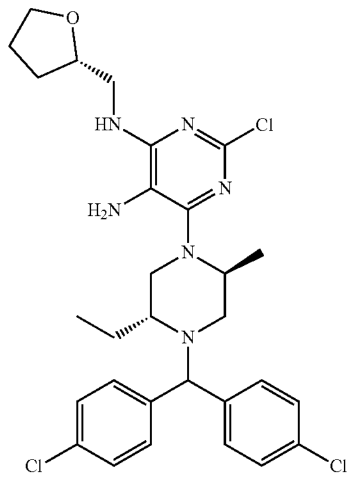 [SMILES: CC[C@@H]1CN(c2nc(Cl)nc(NC[C@@H]3CCCO3)c2N)[C@@H](C)CN1C(c1ccc(Cl)cc1)c1ccc(Cl)cc1]

To a mixture of 2,4,6-trichloro-5-nitropyrimidine (0.120 g, 0.525 mmol, Combi-Blocks, ST-3909) and (2R,5S)-1-(bis(4-chlorophenyl)methyl)-2-ethyl-5-methylpiperazine hydrochloride (Intermediate 38, 0.229 g, 0.573 mmol) in MeCN (10 mL) was added N-ethyl-N-isopropylpropan-2-amine (0.37 mL, 2.1 mmol) was added and the reaction mixture was stirred at rt overnight. The reaction mixture was cooled to 0° C. before (S)-(tetrahydrofuran-2-yl)methanamine (0.029 g, 0.929 mmol, BLD Pharmatech, BD48352) was added and the reaction mixture was warmed to rt and stirred for 30 min. To the reaction mixture was added MeOH (4 mL) and tetrahydroxydiboron (0.141 g, 1.58 mmol, BLD Pharmatech, BD288251) followed by 4,4'-dipyridyl (0.016 g, 0.105 mmol) and the reaction mixture was stirred at rt for 10 min. The reaction mixture was diluted with EtOAc (20 mL) and saturated aqueous $NaHCO_3$ and the resulting mixture was filtered over a pad of Celite. The organic layer was removed, and the aqueous layer was extracted with EtOAc. The combined organic layers were dried over $MgSO_4$, filtered, and concentrated under reduced pressure. The crude material obtained (70 mg) was used directly without further purification. LC-MS calculated for $C_{29}H_{36}Cl_3N_6O$ $(M+H)^+$: m/z=589.2; found 589.3.

Intermediate 40. 6-((2S,5R)-4-(Bis(4-chlorophenyl)methyl)-5-ethyl-2-methylpiperazin-1-yl)-2-chloro-N'—(((R)-tetrahydrofuran-2-yl)methyl)pyrimidine-4,5-diamine

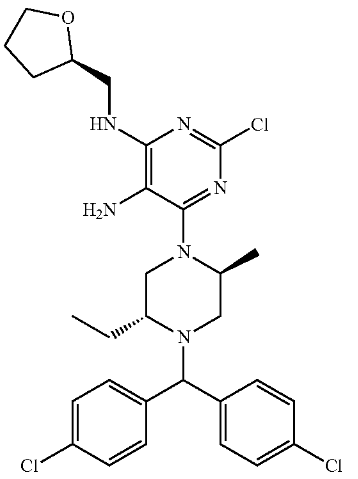 [SMILES: CC[C@@H]1CN(c2nc(Cl)nc(NC[C@H]3CCCO3)c2N)[C@@H](C)CN1C(c1ccc(Cl)cc1)c1ccc(Cl)cc1]

This compound was prepared according to the procedures described in Intermediate 39, with (R)-(tetrahydrofuran-2-yl)methanamine replacing (S)-(tetrahydrofuran-2-yl)methanamine. LC-MS calculated for $C_{29}H_{36}Cl_3N_6O$ $(M+H)^+$: m/z=589.2; found 589.2.

Intermediate 41: (S)-2,6-Dichloro-8-methyl-9-((tetrahydrofuran-2-yl)methyl)-9H-purine

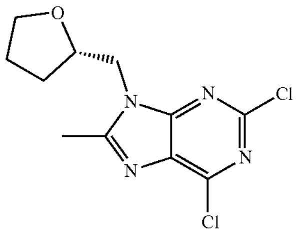 [SMILES: Cc1nc2c(Cl)nc(Cl)nc2n1C[C@@H]1CCCO1]

To a mixture of 2,6-dichloro-8-methylpurine (10.0 g, 49.3 mmol, PharmaBlock PB02898), (S)-(tetrahydrofuran-2-yl)methanol (5.53 g, 54.2 mmol, BLD Pharmatech BD48351), and triphenylphosphine, polymer-bound (100-200 mesh, extent of labeling: ~1.6 mmol/g loading, Aldrich 93094, 62 g, 99 mmol) in THF (500 mL) was added diisopropyl azodicarboxylate (19.2 mL, 98.7 mmol, Aldrich 225541) and the reaction mixture was stirred at rt for 2 h. The mixture was filtered over Celite and the filtrate was concentrated in vacuo. The crude residue was purified by flash column chromatography (330 g $SiO_2$, $CH_2Cl_2$/EtOAc) to afford the desired product (6.8 g, 48% yield) as a white solid. LC-MS calculated for $C_{11}H_{13}Cl_2N_4O$ $(M+H)^+$: m/z=287.0; found 287.0.

Intermediate 42. tert-Butyl (2S,5R)-4-(3,3-difluorocyclobutane-1-carbonyl)-2,5-dimethylpiperazine-1-carboxylate

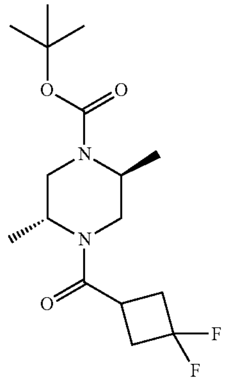 [SMILES: C[C@@H]1CN(C(=O)OC(C)(C)C)[C@@H](C)CN1C(=O)C1CC(F)(F)C1]

A mixture of tert-butyl (2S,5R)-2,5-dimethylpiperazine-1-carboxylate (6.00 g, 28.0 mmol, Combi-Blocks OR-8588) and 3,3-difluorocyclobutane-1-carboxylic acid (4.19 g, 30.8 mmol, Astatech 84107) in MeCN (25 mL) was treated with N,N-diisopropylethylamine (14.7 mL, 84.0 mmol) and HATU (11.2 g, 29.4 mmol, Combi-Blocks OR-0618) and stirred at rt for 30 min. The solvent was removed in vacuo and the residue was diluted with EtOAc and water. The layers were separated and the aqueous layer was extracted with EtOAc. The combined organic layers were washed with brine, dried over $MgSO_4$, concentrated in vacuo, and purified by flash column chromatography (120 g $SiO_2$, EtOAc/hexanes) to give the title compound (8.90 g, 96% yield) as a white solid. LC-MS calculated for $C_{12}H_{19}F_2N_2O_3$$(M-C_4H_8+H)^+$: m/z=277.1; found 277.1.

Intermediate 43. (2R,5S)-1-((3,3-Difluorocyclobutyl)(4-(trifluoromethyl)phenyl)methyl)-2,5-dimethylpiperazine hydrochloride

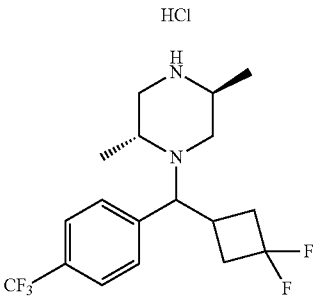 [SMILES: Cl ; C[C@@H]1CN[C@@H](C)CN1C(c1ccc(C(F)(F)F)cc1)C1CC(F)(F)C1]

Step 1: (4-Trifluoromethyl)phenyl)magnesium chloride lithium chloride (1.1 M in THF)

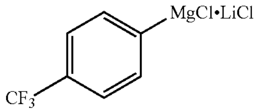

A 1.3 M solution of isopropylmagnesium chloride lithium chloride complex in THF (5.78 mL, 7.52 mmol, Aldrich 656984) was cooled to −78° C. before 1-bromo-4-(trifluoromethyl)benzene (1.14 mL, 8.27 mmol, Aldrich 152692) was added dropwise and the reaction mixture was stirred at −78° C. for 5 min. The reaction mixture was warmed to rt and stirred for an additional 4 h. The mixture obtained was used directly in the next step.

Step 2: tert-Butyl (2S,5R)-4-((3,3-difluorocyclobutyl)(4-(trifluoromethyl)phenyl)methyl)-2,5-dimethylpiperazine-1-carboxylate

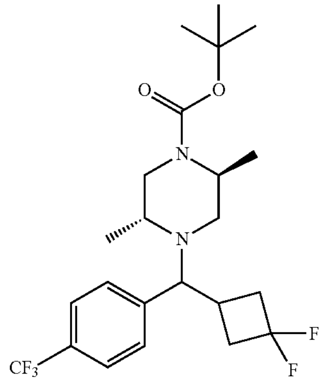 [SMILES: C[C@@H]1CN(C(=O)OC(C)(C)C)[C@@H](C)CN1C(c1ccc(C(F)(F)F)cc1)C1CC(F)(F)C1]

A mixture of tert-butyl (2S,5R)-4-(3,3-difluorocyclobutane-1-carbonyl)-2,5-dimethylpiperazine-1-carboxylate (Intermediate 42, 2.00 g, 6.02 mmol) and chlorocarbonylbis(triphenylphosphine)iridium(I) (0.469 g, 0.602 mmol, Strem 77-0300) in $CH_2Cl_2$ (10 mL) was treated with 1,1,3,3-tetramethyldisiloxane (2.13 mL, 12.0 mmol, Aldrich 235733) and stirred at rt for 15 min. Immediate gas evolution was observed, and the yellow color of the catalyst became bleached over the course of 15 min. The reaction was cooled to −78° C. and stirred for 5 min before (4-(trifluoromethyl)phenyl)magnesium chloride lithium chloride (Step 1, 6.92 mL, 1.1 M in THF, 7.5 mmol) was added dropwise and the reaction mixture was stirred for an additional 5 min. The reaction mixture was warmed to 0° C. and stirred for 30 min. The mixture was quenched with saturated aqueous $NH_4Cl$. After warming to rt, the organic layer was removed and the aqueous layer was extracted with $CH_2Cl_2$. The combined organic layers were dried over $MgSO_4$ and the filtrate was concentrated in vacuo to afford the desired product as a mixture of diastereomers. The crude material obtained was used directly without further purification. LC-MS calculated for $C_{23}H_{32}F_5N_2O_2(M+H)^+$: m/z=463.2; found 463.2.

Step 3: (2R,5S)-1-((3,3-Difluorocyclobutyl)(4-(trifluoromethyl)phenyl)methyl)-2,5-dimethylpiperazine hydrochloride A mixture of tert-butyl (2S,5R)-4-((3,3-difluorocyclobutyl)(4-(trifluoromethyl)phenyl)methyl)-2,5-dimethylpiperazine-1-carboxylate (Step 2) in THF (10 mL) was treated with HCl (4 M in 1,4-dioxane, 10 mL, 40 mmol, Oakwood 094030) and stirred at 60° C. for 1 h. After cooling to rt, the mixture was diluted with diethyl ether and the resulting precipitate was collected by filtration, washed with diethyl ether, and dried under vacuum to afford the desired product (1.50 g, 69% yield over two steps) as a mixture of diastereomers in the form of a white solid. LC-MS calculated for $C_{18}H_{24}F_5N_2$ $(M+H)^+$: m/z=363.2; found 363.2.

Intermediate 44. (2R,5S)-1-((3-Chloro-4-fluorophenyl)(3,3-difluorocyclobutyl)methyl)-2,5-dimethylpiperazine hydrochloride

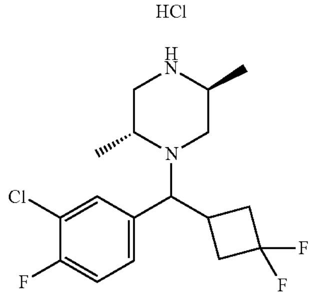 [SMILES: Cl ; C[C@@H]1CN[C@@H](C)CN1C(c1ccc(F)c(Cl)c1)C1CC(F)(F)C1]

Step 1: tert-Butyl (2S,5R)-4-((3-chloro-4-fluorophenyl)(3,3-difluorocyclobutyl)methyl)-2,5-dimethylpiperazine-1-carboxylate

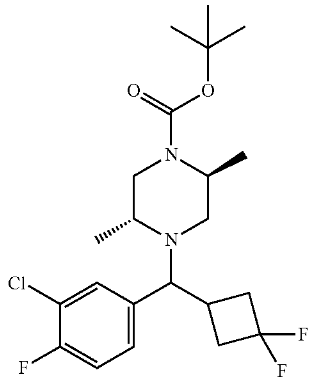 [SMILES: C[C@@H]1CN(C(=O)OC(C)(C)C)[C@@H](C)CN1C(c1ccc(F)c(Cl)c1)C1CC(F)(F)C1]

A mixture of tert-butyl (2S,5R)-4-(3,3-difluorocyclobutane-1-carbonyl)-2,5-dimethylpiperazine-1-carboxylate (Intermediate 42, 1.00 g, 3.01 mmol) and chlorocarbonylbis(triphenylphosphine)iridium(I) (0.235 g, 0.301 mmol, Strem 77-0300) in $CH_2Cl_2$ (10 mL) was treated with 1,1,3,3-tetramethyldisiloxane (1.06 mL, 6.02 mmol, Aldrich 235733) and stirred at rt for 15 min. Immediate gas evolution was observed, and the yellow color of the catalyst became bleached over the course of 15 min. The reaction was cooled to −78° C. and stirred for 5 min before (3-chloro-4-fluorophenyl)magnesium bromide (7.52 mL, 3.76 mmol, 0.5 M in THF, Aldrich 563676) was added dropwise and the reaction mixture was stirred for an additional 5 min. The reaction mixture was warmed to 0° C. and stirred for 30 min. The mixture was quenched with saturated aqueous $NH_4Cl$. After warming to rt, the organic layer was removed and the aqueous layer was extracted with $CH_2Cl_2$. The combined organic layers were dried over $MgSO_4$ and the filtrate was concentrated to afford the desired product as a mixture of diastereomers. The crude material obtained was used directly without further purification. LC-MS calculated for $C_{22}H_{31}ClF_3N_2O_2$ $(M+H)^+$: m/z=447.2; found 447.3.

Step 2: (2R,5S)-1-((3-Chloro-4-fluorophenyl)(3,3-difluorocyclobutyl)methyl)-2,5-dimethylpiperazine hydrochloride A mixture of tert-butyl (2S,5R)-4-((3-chloro-4-fluorophenyl)(3,3-difluorocyclobutyl)methyl)-2,5-dimethylpiperazine-1-carboxylate (Step 1) in THF (5 mL) was treated with HCl (4 M in 1,4-dioxane, 5 mL, 20 mmol, Oakwood 094030) and stirred at 60° C. for 1 h. The mixture was then diluted with diethyl ether and the precipitate was collected by filtration and washed with diethyl ether to afford the desired product (0.56 g, 54% yield over two steps) as mixture of diastereomers in the form of a white solid. LC-MS calculated for $C_{17}H_{23}ClF_3N_2$ $(M+H)^+$: m/z=347.1; found 347.4.

Intermediate 45. (2R,5S)-1-((3,3-Difluorocyclobutyl)(3-fluoro-4-(trifluoromethyl)phenyl)methyl)-2,5-dimethylpiperazine hydrochloride

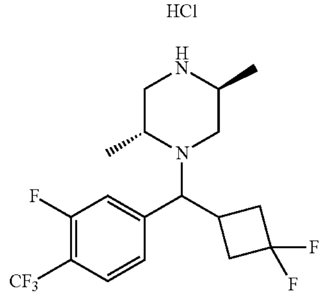 [SMILES: Cl ; C[C@@H]1CN[C@@H](C)CN1C(c1ccc(C(F)(F)F)c(F)c1)C1CC(F)(F)C1]

This compound was prepared according to the procedures described in Intermediate 43, with 4-bromo-2-fluoro-1-(trifluoromethyl)benzene replacing 1-bromo-4-(trifluoromethyl)benzene in Step 1. LC-MS calculated for $C_{18}H_{23}F_6N_2$ $(M+H)^+$: m/z=381.2; found 381.2.

Intermediate 46. (2R,5S)-1-((3,3-Difluorocyclobutyl)(3,4-difluorophenyl)methyl)-2,5-dimethylpiperazine hydrochloride

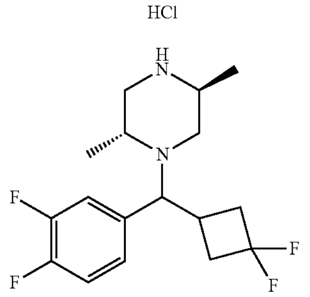 [SMILES: Cl ; C[C@@H]1CN[C@@H](C)CN1C(c1ccc(F)c(F)c1)C1CC(F)(F)C1]

This compound was prepared according to the procedures described in Intermediate 44, with (3,4-difluorophenyl)magnesium bromide (0.5 M in THF, Aldrich 561037) replacing (3-chloro-4-fluorophenyl)magnesium bromide in Step 1. LC-MS calculated for $C_{17}H_{23}F_4N_2$ $(M+H)^+$: m/z=331.2; found 331.1.

Intermediate 47. (2R,5S)-1-((3,4-Dichlorophenyl)(3,3-difluorocyclobutyl)methyl)-2,5-dimethylpiperazine hydrochloride

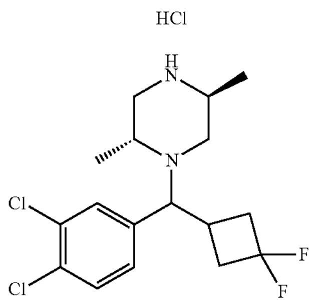 [SMILES: Cl ; C[C@@H]1CN[C@@H](C)CN1C(c1ccc(Cl)c(Cl)c1)C1CC(F)(F)C1]

This compound was prepared according to the procedures described in Intermediate 44, with 3,4-dichlorophenylmagnesium bromide (0.5 M solution in THF, Aldrich 562270) replacing (3-chloro-4-fluorophenyl)magnesium bromide in Step 1. LC-MS calculated for $C_{17}H_{23}Cl_2F_2N_2$ $(M+H)^+$: m/z=363.1; found 363.2.

Intermediate 48. (2R,5S)-1-((4-Chloro-3-fluorophenyl)(3,3-difluorocyclobutyl)methyl)-2,5-dimethylpiperazine hydrochloride

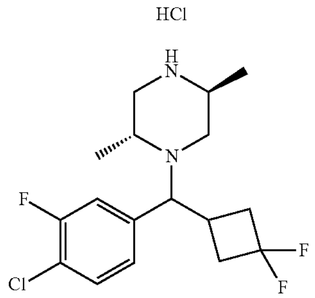 [SMILES: Cl ; C[C@@H]1CN[C@@H](C)CN1C(c1ccc(Cl)c(F)c1)C1CC(F)(F)C1]

Step 1: (4-chloro-3-fluorophenyl)magnesium chloride lithium chloride (1.1 M in THF)

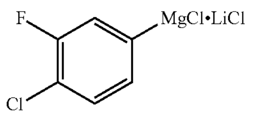

A 1.3 M solution of isopropylmagnesium chloride lithium chloride complex in THF (800 µL, 1.04 mmol, Aldrich 656984) was cooled to −78° C. before 1-chloro-2-fluoro-4-iodobenzene (146 µL, 1.14 mmol, Apollo Scientific PC9033) was added dropwise and the reaction mixture was stirred at −78° C. for 1 h. The reaction mixture was warmed to rt and stirred for 1 h. The mixture obtained was used directly in the next step.

Step 2: tert-Butyl (2S,5R)-4-((4-chloro-3-fluorophenyl)(3,3-difluorocyclobutyl)methyl)-2,5-dimethylpiperazine-1-carboxylate

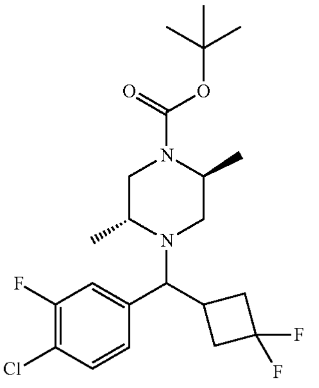 [SMILES: C[C@@H]1CN(C(=O)OC(C)(C)C)[C@@H](C)CN1C(c1ccc(Cl)c(F)c1)C1CC(F)(F)C1]

A mixture of tert-butyl (2S,5R)-4-(3,3-difluorocyclobutane-1-carbonyl)-2,5-dimethylpiperazine-1-carboxylate (Intermediate 42, 250 mg, 0.752 mmol) and chlorocarbonylbis(triphenylphosphine)iridium(I) (59 mg, 0.075 mmol, Strem 77-0300) in $CH_2Cl_2$ (5 mL) was treated with 1,1,3,3-tetramethyldisiloxane (226 μL, 1.50 mmol, Aldrich 235733) and stirred at rt for 15 min. Immediate gas evolution was observed, and the yellow color of the catalyst became bleached over the course of 15 min. Additional chlorocarbonylbis(triphenylphosphine)iridium(I) (59 mg, 0.075 mmol) and 1,1,3,3-tetramethyldisiloxane (226 μL, 1.50 mmol) was added and the reaction mixture was stirred at rt for an additional 15 min. The reaction was cooled to −78° C. and stirred for 5 min before (4-chloro-3-fluorophenyl)magnesium chloride lithium chloride (Step 1, 855 μL, 1.1 M in THF, 0.94 mmol) was added dropwise and the reaction mixture was stirred for an additional 5 min. The reaction mixture was warmed to 0° C. and stirred for 30 min. The mixture was quenched with saturated aqueous $NH_4Cl$. After warming to rt, the organic layer was removed and the aqueous layer was extracted with $CH_2Cl_2$. The combined organic layers were dried over $MgSO_4$ and the filtrate was concentrated in vacuo. The crude residue was purified by flash column chromatography ($SiO_2$, EtOAc/hexanes) to afford the desired product as a mixture of diastereomers. LC-MS calculated for $C_{22}H_{31}ClF_3N_2O_2$ $(M+H)^+$: m/z=447.2; found 447.2.

Step 3: (2R,5S)-1-((4-chloro-3-fluorophenyl)(3,3-difluorocyclobutyl)methyl)-2,5-dimethylpiperazine hydrochloride A mixture of tert-butyl (2S,5R)-4-((4-chloro-3-fluorophenyl)(3,3-difluorocyclobutyl)methyl)-2,5-dimethylpiperazine-1-carboxylate (Step 2) in THF (15 mL) was treated with HCl (4 M in 1,4-dioxane, 5 mL, 20 mmol, Oakwood 094030) and stirred at 60° C. for 1 h. After cooling to rt, the mixture was diluted with diethyl ether (5 mL) and slurried for 30 min. The resulting precipitate was collected by filtration, washed with diethyl ether, and dried under vacuum to afford the desired product as a mixture of diastereomers in the form of a white solid. LC-MS calculated for $C_{17}H_{23}ClF_3N_2(M+H)^+$: m/z=347.2; found 347.1.

Intermediate 49. (2R,5S)-1-((4-Chloro-3-methylphenyl)(3,3-difluorocyclobutyl)methyl)-2,5-dimethylpiperazine hydrochloride

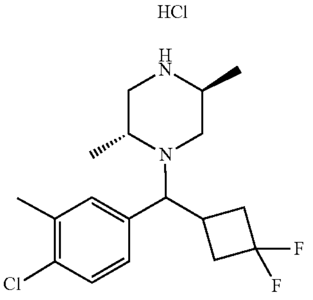 [SMILES: Cl ; Cc1cc(C(C2CC(F)(F)C2)N2C[C@H](C)NC[C@H]2C)ccc1Cl]

This compound was prepared according to the procedures described in Intermediate 44, with (4-chloro-3-methylphenyl)magnesium bromide (0.5 M solution in THF, Synthonix $C_{31776}$) replacing (3-chloro-4-fluorophenyl)magnesium bromide in Step 1. LC-MS calculated for $C_{18}H_{26}ClF_2N_2(M+H)^+$: m/z=343.2; found 343.2.

Intermediate 50. (2R,5S)-1-((3,3-Difluorocyclobutyl)(3,4,5-trifluorophenyl)methyl)-2,5-dimethylpiperazine hydrochloride

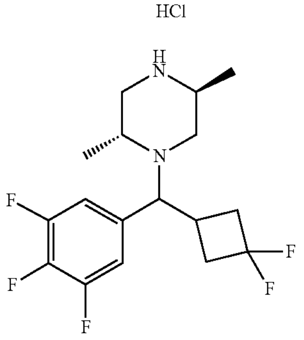 [SMILES: Cl ; C[C@@H]1CN[C@@H](C)CN1C(c1cc(F)c(F)c(F)c1)C1CC(F)(F)C1]

This compound was prepared according to the procedures described in Intermediate 44, with (3,4,5-trifluorophenyl)magnesium bromide (0.5 M solution in THF, Synthonix T31780) replacing (3-chloro-4-fluorophenyl)magnesium bromide in Step 1. LC-MS calculated for $C_{17}H_{22}F_5N_2$ $(M+H)^+$: m/z=349.2; found 349.2.

Intermediate 51: tert-Butyl (2-(2,6-dichloro-9H-purin-9-yl)ethyl)(methyl)carbamate

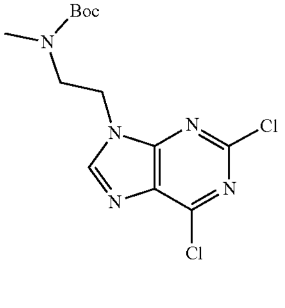 [SMILES: CN(CCn1cnc2c(Cl)nc(Cl)nc21)C(=O)OC(C)(C)C]

To a mixture of 2,6-dichloro-9H-purine (10.0 g, 52.9 mmol, AmBeed A101242), tert-butyl (2-hydroxyethyl)(methyl)carbamate (9.83 mL, 58.2 mmol, BLD Pharmatech, BD29111), and triphenylphosphine, polymer-bound (100-200 mesh, extent of labeling: ~1.6 mmol/g loading, Aldrich 93094, 66.2 g, 106 mmol) in THF (500 mL) was added diisopropyl azodicarboxylate (20.6 mL, 106 mmol, Aldrich 225541) and the reaction mixture was stirred at rt for 2 h. The mixture was filtered over Celite and the filtrate was concentrated. The crude residue was purified by flash column chromatography (330 g $SiO_2$, EtOAc/hexanes) to afford the desired product (8.1 g, 44% yield) as a white solid. LC-MS calculated for $C_{13}H_{18}Cl_2N_5O_2$ $(M+H)^+$: m/z=346.1; found 346.1.

Intermediate 52. (2R,5S)-1-((4-Chlorophenyl)(3,3-difluorocyclobutyl)methyl)-2,5-dimethylpiperazine hydrochloride

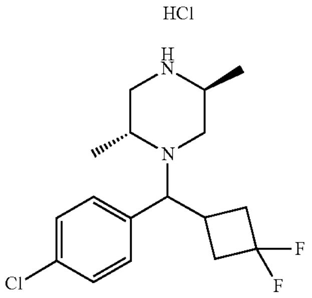

This compound was prepared according to the procedures described in Intermediate 48, with 1-bromo-4-chlorobenzene replacing 1-chloro-2-fluoro-4-iodobenzene in Step 1. LC-MS calculated for $C_{17}H_{24}ClF_2N_2(M+H)^+$: m/z=329.2; found 329.1.

Intermediate 53. (2R,5S)-1-((4-Bromophenyl)(3,3-difluorocyclobutyl)methyl)-2,5-dimethylpiperazine hydrochloride

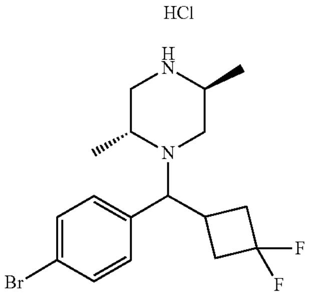 [SMILES: Cl ; C[C@@H]1CN[C@@H](C)CN1C(c1ccc(Cl)cc1)C1CC(F)(F)C1]

This compound was prepared according to the procedures described in Intermediate 48, with 1-bromo-4-iodobenzene replacing 1-chloro-2-fluoro-4-iodobenzene in Step 1. LC-MS calculated for $C_{17}H_{24}BrF_2N_2(M+H)^+$: m/z=373.1; found 373.1.

Intermediate 54. tert-Butyl (2S,5R)-4-(3,3-difluorocyclobutane-1-carbonyl)-5-ethyl-2-methylpiperazine-1-carboxylate

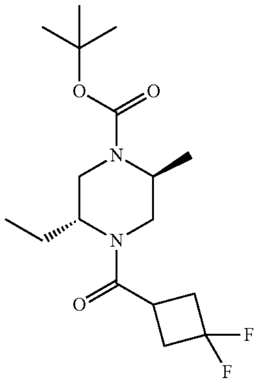 [SMILES: CC[C@@H]1CN(C(=O)OC(C)(C)C)[C@@H](C)CN1C(=O)C1CC(F)(F)C1]

This compound was prepared according to the procedures described in Intermediate 42, with tert-butyl (2S,5R)-5-ethyl-2-methylpiperazine-1-carboxylate (Intermediate 25) replacing tert-butyl (2S,5R)-2,5-dimethylpiperazine-1-carboxylate. LC-MS calculated for $C_{13}H_{21}F_2N_2O_3$ $(M-C_4H_8+H)^+$: m/z=291.2; found 291.1.

Intermediate 55. (2R,5S)-1-((4-Chlorophenyl)(3,3-difluorocyclobutyl)methyl)-2-ethyl-5-methylpiperazine hydrochloride

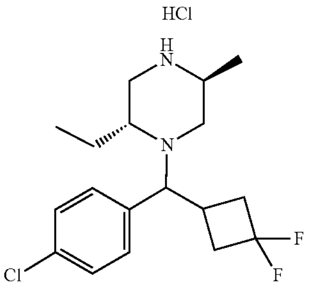 [SMILES: Cl ; CC[C@@H]1CN[C@@H](C)CN1C(c1ccc(Cl)cc1)C1CC(F)(F)C1]

Step 1: (4-Chlorophenyl)magnesium chloride lithium chloride (1.1 M in THF)

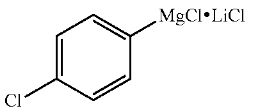

A 1.3 M solution of isopropylmagnesium chloride lithium chloride complex in THF (5.78 mL, 7.52 mmol, Aldrich 656984) was cooled to −78° C. before 1-bromo-4-chlorobenzene (0.96 mL, 8.3 mmol) was added dropwise and the reaction mixture was stirred at −78° C. for 5 min. The reaction mixture was warmed to rt and stirred for an additional 4 h. The mixture obtained was used directly in the next step.

Step 2: tert-Butyl (2S,5R)-4-((4-chlorophenyl)(3,3-difluorocyclobutyl)methyl)-5-ethyl-2-methylpiperazine-1-carboxylate

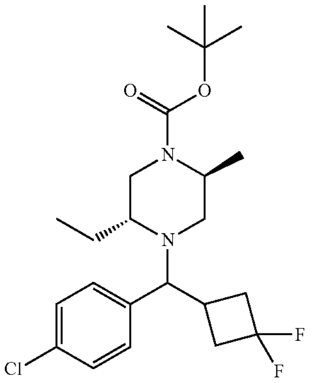 [SMILES: CC[C@@H]1CN(C(=O)OC(C)(C)C)[C@@H](C)CN1C(c1ccc(Cl)cc1)C1CC(F)(F)C1]

A mixture of tert-butyl (2S,5R)-4-(3,3-difluorocyclobutane-1-carbonyl)-5-ethyl-2-methylpiperazine-1-carboxylate (Intermediate 54, 0.800 g, 2.31 mmol) and chlorocarbonylbis(triphenylphosphine)iridium(I) (180 mg, 0.231 mmol, Strem 77-0300) in $CH_2Cl_2$ (5 mL) was treated with 1,1,3,3-tetramethyldisiloxane (816 μL, 4.62 mmol, Aldrich 235733) and stirred at rt for 25 min. The reaction was cooled to −78° C. and stirred for 5 min before (4-chlorophenyl) magnesium chloride lithium chloride (Step 1, 2.89 mL, 1.1 M in THF, 3.2 mmol) was added dropwise and the reaction mixture was stirred for an additional 5 min. The reaction mixture was warmed to 0° C. and stirred for 3 h. The mixture was quenched with saturated aqueous $NH_4Cl$. After warming to rt, the organic layer was removed and the aqueous layer was extracted with $CH_2Cl_2$. The combined organic layers were dried over $MgSO_4$ and the filtrate was concentrated to afford the desired product as a mixture of diastereomers. The crude material obtained was used directly without further purification. LC-MS calculated for $C_{23}H_{34}ClF_2N_2O_2$ $(M+H)^+$: m/z=443.2; found 443.3.

Step 3: (2R,5S)-1-((4-Chlorophenyl)(3,3-difluorocyclobutyl)methyl)-2-ethyl-5-methylpiperazine hydrochloride A mixture of tert-butyl (2S,5R)-4-((4-chlorophenyl)(3,3-difluorocyclobutyl)methyl)-5-ethyl-2-methylpiperazine-1-carboxylate (Step 2) in THF (15 mL) was treated with HCl (4 M in 1,4-dioxane, 5 mL, 20 mmol, Oakwood 094030) and stirred at 60° C. for 30 min. The mixture was then diluted with diethyl ether and the precipitate was collected by filtration and washed with diethyl ether to afford the desired product as mixture of diastereomers in the form of a white solid. LC-MS calculated for $C_{18}H_{26}ClF_2N_2(M+H)^+$: m/z=343.2; found 343.2.

Intermediate 56. tert-Butyl (2S,5R)-2,5-dimethyl-4-(4-(trifluoromethyl)benzoyl)piperazine-1-carboxylate

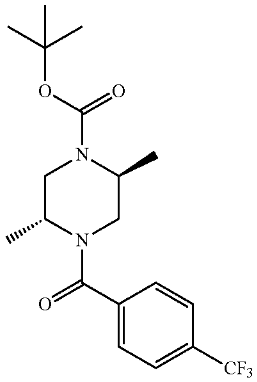 [SMILES: C[C@@H]1CN(C(=O)OC(C)(C)C)[C@@H](C)CN1C(=O)c1ccc(C(F)(F)F)cc1]

A mixture of tert-butyl (2S,5R)-2,5-dimethylpiperazine-1-carboxylate (2.00 g, 9.33 mmol, Combi-Blocks OR-8588), N,N-diisopropylethylamine (3.26 mL, 18.7 mmol), 4-(trifluoromethyl)benzoic acid (1.95 g, 10.3 mmol), and HATU (3.73 g, 9.80 mmol, Combi-Blocks OR-0618) in MeCN (12 mL) was stirred at rt overnight. The reaction mixture was concentrated in vacuo. The crude material was purified by flash column chromatography (120 g $SiO_2$, EtOAc/hexanes) to afford the desired product (3.35 g, 93% yield) as a white solid. LC-MS calculated for $C_{15}H_{18}F_3N_2O_3$ $(M-C_4H_8+H)^+$: m/z=331.1; found 331.2.

Intermediate 57. 2-Chloro-6-((2S,5R)-2,5-dimethyl-4-(2-methyl-1-(4-(trifluoromethyl)phenyl)propyl)piperazin-1-yl)-8-methyl-9H-purine

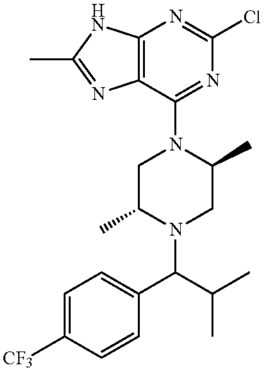 [SMILES: Cc1nc2c(N3C[C@@H](C)N(C(c4ccc(C(F)(F)F)cc4)C(C)C)C[C@@H]3C)nc(Cl)nc2[nH]1]

Step 1: tert-Butyl (2S,5R)-2,5-dimethyl-4-(2-methyl-1-(4-(trifluoromethyl)phenyl)propyl)piperazine-1-carboxylate

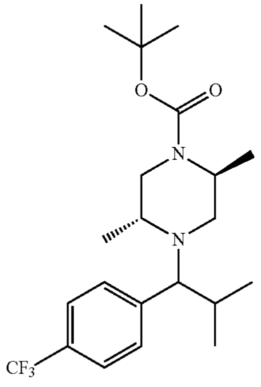 [SMILES: CC(C)C(c1ccc(C(F)(F)F)cc1)N1C[C@H](C)N(C(=O)OC(C)(C)C)C[C@H]1C]

To a mixture of tert-butyl (2S,5R)-2,5-dimethyl-4-(4-(trifluoromethyl)benzoyl)piperazine-1-carboxylate (Intermediate 56, 1.13 g, 2.91 mmol) and chlorocarbonylbis(triphenylphosphine)iridium(I) (0.227 g, 0.291 mmol, Strem 77-0300) in $CH_2Cl_2$ (29 mL) under a nitrogen atmosphere was added 1,1,3,3-tetramethyldisiloxane (1.03 mL, 5.82 mmol, Sigma-Aldrich 235733). The reaction mixture was stirred for 20 min at rt. The reaction mixture was cooled to −78° C. and stirred for 5 min before a 2.0 M solution of isopropylmagnesium chloride in THF (2.80 mL, 3.64 mmol, Sigma-Aldrich 230111) was added dropwise and the mixture was stirred at −78° C. for an additional 5 min. The reaction mixture was warmed to 0° C. and stirred for 1 h before being quenched with saturated aqueous $NH_4Cl$. The layers were separated and the aqueous layer was extracted with $CH_2Cl_2$. The combined organic layers were dried over $Na_2SO_4$ and concentrated under reduced pressure to afford the desired product (0.95 g) as a mixture of diastereomers. The crude material obtained was used directly without further purification. LC-MS calculated for $C_{22}H_{34}F_3N_2O_2(M+H)^+$: m/z=415.3; found 415.3.

Step 2: (2R,5S)-2,5-Dimethyl-1-(2-methyl-1-(4-(trifluoromethyl)phenyl)propyl)piperazine hydrochloride HCl

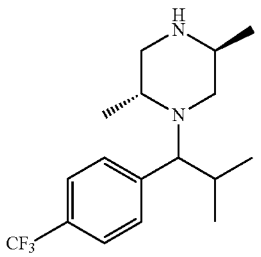

To a mixture of tert-butyl (2S,5R)-2,5-dimethyl-4-(2-methyl-1-(4-(trifluoromethyl)phenyl)propyl)piperazine-1-carboxylate (0.95 g, Step 1) in THF (22.9 mL) was added a 4 molar solution of HCl in 1,4-dioxane (6.86 mL, 27.5 mmol) and the reaction mixture was stirred at 60° C. for 1 h. After cooling to rt, the reaction mixture was diluted with $Et_2O$ (50 mL) and hexanes (25 mL) and slurried for 30 min. The solid precipitate was collected via filtration, washed with $Et_2O$ and hexanes, and dried under vacuum to afford the desired product (0.465 g) as a mixture of diastereomers in the form of a white solid. LC-MS calculated for $C_{17}H_{26}F_3N_2$ $(M+H)^+$: m/z=315.2; found 315.3.

Step 3: 2-Chloro-6-((2S,5R)-2,5-dimethyl-4-(2-methyl-1-(4-(trifluoromethyl)phenyl)propyl)piperazin-1-yl)-8-methyl-9H-purine To a mixture of (2R,5S)-2,5-dimethyl-1-(2-methyl-1-(4-(trifluoromethyl)phenyl)propyl)piperazine hydrochloride (0.465 g, Step 2) in n-BuOH (17 mL) was added 2,6-dichloro-8-methyl-9H-purine (0.60 g, 2.96 mmol, Ambeed A360170) followed by N,N-diisopropylethylamine (0.802 mL, 4.43 mmol) and the reaction mixture was stirred at 90° C. for 2 h. After cooling to rt, the mixture was quenched with saturated aqueous $NaHCO_3$. The layers were separated, and the aqueous layer was extracted with $CH_2Cl_2$. The combined organic layers were dried over $Na_2SO_4$, filtered, and concentrated under reduced pressure. The crude material was purified by flash column chromatography (40 g $SiO_2$, $CH_2Cl_2$/MeOH) to afford the desired product (0.30 g, 11% yield over 3 steps) as a mixture of diastereomers in the form of a yellow oil. LC-MS calculated for $C_{23}H_{29}ClF_3N_6(M+H)^+$: m/z=481.2; found 481.3.

Intermediate 58. tert-Butyl (2S,5R)-2,5-dimethyl-4-(3-(trifluoromethyl)benzoyl)piperazine-1-carboxylate

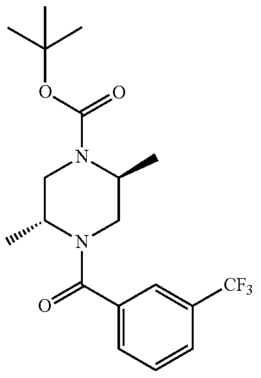 [SMILES: C[C@@H]1CN(C(=O)OC(C)(C)C)[C@@H](C)CN1C(=O)c1cccc(C(F)(F)F)c1]

A mixture of tert-butyl (2S,5R)-2,5-dimethylpiperazine-1-carboxylate (1.10 g, 5.11 mmol, Combi-Blocks OR-8588), N,N-diisopropylethylamine (1.62 mL, 9.30 mmol), 3-(trifluoromethyl)benzoic acid (884 mg, 4.65 mmol), and HATU (1.94 g, 5.11 mmol, Combi-Blocks OR-0618) in MeCN (6.2 mL) was stirred at rt overnight. The reaction mixture was concentrated in vacuo. The crude material was purified by flash column chromatography (120 g $SiO_2$, EtOAc/hexanes) to afford the desired product (1.70 g, 95% yield) as a white solid. LC-MS calculated for $C_{15}H_{18}F_3N_2O_3(M-C_4H_8+H)^+$: m/z=331.1; found 331.1.

Intermediate 59. 2-Chloro-6-((2S,5R)-2,5-dimethyl-4-(2-methyl-1-(3-(trifluoromethyl)phenyl)propyl) piperazin-1-yl)-8-methyl-9H-purine

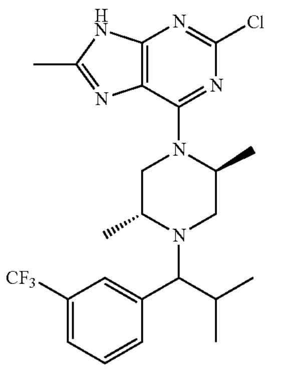 [SMILES: Cc1nc2c(N3C[C@@H](C)N(C(c4cccc(C(F)(F)F)c4)C(C)C)C[C@@H]3C)nc(Cl)nc2[nH]1]

This compound was prepared according to the procedures described in Intermediate 57, with tert-butyl (2S,5R)-2,5-dimethyl-4-(3-(trifluoromethyl)benzoyl)piperazine-1-carboxylate (Intermediate 58) replacing tert-butyl (2S,5R)-2,5-dimethyl-4-(4-(trifluoromethyl)benzoyl)piperazine-1-carboxylate in Step 1. LC-MS calculated for $C_{23}H_{29}ClF_3N_6$ $(M+H)^+$: m/z=481.2; found 481.3.

Intermediate 60. tert-Butyl (2S,5R)-4-(2-fluoro-4-(trifluoromethyl)benzoyl)-2,5-dimethylpiperazine-1-carboxylate

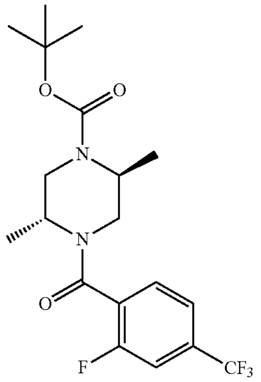

A mixture of tert-butyl (2S,5R)-2,5-dimethylpiperazine-1-carboxylate (1.00 g, 4.67 mmol, Combi-Blocks OR-8588), N,N-diisopropylethylamine (1.63 mL, 9.33 mmol), 2-fluoro-4-(trifluoromethyl)benzoic acid (1.07 g, 5.13 mmol), and HATU (1.86 g, 4.90 mmol, Combi-Blocks OR-0618) in MeCN (6.2 mL) was stirred at rt overnight. The reaction mixture was concentrated in vacuo. The crude material was purified by flash column chromatography (120 g $SiO_2$, EtOAc/hexanes) to afford the desired product (1.67 g, 88% yield) as a white solid. LC-MS calculated for $C_{15}H_{17}F_4N_2O_3(M-C_4H_8+H)^+$: m/z=349.1; found 349.1.

Intermediate 61. 2-Chloro-6-((2S,5R)-4-(1-(2-fluoro-4-(trifluoromethyl)phenyl)-2-methylpropyl)-2,5-dimethylpiperazin-1-yl)-8-methyl-9H-purine

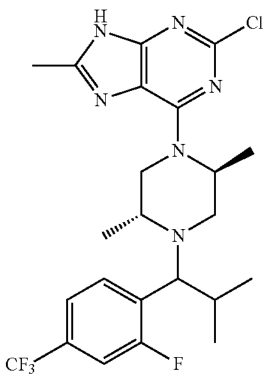 [SMILES: Cc1nc2c(N3C[C@@H](C)N(C(c4ccc(C(F)(F)F)cc4F)C(C)C)C[C@@H]3C)nc(Cl)nc2[nH]1]

This compound was prepared according to the procedures described in Intermediate 57, with tert-butyl (2S,5R)-4-(2-fluoro-4-(trifluoromethyl)benzoyl)-2,5-dimethylpiperazine-1-carboxylate (Intermediate 60) replacing tert-butyl (2S, 5R)-2,5-dimethyl-4-(4-(trifluoromethyl)benzoyl) piperazine-1-carboxylate in Step 1. LC-MS calculated for $C_{23}H_{28}ClF_4N_6$ $(M+H)^+$: m/z=499.2; found 499.3.

Intermediate 62. tert-Butyl (2S,5R)-4-isobutyryl-2,5-dimethylpiperazine-1-carboxylate

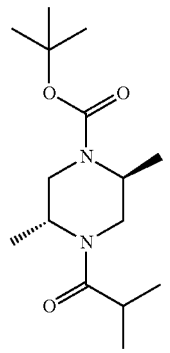

A mixture of tert-butyl (2S,5R)-2,5-dimethylpiperazine-1-carboxylate (20. g, 93 mmol, Combi-Blocks OR-8588) in $CH_2Cl_2$ (933 mL) was cooled to 0° C. before isobutyryl chloride (10.76 mL, 103 mmol) was added followed by triethylamine (39.0 mL, 280 mmol) and the reaction mixture was allowed to warm to rt and stirred overnight. The mixture was transferred to a separatory funnel and the organic phase was washed with 1 M HCl (aq) and brine. The organic phase was dried over $MgSO_4$ and concentrated under reduced pressure to afford the desired product (26 g, 98% yield) as a white solid. The material obtained was used directly without further purification. LC-MS calculated for $C_{15}H_{29}N_2O_3$ $(M+H)^+$: m/z=285.2; found 285.3.

Intermediate 63. (2R,5S)-1-(1-(4-(Difluoromethyl)-3-fluorophenyl)-2-methylpropyl)-2,5-dimethylpiperazine hydrochloride

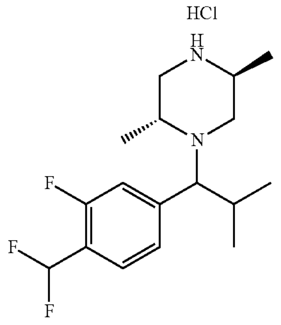 [SMILES: Cl ; CC(C)C(c1ccc(C(F)F)c(F)c1)N1C[C@H](C)NC[C@H]1C]

Step 1: (4-(Difluoromethyl)-3-fluorophenyl)magnesium chloride lithium chloride (0.62M in THF)

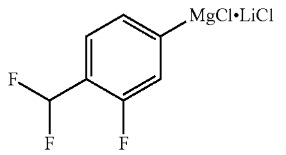

A 1.3 M solution of isopropylmagnesium chloride lithium chloride complex in THF (3.76 mL, 4.89 mmol, Aldrich 656984) was cooled to −78° C. before a mixture of 4-bromo-1-(difluoromethyl)-2-fluorobenzene (1.00 g, 4.44 mmol) in dry THF (3.42 mL total volume) was added dropwise and the reaction mixture was stirred at −78° C. for 5 min. The reaction mixture was warmed to rt and stirred for an additional 4 h. The mixture obtained was used directly in the next step.

Step 2: tert-Butyl (2S,5R)-4-(1-(4-(difluoromethyl)-3-fluorophenyl)-2-methylpropyl)-2,5-dimethylpiperazine-1-carboxylate

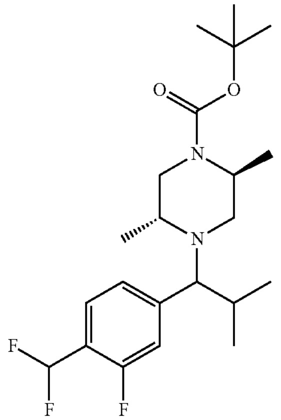 [SMILES: CC(C)C(c1ccc(C(F)F)c(F)c1)N1C[C@H](C)N(C(=O)OC(C)(C)C)C[C@H]1C]

A mixture of tert-butyl (2S,5R)-4-isobutyryl-2,5-dimethylpiperazine-1-carboxylate (Intermediate 62, 1.00 g, 3.52 mmol) and chlorocarbonylbis(triphenylphosphine)iridium (I) (274 mg, 0.352 mmol, Strem 77-0300) in $CH_2Cl_2$ (11.7 mL) was treated with 1,1,3,3-tetramethyldisiloxane (2.13 mL, 12.0 mmol, Aldrich 235733) and stirred at rt for 20 min. The reaction mixture was cooled to −78° C. and stirred for 5 min before (4-(difluoromethyl)-3-fluorophenyl)magnesium chloride lithium chloride (0.62 M in THF) (Step 1, 5.7 mL, 0.62 M in THF, 3.52 mmol) was added dropwise and the reaction mixture was stirred for an additional 5 min before warming to rt and stirring for 1 h. The mixture was quenched with saturated aqueous $NH_4Cl$ and the layers were separated. The organic layer was removed and the aqueous layer was extracted with $CH_2Cl_2$. The combined organic layers were dried over $MgSO_4$ and the filtrate was concentrated in vacuo to afford the desired product as a mixture of diastereomers. The crude material obtained was used directly without further purification. LC-MS calculated for $C_{22}H_{34}F_3N_2O_2(M+H)^+$: m/z=415.3; found 415.4.

Step 3: (2R,5S)-1-(1-(4-(Difluoromethyl)-3-fluorophenyl)-2-methylpropyl)-2,5-dimethylpiperazine hydrochloride A mixture of tert-butyl (2S,5R)-4-(1-(4-(difluoromethyl)-3-fluorophenyl)-2-methylpropyl)-2,5-dimethylpiperazine-1-carboxylate (Step 2) in a 4 M solution of HCl in 1,4-dioxane (10.6 mL, 42.4 mmol) was stirred at 50° C. for 30 min. After cooling to rt, the mixture was diluted with diethyl ether/hexanes (2:1) and slurried at rt for 30 min. The resulting precipitate was collected by filtration, washed with diethyl ether, and dried under vacuum to afford the desired product (875 mg, 79% yield over two steps) as a mixture of diastereomers in the form of a white solid. LC-MS calculated for $C_{17}H_{26}F_3N_2$ $(M+H)^+$: m/z=315.2; found 315.2.

Intermediate 64. tert-Butyl (2S,5R)-4-(3-chloro-4-fluorobenzoyl)-2,5-dimethylpiperazine-1-carboxylate

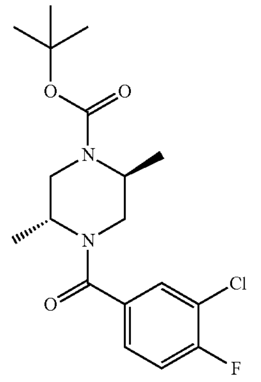 [SMILES: C[C@@H]1CN(C(=O)OC(C)(C)C)[C@@H](C)CN1C(=O)c1ccc(F)c(Cl)c1]

This compound was prepared according to the procedures described in Intermediate 56, with 3-chloro-4-fluorobenzoic acid replacing 4-(trifluoromethyl)benzoic acid. LC-MS calculated for $C_{14}H_{17}ClFN_2O_3(M-C_4H_8+H)^+$: m/z=315.1; found 315.1.

Intermediate 65. 2-Chloro-6-((2S,5R)-4-(1-(3-chloro-4-fluorophenyl)-2-methylpropyl)-2,5-dimethylpiperazin-1-yl)-8-methyl-9H-purine

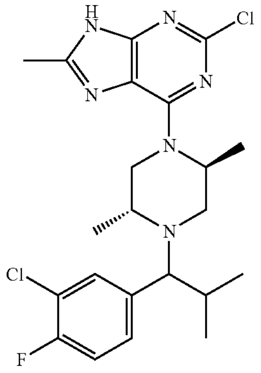 [SMILES: Cc1nc2c(N3C[C@@H](C)N(C(c4ccc(F)c(Cl)c4)C(C)C)C[C@@H]3C)nc(Cl)nc2[nH]1]

This compound was prepared according to the procedures described in Intermediate 57, with tert-butyl (2S,5R)-4-(3-chloro-4-fluorobenzoyl)-2,5-dimethylpiperazine-1-carboxylate (Intermediate 64) replacing tert-butyl (2S,5R)-2,5-dimethyl-4-(4-(trifluoromethyl)benzoyl)piperazine-1-carboxylate in Step 1. LC-MS calculated for $C_{22}H_{28}Cl_2FN_6$ $(M+H)^+$: m/z=465.2; found 465.2.

Intermediate 66. tert-Butyl (2S,5R)-4-(4-chlorobenzoyl)-2,5-dimethylpiperazine-1-carboxylate

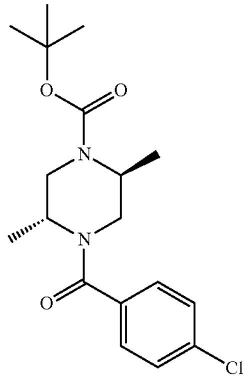 [SMILES: C[C@@H]1CN(C(=O)OC(C)(C)C)[C@@H](C)CN1C(=O)c1ccc(Cl)cc1]

This compound was prepared according to the procedures described in Intermediate 56, with 4-chlorobenzoic acid replacing 4-(trifluoromethyl)benzoic acid. LC-MS calculated for $C_{14}H_{18}ClN_2O_3(M-C_4H_8+H)^+$: m/z=297.1; found 297.2.

Intermediate 67. 2-Chloro-6-((2S,5R)-4-(1-(4-chlorophenyl)-2-methylpropyl)-2,5-dimethylpiperazin-1-yl)-8-methyl-9H-purine

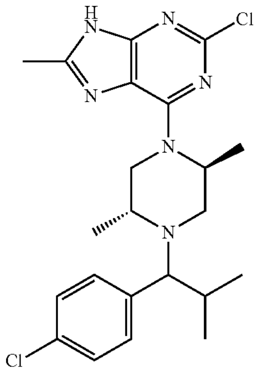 [SMILES: Cc1nc2c(N3C[C@@H](C)N(C(c4ccc(Cl)cc4)C(C)C)C[C@@H]3C)nc(Cl)nc2[nH]1]

This compound was prepared according to the procedures described in Intermediate 57, with tert-butyl (2S,5R)-4-(4-chlorobenzoyl)-2,5-dimethylpiperazine-1-carboxylate (Intermediate 66) replacing tert-butyl (2S,5R)-2,5-dimethyl-4-(4-(trifluoromethyl)benzoyl)piperazine-1-carboxylate in Step 1. LC-MS calculated for $C_{22}H_{29}Cl_2N_6(M+H)^+$: m/z=447.2; found 447.2.

Intermediate 68. (2R,5S)-1-(1-(4-Chlorophenyl)-2-methylpropyl)-2,5-dimethylpiperazine hydrochloride

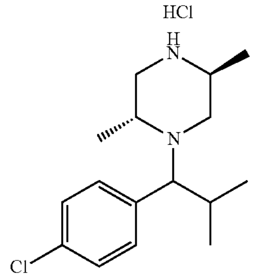 [SMILES: Cl ; CC(C)C(c1ccc(Cl)cc1)N1C[C@H](C)NC[C@H]1C]

This compound was prepared according to the procedures described in Intermediate 57, Steps 1-2 with tert-butyl (2S,5R)-4-(4-chlorobenzoyl)-2,5-dimethylpiperazine-1-carboxylate (Intermediate 66) replacing tert-butyl (2S,5R)-2,5-dimethyl-4-(4-(trifluoromethyl)benzoyl)piperazine-1-carboxylate in Step 1. LC-MS calculated for $C_{16}H_{26}C_1N_2$ $(M+H)^+$: m/z=281.2; found 281.2.

Intermediate 69. tert-Butyl (2S,5R)-4-(4-(difluoromethyl)benzoyl)-2,5-dimethylpiperazine-1-carboxylate

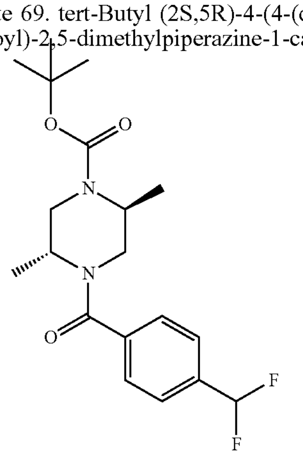

To a mixture of tert-butyl (2S,5R)-2,5-dimethylpiperazine-1-carboxylate (3.74 g, 17.4 mmol, Combi-Blocks OR-8588), N,N-diisopropylethylamine (3.26 mL, 18.7 mmol) and 4-(difluoromethyl)benzoic acid (2.00 g, 11.6 mmol) in MeCN (15.5 mL) was added HATU (4.86 g, 12.8 mmol, Combi-Blocks OR-0618) and N,N-diisopropylethylamine (6.09 mL, 34.9 mmol) and the reaction mixture was stirred at rt overnight. The reaction mixture was concentrated in vacuo, and the crude residue was purified by flash column chromatography ($SiO_2$, EtOAc/hexanes) to afford the desired product (1.90 g, 44% yield). LC-MS calculated for $C_{19}H_{27}F_2N_2O_3(M+H)^+$: m/z=369.2; found 369.2.

Intermediate 70. (2R,5S)-1-((4-(Difluoromethyl)phenyl)(4-methoxyphenyl)methyl)-2,5-dimethylpiperazine hydrochloride

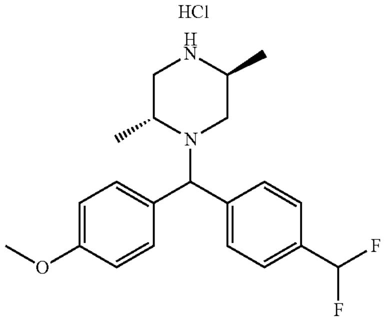 [SMILES: Cl ; COc1ccc(C(c2ccc(C(F)F)cc2)N2C[C@H](C)NC[C@H]2C)cc1]

Step 1: tert-Butyl (2S,5R)-4-((4-(difluoromethyl)phenyl)(4-methoxyphenyl)methyl)-2,5-dimethylpiperazine-1-carboxylate

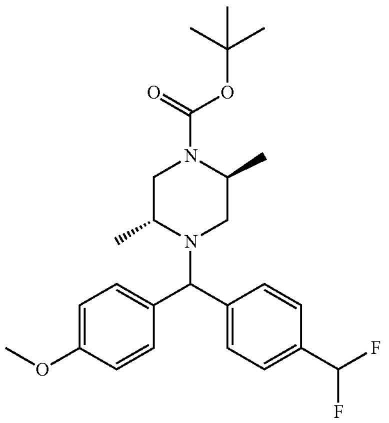 [SMILES: COc1ccc(C(c2ccc(C(F)F)cc2)N2C[C@H](C)N(C(=O)OC(C)(C)C)C[C@H]2C)cc1]

A mixture of tert-butyl (2S,5R)-4-(4-(difluoromethyl)benzoyl)-2,5-dimethylpiperazine-1-carboxylate (Intermediate 69, 500. mg, 1.36 mmol) and chlorocarbonylbis(triphenylphosphine)iridium(I) (106 mg, 0.136 mmol, Strem 77-0300) in $CH_2Cl_2$ (4.52 mL) was treated with 1,1,3,3-tetramethyldisiloxane (0.43 mL, 2.7 mmol, Aldrich 235733) and stirred at rt for 20 min. The reaction mixture was cooled to −78° C. and stirred for 5 min before (4-methoxyphenyl)magnesium bromide (0.5 M in THF, 3.39 mL, 1.70 mmol, Aldrich 470260) was added dropwise and the reaction mixture was stirred for an additional 5 min before warming to rt and stirring overnight. The mixture was quenched with saturated aqueous $NH_4Cl$ and the layers were separated. The organic layer was removed and the aqueous layer was extracted with $CH_2Cl_2$. The combined organic layers were dried over $MgSO_4$ and the filtrate was concentrated to afford the desired product as a mixture of diastereomers. The crude material obtained was used directly without further purification. LC-MS calculated for $C_{26}H_{35}F_2N_2O_3$ $(M+H)^+$: m/z=461.2; found 461.3.

Step 2: (2R,5S)-1-((4-(Difluoromethyl)phenyl)(4-methoxyphenyl)methyl)-2,5-dimethylpiperazine hydrochloride A mixture of tert-butyl (2S,5R)-4-((4-(difluoromethyl)phenyl)(4-methoxyphenyl)methyl)-2,5-dimethylpiperazine-1-carboxylate (Step 1) in a 4 M solution of HCl in 1,4-dioxane (3.13 mL, 12.5 mmol) was stirred at 50° C. for 30 min. After cooling to rt, the mixture was diluted with diethyl ether/hexanes (2:1) and slurried at rt for 10 min. The resulting precipitate was collected by filtration, washed with diethyl ether, and dried under vacuum to afford the desired product as a mixture of diastereomers in the form of a white solid. LC-MS calculated for $C_{21}H_{27}F_2N_2O$ $(M+H)^+$: m/z=361.2; found 361.2.

Intermediate 71. (4-(Difluoromethyl)phenyl)magnesium chloride lithium chloride (0.65 M in THF)

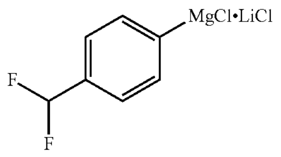

A 1.3 M solution of isopropylmagnesium chloride lithium chloride complex in THF (1.88 mL, 2.45 mmol, Aldrich 656984) was cooled to −78° C. before a mixture of 1-bromo-4-(difluoromethyl)benzene (507 mg, 2.45 mmol) in dry THF (1.88 mL total volume) was added dropwise and the reaction mixture was stirred at −78° C. for 5 min. The reaction mixture was warmed to rt and stirred for an additional 4 h. The mixture obtained was used directly in the next step.

Intermediate 72. (2R,5S)-1-(Bis(4-(difluoromethyl)phenyl)methyl)-2,5-dimethylpiperazine hydrochloride

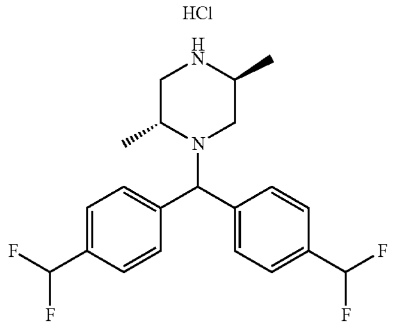 [SMILES: Cl ; C[C@@H]1CN[C@@H](C)CN1C(c1ccc(C(F)F)cc1)c1ccc(C(F)F)cc1]

This compound was prepared according to the procedures described in Intermediate 70, with (4-(difluoromethyl)phenyl)magnesium chloride lithium chloride (Intermediate 71, 0.65 M in THF) replacing (4-methoxyphenyl)magnesium bromide in Step 1. LC-MS calculated for $C_{21}H_{25}F_4N_2$ $(M+H)^+$: m/z=381.2; found 381.3.

Intermediate 73. tert-Butyl (2S,5R)-2,5-dimethyl-4-(5-(trifluoromethyl)picolinoyl)piperazine-1-carboxylate

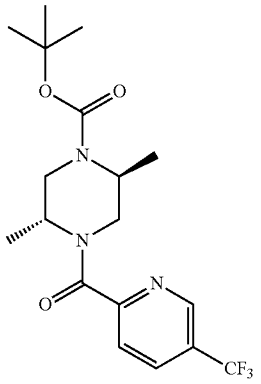 [SMILES: C[C@@H]1CN(C(=O)OC(C)(C)C)[C@@H](C)CN1C(=O)c1ccc(C(F)(F)F)cn1]

A mixture of tert-butyl (2S,5R)-2,5-dimethylpiperazine-1-carboxylate (1.07 g, 5.00 mmol Combi-Blocks OR-8588) and 5-(trifluoromethyl)picolinic acid (0.956 g, 5 mmol, Combi-Blocks PY-1447) in MeCN (25.0 mL) was treated with N,N-diisopropylethylamine (1.75 mL, 10.0 mmol) and HATU (2.00 g, 5.25 mmol, Combi-Blocks OR-0618) and stirred at rt for 30 min. The solvent was removed in vacuo and the crude residue was diluted with EtOAc and water. The layers were separated and the aqueous layer was extracted with EtOAc. The combined organic layers were washed with brine, dried over $MgSO_4$, concentrated in vacuo, and purified by flash column chromatography (40 g $SiO_2$, EtOAc/hexanes) to give the title compound (1.63 g, 84% yield) as a white solid. LC-MS calculated for $C_{14}H_{17}F_3N_3O_3(M-C_4H_8+H)^+$: m/z=332.1; found 332.1.

Intermediate 74: (2R,5S)-2,5-Dimethyl-1-((4-(trifluoromethyl)phenyl)(5-(trifluoromethyl)pyridin-2-yl)methyl)piperazine hydrochloride

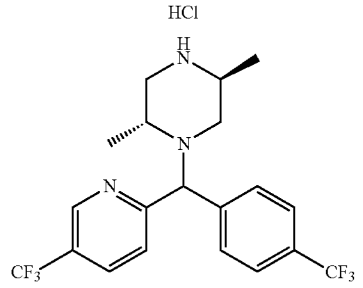 [SMILES: Cl ; C[C@@H]1CN[C@@H](C)CN1C(c1ccc(C(F)(F)F)cc1)c1ccc(C(F)(F)F)cn1]

Step 1: (4-(Trifluoromethyl)phenyl)magnesium chloride lithium chloride (1.1 M in THF)

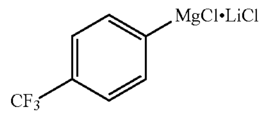

1-Bromo-4-(trifluoromethyl)benzene (1.68 mL, 12.2 mmol, Matrix Scientific 004745) was added to isopropylmagnesium chloride lithium chloride complex (1.3 M in THF, 9.69 mL, 12.6 mmol, Aldrich 656984) dropwise at rt using a tepid water bath to maintain temperature. The mixture was stirred at rt for 4 h. The mixture obtained was used directly in the next step.

Step 2: tert-Butyl (2S,5R)-2,5-dimethyl-4-((4-(trifluoromethyl)phenyl)(5-(trifluoromethyl)pyridin-2-yl)methyl)piperazine-1-carboxylate

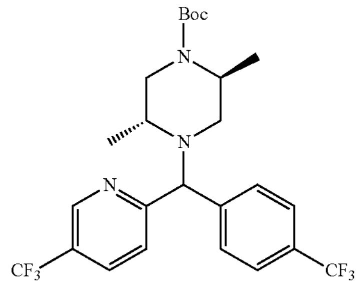 [SMILES: C[C@@H]1CN(C(=O)OC(C)(C)C)[C@@H](C)CN1C(c1ccc(C(F)(F)F)cc1)c1ccc(C(F)(F)F)cn1]

A mixture of tert-butyl (2S,5R)-2,5-dimethyl-4-(5-(trifluoromethyl)picolinoyl)piperazine-1-carboxylate (Intermediate 73, 2.40 g, 6.19 mmol) and chlorocarbonylbis(triphenylphosphine)iridium(I) (0.145 g, 0.186 mmol, Strem 77-0300) in $CH_2Cl_2$ (62 mL) was treated with 1,1,3,3-tetramethyldisiloxane (2.19 mL, 12.4 mmol, Aldrich 235733) and stirred for 15 min at rt. Immediate gas evolution was observed, and the yellow color of the catalyst became bleached over the course of 15 min. Additional chlorocarbonylbis(triphenylphosphine)iridium(I) (0.145 g, 0.186 mmol) and 1,1,3,3-tetramethyldisiloxane (1.10 mL, 6.19 mmol) were added and stirring was continued at rt for another 15 min. The reaction was cooled to −78° C. and stirred for 5 min before (4-(trifluoromethyl)phenyl)magnesium chloride lithium chloride (Step 1, 1.1 M in THF, 7.74 mL, 8.3 mmol) was added dropwise. The reaction was stirred at −78° C. for an additional 5 min, then warmed to 0° C. and stirred for 30 min. The mixture was quenched with saturated aqueous $NH_4Cl$ and the layers were separated. The aqueous layer was extracted with $CH_2Cl_2$ and the combined organic layers were dried over $MgSO_4$ and concentrated in vacuo. The material was purified by flash column chromatography (40 g $SiO_2$, EtOAc/hexanes) to give an orange oil which contained the desired product as a mixture of diastereomers. LC-MS calculated for $C_{25}H_{30}F_6N_3O_2$ $(M+H)^+$: m/z=518.2; found 518.2.

Step 3: (2R,5S)-2,5-Dimethyl-1-((4-(trifluoromethyl)phenyl)(5-(trifluoromethyl)pyridin-2-yl)methyl)piperazine hydrochloride A mixture of tert-butyl (2S,5R)-2,5-dimethyl-4-((4-(trifluoromethyl)phenyl)(5-(trifluoromethyl)pyridin-2-yl)methyl)piperazine-1-carboxylate (Step 2) in THF (12.8 mL) was treated with HCl (4 M in 1,4-dioxane, 12.8 mL, 51.3 mmol) and stirred at 60° C. for 1 h. After cooling to rt, the mixture was diluted with diethyl ether and the resulting precipitate was collected by filtration, washed with diethyl ether, and dried under vacuum to give the desired product (1.30 g, 46% yield over two steps) as mixture of diastereomers in the form of a light orange solid. LC-MS calculated for $C_{20}H_{22}F_6N_3$ $(M+H)^+$: m/z=418.2; found 418.3.

Intermediate 75. tert-Butyl (2-(2-chloro-6-((2S,5R)-2,5-dimethyl-4-((4-(trifluoromethyl)phenyl)(5-(trifluoromethyl)pyridin-2-yl)methyl)piperazin-1-yl)-9H-purin-9-yl)ethyl)(methyl)carbamate

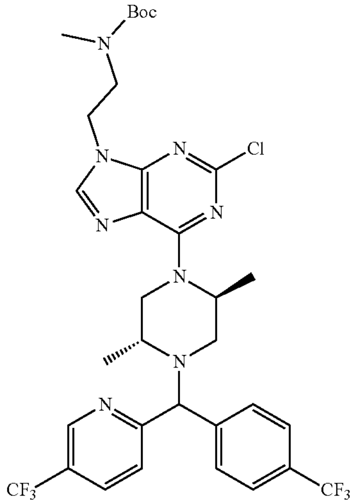 [SMILES: C[C@@H]1CN(c2nc(Cl)nc3c2ncn3CCN(C)C(=O)OC(C)(C)C)[C@@H](C)CN1C(c1ccc(C(F)(F)F)cc1)c1ccc(C(F)(F)F)cn1]

A mixture of (2R,5S)-2,5-dimethyl-1-((4-(trifluoromethyl)phenyl)(5-(trifluoromethyl)pyridin-2-yl)methyl)piperazine hydrochloride (Intermediate 74, 0.567 g, 1.25 mmol), tert-butyl (2-(2,6-dichloro-9H-purin-9-yl)ethyl)(methyl)carbamate (Intermediate 51, 0.433 g, 1.25 mmol), and N,N-diisopropylethylamine (0.655 mL, 3.75 mmol) in n-BuOH (3.12 mL) was stirred at 85° C. overnight. The mixture was cooled to rt, diluted with $CH_2Cl_2$, and quenched with water and 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, EtOAc/hexanes) to the title compound (0.535 g, 59% yield) as a mixture of diastereomers in the form of an orange solid. LC-MS calculated for $C_{33}H_{38}ClF_6N_8O_2$ $(M+H)^+$: m/z=727.3; found 727.4.

Intermediate 76. tert-Butyl (2-(6-((2S,5R)-2,5-dimethyl-4-((4-(trifluoromethyl)phenyl)(5-(trifluoromethyl)pyridin-2-yl)methyl)piperazin-1-yl)-2-hydrazineyl-9H-purin-9-yl)ethyl)(methyl)carbamate

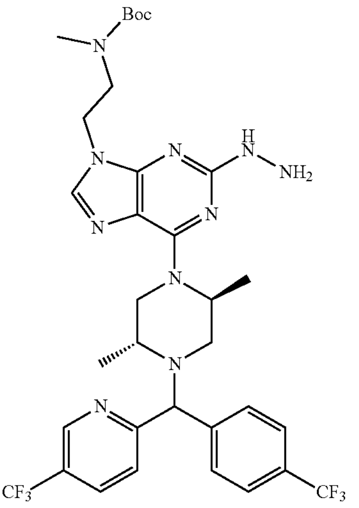 [SMILES: C[C@@H]1CN(c2nc(NN)nc3c2ncn3CCN(C)C(=O)OC(C)(C)C)[C@@H](C)CN1C(c1ccc(C(F)(F)F)cc1)c1ccc(C(F)(F)F)cn1]

A mixture of tert-butyl (2-(2-chloro-6-((2S,5R)-2,5-dimethyl-4-((4-(trifluoromethyl)phenyl)(5-(trifluoromethyl)pyridin-2-yl)methyl)piperazin-1-yl)-9H-purin-9-yl)ethyl)(methyl)carbamate (Intermediate 75, 0.535 g, 0.735 mmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (31.4 mg, 37.0 μmol, Aldrich 745979), and cesium carbonate (0.716 g, 2.20 mmol) was taken up in THF (3.7 mL) and treated with hydrazine hydrate (0.230 mL, 3.67 mmol). The mixture was stirred at 60° C. for 30 min, cooled to rt, and filtered through $MgSO_4$ in a SiliaPrep SPE thiol cartridge (500 mg, SiliCycle SPE-R51030B-06P). The filtrate was concentrated in vacuo and the crude residue was purified by flash column chromatography (24 g $SiO_2$, MeOH/$CH_2Cl_2$) to give the title compound (0.419 g, 79% yield) as a mixture of diastereomers in the form of a white foam. LC-MS calculated for $C_{33}H_{41}F_6N_{10}O_2(M+H)^+$: m/z=723.3; found 723.4.

Intermediate 77. tert-Butyl (2-(4-((2S,5R)-2,5-dimethyl-4-((4-(trifluoromethyl)phenyl)(5-(trifluoromethyl)pyridin-2-yl)methyl)piperazin-1-yl)-1H-[1,2,4]triazolo[3,4-b]purin-1-yl)ethyl)(methyl)carbamate

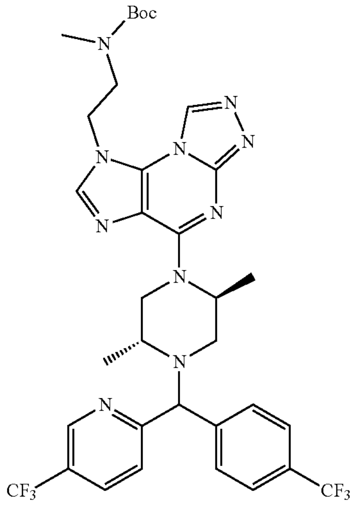 [SMILES: C[C@@H]1CN(c2nc3nncn3c3c2ncn3CCN(C)C(=O)OC(C)(C)C)[C@@H](C)CN1C(c1ccc(C(F)(F)F)cc1)c1ccc(C(F)(F)F)cn1]

A mixture of tert-butyl (2-(6-((2S,5R)-2,5-dimethyl-4-((4-(trifluoromethyl)phenyl)(5-(trifluoromethyl)pyridin-2-yl)methyl)piperazin-1-yl)-2-hydrazineyl-9H-purin-9-yl)ethyl)(methyl)carbamate (Intermediate 76, 0.419 g, 0.579 mmol), acetic acid (1.66 mL, 29.0 mmol) and triethyl orthoformate (0.483 mL, 2.90 mmol) was stirred at 95° C. for 1 h. The reaction was cooled to rt, diluted with $CH_2Cl_2$, and quenched with 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, MeOH/$CH_2Cl_2$) to give the title compound (0.262 g, 62% yield) as a mixture of diastereomers in the form of an off-white solid. LC-MS calculated for $C_{34}H_{39}F_6N_{10}O_2$ $(M+H)^+$: m/z=733.3; found 733.3.

Intermediate 78. tert-Butyl (2S,5R)-4-(5-fluoro-6-(trifluoromethyl)picolinoyl)-2,5-dimethylpiperazine-1-carboxylate

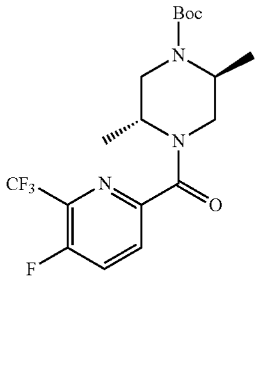 [SMILES: C[C@@H]1CN(C(=O)OC(C)(C)C)[C@@H](C)CN1C(=O)c1ccc(F)c(C(F)(F)F)n1]

A mixture of tert-butyl (2S,5R)-2,5-dimethylpiperazine-1-carboxylate (0.292 g, 1.36 mmol Combi-Blocks OR-8588) and 5-fluoro-6-(trifluoromethyl)picolinic acid (0.285 g, 1.36 mmol, Enamine, EN300-1696814) in MeCN (6.80 mL) was treated with N,N-diisopropylethylamine (0.480 ml, 2.73 mmol) and HATU (0.544 g, 1.43 mmol) and stirred at rt for 30 min. The solvent was removed in vacuo and the crude residue was diluted with EtOAc and water. The layers were separated and the aqueous layer was extracted with EtOAc. The combined organic layers were washed with brine, dried over $MgSO_4$, and concentrated in vacuo. The crude residue was purified by flash column chromatography (24 g $SiO_2$, EtOAc/hexanes) to give the title compound (0.466 g, 84% yield) as a white solid. LC-MS calculated for $C_{13}H_{16}F_4N_{30}$ $(M-C_5H_8O_2+H)^+$: m/z=306.1; found 306.1.

Intermediate 79. tert-Butyl (2S,5R)-4-((5-fluoro-6-(trifluoromethyl)pyridin-2-yl)(4-fluorophenyl)methyl)-2,5-dimethylpiperazine-1-carboxylate

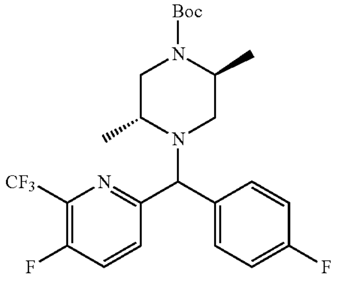 [SMILES: C[C@@H]1CN(C(=O)OC(C)(C)C)[C@@H](C)CN1C(c1ccc(F)cc1)c1ccc(F)c(C(F)(F)F)n1]

A mixture of tert-butyl (2S,5R)-4-(5-fluoro-6-(trifluoromethyl)picolinoyl)-2,5-dimethylpiperazine-1-carboxylate (Intermediate 78, 0.722 g, 1.78 mmol) and chlorocarbonylbis(triphenylphosphine)iridium(I) (69.0 mg, 89.0 μmol, Strem 77-0300) in $CH_2Cl_2$ (17.8 mL) was treated with 1,1,3,3-tetramethyldisiloxane (0.630 mL, 3.56 mmol, Aldrich 235733) and stirred for 15 min at rt. Immediate gas evolution was observed, and the yellow color of the catalyst became bleached over the course of 15 min. Additional chlorocarbonylbis(triphenylphosphine)iridium(I) (69.0 mg, 89.0 μmol) and 1,1,3,3-tetramethyldisiloxane (0.315 mL, 1.78 mmol) were added and stirring was continued at rt for another 15 min. The reaction was cooled to −78° C. and stirred for 5 min before (4-fluorophenyl)magnesium bromide (2.23 mL, 2.23 mmol, Aldrich 328820) was added was added dropwise. The reaction mixture was stirred for an additional 5 min at −78° C., warmed to 0° C., and stirred for 30 min. The mixture was quenched with saturated aqueous $NH_4Cl$ and the layers were separated. The aqueous layer was extracted with $CH_2Cl_2$ and the combined organic layers were dried over $MgSO_4$ and concentrated in vacuo. The material was purified by flash column chromatography (24 g $SiO_2$, EtOAc/hexanes) to give the desired product (0.609 g, 70% yield) as mixture of diastereomers in the form of a white, foamy solid. LC-MS calculated for $C_{24}H_{29}F_5N_3O_2$ $(M+H)^+$: m/z=486.2; found 486.3.

Intermediate 80. (2R,5S)-1-((5-Fluoro-6-(trifluoromethyl)pyridin-2-yl)(4-fluorophenyl)methyl)-2,5-dimethylpiperazine hydrochloride

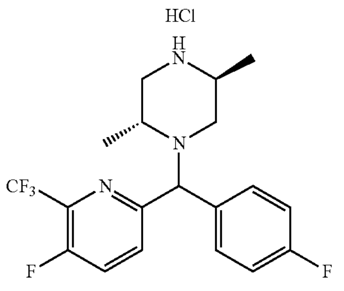 [SMILES: Cl ; C[C@@H]1CN[C@@H](C)CN1C(c1ccc(F)cc1)c1ccc(F)c(C(F)(F)F)n1]

A mixture of tert-butyl (2S,5R)-4-((5-fluoro-6-(trifluoromethyl)pyridin-2-yl)(4-fluorophenyl)methyl)-2,5-dimethylpiperazine-1-carboxylate (Intermediate 79, 0.609 g, 1.25 mmol) in THF (3.10 mL) was treated with HCl (4 M in 1,4-dioxane, 3.12 mL, 12.5 mmol) and stirred at 60° C. for 1 h. After cooling to rt, the mixture was diluted with diethyl ether and the resulting precipitate was collected by filtration, washed with diethyl ether, and dried under vacuum to give the desired product (0.447 g, 85% yield) as a mixture of diastereomers in the form of a light yellow solid. LC-MS calculated for $C_{19}H_{21}F_5N_3$ $(M+H)^+$: m/z=386.2; found 386.2.

Intermediate 81: 2-Chloro-6-((2S,5R)-4-((5-fluoro-6-(trifluoromethyl)pyridin-2-yl)(4-fluorophenyl)methyl)-2,5-dimethylpiperazin-1-yl)-8-methyl-9-(((S)-tetrahydrofuran-2-yl)methyl)-9H-purine

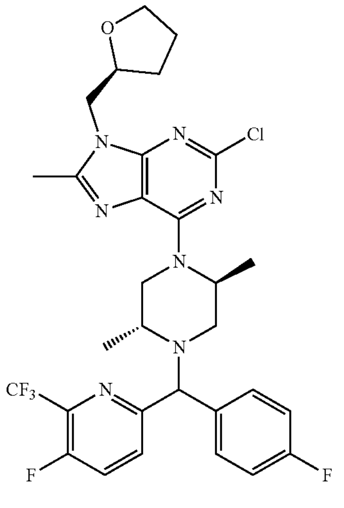 [SMILES: Cc1nc2c(N3C[C@@H](C)N(C(c4ccc(F)cc4)c4ccc(F)c(C(F)(F)F)n4)C[C@@H]3C)nc(Cl)nc2n1C[C@@H]1CCCO1]

A mixture of (2R,5S)-1-((5-fluoro-6-(trifluoromethyl)pyridin-2-yl)(4-fluorophenyl)methyl)-2,5-dimethylpiperazine hydrochloride (Intermediate 80, 0.447 g, 1.06 mmol), (S)-2,6-dichloro-8-methyl-9-((tetrahydrofuran-2-yl)methyl)-9H-purine (Intermediate 41, 0.304 g, 1.06 mmol), and N,N-diisopropylethylamine (0.560 mL, 3.18 mmol) in n-BuOH (2.65 mL) was stirred at 85° C. overnight. The mixture was cooled to rt, diluted with $CH_2Cl_2$, and quenched with water and 1 M NaOH. The layers were separated and the aqueous layer was extracted with $CH_2Cl_2$. The combined organic layers were dried over $MgSO_4$, concentrated in vacuo, and purified by flash column chromatography (24 g $SiO_2$, EtOAc/hexanes) to give the title compound (0.416 g, 62% yield) as a mixture of diastereomers in the form of an orange solid. LC-MS calculated for $C_{30}H_{32}ClF_5N_7O$ $(M+H)^+$: m/z=636.2; found 636.2.

Intermediate 82. 6-((2S,5R)-4-((5-Fluoro-6-(trifluoromethyl)pyridin-2-yl)(4-fluorophenyl)methyl)-2,5-dimethylpiperazin-1-yl)-2-hydrazineyl-8-methyl-9-(((S)-tetrahydrofuran-2-yl)methyl)-9H-purine

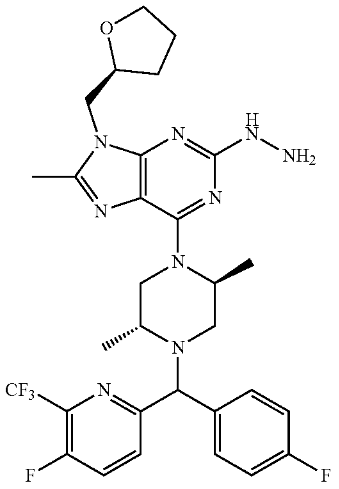 [SMILES: Cc1nc2c(N3C[C@@H](C)N(C(c4ccc(F)cc4)c4ccc(F)c(C(F)(F)F)n4)C[C@@H]3C)nc(NN)nc2n1C[C@@H]1CCCO1]

A mixture of 2-chloro-6-((2S,5R)-4-((5-fluoro-6-(trifluoromethyl)pyridin-2-yl)(4-fluorophenyl)methyl)-2,5-dimethylpiperazin-1-yl)-8-methyl-9-(((S)-tetrahydrofuran-2-yl)methyl)-9H-purine (Intermediate 81, 0.416 g, 0.653 mmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (27.9 mg, 33.0 μmol, Aldrich 745979), and cesium carbonate (0.639 g, 2.20 mmol) was taken up in THF (3.2 mL) and treated with hydrazine hydrate (0.203 mL, 3.67 mmol). The mixture was stirred at 60° C. for 30 min, cooled to rt, and filtered through $MgSO_4$ in a SiliaPrep SPE thiol cartridge (500 mg, SiliCycle SPE-R51030B-06P). The filtrate was concentrated in vacuo and the crude residue was purified by flash column chromatography (24 g $SiO_2$, $MeOH/CH_2Cl_2$) to give the title compound (0.355 g, 86% yield) as a mixture of diastereomers in the form of a white foam. LC-MS calculated for $C_{30}H_{35}F_5N_9O$ $(M+H)^+$: m/z=632.3; found 632.3.

Intermediate 83. (2R,5S)-1-(Bis(4-chlorophenyl) methyl)-2,5-dimethylpiperazine hydrochloride

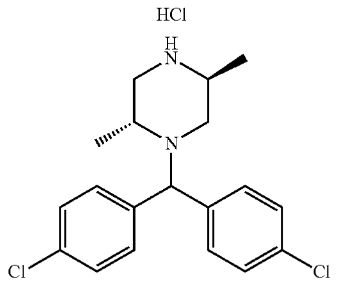 [SMILES: Cl ; C[C@@H]1CN[C@@H](C)CN1C(c1ccc(Cl)cc1)c1ccc(Cl)cc1]

Step 1: tert-Butyl (2S,5R)-4-(bis(4-chlorophenyl) methyl)-2,5-dimethylpiperazine-1-carboxylate

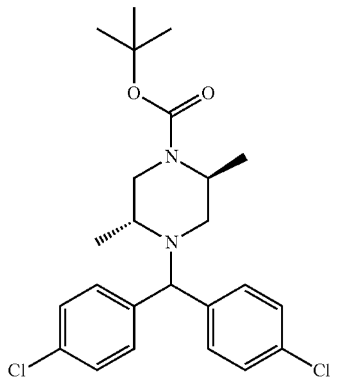 [SMILES: C[C@@H]1CN(C(=O)OC(C)(C)C)[C@@H](C)CN1C(c1ccc(Cl)cc1)c1ccc(Cl)cc1]

In a 20 mL microwave vial with a stir bar, a mixture of tert-butyl (2S,5R)-2,5-dimethylpiperazine-1-carboxylate (1.11 g, 5.19 mmol, Combi-Blocks OR-8588), 4,4'-(chloromethylene)bis(chlorobenzene) (1.41 g, 5.19 mmol, A2B Chem AC49945), and N,N-diisopropylethylamine (1.81 mL, 10.4 mmol) in MeCN (13 mL) was irradiated at 115° C. in a microwave reactor for 4 h. A second reaction was set up in parallel in a separate vessel, and after cooling to rt the two reaction mixtures were combined and concentrated in vacuo. The crude residue was diluted with EtOAc and water and the layers were separated. The organic layer was removed, and the aqueous layer was extracted with EtOAc. The combined organic layers were washed with brine, dried over $MgSO_4$, and concentrated in vacuo. The crude residue was purified by flash column chromatography (40 g $SiO_2$, EtOAc/hexanes) to give the title compound as a white solid. LC-MS calculated for $C_{24}H_{31}Cl_2N_2O_2$ $(M+H)^+$: m/z=449.2; found 449.2.

Step 2: (2R,5S)-1-(Bis(4-chlorophenyl)methyl)-2,5-dimethylpiperazine hydrochloride A mixture of tert-butyl (2S,5R)-4-(bis(4-chlorophenyl) methyl)-2,5-dimethylpiperazine-1-carboxylate (Step 1) in THF (26 mL) was treated with HCl (4 M in 1,4-dioxane, 26 mL, 104 mmol) and the reaction mixture was stirred at 60° C. for 1 h. After cooling to rt, the mixture was diluted with diethyl ether (100 mL). The solid precipitate that formed was collected by filtration, washed with diethyl ether, and dried under vacuum to give the title compound (2.44 g, 610% yield over two steps) as a white solid. LC-MS calculated for $C_{19}H_{23}Cl_2N_2(M+H)^+$: m/z=349.1; found 349.2.

Intermediate 84: 6-((2S,5R)-4-(Bis(4-chlorophenyl) methyl)-2,5-dimethylpiperazin-1-yl)-2-chloro-5-nitro-N—(((R)-tetrahydrofuran-2-yl)methyl)pyrimidin-4-amine

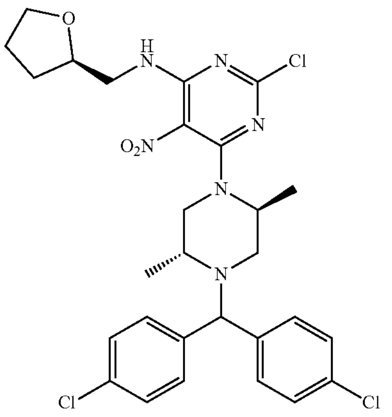 [SMILES: C[C@@H]1CN(c2nc(Cl)nc(NC[C@H]3CCCO3)c2[N+](=O)[O-])[C@@H](C)CN1C(c1ccc(Cl)cc1)c1ccc(Cl)cc1]

A suspension of (2R,5S)-1-(bis(4-chlorophenyl)methyl)-2,5-dimethylpiperazine hydrochloride (Intermediate 83, 0.507 g, 1.20 mmol) and 2,4,6-trichloro-5-nitropyrimidine (0.274 g, 1.2 mmol, Combi-Blocks ST-3909) in $CH_2Cl_2$ (6 mL) was cooled to −40° C. N,N-diisopropylethylamine (0.838 mL, 4.80 mmol) was added and the mixture was stirred at −40° C. for 30 min. A solution of (R)-(tetrahydrofuran-2-yl)methanamine (0.121 g, 1.20 mmol, BLDpharm BD46980) in $CH_2Cl_2$ (3 mL) was added to the reaction mixture, and after the transfer was complete the mixture was warmed to 0° C. and stirred for 30 min. The reaction was quenched with saturated aqueous $NaHCO_3$ and diluted with $CH_2Cl_2$. The layers were separated and the aqueous layer was extracted with $CH_2Cl_2$. The combined organic layers were dried over $MgSO_4$ and concentrated in vacuo. The crude residue was purified by flash column chromatography (24 g $SiO_2$, EtOAc/hexanes) to give the title compound (0.461 g, 63% yield) as a yellow oil. LC-MS calculated for $C_{28}H_{32}Cl_3N_6O_3$ $(M+H)^+$: m/z=605.2; found 605.3.

Intermediate 85. tert-Butyl (2S,5R)-4-(4-bromobenzoyl)-2,5-dimethylpiperazine-1-carboxylate

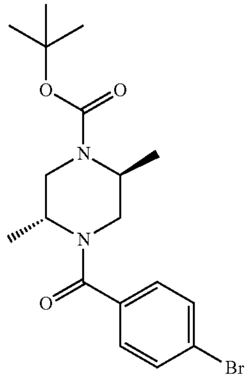 [SMILES: C[C@@H]1CN(C(=O)OC(C)(C)C)[C@@H](C)CN1C(=O)c1ccc(Br)cc1]

To a mixture of tert-butyl (2S,5R)-2,5-dimethylpiperazine-1-carboxylate (1.07 g, 5.00 mmol, Combi-Blocks OR-8588) and 4-bromobenzoyl chloride (1.15 g, 5.25 mmol) in $CH_2Cl_2$ (25 mL) in a tepid water bath was added N,N-diisopropylethylamine (1.75 mL, 10.0 mmol) and the mixture was stirred overnight. Saturated aqueous $NaHCO_3$ was added and the mixture was stirred 15 min. The layers were separated and the organic layer was washed with 1 M HCl, brine, dried over $MgSO_4$, and concentrated in vacuo to give the title compound (1.99 g, 5.00 mmol, 100% yield) as a white solid. LC-MS calculated for $C_{14}H_{18}BrN_2O_3(M-C_4H_8+H)^+$: m/z=341.1; found 341.

Intermediate 86. (2R,5S)-1-(Bis(4-bromophenyl)methyl)-2,5-dimethylpiperazine hydrochloride

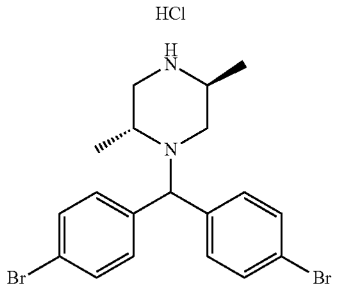 [SMILES: Cl ; C[C@@H]1CN[C@@H](C)CN1C(c1ccc(Br)cc1)c1ccc(Br)cc1]

Step 1: (4-Bromophenyl)magnesium chloride lithium chloride (0.5M in THF)

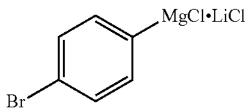

To a solution of 1-bromo-4-iodobenzene (2.492 g, 8.81 mmol, TCI B0604) in THF (10.5 mL total volume) was added isopropylmagnesium chloride lithium chloride complex (1.3 M in THF, 7.12 mL, 9.25 mmol, Aldrich 656984) dropwise at −20° C. and the reaction was stirred at this temperature for 30 min. The turbid mixture obtained was used directly in the next step.

Step 2: tert-Butyl (2S,5R)-4-(bis(4-bromophenyl)methyl)-2,5-dimethylpiperazine-1-carboxylate

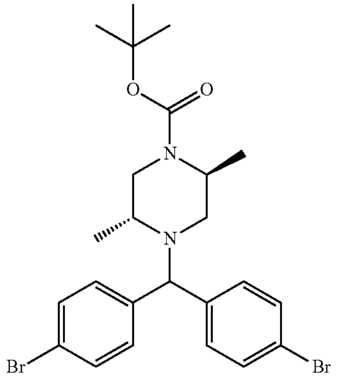 [SMILES: C[C@@H]1CN(C(=O)OC(C)(C)C)[C@@H](C)CN1C(c1ccc(Br)cc1)c1ccc(Br)cc1]

A mixture of tert-butyl (2S,5R)-4-(4-bromobenzoyl)-2,5-dimethylpiperazine-1-carboxylate (Intermediate 85, 1.40 g, 3.52 mmol) and chlorocarbonylbis(triphenylphosphine)iridium(I) (0.082 g, 0.106 mmol, Strem 77-0300) in $CH_2Cl_2$ (35 mL) was treated with 1,1,3,3-tetramethyldisiloxane (1.25 mL, 7.07 mmol, Aldrich 235733) and stirred for 15 min at rt. Immediate gas evolution was observed, and the yellow color of the catalyst became bleached over the course of 15 min. Additional chlorocarbonylbis(triphenylphosphine)iridium(I) (0.082 g, 0.106 mmol) and 1,1,3,3-tetramethyldisiloxane (623 μL, 3.52 mmol) was added and stirring was continued at rt for 15 min. The reaction was cooled to −78° C. and stirred for 5 min before (4-bromophenyl)magnesium chloride lithium chloride (Step 1, 0.5 M in THF, 8.8 mL, 4.4 mmol) was added dropwise. The reaction was stirred at −78° C. for an additional 5 min, then warmed to 0° C. and stirred for 30 min. The mixture was quenched with saturated aqueous $NH_4Cl$ and the layers were separated. The aqueous layer was extracted with $CH_2Cl_2$ and the combined organic layers were dried over $MgSO_4$ and concentrated in vacuo. The material was purified by flash column chromatography (40 g $SiO_2$, EtOAc/hexanes) to afford the desired product. LC-MS calculated for $C_{24}H_{31}Br_2N_2O_2$ $(M+H)^+$: m/z=537.1; found 537.2.

Step 3: (2R,5S)-1-(Bis(4-bromophenyl)methyl)-2,5-dimethylpiperazine hydrochloride A mixture of tert-butyl (2S,5R)-4-(bis(4-bromophenyl)methyl)-2,5-dimethylpiperazine-1-carboxylate (Step 2) in THF (8.81 mL) was treated with HCl (4 M in 1,4-dioxane, 8.81 mL, 35.2 mmol) and stirred at 60° C. for 30 min. After cooling to rt, the mixture was diluted with diethyl ether (100 mL). The resulting precipitate was collected by filtration, washed with diethyl ether, and dried under vacuum to afford the desired product (1.52 g, 91% yield over two steps) as a white solid. LC-MS calculated for $C_{19}H_{23}Br_2N_2(M+H)^+$: m/z=437.0; found 437.1.

Intermediate 87. Bis(5-(trifluoromethyl)pyridin-2-yl)methyl methanesulfonate

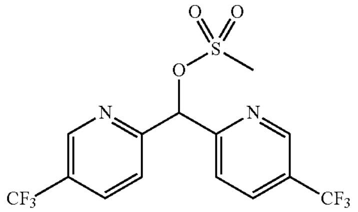 [SMILES: CS(=O)(=O)OC(c1ccc(C(F)(F)F)cn1)c1ccc(C(F)(F)F)cn1]

Step 1: Bis(5-(trifluoromethyl)pyridin-2-yl)methanol

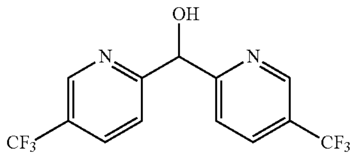 [SMILES: OC(c1ccc(C(F)(F)F)cn1)c1ccc(C(F)(F)F)cn1]

To a mixture of 2-bromo-5-(trifluoromethyl)pyridine (2.64 g, 11.7 mmol, Aldrich 661120) in $Et_2O$ (47 mL) at 0° C. was added isopropylmagnesium chloride lithium chloride complex (1.3 M in THF, 9.43 mL, 12.3 mmol, Aldrich 656984) dropwise over 5 min. The light orange solution became dark red over time. After stirring at 0° C. for 2 h, a solution of 5-(trifluoromethyl)picolinaldehyde (2.04 g, 11.7 mmol, Combi-Blocks PY-1433) in $Et_2O$ (10 mL) was added. A precipitate formed immediately. The reaction mixture was stirred at 0° C. for 5 min, then quenched with sat. aq. $NH_4Cl$. After warming to rt, the layers were separated. The organic layer was removed and the aqueous layer was extracted with EtOAc. The combined organic layers were dried over $MgSO_4$ and concentrated in vacuo. The crude residue was purified by flash column chromatography (40 g $SiO_2$, EtOAc/hexanes) to give the title compound (1.98 g, 60% yield) as an orange solid. LC-MS calculated for $C_{13}H_9F_6N_2O$ $(M+H)^+$: m/z=323.1; found 323.1.

Step 2: Bis(5-(trifluoromethyl)pyridin-2-yl)methyl methanesulfonate

A mixture of bis(5-(trifluoromethyl)pyridin-2-yl)methanol (1.98 g, 6.14 mmol) and N,N-diisopropylethylamine (3.22 mL, 18.42 mmol) in $CH_2Cl_2$ (12.3 mL) was cooled to 0° C. Methanesulfonyl chloride (0.718 mL, 9.21 mmol) was added dropwise and the reaction mixture was stirred at 0° C. for 1 h. The mixture was diluted with water and after warming to rt the layers were separated. The organic layer was removed and the aqueous layer was extracted with $CH_2Cl_2$. The combined organic layers were dried over $MgSO_4$ and concentrated in vacuo. The crude residue was purified by flash column chromatography (40 g $SiO_2$, EtOAc/hexanes) to give the title compound (2.33 g, 95% yield) as an orange solid. LC-MS calculated for $C_{14}H_{11}F_6N_2O_3S$ $(M+H)^+$: m/z=401.0; found 401.1.

Intermediate 88. (2R,5S)-1-(Bis(5-(trifluoromethyl)pyridin-2-yl)methyl)-2,5-dimethylpiperazine dihydrochloride

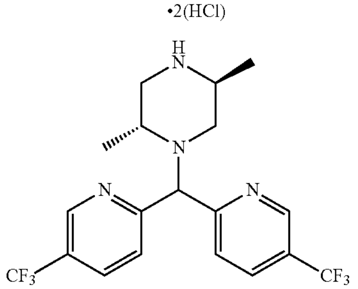

Step 1: tert-Butyl (2S,5R)-4-(bis(5-(trifluoromethyl)pyridin-2-yl)methyl)-2,5-dimethylpiperazine-1-carboxylate

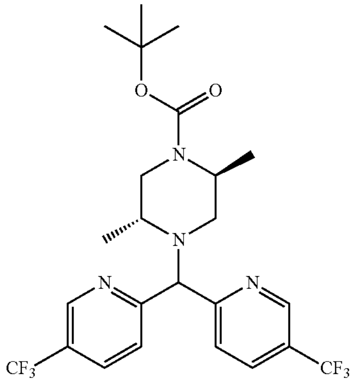 [SMILES: C[C@@H]1CN(C(=O)OC(C)(C)C)[C@@H](C)CN1C(c1ccc(C(F)(F)F)cn1)c1ccc(C(F)(F)F)cn1]

A mixture of tert-butyl (2S,5R)-2,5-dimethylpiperazine-1-carboxylate (1.32 g, 6.14 mmol, Combi-Blocks OR-8588), bis(5-(trifluoromethyl)pyridin-2-yl)methyl methanesulfonate (Intermediate 87, 2.33 g, 5.81 mmol) and N,N-diisopropylethylamine (3.22 mL, 18.2 mmol) in MeCN (30 mL) was stirred at 85° C. overnight. After cooling to rt, the reaction mixture was concentrated in vacuo. The crude residue was taken up in EtOAc and sat. aq. $NaHCO_3$ was added. The layers were separated and the aqueous layer was extracted with EtOAc. The combined organic layers were washed with brine, dried over $Na_2SO_4$, and concentrated in vacuo. The crude residue was purified by flash column chromatography (40 g $SiO_2$, EtOAc/hexanes) to give the title compound as an orange oil. LC-MS calculated for $C_{24}H_{29}F_6N_4O_2(M+H)^+$: m/z=519.2; found 519.2.

Step 2: (2R,5S)-1-(Bis(5-(trifluoromethyl)pyridin-2-yl)methyl)-2,5-dimethylpiperazine dihydrochloride To a mixture of tert-butyl (2S,5R)-4-(bis(5-(trifluoromethyl)pyridin-2-yl)methyl)-2,5-dimethylpiperazine-1-carboxylate (Step 1) in THF (15 mL) was added HCl (4 M in 1,4-dioxane, 15.4 mL, 61.4 mmol) and the reaction mixture was stirred at 60° C. for 1 h. After cooling to rt, the mixture was diluted with diethyl ether (100 mL). The resulting precipitate was collected by filtration, washed with diethyl ether, and dried under vacuum to give the title compound (1.24 g, 43% yield over two steps) as a green solid. LC-MS calculated for $C_{19}H_{21}F_6N_4$ $(M+H)^+$: m/z=419.2; found 419.3.

Intermediate 89. tert-Butyl (2S,5R)-2,5-dimethyl-4-((trans)-3-(trifluoromethyl)cyclobutane-1-carbonyl)piperazine-1-carboxylate

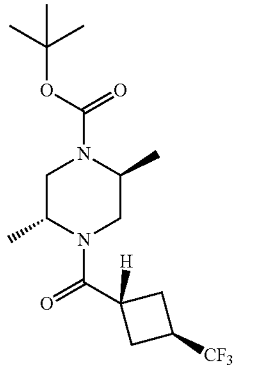 [SMILES: C[C@@H]1CN(C(=O)OC(C)(C)C)[C@@H](C)CN1C(=O)[C@H]1C[C@H](C(F)(F)F)C1]

This compound was prepared according to the procedure described for Intermediate 73, with (trans)-3-(trifluoromethyl)cyclobutane-1-carboxylic acid (Pharmablock PBLL1673) replacing 5-(trifluoromethyl)picolinic acid. LC-MS calculated for $C_{13}H_{20}F_3N_2O_3$ $(M-C_4H_8+H)^+$: m/z=309.1; found 309.1.

Intermediate 90. (2R,5S)-1-((3-Chloro-4-fluorophenyl)((trans)-3-(trifluoromethyl)cyclobutyl)methyl)-2,5-dimethylpiperazine hydrochloride

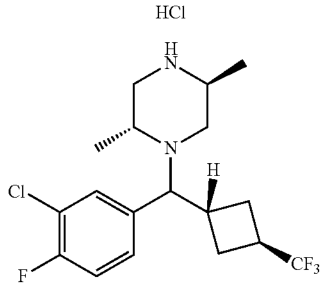 [SMILES: Cl ; C[C@@H]1CN[C@@H](C)CN1C(c1ccc(F)c(Cl)c1)[C@H]1C[C@H](C(F)(F)F)C1]

Step 1: tert-Butyl (2S,5R)-4-((3-chloro-4-fluorophenyl)((trans)-3-(trifluoromethyl)cyclobutyl)methyl)-2,5-dimethylpiperazine-1-carboxylate

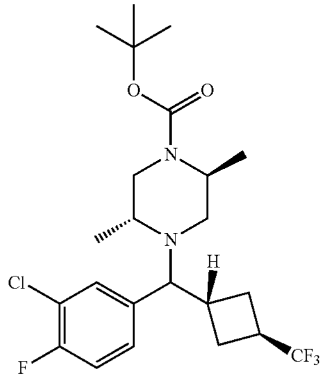 [SMILES: C[C@@H]1CN(C(=O)OC(C)(C)C)[C@@H](C)CN1C(c1ccc(F)c(Cl)c1)[C@H]1C[C@H](C(F)(F)F)C1]

A mixture of tert-butyl (2S,5R)-2,5-dimethyl-4-((trans)-3-(trifluoromethyl)cyclobutane-1-carbonyl)piperazine-1-carboxylate (Intermediate 89, 182 mg, 0.500 mmol) and chlorocarbonylbis(triphenylphosphine)iridium(I) (19.5 mg, 0.025 mmol, Strem 77-0300) in $CH_2Cl_2$ (5 mL) was treated with 1,1,3,3-tetramethyldisiloxane (177 μL, 1.00 mmol, Aldrich 235733) and stirred at rt for 15 min. Additional chlorocarbonylbis(triphenylphosphine)iridium(I) (19.5 mg, 0.025 mmol) and 1,1,3,3-tetramethyldisiloxane (88 μL, 0.5 mmol) was added and stirring was continued at rt for 15 min. The reaction was cooled to −78° C. and stirred for 5 min before (3-chloro-4-fluorophenyl)magnesium bromide (1.25 mL, 0.625 mmol, 0.5 M in THF, Aldrich 563676) was added dropwise and the reaction mixture was stirred for an additional 5 min. The reaction mixture was warmed to 0° C. and stirred for 30 min. The mixture was quenched with saturated aqueous $NH_4Cl$. After warming to rt, the organic layer was removed and the aqueous layer was extracted with $CH_2Cl_2$. The combined organic layers were dried over $MgSO_4$ and the filtrate was concentrated to afford the desired product as a mixture of diastereomers. The crude material obtained was used directly without further purification. LC-MS calculated for $C_{23}H_{32}ClF_4N_2O_2$ $(M+H)^+$: m/z=479.2; found 479.2.

Step 2: (2R,5S)-1-((3-Chloro-4-fluorophenyl)((trans)-3-(trifluoromethyl)cyclobutyl)methyl)-2,5-dimethylpiperazine hydrochloride A mixture of tert-butyl (2S,5R)-4-((3-chloro-4-fluorophenyl)((trans)-3-(trifluoromethyl)cyclobutyl)methyl)-2,5-dimethylpiperazine-1-carboxylate (Step 1) in THF (1.25 mL) and HCl (4 M in 1,4-dioxane, 1.25 mL, 5.00 mmol) was stirred at 60° C. for 1 h. After cooling to rt, the mixture was concentrated in vacuo to afford the desired product as a white solid. The crude material obtained was used directly without further purification. LC-MS calculated for $C_{11}H_{24}ClF_4N_2(M+H)^+$: m/z=379.2; found 379.2.

Intermediate 91: (2R,5S)-2,5-Dimethyl-1-(((trans)-3-(trifluoromethyl)cyclobutyl)(4-(trifluoromethyl)phenyl)methyl)piperazine hydrochloride

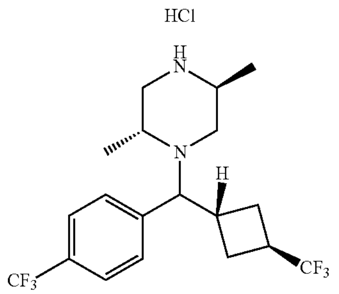 [SMILES: Cl ; C[C@@H]1CN[C@@H](C)CN1C(c1ccc(C(F)(F)F)cc1)[C@H]1C[C@H](C(F)(F)F)C1]

This compound was prepared according to the procedures described for Intermediate 43, with tert-butyl (2S,5R)-2,5-dimethyl-4-((trans)-3-(trifluoromethyl)cyclobutane-1-carbonyl)piperazine-1-carboxylate (Intermediate 89) replacing tert-butyl (2S,5R)-4-(3,3-difluorocyclobutane-1-carbonyl)-2,5-dimethylpiperazine-1-carboxylate. LC-MS calculated for $C_{19}H_{25}F_6N_2$ $(M+H)^+$: m/z=395.2; found 395.3.

Intermediate 92. tert-Butyl (2S,5R)-4-(4,4-difluorocyclohexane-1-carbonyl)-2,5-dimethylpiperazine-1-carboxylate

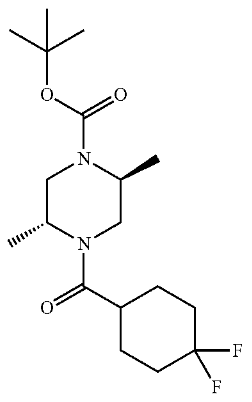 [SMILES: C[C@@H]1CN(C(=O)OC(C)(C)C)[C@@H](C)CN1C(=O)C1CCC(F)(F)CC1]

This compound was prepared according to the procedure described for Intermediate 73, with 4,4-difluorocyclohexanecarboxylic acid (Combi-Blocks, OS-1238) replacing 5-(trifluoromethyl)picolinic acid. LC-MS calculated for $C_{14}H_{23}F_2N_2O_3(M-C_4H_8+H)^+$: m/z=305.2; found 305.2.

Intermediate 93. (2R,5S)-1-((4,4-Difluorocyclohexyl)(4-(trifluoromethyl)phenyl)methyl)-2,5-dimethylpiperazine hydrochloride

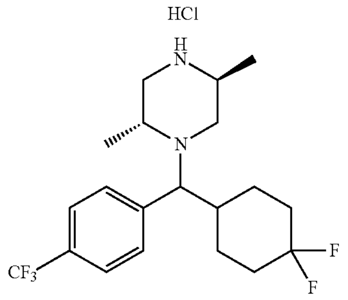 [SMILES: Cl ; C[C@@H]1CN[C@@H](C)CN1C(c1ccc(C(F)(F)F)cc1)C1CCC(F)(F)CC1]

This compound was prepared according to the procedures described for Intermediate 43, with tert-butyl (2S,5R)-4-(4,4-difluorocyclohexane-1-carbonyl)-2,5-dimethylpiperazine-1-carboxylate (Intermediate 92) replacing tert-butyl (2S,5R)-4-(3,3-difluorocyclobutane-1-carbonyl)-2,5-dimethylpiperazine-1-carboxylate. LC-MS calculated for $C_{20}H_{28}F_5N_2(M+H)^+$: m/z=391.2; found 391.2.

Intermediate 94: tert-Butyl (2S,5R)-2,5-dimethyl-4-(4-(trifluoromethoxy)benzoyl)piperazine-1-carboxylate

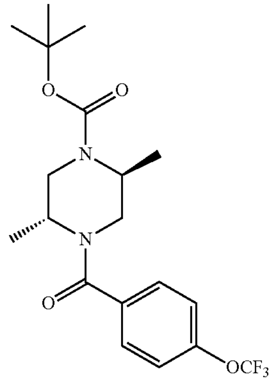 [SMILES: C[C@@H]1CN(C(=O)OC(C)(C)C)[C@@H](C)CN1C(=O)c1ccc(OC(F)(F)F)cc1]

To a mixture of tert-butyl (2S,5R)-2,5-dimethylpiperazine-1-carboxylate (0.500 g, 2.33 mmol, Combi-Blocks OR-8588) in THF (11.7 mL) was added 4-(trifluoromethoxy)benzoyl chloride (0.460 mL, 2.92 mmol, Aldrich 249475) followed by N,N-diisopropylethylamine (1.22 mL, 7.00 mmol) and the reaction mixture was stirred at rt overnight. The mixture was diluted with water and the layers were separated. The organic layer was removed and the aqueous layer was extracted with EtOAc. The combined organic layers were dried over $MgSO_4$ and concentrated in vacuo. The crude residue was purified by flash column chromatography (40 g $SiO_2$, EtOAc/hexanes) to give the desired product in quantitative yield (0.952 g) as a white solid. LC-MS calculated for $C_{15}H_{18}F_3N_2O_4$ $(M-C_4H_8+H)^+$: m/z=347.1; found 347.1.

Intermediate 95. tert-Butyl (2-(6-((2S,5R)-4-(bis(4-fluorophenyl)methyl)-5-ethyl-2-methylpiperazin-1-yl)-2-chloro-9H-purin-9-yl)ethyl)(methyl)carbamate

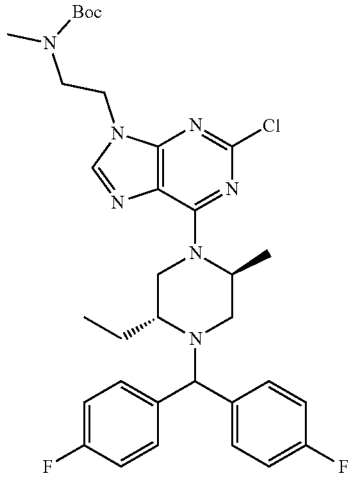 [SMILES: CC[C@@H]1CN(c2nc(Cl)nc3c2ncn3CCN(C)C(=O)OC(C)(C)C)[C@@H](C)CN1C(c1ccc(F)cc1)c1ccc(F)cc1]

This compound was prepared according to the procedures described in Intermediate 35, with 2-(4-((2S,5R)-4-(bis(4-fluorophenyl)methyl)-5-ethyl-2-methylpiperazin-1-yl)-1H-[1,2,4]triazolo[3,4-b]purin-1-yl)-N,N-dimethylethan-1- amine (Intermediate 37) replacing 6-((2S,5R)-4-(bis(4-fluorophenyl)methyl)-2,5-dimethylpiperazin-1-yl)-2-chloro-9H-purine. LC-MS calculated for $C_{33}H_{41}ClF_2N_7O_2$ $(M+H)^+$: m/z=640.3; found 640.3.

Intermediate 96. 2-Chloro-6-((2S,5R)-2,5-dimethyl-4-(2-methyl-1-(4-(trifluoromethoxy)phenyl)propyl)piperazin-1-yl)-8-methyl-9H-purine

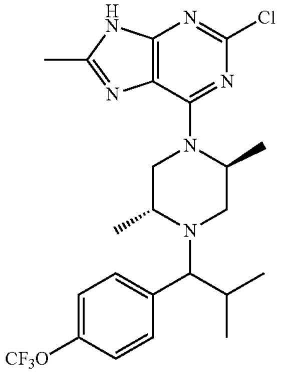

This compound was prepared according to the procedures described for Intermediate 57, with tert-butyl (2S,5R)-2,5-dimethyl-4-(4-(trifluoromethoxy)benzoyl)piperazine-1-carboxylate (Intermediate 94) replacing tert-butyl (2S,5R)-2,5-dimethyl-4-(4-(trifluoromethyl)benzoyl)piperazine-1-carboxylate in Step 1. LC-MS calculated for $C_{23}H_{29}ClF_3N_6O$ $(M+H)^+$: m/z=497.2; found 497.3.

Intermediate 97. (2R,5S)-1-((4-Fluorophenyl)(3,3-difluorocyclobutyl)methyl)-2-ethyl-5-methylpiperazine hydrochloride

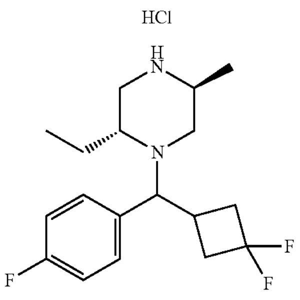 [SMILES: Cl ; CC[C@@H]1CN[C@@H](C)CN1C(c1ccc(F)cc1)C1CC(F)(F)C1]

This compound was prepared according to the procedures described in Intermediate 55, with (4-fluorophenyl)magnesium bromide (1.0 M solution in THF, Aldrich 328820) replacing (4-chlorophenyl)magnesium chloride lithium chloride. LC-MS calculated for $C_{18}H_{26}F_3N_2$ $(M+H)^+$: m/z=327.2; found 327.2.

Intermediate 98. tert-Butyl (2S,5S)-4-(3,3-difluorocyclobutane-1-carbonyl)-5-(hydroxymethyl)-2-methylpiperazine-1-carboxylate

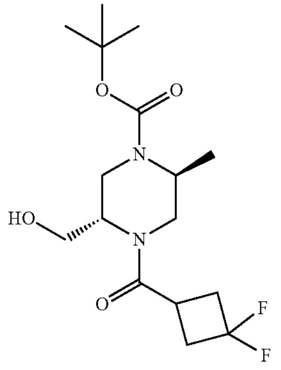 [SMILES: C[C@H]1CN(C(=O)C2CC(F)(F)C2)[C@H](CO)CN1C(=O)OC(C)(C)C]

This compound was prepared according to the procedures described in Intermediate 42, with tert-butyl (2S,5S)-5-(hydroxymethyl)-2-methylpiperazine-1-carboxylate (PharmaBlock PBHA542) replacing tert-butyl (2S,5R)-2,5-dimethylpiperazine-1-carboxylate. LC-MS calculated for $C_{12}H_{19}F_2N_2O_4(M-C_4H_8+H)^+$: m/z=293.1; found 293.1.

Intermediate 99. ((2S,5S)-1-((3,3-Difluorocyclobutyl)(4-(trifluoromethyl)phenyl)methyl)-5-methylpiperazin-2-yl)methanol hydrochloride

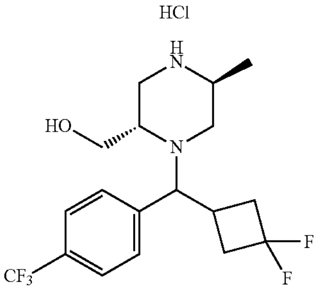 [SMILES: Cl ; C[C@H]1CN(C(c2ccc(C(F)(F)F)cc2)C2CC(F)(F)C2)[C@H](CO)CN1]

This compound was prepared according to the procedures described in Intermediate 43, with tert-butyl (2S,5S)-4-(3,3-difluorocyclobutane-1-carbonyl)-5-(hydroxymethyl)-2-methylpiperazine-1-carboxylate (Intermediate 98) replacing tert-butyl (2S,5R)-4-(3,3-difluorocyclobutane-1-carbonyl)-2,5-dimethylpiperazine-1-carboxylate (Intermediate 42). LC-MS calculated for $C_{18}H_{24}F_5N_2O(M+H)^+$: m/z=379.2; found 379.3.

Intermediate 100. 1-((2S,5S)-1-(Bis(4-fluorophenyl)methyl)-5-methylpiperazin-2-yl)ethan-1-ol hydrochloride

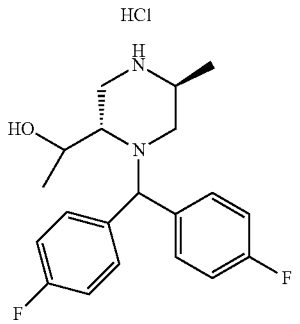 [SMILES: Cl ; CC(O)[C@@H]1CN[C@@H](C)CN1C(c1ccc(F)cc1)c1ccc(F)cc1]

Step 1: tert-Butyl (2S,5S)-4-(bis(4-fluorophenyl)methyl)-5-formyl-2-methylpiperazine-1-carboxylate

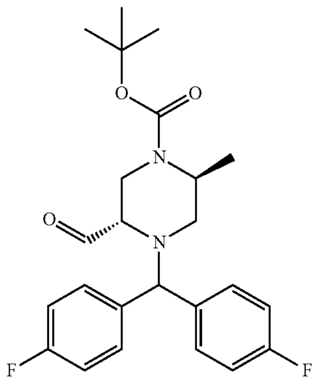 [SMILES: C[C@H]1CN(C(c2ccc(F)cc2)c2ccc(F)cc2)[C@H](C=O)CN1C(=O)OC(C)(C)C]

To a mixture of tert-butyl (2S,5S)-4-(bis(4-fluorophenyl)methyl)-5-(hydroxymethyl)-2-methylpiperazine-1-carboxylate (Intermediate 13, 200. mg, 0.462 mmol) and sodium bicarbonate (117 mg, 1.39 mmol) in $CH_2Cl_2$ (5 mL) was added 1,1,1-tris(acetyloxy)-1,1-dihydro-1,2-benziodoxol-3-(1H)-one (294 mg, 0.694 mmol, Oakwood 011794) and the reaction mixture was stirred at rt for 1 h. The mixture was quenched with 1:1 saturated aqueous $NaHCO_3$ and $Na_2S_2O_3$. The organic layer was removed, and the aqueous layer was extracted with $CH_2Cl_2$. The combined organic layers were dried over $MgSO_4$ and the filtrate was concentrated to afford the desired product. The crude material obtained was used directly without further purification. LC-MS calculated for $C_{24}H_{29}F_2N_2O_3(M+H)^+$: m/z=431.2; found 431.3.

Step 2: tert-Butyl (2S,5S)-4-(bis(4-fluorophenyl)methyl)-5-(1-hydroxyethyl)-2-methylpiperazine-1-carboxylate

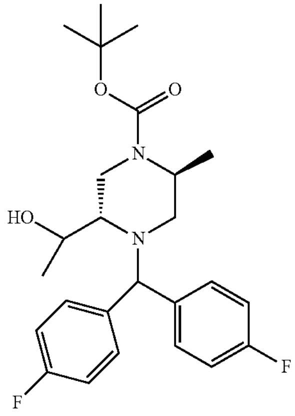 [SMILES: CC(O)[C@@H]1CN(C(=O)OC(C)(C)C)[C@@H](C)CN1C(c1ccc(F)cc1)c1ccc(F)cc1]

A mixture of tert-butyl (2S,5S)-4-(bis(4-fluorophenyl)methyl)-5-formyl-2-methylpiperazine-1-carboxylate (Step 1) in THF (5 mL) was cooled to −78° C. before methylmagnesium bromide (0.33 mL, 0.46 mmol, 1.4 M in THF/toluene (1:3), Aldrich 282235) was added dropwise and the reaction mixture was stirred at −78° C. for 30 min. The mixture was quenched with saturated aqueous $NH_4Cl$. After warming to rt, the organic layer was removed and the aqueous layer was extracted with EtOAc. The combined organic layers were dried over $MgSO_4$ and the filtrate was concentrated to afford the desired product as a mixture of diastereomers. The crude material obtained was used directly without further purification. LC-MS calculated for $C_{25}H_{33}F_2N_2O_3(M+H)^+$: m/z=447.2; found 447.3.

Step 3: 1-((2S,5S)-1-(Bis(4-fluorophenyl)methyl)-5-methylpiperazin-2-yl)ethan-1-ol hydrochloride A mixture of tert-butyl (2S,5S)-4-(bis(4-fluorophenyl)methyl)-5-(1-hydroxyethyl)-2-methylpiperazine-1-carboxylate (Step 2) in THF (5 mL) was treated with HCl (4 M in 1,4-dioxane, 2 mL, 8 mmol, Oakwood 094030) and the reaction mixture was stirred at 60° C. for 1 h. After cooling to rt, the mixture was diluted with diethyl ether and the resulting precipitate was collected by filtration, washed with diethyl ether, and dried under vacuum to afford the desired product (50.0 mg, 31% yield over 3 steps) as a mixture of diastereomers in the form of a white solid. LC-MS calculated for $C_{20}H_{25}F_2N_2O(M+H)^+$: m/z=347.2; found 347.2.

Intermediate 101. tert-Butyl (2S,5R)-4-(4-(difluoromethoxy)benzoyl)-5-ethyl-2-methylpiperazine-1-carboxylate

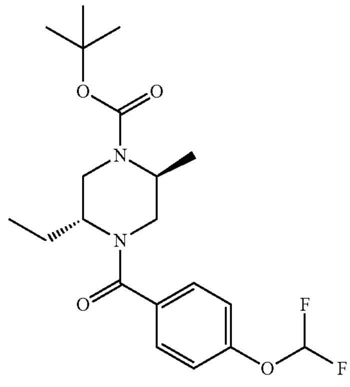 [SMILES: CC[C@@H]1CN(C(=O)OC(C)(C)C)[C@@H](C)CN1C(=O)c1ccc(OC(F)F)cc1]

A mixture of tert-butyl (2S,5R)-5-ethyl-2-methylpiperazine-1-carboxylate (Intermediate 25, 500 mg, 2.2 mmol) and 4-(difluoromethoxy)benzoic acid (453 mg, 2.4 mmol) in DMF (10 mL) was treated with N,N-diisopropylethylamine (1.15 mL, 6.6 mmol) and HATU (1.67 g, 4.4 mmol) and the reaction mixture was stirred at rt for overnight. The mixture was diluted with EtOAc and water. The layers were separated and the organic layer was washed three times with water, dried over $Na_2SO_4$, and concentrated in vacuo. The crude residue was purified by flash column chromatography ($SiO_2$, EtOAc/hexanes) to give the title compound as a white solid. LCMS calculated for $C_{16}H_{21}F_2N_2O_4(M-C_4H_8+H)^+$: m/z=343.2; found 343.2.

Intermediate 102. (2R,5S)-1-(1-(4-(Difluoromethoxy)phenyl)-2-methylpropyl)-2-ethyl-5-methylpiperazine hydrochloride

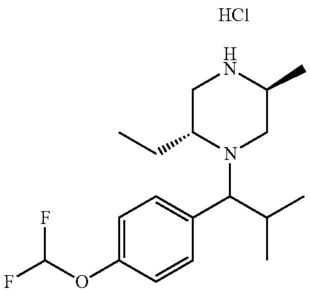 [SMILES: Cl ; CC[C@@H]1CN[C@@H](C)CN1C(c1ccc(OC(F)F)cc1)C(C)C]

Step 1: tert-Butyl (2S,5R)-4-(1-(4-(difluoromethoxy)phenyl)-2-methylpropyl)-5-ethyl-2-methylpiperazine-1-carboxylate

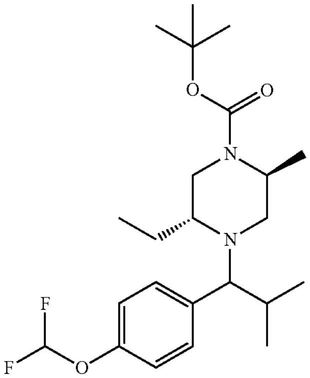 [SMILES: CC[C@@H]1CN(C(=O)OC(C)(C)C)[C@@H](C)CN1C(c1ccc(OC(F)F)cc1)C(C)C]

A mixture of tert-butyl (2S,5R)-4-(4-(difluoromethoxy)benzoyl)-5-ethyl-2-methylpiperazine-1-carboxylate (Intermediate 101, 100. mg, 0.25 mmol) and chlorocarbonylbis(triphenylphosphine)iridium(I) (2.0 mg, 0.0025 mmol) in $CH_2Cl_2$ (2.5 mL) was treated with 1,1,3,3-tetramethyldisiloxane (0.088 mL, 0.50 mmol) and stirred at rt for 15 min. Immediate gas evolution was observed, and the yellow color of the catalyst became bleached over the course of 15 min. The reaction was cooled to −78° C. and stirred for 5 min before isopropylmagnesium chloride lithium chloride (0.384 mL, 1.3 M in THF, 0.50 mmol) was added dropwise and the reaction mixture was stirred for an additional 5 min. The reaction mixture was warmed to 0° C. and stirred for 30 min. The mixture was quenched with saturated aqueous $NH_4Cl$. After warming to rt, the organic layer was removed and the aqueous layer was extracted with $CH_2Cl_2$. The combined organic layers were dried over $MgSO_4$ and the filtrate was concentrated. The crude residue was purified by flash column chromatography ($SiO_2$, EtOAc/hexanes) to afford desired product as a mixture of diastereomers. LCMS calculated for $C_{23}H_{37}F_2N_2O_3(M+H)^+$: m/z=427.3; found 427.3.

Step 2: (2R,5S)-1-(1-(4-(Difluoromethoxy)phenyl)-2-methylpropyl)-2-ethyl-5-methylpiperazine hydrochloride To a mixture of tert-butyl (2S,5R)-4-(1-(4-(difluoromethoxy)phenyl)-2-methylpropyl)-5-ethyl-2-methylpiperazine-1-carboxylate (Step 1) in $CH_2Cl_2$ (1.0 mL) was added a 4 molar solution of HCl in 1,4-dioxane (0.25 mL, 1.0 mmol), and the reaction mixture was allowed to stir at rt for 4 h. The reaction mixture was concentrated in vacuo to afford the desired product as a mixture of diastereomers. The crude material obtained was used directly without further purification. LC-MS calculated for $C_{18}H_{29}F_2N_2O$ $(M+H)^+$: m/z=327.2; found 327.3.

Intermediate 103. tert-Butyl (2S,5R)-4-(4-cyanobenzoyl)-5-ethyl-2-methylpiperazine-1-carboxylate

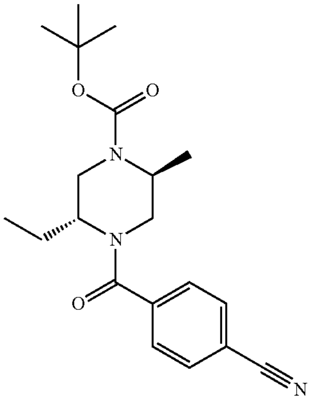 [SMILES: CC[C@@H]1CN(C(=O)OC(C)(C)C)[C@@H](C)CN1C(=O)c1ccc(C#N)cc1]

A mixture of tert-butyl (2S,5R)-5-ethyl-2-methylpiperazine-1-carboxylate (Intermediate 25, 0.800 g, 3.5 mmol) and 4-cyanobenzoic acid (567 mg, 3.9 mmol) in DMF (15 mL) was treated with N,N-diisopropylethylamine (1.84 mL, 10.5 mmol) and HATU (2.6 g, 7.0 mmol) and the reaction mixture was stirred at rt overnight. The mixture was diluted with EtOAc and water. The layers were separated and the organic layer was washed three times with water, dried over $Na_2SO_4$, and concentrated in vacuo. The crude residue was purified by flash column chromatography ($SiO_2$, EtOAc/hexanes) to give the title compound (1.07 g, 85% yield) as a white solid. LCMS calculated for $C_{16}H_{20}N_3O_3(M-C_4H_8+H)^+$: m/z=302.2; found 302.2.

Intermediates 104 and 105. tert-Butyl (2S,5R)-4-((S)-(4-cyanophenyl)(4-fluorophenyl)methyl)-5-ethyl-2-methylpiperazine-1-carboxylate and tert-butyl (2S,5R)-4-((R)-(4-cyanophenyl)(4-fluorophenyl)methyl)-5-ethyl-2-methylpiperazine-1-carboxylate

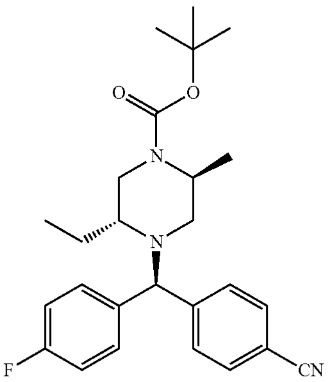

and

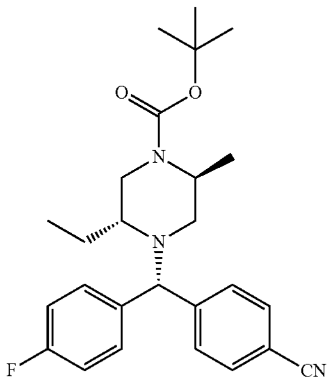

A mixture of tert-butyl (2S,5R)-4-(4-cyanobenzoyl)-5-ethyl-2-methylpiperazine-1-carboxylate (Intermediate 103, 350 mg, 0.98 mmol) and chlorocarbonylbis(triphenylphosphine)iridium(I) (7.6 mg, 0.0098 mmol) in $CH_2Cl_2$ (10 mL) was treated with 1,1,3,3-tetramethyldisiloxane (0.35 mL, 2.0 mmol) and stirred at rt for 15 min. Immediate gas evolution was observed, and the yellow color of the catalyst became bleached over the course of 15 min. The reaction was cooled to −78° C. and stirred for 5 min before (4-fluorophenyl) magnesium bromide (1.0 M in THF, 1.18 mL, 1.18 mmol) was added dropwise and the reaction mixture was stirred for an additional 5 min. The reaction mixture was warmed to 0° C. and stirred for 30 min. The mixture was quenched with saturated aqueous $NH_4Cl$. After warming to rt, the organic layer was removed and the aqueous layer was extracted with $CH_2Cl_2$. The combined organic layers were dried over $Na_2SO_4$, filtered, and the filtrate was concentrated in vacuo. The crude residue containing a mixture of diastereomers was purified by flash column chromatography ($SiO_2$, EtOAc/hexanes) to afford each desired product as a single diastereomer.

Intermediate 104: Retention time on LCMS $t_r$=1.82 min, LCMS calculated for $C_{26}H_{33}FN_3O_2(M+H)^+$: m/z=438.3; found 438.3.

Intermediate 105: Retention time on LCMS $t_r$=1.84 min, LCMS calculated for $C_{26}H_{33}FN_3O_2(M+H)^+$: m/z=438.3; found 438.3.

Intermediate 106. 4-(((2R,5S)-2-Ethyl-5-methylpiperazin-1-yl)(4-fluorophenyl)methyl)benzonitrile hydrochloride

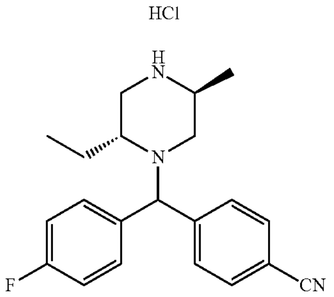 [SMILES: Cl ; CC[C@@H]1CN[C@@H](C)CN1C(c1ccc(F)cc1)c1ccc(C#N)cc1]

To a mixture of tert-butyl (2S,5R)-4-((4-cyanophenyl)(4-fluorophenyl)methyl)-5-ethyl-2-methylpiperazine-1-carboxylate (Intermediate 104, 428 mg, 0.98 mmol) in $CH_2Cl_2$ (1.0 mL) was added a 4 molar solution of HCl in 1,4-dioxane (0.25 mL, 1.0 mmol), and the reaction mixture was allowed to stir at rt for 4 h. The reaction mixture was concentrated in vacuo, and the crude residue was used for next step without further purification. LC-MS calculated for $C_{21}H_{25}FN_3$ $(M+H)^+$: m/z=338.2; found 338.2.

Intermediate 107. 4-(((2R,5S)-2-Ethyl-5-methylpiperazin-1-yl)(4-fluorophenyl)methyl)benzonitrile hydrochloride

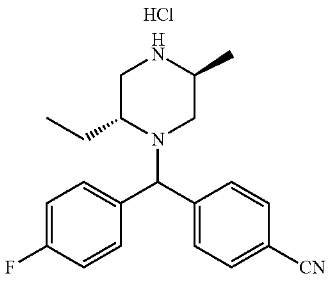 [SMILES: Cl ; CC[C@@H]1CN[C@@H](C)CN1C(c1ccc(F)cc1)c1ccc(C#N)cc1]

This compound was prepared according to the procedures described in Intermediate 106, with tert-butyl (2S,5R)-4-((4-cyanophenyl)(4-fluorophenyl)methyl)-5-ethyl-2-methylpiperazine-1-carboxylate (Intermediate 105) replacing Intermediate 104. LC-MS calculated for $C_{21}H_{25}FN_3$ $(M+H)^+$: m/z=338.2; found 338.2.

Intermediate 108. (2R,5S)-1-(Bis(4-(trifluoromethyl)phenyl)methyl)-2,5-dimethylpiperazine hydrochloride

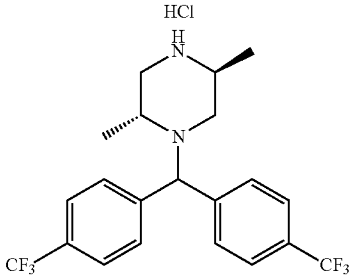 [SMILES: Cl ; C[C@@H]1CN[C@@H](C)CN1C(c1ccc(C(F)(F)F)cc1)c1ccc(C(F)(F)F)cc1]

This compound was prepared according to the procedures described for Intermediate 74, with tert-butyl (2S,5R)-2,5-dimethyl-4-(4-(trifluoromethyl)benzoyl)piperazine-1-carboxylate (Intermediate 56) replacing tert-butyl (2S,5R)-2,5-dimethyl-4-(5-(trifluoromethyl)picolinoyl)piperazine-1-carboxylate in Step 2. LCMS calculated for $C_{21}H_{23}F_6N_2$ $(M+H)^+$: m/z=417.2; found 417.2.

Intermediate 109. 6-((2S,5R)-4-(Bis(4-(trifluoromethyl)phenyl)methyl)-2,5-dimethylpiperazin-1-yl)-2-chloro-8-methyl-9H-purine

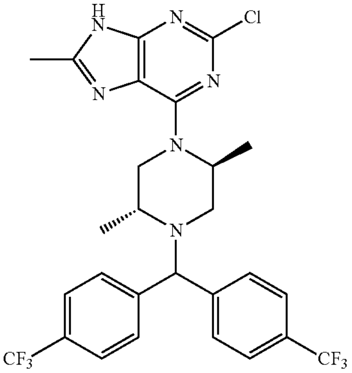 [SMILES: Cc1nc2c(N3C[C@@H](C)N(C(c4ccc(C(F)(F)F)cc4)c4ccc(C(F)(F)F)cc4)C[C@@H]3C)nc(Cl)nc2[nH]1]

This compound was prepared according to the procedures described for Intermediate 23, with (2R,5S)-1-(bis(4-(trifluoromethyl)phenyl)methyl)-2,5-dimethylpiperazine hydrochloride (Intermediate 108) replacing (2R,5S)-1-(bis(4-fluorophenyl)methyl)-2,5-dimethylpiperazine hydrochloride. LCMS calculated for $C_{26}H_{24}ClF_6N_6(M+H)^+$: m/z=569.2; found 569.2.

Intermediate 110. (2R,5S)-1-((3,3-Difluorocyclobutyl)(4-(difluoromethyl)-3-fluorophenyl)methyl)-2,5-dimethylpiperazine hydrochloride

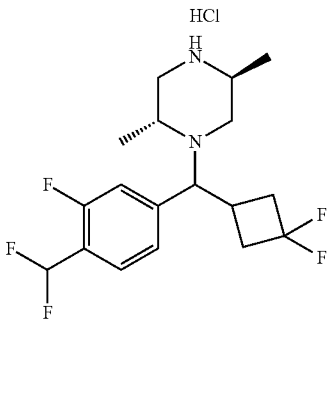 [SMILES: Cl ; C[C@@H]1CN[C@@H](C)CN1C(c1ccc(C(F)F)c(F)c1)C1CC(F)(F)C1]

This compound was prepared according to the procedures described in Intermediate 63, with tert-butyl (2S,5R)-4-(3,3-difluorocyclobutane-1-carbonyl)-2,5-dimethylpiperazine-1-carboxylate (Intermediate 42) replacing tert-butyl (2S,5R)-4-isobutyryl-2,5-dimethylpiperazine-1-carboxylate (Intermediate 62) in Step 2. LC-MS calculated for $C_{18}H_{24}F_5N_2$ $(M+H)^+$: m/z=363.2; found 363.2.

Intermediate 111: ((2S,5S)-1-(Bis(4-chlorophenyl)methyl)-5-methylpiperazin-2-yl)methanol hydrochloride

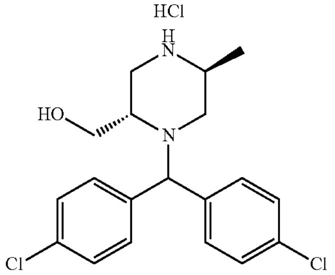 [SMILES: Cl ; C[C@H]1CN(C(c2ccc(Cl)cc2)c2ccc(Cl)cc2)[C@H](CO)CN1]

This compound was prepared according to the procedures described in Intermediate 38, with tert-butyl (2S,5S)-5-(hydroxymethyl)-2-methylpiperazine-1-carboxylate (PharmaBlock PBHA542) replacing tert-butyl (2S,5R)-5-ethyl-2-methylpiperazine-1-carboxylate (Intermediate 25) in Step 1. LC-MS calculated for $C_{19}H_{23}Cl_2N_2O(M+H)^+$: m/z=365.1; found 365.2.

Intermediate 112. (2R,5S)-1-(1-(4-Bromophenyl)-2-methylpropyl)-2,5-dimethylpiperazine hydrochloride

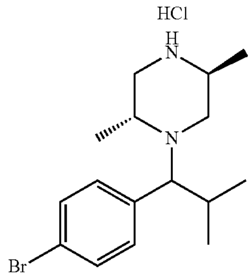 [SMILES: Cl ; CC(C)C(c1ccc(Br)cc1)N1C[C@H](C)NC[C@H]1C]

This compound was prepared according to the procedures described in Intermediate 57, Steps 1-2 with tert-butyl (2S,5R)-4-(4-bromobenzoyl)-2,5-dimethylpiperazine-1-carboxylate (Intermediate 85) replacing tert-butyl (2S,5R)-2,5-dimethyl-4-(4-(trifluoromethyl)benzoyl)piperazine-1-carboxylate in Step 1. LC-MS calculated for $C_{16}H_{26}BrN_2$ $(M+H)^+$: m/z=325.1; found 325.2.

Intermediate 113. 6-((2S,5R)-4-(Bis(4-chlorophenyl)methyl)-2,5-dimethylpiperazin-1-yl)-2-chloro-9H-purine

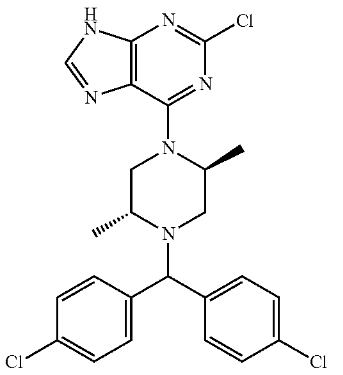 [SMILES: C[C@@H]1CN(c2nc(Cl)nc3[nH]cnc23)[C@@H](C)CN1C(c1ccc(Cl)cc1)c1ccc(Cl)cc1]

This compound was prepared according to the procedures described in Intermediate 21, with (2R,5S)-1-(bis(4-chlorophenyl)methyl)-2,5-dimethylpiperazine hydrochloride (Intermediate 83) replacing (2R,5S)-1-(bis(4-fluorophenyl)methyl)-2,5-dimethylpiperazine hydrochloride. LC-MS calculated for $C_{24}H_{24}Cl_3N_6(M+H)^+$: m/z=501.1; found 501.2.

Intermediate 114: (2R,5S)-1-((3-Chloro-4-fluorophenyl)(4-chlorophenyl)methyl)-2,5-dimethylpiperazine hydrochloride

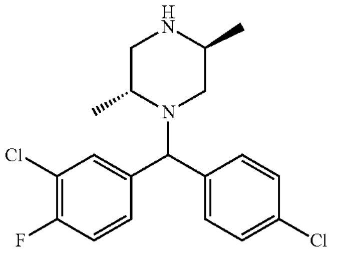

This compound was prepared according to the procedures described in Intermediate 44, with tert-butyl (2S,5R)-4-(4-chlorobenzoyl)-2,5-dimethylpiperazine-1-carboxylate (Intermediate 66) replacing tert-butyl (2S,5R)-4-(3,3-difluorocyclobutane-1-carbonyl)-2,5-dimethylpiperazine-1-carboxylate. LC-MS calculated for $C_{19}H_{22}Cl_2FN_2$ $(M+H)^+$: m/z=367.1; found 367.2.

Intermediate 115. (2R,5S)-1-((3-Chloro-4-fluorophenyl)(4-bromophenyl)methyl)-2,5-dimethylpiperazine hydrochloride

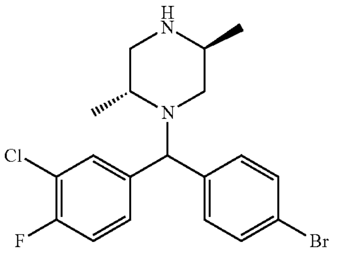

This compound was prepared according to the procedures described in Intermediate 44, with tert-butyl (2S,5R)-4-(4-bromobenzoyl)-2,5-dimethylpiperazine-1-carboxylate (Intermediate 85) replacing tert-butyl (2S,5R)-4-(3,3-difluorocyclobutane-1-carbonyl)-2,5-dimethylpiperazine-1-carboxylate. LC-MS calculated for $C_{19}H_{22}BrClFN_2$ $(M+H)^+$: m/z=411.1; found 411.1.

Example 1. 4-((2S,5R)-4-(Bis(4-fluorophenyl)methyl)-2,5-dimethylpiperazin-1-yl)thiazolo[4,5-e][1,2,4]triazolo[4,3-a]pyrimidine

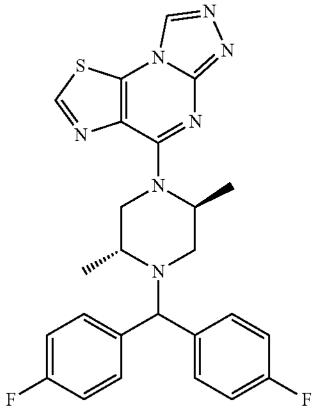 [SMILES: C[C@@H]1CN(c2nc3nncn3c3scnc23)[C@@H](C)CN1C(c1ccc(F)cc1)c1ccc(F)cc1]

Step 1. 7-((2S,5R)-4-(Bis(4-fluorophenyl)methyl)-2,5-dimethylpiperazin-1-yl)-5-hydrazineylthiazolo[5,4-d]pyrimidine

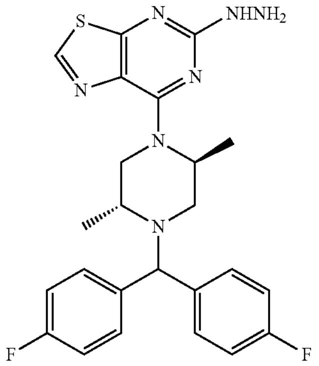 [SMILES: C[C@@H]1CN(c2nc(NN)nc3scnc23)[C@@H](C)CN1C(c1ccc(F)cc1)c1ccc(F)cc1]

To a mixture of 7-((2S,5R)-4-(bis(4-fluorophenyl)methyl)-2,5-dimethylpiperazin-1-yl)-5-chlorothiazolo[5,4-d]pyrimidine (Intermediate 2, 48.6 mg, 0.100 mmol), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (17.1 mg, 0.020 mmol, Aldrich 745979) and cesium carbonate (65.2 mg, 0.200 mmol) was added a 1 molar solution of hydrazine in THF (0.50 mL, 0.50 mmol, Aldrich 433632) and the reaction mixture was stirred at 60° C. for 30 min. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude material obtained was used directly without further purification. LC-MS calculated for $C_{24}H_{26}F_2N_7S$ $(M+H)^+$: m/z=482.2; found 482.2.

Step 2. 4-((2S,5R)-4-(Bis(4-fluorophenyl)methyl)-2,5-dimethylpiperazin-1-yl)thiazolo[4,5-e][1,2,4]triazolo[4,3-a]pyrimidine A mixture of 7-((2S,5R)-4-(bis(4-fluorophenyl)methyl)-2,5-dimethylpiperazin-1-yl)-5-hydrazineylthiazolo[5,4-d]pyrimidine (Step 1), trimethyl orthoformate (111 μL, 1.0 mmol), and AcOH (6 mg, 0.1 mmol) was stirred at 100° C. for 30 min. After cooling to rt, the reaction mixture was diluted with acetonitrile, water, and several drops of TFA, and the mixture was filtered and purified by prep-HPLC (Sunfire C18 column, eluting with a gradient of acetonitrile/water containing 0.1% TFA, at flow rate of 60 mL/min) to afford the desired product as its TFA salt. LC-MS calculated for $C_{25}H_{24}F_2N_7S$ $(M+H)^+$: m/z=492.2; found 492.1.

Example 2. 4-((2S,5R)-4-(Bis(4-fluorophenyl)methyl)-2,5-dimethylpiperazin-1-yl)-8-methylthiazolo[4,5-e][1,2,4]triazolo[4,3-a]pyrimidine

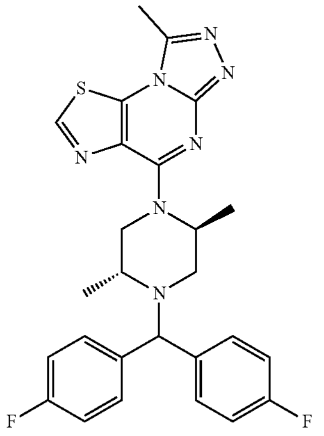 [SMILES: Cc1nnc2nc(N3C[C@@H](C)N(C(c4ccc(F)cc4)c4ccc(F)cc4)C[C@@H]3C)c3ncsc3n12]

This compound was prepared according to the procedures described in Example 1, with triethyl orthoacetate replacing trimethyl orthoformate in Step 2. LC-MS calculated for $C_{26}H_{26}F_2N_7S$ $(M+H)^+$: m/z=506.2; found 506.1.

Example 3. 4-((2S,5R)-4-(Bis(4-fluorophenyl)methyl)-2,5-dimethylpiperazin-1-yl)-2-(difluoromethyl)thiazolo[4,5-e][1,2,4]triazolo[4,3-a]pyrimidine

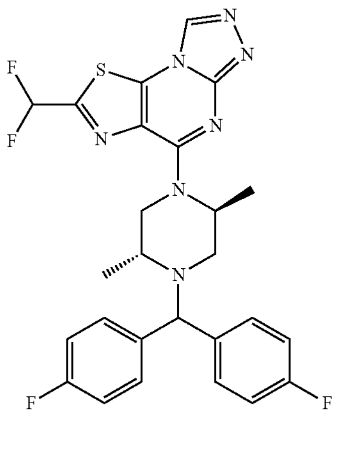 [SMILES: C[C@@H]1CN(c2nc3nncn3c3sc(C(F)F)nc23)[C@@H](C)CN1C(c1ccc(F)cc1)c1ccc(F)cc1]

This compound was prepared according to the procedures described in Example 1, with 7-((2S,5R)-4-(bis(4-fluorophenyl)methyl)-2,5-dimethylpiperazin-1-yl)-5-chloro-2-(difluoromethyl)thiazolo[5,4-d]pyrimidine (Intermediate 4) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{26}H_{24}F_4N_7S$ $(M+H)^+$: m/z=542.2; found 542.1.

Example 4. 3-(4-((2S,5R)-4-(Bis(4-fluorophenyl)methyl)-2,5-dimethylpiperazin-1-yl)thiazolo[4,5-e][1,2,4]triazolo[4,3-a]pyrimidin-2-yl)propanenitrile

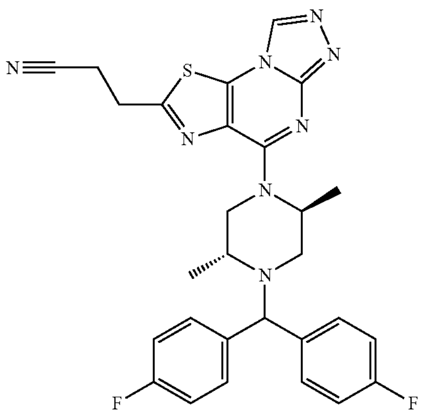 [SMILES: C[C@@H]1CN(c2nc3nncn3c3sc(CCC#N)nc23)[C@@H](C)CN1C(c1ccc(F)cc1)c1ccc(F)cc1]

Step 1. 3-(7-((2S,5R)-4-(Bis(4-fluorophenyl)methyl)-2,5-dimethylpiperazin-1-yl)-5-hydrazineylthiazolo[5,4-d]pyrimidin-2-yl)propanenitrile

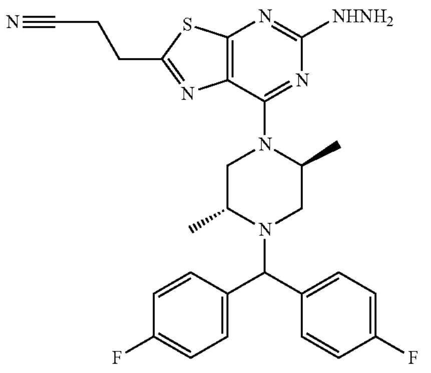 [SMILES: C[C@@H]1CN(c2nc(NN)nc3sc(CCC#N)nc23)[C@@H](C)CN1C(c1ccc(F)cc1)c1ccc(F)cc1]

To a mixture of 3-(7-((2S,5R)-4-(bis(4-fluorophenyl)methyl)-2,5-dimethylpiperazin-1-yl)-5-chlorothiazolo[5,4-d]pyrimidin-2-yl)propanenitrile (Intermediate 5, 87.9 mg, 0.163 mmol), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (28 mg, 0.033 mmol, Aldrich 745979) and cesium carbonate (106 mg, 0.326 mmol) was added a 1 molar solution of hydrazine in THF (0.82 mL, 0.82 mmol) and the reaction mixture was stirred at 60° C. for 30 min. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude material obtained was used directly without further purification. LC-MS calculated for $C_{27}H_{29}F_2N_8S$ $(M+H)^+$: m/z=535.2; found 535.2.

Step 2. 3-(4-((2S,5R)-4-(Bis(4-fluorophenyl)methyl)-2,5-dimethylpiperazin-1-yl)thiazolo[4,5-e][2,4]triazolo[4,3-a]pyrimidin-2-yl)propanenitrile A mixture of 3-(7-((2S,5R)-4-(bis(4-fluorophenyl)methyl)-2,5-dimethylpiperazin-1-yl)-5-hydrazineylthiazolo[5,4-d]pyrimidin-2-yl)propanenitrile (Step 1), trimethyl orthoformate (0.18 mL, 1.6 mmol), and AcOH (10 mg, 0.17 mmol) was stirred at 100° C. for 30 min. After cooling to rt, the reaction mixture was diluted with acetonitrile, water, and several drops of TFA, and the mixture was filtered and purified by prep-HPLC (Sunfire C18 column, eluting with a gradient of acetonitrile/water containing 0.1% TFA, at flow rate of 60 mL/min) to afford the desired product as its TFA salt. LC-MS calculated for $C_{28}H_{27}F_2N_8S$ $(M+H)^+$: m/z=545.2; found 545.2.

Example 5. 4-((2S,5R)-4-(Bis(4-fluorophenyl)methyl)-2,5-dimethylpiperazin-1-yl)-2-(1H-pyrazol-4-yl)thiazolo[4,5-e][1,2,4]triazolo[4,3-a]pyrimidine

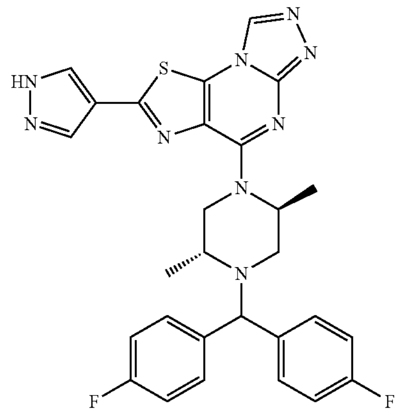 [SMILES: C[C@@H]1CN(c2nc3nncn3c3sc(-c4cn[nH]c4)nc23)[C@@H](C)CN1C(c1ccc(F)cc1)c1ccc(F)cc1]

Step 1. 7-((2S,5R)-4-(Bis(4-fluorophenyl)methyl)-2,5-dimethylpiperazin-1-yl)-5-chloro-2-(1-(1-ethoxyethyl)-1H-pyrazol-4-yl)thiazolo[5,4-d]pyrimidine

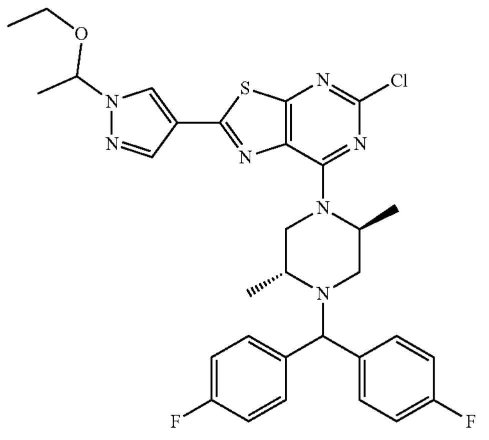 [SMILES: CCOC(C)n1cc(-c2nc3c(N4C[C@@H](C)N(C(c5ccc(F)cc5)c5ccc(F)cc5)C[C@@H]4C)nc(Cl)nc3s2)cn1]

A mixture of 7-((2S,5R)-4-(bis(4-fluorophenyl)methyl)-2,5-dimethylpiperazin-1-yl)-5-chloro-2-idothiazolo[5,4-d]pyrimidine (Intermediate 3, 40.0 mg, 0.065 mmol), 1-(1-ethoxyethyl)-4-(4,4,5,5-tetramethyl-1,3,2-dioxaborolan-2-yl)-1H-pyrazole (17.4 mg, 0.065 mmol, AstaTech 26684), 1,1'-bis(diphenylphosphino)ferrocene-palladium(II)dichloride dichloromethane complex (5.3 mg, 6.5 μmol, Combi-Blocks ST-8328), $K_3PO_4$ (27.7 mg, 0.13 mmol) in 1,4-dioxane/$H_2O$ (5:1, 0.33 mL) was purged with $N_2$ and stirred at 80° C. for 2 h. After cooling to rt, the reaction mixture was diluted with sat. aq. $NaHCO_3$ and extracted with $CH_2Cl_2$. The combined organic layers were filtered through a pad of $MgSO_4$ in a SiliaPrep SPE thiol cartridge (500 mg, SiliCycle SPE-R51030B-06P). The filtrate was concentrated, and the crude material obtained was used directly without further purification. LC-MS calculated for $C_{31}H_{33}ClF_2N_7OS$ $(M+H)^+$: m/z=624.2; found 624.2.

Step 2. 7-((2S,5R)-4-(Bis(4-fluorophenyl)methyl)-2,5-dimethylpiperazin-1-yl)-2-(1-(1-ethoxyethyl)-1H-pyrazol-4-yl)-5-hydrazineylthiazolo[5,4-d]pyrimidine

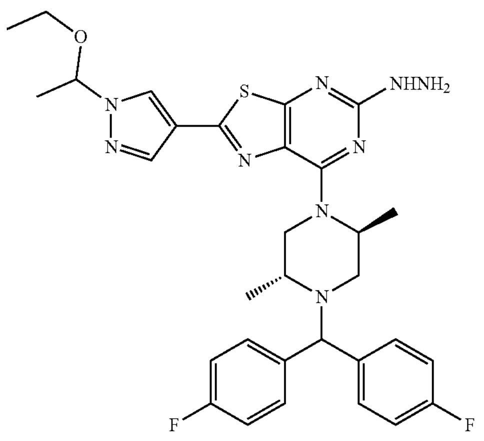 [SMILES: CCOC(C)n1cc(-c2nc3c(N4C[C@@H](C)N(C(c5ccc(F)cc5)c5ccc(F)cc5)C[C@@H]4C)nc(NN)nc3s2)cn1]

To a mixture of 7-((2S,5R)-4-(bis(4-fluorophenyl)methyl)-2,5-dimethylpiperazin-1-yl)-5-chloro-2-(1-(1-ethoxyethyl)-1H-pyrazol-4-yl)thiazolo[5,4-d]pyrimidine (Step 1), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (11.2 mg, 0.013 mmol, Aldrich 745979) and cesium carbonate (42.6 mg, 0.13 mmol) was added a 1 molar solution of hydrazine in THF (327 μL, 0.327 mmol) and the mixture stirred at 60° C. for 30 min. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude material obtained was used directly without further purification. LC-MS calculated for $C_{31}H_{36}F_2N_9OS$ $(M+H)^+$: m/z=620.3; found 620.4.

Step 3. 4-((2S,5R)-4-(Bis(4-fluorophenyl)methyl)-2,5-dimethylpiperazin-1-yl)-2-(1-(1-ethoxyethyl)-1H-pyrazol-4-yl)thiazolo[4,5-e][1,2,4]triazolo[4,3-a]pyrimidine

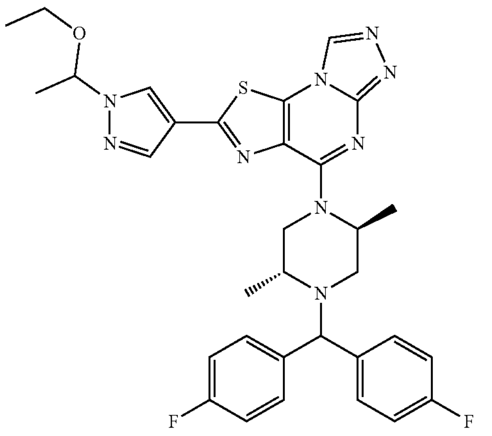 [SMILES: CCOC(C)n1cc(-c2nc3c(N4C[C@@H](C)N(C(c5ccc(F)cc5)c5ccc(F)cc5)C[C@@H]4C)nc4nncn4c3s2)cn1]

A mixture of 7-((2S,5R)-4-(bis(4-fluorophenyl)methyl)-2,5-dimethylpiperazin-1-yl)-2-(1-(1-ethoxyethyl)-1H-pyrazol-4-yl)-5-hydrazinylthiazolo[5,4-d]pyrimidine (Step 2), trimethyl orthoformate (72 μL, 0.65 mmol), and AcOH (4 mg, 0.07 mmol) was stirred at 100° C. for 30 min. After cooling to rt, the reaction mixture was diluted with $CH_2Cl_2$ and filtered over a pad of $MgSO_4$. The filtrate was concentrated, and the crude material obtained was used directly without further purification. LC-MS calculated for $C_{32}H_{34}F_2N_9OS$ $(M+H)^+$: m/z=630.3; found 630.3.

Step 4. 4-((2S,5R)-4-(Bis(4-fluorophenyl)methyl)-2,5-dimethylpiperazin-1-yl)-2-(1H-pyrazol-4-yl)thiazolo[4,5-e][1,2,4]triazolo[4,3-a]pyrimidine To a mixture of 4-((2S,5R)-4-(bis(4-fluorophenyl)methyl)-2,5-dimethylpiperazin-1-yl)-2-(1-(1-ethoxyethyl)-1H-pyrazol-4-yl)thiazolo[4,5-e][1,2,4]triazolo[4,3-a]pyrimidine (Step 3) in MeOH (0.33 mL) was added a 4 molar solution of HCl in 1,4-dioxane (163 μL, 0.65 mmol) and the mixture was stirred at 60° C. for 15 mins. After cooling to rt, the reaction mixture was diluted with acetonitrile, water, and several drops of TFA, and the mixture was filtered and purified by prep-HPLC (Sunfire C18 column, eluting with a gradient of acetonitrile/water containing 0.10% TFA, at flow rate of 60 mL/min) to afford the desired product as its TFA salt. LC-MS calculated for $C_{28}H_{26}F_2N_9S$ $(M+H)^+$: m/z=558.2; found 558.1.

Example 6. 4-((2S,5R)-4-(Bis(4-fluorophenyl)methyl)-2,5-dimethylpiperazin-1-yl)-1-methyl-1H-pyrazolo[4,3-e][1,2,4]triazolo[4,3-a]pyrimidine

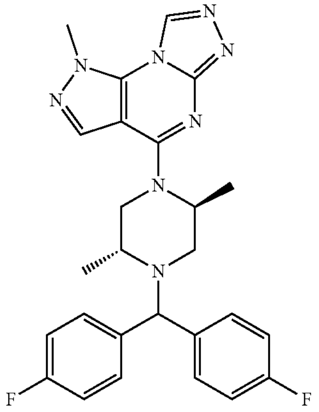 [SMILES: C[C@@H]1CN(c2nc3nncn3c3c2cnn3C)[C@@H](C)CN1C(c1ccc(F)cc1)c1ccc(F)cc1]

This compound was prepared according to the procedures described in Example 1, with 4-((2S,5R)-4-(bis(4-fluorophenyl)methyl)-2,5-dimethylpiperazin-1-yl)-6-chloro-1-methyl-1H-pyrazolo[3,4-d]pyrimidine (Intermediate 6) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{26}H_{27}F_2N_8$ $(M+H)^+$: m/z=489.2; found 489.2. $^1H$ NMR (500 MHz, DMSO-$d_6$, 70° C.) δ 9.56 (s, 1H), 8.48 (s, 1H), 7.66-7.52 (m, 4H), 7.21-7.09 (m, 4H), 4.96 (br s, 1H), 4.71 (s, 1H), 4.59-4.36 (br m, 1H), 4.31 (s, 3H), 3.91-3.74 (br m, 1H), 3.28-3.19 (m, 1H), 2.79 (dd, J=12.4, 4.1 Hz, 1H), 2.52-2.45 (m, 1H), 1.51 (d, J=6.7 Hz, 3H), 0.94 (d, J=6.5 Hz, 3H).

Example 7. 5-((2S,5R)-4-(Bis(4-fluorophenyl)methyl)-2,5-dimethylpiperazin-1-yl)furo[2,3-e][1,2,4]triazolo[4,3-a]pyrimidine

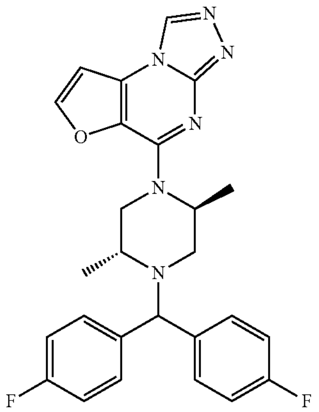 [SMILES: C[C@@H]1CN(c2nc3nncn3c3ccoc23)[C@@H](C)CN1C(c1ccc(F)cc1)c1ccc(F)cc1]

This compound was prepared according to the procedures described in Example 1, with 4-((2S,5R)-4-(bis(4-fluorophenyl)methyl)-2,5-dimethylpiperazin-1-yl)-2-chlorofuro[3,2-d]pyrimidine (Intermediate 7) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{26}H_{25}F_2N_6O$ $(M+H)^+$: m/z=475.2; found 475.2. $^1$H NMR (500 MHz, DMSO-$d_6$, 70° C.) δ 9.41 (s, 1H), 8.45 (d, J=2.3 Hz, 1H), 7.66-7.53 (m, 5H), 7.21-7.09 (m, 4H), 5.13-5.04 (m, 1H), 4.71 (s, 1H), 4.63 (d, J=13.5 Hz, 1H), 3.88 (br s, 1H), 3.28-3.20 (m, 1H), 2.86-2.79 (m, 1H), 2.54-2.46 (m, 1H), 1.54 (d, J=6.7 Hz, 3H), 0.97 (d, J=6.5 Hz, 3H).

Example 8. 5-((2S,5R)-4-(Bis(4-fluorophenyl)methyl)-2,5-dimethylpiperazin-1-yl)thieno[2,3-e][1,2,4]triazolo[4,3-a]pyrimidine

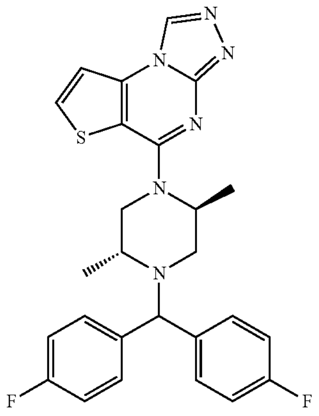 [SMILES: C[C@@H]1CN(c2nc3nncn3c3ccsc23)[C@@H](C)CN1C(c1ccc(F)cc1)c1ccc(F)cc1]

This compound was prepared according to the procedures described in Example 1, with 4-((2S,5R)-4-(bis(4-fluorophenyl)methyl)-2,5-dimethylpiperazin-1-yl)-2-chlorothieno[3,2-d]pyrimidine (Intermediate 8) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{26}H_{25}F_2N_6S$ $(M+H)^+$: m/z=491.2; found 491.2.

Example 9. 4-((2S,5R)-4-(Bis(4-fluorophenyl)methyl)-2,5-dimethylpiperazin-1-yl)-1-methyl-1H-[1,2,4]triazolo[3,4-b]purine

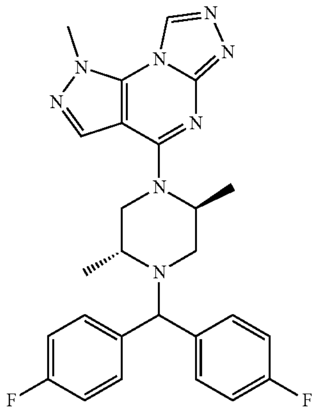 [SMILES: C[C@@H]1CN(c2nc3nncn3c3c2cnn3C)[C@@H](C)CN1C(c1ccc(F)cc1)c1ccc(F)cc1]

This compound was prepared according to the procedures described in Example 1, with 6-((2S,5R)-4-(bis(4-fluorophenyl)methyl)-2,5-dimethylpiperazin-1-yl)-2-chloro-9-methyl-9H-purine (Intermediate 9) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{26}H_{27}F_2N_8(M+H)^+$: m/z=489.2; found 489.1.

Example 10. 5-((2S,5R)-4-(Bis(4-fluorophenyl)methyl)-2,5-dimethylpiperazin-1-yl)-6-ethyl-6H-pyrrolo[2,3-e][1,2,4]triazolo[4,3-a]pyrimidine

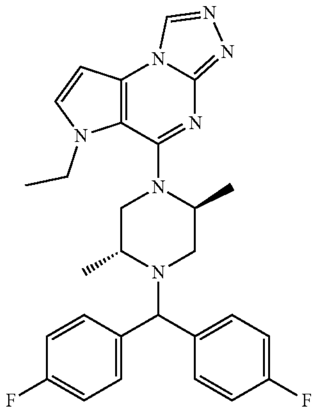 [SMILES: CCn1ccc2c1c(N1C[C@@H](C)N(C(c3ccc(F)cc3)c3ccc(F)cc3)C[C@@H]1C)nc1nncn12]

This compound was prepared according to the procedures described in Example 1, with 4-((2S,5R)-4-(bis(4-fluorophenyl)methyl)-2,5-dimethylpiperazin-1-yl)-2-chloro-5-ethyl-5H-pyrrolo[3,2-d]pyrimidine (Intermediate 10) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{28}H_{30}F_2N_7(M+H)^+$: m/z=502.3; found 502.1.

Example 11. 5-((2S,5R)-4-(Bis(4-fluorophenyl)methyl)-2,5-dimethylpiperazin-1-yl)thieno[2,3-e][1,2,4]triazolo[4,3-a]pyridine

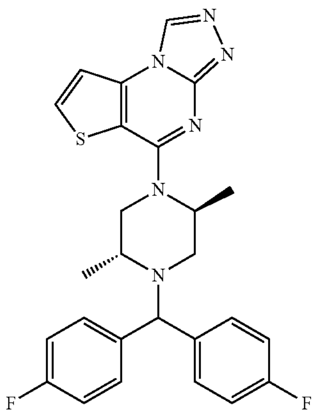 [SMILES: C[C@@H]1CN(c2nc3nncn3c3ccsc23)[C@@H](C)CN1C(c1ccc(F)cc1)c1ccc(F)cc1]

This compound was prepared according to the procedures described in Example 1, with 7-((2S,5R)-4-(bis(4-fluorophenyl)methyl)-2,5-dimethylpiperazin-1-yl)-5-chlorothieno[3,2-b]pyridine (Intermediate 11) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{27}H_{26}F_2N_5S$ $(M+H)^+$: m/z=490.2; found 490.1.

Example 12. 4-((2S,5R)-4-(Bis(4-fluorophenyl)methyl)-2,5-dimethylpiperazin-1-yl)-1,3-dimethyl-1H-pyrazolo[4,3-e][1,2,4]triazolo[4,3-a]pyridine

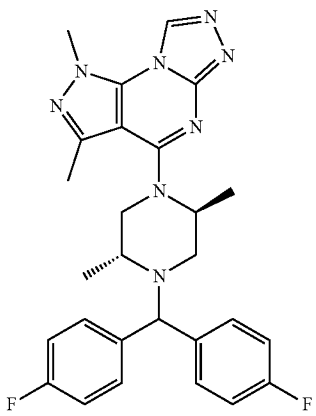 [SMILES: Cc1nn(C)c2c1c(N1C[C@@H](C)N(C(c3ccc(F)cc3)c3ccc(F)cc3)C[C@@H]1C)nc1nncn12]

This compound was prepared according to the procedures described in Example 1, with 4-((2S,5R)-4-(bis(4-fluorophenyl)methyl)-2,5-dimethylpiperazin-1-yl)-6-chloro-1,3-dimethyl-1H-pyrazolo[3,4-b]pyridine (Intermediate 12) replacing 7-((2S,5R)-4-(bis(4-fluorophenyl)methyl)-2,5-dimethylpiperazin-1-yl)-5-chlorothiazolo[5,4-d]pyrimidine in Step 1. LC-MS calculated for $C_{28}H_{30}F_2N_7(M+H)^+$: m/z=502.3; found 502.3.

Example 13. 4-((2S,5S)-4-(Bis(4-fluorophenyl)methyl)-5-(methoxymethyl)-2-methylpiperazin-1-yl)thiazolo[4,5-e][1,2,4]triazolo[4,3-a]pyrimidine

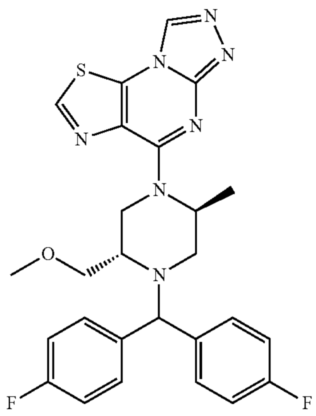 [SMILES: COC[C@@H]1CN(c2nc3nncn3c3scnc23)[C@@H](C)CN1C(c1ccc(F)cc1)c1ccc(F)cc1]

Step 1. 7-((2S,5S)-4-(Bis(4-fluorophenyl)methyl)-5-(methoxymethyl)-2-methylpiperazin-1-yl)-5-chlorothiazolo[5,4-d]pyrimidine

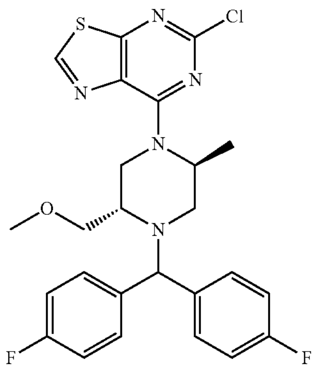 [SMILES: COC[C@@H]1CN(c2nc(Cl)nc3scnc23)[C@@H](C)CN1C(c1ccc(F)cc1)c1ccc(F)cc1]

To a mixture of 5,7-dichlorothiazolo[5,4-d]pyrimidine (51 mg, 0.25 mmol, PharmaBlock PB03220) and (2S,5S)-1-(bis(4-fluorophenyl)methyl)-2-(methoxymethyl)-5-methylpiperazine hydrochloride (Intermediate 14, 95 mg, 0.25 mmol) in 1-butanol (1.2 mL) was added N-ethyl-N-isopropylpropan-2-amine (0.13 mL, 0.75 mmol) and the reaction mixture was stirred at 60° C. for 4 h. The reaction mixture was concentrated in vacuo and the crude residue was purified by flash column chromatography ($SiO_2$, EtOAc/hexanes). LC-MS calculated for $C_{25}H_{25}ClF_2N_5OS$ $(M+H)^+$: m/z=516.1; found 516.0.

Step 2. 7-((2S,5S)-4-(Bis(4-fluorophenyl)methyl)-5-(methoxymethyl)-2-methylpiperazin-1-yl)-5-hydrazineylthiazolo[5,4-d]pyrimidine

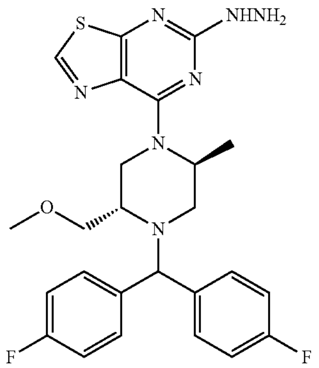 [SMILES: COC[C@@H]1CN(c2nc(NN)nc3scnc23)[C@@H](C)CN1C(c1ccc(F)cc1)c1ccc(F)cc1]

A mixture of 7-((2S,5S)-4-(bis(4-fluorophenyl)methyl)-5-(methoxymethyl)-2-methylpiperazin-1-yl)-5-chlorothiazolo[5,4-d]pyrimidine (Step 1), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (42.3 mg, 0.050 mmol, Aldrich 745979) and cesium carbonate (161 mg, 0.5 mmol) in a 1 molar solution of hydrazine in THF (1.2 mL, 1.2 mmol, Aldrich 433632) was stirred at 60° C. for 1 h. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude material obtained was used directly without further purification. LC-MS calculated for $C_{25}H_{28}F_2N_7OS$ $(M+H)^+$: m/z=512.2; found 512.3.

Step 3. 4-((2S,5S)-4-(Bis(4-fluorophenyl)methyl)-5-(methoxymethyl)-2-methylpiperazin-1-yl)thiazolo[4,5-e][1,2,4]triazolo[4,3-a]pyrimidine A mixture of 7-((2S,5S)-4-(bis(4-fluorophenyl)methyl)-5-(methoxymethyl)-2-methylpiperazin-1-yl)-5-hydrazineylthiazolo[5,4-d]pyrimidine (Step 2), trimethyl orthoformate (0.28 mL, 2.5 mmol), and AcOH (15 mg, 0.25 mmol) was stirred at 100° C. for 1 h. After cooling to rt, the reaction mixture was diluted with acetonitrile, water, and several drops of TFA, and the mixture was filtered and purified by prep-HPLC (Sunfire C18 column, eluting with a gradient of acetonitrile/water containing 0.1% TFA, at flow rate of 60 mL/min) to afford the desired product as its TFA salt. LC-MS calculated for $C_{26}H_{26}F_2N_7OS$ $(M+H)^+$: m/z=522.2; found 522.2.

Example 14. 2-((2R,5S)-1-(Bis(4-fluorophenyl)methyl)-5-methyl-4-(thiazolo[4,5-e][1,2,4]triazolo[4,3-a]pyrimidin-4-yl)piperazin-2-yl)acetonitrile

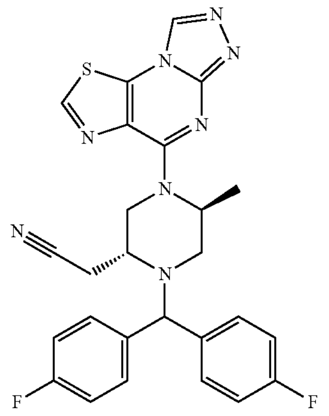 [SMILES: C[C@H]1CN(C(c2ccc(F)cc2)c2ccc(F)cc2)[C@H](CC#N)CN1c1nc2nncn2c2scnc12]

Step 1. 2-((2R,5S)-1-(Bis(4-fluorophenyl)methyl)-4-(5-hydrazineylthiazolo[5,4-d]pyrimidin-7-yl)-5-methylpiperazin-2-yl)acetonitrile

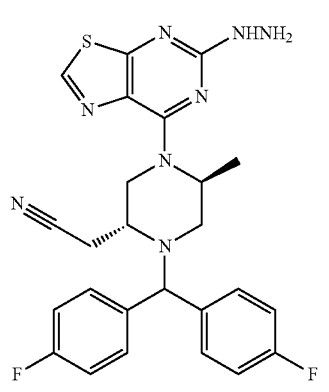

A mixture of 2-((2R,5S)-1-(bis(4-fluorophenyl)methyl)-4-(5-chlorothiazolo[5,4-d]pyrimidin-7-yl)-5-methylpiperazin-2-yl)acetonitrile (Intermediate 16, 42.5 mg, 0.083 mmol), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (14.2 mg, 0.017 mmol, Aldrich 745979) and cesium carbonate (54.2 mg, 0.17 mmol) in a 1 molar solution of hydrazine in THF (416 µL, 0.42 mmol, Aldrich 433632) was stirred at 60° C. for 30 min. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude material obtained was used directly without further purification. LC-MS calculated for $C_{25}H_{25}F_2N_8S$ $(M+H)^+$: m/z=507.2; found 507.2.

Step 2. 2-((2R,5S)-1-(Bis(4-fluorophenyl)methyl)-5-methyl-4-(thiazolo[4,5-e][1,2,4]triazolo[4,3-a]pyrimidin-4-yl)piperazin-2-yl)acetonitrile A mixture of 2-((2R,5S)-1-(bis(4-fluorophenyl)methyl)-4-(5-hydrazineylthiazolo[5,4-d]pyrimidin-7-yl)-5-methylpiperazin-2-yl)acetonitrile (Step 1), trimethyl orthoformate (92 µL, 0.83 mmol), and AcOH (5 mg, 0.08 mmol) was stirred at 100° C. for 30 min. After cooling to rt, the reaction mixture was diluted with acetonitrile and water and several drops of TFA, and the mixture was filtered and purified by prep-HPLC (Sunfire C18 column, eluting with a gradient of acetonitrile/water containing 0.1% TFA, at flow rate of 60 mL/min) to afford the desired product as its TFA salt. LC-MS calculated for $C_{26}H_{23}F_2N_8S$ $(M+H)^+$: m/z=517.2; found 517.1. $^1H$ NMR (500 MHz, DMSO-$d_6$, 80° C.) δ 9.42 (s, 1H), 9.29 (s, 1H), 7.66-7.59 (m, 2H), 7.59-7.51 (m, 2H), 7.24-7.12 (m, 4H), 5.73-5.39 (br m, 2H), 4.93 (s, 1H), 3.85 (dd, J=13.9, 3.5 Hz, 1H), 3.41-3.34 (m, 1H), 2.82-2.75 (m, 3H), 2.58-2.52 (m, 1H), 1.50 (d, J=6.6 Hz, 3H).

Example 15. 2-((2R,5S)-1-(Bis(4-fluorophenyl)methyl)-4-(8-cyclopropylthiazolo[4,5-e][1,2,4]triazolo[4,3-a]pyrimidin-4-yl)-5-methylpiperazin-2-yl)acetonitrile

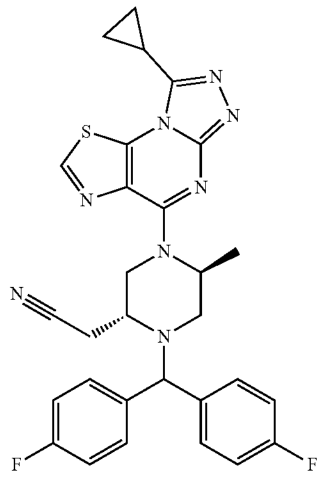 [SMILES: C[C@H]1CN(C(c2ccc(F)cc2)c2ccc(F)cc2)[C@H](CC#N)CN1c1nc2nnc(C3CC3)n2c2scnc12]

This compound was prepared according to the procedures described in Example 14, with (trimethoxymethyl)cyclopropane (AstaTech $C_{77493}$) replacing trimethyl orthoformate in Step 2. LC-MS calculated for $C_{29}H_{27}F_2N_8S$ $(M+H)^+$: m/z=557.2; found 557.1.

Example 16. 2-((2R,5S)-1-(Bis(4-fluorophenyl)methyl)-5-methyl-4-(1-methyl-1H-[1,2,4]triazolo[3,4-b]purin-4-yl)piperazin-2-yl)acetonitrile

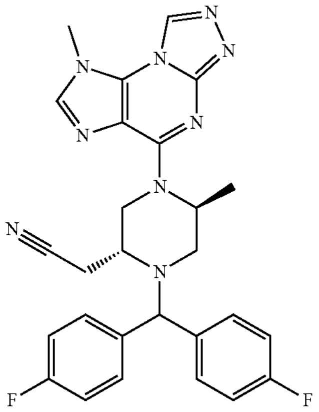 [SMILES: C[C@H]1CN(C(c2ccc(F)cc2)c2ccc(F)cc2)[C@H](CC#N)CN1c1nc2nncn2c2c1ncn2C]

This compound was prepared according to the procedures described in Example 14, with 2-((2R,5S)-1-(bis(4-fluorophenyl)methyl)-4-(2-chloro-9-methyl-9H-purin-6-yl)-5-methylpiperazin-2-yl)acetonitrile (Intermediate 17) replacing 2-((2R,5S)-1-(bis(4-fluorophenyl)methyl)-4-(5-chlorothiazolo[5,4-d]pyrimidin-7-yl)-5-methylpiperazin-2-yl)acetonitrile in Step 1. LC-MS calculated for $C_{27}H_{26}F_2N_9$ $(M+H)^+$: m/z=514.2; found 514.1.

Example 17. (R)-3-(1-(Bis(4-fluorophenyl)methyl)-4-(thiazolo[4,5-e][1,2,4]triazolo[4,3-a]pyrimidin-4-yl)piperazin-2-yl)propanenitrile

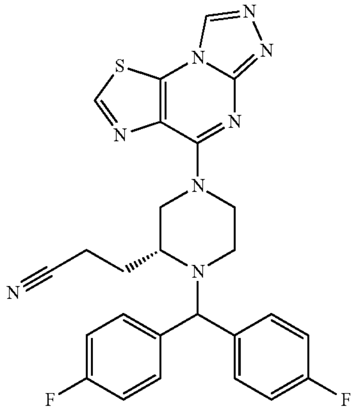 [SMILES: N#CCC[C@@H]1CN(c2nc3nncn3c3scnc23)CCN1C(c1ccc(F)cc1)c1ccc(F)cc1]

This compound was prepared according to the procedures described in Example 14, with (R)-3-(1-(bis(4-fluorophenyl)methyl)-4-(5-chlorothiazolo[5,4-d]pyrimidin-7-yl)piperazin-2-yl)propanenitrile (Intermediate 20) replacing 2-((2R,5S)-1-(bis(4-fluorophenyl)methyl)-4-(5-chlorothiazolo[5,4-d]pyrimidin-7-yl)-5-methylpiperazin-2-yl)acetonitrile in Step 1. LC-MS calculated for $C_{26}H_{23}F_2N_8S$ $(M+H)^+$: m/z=517.2; found 517.2. $^1H$ NMR (500 MHz, DMSO-$d_6$, 70° C.) δ 9.45 (s, 1H), 9.30 (s, 1H), 7.61-7.52 (m, 4H), 7.19-7.10 (m, 4H), 5.40-4.95 (br m, 2H), 5.20 (s, 1H), 3.79 (dd, J=14.1, 3.1 Hz, 1H), 3.65 (t, J=12.2 Hz, 1H), 2.98 (ddt, J=8.5, 5.7, 2.8 Hz, 1H), 2.87 (ddd, J=14.6, 11.7, 3.3 Hz, 1H), 2.70 (dt, J=13.5, 3.2 Hz, 1H), 2.54-2.44 (m, 1H), 2.38 (dt, J=17.1, 7.7 Hz, 1H), 2.03-1.93 (m, 1H), 1.78 (dtd, J=14.0, 8.3, 5.8 Hz, 1H).

Example 18. 4-((2S,5R)-4-(Bis(4-fluorophenyl)methyl)-2,5-dimethylpiperazin-1-yl)-1-(cyclopropylmethyl)-1H-[1,2,4]triazolo[3,4-b]purine

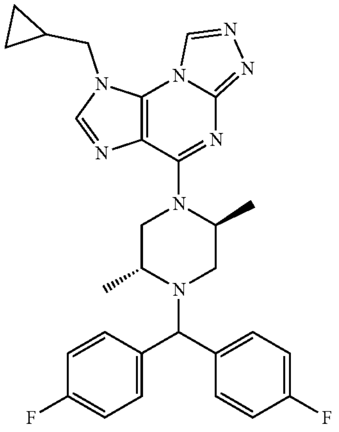 [SMILES: C[C@@H]1CN(c2nc3nncn3c3c2ncn3CC2CC2)[C@@H](C)CN1C(c1ccc(F)cc1)c1ccc(F)cc1]

Step 1. 6-((2S,5R)-4-(Bis(4-fluorophenyl)methyl)-2,5-dimethylpiperazin-1-yl)-2-chloro-9-(cyclopropylmethyl)-9H-purine

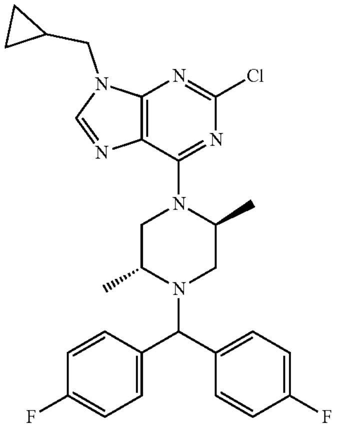 [SMILES: C[C@@H]1CN(c2nc(Cl)nc3c2ncn3CC2CC2)[C@@H](C)CN1C(c1ccc(F)cc1)c1ccc(F)cc1]

To a mixture of 6-((2S,5R)-4-(bis(4-fluorophenyl)methyl)-2,5-dimethylpiperazin-1-yl)-2-chloro-9H-purine (Intermediate 21, 1.31 g, 2.79 mmol) in $CH_3CN$ (27.9 mL) was added cesium carbonate (2.73 g, 8.38 mmol) followed by (bromomethyl)cyclopropane (0.543 mL, 5.59 mmol, Matrix 006642) and the reaction mixture was stirred at 25° C. for 12 h. The reaction mixture was filtered, and the filtrate was concentrated. To the crude residue was added $CH_2Cl_2$ (50 mL) and the mixture was cooled in an ice-bath and slurried for 30 mins. The solid precipitate was collected via filtration and dried to afford the desired product (1.20 g, 82% yield) as a white solid. LC-MS calculated for $C_{28}H_{30}ClF_2N_6$ $(M+H)^+$: m/z=523.2; found 523.2.

Step 2. 6-((2S,5R)-4-(Bis(4-fluorophenyl)methyl)-2,5-dimethylpiperazin-1-yl)-9-(cyclopropylmethyl)-2-hydrazineyl-9H-purine

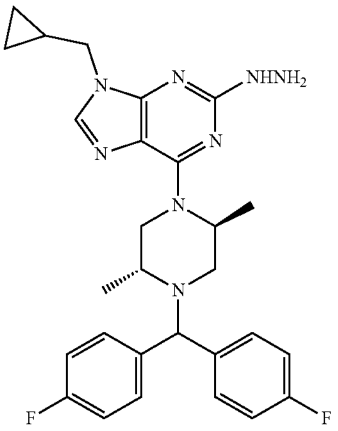 [SMILES: C[C@@H]1CN(c2nc(NN)nc3c2ncn3CC2CC2)[C@@H](C)CN1C(c1ccc(F)cc1)c1ccc(F)cc1]

To a mixture of 6-((2S,5R)-4-(bis(4-fluorophenyl)methyl)-2,5-dimethylpiperazin-1-yl)-2-chloro-9-(cyclopropylmethyl)-9H-purine (1.10 g, 2.10 mmol), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (90 mg, 0.11 mmol, Strem 46-0325) and cesium carbonate (1.37 g, 4.21 mmol) was added a 1 molar solution of hydrazine in THF (5.26 mL, 5.26 mmol) and the mixture was purged with nitrogen and stirred at 60° C. for 1 h. After cooling to rt, the reaction mixture was diluted with $CH_2Cl_2$ and filtered over a pad of Celite. The filtrate was concentrated, and the crude material obtained was used directly without further purification. LC-MS calculated for $C_{28}H_{33}F_2N_8$ $(M+H)^+$: m/z=519.3; found 519.3.

Step 3. 4-((2S,5R)-4-(Bis(4-fluorophenyl)methyl)-2,5-dimethylpiperazin-1-yl)-1-(cyclopropylmethyl)-1H-[1,2,4]triazolo[3,4-b]purine A mixture of 6-((2S,5R)-4-(bis(4-fluorophenyl)methyl)-2,5-dimethylpiperazin-1-yl)-9-(cyclopropylmethyl)-2-hydrazineyl-9H-purine (Step 2), triethyl orthoformate (3.5 mL, 21 mmol), and AcOH (0.12 mL, 2.1 mmol) was stirred at 95° C. overnight. After cooling to rt, the reaction mixture was diluted with acetonitrile and water and purified by prep-HPLC (Sunfire C18 column, eluting with a gradient of acetonitrile/water containing 0.1% TFA, at flow rate of 60 mL/min) to afford the desired product as its TFA salt. Fractions containing the desired product were concentrated, and the material was re-purified by prep-HPLC (Sunfire C18 column, eluting with a gradient of acetonitrile/water containing 0.1% $NH_4OH$, at flow rate of 60 mL/min) to afford the desired product. LC-MS calculated for $C_{29}H_{31}F_2N_8$ $(M+H)^+$: m/z=529.3; found 529.4. $^1H$ NMR (500 MHz, DMSO-$d_6$) (mixture of rotamers) δ 9.26 (s, 1H), 8.15 (s, 1H), 7.63-7.54 (m, 4H), 7.14 (td, J=8.8, 4.1 Hz, 4H), 6.24-5.96 (m, 0.4H), 5.92-5.68 (m, 0.6H), 5.20-4.96 (m, 0.6H) 4.71-4.53 (m, 1.4H), 4.42-4.30 (m, 2H), 3.80-3.62 (m, 0.6H), 3.53-3.37 (m, 0.4H), 3.18-3.01 (m, 1H), 2.81-2.64 (m, 1H), 2.40 (d, J=12.0 Hz, 1H), 1.43 (d, J=6.6 Hz, 3H), 1.33 (tt, J=7.6, 4.8 Hz, 1H), 0.90 (d, J=6.5 Hz, 3H), 0.64-0.54 (m, 2H), 0.50-0.42 (m, 2H).

Example 19. 4-((2S,5R)-4-(Bis(4-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine

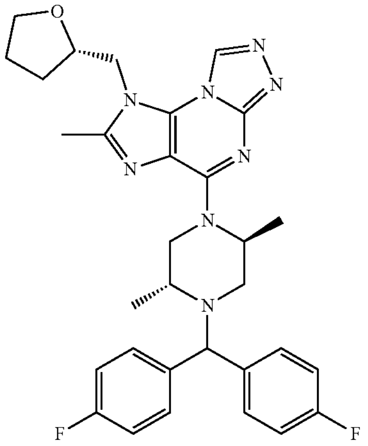 [SMILES: Cc1nc2c(N3C[C@@H](C)N(C(c4ccc(F)cc4)c4ccc(F)cc4)C[C@@H]3C)nc3nncn3c2n1C[C@@H]1CCCO1]

Step 1. 6-((2S,5R)-4-(Bis(4-fluorophenyl)methyl)-2,5-dimethylpiperazin-1-yl)-2-chloro-8-methyl-9-(((S)-tetrahydrofuran-2-yl)methyl)-9H-purine

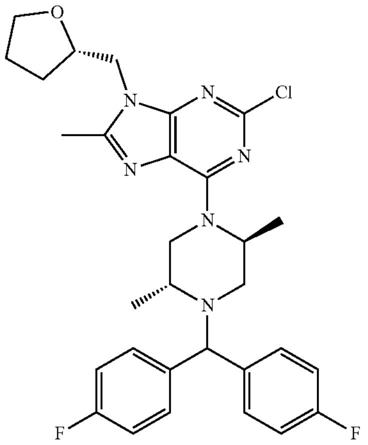 [SMILES: Cc1nc2c(N3C[C@@H](C)N(C(c4ccc(F)cc4)c4ccc(F)cc4)C[C@@H]3C)nc(Cl)nc2n1C[C@@H]1CCCO1]

To a mixture of 6-((2S,5R)-4-(bis(4-fluorophenyl)methyl)-2,5-dimethylpiperazin-1-yl)-2-chloro-8-methyl-9H-purine (Intermediate 23, 300. mg, 0.621 mmol) and cesium carbonate (1.01 g, 3.10 mmol) in N,N-dimethylformamide (1.6 mL) was added (S)-(tetrahydrofuran-2-yl)methyl methanesulfonate (Intermediate 22, 224 mg, 1.24 mmol) and the mixture was stirred at 75° C. overnight. After cooling to rt, the reaction mixture was diluted with aqueous LiCl (5% w/v) and extracted with EtOAc. The combined organic phases were washed with three times with water, dried over $MgSO_4$, and concentrated under reduced pressure. The crude residue was purified by flash column chromatography ($SiO_2$, EtOAc/hexanes) to afford the desired product (190.7 mg, 54% yield) as an orangish-brown waxy solid. LC-MS calculated for $C_{30}H_{34}ClF_2N_6O$ $(M+H)^+$: m/z=567.2; found 567.3.

Step 2. 6-((2S,5R)-4-(Bis(4-fluorophenyl)methyl)-2,5-dimethylpiperazin-1-yl)-2-hydrazineyl-8-methyl-9-(((S)-tetrahydrofuran-2-yl)methyl)-9H-purine

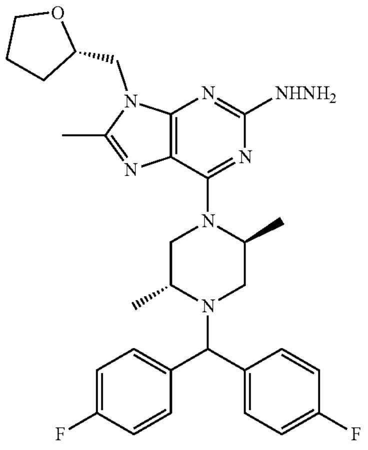 [SMILES: Cc1nc2c(N3C[C@@H](C)N(C(c4ccc(F)cc4)c4ccc(F)cc4)C[C@@H]3C)nc(NN)nc2n1C[C@@H]1CCCO1]

To a mixture of 6-((2S,5R)-4-(bis(4-fluorophenyl)methyl)-2,5-dimethylpiperazin-1-yl)-2-chloro-8-methyl-9-(((S)-tetrahydrofuran-2-yl)methyl)-9H-purine (190.7 mg, 0.336 mmol) methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (28.7 mg, 0.034 mmol, Aldrich 745979), and cesium carbonate (219 mg, 0.673 mmol) was added a 1 molar solution of hydrazine in THF (1.68 mL, 1.68 mmol) and the mixture was stirred at 60° C. for 30 min. After cooling to rt, the reaction mixture was filtered through a pad of $MgSO_4$ in a SiliaPrep SPE thiol cartridge (SiliCycle SPE-R51030B-06P). The filtrate was concentrated, and the crude material obtained was used directly without further purification. LC-MS calculated for $C_{30}H_{37}F_2N_8O$ $(M+H)^+$: m/z=563.3; found 563.4.

Step 3. 4-((2S,5R)-4-(Bis(4-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine A mixture of 6-((2S,5R)-4-(bis(4-fluorophenyl)methyl)-2,5-dimethylpiperazin-1-yl)-2-hydrazineyl-8-methyl-9-(((S)-tetrahydrofuran-2-yl)methyl)-9H-purine (Step 2), triethyl orthoformate (1.12 mL, 6.73 mmol), and AcOH (38.5 μL, 0.673 mmol) was stirred at 85° C. overnight. After cooling to rt, the reaction mixture was diluted with acetonitrile and water and purified by prep-HPLC (Sunfire C18 column, eluting with a gradient of acetonitrile/water containing 0.1% $NH_4OH$, at flow rate of 60 mL/min) to afford the desired product. LC-MS calculated for $C_{31}H_{35}F_2N_8O$ $(M+H)^+$: m/z=573.3; found 573.3. $^1H$ NMR (500 MHz, DMSO-$d_6$) (mixture of rotamers) δ 9.48 (s, 1H), 7.65-7.53 (m, 4H), 7.19-7.12 (m, 4H), 6.25-6.17 (m, 0.4H), 5.96-5.88 (m, 0.6H), 5.09-5.03 (m, 0.6H), 4.75-4.60 (m, 2.4H), 4.58-4.49 (m, 1H), 4.14-4.05 (m, 1H), 3.88-3.82 (m, 0.6H), 3.72-3.65 (m, 1H), 3.65-3.59 (m, 0.4H), 3.59-3.51 (m, 1H), 3.24-3.09 (m, 1H), 2.81-2.68 (m, 1H), 2.59-2.54 (m, 3H), 2.47-2.38 (m, 1H), 2.17-2.07 (m, 1H), 1.99-1.88 (m, 1H), 1.88-1.76 (m, 1H), 1.76-1.65 (m, 1H), 1.54-1.49 (m, 1.2H), 1.49-1.42 (m, 1.8H), 0.93-0.87 (m, 3H).

Example 20. 4-((2S,5R)-4-(Bis(4-fluorophenyl)methyl)-5-ethyl-2-methylpiperazin-1-yl)-2-methyl-1-(((S)-tetrahydrofuran-2-yl)methyl)-1H-[1,2,4]triazolo[3,4-b]purine

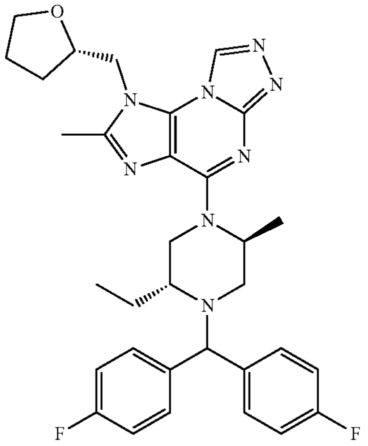 [SMILES: CC[C@@H]1CN(c2nc3nncn3c3c2nc(C)n3C[C@@H]2CCCO2)[C@@H](C)CN1C(c1ccc(F)cc1)c1ccc(F)cc1]

Step 1. 6-((2S,5R)-4-(Bis(4-fluorophenyl)methyl)-5-ethyl-2-methylpiperazin-1-yl)-2-chloro-8-methyl-9-(((S)-tetrahydrofuran-2-yl)methyl)-9H-purine

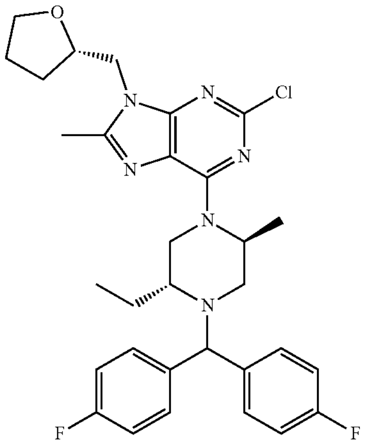 [SMILES: CC[C@@H]1CN(c2nc(Cl)nc3c2nc(C)n3C[C@@H]2CCCO2)[C@@H](C)CN1C(c1ccc(F)cc1)c1ccc(F)cc1]

To a mixture of 6-((2S,5R)-4-(bis(4-fluorophenyl)methyl)-5-ethyl-2-methylpiperazin-1-yl)-2-chloro-8-methyl-9H-purine (Intermediate 27, 256 mg, 0.515 mmol) and (S)-(tetrahydrofuran-2-yl)methyl methanesulfonate (Intermediate 22, 186 mg, 1.03 mmol) in $CH_3CN$ (2.6 mL) was added cesium carbonate (503 mg, 1.54 mmol) and the mixture was stirred at 90° C. for 2 h. After cooling to rt, the reaction mixture was diluted with saturated aqueous $NaHCO_3$ and extracted with $CH_2Cl_2$. The combined organic phases were dried over $MgSO_4$, concentrated, and the crude residue was purified by flash column chromatography to afford the desired product (279 mg, 93% yield) as a light yellow waxy solid. LC-MS calculated for $C_{31}H_{36}ClF_2N_6O$ $(M+H)^+$: m/z=581.3; found 581.3.

Step 2. 6-((2S,5R)-4-(Bis(4-fluorophenyl)methyl)-5-ethyl-2-methylpiperazin-1-yl)-2-hydrazineyl-8-methyl-9-(((S)-tetrahydrofuran-2-yl)methyl)-9H-purine

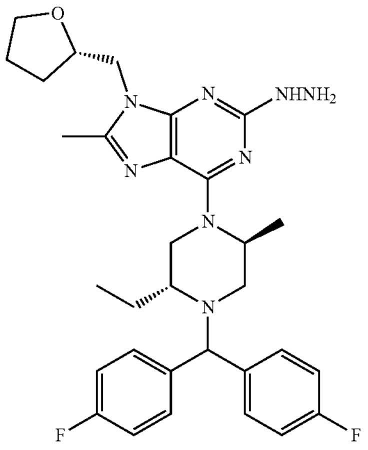 [SMILES: CC[C@@H]1CN(c2nc(NN)nc3c2nc(C)n3C[C@@H]2CCCO2)[C@@H](C)CN1C(c1ccc(F)cc1)c1ccc(F)cc1]

To a mixture of 6-((2S,5R)-4-(bis(4-fluorophenyl)methyl)-5-ethyl-2-methylpiperazin-1-yl)-2-chloro-8-methyl-9-(((S)-tetrahydrofuran-2-yl)methyl)-9H-purine (279 mg, 0.480 mmol), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (20.5 mg, 0.024 mmol, Aldrich 745979) and cesium carbonate (782 mg, 2.4 mmol) was added a 1 molar solution of hydrazine in THF (2.4 mL, 2.4 mmol) and the mixture was purged with nitrogen and stirred at 60° C. for 30 min. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude material obtained was used directly without further purification. LC-MS calculated for $C_{31}H_{39}F_2N_8O$ $(M+H)^+$: m/z=577.3; found 577.3.

Step 3. 4-((2S,5R)-4-(Bis(4-fluorophenyl)methyl)-5-ethyl-2-methylpiperazin-1-yl)-2-methyl-1-(((S)-tetrahydrofuran-2-yl)methyl)-1H-[1,2,4]triazolo[3,4-b]purine A mixture of 6-((2S,5R)-4-(bis(4-fluorophenyl)methyl)-5-ethyl-2-methylpiperazin-1-yl)-2-hydrazineyl-8-methyl-9-(((S)-tetrahydrofuran-2-yl)methyl)-9H-purine (Step 2), triethyl orthoformate (0.8 mL, 4.8 mmol), and AcOH (29 mg, 0.48 mmol) was stirred at 90° C. for 1 h. After cooling to rt, the reaction mixture was diluted with acetonitrile, water, and several drops of TFA, and the mixture was filtered and purified by prep-HPLC (Sunfire C18 column, eluting with a gradient of acetonitrile/water containing 0.10% TFA, at flow rate of 60 mL/min) to afford the desired product as its TFA salt. LC-MS calculated for $C_{32}H_{37}F_2N_8O$ $(M+H)^+$: m/z=587.3; found 587.3. $^1H$ NMR (500 MHz, DMSO-$d_6$) (mixture of rotamers) δ 9.49 (s, 0.6H), 9.48 (s, 0.4H), 7.64-7.53 (m, 4H), 7.22-7.11 (m, 4H), 6.21-6.13 (m, 0.4H), 6.13-6.07 (m, 0.6H), 5.07-4.99 (m, 0.6H), 4.88-4.82 (m, 0.4H), 4.80 (s, 1H), 4.73 (dd, J=7.2, 2.5 Hz, 0.4H), 4.70 (dd, J=7.2, 2.5 Hz, 0.6H), 4.58-4.54 (m, 0.6H), 4.54-4.50 (m, 0.4H), 4.14-4.05 (m, 1H), 3.80-3.73 (m, 0.6H), 3.73-3.66 (m, 1H), 3.59-3.51 (m, 1.4H), 2.81-2.61 (m, 2H), 2.58 (s, 1.2H), 2.56 (s, 1.8H), 2.51-2.41 (m, 1H), 2.16-2.08 (m, 1H), 1.98-1.88 (m, 1H), 1.87-1.77 (m, 1H), 1.76-1.67 (m, 1H), 1.60-1.49 (m, 2.2H), 1.46 (d, J=6.7 Hz, 1.8H), 1.43-1.33 (m, 1H), 0.69-0.60 (m, 3H).

Example 21. 4-((2S,5R)-4-(Bis(4-fluorophenyl)methyl)-2,5-diethylpiperazin-1-yl)-1-(cyclopropylmethyl)-1H-[1,2,4]triazolo[3,4-b]purine

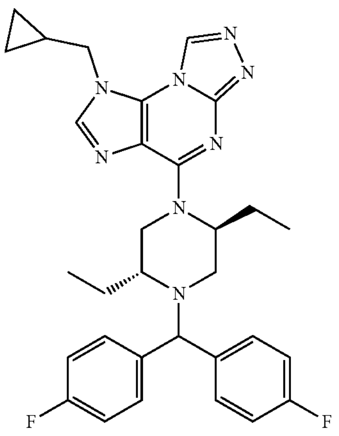 [SMILES: CC[C@H]1CN(C(c2ccc(F)cc2)c2ccc(F)cc2)[C@H](CC)CN1c1nc2nncn2c2c1ncn2CC1CC1]

Step 1. 6-((2S,5R)-4-(Bis(4-fluorophenyl)methyl)-2,5-diethylpiperazin-1-yl)-2-chloro-9-(cyclopropylmethyl)-9H-purine

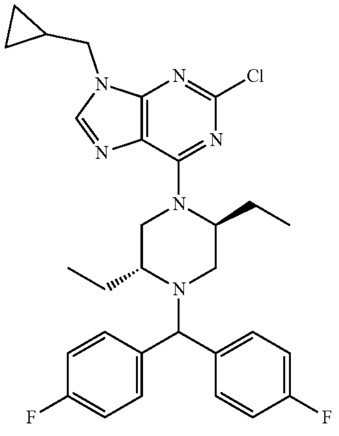 [SMILES: CC[C@H]1CN(C(c2ccc(F)cc2)c2ccc(F)cc2)[C@H](CC)CN1c1nc(Cl)nc2c1ncn2CC1CC1]

To a mixture of 6-((2S,5R)-4-(bis(4-fluorophenyl)methyl)-2,5-diethylpiperazin-1-yl)-2-chloro-9H-purine (Intermediate 30, 0.277 g, 0.557 mmol) in $CH_3CN$ (2 mL) was added cesium carbonate (0.544 g, 1.67 mmol) followed by (bromomethyl)cyclopropane (86 μL, 0.89 mmol, Matrix Scientific 006642) and the reaction mixture was stirred at 60° C. for 12 h. After cooling to rt, the reaction mixture was concentrated in vacuo, and the crude residue was diluted with $CH_2Cl_2$ and extracted with saturated aqueous $NaHCO_3$. The combined organic layers were dried over $MgSO_4$ and the filtrate was concentrated. The crude material obtained was used directly without further purification. LC-MS calculated for $C_{30}H_{34}ClF_2N_6$$(M+H)^+$: m/z=551.3; found 551.3.

Step 2. 6-((2S,5R)-4-(Bis(4-fluorophenyl)methyl)-2,5-diethylpiperazin-1-yl)-9-(cyclopropylmethyl)-2-hydrazineyl-9H-purine

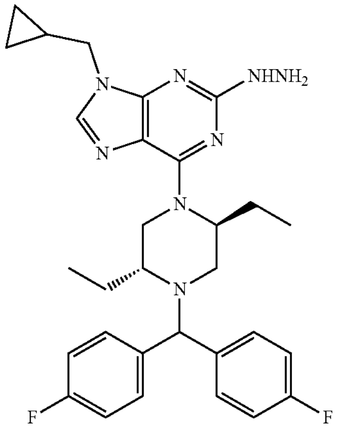 [SMILES: CC[C@H]1CN(C(c2ccc(F)cc2)c2ccc(F)cc2)[C@H](CC)CN1c1nc(NN)nc2c1ncn2CC1CC1]

To a mixture of 6-((2S,5R)-4-(bis(4-fluorophenyl)methyl)-2,5-diethylpiperazin-1-yl)-2-chloro-9-(cyclopropylmethyl)-9H-purine (Step 1), [(2-di-tert-butylphosphino-3,6-dimethoxy-2',4',6'-triisopropyl-1,1'-biphenyl)-2-(2'-amino-1,1'-biphenyl)]palladium(II) methanesulfonate (24 mg, 0.028 mmol, Aldrich 745979) and cesium carbonate (0.544 g, 1.671 mmol) in 1,4-dioxane (2 mL) was added a 1 molar solution of hydrazine in THF (2.78 mL, 2.78 mmol) and the mixture was purged with nitrogen and stirred at 60° C. for 1 h. After cooling to rt, the reaction mixture was diluted with $CH_2Cl_2$ and filtered over a pad of Celite. The filtrate was concentrated, and the crude material obtained was used directly without further purification. LC-MS calculated for $C_{30}H_{37}F_2N_8$ $(M+H)^+$: m/z=547.3; found 547.3.

Step 3. 4-((2S,5R)-4-(Bis(4-fluorophenyl)methyl)-2,5-diethylpiperazin-1-yl)-1-(cyclopropylmethyl)-1H-[1,2,4]triazolo[3,4-b]purine A mixture of 6-((2S,5R)-4-(bis(4-fluorophenyl)methyl)-2,5-diethylpiperazin-1-yl)-9-(cyclopropylmethyl)-2-hydrazineyl-9H-purine (Step 2), triethyl orthoformate (2.3 mL, 14 mmol), and AcOH (0.032 mL, 0.56 mmol) was stirred at 90° C. for 1 h. After cooling to rt, the reaction mixture was diluted with acetonitrile and water and purified by prep-HPLC (Sunfire C18 column, eluting with a gradient of acetonitrile/water containing 0.10% $NH_4OH$, at flow rate of 60 mL/min) to afford the desired product. Fractions containing the desired product were concentrated, and the material was re-purified by prep-HPLC (Sunfire C18 column, eluting with a gradient of acetonitrile/water containing 0.1% TFA, at flow rate of 60 mL/min) to afford the desired product as its TFA salt. LC-MS calculated for $C_{31}H_{35}F_2N_8$ $(M+H)^+$: m/z=557.3; found 557.3. $^1H$ NMR (500 MHz, DMSO-$d_6$) (mixture of rotamers) δ 9.62 (s, 1H), 8.46 (s, 0.5H), 8.45 (s, 0.5H), 7.64-7.54 (m, 4H), 7.22-7.12 (m, 4H), 6.19-6.09 (m, 0.5H), 6.09-6.00 (m, 0.5H), 4.98-4.89 (m, 1H), 4.80 (s, 1H), 4.47-4.32 (m, 2H), 3.81-3.72 (m, 0.5H), 3.56-3.43 (m, 0.5H), 2.76-2.62 (m, 2H), 2.62-2.54 (m, 1H), 2.22-2.14 (m, 0.5H), 2.12-2.01 (m, 1.5H), 1.61-1.47 (m, 1H), 1.47-1.30 (m, 2H), 0.86-0.77 (m, 3H), 0.71-0.61 (m, 3.5H), 0.62-0.55 (m, 1.5H), 0.55-0.48 (m, 2H).

Examples 22 and 23. 1-(Cyclopropylmethyl)-4-((2S,5R)-4-((S)-1-(4-fluorophenyl)-2-methylpropyl)-2,5-dimethylpiperazin-1-yl)-1H-[1,2,4]triazolo[3,4-b]purine and 1-(cyclopropylmethyl)-4-((2S,5R)-4-((R)-1-(4-fluorophenyl)-2-methylpropyl)-2,5-dimethylpiperazin-1-yl)-1H-[1,2,4]triazolo[3,4-b]purine

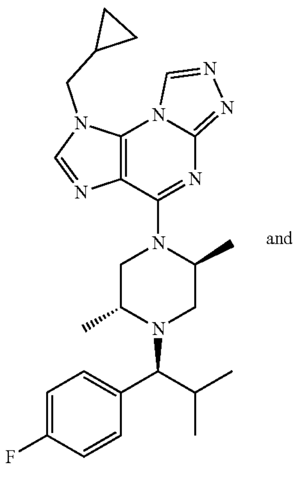

and

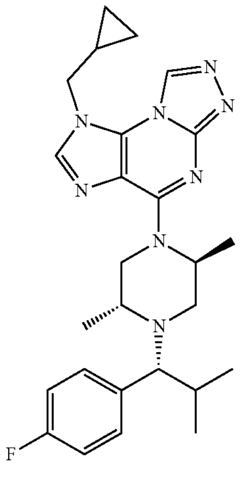

Step 1: 2-Chloro-9-(cyclopropylmethyl)-6-((2S,5R)-4-(1-(4-fluorophenyl)-2-methylpropyl)-2,5-dimethylpiperazin-1-yl)-9H-purine

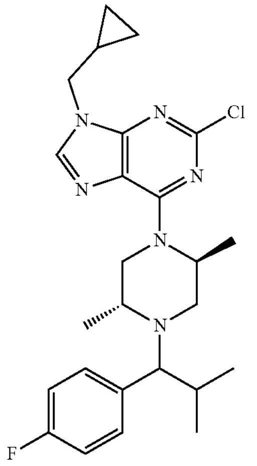 [SMILES: CC(C)C(c1ccc(F)cc1)N1C[C@H](C)N(c2nc(Cl)nc3c2ncn3CC2CC2)C[C@H]1C]

To a mixture of 2-chloro-6-((2S,5R)-4-(1-(4-fluorophenyl)-2-methylpropyl)-2,5-dimethylpiperazin-1-yl)-9H-purine (Intermediate 32, 1.00 g, 2.40 mmol) and cesium carbonate (3.91 g, 12.0 mmol) in MeCN (6.00 mL) was added (bromomethyl)cyclopropane (0.349 mL, 3.60 mmol) and the reaction mixture was stirred at 50° C. for 1 h. The mixture was cooled to rt, filtered, and concentrated in vacuo. The crude residue purified by flash column chromatography (24 g $SiO_2$, EtOAc/hexanes) to give the desired product (0.919 g, 81% yield) as a mixture of diastereomers in the form of a white solid. LC-MS calculated for $C_{25}H_{33}ClFN_6$ $(M+H)^+$: m/z=471.2; found 471.2.

Step 2: 9-(Cyclopropylmethyl)-6-((2S,5R)-4-(1-(4-fluorophenyl)-2-methylpropyl)-2,5-dimethylpiperazin-1-yl)-2-hydrazineyl-9H-purine

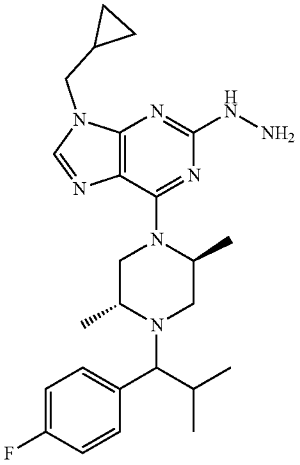 [SMILES: CC(C)C(c1ccc(F)cc1)N1C[C@H](C)N(c2nc(NN)nc3c2ncn3CC2CC2)C[C@H]1C]

To a mixture 2-chloro-9-(cyclopropylmethyl)-6-((2S,5R)-4-(1-(4-fluorophenyl)-2-methylpropyl)-2,5-dimethylpiperazin-1-yl)-9H-purine (Step 1, 0.589 g, 1.25 mmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (26.7 mg, 0.031 mmol, Aldrich 745979) and cesium carbonate (1.22 g, 3.75 mmol) under a nitrogen atmosphere was added a 1 molar solution of hydrazine in THF (6.25 mL, 6.25 mmol) and the reaction mixture was stirred at 60° C. for 30 min. After cooling to rt, the mixture was filtered through a pad of $MgSO_4$ in a SiliaPrep SPE thiol cartridge (SiliCycle SPE-R51030B-06P). The filtrate was concentrated, and the crude material obtained (mixture of diastereomers) was used directly without further purification. LC-MS calculated for $C_{25}H_{36}FN_s(M+H)^+$: m/z=467.3; found 467.3.

Step 3. 1-(Cyclopropylmethyl)-4-((2S,5R)-4-((S)-1-(4-fluorophenyl)-2-methylpropyl)-2,5-dimethylpiperazin-1-yl)-1H-[1,2,4]triazolo[3,4-b]purine and 1-(cyclopropylmethyl)-4-((2S,5R)-4-((R)-1-(4-fluorophenyl)-2-methylpropyl)-2,5-dimethylpiperazin-1-yl)-1H-[1,2,4]triazolo[3,4-b]purine A mixture of 9-(cyclopropylmethyl)-6-((2S,5R)-4-(1-(4-fluorophenyl)-2-methylpropyl)-2,5-dimethylpiperazin-1-yl)-2-hydrazineyl-9H-purine (Step 2), triethyl orthoformate (2.08 mL, 12.5 mmol), and trifluoroacetic acid (9.63 µL, 0.125 mmol) was stirred at 85° C. for 16 h. The diastereomeric mixture was diluted with acetonitrile, water, and several drops of TFA, and the mixture was filtered and purified by prep-HPLC (XBridge C18 column, eluting with a gradient of acetonitrile/water containing 0.15% $NH_4OH$, at a flow rate of 60 mL/min.). Fractions containing the desired product were concentrated in vacuo, and the material obtained was purified a second time by prep-HPLC (Sunfire C18 column, eluting with a gradient of acetonitrile/water containing 0.1% TFA, at flow rate of 60 mL/min) to afford each diastereomer as its TFA salt.

Example 22: Retention time on LCMS $t_r$=1.13 min, LC-MS calculated for $C_{26}H_{34}FN_8$ $(M+H)^+$: m/z=477.3; found 477.3. $^1H$ NMR (500 MHz, DMF-$d_7$) (mixture of rotamers) δ 10.17-10.12 (m, J=5.6 Hz, 1H), 8.89 (s, 0.4H), 8.81 (s, 0.6H), 7.68-7.54 (m, 2H), 7.53-7.40 (m, 2H), 6.35-6.23 (m, 0.4H), 6.16-6.02 (m, 0.6H), 5.29-5.10 (m, 0.6H), 4.92-4.74 (m, 2.4H), 3.99-3.81 (m, 0.6H), 3.74-3.47 (m, 1.4H), 3.37-3.19 (m, 1H), 3.16-3.11 (m, 1H), 2.88-2.75 (m, 1H), 2.61-2.43 (m, 1H), 1.88-1.68 (m, 2.2H), 1.62 (d, J=6.3 Hz, 1.8H), 1.22-1.10 (m, 2.4H), 1.09-0.72 (m, 10.6H)

Example 23: Retention time on LCMS $t_r$=1.20 min, LC-MS calculated for $C_{26}H_{34}FNs$ $(M+H)^+$: m/z=477.3; found 477.3. $^1H$ NMR (500 MHz, DMF-$d_7$) (mixture of rotamers) δ 10.00 (s, 1H), 8.79-8.70 (m, 1H), 7.69-7.55 (m, 2H), 7.43-7.36 (m, 2H), 6.44-6.36 (m, 0.4H), 6.36-6.29 (m, 0.6H), 5.37-5.30 (m, 0.6H), 5.09-5.03 (m, 0.4H), 4.87-4.79 (m, 2H), 4.22-4.16 (m, 0.6H), 3.95-3.80 (m, 1.4H), 3.68-3.54 (m, 1H), 2.97-2.85 (m, 1H), 2.67-2.56 (m, 1H), 2.56-2.44 (m, 1H), 1.81-1.71 (m, 1H), 1.70-1.59 (m, 3H), 1.24-1.20 (m, 3H), 1.04-0.93 (m, 6H), 0.93-0.87 (m, 2H), 0.83-0.75 (m, 2H)

Examples 24 and 25. 1-(Cyclopropylmethyl)-4-((2S,5R)-4-((S)-(4-fluorophenyl)(5-(trifluoromethoxy)pyridin-2-yl)methyl)-2,5-dimethylpiperazin-1-yl)-1H-[1,2,4]triazolo[3,4-b]purine and 1-(cyclopropylmethyl)-4-((2S,5R)-4-((R)-(4-fluorophenyl)(5-(trifluoromethoxy)pyridin-2-yl)methyl)-2,5-dimethylpiperazin-1-yl)-1H-[1,2,4]triazolo[3,4-b]purine

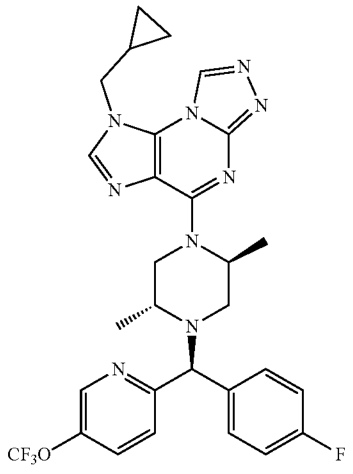

and

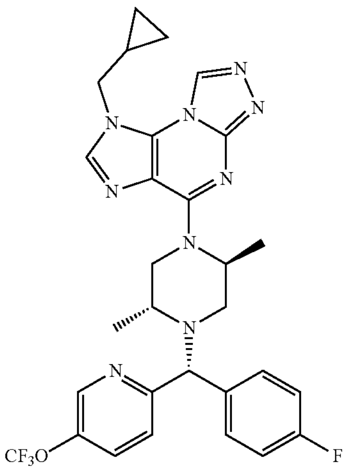

Step 1. 2-Chloro-9-(cyclopropylmethyl)-6-((2S,5R)-4-((4-fluorophenyl)(5-(trifluoromethoxy)pyridin-2-yl)methyl)-2,5-dimethylpiperazin-1-yl)-9H-purine

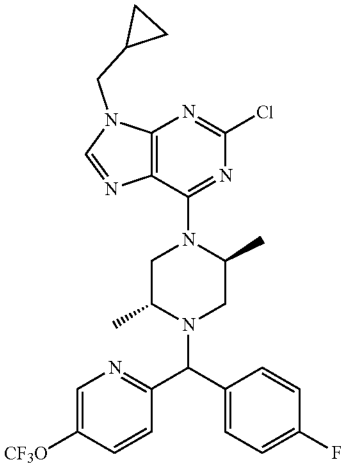

To a suspension of 2-chloro-6-((2S,5R)-4-((4-fluorophenyl)(5-(trifluoromethoxy)pyridin-2-yl)methyl)-2,5-dimethylpiperazin-1-yl)-9H-purine (Intermediate 34, 0.500 g, 0.933 mmol) and cesium carbonate (1.520 g, 4.66 mmol) in MeCN (4.66 mL) was added (bromomethyl)cyclopropane (0.136 mL, 1.399 mmol) and the mixture was stirred at 50° C. for 1 h. The mixture was cooled to rt, filtered, and concentrated under in vacuo. The residue was purified by flash column chromatography (24 g $SiO_2$, EtOAc/hexanes) to give the desired product (0.496 g, 90% yield) as a mixture of diastereomers in the form of a light orange solid. LC-MS calculated for $C_{28}H_{29}ClF_4N_7O$ $(M+H)^+$: m/z=590.2; found 590.2.

Step 2. 9-(Cyclopropylmethyl)-6-((2S,5R)-4-((4-fluorophenyl)(5-(trifluoromethoxy)pyridin-2-yl)methyl)-2,5-dimethylpiperazin-1-yl)-2-hydrazineyl-9H-purine

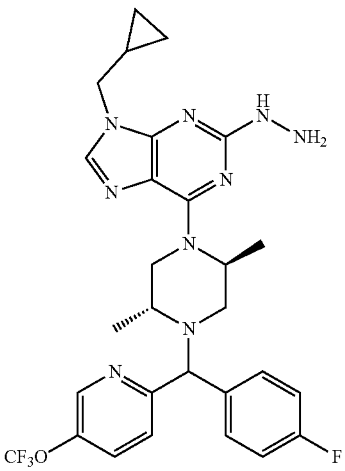

To a mixture 2-chloro-9-(cyclopropylmethyl)-6-((2S,5R)-4-((4-fluorophenyl)(5-(trifluoromethoxy)pyridin-2-yl)

methyl)-2,5-dimethylpiperazin-1-yl)-9H-purine (Step 1, 0.496 g, 0.840 mmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (18.0 mg, 0.021 mmol, Aldrich 745979), and cesium carbonate (0.821 g, 2.52 mmol) under a nitrogen atmosphere was added a 1 molar solution of hydrazine in THF (4.20 mL, 4.20 mmol) and the reaction mixture was stirred at 60° C. for 30 min. After cooling to rt, the mixture was filtered through a pad of $MgSO_4$ in a SiliaPrep SPE thiol cartridge (SiliCycle SPE-R51030B-06P). The filtrate was concentrated, and the crude material obtained (mixture of diastereomers) was used directly without further purification. LC-MS calculated for $C_{28}H_{32}F_4N_9O$ $(M+H)^+$: m/z=586.3; found 586.3.

Step 3: 1-(Cyclopropylmethyl)-4-((2S,5R)-4-((S)-(4-fluorophenyl)(5-(trifluoromethoxy)pyridin-2-yl)methyl)-2,5-dimethylpiperazin-1-yl)-1H-[1,2,4]triazolo[3,4-b]purine and 1-(cyclopropylmethyl)-4-((2S,5R)-4-((R)-(4-fluorophenyl)(5-(trifluoromethoxy)pyridin-2-yl)methyl)-2,5-dimethylpiperazin-1-yl)-1H-[1,2,4]triazolo[3,4-b]purine A mixture of 9-(cyclopropylmethyl)-6-((2S,5R)-4-((4-fluorophenyl)(5-(trifluoromethoxy)pyridin-2-yl)methyl)-2,5-dimethylpiperazin-1-yl)-2-hydrazineyl-9H-purine (Step 2), triethyl orthoformate (1.40 mL, 8.40 mmol), and trifluoroacetic acid (6.47 µL, 0.084 mmol) was stirred at 85° C. for 16 h. The diastereomeric mixture was diluted with acetonitrile, water, and several drops of TFA, and the mixture was filtered and purified by prep-HPLC (XBridge C18 column, eluting with a gradient of acetonitrile/water containing 0.150% $NH_4OH$, at a flow rate of 60 mL/min.). Fractions containing the desired product were concentrated in vacuo, and the material obtained was purified a second time by prep-HPLC (Sunfire C18 column, eluting with a gradient of acetonitrile/water containing 0.10% TFA, at flow rate of 60 mL/min) to afford each diastereomer as its TFA salt.

Example 24: Retention time on LCMS $t_r$=1.41 min, LC-MS calculated for $C_{29}H_{30}F_4N_9O$ $(M+H)^+$: m/z=596.3; found 596.3. $^1H$ NMR (600 MHz, DMSO-$d_6$) δ 9.64 (s, 1H), 8.56 (s, 1H), 8.48-8.42 (m, 1H), 7.97-7.93 (m, 2H), 7.68-7.61 (m, 2H), 7.23-7.17 (m, 2H), 6.25-6.18 (m, 0.4H), 5.97-5.92 (m, 0.6H), 5.16-5.08 (m, 0.6H), 4.84 (s, 1H), 4.70-4.65 (m, 0.4H), 4.46-4.35 (m, 2H), 3.95-3.90 (m, 0.6H), 3.69-3.64 (m, 0.4H), 3.29-3.11 (m, 1H), 2.97-2.79 (m, 1H), 2.46-2.33 (m, 1H), 1.55 (d, J=6.6 Hz, 1.2H), 1.50 (d, J=6.8 Hz, 1.8H), 1.43-1.35 (m, 1H), 0.95-0.91 (m, 3H), 0.68-0.60 (m, 2H), 0.52-0.48 (m, 2H).

Example 25: Retention time on LCMS $t_r$=1.49 min, LC-MS calculated for $C_{29}H_{30}F_4N_9O$ $(M+H)^+$: m/z=596.3; found 596.3. $^1H$ NMR (600 MHz, DMSO-$d_6$) δ 9.62 (s, 1H), 8.62 (s, 1H), 8.47-8.40 (m, 1H), 7.92-7.89 (m, 2H), 7.65-7.59 (m, 2H), 7.22-7.15 (m, 2H), 6.25-6.15 (m, 0.4H), 5.97-5.90 (m, 0.6H), 5.15-5.05 (m, 0.6H), 4.88 (s, 1H), 4.71-4.61 (m, 0.4H), 4.47-4.35 (m, 2H), 3.93-3.87 (m, 0.6H), 3.69-3.60 (m, 0.4H), 3.18-3.05 (m, 1H), 2.87-2.73 (m, 1H), 2.50-2.39 (m, 1H), 1.54-1.45 (m, 3H), 1.45-1.34 (m, 1H), 0.99-0.94 (m, 3H), 0.69-0.60 (m, 2H), 0.54-0.47 (m, 2H).

Examples 26 and 27. 4-((2S,5R)-4-((S)-(4-Fluorophenyl)(5-(trifluoromethoxy)pyridin-2-yl)methyl)-2,5-dimethylpiperazin-1-yl)-1-(((S)-tetrahydrofuran-2-yl)methyl)-1H-[1,2,4]triazolo[3,4-b]purine and 4-((2S,5R)-4-((R)-(4-fluorophenyl)(5-(trifluoromethoxy)pyridin-2-yl)methyl)-2,5-dimethylpiperazin-1-yl)-1-(((S)-tetrahydrofuran-2-yl)methyl)-1H-[1,2,4]triazolo[3,4-b]purine

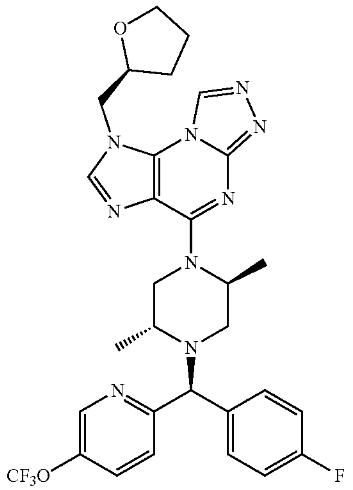

and

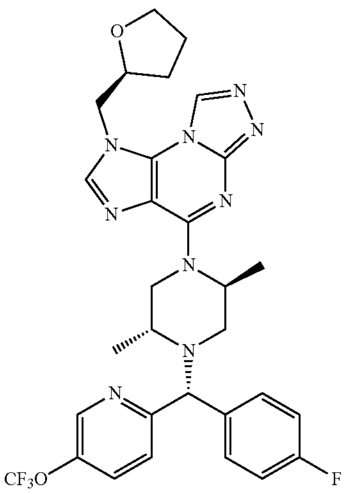

Step 1: 2-Chloro-6-((2S,5R)-4-((4-fluorophenyl)(5-(trifluoromethoxy)pyridin-2-yl)methyl)-2,5-dimethylpiperazin-1-yl)-9-(((S)-tetrahydrofuran-2-yl)methyl)-9H-purine

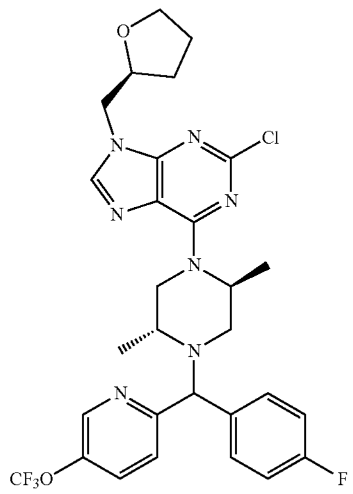

To a mixture of 2-chloro-6-((2S,5R)-4-((4-fluorophenyl)(5-(trifluoromethoxy)pyridin-2-yl)methyl)-2,5-dimethylpiperazin-1-yl)purine (Intermediate 34, 0.364 g, 0.679 mmol) and (S)-(tetrahydrofuran-2-yl)methyl methanesulfonate (Intermediate 22, 0.184 g, 1.019 mmol) in MeCN (1.70 mL) was added cesium carbonate (1.106 g, 3.40 mmol) and the suspension was stirred at 85° C. for 16 h. The mixture was cooled to rt, filtered, and concentrated under in vacuo. The residue was purified by flash column chromatography (24 g $SiO_2$, EtOAc/hexanes) to give the desired product (0.380 g, 90% yield) as a mixture of diastereomers in the form of a light orange solid. LC-MS calculated for $C_{29}H_{31}ClF_4N_7O_2$ $(M+H)^+$: m/z=620.2; found 620.2.

Step 2: 6-((2S,5R)-4-((4-Fluorophenyl)(5-(trifluoromethoxy)pyridin-2-yl)methyl)-2,5-dimethylpiperazin-1-yl)-2-hydrazineyl-9-(((S)-tetrahydrofuran-2-yl)methyl)-9H-purine

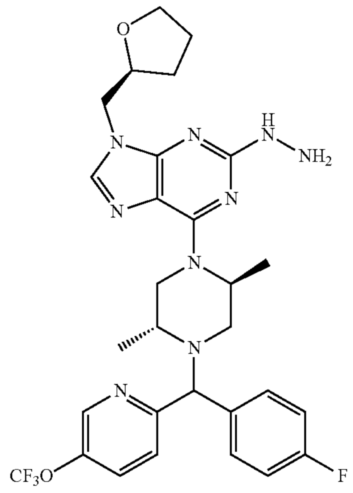

To a mixture of 2-chloro-6-((2S,5R)-4-((4-fluorophenyl)(5-(trifluoromethoxy)pyridin-2-yl)methyl)-2,5-dimethylpiperazin-1-yl)-9-(((S)-tetrahydrofuran-2-yl)methyl)-9H-purine (Step 1, 0.380 g, 0.612 mmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (13.1 mg, 0.015 mmol, Aldrich 745979), and cesium carbonate (0.598 g, 1.84 mmol) under a nitrogen atmosphere was added a 1 molar solution of hydrazine in THF (3.06 mL, 3.06 mmol) and the reaction mixture was stirred at 60° C. for 30 min. After cooling to rt, the mixture was filtered through a pad of $MgSO_4$ in a SiliaPrep SPE thiol cartridge (SiliCycle SPE-R51030B-06P). The filtrate was concentrated, and the crude material obtained (mixture of diastereomers) was used directly without further purification. LC-MS calculated for $C_{29}H_{34}F_4N_9O_2(M+H)^+$: m/z=616.3; found 616.3.

Step 3: 4-((2S,5R)-4-((S)-(4-Fluorophenyl)(5-(trifluoromethoxy)pyridin-2-yl)methyl)-2,5-dimethylpiperazin-1-yl)-1-(((S)-tetrahydrofuran-2-yl)methyl)-1H-[1,2,4]triazolo[3,4-b]purine and 4-((2S,5R)-4-((R)-(4-fluorophenyl)(5-(trifluoromethoxy)pyridin-2-yl)methyl)-2,5-dimethylpiperazin-1-yl)-1-(((S)-tetrahydrofuran-2-yl)methyl)-1H-[1,2,4]triazolo[3,4-b]purine A mixture of 6-((2S,5R)-4-((4-fluorophenyl)(5-(trifluoromethoxy)pyridin-2-yl)methyl)-2,5-dimethylpiperazin-1-yl)-2-hydrazineyl-9-(((S)-tetrahydrofuran-2-yl)methyl)-9H-purine (Step 2), triethyl orthoformate (1.02 mL, 6.12 mmol), and trifluoroacetic acid (4.71 μL, 0.061 mmol) was stirred at 85° C. for 16 h. The diastereomeric mixture was diluted with acetonitrile, water, and several drops of TFA, and the mixture was filtered and purified by prep-HPLC (XBridge C18 column, eluting with a gradient of acetonitrile/water containing 0.150% $NH_4OH$, at a flow rate of 60 mL/min.). Fractions containing the desired product were concentrated in vacuo, and the material obtained was purified a second time by prep-HPLC (Sunfire C18 column, eluting with a gradient of acetonitrile/water containing 0.10% TFA, at flow rate of 60 mL/min) to afford each diastereomer as its TFA salt.

Example 26: Retention time on LCMS $t_r$=1.38 min, LC-MS calculated for $C_{30}H_{32}F_4N_9O_2(M+H)^+$: m/z=626.3; found 626.2. $^1$H NMR (500 MHz, DMF-$d_7$) (mixture of rotamers) δ 9.72 (s, 1H), 8.64-8.59 (m, 1H), 8.51-8.44 (m, 1H), 8.12-8.07 (m, 1H), 8.03-7.96 (m, 1H), 7.78-7.72 (m, 2H), 7.27-7.19 (m, 2H), 6.37-6.30 (m, 0.4H), 6.12-6.05 (m, 0.6H), 5.30-5.22 (m, 0.6H), 5.09-5.03 (m, 1H), 4.93 (s, 1H), 4.87-4.78 (m, 1.4H), 4.38-4.32 (m, 1H), 4.08-4.00 (m, 0.6H), 3.82-3.74 (m, 1.4H), 3.68-3.60 (m, 1H), 3.35-3.31 (m, 1H), 3.09-2.95 (m, 1H), 2.55-2.49 (m, 1H), 2.24-2.11 (m, 1H), 1.93-1.77 (m, 3H), 1.68-1.56 (m, 3H), 1.04-1.00 (m, 3H).

Example 27: Retention time on LCMS $t_r$=1.47 min LC-MS calculated for $C_{30}H_{32}F_4N_9O_2$ $(M+H)^+$: m/z=626.3; found 626.2. $^1$H NMR (500 MHz, DMF-$d_7$) (mixture of rotamers) δ 9.72-9.68 (m, 1H), 8.68-8.64 (m, 1H), 8.46 (s, 1H), 8.08-8.04 (m, 1H), 7.99-7.93 (m, 1H), 7.77-7.69 (m, 2H), 7.27-7.18 (m, 2H), 6.39-6.25 (m, 0.4H), 6.12-6.00 (m, 0.6H), 5.31-5.18 (m, 0.6H), 5.09-5.02 (m, 1H), 4.97 (s, 1H), 4.89-4.73 (m, 1.4H), 4.38-4.30 (m, 1H), 4.05-3.93 (m, 0.6H), 3.82-3.74 (m, 1.4H), 3.68-3.60 (m, 1H), 3.25-3.22 (m, 1H), 3.01-2.84 (m, 1H), 2.60-2.54 (m, 1H), 2.24-2.14 (m, 1H), 1.94-1.77 (m, 3H), 1.63-1.55 (m, 3H), 1.07-1.02 (m, 3H).

Example 28. 2-(4-((2S,5R)-4-(Bis(4-fluorophenyl)methyl)-2,5-dimethylpiperazin-1-yl)-1H-[1,2,4]triazolo[3,4-b]purin-1-yl)-N,N-dimethylethan-1-amine

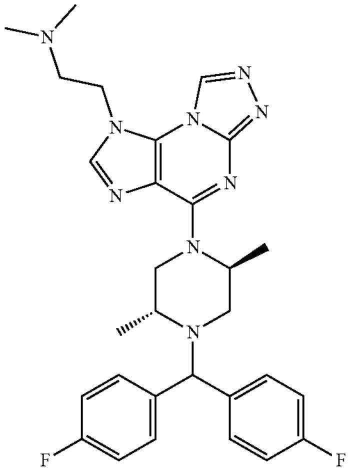 [SMILES: C[C@@H]1CN(c2nc3nncn3c3c2ncn3CCN(C)C)[C@@H](C)CN1C(c1ccc(F)cc1)c1ccc(F)cc1]

Step 1. 2-(6-((2S,5R)-4-(Bis(4-fluorophenyl)methyl)-2,5-dimethylpiperazin-1-yl)-2-chloro-9H-purin-9-yl)-N,N-dimethylethan-1-amine

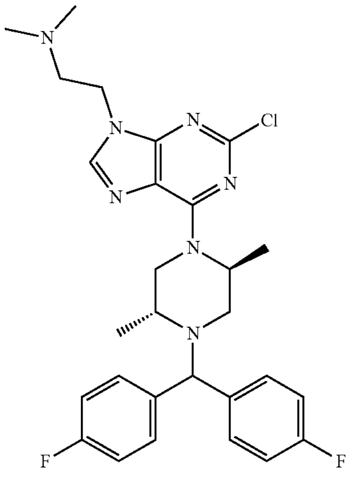 [SMILES: C[C@@H]1CN(c2nc(Cl)nc3c2ncn3CCN(C)C)[C@@H](C)CN1C(c1ccc(F)cc1)c1ccc(F)cc1]

A mixture of 6-((2S,5R)-4-(bis(4-fluorophenyl)methyl)-2,5-dimethylpiperazin-1-yl)-2-chloro-9H-purine (Intermediate 21, 2.33 g, 4.97 mmol) in DMF (24.8 mL) was added cesium carbonate (4.86 g, 14.9 mmol) and 2-bromo-N,N-dimethylethan-1-amine hydrobromide (1.74 g, 7.47 mmol, AstaTech 010701) and the reaction mixture was stirred at 80° C. overnight. After cooling to rt, additional cesium carbonate (1.62 g, 4.97 mmol) and 2-bromo-N,N-dimethylethan-1-amine hydrobromide (1.74 g, 7.47 mmol) was added and the reaction mixture was stirred at 80° C. for 1 h. The reaction mixture was filtered and the filtrate was concentrated. The crude residue was purified by flash column chromatography (40 g $SiO_2$, eluting with a gradient of 0-10% MeOH in $CH_2Cl_2$) to afford the desired product (1.45 g, 54% yield) as a yellow waxy solid. LC-MS calculated for $C_{28}H_{33}ClF_2N_7(M+H)^+$: m/z=540.2; found 540.2.

Step 2. 2-(6-((2S,5R)-4-(Bis(4-fluorophenyl)methyl)-2,5-dimethylpiperazin-1-yl)-2-hydrazineyl-9H-purin-9-yl)-N,N-dimethylethan-1-amine

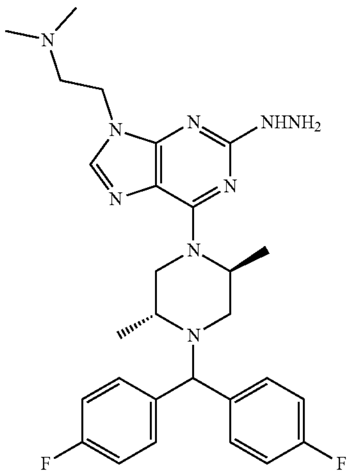 [SMILES: C[C@@H]1CN(c2nc(NN)nc3c2ncn3CCN(C)C)[C@@H](C)CN1C(c1ccc(F)cc1)c1ccc(F)cc1]

A mixture of 2-(6-((2S,5R)-4-(bis(4-fluorophenyl)methyl)-2,5-dimethylpiperazin-1-yl)-2-chloro-9H-purin-9-yl)-N,N-dimethylethan-1-amine (1.45 g, 2.68 mmol), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (46 mg, 0.054 mmol, Strem 46-0325), and cesium carbonate (1.75 g, 5.37 mmol) in a 1 molar solution of hydrazine in THF (6.71 mL, 6.71 mmol) was purged with nitrogen and stirred at 60° C. for 1 h. After cooling to rt, the reaction mixture was diluted with $CH_2Cl_2$ and filtered through a pad of $MgSO_4$ in a SiliaPrep SPE thiol cartridge (SiliCycle SPE-R51030B-06P). The filtrate was concentrated and the crude material obtained was used directly without further purification. LC-MS calculated for $C_{28}H_{36}F_2N_9$ $(M+H)^+$: m/z=536.3; found 536.3.

Step 3. 2-(4-((2S,5R)-4-(Bis(4-fluorophenyl)methyl)-2,5-dimethylpiperazin-1-yl)-1H-[1,2,4]triazolo[3,4-b]purin-1-yl)-N,N-dimethylethan-1-amine A mixture of 2-(6-((2S,5R)-4-(bis(4-fluorophenyl)methyl)-2,5-dimethylpiperazin-1-yl)-2-hydrazineyl-9H-purin-9-yl)-N,N-dimethylethan-1-amine (Step 2), triethyl orthoformate (4.5 mL, 27 mmol), and AcOH (154 μL, 2.68 mmol) was stirred at 90° C. overnight. After cooling to rt, the reaction mixture was diluted with acetonitrile and concentrated in vacuo. To the residue was added acetonitrile and water, and the mixture was filtered and purified by prep-HPLC (Sunfire C18 column, eluting with a gradient of acetonitrile/water containing 0.1% TFA, at flow rate of 60 mL/min) to afford the desired product as its TFA salt. Fractions containing the desired product were concentrated, and the material was re-purified by prep-HPLC (Sunfire C18 column, eluting with a gradient of acetonitrile/water containing 0.1% $NH_4OH$, at flow rate of 60 mL/min) to afford the desired product. LC-MS calculated for $C_{29}H_{34}F_2N_9$ $(M+H)^+$: m/z=546.3; found 546.3. $^1H$ NMR (600 MHz, DMSO-$d_6$) (mixture of rotamers) δ 9.20 (s, 1H), 8.03 (s, 1H), 7.62-7.54 (m, 4H), 7.18-7.11 (m, 4H), 6.19-6.00 (m, 0.4H), 5.89-5.70 (m, 0.6H), 5.16-4.97 (m, 0.6H), 4.65 (s, 1H), 4.62-4.50 (m, 2.4H), 3.82-3.59 (m, 0.6H), 3.55-3.36 (m, 0.4H), 3.20-2.99 (m, 1H), 2.82-2.60 (m, 3H), 2.45-2.34 (m, 1H), 2.15 (s, 6H), 1.42 (d, J=6.6 Hz, 3H), 0.90 (d, J=6.5 Hz, 3H).

Example 29. 4-((2S,5R)-4-(Bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine

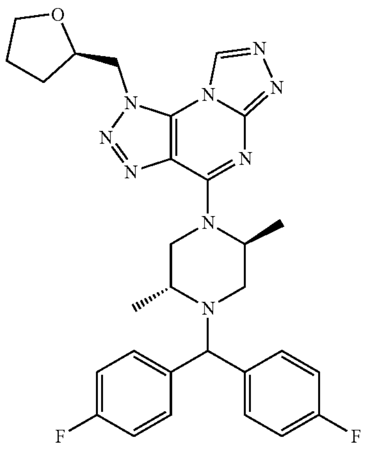 [SMILES: C[C@@H]1CN(c2nc3nncn3c3c2nnn3C[C@H]2CCCO2)[C@@H](C)CN1C(c1ccc(F)cc1)c1ccc(F)cc1]

Step 1: 6-((2S,5R)-4-(Bis(4-fluorophenyl)methyl)-2,5-dimethylpiperazin-1-yl)-2-chloro-5-nitro-N—(((R)-tetrahydrofuran-2-yl)methyl)pyrimidin-4-amine

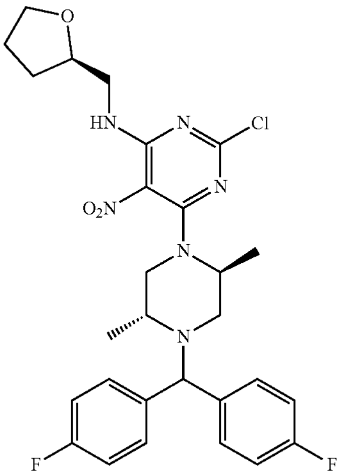 [SMILES: C[C@@H]1CN(c2nc(Cl)nc(NC[C@H]3CCCO3)c2[N+](=O)[O-])[C@@H](C)CN1C(c1ccc(F)cc1)c1ccc(F)cc1]

A mixture of 2,4,6-trichloro-5-nitropyrimidine (2.00 g, 8.76 mmol, Combi-Blocks, ST-3909) and (2R,5S)-1-(bis(4-fluorophenyl)methyl)-2,5-dimethylpiperazine hydrochloride (Intermediate 1, 3.41 g, 9.66 mmol) in $CH_3CN$ (100 mL) was cooled to 0° C. in an ice-bath before N-ethyl-N-isopropylpropan-2-amine (6.12 mL, 35.0 mmol) was added and the reaction mixture was stirred at 0° C. for 30 min. To the mixture was added (R)-(tetrahydrofuran-2-yl)methanamine (0.886 g, 8.76 mmol, BLD Pharmatech, BD46980) and the reaction mixture was warmed to rt and stirred for 30 min. The mixture was diluted with saturated aqueous $NaHCO_3$ and extracted with EtOAc. The organic layer was removed, and the aqueous layer was extracted with EtOAc. The combined organic layers were dried over $MgSO_4$, filtered, and concentrated under reduced pressure to afford the desired product. The crude material obtained was used directly without further purification. LC-MS calculated for $C_{28}H_{32}ClF_2N_6O_3$ $(M+H)^+$: m/z=573.2; found 573.2.

Step 2. 6-((2S,5R)-4-(Bis(4-fluorophenyl)methyl)-2,5-dimethylpiperazin-1-yl)-2-chloro-$N^4$-(((R)-tetrahydrofuran-2-yl)methyl)pyrimidine-4,5-diamine

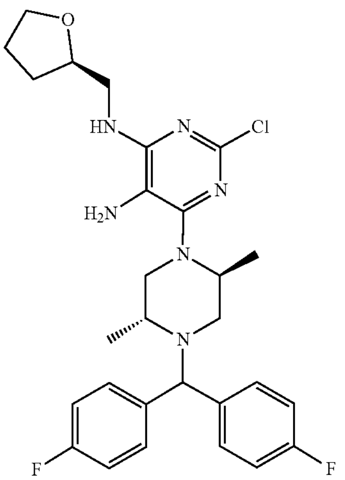 [SMILES: C[C@@H]1CN(c2nc(Cl)nc(NC[C@H]3CCCO3)c2N)[C@@H](C)CN1C(c1ccc(F)cc1)c1ccc(F)cc1]

To a mixture of 6-((2S,5R)-4-(bis(4-fluorophenyl)methyl)-2,5-dimethylpiperazin-1-yl)-2-chloro-5-nitro-N—(((R)-tetrahydrofuran-2-yl)methyl)pyrimidin-4-amine (Step 1) in saturated aqueous $NH_4Cl$ (20 mL)/MeOH (20 mL)/THF (20 mL) was added iron (1.95 g, 35.0 mmol) and the reaction mixture was stirred at 65° C. overnight. After cooling to rt, the reaction mixture was diluted with EtOAc (100 mL) and saturated aqueous $NaHCO_3$ and the resulting mixture was filtered over a pad of Celite. The organic layer was removed, and the aqueous layer was extracted with EtOAc. The combined organic layers were dried over $MgSO_4$, filtered, and concentrated under reduced pressure to afford the desired product. The crude material obtained was used directly without further purification. LC-MS calculated for $C_{28}H_{34}ClF_2N_6O$ $(M+H)^+$: m/z=543.2; found 543.2.

Step 3. 7-((2S,5R)-4-(Bis(4-fluorophenyl)methyl)-2,5-dimethylpiperazin-1-yl)-5-chloro-3-(((R)-tetrahydrofuran-2-yl)methyl)-3H-[1,2,3]triazolo[4,5-d]pyrimidine

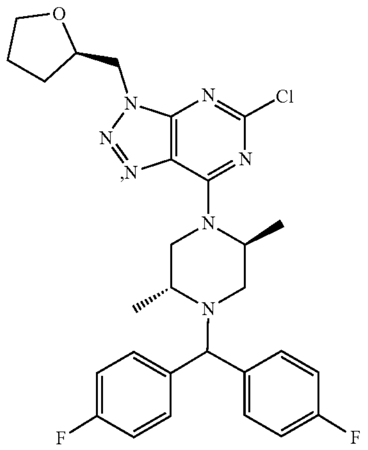

To a mixture of 6-((2S,5R)-4-(bis(4-fluorophenyl)methyl)-2,5-dimethylpiperazin-1-yl)-2-chloro-$N^4$-(((R)-tetrahydrofuran-2-yl)methyl)pyrimidine-4,5-diamine (Step 2) and AcOH (2.0 mL, 35 mmol) in water (20 mL) and THF (20 mL) was added sodium nitrite (2.42 g, 35.0 mmol) and the reaction mixture was stirred at rt for 30 min. The mixture was diluted with EtOAc (100 mL) and the aqueous layer was adjusted to pH=8 with saturated aqueous $NaHCO_3$. The organic layer was removed, and the aqueous layer was extracted with EtOAc. The organic phases were combined, dried over $MgSO_4$, filtered, and concentrated under reduced pressure. The crude residue was purified by flash column chromatography ($SiO_2$, 0-10% EtOAc/$CH_2Cl_2$) to afford the desired product (2.8 g, 58% yield over 3 steps) as a yellow solid. LC-MS calculated for $C_{28}H_{31}ClF_2N_7O$ $(M+H)^+$: m/z=554.2; found 554.2.

Step 4. 7-((2S,5R)-4-(Bis(4-fluorophenyl)methyl)-2,5-dimethylpiperazin-1-yl)-5-hydrazineyl-3-(((R)-tetrahydrofuran-2-yl)methyl)-3H-[1,2,3]triazolo[4,5-d]pyrimidine

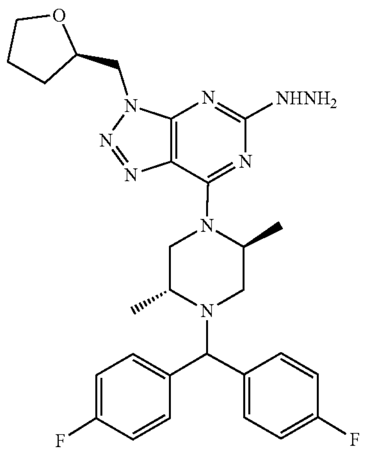 [SMILES: C[C@@H]1CN(c2nc(NN)nc3c2nnn3C[C@H]2CCCO2)[C@@H](C)CN1C(c1ccc(F)cc1)c1ccc(F)cc1]

To a mixture of 7-((2S,5R)-4-(bis(4-fluorophenyl)methyl)-2,5-dimethylpiperazin-1-yl)-5-chloro-3-(((R)-tetrahydrofuran-2-yl)methyl)-3H-[1,2,3]triazolo[4,5-d]pyrimidine (2.8 g, 5.1 mmol), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (0.374 g, 0.438 mmol, Aldrich 745979) and cesium carbonate (2.85 g, 8.76 mmol) in 1,4-dioxane (100 mL) was added hydrazine (0.561 g, 17.5 mmol) and the mixture was purged with nitrogen and stirred at 90° C. for 1 h. After cooling to rt, the reaction mixture was diluted with $CH_2Cl_2$ and filtered over a pad of Celite. The filtrate was concentrated under reduced pressure, and the crude residue was purified by flash column chromatography ($SiO_2$, 0-5% MeOH/$CH_2Cl_2$) to afford the desired product (2.5 g, 90% yield) as a yellow solid. LC-MS calculated for $C_{28}H_{34}F_2N_9O$ $(M+H)^+$: m/z=550.3; found 550.7.

Step 5. 4-((2S,5R)-4-(Bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine To a mixture of 7-((2S,5R)-4-(bis(4-fluorophenyl)methyl)-2,5-dimethylpiperazin-1-yl)-5-hydrazineyl-3-(((R)-tetrahydrofuran-2-yl)methyl)-3H-[1,2,3]triazolo[4,5-d]pyrimidine (2.5 g, 4.5 mmol) and AcOH (2.0 mL, 35 mmol) was added triethyl orthoformate (6.49 g, 43.8 mmol) and the reaction mixture was stirred at 95° C. for 1 h. After cooling to rt, the reaction mixture was concentrated under reduced pressure, and to the crude residue was added $CH_3CN$ (10 mL) and saturated aqueous $NaHCO_3$. The mixture was extracted with EtOAc (3×100 mL), and the combined organic phases were dried over $MgSO_4$, filtered, and concentrated under reduced pressure. The crude residue was purified by flash column chromatography ($SiO_2$, 0-70% EtOAc/$CH_2Cl_2$ followed by 5% MeOH/$CH_2Cl_2$) to afford the desired product (1.8 g, 71% yield) as a white solid. The product was recrystallized from $CH_2Cl_2$/MTBE/hexanes (20 mL/20 mL/20 mL) and the solid precipitate was filtered, washed with MTBE/hexanes (1:3), and dried under vacuum to afford the desired product (1.1 g). LC-MS calculated for $C_{29}H_{32}F_2N_9O$ $(M+H)^+$: m/z=560.3; found 560.3. $^1H$ NMR (600 MHz, DMSO-$d_6$) (mixture of rotamers) δ 9.32 (s, 1H), 7.64-7.57 (m, 4H), 7.19-7.13 (m, 4H), 5.86 (m, 0.5H), 5.59-5.48 (m, 0.5H), 5.13-5.06 (m, 1.5H), 4.93-4.86 (m, 1H), 4.68 (s, 1H), 4.66-4.61 (m, 0.5H), 4.29-4.22 (m, 1H), 3.97-3.84 (m, 0.5H), 3.59-3.46 (m, 2.5H), 3.23-3.11 (m, 1H), 2.88-2.78 (m, 0.5H), 2.77-2.68 (m, 0.5H), 2.48-2.43 (m, 1H), 2.14-2.06 (m, 1H), 1.82-1.70 (m, 3H), 1.52-1.44 (m, 3H), 0.93 (d, J=6.5 Hz, 3H).

Example 30. 4-((2S,5R)-4-(Bis(4-fluorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine

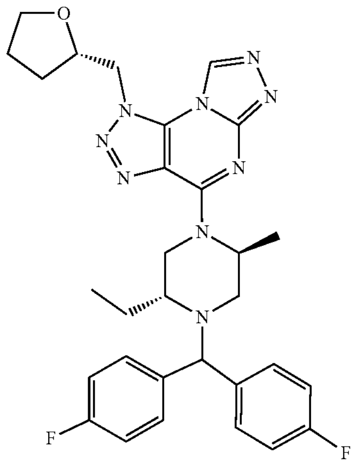

Step 1: 6-((2S,5R)-4-(Bis(4-fluorophenyl)methyl)-5-ethyl-2-methylpiperazin-1-yl)-2-chloro-N—(((S)-tetrahydrofuran-2-yl)methyl)pyrimidine-4,5-diamine

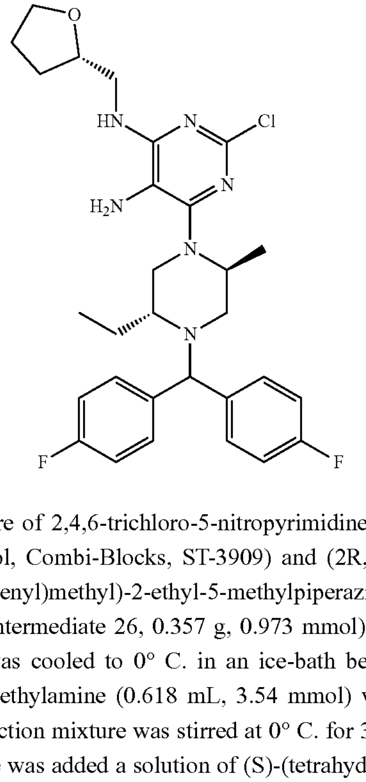

A mixture of 2,4,6-trichloro-5-nitropyrimidine (0.202 g, 0.884 mmol, Combi-Blocks, ST-3909) and (2R,5S)-1-(bis(4-fluorophenyl)methyl)-2-ethyl-5-methylpiperazine hydrochloride (Intermediate 26, 0.357 g, 0.973 mmol) in MeCN (15 mL) was cooled to 0° C. in an ice-bath before N,N-diisopropylethylamine (0.618 mL, 3.54 mmol) was added and the reaction mixture was stirred at 0° C. for 30 min. To the mixture was added a solution of (S)-(tetrahydrofuran-2-yl)methanamine (0.094 g, 0.929 mmol, BLD Pharmatech, BD48352) in MeCN (1 mL) and the reaction mixture was warmed to rt and stirred for 30 min. To the mixture was added tetrahydroxydiboron (0.238 g, 2.65 mmol, BLD Pharmatech, BD288251) followed by MeOH (5 mL) and the reaction mixture was cooled to 0° C. A mixture of 4,4'-dipyridyl (0.014 g, 0.088 mmol) in MeOH (1 mL) was added dropwise and the reaction mixture was stirred at 0° C. for 10 min. After warming to rt, the reaction mixture was diluted with EtOAc (20 mL) and saturated aqueous $NaHCO_3$ and the resulting mixture was filtered over a pad of Celite. The organic layer was removed, and the aqueous layer was extracted with EtOAc. The combined organic layers were dried over $MgSO_4$, filtered, and concentrated under reduced pressure. The residue was purified by flash column chromatography ($SiO_2$, 0-2% MeOH in $CH_2Cl_2$) to afford the desired product. LC-MS calculated for $C_{29}H_{36}ClF_2N_6O$ $(M+H)^+$: m/z=557.2; found 557.2.

Step 2. 7-((2S,5R)-4-(Bis(4-fluorophenyl)methyl)-5-ethyl-2-methylpiperazin-1-yl)-5-chloro-3-(((S)-tetrahydrofuran-2-yl)methyl)-3H-[1,2,3]triazolo[4,5-d]pyrimidine

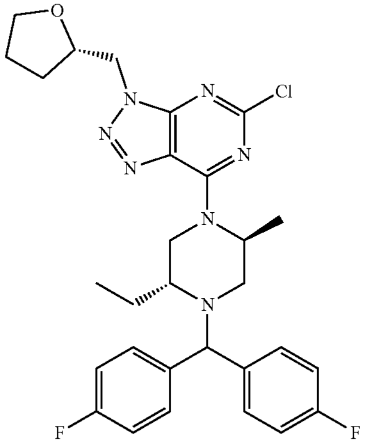 [SMILES: CC[C@@H]1CN(c2nc(Cl)nc3c2nnn3C[C@@H]2CCCO2)[C@@H](C)CN1C(c1ccc(F)cc1)c1ccc(F)cc1]

To a mixture of 6-((2S,5R)-4-(bis(4-fluorophenyl)methyl)-5-ethyl-2-methylpiperazin-1-yl)-2-chloro-$N^4$—(((S)-tetrahydrofuran-2-yl)methyl)pyrimidine-4,5-diamine (Step 1) and AcOH (0.3 mL, 5 mmol) in water (4 mL) and THF (4 mL) was added sodium nitrite (0.183 g, 2.65 mmol) and the reaction mixture was stirred at rt for 30 min. The mixture was diluted with EtOAc (20 mL) and the aqueous layer was adjusted to pH=8 with saturated aqueous $NaHCO_3$. The organic layer was removed, and the aqueous layer was extracted with EtOAc. The organic phases were combined, dried over $MgSO_4$, filtered, and concentrated under reduced pressure. The crude residue was purified by flash column chromatography ($SiO_2$, 0-10% EtOAc/$CH_2Cl_2$) to afford the desired product. LC-MS calculated for $C_{29}H_{33}ClF_2N_7O$ $(M+H)^+$: m/z=568.2; found 568.2.

Step 3. 7-((2S,5R)-4-(Bis(4-fluorophenyl)methyl)-5-ethyl-2-methylpiperazin-1-yl)-5-hydrazineyl-3-(((S)-tetrahydrofuran-2-yl)methyl)-3H-[1,2,3]triazolo[4,5-d]pyrimidine

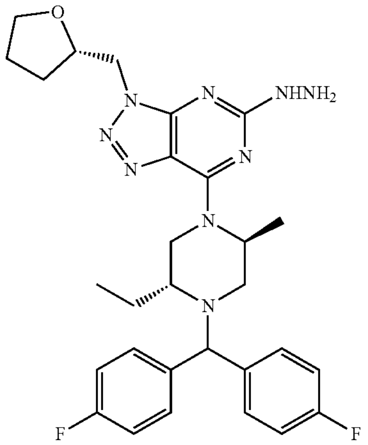 [SMILES: CC[C@@H]1CN(c2nc(NN)nc3c2nnn3C[C@@H]2CCCO2)[C@@H](C)CN1C(c1ccc(F)cc1)c1ccc(F)cc1]

To a mixture of 7-((2S,5R)-4-(bis(4-fluorophenyl)methyl)-5-ethyl-2-methylpiperazin-1-yl)-5-chloro-3-(((S)-tetrahydrofuran-2-yl)methyl)-3H-[1,2,3]triazolo[4,5-d]pyrimidine (Step 2) in MeCN (10 mL) was added hydrazine hydrate (0.86 mL, 18 mmol, Aldrich 225819) and the mixture was stirred at 90° C. for 1 h. After cooling to rt, the reaction mixture was concentrated under reduced pressure, and the crude residue was purified by flash column chromatography ($SiO_2$, 0-5% $MeOH/CH_2Cl_2$) to afford the desired product (0.13 g, 26% yield over 3 steps) as an off-white solid. LC-MS calculated for $C_{29}H_{36}F_2N_9O$ $(M+H)^+$: m/z=564.3; found 564.4.

Step 4. 4-((2S,5R)-4-(Bis(4-fluorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine To a mixture of 7-((2S,5R)-4-(bis(4-fluorophenyl)methyl)-5-ethyl-2-methylpiperazin-1-yl)-5-hydrazineyl-3-(((S)-tetrahydrofuran-2-yl)methyl)-3H-[1,2,3]triazolo[4,5-d]pyrimidine (0.13 g, 0.23 mmol) in AcOH (2 mL) was added triethyl orthoformate (1.31 g, 8.84 mmol) and the reaction mixture was stirred at 95° C. for 1 h. After cooling to rt, the reaction mixture was concentrated under reduced pressure, and to the crude residue was added MeCN (2 mL) and saturated aqueous $NaHCO_3$. The mixture was extracted with EtOAc (3×20 mL), and the combined organic phases were dried over $MgSO_4$, filtered, and concentrated under reduced pressure. The crude residue was purified by flash column chromatography ($SiO_2$, 0-5% $MeOH/CH_2Cl_2$) to afford the desired product (90 mg, 68% yield) as a white solid. To a mixture of the product in 1:1 $MeCN/H_2O$ (20 mL) was added TFA (23 μL, 0.3 mmol) and the resulting mixture was lyophilized to afford the desired product as its TFA salt. LC-MS calculated for $C_{30}H_{34}F_2N_9O$ $(M+H)^+$: m/z=574.3; found 574.4. $^1H$ NMR (600 MHz, DMSO-$d_6$) (mixture of rotamers) δ 9.55 (s, 1H), 7.65-7.55 (m, 4H), 7.21-7.13 (m, 4H), 5.92-5.83 (m, 0.4H), 5.82-5.73 (m, 0.6H), 5.23-5.14 (m, 1H), 5.13-5.04 (m, 0.6H), 5.01-4.93 (m, 1H), 4.92-4.85 (m, 0.4H), 4.82 (s, 1H), 4.28-4.20 (m, 1H), 3.98-3.90 (m, 0.6H), 3.65-3.54 (m, 1.4H), 3.54-3.47 (m, 1H), 2.88-2.67 (m, 2H), 2.55-2.49 (m, 1H), 2.16-2.06 (m, 1H), 1.82-1.62 (m, 3H), 1.62-1.47 (m, 4H), 1.47-1.36 (m, 1H), 0.66 (t, J=7.4 Hz, 1.2H), 0.59 (t, J=7.4 Hz, 1.8H).

Example 31. 4-((2S,5R)-4-(Bis(4-fluorophenyl)methyl)-2,5-diethylpiperazin-1-yl)-1-(((S)-tetrahydrofuran-2-yl)methyl)-1H-[1,2,3]triazolo[4,5-e][1,2,4]triazolo[4,3-a]pyrimidine

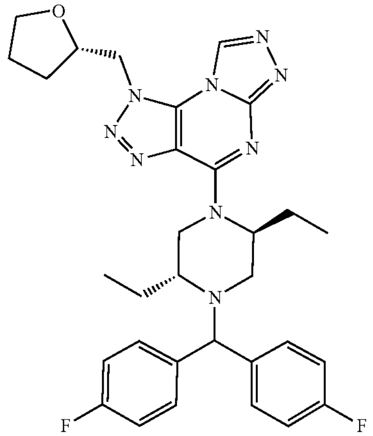 [SMILES: CC[C@H]1CN(C(c2ccc(F)cc2)c2ccc(F)cc2)[C@H](CC)CN1c1nc2nncn2c2c1nnn2C[C@@H]1CCCO1]

Step 1: 6-((2S,5R)-4-(Bis(4-fluorophenyl)methyl)-2,5-diethylpiperazin-1-yl)-2-chloro-5-nitro-N—(((S)-tetrahydrofuran-2-yl)methyl)pyrimidin-4-amine

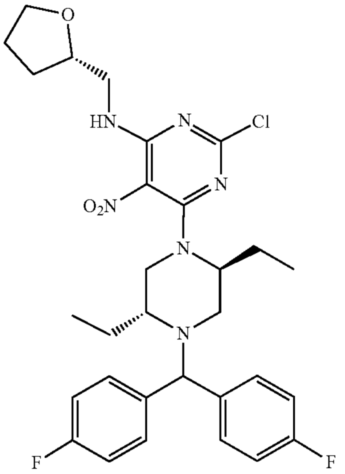 [SMILES: CC[C@H]1CN(C(c2ccc(F)cc2)c2ccc(F)cc2)[C@H](CC)CN1c1nc(Cl)nc(NC[C@@H]2CCCO2)c1[N+](=O)[O-]]

A mixture of 2,4,6-trichloro-5-nitropyrimidine (0.100 g, 0.438 mmol, Combi-Blocks, ST-3909) and (2R,5S)-1-(bis(4-fluorophenyl)methyl)-2,5-diethylpiperazine hydrochloride (Intermediate 29, 0.183 g, 0.48 mmol) in MeCN (10 mL) was cooled to 0° C. in an ice-bath before N,N-diisopropylethylamine (0.3 mL, 1.7 mmol) was added and the reaction mixture was stirred at 0° C. for 30 min. To the mixture was added (S)-(tetrahydrofuran-2-yl)methanamine (0.886 g, 8.76 mmol, BLD Pharmatech, BD48352) and the reaction mixture was warmed to rt and stirred for 30 min. The mixture was diluted with saturated aqueous $NaHCO_3$ and extracted with EtOAc. The organic layer was removed, and the aqueous layer was extracted with EtOAc. The combined organic layers were dried over $MgSO_4$, filtered, and concentrated under reduced pressure to afford the desired product. The crude material obtained was used directly without further purification. LC-MS calculated for $C_{30}H_{36}ClF_2NO_3$ (M+H)$^+$: m/z=601.2; found 601.3.

Step 2. 6-((2S,5R)-4-(Bis(4-fluorophenyl)methyl)-2,5-diethylpiperazin-1-yl)-2-chloro-$N^4$—(((S)-tetrahydrofuran-2-yl)methyl)pyrimidine-4,5-diamine

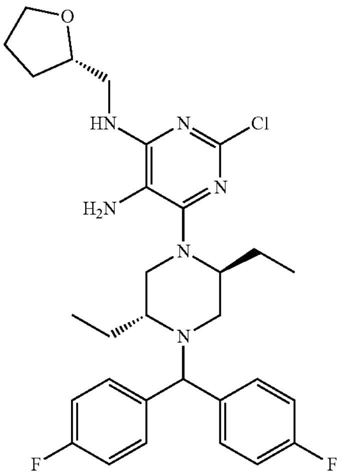 [SMILES: CC[C@H]1CN(C(c2ccc(F)cc2)c2ccc(F)cc2)[C@H](CC)CN1c1nc(Cl)nc(NC[C@@H]2CCCO2)c1N]

To a mixture of 6-((2S,5R)-4-(bis(4-fluorophenyl)methyl)-2,5-diethylpiperazin-1-yl)-2-chloro-5-nitro-N—(((S)-tetrahydrofuran-2-yl)methyl)pyrimidin-4-amine (Step 1) in saturated aqueous $NH_4Cl$ (2 mL)/MeOH (2 mL)/THF (2 mL) was added iron (98 mg, 1.75 mmol) and the reaction mixture was stirred at 65° C. overnight. After cooling to rt, the reaction mixture was diluted with $CH_2Cl_2$ (10 mL) and saturated aqueous $NaHCO_3$ and the resulting mixture was filtered over a pad of Celite. The organic layer was removed, and the aqueous layer was extracted with $CH_2Cl_2$. The combined organic layers were dried over $Na_2SO_4$, filtered, and concentrated under reduced pressure to afford the desired product. The crude material obtained was used directly without further purification. LC-MS calculated for $C_{30}H_{38}ClF_2N_6O$ (M+H)$^+$: m/z=571.3; found 571.3.

Step 3. 7-((2S,5R)-4-(Bis(4-fluorophenyl)methyl)-2,5-diethylpiperazin-1-yl)-5-chloro-3-(((S)-tetrahydrofuran-2-yl)methyl)-3H-[1,2,3]triazolo[4,5-d]pyrimidine

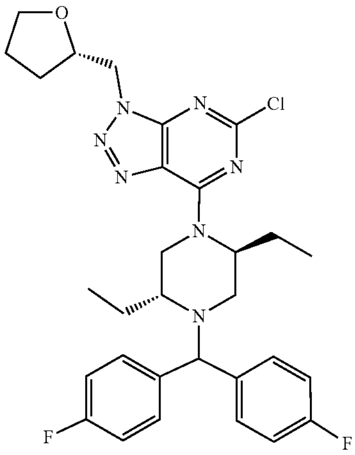

To a mixture of 6-((2S,5R)-4-(bis(4-fluorophenyl)methyl)-2,5-diethylpiperazin-1-yl)-2-chloro-$N^4$—(((S)-tetrahydrofuran-2-yl)methyl)pyrimidine-4,5-diamine (Step 2) and AcOH (0.38 mL, 6.6 mmol) in water (2 mL) and THF (2 mL) was added sodium nitrite (0.121 g, 1.75 mmol) and the reaction mixture was stirred at rt for 30 min. The mixture was diluted with EtOAc and extracted with saturated aqueous $NaHCO_3$. The organic layer was removed, and the aqueous layer was extracted with EtOAc. The organic phases were combined, dried over $MgSO_4$, filtered, and concentrated under reduced pressure. The crude residue was purified by flash column chromatography ($SiO_2$, 0-10% EtOAc/$CH_2Cl_2$) to afford the desired product (0.19 g, 75% yield over 3 steps). LC-MS calculated for $C_{30}H_{35}ClF_2N_7O$ (M+H)$^+$: m/z=582.3; found 582.3.

Step 4. 7-((2S,5R)-4-(Bis(4-fluorophenyl)methyl)-2,5-diethylpiperazin-1-yl)-5-hydrazineyl-3-(((S)-tetrahydrofuran-2-yl)methyl)-3H-[1,2,3]triazolo[4,5-d]pyrimidine

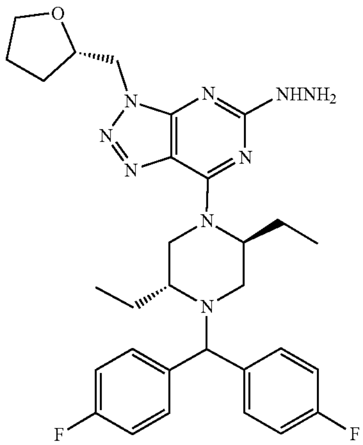 [SMILES: CC[C@H]1CN(C(c2ccc(F)cc2)c2ccc(F)cc2)[C@H](CC)CN1c1nc(NN)nc2c1nnn2C[C@@H]1CCCO1]

To a mixture of 7-((2S,5R)-4-(bis(4-fluorophenyl)methyl)-2,5-diethylpiperazin-1-yl)-5-chloro-3-(((S)-tetrahydrofuran-2-yl)methyl)-3H-[1,2,3]triazolo[4,5-d]pyrimidine (Step 3) in MeCN (10 mL) was added hydrazine hydrate (0.43 mL, 8.8 mmol, Aldrich 225819) and the mixture was stirred at 90° C. for 1 h. After cooling to rt, the reaction mixture was concentrated under reduced pressure, and the crude residue was purified by flash column chromatography ($SiO_2$, 0-5% MeOH/$CH_2Cl_2$) to afford the desired product (0.15 g, 80% yield) as an off-white solid. LC-MS calculated for $C_{30}H_{38}F_2N_9O$ (M+H)$^+$: m/z=578.3; found 578.7.

Step 5. 4-((2S,5R)-4-(Bis(4-fluorophenyl)methyl)-2,5-diethylpiperazin-1-yl)-1-(((S)-tetrahydrofuran-2-yl)methyl)-1H-[1,2,3]triazolo[4,5-e][1,2,4]triazolo[4,3-a]pyrimidine To a mixture of 7-((2S,5R)-4-(bis(4-fluorophenyl)methyl)-2,5-diethylpiperazin-1-yl)-5-hydrazineyl-3-(((S)-tetrahydrofuran-2-yl)methyl)-3H-[1,2,3]triazolo[4,5-d]pyrimidine (0.15 g, 0.23 mmol) in AcOH (2 mL) was added triethyl orthoformate (0.324 g, 2.19 mmol) and the reaction mixture was stirred at 90° C. for 1 h. After cooling to rt, the reaction mixture was concentrated under reduced pressure, and the crude residue was diluted with acetonitrile, water, and several drops of TFA and purified by prep-HPLC (Sunfire C18 column, eluting with a gradient of acetonitrile/water containing 0.10% TFA, at flow rate of 60 mL/min) to afford the desired product as its TFA salt. LC-MS calculated for $C_{31}H_{36}F_2N_9O$ $(M+H)^+$: m/z=588.3; found 588.3. $^1H$ NMR (500 MHz, DMSO-$d_6$) (mixture of rotamers) δ 9.58 (s, 1H), 7.68-7.50 (m, 4H), 7.23-7.10 (m, 4H), 5.86-5.77 (m, 0.5H), 5.77-5.69 (m, 0.5H), 5.23-5.15 (m, 1H), 5.04-4.87 (m, 2H), 4.86-4.75 (m, 1H), 4.30-4.20 (m, 1H), 3.96-3.86 (m, 0.5H), 3.66-3.57 (m, 1H), 3.56-3.45 (m, 1.5H), 2.81-2.54 (m, 3H), 2.27-1.98 (m, 3H), 1.83-1.30 (m, 5H), 0.85-0.77 (m, 3H), 0.65 (t, J=7.3 Hz, 1.5H), 0.53 (t, J=7.3 Hz, 1.5H).

Example 32. 4-((2S,5R)-4-(Bis(4-fluorophenyl)methyl)-5-ethyl-2-methylpiperazin-1-yl)-1-(((R)-tetrahydrofuran-2-yl)methyl)-1H-[1,2,3]triazolo[4,5-e][1,2,4]triazolo[4,3-a]pyrimidine

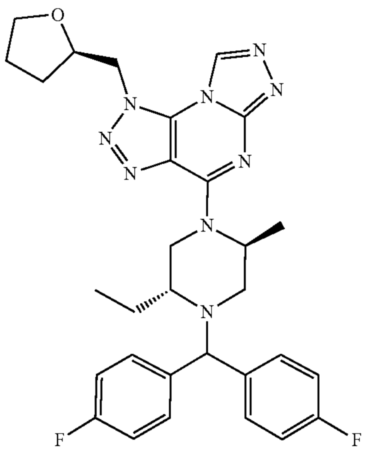 [SMILES: CC[C@@H]1CN(c2nc3nncn3c3c2nnn3C[C@H]2CCCO2)[C@@H](C)CN1C(c1ccc(F)cc1)c1ccc(F)cc1]

This compound was prepared according to the procedures described in Example 31, with (2R,5S)-1-(bis(4-fluorophenyl)methyl)-2-ethyl-5-methylpiperazine hydrochloride (Intermediate 26) replacing (2R,5S)-1-(bis(4-fluorophenyl)methyl)-2,5-diethylpiperazine hydrochloride and (R)-(tetrahydrofuran-2-yl)methanamine replacing (S)-(tetrahydrofuran-2-yl)methanamine in Step 1. LC-MS calculated for $C_{30}H_{34}F_2N_9O$ $(M+H)^+$: m/z=574.3; found 574.4. $^1H$ NMR (600 MHz, DMSO-$d_6$) (mixture of rotamers) δ 9.60 (s, 1H), 7.68-7.51 (m, 4H), 7.24-7.10 (m, 4H), 5.90-5.82 (m, 0.4H), 5.82-5.74 (m, 0.6H), 5.24-5.16 (m, 1H), 5.12-5.05 (m, 0.6H), 5.05-4.95 (m, 1H), 4.92-4.77 (m, 1.4H), 4.33-4.24 (m, 1H), 4.01-3.92 (m, 0.6H), 3.63-3.49 (m, 2.4H), 2.89-2.67 (m, 2H), 2.57-2.50 (m, 1H), 2.15-2.06 (m, 1H), 1.84-1.35 (m, 8H), 0.67 (t, J=7.3 Hz, 1.2H), 0.60 (t, J=7.3 Hz, 1.8H).

Example 33. 4-((2S,5R)-4-(Bis(4-fluorophenyl)methyl)-2,5-diethylpiperazin-1-yl)-1-(((R)-tetrahydrofuran-2-yl)methyl)-1H-[1,2,3]triazolo[4,5-e][1,2,4]triazolo[4,3-a]pyrimidine

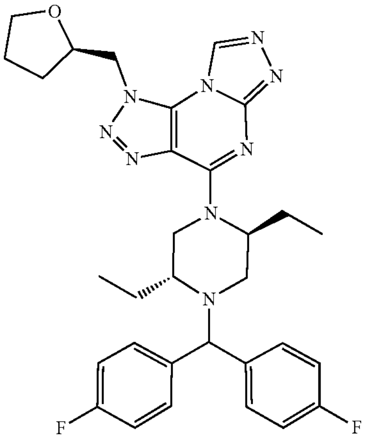 [SMILES: CC[C@H]1CN(C(c2ccc(F)cc2)c2ccc(F)cc2)[C@H](CC)CN1c1nc2nncn2c2c1nnn2C[C@H]1CCCO1]

This compound was prepared according to the procedures described in Example 31, with (R)-(tetrahydrofuran-2-yl)methanamine replacing (S)-(tetrahydrofuran-2-yl)methanamine in Step 1. LC-MS calculated for $C_{31}H_{36}F_2N_9O$ $(M+H)^+$: m/z=588.3; found 588.3. $^1H$ NMR (500 MHz, DMSO-$d_6$) (mixture of rotamers) δ 9.59-9.55 (m, 1H), 7.65-7.56 (m, 4H), 7.21-7.14 (m, 4H), 5.85-5.78 (m, 0.5H), 5.75-5.67 (m, 0.5H), 5.23-5.15 (m, 1H), 5.03-4.89 (m, 2H), 4.82 (s, 1H), 4.33-4.25 (m, 1H), 3.94-3.88 (m, 0.5H), 3.65-3.47 (m, 2.5H), 2.76-2.70 (m, 3H), 2.20-2.05 (m, 3H), 1.84-1.66 (m, 3H), 1.63-1.49 (m, 1H), 1.47-1.32 (m, 1H), 0.86-0.78 (m, 3H), 0.66 (t, J=7.3 Hz, 1.5H), 0.56 (t, J=7.3 Hz, 1.5H).

Example 34. 2-(4-((2S,5R)-4-(Bis(4-fluorophenyl)methyl)-2,5-dimethylpiperazin-1-yl)-1H-[1,2,4]triazolo[3,4-b]purin-1-yl-2-d)-N,N-dimethylethan-1-amine

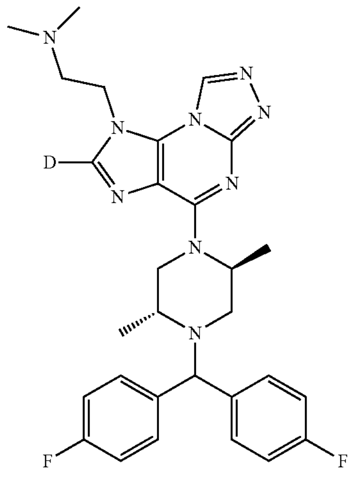 [SMILES: [2H]c1nc2c(N3C[C@@H](C)N(C(c4ccc(F)cc4)c4ccc(F)cc4)C[C@@H]3C)nc3nncn3c2n1CCN(C)C]

Step 1: tert-Butyl (2-(6-((2S,5R)-4-(bis(4-fluorophenyl)methyl)-2,5-dimethylpiperazin-1-yl)-2-chloro-9H-purin-9-yl-8-d)ethyl)(methyl)carbamate

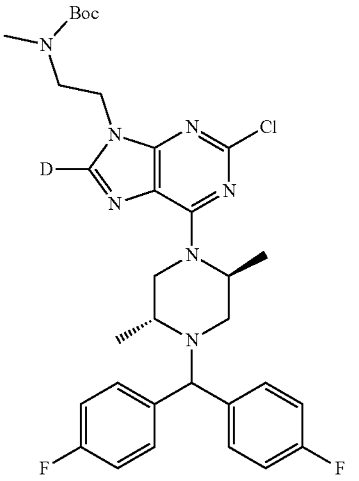 [SMILES: [2H]c1nc2c(N3C[C@@H](C)N(C(c4ccc(F)cc4)c4ccc(F)cc4)C[C@@H]3C)nc(Cl)nc2n1CCN(C)C(=O)OC(C)(C)C]

A mixture of tert-butyl (2-(6-((2S,5R)-4-(bis(4-fluorophenyl)methyl)-2,5-dimethylpiperazin-1-yl)-2-chloro-9H-purin-9-yl)ethyl)(methyl)carbamate (Intermediate 35, 850 mg, 1.36 mmol) in THF (20 mL) was cooled to −78° C. before a 2.5 M solution of n-butyllithium (1.1 mL, Aldrich 230707) was added dropwise and the reaction mixture was stirred at −78° C. for 30 min. Methanol-$d_4$ (73 mg, 2.04 mmol) was added dropwise and the mixture was stirred at −78° C. for 1 h. The reaction was quenched with saturated aqueous $NH_4Cl$. After warming to rt, the mixture was diluted with saturated aqueous $NaHCO_3$ and extracted with $CH_2Cl_2$. The combined organic layers were dried over $MgSO_4$, filtered, and concentrated under reduced pressure. The residue was purified by flash column chromatography ($SiO_2$, 0-50% EtOAc/hexanes followed by 0-3% MeOH/$CH_2Cl_2$) to afford the desired product (730 mg, 86% yield). LC-MS calculated for $C_{32}H_{38}DClF_2N_7O_2$ $(M+H)^+$: m/z=627.3; found 627.4.

Step 2. tert-Butyl (2-(6-((2S,5R)-4-(bis(4-fluorophenyl)methyl)-2,5-dimethylpiperazin-1-yl)-2-hydrazineyl-9H-purin-9-yl-8-d)ethyl)(methyl)carbamate

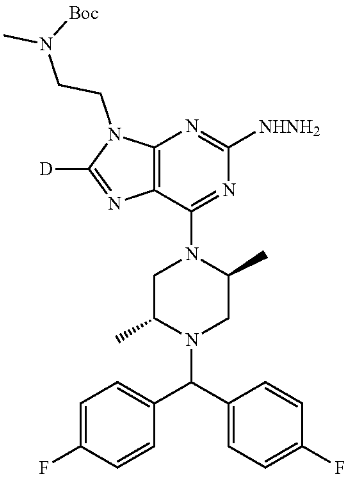 [SMILES: [2H]c1nc2c(N3C[C@@H](C)N(C(c4ccc(F)cc4)c4ccc(F)cc4)C[C@@H]3C)nc(NN)nc2n1CCN(C)C(=O)OC(C)(C)C]

To a mixture of tert-butyl (2-(6-((2S,5R)-4-(bis(4-fluorophenyl)methyl)-2,5-dimethylpiperazin-1-yl)-2-chloro-9H-purin-9-yl-8-d)ethyl)(methyl)carbamate (730 mg, 1.16 mmol) in 1,4-dioxane (4 mL) was added hydrazine hydrate (1.36 g, 27.2 mmol, Aldrich 225819) and the mixture was stirred at 115° C. overnight. After cooling to rt, the mixture was diluted with saturated aqueous $NaHCO_3$ and extracted with EtOAc. The combined organic layers were dried over $MgSO_4$, filtered, and concentrated under reduced pressure. The residue was purified by flash column chromatography ($SiO_2$, 0-10% MeOH/$CH_2Cl_2$) to afford the desired product (570 mg, 79% yield). LC-MS calculated for $C_{32}H_{41}DF_2N_9O_2$ $(M+H)^+$: m/z=623.3; found 623.5.

Step 3. tert-Butyl (2-(4-((2S,5R)-4-(bis(4-fluorophenyl)methyl)-2,5-dimethylpiperazin-1-yl)-1H-[1,2,4]triazolo[3,4-b]purin-1-yl-2-d)ethyl)(methyl)carbamate

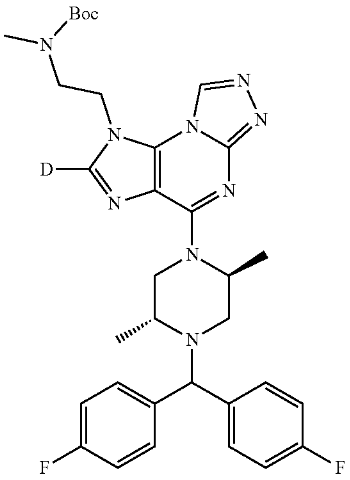 [SMILES: [2H]c1nc2c(N3C[C@@H](C)N(C(c4ccc(F)cc4)c4ccc(F)cc4)C[C@@H]3C)nc3nncn3c2n1CCN(C)C(=O)OC(C)(C)C]

To a mixture of tert-butyl (2-(6-((2S,5R)-4-(bis(4-fluorophenyl)methyl)-2,5-dimethylpiperazin-1-yl)-2-hydrazineyl-9H-purin-9-yl-8-d)ethyl)(methyl)carbamate (570 mg, 0.915 mmol) in AcOH (5 mL) was added triethyl orthoformate (0.45 mL, 2.7 mmol) and the reaction mixture was stirred at 95° C. overnight. After cooling to rt, the mixture was diluted with saturated aqueous $NaHCO_3$ and extracted with EtOAc. The combined organic layers were dried over $MgSO_4$, filtered, and concentrated under reduced pressure. The residue was purified by flash column chromatography ($SiO_2$, 0-10% MeOH/$CH_2Cl_2$) to afford the desired product (260 mg, 45% yield). LC-MS calculated for $C_{33}H_{39}DF_2N_9O_2$ $(M+H)^+$: m/z=633.3; found 633.4.

Step 4. 2-(4-((2S,5R)-4-(Bis(4-fluorophenyl)methyl)-2,5-dimethylpiperazin-1-yl)-1H-[1,2,4]triazolo[3,4-b]purin-1-yl-2-d)-N,N-dimethylethan-1-amine To a mixture of tert-butyl (2-(4-((2S,5R)-4-(bis(4-fluorophenyl)methyl)-2,5-dimethylpiperazin-1-yl)-1H-[1,2,4]triazolo[3,4-b]purin-1-yl-2-d)ethyl)(methyl)carbamate (260 mg, 0.411 mmol) in $CH_2Cl_2$ (2 mL) was added TFA (2.1 mL, 27 mmol) and the reaction mixture was stirred at rt for 1 h. The reaction mixture was concentrated in vacuo, and to the crude residue was added THF (10 mL) followed by a 37% solution of formaldehyde in $H_2O$ (110 mg, 1.4 mmol) and the reaction mixture was stirred at rt for 10 min before sodium triacetoxyborohydride (288 mg, 1.36 mmol) was added and the reaction mixture was stirred at rt for 2 h. After cooling to rt, the reaction mixture was diluted with saturated aqueous $NaHCO_3$ and extracted with EtOAc (3×20 mL). The combined organic layers were dried over $MgSO_4$, filtered, and concentrated in vacuo. The residue was purified by flash column chromatography ($SiO_2$, 0-12% MeOH in $CH_2Cl_2$) to afford the desired product (190 mg, 85% yield). To a mixture of the product in 1:1 MeCN/$H_2O$ (20 mL) was added TFA (52 μL, 0.68 mmol) and the resulting mixture was lyophilized to afford the desired product as its TFA salt. LC-MS calculated for $C_{29}H_{33}DF_2N_9$ $(M+H)^+$: m/z=547.3; found 547.3. $^1H$ NMR (600 MHz, DMSO-$d_6$) (mixture of rotamers) δ 9.59 (s, 1H), 7.65-7.56 (m, 4H), 7.21-7.14 (m, 4H), 6.20-6.12 (m, 0.4H), 5.92-5.86 (m, 0.6H), 5.14-5.07 (m, 0.6H), 5.01-4.94 (m, 2H), 4.72-4.63 (m, 1.4H), 3.93-3.85 (m, 0.6H), 3.71-3.61 (m, 2.4H), 3.27-3.13 (m, 1H), 2.89 (s, 6H), 2.81-2.69 (m, 1H), 2.54-2.43 (m, 1H), 1.57-1.45 (m, 3H), 0.96-0.85 (m, 3H).

Example 35. 2-(4-((2S,5R)-4-(Bis(4-fluorophenyl)methyl)-2,5-diethylpiperazin-1-yl)-1H-[1,2,4]triazolo[3,4-b]purin-1-yl)-N,N-dimethylethan-1-amine

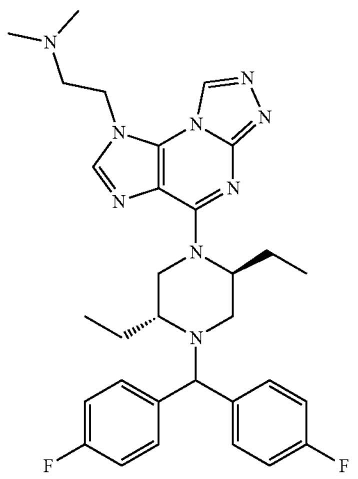 [SMILES: CC[C@H]1CN(C(c2ccc(F)cc2)c2ccc(F)cc2)[C@H](CC)CN1c1nc2nncn2c2c1ncn2CCN(C)C]

This compound was prepared according to the procedures described in Example 34, with tert-butyl (2-(6-((2S,5R)-4-(bis(4-fluorophenyl)methyl)-2,5-diethylpiperazin-1-yl)-2-chloro-9H-purin-9-yl)ethyl)(methyl)carbamate (Intermediate 36) replacing tert-butyl (2-(6-((2S,5R)-4-(bis(4-fluorophenyl)methyl)-2,5-dimethylpiperazin-1-yl)-2-chloro-9H-purin-9-yl-8-d)ethyl)(methyl)carbamate in Step 2. LC-MS calculated for $C_{31}H_{38}F_2N_9$ $(M+H)^+$: m/z=574.3; found 574.3.

Example 36. 2-(4-((2S,5R)-4-(Bis(4-fluorophenyl)methyl)-2,5-diethylpiperazin-1-yl)-1H-[1,2,4]triazolo[3,4-b]purin-1-yl-2-d)-N,N-dimethylethan-1-amine

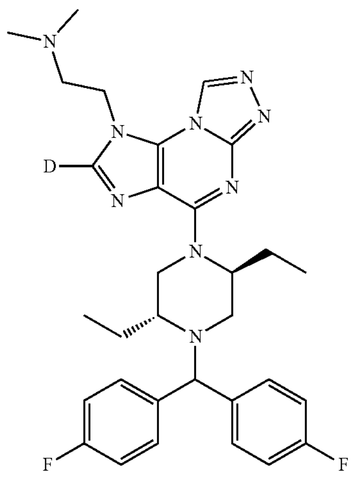 [SMILES: [2H]c1nc2c(N3C[C@@H](CC)N(C(c4ccc(F)cc4)c4ccc(F)cc4)C[C@@H]3CC)nc3nncn3c2n1CCN(C)C]

This compound was prepared according to the procedures described in Example 34, with tert-butyl (2-(6-((2S,5R)-4-(bis(4-fluorophenyl)methyl)-2,5-diethylpiperazin-1-yl)-2-chloro-9H-purin-9-yl)ethyl)(methyl)carbamate (Intermediate 36) replacing tert-butyl (2-(6-((2S,5R)-4-(bis(4-fluorophenyl)methyl)-2,5-dimethylpiperazin-1-yl)-2-chloro-9H-purin-9-yl)ethyl)(methyl)carbamate in Step 1. LC-MS calculated for $C_{31}H_{37}DF_2N_9(M+H)^+$: m/z=575.3; found 575.3.

Example 37. 2-(4-((2S,5R)-4-(Bis(4-fluorophenyl)methyl)-5-ethyl-2-methylpiperazin-1-yl)-1H-[1,2,4]triazolo[3,4-b]purin-1-yl)-N,N-dimethylethan-1-amine

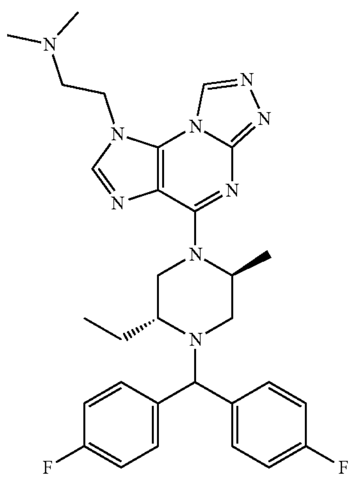 [SMILES: CC[C@@H]1CN(c2nc3nncn3c3c2ncn3CCN(C)C)[C@@H](C)CN1C(c1ccc(F)cc1)c1ccc(F)cc1]

This compound was prepared according to the procedures described in Example 28, with 6-((2S,5R)-4-(bis(4-fluorophenyl)methyl)-5-ethyl-2-methylpiperazin-1-yl)-2-chloro-9H-purine (Intermediate 37) replacing 6-((2S,5R)-4-(bis(4-fluorophenyl)methyl)-2,5-dimethylpiperazin-1-yl)-2- chloro-9H-purine in Step 1. LC-MS calculated for $C_{30}H_{36}F_2N_9$ $(M+H)^+$: m/z=560.3; found 560.4.

Example 38. 2-(4-((2S,5R)-4-(Bis(4-fluorophenyl)methyl)-5-ethyl-2-methylpiperazin-1-yl)-1H-[1,2,4]triazolo[3,4-b]purin-1-yl-2-d)-N,N-dimethylethan-1-amine

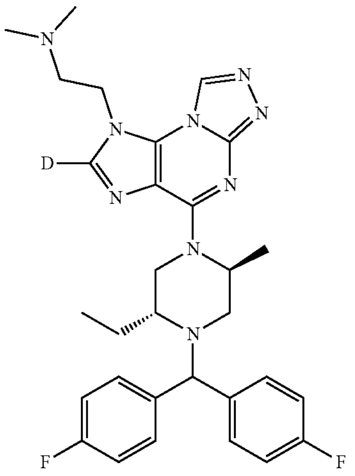 [SMILES: [2H]c1nc2c(N3C[C@@H](CC)N(C(c4ccc(F)cc4)c4ccc(F)cc4)C[C@@H]3C)nc3nncn3c2n1CCN(C)C]

This compound was prepared according to the procedures described in Example 34, with tert-Butyl (2-(6-((2S,5R)-4-(bis(4-fluorophenyl)methyl)-5-ethyl-2-methylpiperazin-1-yl)-2-chloro-9H-purin-9-yl)ethyl)(methyl)carbamate (Intermediate 95) replacing tert-butyl (2-(6-((2S,5R)-4-(bis(4-fluorophenyl)methyl)-2,5-dimethylpiperazin-1-yl)-2-chloro-9H-purin-9-yl)ethyl)(methyl)carbamate in Step 1. LC-MS calculated for $C_{30}H_{35}DF_2N_9(M+H)^+$: m/z=561.3; found 561.4.

Example 39. 4-((2S,5R)-4-(Bis(4-chlorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine

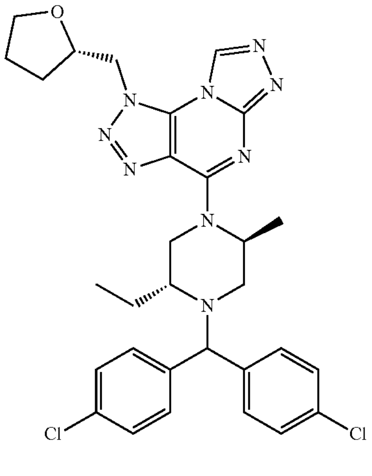 [SMILES: CC[C@@H]1CN(c2nc3nncn3c3c2nnn3C[C@@H]2CCCO2)[C@@H](C)CN1C(c1ccc(Cl)cc1)c1ccc(Cl)cc1]

This compound was prepared according to the procedures described in Example 30, with 6-((2S,5R)-4-(bis(4-chlorophenyl)methyl)-5-ethyl-2-methylpiperazin-1-yl)-2-chloro-$N^4$—(((S)-tetrahydrofuran-2-yl)methyl)pyrimidine-4,5-diamine (Intermediate 39) replacing 6-((2S,5R)-4-(bis(4-fluorophenyl)methyl)-5-ethyl-2-methylpiperazin-1-yl)-2-chloro-$N^4$—(((S)-tetrahydrofuran-2-yl)methyl)pyrimidine-4,5-diamine in Step 2. LC-MS calculated for $C_{30}H_{34}C_{12}N_9O$ $(M+H)^+$: m/z=606.2; found 606.3. $^1H$ NMR (500 MHz, DMSO-$d_6$) (mixture of rotamers) δ 9.61-9.57 (m, 1H), 7.63-7.56 (m, 4H), 7.44-7.37 (m, 4H), 5.92-5.84 (m, 0.4H), 5.83-5.75 (m, 0.6H), 5.25-5.16 (m, 1H), 5.13-5.04 (m, 0.6H), 5.03-4.95 (m, 1H), 4.92-4.86 (m, 0.4H), 4.84 (s, 1H), 4.29-4.20 (m, 1H), 4.00-3.93 (m, 0.6H), 3.67-3.56 (m, 1.4H), 3.55-3.47 (m, 1H), 2.89-2.71 (m, 2H), 2.56-2.51 (m, 1H), 2.17-2.06 (m, 1H), 1.83-1.63 (m, 3H), 1.63-1.47 (m, 4H), 1.47-1.36 (m, 1H), 0.67 (t, J=7.3 Hz, 1.2H), 0.60 (t, J=7.3 Hz, 1.8H).

Example 40. 4-((2S,5R)-4-(Bis(4-chlorophenyl)methyl)-5-ethyl-2-methylpiperazin-1-yl)-1-(((R)-tetrahydrofuran-2-yl)methyl)-1H-[1,2,3]triazolo[4,5-e][1,2,4]triazolo[4,3-a]pyrimidine

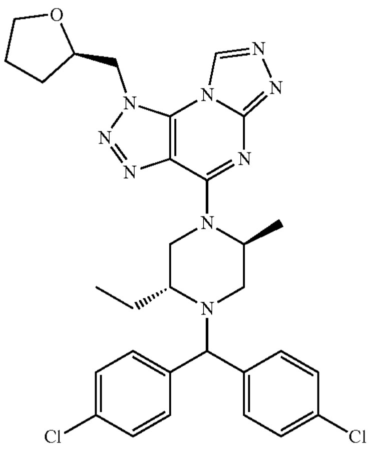 [SMILES: CC[C@@H]1CN(c2nc3nncn3c3c2nnn3C[C@H]2CCCO2)[C@@H](C)CN1C(c1ccc(Cl)cc1)c1ccc(Cl)cc1]

This compound was prepared according to the procedures described in Example 30, with 6-((2S,5R)-4-(bis(4-chlorophenyl)methyl)-5-ethyl-2-methylpiperazin-1-yl)-2-chloro-$N^4$-(((R)-tetrahydrofuran-2-yl)methyl)pyrimidine-4,5-diamine (Intermediate 40) replacing 6-((2S,5R)-4-(bis(4-fluorophenyl)methyl)-5-ethyl-2-methylpiperazin-1-yl)-2-chloro-$N^4$—(((S)-tetrahydrofuran-2-yl)methyl)pyrimidine-4,5-diamine in Step 2. LC-MS calculated for $C_{30}H_{34}C_{12}N_9O$ $(M+H)^+$: m/z=606.2; found 606.3. $^1H$ NMR (500 MHz, DMSO-$d_6$) (mixture of rotamers) δ 9.58 (s, 1H), 7.63-7.56 (m, 4H), 7.43-7.37 (m, 4H), 5.89-5.82 (m, 0.4H), 5.81-5.75 (m, 0.6H), 5.24-5.16 (m, 1H), 5.12-5.05 (m, 0.6H), 5.04-4.95 (m, 1H), 4.91-4.81 (m, 1.4H), 4.33-4.24 (m, 1H), 4.00-3.92 (m, 0.6H), 3.65-3.49 (m, 2.4H), 2.89-2.69 (m, 2H), 2.56-2.51 (m, 1H), 2.15-2.05 (m, 1H), 1.83-1.61 (m, 3H), 1.61-1.48 (m, 4H), 1.47-1.37 (m, 1H), 0.67 (t, J=7.4 Hz, 1.2H), 0.61 (t, J=7.4 Hz, 1.8H).

Example 41. 4-((2S,5R)-4-(Bis(4-chlorophenyl)methyl)-5-ethyl-2-methylpiperazin-1-yl)-2-methyl-1-(((S)-tetrahydrofuran-2-yl)methyl)-1H-[1,2,4]triazolo[3,4-b]purine

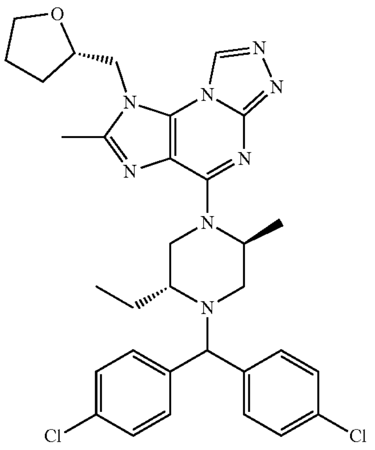 [SMILES: CC[C@@H]1CN(c2nc3nncn3c3c2nc(C)n3C[C@@H]2CCCO2)[C@@H](C)CN1C(c1ccc(Cl)cc1)c1ccc(Cl)cc1]

Step 1. 6-((2S,5R)-4-(Bis(4-chlorophenyl)methyl)-5-ethyl-2-methylpiperazin-1-yl)-2-chloro-8-methyl-9-(((S)-tetrahydrofuran-2-yl)methyl)-9H-purine

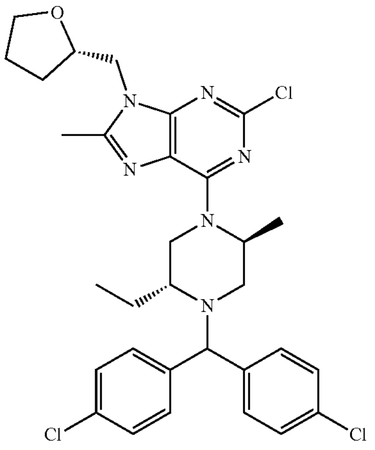 [SMILES: CC[C@@H]1CN(c2nc(Cl)nc3c2nc(C)n3C[C@@H]2CCCO2)[C@@H](C)CN1C(c1ccc(Cl)cc1)c1ccc(Cl)cc1]

A mixture of 6-((2S,5R)-4-(bis(4-chlorophenyl)methyl)-5-ethyl-2-methylpiperazin-1-yl)-2-chloro-N[4]—(((S)-tetrahydrofuran-2-yl)methyl)pyrimidine-4,5-diamine (Intermediate 39, 20 mg, 0.034 mmol) and triethyl orthoacetate (11 mg, 0.068 mmol) in AcOH (2 mL) was stirred at 100° C. for 2 h. After cooling to rt, the mixture was diluted with saturated aqueous $NaHCO_3$ and extracted with EtOAc. The combined organic layers were dried over $MgSO_4$, filtered, and concentrated under reduced pressure to afford the desired product. The crude material obtained was used directly without further purification. LC-MS calculated for $C_{31}H_{36}Cl_3N_6O$ $(M+H)^+$: m/z=613.2; found 613.3.

Step 2. 6-((2S,5R)-4-(Bis(4-chlorophenyl)methyl)-5-ethyl-2-methylpiperazin-1-yl)-2-hydrazineyl-8-methyl-9-(((S)-tetrahydrofuran-2-yl)methyl)-9H-purine

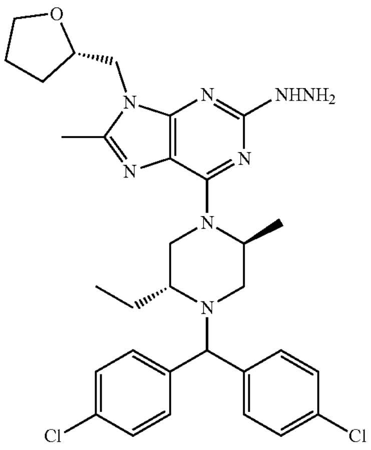 [SMILES: CC[C@@H]1CN(c2nc(NN)nc3c2nc(C)n3C[C@@H]2CCCO2)[C@@H](C)CN1C(c1ccc(Cl)cc1)c1ccc(Cl)cc1]

To a mixture of 6-((2S,5R)-4-(bis(4-chlorophenyl)methyl)-5-ethyl-2-methylpiperazin-1-yl)-2-chloro-8-methyl-9-(((S)-tetrahydrofuran-2-yl)methyl)-9H-purine (Step 1) in 1,4-dioxane (4 mL) was added hydrazine hydrate (33.9 mg, 0.678 mmol, Aldrich 225819) and the mixture was stirred at 120° C. overnight. After cooling to rt, the mixture was diluted with saturated aqueous $NaHCO_3$ and extracted with EtOAc. The combined organic layers were dried over $MgSO_4$, filtered, and concentrated under reduced pressure to afford the desired product. The crude material obtained was used directly without further purification. LC-MS calculated for $C_{31}H_{39}Cl_2N_8O$ $(M+H)^+$: m/z=609.3; found 609.4.

Step 3. 4-((2S,5R)-4-(Bis(4-chlorophenyl)methyl)-5-ethyl-2-methylpiperazin-1-yl)-2-methyl-1-(((S)-tetrahydrofuran-2-yl)methyl)-1H-[1,2,4]triazolo[3,4-b]purine A mixture of 6-((2S,5R)-4-(bis(4-chlorophenyl)methyl)-5-ethyl-2-methylpiperazin-1-yl)-2-hydrazineyl-8-methyl-9-(((S)-tetrahydrofuran-2-yl)methyl)-9H-purine (Step 2) and triethyl orthoformate (10.1 mg, 0.068 mmol) in AcOH (2 mL) was stirred at 90° C. for 1 h. After cooling to rt, the reaction mixture was concentrated in vacuo, and the crude residue was diluted with acetonitrile, water, and TFA and purified by prep-HPLC (Sunfire C18 column, eluting with a gradient of acetonitrile/water containing 0.10% TFA, at flow rate of 60 mL/min) to afford the desired product as its TFA salt. LC-MS calculated for $C_{32}H_{37}Cl_2N_8O$ $(M+H)^+$: m/z=619.2; found 619.3. $^1H$ NMR (500 MHz, DMSO-$d_6$) (mixture of rotamers) δ 9.51-9.47 (m, 1H), 7.62-7.53 (m, 4H), 7.43-7.36 (m, 4H), 6.21-6.14 (m, 0.4H), 6.14-6.07 (m, 0.6H), 5.08-4.99 (m, 0.6H), 4.88-4.82 (m, 0.4H), 4.81 (s, 1H), 4.76-4.67 (m, 1H), 4.58-4.50 (m, 1H), 4.14-4.05 (m, 1H), 3.80-3.72 (m, 0.6H), 3.74-3.65 (m, 1H), 3.59-3.51 (m, 1.4H), 2.82-2.61 (m, 2H), 2.58 (s, 1.2H), 2.56 (s, 1.8H), 2.52-2.41 (m, 1H), 2.17-2.07 (m, 1H), 1.98-1.87 (m, 1H), 1.88-1.75 (m, 1H), 1.77-1.66 (m, 1H), 1.60-1.44 (m, 4H), 1.45-1.33 (m, 1H), 0.69-0.60 (m, 3H).

Example 42. 4-((2S,5R)-4-(Bis(4-chlorophenyl)methyl)-5-ethyl-2-methylpiperazin-1-yl)-2-methyl-1-(((R)-tetrahydrofuran-2-yl)methyl)-1H-[1,2,4]triazolo[3,4-b]purine

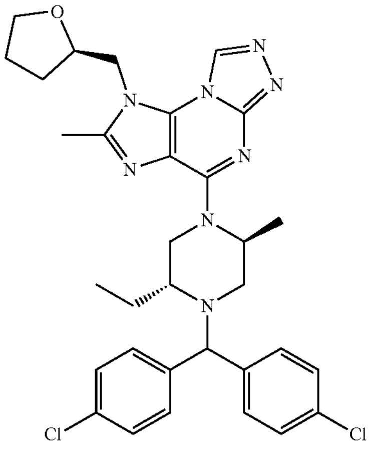 [SMILES: CC[C@@H]1CN(c2nc3nncn3c3c2nc(C)n3C[C@H]2CCCO2)[C@@H](C)CN1C(c1ccc(Cl)cc1)c1ccc(Cl)cc1]

This compound was prepared according to the procedures described in Example 41, with 6-((2S,5R)-4-(bis(4-chlorophenyl)methyl)-5-ethyl-2-methylpiperazin-1-yl)-2-chloro-$N^4$-(((R)-tetrahydrofuran-2-yl)methyl)pyrimidine-4,5-diamine (Intermediate 40) replacing 6-((2S,5R)-4-(bis(4-chlorophenyl)methyl)-5-ethyl-2-methylpiperazin-1-yl)-2-chloro-$N^4$—(((S)-tetrahydrofuran-2-yl)methyl)pyrimidine-4,5-diamine in Step 1. LC-MS calculated for $C_{32}H_{37}C_{12}N_8O$ $(M+H)^+$: m/z=619.2; found 619.3. $^1$H NMR (500 MHz, DMSO-$d_6$) (mixture of rotamers) δ 9.51-9.47 (m, 1H), 7.62-7.51 (m, 4H), 7.44-7.35 (m, 4H), 6.23-6.15 (m, 0.4H), 6.15-6.08 (m, 0.6H), 5.09-5.00 (m, 0.6H), 4.88-4.77 (m, 1.4H), 4.77-4.69 (m, 1H), 4.58-4.49 (m, 1H), 4.16-4.08 (m, 1H), 3.82-3.74 (m, 0.6H), 3.74-3.64 (m, 1H), 3.63-3.51 (m, 1.4H), 2.81-2.63 (m, 2H), 2.58 (s, 1.2H), 2.56 (s, 1.8H), 2.51-2.43 (m, 1H), 2.18-2.08 (m, 1H), 1.99-1.88 (m, 1H), 1.88-1.77 (m, 1H), 1.76-1.63 (m, 1H), 1.60-1.32 (m, 5H), 0.70-0.58 (m, 3H).

Example 43. 4-((2S,5R)-4-((3,3-Difluorocyclobutyl)(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine

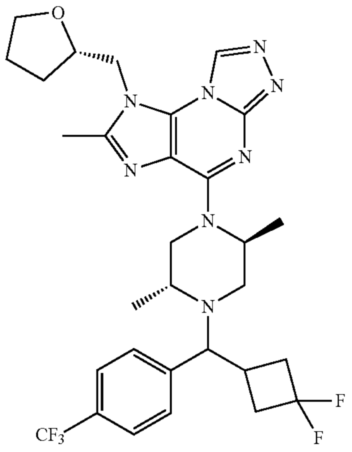

Step 1. 2-Chloro-6-((2S,5R)-4-((3,3-difluorocyclobutyl)(4-(trifluoromethyl)phenyl)methyl)-2,5-dimethylpiperazin-1-yl)-8-methyl-9-(((S)-tetrahydrofuran-2-yl)methyl)-9H-purine

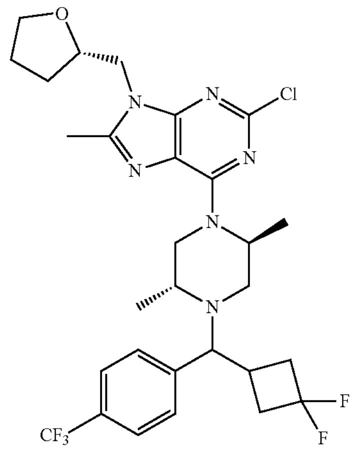 [SMILES: Cc1nc2c(N3C[C@@H](C)N(C(c4ccc(C(F)(F)F)cc4)C4CC(F)(F)C4)C[C@@H]3C)nc(Cl)nc2n1C[C@@H]1CCCO1]

To a mixture of (S)-2,6-dichloro-8-methyl-9-((tetrahydrofuran-2-yl)methyl)-9H-purine (Intermediate 41, 1.44 g, 5.01 mmol) and (2R,5S)-1-((3,3-difluorocyclobutyl)(4-(trifluoromethyl)phenyl)methyl)-2,5-dimethylpiperazine hydrochloride (Intermediate 43, 2.00 g, 5.01 mmol) in 1-butanol (8 mL) was added N,N-diisopropylethylamine (2.63 mL, 15.0 mmol) and the mixture was stirred at 90° C. overnight. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$ and the filtrate was concentrated to afford the desired product as a mixture of diastereomers. The crude material obtained was used directly without further purification. LC-MS calculated for $C_{29}H_{35}ClF_5N_6O$ $(M+H)^+$: m/z=613.3; found 613.3.

Step 2. 6-((2S,5R)-4-((3,3-Difluorocyclobutyl)(4-(trifluoromethyl)phenyl)methyl)-2,5-dimethylpiperazin-1-yl)-2-hydrazineyl-8-methyl-9-(((S)-tetrahydrofuran-2-yl)methyl)-9H-purine

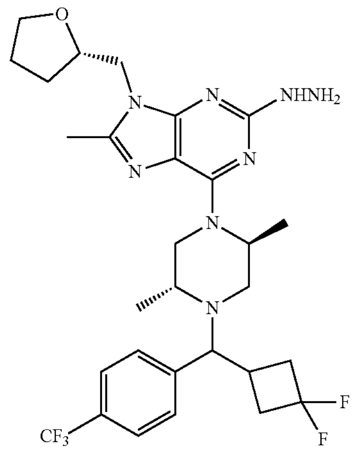 [SMILES: Cc1nc2c(N3C[C@@H](C)N(C(c4ccc(C(F)(F)F)cc4)C4CC(F)(F)C4)C[C@@H]3C)nc(NN)nc2n1C[C@@H]1CCCO1]

To a mixture of 2-chloro-6-((2S,5R)-4-((3,3-difluorocyclobutyl)(4-(trifluoromethyl)phenyl)methyl)-2,5-dimethylpiperazin-1-yl)-8-methyl-9-(((S)-tetrahydrofuran-2-yl)methyl)-9H-purine (Step 1), cesium carbonate (3.27 g, 10.03 mmol), and methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (0.428 g, 0.501 mmol, Aldrich 745979) in 1,4-dioxane (4 mL) was added hydrazine (0.79 mL, 25 mmol), and the mixture was purged with nitrogen and stirred at 90° C. for 1 h. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude residue was purified by flash column chromatography (40 g $SiO_2$, 0-5% MeOH/$CH_2Cl_2$) to afford the desired product (1.50 g, 49% yield over 2 steps) as a mixture of diastereomers in the form of an off-white solid. LC-MS calculated for $C_{29}H_{38}F_5N_8O$ $(M+H)^+$: m/z=609.3; found 609.4.

Step 3. 4-((2S,5R)-4-((3,3-Difluorocyclobutyl)(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine To a mixture of 6-((2S,5R)-4-((3,3-difluorocyclobutyl)(4-(trifluoromethyl)phenyl)methyl)-2,5-dimethylpiperazin-1-yl)-2-hydrazineyl-8-methyl-9-(((S)-tetrahydrofuran-2-yl)methyl)-9H-purine (1.50 g, 2.46 mmol) in AcOH (2.87 mL, 50.1 mmol) was added triethyl orthoformate (1.85 mL, 11.1 mmol) and the reaction mixture was stirred at 90° C. for 1 h. After cooling to rt, the reaction mixture was diluted with acetonitrile, water, and several drops of TFA, and the diastereomeric mixture was filtered and purified by prep-HPLC (Sunfire C18 column, eluting with a gradient of acetonitrile/water containing 0.10% TFA, at flow rate of 60 mL/min) to afford the major diastereomer as a single stereoisomer as its TFA salt. LC-MS calculated for $C_{30}H_{36}F_5N_8O$ $(M+H)^+$: m/z=619.3; found 619.3. $^1H$ NMR (500 MHz, DMSO-$d_6$) (mixture of rotamers) δ 9.48 (s, 1H), 7.81-7.70 (m, 2H), 7.68-7.56 (m, 2H), 6.20-5.99 (m, 0.4H), 5.90-5.64 (m, 0.6H), 5.06-4.80 (m, 0.6H), 4.79-4.64 (m, 1H), 4.62-4.40 (m, 1.4H), 4.18-4.04 (m, 1H), 3.81-3.64 (m, 2H), 3.64-3.46 (m, 1.6H), 3.46-3.27 (m, 0.4H), 3.16-2.97 (m, 1H), 2.95-2.74 (m, 2H), 2.74-2.52 (m, 5H), 2.47-2.31 (m, 1H), 2.29-2.09 (m, 2H), 2.09-1.98 (m, 1H), 1.98-1.88 (m, 1H), 1.88-1.77 (m, 1H), 1.77-1.66 (m, 1H), 1.58-1.27 (m, 3H), 1.09-0.81 (m, 3H).

Example 44. 4-((2S,5R)-4-((3-Chloro-4-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine

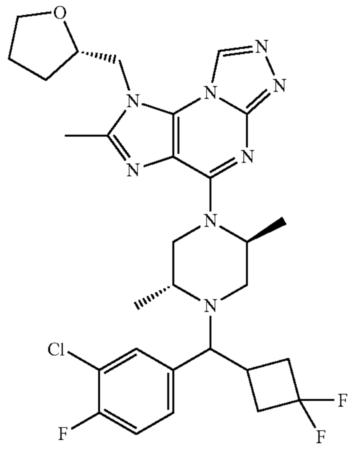 [SMILES: Cc1nc2c(N3C[C@@H](C)N(C(c4ccc(F)c(Cl)c4)C4CC(F)(F)C4)C[C@@H]3C)nc3nncn3c2n1C[C@@H]1CCCO1]

Step 1. 2-Chloro-6-((2S,5R)-4-((3-chloro-4-fluorophenyl)(3,3-difluorocyclobutyl)methyl)-2,5-dimethylpiperazin-1-yl)-8-methyl-9-(((S)-tetrahydrofuran-2-yl)methyl)-9H-purine

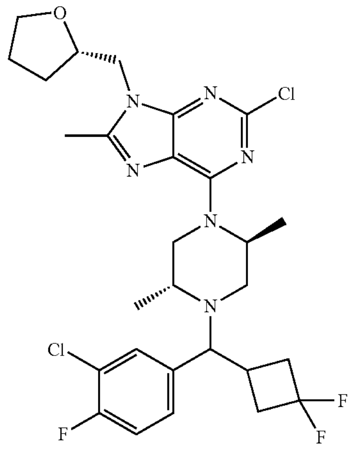 [SMILES: Cc1nc2c(N3C[C@@H](C)N(C(c4ccc(F)c(Cl)c4)C4CC(F)(F)C4)C[C@@H]3C)nc(Cl)nc2n1C[C@@H]1CCCO1]

To a mixture of (S)-2,6-dichloro-8-methyl-9-((tetrahydrofuran-2-yl)methyl)-9H-purine (Intermediate 41, 0.90 g, 3.13 mmol) and (2R,5S)-1-((3-chloro-4-fluorophenyl)(3,3-difluorocyclobutyl)methyl)-2,5-dimethylpiperazine hydrochloride (Intermediate 44, 1.20 g, 3.13 mmol) in n-BuOH (4 mL) was added N,N-diisopropylethylamine (1.64 mL, 9.39 mmol) and the mixture was stirred at 90° C. overnight. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$ and the filtrate was concentrated to afford the desired product as a mixture of diastereomers. The crude material obtained was used directly without further purification. LC-MS calculated for $C_{28}H_{34}Cl_2F_3N_6O$ $(M+H)^+$: m/z=597.2; found 597.1.

Step 2. 6-((2S,5R)-4-((3-Chloro-4-fluorophenyl)(3,3-difluorocyclobutyl)methyl)-2,5-dimethylpiperazin-1-yl)-2-hydrazineyl-8-methyl-9-(((S)-tetrahydrofuran-2-yl)methyl)-9H-purine

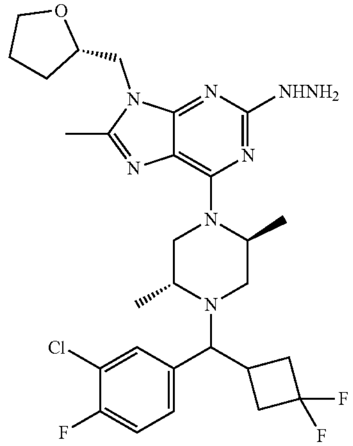 [SMILES: Cc1nc2c(N3C[C@@H](C)N(C(c4ccc(F)c(Cl)c4)C4CC(F)(F)C4)C[C@@H]3C)nc(NN)nc2n1C[C@@H]1CCCO1]

To a mixture of 2-chloro-6-((2S,5R)-4-((3-chloro-4-fluorophenyl)(3,3-difluorocyclobutyl)methyl)-2,5-dimethylpiperazin-1-yl)-8-methyl-9-(((S)-tetrahydrofuran-2-yl)methyl)-9H-purine (Step 1) in 1,4-dioxane (4 mL) was added hydrazine (0.49 mL, 16 mmol), and the mixture was stirred at 120° C. overnight. After cooling to rt, the reaction mixture was concentrated, and the crude residue was purified by flash column chromatography (40 g $SiO_2$, 0-5% MeOH/$CH_2Cl_2$) to afford the desired product (810 mg, 44% yield over 2 steps) as a mixture of diastereomers in the form of an off-white solid. LC-MS calculated for $C_{28}H_{37}ClF_3N_8O$ $(M+H)^+$: m/z=593.3; found 593.4.

Step 3. 4-((2S,5R)-4-((3-Chloro-4-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine To a mixture of 6-((2S,5R)-4-((3-chloro-4-fluorophenyl)(3,3-difluorocyclobutyl)methyl)-2,5-dimethylpiperazin-1-yl)-2-hydrazineyl-8-methyl-9-(((S)-tetrahydrofuran-2-yl)methyl)-9H-purine (810 mg, 1.37 mmol) in AcOH (1.79 mL, 31.3 mmol) was added triethyl orthoformate (1.15 mL, 6.91 mmol) and the reaction mixture was stirred at 90° C. for 1 h. After cooling to rt, the reaction mixture was diluted with acetonitrile, water, and several drops of TFA, and the diastereomeric mixture was filtered and purified by prep-HPLC (Sunfire C18 column, eluting with a gradient of acetonitrile/water containing 0.10% TFA, at flow rate of 60 mL/min) to afford the major diastereomer as a single stereoisomer as its TFA salt. LC-MS calculated for $C_{29}H_{35}ClF_3N_8O$ $(M+H)^+$: m/z=603.3; found 603.8. $^1H$ NMR (600 MHz, DMSO-$d_6$) (mixture of rotamers) δ 9.49 (s, 1H), 7.73-7.53 (m, 1H), 7.52-7.32 (m, 2H), 6.19-5.95 (m, 0.4H), 5.89-5.69 (m, 0.6H), 5.00-4.81 (m, 0.6H), 4.79-4.65 (m, 1H), 4.64-4.44 (m, 1.4H), 4.16-4.06 (m, 1H), 3.80-3.24 (m, 4H), 3.19-2.95 (m, 1H), 2.94-2.74 (m, 2H), 2.73-2.52 (m, 5H), 2.45-2.29 (m, 1H), 2.28-2.09 (m, 2H), 2.08-1.98 (m, 1H), 1.98-1.89 (m, 1H), 1.88-1.78 (m, 1H), 1.77-1.68 (m, 1H), 1.59-1.27 (m, 3H), 1.10-0.84 (m, 3H).

Example 45. 4-((2S,5R)-4-((3,3-Difluorocyclobutyl)(3-fluoro-4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine

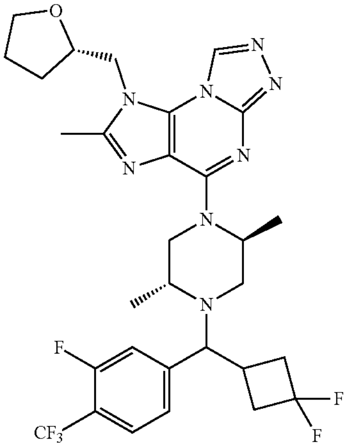 [SMILES: Cc1nc2c(N3C[C@@H](C)N(C(c4ccc(C(F)(F)F)c(F)c4)C4CC(F)(F)C4)C[C@@H]3C)nc3nncn3c2n1C[C@@H]1CCCO1]

Step 1. 2-Chloro-6-((2S,5R)-4-((3,3-difluorocyclobutyl)(3-fluoro-4-(trifluoromethyl)phenyl)methyl)-2,5-dimethylpiperazin-1-yl)-8-methyl-9-(((S)-tetrahydrofuran-2-yl)methyl)-9H-purine

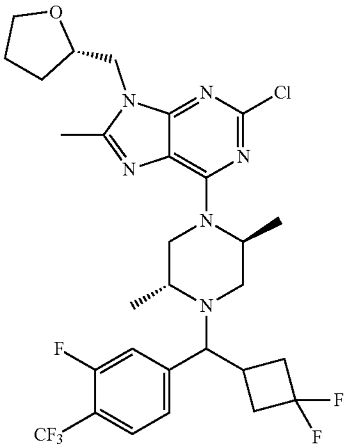 [SMILES: Cc1nc2c(N3C[C@@H](C)N(C(c4ccc(C(F)(F)F)c(F)c4)C4CC(F)(F)C4)C[C@@H]3C)nc(Cl)nc2n1C[C@@H]1CCCO1]

To a mixture of (S)-2,6-dichloro-8-methyl-9-((tetrahydrofuran-2-yl)methyl)-9H-purine (Intermediate 41, 0.207 g, 0.720 mmol) and (2R,5S)-1-((3,3-difluorocyclobutyl)(3-fluoro-4-(trifluoromethyl)phenyl)methyl)-2,5-dimethylpiperazine hydrochloride (Intermediate 45, 0.30 g, 0.72 mmol) in n-BuOH (4 mL) was added N,N-diisopropylethylamine (0.38 mL, 2.16 mmol) and the mixture was stirred at 90° C. overnight. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$ and the filtrate was concentrated in vacuo to afford the desired product as a mixture of diastereomers. The crude material obtained was used directly without further purification. LC-MS calculated for $C_{29}H_{34}ClF_6N_6O$ $(M+H)^+$: m/z=631.2; found 631.3.

Step 2. 6-((2S,5R)-4-((3,3-Difluorocyclobutyl)(3-fluoro-4-(trifluoromethyl)phenyl)methyl)-2,5-dimethylpiperazin-1-yl)-2-hydrazineyl-8-methyl-9-(((S)-tetrahydrofuran-2-yl)methyl)-9H-purine

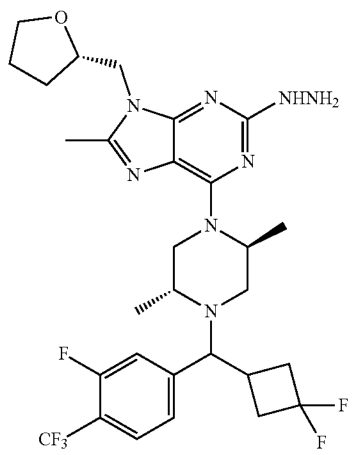

To a mixture of 2-chloro-6-((2S,5R)-4-((3,3-difluorocyclobutyl)(3-fluoro-4-(trifluoromethyl)phenyl)methyl)-2,5-dimethylpiperazin-1-yl)-8-methyl-9-(((S)-tetrahydrofuran-2-yl)methyl)-9H-purine (Step 1), cesium carbonate (0.47 g, 1.44 mmol), and methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (0.061 g, 0.072 mmol, Aldrich 745979) in 1,4-dioxane (4 mL) was added hydrazine (0.11 mL, 3.6 mmol), and the mixture was purged with nitrogen and stirred at 90° C. for 1 h. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude residue was purified by flash column chromatography (24 g $SiO_2$, 0-5% $MeOH/CH_2Cl_2$) to afford the desired product (278 mg, 62% yield over 2 steps) as a mixture of diastereomers in the form of an off-white solid. LC-MS calculated for $C_{29}H_{37}F_6N_8O$ $(M+H)^+$: m/z=627.3; found 627.4.

Step 3. 4-((2S,5R)-4-((3,3-Difluorocyclobutyl)(3-fluoro-4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine To a mixture of 6-((2S,5R)-4-((3,3-difluorocyclobutyl)(3-fluoro-4-(trifluoromethyl)phenyl)methyl)-2,5-dimethylpiperazin-1-yl)-2-hydrazineyl-8-methyl-9-(((S)-tetrahydrofuran-2-yl)methyl)-9H-purine (278 mg, 0.444 mmol) in AcOH (0.41 mL, 7.2 mmol) was added triethyl orthoformate (0.26 mL, 1.6 mmol) and the reaction mixture was stirred at 90° C. for 1 h. After cooling to rt, the reaction mixture was diluted with acetonitrile, water, and several drops of TFA, and the diastereomeric mixture was filtered and purified by prep-HPLC (Sunfire C18 column, eluting with a gradient of acetonitrile/water containing 0.10% TFA, at flow rate of 60 mL/min) to afford the major diastereomer as a single stereoisomer as its TFA salt. Retention time on LC-MS $t_r$=1.59 min. LC-MS calculated for $C_{30}H_{35}F_6N_8O$ $(M+H)^+$: m/z=637.3; found 637.5. $^1H$ NMR (500 MHz, DMSO-$d_6$) (mixture of rotamers) δ 9.49 (s, 1H), 7.87-7.75 (m, 1H), 7.64-7.52 (m, 1H), 7.52-7.39 (m, 1H), 6.19-6.02 (m, 0.4H), 5.91-5.69 (m, 0.6H), 5.00-4.81 (m, 0.6H), 4.76-4.65 (m, 1H), 4.61-4.41 (m, 1.4H), 4.16-4.06 (m, 1H), 3.86-3.66 (m, 2H), 3.65-3.50 (m, 1.6H), 3.48-3.30 (m, 0.4H), 3.13-3.01 (m, 1H), 2.94-2.76 (m, 2H), 2.76-2.54 (m, 5H), 2.46-2.31 (m, 1H), 2.31-1.99 (m, 3H), 1.98-1.88 (m, 1H), 1.88-1.77 (m, 1H), 1.77-1.67 (m, 1H), 1.57-1.28 (m, 3H), 1.06-0.88 (m, 3H).

Examples 46 and 47. 4-((2S,5R)-4-((S)-(3,3-Difluorocyclobutyl)(3,4-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-(3,3-difluorocyclobutyl)(3,4-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine

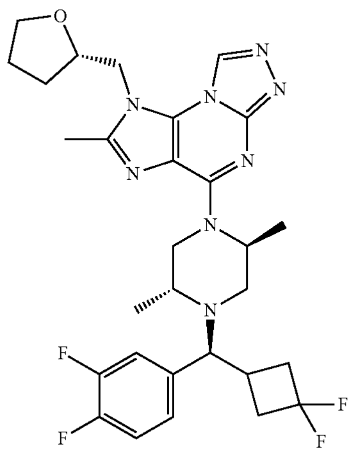

and

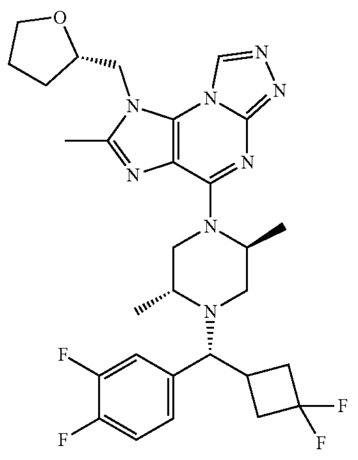

Step 1. 2-Chloro-6-((2S,5R)-4-((3,3-difluorocyclobutyl)(3,4-difluorophenyl)methyl)-2,5-dimethylpiperazin-1-yl)-8-methyl-9-(((S)-tetrahydrofuran-2-yl)methyl)-9H-purine

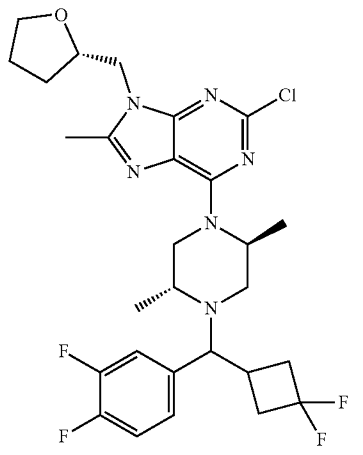 [SMILES: Cc1nc2c(N3C[C@@H](C)N(C(c4ccc(F)c(F)c4)C4CC(F)(F)C4)C[C@@H]3C)nc(Cl)nc2n1C[C@@H]1CCCO1]

To a mixture of (S)-2,6-dichloro-8-methyl-9-((tetrahydrofuran-2-yl)methyl)-9H-purine (Intermediate 41, 0.235 g, 0.818 mmol) and (2R,5S)-1-((3,3-difluorocyclobutyl)(3,4-difluorophenyl)methyl)-2,5-dimethylpiperazine hydrochloride (Intermediate 46, 0.300 g, 0.818 mmol) in n-BuOH (4 mL) was added N,N-diisopropylethylamine (0.43 mL, 2.45 mmol) and the mixture was stirred at 90° C. overnight. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$ and the filtrate was concentrated in vacuo to afford the desired product as a mixture of diastereomers. The crude material obtained was used directly without further purification. LC-MS calculated for $C_{28}H_{34}ClF_4N_6O$ $(M+H)^+$: m/z=581.2; found 581.3.

Step 2. 6-((2S,5R)-4-((3,3-Difluorocyclobutyl)(3,4-difluorophenyl)methyl)-2,5-dimethylpiperazin-1-yl)-2-hydrazineyl-8-methyl-9-(((S)-tetrahydrofuran-2-yl)methyl)-9H-purine

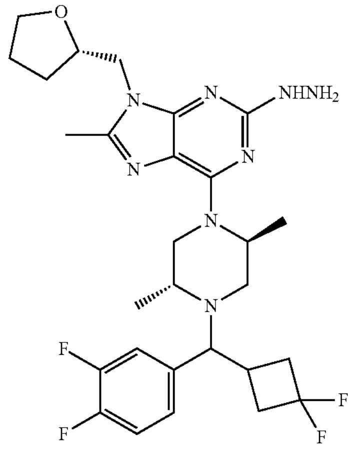 [SMILES: Cc1nc2c(N3C[C@@H](C)N(C(c4ccc(F)c(F)c4)C4CC(F)(F)C4)C[C@@H]3C)nc(NN)nc2n1C[C@@H]1CCCO1]

To a mixture of 2-chloro-6-((2S,5R)-4-((3,3-difluorocyclobutyl)(3,4-difluorophenyl)methyl)-2,5-dimethylpiperazin-1-yl)-8-methyl-9-(((S)-tetrahydrofuran-2-yl)methyl)-9H-purine (Step 1), cesium carbonate (0.533 g, 1.636 mmol), and methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (0.070 g, 0.082 mmol, Aldrich 745979) in 1,4-dioxane (4 mL) was added hydrazine (0.128 mL, 4.09 mmol), and the mixture was purged with nitrogen and stirred at 90° C. for 1 h. After cooling to rt, the reaction mixture was diluted with $CH_2Cl_2$ and filtered through a pad of $MgSO_4$ in a SiliaPrep SPE thiol cartridge (500 mg, SiliCycle SPE-R51030B-06P). The filtrate was concentrated, and the crude residue was purified by flash column chromatography (40 g $SiO_2$, 0-5% MeOH/$CH_2Cl_2$) to afford the desired product (0.210 g, 45% yield over 2 steps) as a mixture of diastereomers in the form of an off-white solid. LC-MS calculated for $C_{28}H_{37}F_4N_8O$ $(M+H)^+$: m/z=577.3; found 577.4.

Step 3. 4-((2S,5R)-4-((S)-(3,3-Difluorocyclobutyl)(3,4-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-(3,3-difluorocyclobutyl)(3,4-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine To a mixture of 6-((2S,5R)-4-((3,3-difluorocyclobutyl)(3,4-difluorophenyl)methyl)-2,5-dimethylpiperazin-1-yl)-2-hydrazineyl-8-methyl-9-(((S)-tetrahydrofuran-2-yl)methyl)-9H-purine (0.210 g, 0.364 mmol) in AcOH (0.47 mL, 8.2 mmol) was added triethyl orthoformate (0.30 mL, 1.8 mmol) and the reaction mixture was stirred at 90° C. for 1 h. After cooling to rt, the reaction mixture was diluted with acetonitrile, water, and several drops of TFA, and the diastereomeric mixture was filtered and purified by prep-HPLC (Sunfire C18 column, eluting with a gradient of acetonitrile/water containing 0.1% TFA, at flow rate of 60 mL/min) to afford each diastereomer as its TFA salt.

Example 46: Retention time on LC-MS $t_r$=1.46 min, LC-MS calculated for $C_{29}H_{35}F_4N_8O$ $(M+H)^+$: m/z=587.3; found 587.4. $^1H$ NMR (600 MHz, DMSO-$d_6$) (mixture of rotamers) δ 9.50 (s, 1H), 7.57-7.37 (m, 2H), 7.34-7.16 (m, 1H), 6.17-6.01 (m, 0.4H), 5.89-5.70 (m, 0.6H), 5.00-4.82 (m, 0.6H), 4.79-4.66 (m, 1H), 4.62-4.46 (m, 1.4H), 4.16-4.07 (m, 1H), 3.74-3.50 (m, 3.6H), 3.45-3.31 (m, 0.4H), 3.12-2.94 (m, 1H), 2.94-2.73 (m, 2H), 2.72-2.53 (m, 5H), 2.45-2.30 (m, 1H), 2.30-2.10 (m, 2H), 2.10-1.99 (m, 1H), 1.99-1.89 (m, 1H), 1.89-1.79 (m, 1H), 1.79-1.68 (m, 1H), 1.54-1.29 (m, 3H), 1.07-0.82 (m, 3H).

Example 47: Retention time on LC-MS $t_r$=1.43 min, LC-MS calculated for $C_{29}H_{35}F_4N_8O$ $(M+H)^+$: m/z=587.3; found 587.4.

Examples 48 and 49. 4-((2S,5R)-4-((S)-(3,4-Dichlorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-(3,4-dichlorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine

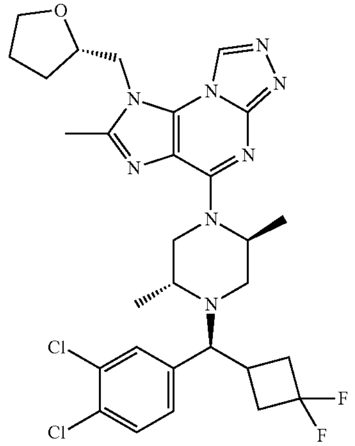

and

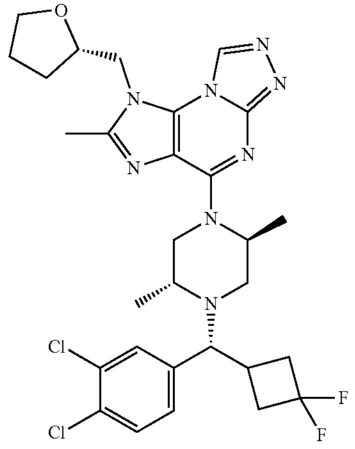

This compound was prepared according to the procedures described in Example 44, with (2R,5S)-1-((3,4-dichlorophenyl)(3,3-difluorocyclobutyl)methyl)-2,5-dimethylpiperazine hydrochloride (Intermediate 47) replacing (2R,5S)-1-((3-chloro-4-fluorophenyl)(3,3-difluorocyclobutyl)methyl)-2,5-dimethylpiperazine hydrochloride in Step 1. In Step 3 the diastereomeric mixture was filtered and purified by prep-HPLC (Sunfire C18 column, eluting with a gradient of acetonitrile/water containing 0.10% TFA, at flow rate of 60 mL/min) to afford each diastereomer as its TFA salt.

Example 48: Retention time on LC-MS $t_r$=3.96 min, LC-MS calculated for $C_{29}H_{35}Cl_2F_2N_8O$ $(M+H)^+$: m/z=619.2; found 619.2. $^1H$ NMR (500 MHz, DMSO-$d_6$) (mixture of rotamers) δ 9.49 (s, 1H), 7.72-7.61 (m, 2H), 7.47-7.36 (m, 1H), 6.18-5.98 (m, 0.4H), 5.89-5.69 (m, 0.6H), 4.99-4.81 (m, 0.6H), 4.79-4.66 (m, 1H), 4.61-4.45 (m, 1.4H), 4.17-4.06 (m, 1H), 3.76-3.51 (m, 3.6H), 3.46-3.29 (m, 0.4H), 3.14-2.97 (m, 1H), 2.93-2.75 (m, 2H), 2.73-2.54 (m, 5H), 2.44-2.29 (m, 1H), 2.29-2.09 (m, 2H), 2.09-1.99 (m, 1H), 1.99-1.89 (m, 1H), 1.89-1.79 (m, 1H), 1.78-1.67 (m, 1H), 1.56-1.27 (m, 3H), 1.02-0.87 (m, 3H).

Example 49: Retention time on LC-MS $t_r$=3.92 min, LC-MS calculated for $C_{29}H_{35}Cl_2F_2N_8O$ $(M+H)^+$: m/z=619.2; found 619.3.

Example 50. 4-((2S,5R)-4-((4-Chloro-3-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine

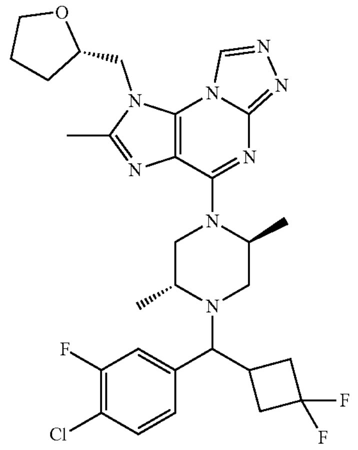

Step 1. 2-Chloro-6-((2S,5R)-4-((4-chloro-3-fluorophenyl)(3,3-difluorocyclobutyl)methyl)-2,5-dimethylpiperazin-1-yl)-8-methyl-9-(((S)-tetrahydrofuran-2-yl)methyl)-9H-purine

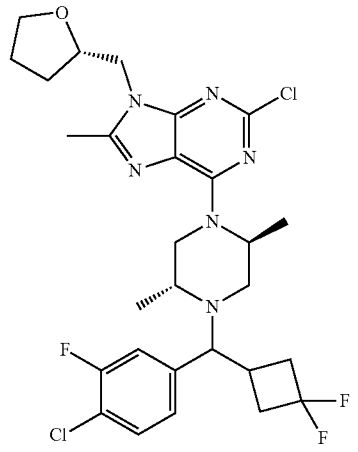 [SMILES: Cc1nc2c(N3C[C@@H](C)N(C(c4ccc(Cl)c(F)c4)C4CC(F)(F)C4)C[C@@H]3C)nc(Cl)nc2n1C[C@@H]1CCCO1]

To a mixture of (S)-2,6-dichloro-8-methyl-9-((tetrahydrofuran-2-yl)methyl)-9H-purine (Intermediate 41, 75 mg, 0.26 mmol) and (2R,5S)-1-((4-chloro-3-fluorophenyl)(3,3-difluorocyclobutyl)methyl)-2,5-dimethylpiperazine hydrochloride (Intermediate 48, 100 mg, 0.26 mmol) in n-BuOH (4 mL) was added N,N-diisopropylethylamine (0.14 mL, 0.8 mmol) and the mixture was stirred at 90° C. overnight. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$ and the filtrate was concentrated in vacuo to afford the desired product as a mixture of diastereomers. The crude material obtained was used directly without further purification. LC-MS calculated for $C_{28}H_{34}Cl_2F_3N_6O$ $(M+H)^+$: m/z=597.2; found 597.3.

Step 2. 6-((2S,5R)-4-((4-Chloro-3-fluorophenyl)(3,3-difluorocyclobutyl)methyl)-2,5-dimethylpiperazin-1-yl)-2-hydrazineyl-8-methyl-9-(((S)-tetrahydrofuran-2-yl)methyl)-9H-purine

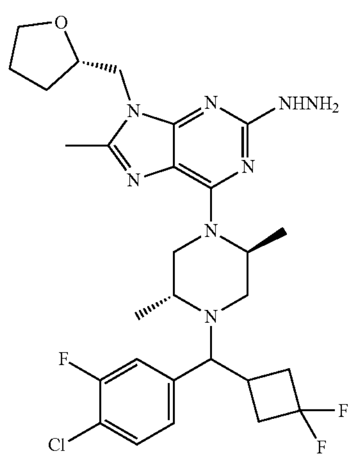 [SMILES: Cc1nc2c(N3C[C@@H](C)N(C(c4ccc(Cl)c(F)c4)C4CC(F)(F)C4)C[C@@H]3C)nc(NN)nc2n1C[C@@H]1CCCO1]

To a mixture of 2-chloro-6-((2S,5R)-4-((4-chloro-3-fluorophenyl)(3,3-difluorocyclobutyl)methyl)-2,5-dimethylpiperazin-1-yl)-8-methyl-9-(((S)-tetrahydrofuran-2-yl)methyl)-9H-purine (Step 1) in 1,4-dioxane (4 mL) was added hydrazine (41 μL, 1.3 mmol), and the mixture was stirred at 120° C. overnight. After cooling to rt, the reaction mixture was concentrated, and the crude residue was purified by flash column chromatography ($SiO_2$, 0-5% $MeOH/CH_2Cl_2$) to afford the desired product (37 mg, 24% yield over 2 steps) as a mixture of diastereomers in the form of an off-white solid. LC-MS calculated for $C_{28}H_{37}ClF_3N_8O$ $(M+H)^+$: m/z=593.3; found 593.4.

Step 3. 4-((2S,5R)-4-((4-Chloro-3-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine To a mixture of 6-((2S,5R)-4-((4-chloro-3-fluorophenyl)(3,3-difluorocyclobutyl)methyl)-2,5-dimethylpiperazin-1-yl)-2-hydrazineyl-8-methyl-9-(((S)-tetrahydrofuran-2-yl)methyl)-9H-purine (37 mg, 0.062 mmol) in AcOH (0.15 mL, 2.6 mmol) was added triethyl orthoformate (0.1 mL, 0.6 mmol) and the reaction mixture was stirred at 90° C. for 1 h. After cooling to rt, the reaction mixture was diluted with acetonitrile, water, and several drops of TFA, and the diastereomeric mixture was filtered and purified by prep-HPLC (Sunfire C18 column, eluting with a gradient of acetonitrile/water containing 0.10% TFA, at flow rate of 60 mL/min) to afford the major diastereomer as a single stereoisomer as its TFA salt. LC-MS calculated for $C_{29}H_{35}ClF_3N_8O$ $(M+H)^+$: m/z=603.3; found 603.4. $^1H\{19F\}$ NMR (500 MHz, DMSO-$d_6$) (mixture of rotamers) δ 9.47 (s, 1H), 7.60 (d, J=8.2 Hz, 1H), 7.46 (s, 1H), 7.26 (d, J=8.2 Hz, 1H), 6.19-5.97 (m, 0.4H), 5.88-5.65 (m, 0.6H), 5.00-4.81 (m, 0.6H), 4.80-4.64 (m, 1H), 4.63-4.41 (m, 1.4H), 4.16-4.05 (m, 1H), 3.74-3.51 (m, 3.6H), 3.45-3.32 (m, 0.4H), 3.09-2.97 (m, 1H), 2.91-2.74 (m, 2H), 2.73-2.53 (m, 5H), 2.42-2.31 (m, 1H), 2.28-2.09 (m, 2H), 2.08-2.01 (m, 1H), 1.97-1.89 (m, 1H), 1.88-1.77 (m, 1H), 1.77-1.66 (m, 1H), 1.54-1.29 (m, 3H), 1.00-0.87 (m, 3H).

Example 51. 4-((2S,5R)-4-((4-Chloro-3-methylphenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine

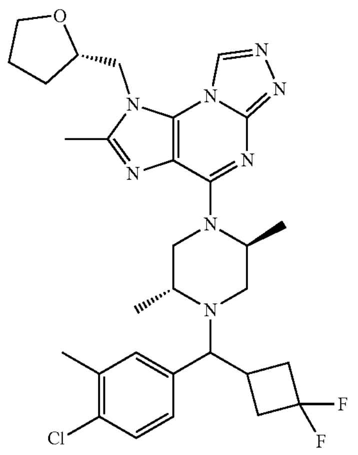 [SMILES: Cc1cc(C(C2CC(F)(F)C2)N2C[C@H](C)N(c3nc4nncn4c4c3nc(C)n4C[C@@H]3CCCO3)C[C@H]2C)ccc1Cl]

This compound was prepared according to the procedures described in Example 44, with (2R,5S)-1-((4-chloro-3-methylphenyl)(3,3-difluorocyclobutyl)methyl)-2,5-dimethylpiperazine hydrochloride (Intermediate 49) replacing (2R,5S)-1-((3-chloro-4-fluorophenyl)(3,3-difluorocyclobutyl)methyl)-2,5-dimethylpiperazine hydrochloride in Step 1. LC-MS calculated for $C_{30}H_{38}CF_2N_8O$ $(M+H)^+$: m/z=599.3; found 599.3.

Example 52. 4-((2S,5R)-4-((3,3-Difluorocyclobutyl)(3,4,5-trifluorophenyl)methyl)-2,5-dimethylpiperazin-1-yl)-2-methyl-1-(((S)-tetrahydrofuran-2-yl)methyl)-1H-[1,2,4]triazolo[3,4-b]purine

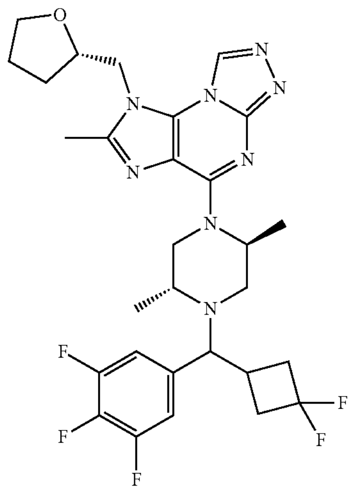 [SMILES: Cc1nc2c(N3C[C@@H](C)N(C(c4cc(F)c(F)c(F)c4)C4CC(F)(F)C4)C[C@@H]3C)nc3nncn3c2n1C[C@@H]1CCCO1]

This compound was prepared according to the procedures described in Example 44, with (2R,5S)-1-((3,3-difluorocyclobutyl)(3,4,5-trifluorophenyl)methyl)-2,5-dimethylpiperazine hydrochloride (Intermediate 50) replacing (2R,5S)-1-((3-chloro-4-fluorophenyl)(3,3-difluorocyclobutyl)methyl)-2,5-dimethylpiperazine hydrochloride in Step 1. LC-MS calculated for $C_{29}H_{34}F_5N_8O$ $(M+H)^+$: m/z=605.3; found 605.3.

Examples 53-56

Examples 53-56 of Table 2 were prepared in accordance with the synthetic protocols set forth in Example 43 using the indicated aryl halides for Grignard formation as described in Intermediate 43.

TABLE 2

| Ex. | Name | Structure | Aryl Halide Starting Material | Analytical data |
|---|---|---|---|---|
| 53 | 4-((2S,5R)-4-((3,3-Difluorocyclobutyl)(2,5-difluorophenyl)methyl)-2,5-dimethylpiperazin-1-yl)-2-methyl-1-(((S)-tetrahydrofuran-2-yl)methyl)-1H-[1,2,4]triazolo[3,4-b]purine | 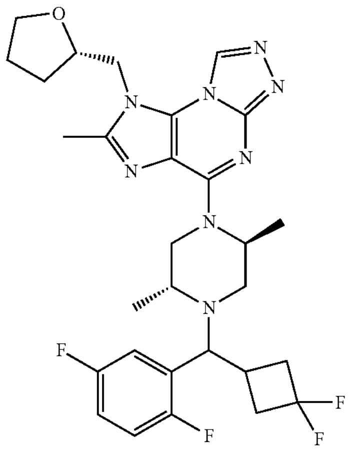 [SMILES: Cc1nc2c(N3C[C@@H](C)N(C(c4cc(F)ccc4F)C4CC(F)(F)C4)C[C@@H]3C)nc3nncn3c2n1C[C@@H]1CCCO1] | 1,4-Difluoro-2-iodobenzene | LC-MS $[M + H]^+$: found 587.3 |
| 54 | 4-((2S,5R)-4-((3,3-Difluorocyclobutyl)(3-(difluoromethyl)-4-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine | 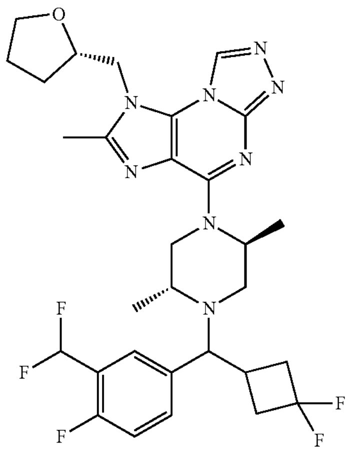 [SMILES: Cc1nc2c(N3C[C@@H](C)N(C(c4ccc(F)c(C(F)F)c4)C4CC(F)(F)C4)C[C@@H]3C)nc3nncn3c2n1C[C@@H]1CCCO1] | 2-(Difluoromethyl)-1-fluoro-4-iodobenzene | LC-MS $[M + H]^+$: found 619.3 |
| 55 | 4-((2S,5R)-4-((3,3-Difluorocyclobutyl)(3-methyl-4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine | 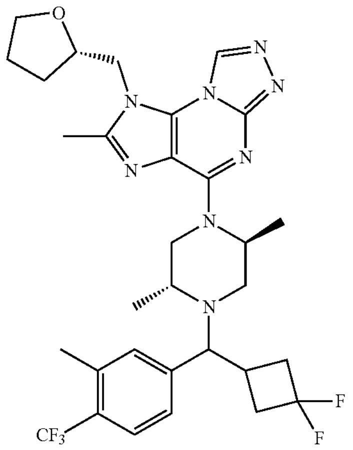 | 4-Iodo-2-methyl-1-(trifluoromethyl)benzene | LC-MS $[M + H]^+$: found 633.4 |

TABLE 2-continued

| Ex. | Name | Structure | Aryl Halide Starting Material | Analytical data |
|---|---|---|---|---|
| 56 | 4-((2S,5R)-4-((2,5-Difluoro-4-(trifluoromethyl)phenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 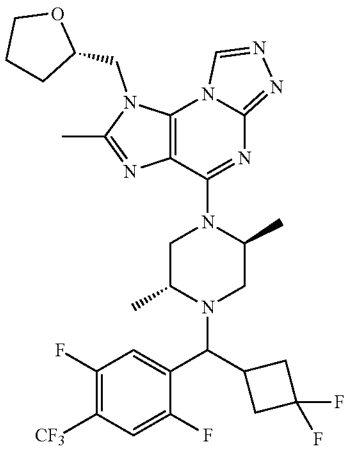 [SMILES: Cc1nc2c(N3C[C@@H](C)N(C(c4cc(F)c(C(F)(F)F)cc4F)C4CC(F)(F)C4)C[C@@H]3C)nc3nncn3c2n1C[C@@H]1CCCO1] | 1-Bromo-2,5-difluoro-4-(trifluoromethyl)benzene | LC-MS $[M+H]^+$: found 655.3 |

Examples 57-63

Examples 57-63 of Table 3 were prepared in accordance with the synthetic protocols set forth in Example 50 using the indicated aryl halides for Grignard formation as described in Intermediate 48.

TABLE 3

| Ex. | Name | Structure | Aryl Halide Starting Material | Analytical data |
|---|---|---|---|---|
| 57 | 4-((2S,5R)-4-((3-Chloro-2,4-difluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 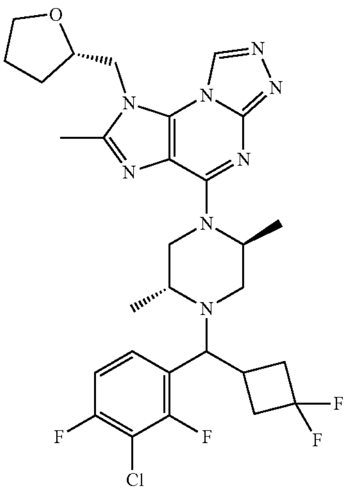 [SMILES: Cc1nc2c(N3C[C@@H](C)N(C(c4ccc(F)c(Cl)c4F)C4CC(F)(F)C4)C[C@@H]3C)nc3nncn3c2n1C[C@@H]1CCCO1] | 1-Bromo-3-chloro-2,4-difluorobenzene | LC-MS $[M+H]^+$: found 621.2 |

TABLE 3-continued

| Ex. | Name | Structure | Aryl Halide Starting Material | Analytical data |
|---|---|---|---|---|
| 58 | 4-((2S,5R)-4-((3-Chloro-4-(trifluoromethyl)phenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 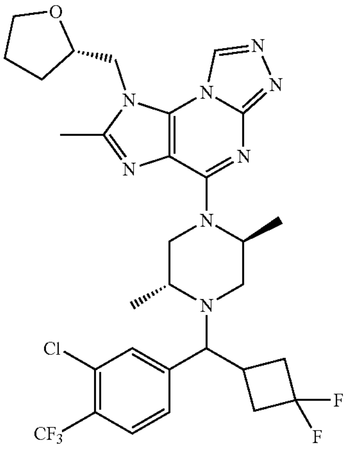 | 2-Chloro-4-iodo-1-(trifluoromethyl)benzene | LC-MS $[M + H]^+$: found 653.2 |
| 59 | 4-((2S,5R)-4-((4-Chloro-3-(trifluoromethyl)phenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 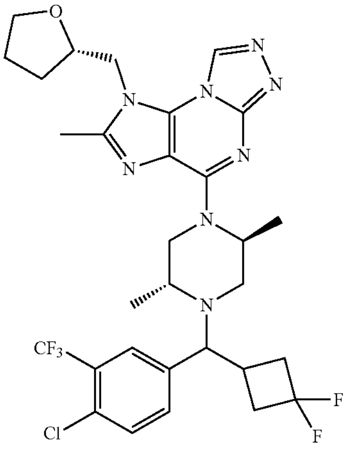 | 4-Bromo-1-chloro-2-(trifluoromethyl)benzene | LC-MS $[M + H]^+$: found 653.3 |
| 60 | 4-((2S,5R)-4-((4-Chlorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 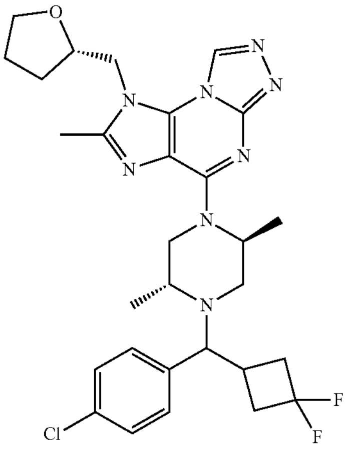 [SMILES: Cc1nc2c(N3C[C@@H](C)N(C(c4ccc(Cl)cc4)C4CC(F)(F)C4)C[C@@H]3C)nc3nncn3c2n1C[C@@H]1CCCO1] | 1-Bromo-4-chlorobenzene | LC-MS $[M + H]^+$: found 585.3 |

TABLE 3-continued

| Ex. | Name | Structure | Aryl Halide Starting Material | Analytical data |
|---|---|---|---|---|
| 61 | 4-((2S,5R)-4-((4-Bromophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 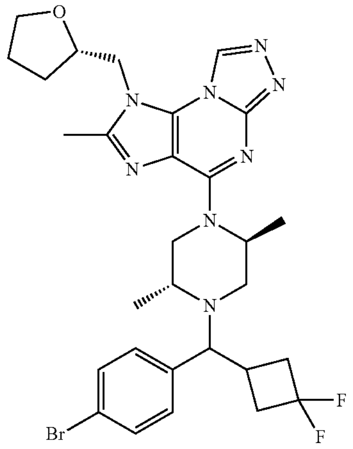 [SMILES: Cc1nc2c(N3C[C@@H](C)N(C(c4ccc(Br)cc4)C4CC(F)(F)C4)C[C@@H]3C)nc3nncn3c2n1C[C@@H]1CCCO1] | 1-Bromo-4-iodobenzene | LC-MS $[M + H]^+$: found 629.3 |
| 62 | 4-((2S,5R)-4-((3-Bromo-4-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 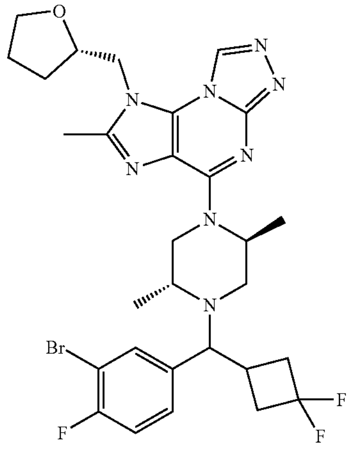 [SMILES: Cc1nc2c(N3C[C@@H](C)N(C(c4ccc(F)c(Br)c4)C4CC(F)(F)C4)C[C@@H]3C)nc3nncn3c2n1C[C@@H]1CCCO1] | 2-Bromo-1-fluoro-4-iodobenzene | LC-MS $[M + H]^+$: found 647.1 |
| 63 | 4-((2S,5R)-4-((4-Bromo-3-fluorophenyl)(3,3-difluorocyclobutyl)methyl)-2,5-dimethylpiperazin-1-yl)-2-methyl-1-(((S)-tetrahydrofuran-2-yl)methyl)-1H-[1,2,4]triazolo[3,4-b]purine | 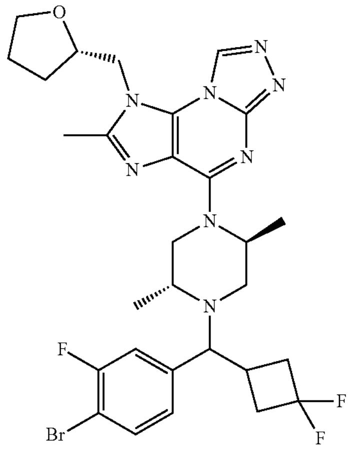 [SMILES: Cc1nc2c(N3C[C@@H](C)N(C(c4ccc(Br)c(F)c4)C4CC(F)(F)C4)C[C@@H]3C)nc3nncn3c2n1C[C@@H]1CCCO1] | 1-Bromo-2-fluoro-4-iodobenzene | LC-MS $[M + H]^+$: found 647.2 |

Example 64. 2-(4-((2S,5R)-4-((4-Chlorophenyl)(3,3-difluorocyclobutyl)methyl)-2,5-dimethylpiperazin-1-yl)-1H-[1,2,4]triazolo[3,4-b]purin-1-yl)-N,N-dimethylethan-1-amine

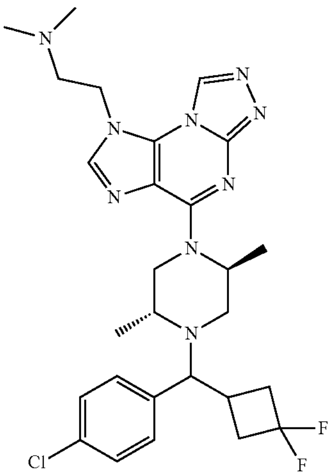 [SMILES: C[C@@H]1CN(c2nc3nncn3c3c2ncn3CCN(C)C)[C@@H](C)CN1C(c1ccc(Cl)cc1)C1CC(F)(F)C1]

Step 1. tert-Butyl (2-(2-chloro-6-((2S,5R)-4-((4-chlorophenyl)(3,3-difluorocyclobutyl)methyl)-2,5-dimethylpiperazin-1-yl)-9H-purin-9-yl)ethyl)(methyl)carbamate

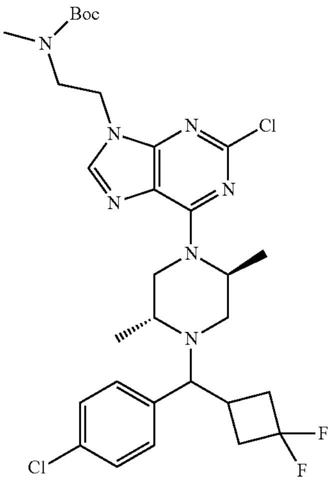 [SMILES: C[C@@H]1CN(c2nc(Cl)nc3c2ncn3CCN(C)C(=O)OC(C)(C)C)[C@@H](C)CN1C(c1ccc(Cl)cc1)C1CC(F)(F)C1]

To a mixture of tert-butyl (2-(2,6-dichloro-9H-purin-9-yl)ethyl)(methyl)carbamate (Intermediate 51, 85.0 mg, 0.246 mmol) and (2R,5S)-1-((4-chlorophenyl)(3,3-difluorocyclobutyl)methyl)-2,5-dimethylpiperazine hydrochloride (Intermediate 52, 90.0 mg, 0.246 mmol) in n-BuOH (4 mL) was added N,N-diisopropylethylamine (0.12 mL, 0.7 mmol) and the mixture was stirred at 90° C. overnight. After cooling to rt, the mixture was concentrated in vacuo, and the residue was taken up in $CH_2Cl_2$ and washed with saturated aqueous $NaHCO_3$. The organic layer was removed, and the aqueous layer was extracted with $CH_2Cl_2$. The combined organic layers were dried over $MgSO_4$ and the filtrate was concentrated in vacuo to afford the desired product as a mixture of diastereomers. The crude material obtained was used directly without further purification. LC-MS calculated for $C_{30}H_{40}Cl_2F_2N_7O_2(M+H)^+$: m/z=638.3; found 638.4.

Step 2. tert-Butyl (2-(6-((2S,5R)-4-((4-chlorophenyl)(3,3-difluorocyclobutyl)methyl)-2,5-dimethylpiperazin-1-yl)-2-hydrazineyl-9H-purin-9-yl)ethyl)(methyl)carbamate

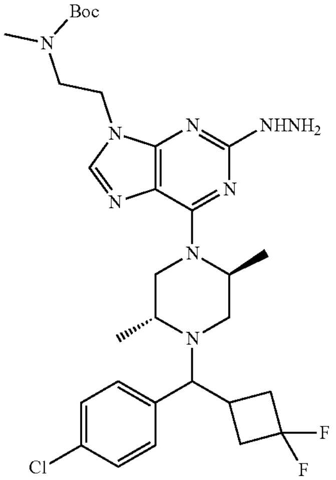 [SMILES: C[C@@H]1CN(c2nc(NN)nc3c2ncn3CCN(C)C(=O)OC(C)(C)C)[C@@H](C)CN1C(c1ccc(Cl)cc1)C1CC(F)(F)C1]

To a mixture of tert-butyl (2-(2-chloro-6-((2S,5R)-4-((4-chlorophenyl)(3,3-difluorocyclobutyl)methyl)-2,5-dimethylpiperazin-1-yl)-9H-purin-9-yl)ethyl)(methyl)carbamate (Step 1) in 1,4-dioxane (3 mL) was added hydrazine (39 μL, 1.2 mmol), and the mixture was stirred at 120° C. overnight. After cooling to rt, the reaction mixture was concentrated, and the crude residue was purified by flash column chromatography ($SiO_2$, 0-5% $MeOH/CH_2Cl_2$) to afford the desired product (30.2 mg, 19% yield over 2 steps) as a mixture of diastereomers in the form of a white solid. LC-MS calculated for $C_{30}H_{43}ClF_2N_9O_2$ $(M+H)^+$: m/z=634.3; found 634.3.

Step 3. tert-Butyl (2-(4-((2S,5R)-4-((4-chlorophenyl)(3,3-difluorocyclobutyl)methyl)-2,5-dimethylpiperazin-1-yl)-1H-[1,2,4]triazolo[3,4-b]purin-1-yl)ethyl)(methyl)carbamate

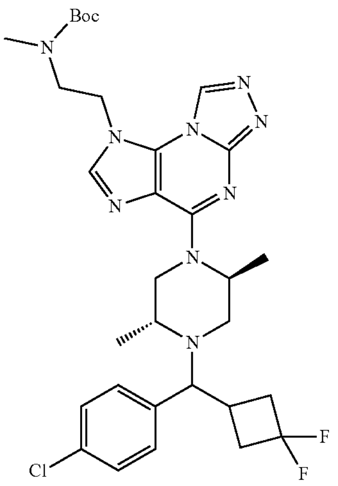 [SMILES: C[C@@H]1CN(c2nc3nncn3c3c2ncn3CCN(C)C(=O)OC(C)(C)C)[C@@H](C)CN1C(c1ccc(Cl)cc1)C1CC(F)(F)C1]

To a mixture of tert-butyl (2-(6-((2S,5R)-4-((4-chlorophenyl)(3,3-difluorocyclobutyl)methyl)-2,5-dimethylpiperazin-1-yl)-2-hydrazineyl-9H-purin-9-yl)ethyl)(methyl)carbamate (30.2 mg, 0.048 mmol) in AcOH (28 μL, 0.49 mmol) was added triethyl orthoformate (0.205 mL, 1.23 mmol) and the reaction mixture was stirred at 90° C. for 1 h. After cooling to rt, the reaction mixture was diluted with toluene and concentrated in vacuo to afford the desired product as a mixture of diastereomers. The crude material obtained was used directly without further purification. LC-MS calculated for $C_{31}H_{41}ClF_2N_9O_2$ $(M+H)^+$: m/z=644.3; found 644.4.

Step 4. 2-(4-((2S,5R)-4-((4-Chlorophenyl)(3,3-difluorocyclobutyl)methyl)-2,5-dimethylpiperazin-1-yl)-1H-[1,2,4]triazolo[3,4-b]purin-1-yl)-N,N-dimethylethan-1-amine To a mixture of tert-butyl (2-(4-((2S,5R)-4-((4-chlorophenyl)(3,3-difluorocyclobutyl)methyl)-2,5-dimethylpiperazin-1-yl)-1H-[1,2,4]triazolo[3,4-b]purin-1-yl)ethyl)(methyl)carbamate (Step 3) in $CH_2Cl_2$ (2 mL) was added trifluoroacetic acid (1 mL) and the reaction mixture was stirred at rt for 30 min. The mixture was concentrated in vacuo, and to the crude residue was added THF (3 mL) followed by formaldehyde (37 wt % in water, 0.110 mL, 1.478 mmol) and the reaction mixture was stirred at rt for 15 min. Sodium triacetoxyborohydride (157 mg, 0.739 mmol) was added and the reaction mixture was stirred at rt for 15 min. The mixture was treated with 1 M HCl (aq) and diluted with acetonitrile, water, and several drops of TFA. The diastereomeric mixture was filtered and purified by prep-HPLC (Sunfire C18 column, eluting with a gradient of acetonitrile/water containing 0.1% TFA, at flow rate of 60 mL/min) to afford the major diastereomer as a single stereoisomer as its TFA salt. LC-MS calculated for $C_{27}H_{35}ClF_2N_9$ $(M+H)^+$: m/z=558.3; found 558.3. $^1H$ NMR (500 MHz, DMSO-$d_6$, 100° C.) δ 9.43 (s, 1H), 8.31 (s, 1H), 7.45-7.37 (m, 4H), 5.48 (s, 1H), 5.20 (s, 1H), 4.92 (t, J=6.7 Hz, 2H), 3.63 (d, J=9.7 Hz, 1H), 3.59 (t, J=6.7 Hz, 2H), 3.50 (dd, J=13.5, 4.3 Hz, 1H), 3.08 (dd, J=12.1, 4.9 Hz, 1H), 2.96-2.91 (m, 1H), 2.84 (s, 6H), 2.82-2.75 (m, 1H), 2.71-2.63 (m, 2H), 2.44-2.32 (m, 1H), 2.31-2.20 (m, 1H), 2.10-1.96 (m, 1H), 1.43 (d, J=6.5 Hz, 3H), 0.95 (d, J=6.4 Hz, 3H).

Example 65. 2-(4-((2S,5R)-4-((4-Bromophenyl)(3,3-difluorocyclobutyl)methyl)-2,5-dimethylpiperazin-1-yl)-1H-[1,2,4]triazolo[3,4-b]purin-1-yl)-N,N-dimethylethan-1-amine

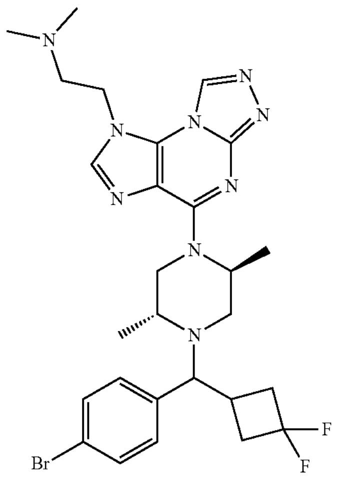 [SMILES: C[C@@H]1CN(c2nc3nncn3c3c2ncn3CCN(C)C)[C@@H](C)CN1C(c1ccc(Br)cc1)C1CC(F)(F)C1]

This compound was prepared according to the procedures described in Example 64, with (2R,5S)-1-((4-bromophenyl)(3,3-difluorocyclobutyl)methyl)-2,5-dimethylpiperazine hydrochloride (Intermediate 53) replacing (2R,5S)-1-((4-chlorophenyl)(3,3-difluorocyclobutyl)methyl)-2,5-dimethylpiperazine hydrochloride in Step 1. LC-MS calculated for $C_{27}H_{35}BrF_2N_9(M+H)^+$: m/z=602.2; found 602.3.

Example 66. 2-(4-((2S,5R)-4-((4-Chlorophenyl)(3,3-difluorocyclobutyl)methyl)-5-ethyl-2-methylpiperazin-1-yl)-1H-[1,2,4]triazolo[3,4-b]purin-1-yl)-N,N-dimethylethan-1-amine

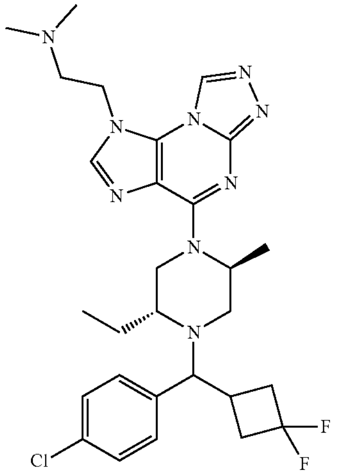 [SMILES: CC[C@@H]1CN(c2nc3nncn3c3c2ncn3CCN(C)C)[C@@H](C)CN1C(c1ccc(Cl)cc1)C1CC(F)(F)C1]

This compound was prepared according to the procedures described in Example 64, with (2R,5S)-1-((4-chlorophenyl)(3,3-difluorocyclobutyl)methyl)-2-ethyl-5-methylpiperazine hydrochloride (Intermediate 55) replacing (2R,5S)-1-((4-chlorophenyl)(3,3-difluorocyclobutyl)methyl)-2,5-dimethylpiperazine hydrochloride in Step 1. LC-MS calculated for $C_{28}H_{37}ClF_2N_9(M+H)^+$: m/z=572.3; found 572.4.

Examples 67 and 68. 4-((2S,5R)-2,5-Dimethyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine and 4-((2S,5R)-2,5-dimethyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine

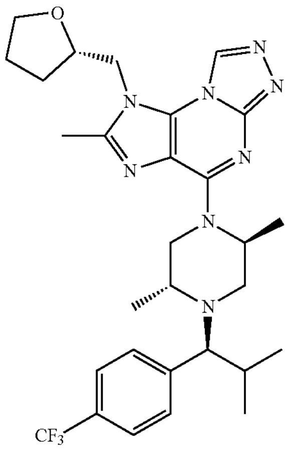

and

-continued

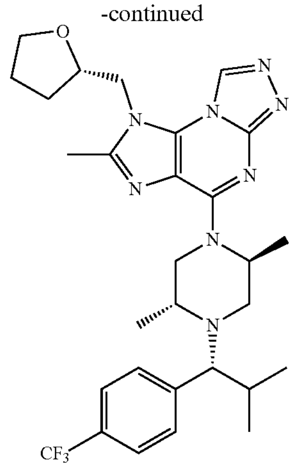

Step 1. 2-Chloro-6-((2S,5R)-2,5-dimethyl-4-(2-methyl-(4-(trifluoromethyl)phenyl)propyl)piperazin-1-yl)-8-methyl-9-(((S)-tetrahydrofuran-2-yl)methyl)-9H-purine

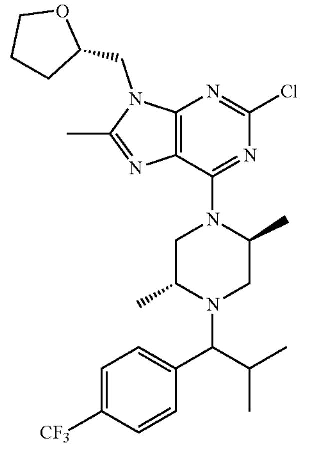 [SMILES: Cc1nc2c(N3C[C@@H](C)N(C(c4ccc(C(F)(F)F)cc4)C(C)C)C[C@@H]3C)nc(Cl)nc2n1C[C@@H]1CCCO1]

To a mixture of 2-chloro-6-((2S,5R)-2,5-dimethyl-4-(2-methyl-1-(4-(trifluoromethyl)phenyl)propyl)piperazin-1-yl)-8-methyl-9H-purine (Intermediate 57, 190 mg, 0.395 mmol) and cesium carbonate (0.644 g, 1.98 mmol) in acetonitrile (2.0 mL) was added (S)-(tetrahydrofuran-2-yl) methyl methanesulfonate (Intermediate 22, 214.0 mg, 1.19 mmol) and the mixture was stirred at 90° C. overnight. After cooling to rt, the reaction mixture was filtered to remove insoluble solids and the resulting filtrate was concentrated under reduced pressure to afford the desired product as a mixture of diastereomers. The crude residue was used in the next step without further purification. LC-MS calculated for $C_{28}H_{37}ClF_3N_6O$ $(M+H)^+$: m/z=565.3; found 565.3.

Step 2. 6-((2S,5R)-2,5-Dimethyl-4-(2-methyl-1-(4-(trifluoromethyl)phenyl)propyl)piperazin-1-yl)-2-hydrazineyl-8-methyl-9-(((S)-tetrahydrofuran-2-yl)methyl)-9H-purine

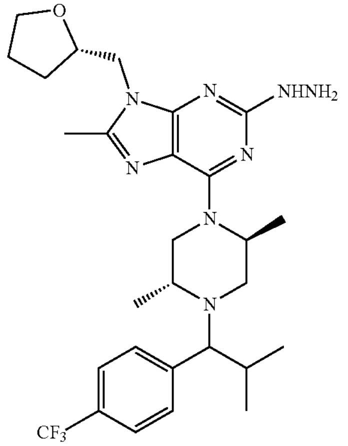 [SMILES: Cc1nc2c(N3C[C@@H](C)N(C(c4ccc(C(F)(F)F)cc4)C(C)C)C[C@@H]3C)nc(NN)nc2n1C[C@@H]1CCCO1]

To a mixture of 2-chloro-6-((2S,5R)-2,5-dimethyl-4-(2-methyl-1-(4-(trifluoromethyl)phenyl)propyl)piperazin-1-yl)-8-methyl-9-(((S)-tetrahydrofuran-2-yl)methyl)-9H-purine (Step 1) was added methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (67.5 mg, 0.079 mmol, Aldrich 745979), and cesium carbonate (386 mg, 1.19 mmol) in THF (1.98 mL) was added hydrazine (62 μL, 2.0 mmol) and the mixture was stirred at 60° C. for 1 h. After cooling to rt, the reaction mixture was filtered through a pad of $MgSO_4$ in a SiliaPrep SPE thiol cartridge (500 mg, SiliCycle SPE-R51030B-06P). The filtrate was concentrated to afford the desired product as a mixture of diastereomers. The crude material obtained was used directly without further purification. LC-MS calculated for $C_{28}H_{40}F_3N_8O$ $(M+H)^+$: m/z=561.3; found 561.3.

Step 3. 4-((2S,5R)-2,5-Dimethyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine and 4-((2S,5R)-2,5-dimethyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine A mixture of 6-((2S,5R)-2,5-dimethyl-4-(2-methyl-1-(4-(trifluoromethyl)phenyl)propyl)piperazin-1-yl)-2-hydrazineyl-8-methyl-9-(((S)-tetrahydrofuran-2-yl)methyl)-9H-purine (Step 2), triethyl orthoformate (329 μL, 1.98 mmol), and AcOH (1.13 mL, 19.8 mmol) was stirred at 85° C. overnight. After cooling to rt, the diastereomeric mixture was diluted with acetonitrile and water and purified by prep-HPLC (Sunfire C18 column, eluting with a gradient of acetonitrile/water containing 0.10% TFA, at flow rate of 60 mL/min) to afford each diastereomer as its TFA salt.

Example 67: Retention time on LC-MS $t_r$=1.248 min, LC-MS calculated for $C_{29}H_{38}F_3N_8O$ $(M+H)^+$: m/z=571.3; found 571.4. $^1H$ NMR (500 MHz, DMSO-$d_6$) (mixture of rotamers) δ 9.47 (s, 1H), 7.74 (d, J=7.8 Hz, 2H), 7.52 (d, J=7.8 Hz, 2H), 6.18-5.90 (m, 0.4H), 5.89-5.61 (m, 0.6H), 5.05-4.85 (m, 0.6H), 4.78-4.46

(m, 2.4H), 4.15-4.07 (m, 1H), 3.74-3.66 (m, 1H), 3.65-3.34 (m, 3H), 3.06-2.98 (m, 1H), 2.89-2.77 (m, 1H), 2.71-2.53 (m, 4H), 2.38-2.29 (m, 1H), 2.17-2.08 (m, 1H), 1.98-1.88 (m, 1H), 1.88-1.77 (m, 1H), 1.77-1.66 (m, 1H), 1.53-1.29 (m, 3H), 0.98-0.87 (m, 3H), 0.86-0.66 (m, 6H).

Example 68: Retention time on LC-MS $t_r$=1.297 min, LC-MS calculated for $C_{29}H_{38}F_3N_8O$ $(M+H)^+$: m/z=571.3; found 571.4. $^1H$ NMR (500 MHz, DMSO-$d_6$) (mixture of rotamers) δ 9.50-9.46 (m, 1H), 7.74-7.67 (m, 2H), 7.59-7.51 (m, 2H), 6.19-6.10 (m, 0.4H), 6.05-5.95 (m, 0.6H), 5.03-4.94 (m, 0.6H), 4.76-4.67 (m, 1.4H), 4.60-4.48 (m, 1H), 4.14-4.05 (m, 1H), 3.92-3.83 (m, 0.6H), 3.74-3.51 (m, 3.4H), 3.47-3.40 (m, 1H), 2.71-2.58 (m, 2.8H), 2.56 (s, 1.2H), 2.34-2.23 (m, 2H), 2.17-2.07 (m, 1H), 1.98-1.88 (m, 1H), 1.88-1.77 (m, 1H), 1.77-1.65 (m, 1H), 1.41 (d, J=6.6 Hz, 1.2H), 1.35 (d, J=6.8 Hz, 1.8H), 0.96 (d, J=6.4 Hz, 1.8H), 0.91 (d, J=6.4 Hz, 1.2H), 0.81-0.68 (m, 6H).

Examples 69 and 70. 4-((2S,5R)-2,5-Dimethyl-4-((S)-2-methyl-1-(3-(trifluoromethyl)phenyl)propyl)piperazin-1-yl)-2-methyl-1-(((S)-tetrahydrofuran-2-yl)methyl)-1H-[1,2,4]triazolo[3,4-b]purine and 4-((2S,5R)-2,5-dimethyl-4-((R)-2-methyl-1-(3-(trifluoromethyl)phenyl)propyl)piperazin-1-yl)-2-methyl-1-(((S)-tetrahydrofuran-2-yl)methyl)-1H-[1,2,4]triazolo[3,4-b]purine

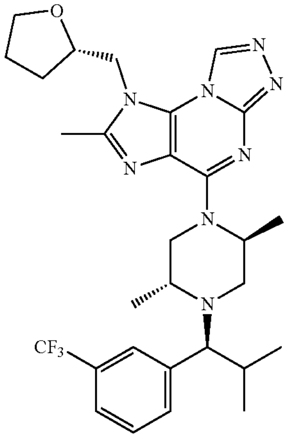

and

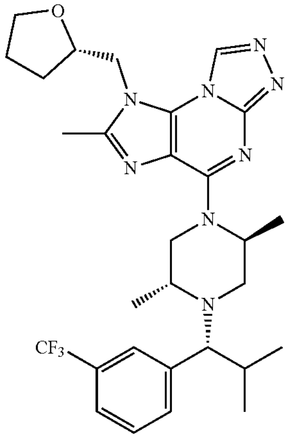

These compounds were prepared according to the procedures described in Examples 67 and 68, with 2-chloro-6-((2S,5R)-2,5-dimethyl-4-(2-methyl-1-(3-(trifluoromethyl)phenyl)propyl)piperazin-1-yl)-8-methyl-9H-purine (Intermediate 59) replacing 2-chloro-6-((2S,5R)-2,5-dimethyl-4-(2-methyl-1-(4-(trifluoromethyl)phenyl)propyl)piperazin-1-yl)-8-methyl-9H-purine in Step 1.

Example 69: Retention time on LC-MS $t_r$=1.449 min, LC-MS calculated for $C_{29}H_{38}F_3N_8O$ $(M+H)^+$: m/z=571.3; found 571.4. $^1H$ NMR (500 MHz, DMF-$d_7$, −15° C.) (mixture of rotamers) δ 9.82-9.74 (m, 1H), 7.88-7.66 (m, 4H), 6.23-6.09 (m, 0.3H), 6.01-5.87 (m, 0.7H), 5.14-4.91 (m, 1.7H), 4.86-4.76 (m, 1H), 4.73-4.61 (m, 0.3H), 4.35-4.23 (m, 1H), 3.88-3.80 (m, 1H), 3.78-3.68 (m, 0.7H), 3.68-3.54 (m, 2H), 3.53-3.44 (m, 0.3H), 3.22-3.09 (m, 1H), 2.99-2.86 (m, 1H), 2.78-2.69 (m, 4H), 2.51-2.35 (m, 1H), 2.29-2.17 (m, 1H), 2.07-1.97 (m, 1H), 1.96-1.79 (m, 2H), 1.62-1.39 (m, 3H), 1.10-0.92 (m, 3H), 0.91-0.67 (m, 6H).

Example 70: Retention time on LC-MS $t_r$=1.536 min, LC-MS calculated for $C_{29}H_{38}F_3N_8O$ $(M+H)^+$: m/z=571.3; found 571.4. $^1H$ NMR (500 MHz, DMSO-$d_6$) (mixture of rotamers) δ 9.52-9.47 (m, 1H), 7.81-7.49 (m, 4H), 6.20-6.10 (m, 0.4H), 6.07-5.96 (m, 0.6H), 5.05-4.92 (m, 0.6H), 4.75-4.70 (m, 1.4H), 4.58-4.51 (m, 1H), 4.14-4.07 (m, 1H), 3.97-3.83 (m, 0.6H), 3.72-3.66 (m, 1.4H), 3.60-3.53 (m, 2H), 3.51-3.43 (m, 1H), 2.70-2.62 (m, 2.8H), 2.57 (s, 1.2H), 2.39-2.20 (m, 2H), 2.13-2.09 (m, 1H), 1.98-1.89 (m, 1H), 1.88-1.78 (m, 1H), 1.74-1.67 (m, 1H), 1.41 (d, J=6.6 Hz, 1.2H), 1.34 (d, J=6.7 Hz, 1.8H), 1.05-0.89 (m, 3H), 0.81-0.68 (m, 6H).

Examples 71 and 72. 4-((2S,5R)-4-((S)-1-(2-Fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(2-fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine

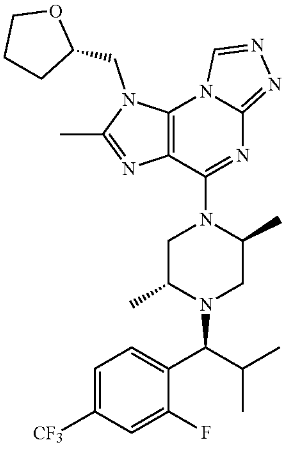

and

-continued

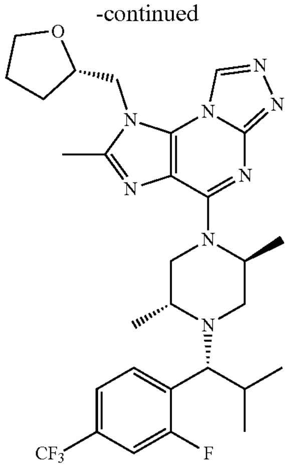

These compounds were prepared according to the procedures described in Examples 67 and 68, with 2-chloro-6-((2S,5R)-4-(1-(2-fluoro-4-(trifluoromethyl)phenyl)-2-methylpropyl)-2,5-dimethylpiperazin-1-yl)-8-methyl-9H-purine (Intermediate 61) replacing 2-chloro-6-((2S,5R)-2,5-dimethyl-4-(2-methyl-1-(4-(trifluoromethyl)phenyl)propyl)piperazin-1-yl)-8-methyl-9H-purine in Step 1.

Example 71: Retention time on LC-MS $t_r$=4.066 min, LC-MS calculated for $C_{29}H_{37}F_4N_8O$ $(M+H)^+$: m/z=589.3; found 589.4. $^1$H NMR (500 MHz, DMSO-$d_6$) (mixture of rotamers) δ 9.48 (s, 1H), 7.74-7.63 (m, 3H), 6.03-5.85 (m, 0.4H), 5.85-5.70 (m, 0.6H), 4.98-4.80 (m, 0.6H), 4.79-4.63 (m, 1H), 4.60-4.44 (m, 1.4H), 4.18-4.05 (m, 1H), 3.87-3.73 (m, 1H), 3.74-3.66 (m, 1H), 3.66-3.51 (m, 1.6H), 3.49-3.36 (m, 0.4H), 3.15-3.05 (m, 1H), 2.83-2.72 (m, 1H), 2.69-2.53 (m, 4H), 2.45-2.34 (m, 1H), 2.18-2.08 (m, 1H), 1.98-1.88 (m, 1H), 1.88-1.77 (m, 1H), 1.77-1.66 (m, 1H), 1.48-1.25 (m, 3H), 0.97 (d, J=6.4 Hz, 3H), 0.93-0.81 (m, 3H), 0.71 (d, J=6.4 Hz, 3H).

Example 72: Retention time on LC-MS $t_r$=4.621 min, LC-MS calculated for $C_{29}H_{37}F_4N_8)$ $(M+H)_1$: m/z=589.3; found 589.4. $^1$H NMR (500 MHz, DMSO-$d_6$) (mixture of rotamers) δ 9.51-9.47 (m, 1H), 7.81-7.71 (m, 1H), 7.69-7.58 (m, 2H), 6.22-6.14 (m, 0.4H), 6.02-5.96 (m, 0.6H), 5.04-4.96 (m, 0.6H), 4.77-4.65 (m, 1.4H), 4.59-4.49 (m, 1H), 4.15-4.05 (m, 1H), 3.90-3.84 (m, 0.6H), 3.83-3.75 (m, 1H), 3.73-3.60 (m, 1.4H), 3.60-3.50 (m, 2H), 2.76-2.55 (m, 4), 2.42-2.29 (m, 2H), 2.17-2.05 (m, 1H), 1.98-1.88 (m, 1H), 1.88-1.76 (m, 1H), 1.77-1.65 (m, 1H), 1.42 (d, J=6.6 Hz, 1.2H), 1.35 (d, J=6.7 Hz, 1.8H), 0.98-0.72 (m, 9H).

Examples 73-80

Examples 73-80 of Table 4 were prepared in accordance with the synthetic protocols set forth in Examples 67 and 68 using the indicated carboxylic acid starting material as described in Intermediate 56.

TABLE 4

| Ex. | Name | Structure | Starting Material | Analytical data |
|---|---|---|---|---|
| 73 and 74 | 4-((2S,5R)-4-((S)-1-(4-(Difluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-(difluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 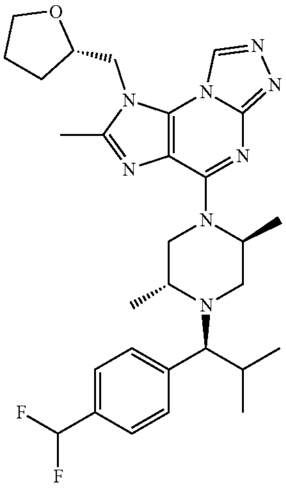 [SMILES: Cc1nc2c(N3C[C@@H](C)N([C@H](c4ccc(C(F)F)cc4)C(C)C)C[C@@H]3C)nc3nncn3c2n1C[C@@H]1CCCO1] and | 4-(Difluoromethyl)benzoic acid | Example 73: Retention time on LC-MS $t_r$ = 1.288 min, LC-MS $[M + H]^+$: found 553.4. Example 74: Retention time on LC-MS $t_r$ = 1.344 min, LC-MS $[M + H]^+$: found 553.4. |

TABLE 4-continued

| Ex. | Name | Structure | Starting Material | Analytical data |
|---|---|---|---|---|
| | | 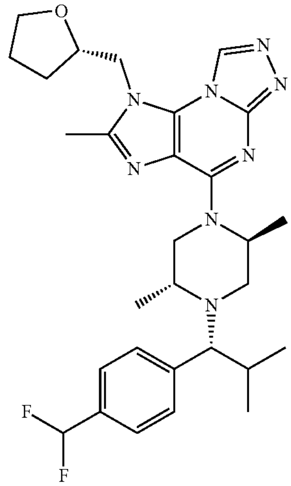 [SMILES: Cc1nc2c(N3C[C@@H](C)N([C@@H](c4ccc(C(F)F)cc4)C(C)C)C[C@@H]3C)nc3nncn3c2n1C[C@@H]1CCCO1] | | |
| 75 and 76 | 4-((2S,5R)-4-((S)-1-(4-(Difluoromethoxy)-2-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-(difluoromethoxy)-2-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 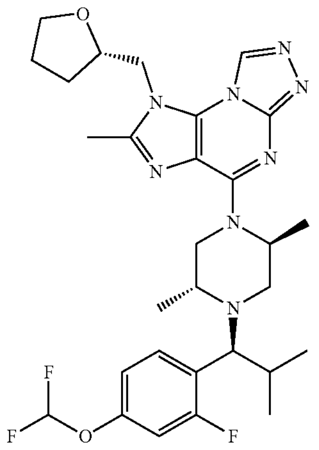 [SMILES: Cc1nc2c(N3C[C@@H](C)N([C@H](c4ccc(OC(F)F)cc4F)C(C)C)C[C@@H]3C)nc3nncn3c2n1C[C@@H]1CCCO1] and 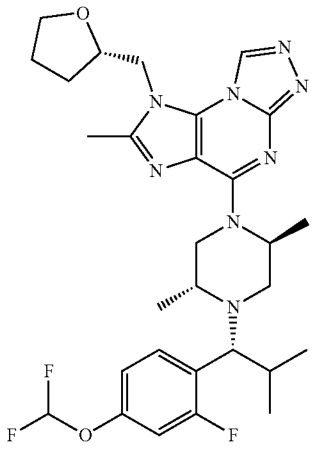 [SMILES: Cc1nc2c(N3C[C@@H](C)N([C@@H](c4ccc(OC(F)F)cc4F)C(C)C)C[C@@H]3C)nc3nncn3c2n1C[C@@H]1CCCO1] | 4-(Difluoromethoxy)-2-fluorobenzoic acid | Example 75: Retention time on LC-MS $t_r$ = 1.342 min, LC-MS $[M + H]^+$: found 587.4. Example 76: Retention time on LC-MS $t_r$ = 1.388 min, LC-MS $[M + H]^+$: found 587.4. |

TABLE 4-continued

| Ex. | Name | Structure | Starting Material | Analytical data |
|---|---|---|---|---|
| 77 and 78 | 4-((2S,5R)-4-((S)-1-(4-Methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 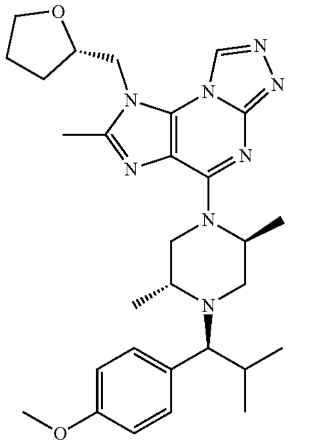 [SMILES: COc1ccc([C@H](C(C)C)N2C[C@H](C)N(c3nc4nncn4c4c3nc(C)n4C[C@@H]3CCCO3)C[C@H]2C)cc1] and 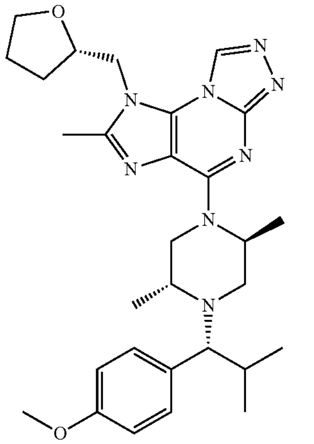 [SMILES: COc1ccc([C@@H](C(C)C)N2C[C@H](C)N(c3nc4nncn4c4c3nc(C)n4C[C@@H]3CCCO3)C[C@H]2C)cc1] | 4-Methoxybenzoic acid | Example 77: Retention time on LC-MS $t_r$ = 0.751 min, LC-MS [M + H]$^+$: found 533.3. Example 78: Retention time on LC-MS $t_r$ = 0.843 min, LC-MS [M + H]$^+$: found 533.3. |
| 79 and 80 | 4-((2S,5R)-4-((S)-1-(4-(Difluoromethoxy)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-(difluoromethoxy)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 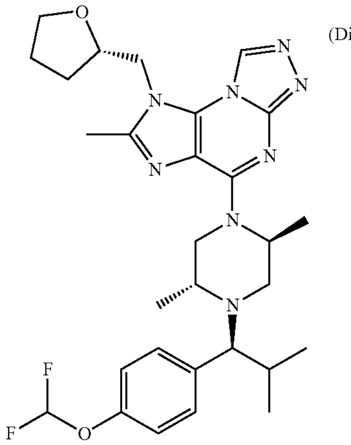 and | 4-(Difluoromethoxy)benzoic acid | Example 79: Retention time on LC-MS $t_r$ = 0.970 min, LC-MS [M + H]$^+$: found 569.3. Example 80: Retention time on LC-MS $t_r$ = 1.03 min, LC-MS [M + H]$^+$: found 569.3. |

TABLE 4-continued

| Ex. | Name | Structure | Starting Material | Analytical data |
|---|---|---|---|---|
| | | 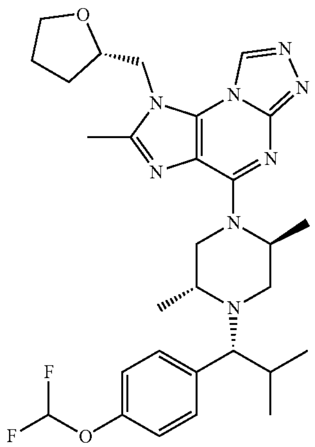 [SMILES: Cc1nc2c(N3C[C@@H](C)N([C@@H](c4ccc(OC(F)F)cc4)C(C)C)C[C@@H]3C)nc3nncn3c2n1C[C@@H]1CCCO1] | | |

Example 81. 4-((2S,5R)-4-(1-(4-(Difluoromethyl)-3-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine

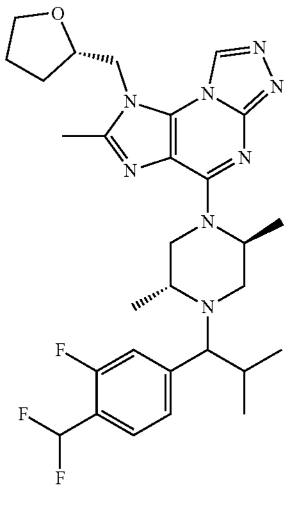 [SMILES: Cc1nc2c(N3C[C@@H](C)N(C(c4ccc(C(F)F)c(F)c4)C(C)C)C[C@@H]3C)nc3nncn3c2n1C[C@@H]1CCCO1]

Step 1. 2-Chloro-6-((2S,5R)-4-(1-(4-(difluoromethyl)-3-fluorophenyl)-2-methylpropyl)-2,5-dimethylpiperazin-1-yl)-8-methyl-9-(((S)-tetrahydrofuran-2-yl)methyl)-9H-purine

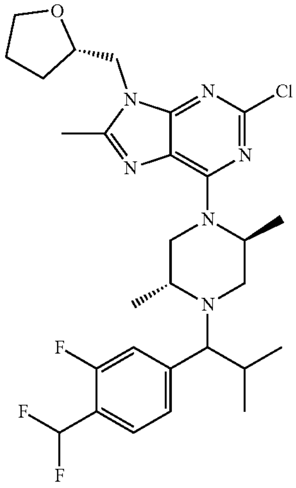 [SMILES: Cc1nc2c(N3C[C@@H](C)N(C(c4ccc(C(F)F)c(F)c4)C(C)C)C[C@@H]3C)nc(Cl)nc2n1C[C@@H]1CCCO1]

To a mixture of (S)-2,6-dichloro-8-methyl-9-((tetrahydrofuran-2-yl)methyl)-9H-purine (Intermediate 41, 274 mg, 0.954 mmol) and (2R,5S)-1-(1-(4-(difluoromethyl)-3-fluorophenyl)-2-methylpropyl)-2,5-dimethylpiperazine hydrochloride (Intermediate 63, 300 mg, 0.855 mmol) in n-BuOH (3 mL) was added N,N-diisopropylethylamine (0.50 mL, 2.9 mmol) and the mixture was stirred at 95° C. overnight. After cooling to rt, the mixture was concentrated in vacuo, and the crude residue was purified directly by flash column chromatography ($SiO_2$, $MeOH/CH_2Cl_2$) to afford the desired product as a mixture of diastereomers. LC-MS calculated for $C_{28}H_{37}ClF_3N_6O$ $(M+H)^+$: m/z=565.3; found 565.4.

Step 2. 6-((2S,5R)-4-(1-(4-(Difluoromethyl)-3-fluorophenyl)-2-methylpropyl)-2,5-dimethylpiperazin-1-yl)-2-hydrazineyl-8-methyl-9-(((S)-tetrahydrofuran-2-yl methyl)-9H-purine

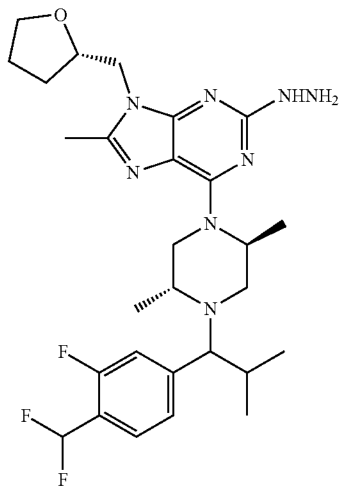 [SMILES: Cc1nc2c(N3C[C@@H](C)N(C(c4ccc(C(F)F)c(F)c4)C(C)C)C[C@@H]3C)nc(NN)nc2n1C[C@@H]1CCCO1]

To a mixture of 2-chloro-6-((2S,5R)-4-(1-(4-(difluoromethyl)-3-fluorophenyl)-2-methylpropyl)-2,5-dimethylpiperazin-1-yl)-8-methyl-9-(((S)-tetrahydrofuran-2-yl)methyl)-9H-purine (Step 1) in 1,4-dioxane (3 mL) was added hydrazine (180 μL, 5.73 mmol) and the reaction mixture was stirred at 120° C. overnight. After cooling to rt, the reaction mixture was concentrated, and the crude residue was purified directly by flash column chromatography ($SiO_2$, MeOH/$CH_2Cl_2$) to afford the desired product as a mixture of diastereomers. LC-MS calculated for $C_{28}H_{40}F_3N_8O$ $(M+H)^+$: m/z=561.3; found 561.4.

Step 3. 4-((2S,5R)-4-(1-(4-(Difluoromethyl)-3-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine A mixture of 6-((2S,5R)-4-(1-(4-(difluoromethyl)-3-fluorophenyl)-2-methylpropyl)-2,5-dimethylpiperazin-1-yl)-2-hydrazineyl-8-methyl-9-(((S)-tetrahydrofuran-2-yl)methyl)-9H-purine (Step 2) in triethyl orthoformate (794 μL, 4.77 mmol) and AcOH (2.73 mL, 47.7 mmol) was stirred at 85° C. for 1 h. After cooling to rt, the reaction mixture was concentrated in vacuo. The crude residue was taken up in acetonitrile, water, and several drops of TFA, and the diastereomeric mixture was filtered and purified by prep-HPLC (Sunfire C18 column, eluting with a gradient of acetonitrile/water containing 0.10% TFA, at flow rate of 60 mL/min) to afford the major diastereomer as a single stereoisomer as its TFA salt. LC-MS calculated for $C_{29}H_{38}F_3N_8O$ $(M+H)^+$: m/z=571.3; found 571.4.

Examples 82-85

Examples 82-85 of Table 5 were prepared in accordance with the synthetic protocols set forth in Example 81 using the indicated aryl halides for Grignard formation as described in Intermediate 63.

TABLE 5

| Ex. | Name | Structure | Aryl Halide Starting Material | Analytical data |
|---|---|---|---|---|
| 82 | 4-((2S,5R)-4-(1-(3-(Difluoromethyl)-4-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 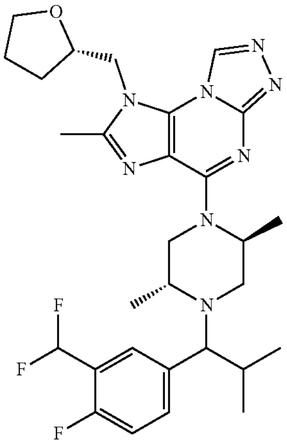 [SMILES: Cc1nc2c(N3C[C@@H](C)N(C(c4ccc(F)c(C(F)F)c4)C(C)C)C[C@@H]3C)nc3nncn3c2n1C[C@@H]1CCCO1] | 4-Bromo-2-(difluoromethyl)-1-fluorobenzene | LC-MS $[M+H]^+$: found 571.4 |

TABLE 5-continued

| Ex. | Name | Structure | Aryl Halide Starting Material | Analytical data |
|---|---|---|---|---|
| 83 | 4-((2S,5R)-4-(1-(3-Fluoro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 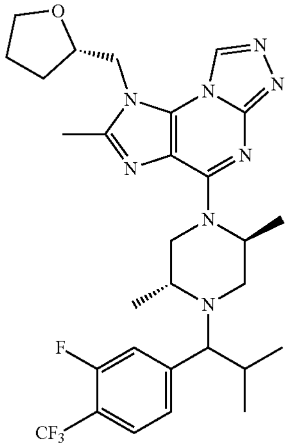 [SMILES: Cc1nc2c(N3C[C@@H](C)N(C(c4ccc(C(F)(F)F)c(F)c4)C(C)C)C[C@@H]3C)nc3nncn3c2n1C[C@@H]1CCCO1] | 4-Bromo-2-fluoro-1-(trifluoromethyl)benzene | LC-MS $[M + H]^+$: found 589.3 |
| 84 | 4-((2S,5R)-4-(1-(4-Fluoro-3-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 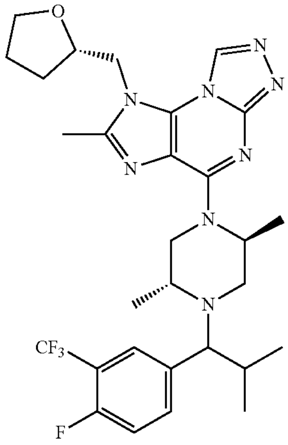 [SMILES: Cc1nc2c(N3C[C@@H](C)N(C(c4ccc(F)c(C(F)(F)F)c4)C(C)C)C[C@@H]3C)nc3nncn3c2n1C[C@@H]1CCCO1] | 1-Fluoro-4-iodo-2-(trifluoromethyl)benzene | LC-MS $[M + H]^+$: found 589.4 |
| 85 | 4-((2S,5R)-4-(1-(3-Chloro-4-(trifluoromethyl)phenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 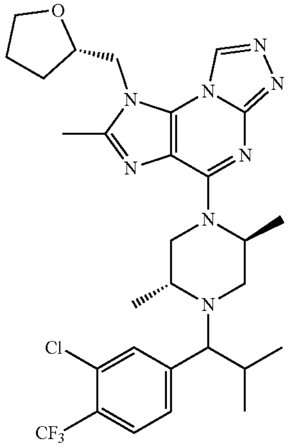 [SMILES: Cc1nc2c(N3C[C@@H](C)N(C(c4ccc(C(F)(F)F)c(Cl)c4)C(C)C)C[C@@H]3C)nc3nncn3c2n1C[C@@H]1CCCO1] | 4-Bromo-2-chloro-1-(trifluoromethyl)benzene | LC-MS $[M + H]^+$: found 605.5 |

Examples 86 and 87. 4-((2S,5R)-4-((S)-1-(3-Chloro-4-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(3-chloro-4-fluorophenyl)-2-methylpropyl)-2,5-dimethylpiperazin-1-yl)-2-methyl-11-(((S)-tetrahydrofuran-2-yl)methyl)-1H-[1,2,4]triazolo[3,4-b]purine

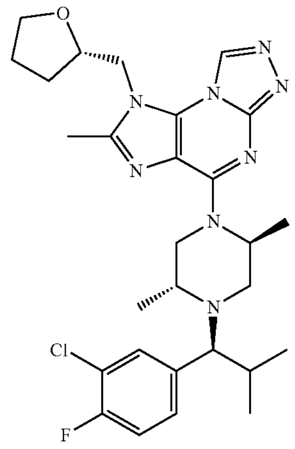

and

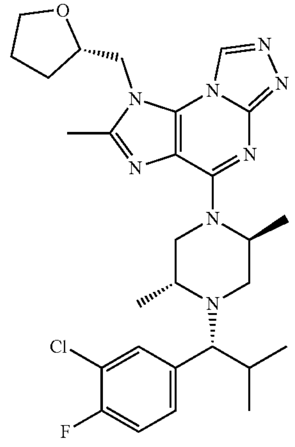

Step 1. 2-Chloro-6-((2S,5R)-4-(1-(3-chloro-4-fluorophenyl)-2-methylpropyl)-2,5-dimethylpiperazin-1-yl)-8-methyl-9-(((S)-tetrahydrofuran-2-yl)methyl)-9H-purine

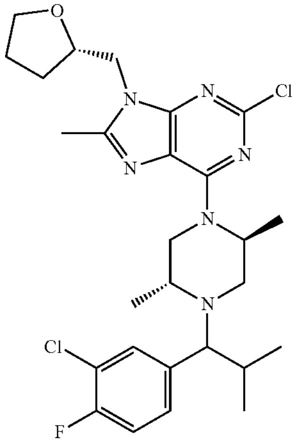 [SMILES: Cc1nc2c(N3C[C@@H](C)N(C(c4ccc(F)c(Cl)c4)C(C)C)C[C@@H]3C)nc(Cl)nc2n1C[C@@H]1CCCO1]

A mixture of 2-chloro-6-((2S,5R)-4-(1-(3-chloro-4-fluorophenyl)-2-methylpropyl)-2,5-dimethylpiperazin-1-yl)-8-methyl-9H-purine (Intermediate 65, 800. mg, 1.72 mmol), (S)-(tetrahydrofuran-2-yl)methyl methanesulfonate (Intermediate 22, 929 mg, 5.16 mmol) and cesium carbonate (2.80 g, 8.59 mmol) in acetonitrile (8.59 mL) was stirred at 90° C. overnight. After cooling to rt, the reaction mixture was filtered to remove insoluble solids and the resulting filtrate was concentrated under reduced pressure to afford the desired product as a mixture of diastereomers. The crude residue was used in the next step without further purification. LC-MS calculated for $C_{27}H_{36}Cl_2FN_6O$ $(M+H)^+$: m/z=549.2; found 549.3.

Step 2. 6-((2S,5R)-4-(1-(3-Chloro-4-fluorophenyl)-2-methylpropyl)-2,5-dimethylpiperazin-1-yl)-2-hydrazineyl-8-methyl-9-(((S)-tetrahydrofuran-2-yl)methyl)-9H-purine

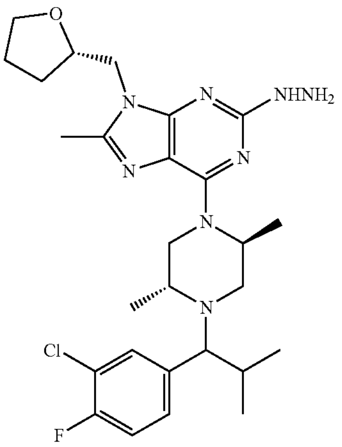 [SMILES: Cc1nc2c(N3C[C@@H](C)N(C(c4ccc(F)c(Cl)c4)C(C)C)C[C@@H]3C)nc(NN)nc2n1C[C@@H]1CCCO1]

To a mixture of 2-chloro-6-((2S,5R)-4-(1-(3-chloro-4-fluorophenyl)-2-methylpropyl)-2,5-dimethylpiperazin-1-yl)-8-methyl-9-(((S)-tetrahydrofuran-2-yl)methyl)-9H-purine (Step 1) in 1,4-dioxane (8.59 mL) was added hydrazine (270 μL, 8.59 mmol) and the reaction mixture was stirred at 110° C. for 2 d. After cooling to rt, the reaction mixture was concentrated, and the crude residue was purified directly by flash column chromatography ($SiO_2$, $MeOH/CH_2Cl_2$) to afford the desired product as a mixture of diastereomers. LC-MS calculated for $C_{27}H_{39}ClFN_8O$ $(M+H)^+$: m/z=545.3; found 545.3.

Step 3. 4-((2S,5R)-4-((S)-1-(3-Chloro-4-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(3-chloro-4-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine A mixture of 6-((2S,5R)-4-(1-(3-chloro-4-fluorophenyl)-2-methylpropyl)-2,5-dimethylpiperazin-1-yl)-2-hydrazineyl-8-methyl-9-(((S)-tetrahydrofuran-2-yl)methyl)-9H-purine (Step 2), triethyl orthoformate (1.43 mL, 8.59 mmol), and AcOH (4.92 mL, 86 mmol) was stirred at 85° C. for 1 h. After cooling to rt, the diastereomeric mixture was diluted with acetonitrile and water and purified by prep-HPLC (Sunfire C18 column, eluting with a gradient of acetonitrile/water containing 0.1% TFA, at flow rate of 60 mL/min) to afford each diastereomer as its TFA salt.

Example 86: Retention time on LC-MS $t_r$=1.325 min, LC-MS calculated for $C_{28}H_{37}ClFN_8O$ $(M+H)^+$: m/z=555.3; found 555.3.

Example 87: Retention time on LC-MS $t_r$=1.419 min, LC-MS calculated for $C_{28}H_{37}ClFN_8O$ $(M+H)^+$: m/z=555.3; found 555.3.

Examples 88 and 89. 4-((2S,5R)-4-((S)-1-(4-Chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine

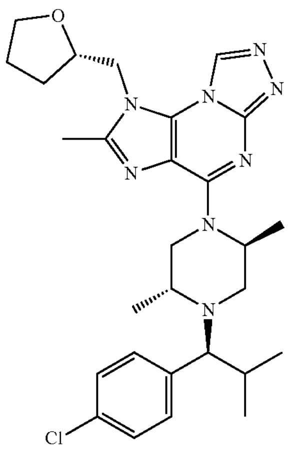

and

-continued

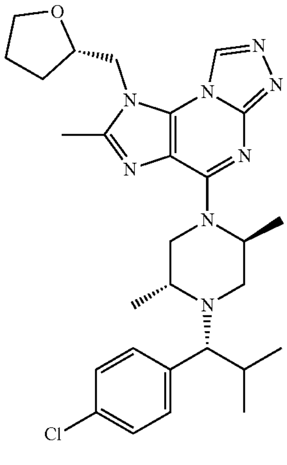

These compounds were prepared according to the procedures described in Examples 86 and 87, with 2-chloro-6-((2S,5R)-4-(1-(4-chlorophenyl)-2-methylpropyl)-2,5-dimethylpiperazin-1-yl)-8-methyl-9H-purine (Intermediate 67) replacing 2-chloro-6-((2S,5R)-4-(1-(3-chloro-4-fluorophenyl)-2-methylpropyl)-2,5-dimethylpiperazin-1-yl)-8-methyl-9H-purine in Step 1.

Example 88: Retention time on LC-MS $t_r$=1.226 min, LC-MS calculated for $C_{28}H_{38}ClN_8O$ $(M+H)^+$: m/z=537.3; found 537.3.

Example 89: Retention time on LC-MS $t_r$=1.295 min, LC-MS calculated for $C_{28}H_{38}ClN_8O$ $(M+H)^+$: m/z=537.3; found 537.3.

Examples 90 and 91. 2-(4-((2S,5R)-4-((S)-1-(4-Chlorophenyl)-2-methylpropyl)-2,5-dimethylpiperazin-1-yl)-1H-[1,2,4]triazolo[3,4-b]purin-1-yl)-N,N-dimethylethan-1-amine and 2-(4-((2S,5R)-4-((R)-1-(4-chlorophenyl)-2-methylpropyl)-2,5-dimethylpiperazin-1-yl)-1H-[1,2,4]triazolo[3,4-b]purin-1-yl)-N,N-dimethylethan-1-amine

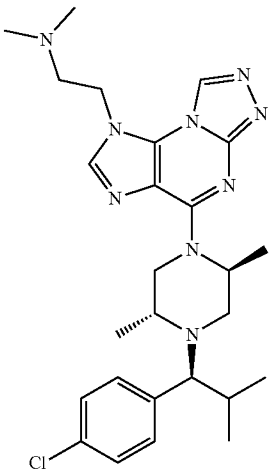

and

-continued

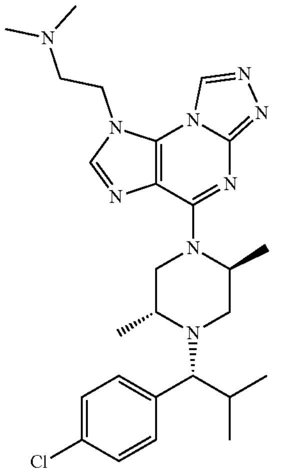

This compound was prepared according to the procedures described in Example 64, with (2R,5S)-1-(1-(4-chlorophenyl)-2-methylpropyl)-2,5-dimethylpiperazine hydrochloride (Intermediate 68) replacing (2R,5S)-1-((4-chlorophenyl)(3,3-difluorocyclobutyl)methyl)-2,5-dimethylpiperazine hydrochloride in Step 1. In Step 3 the diastereomeric mixture was filtered and purified by prep-HPLC (Sunfire C18 column, eluting with a gradient of acetonitrile/water containing 0.1% TFA, at flow rate of 60 mL/min) to afford each diastereomer as its TFA salt.

Example 90: Retention time on LC-MS $t_r$=0.818 min, LC-MS calculated for $C_{26}H_{37}ClN_9$ $(M+H)^+$: m/z=510.3; found 510.3.

Example 91: Retention time on LC-MS $t_r$=0.851 min, LC-MS calculated for $C_{26}H_{37}ClN_9$ $(M+H)^+$: m/z=510.3; found 510.3.

Example 92. 4-((2S,5R)-4-((4-(Difluoromethyl)phenyl)(4-methoxyphenyl)methyl)-2,5-dimethylpiperazin-1-yl)-2-methyl-1-(((S)-tetrahydrofuran-2-yl)methyl)-1H-[1,2,4]triazolo[3,4-b]purine

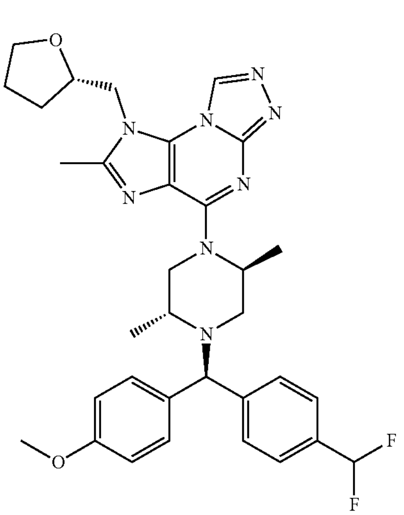 [SMILES: COc1ccc([C@H](c2ccc(C(F)F)cc2)N2C[C@H](C)N(c3nc4nncn4c4c3nc(C)n4C[C@@H]3CCCO3)C[C@H]2C)cc1]

Step 1. 2-Chloro-6-((2S,5R)-4-((4-(difluoromethyl)phenyl)(4-methoxyphenyl)methyl)-2,5-dimethylpiperazin-1-yl)-8-methyl-9-(((S)-tetrahydrofuran-2-yl)methyl)-9H-purine

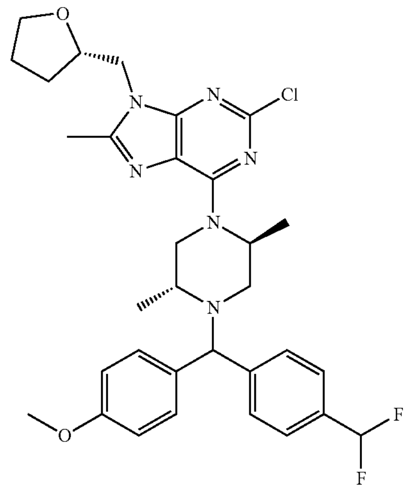 [SMILES: COc1ccc(C(c2ccc(C(F)F)cc2)N2C[C@H](C)N(c3nc(Cl)nc4c3nc(C)n4C[C@@H]3CCCO3)C[C@H]2C)cc1]

To a mixture of (S)-2,6-dichloro-8-methyl-9-((tetrahydrofuran-2-yl)methyl)-9H-purine (Intermediate 41, 76.0 mg, 0.264 mmol) and (2R,5S)-1-((4-(difluoromethyl)phenyl)(4-methoxyphenyl)methyl)-2,5-dimethylpiperazine hydrochloride (Intermediate 70, 95 mg, 1.3 mmol) in 1-butanol (661 μL) was added N-ethyl-N-isopropylpropan-2-amine (230 μL, 0.8 mmol) and the mixture was stirred at 90° C. for 2 h. After cooling to rt, the mixture was concentrated in vacuo, and the crude residue was purified directly by flash column chromatography ($SiO_2$, $MeOH/CH_2Cl_2$) to afford the desired product as a mixture of diastereomers. The crude material obtained was used directly without further purification. LC-MS calculated for $C_{32}H_{38}ClF_2N_6O_2$ $(M+H)^+$: m/z=611.3; found 611.4.

Step 2. 6-((2S,5R)-4-((4-(difluoromethyl)phenyl)(4-methoxyphenyl)methyl)-2,5-dimethylpiperazin-1-yl)-2-hydrazineyl-8-methyl-9-(((S)-tetrahydrofuran-2-yl)methyl)-9H-purine

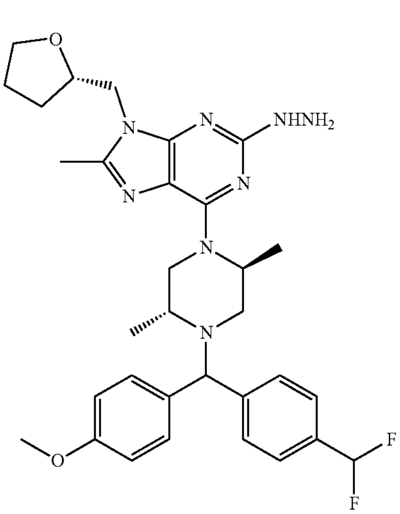 [SMILES: COc1ccc(C(c2ccc(C(F)F)cc2)N2C[C@H](C)N(c3nc(NN)nc4c3nc(C)n4C[C@@H]3CCCO3)C[C@H]2C)cc1]

To a mixture of 2-chloro-6-((2S,5R)-4-((4-(difluoromethyl)phenyl)(4-methoxyphenyl)methyl)-2,5-dimethylpiperazin-1-yl)-8-methyl-9-(((S)-tetrahydrofuran-2-yl)methyl)-9H-purine (369 mg, 0.604 mmol) in 1,4-dioxane (3.0 mL) was added hydrazine (114 μL, 3.62 mmol), and the mixture was stirred at 120° C. overnight. After cooling to rt, the reaction mixture was concentrated, and the crude residue was purified directly by flash column chromatography ($SiO_2$, $MeOH/CH_2Cl_2$) to afford the desired product as a mixture of diastereomers in the form of an off-white solid. LC-MS calculated for $C_{32}H_{41}F_2N_8O_2$ $(M+H)^+$: m/z=607.3; found 607.5.

Step 3. 4-((2S,5R)-4-((S)-(4-(Difluoromethyl)phenyl)(4-methoxyphenyl)methyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-(4-(difluoromethyl)phenyl)(4-methoxyphenyl)methyl)-2,5-dimethylpiperazin-1-yl)-2-methyl-1-(((S)-tetrahydrofuran-2-yl)methyl)-1H-[1,2,4]triazolo[3,4-b]purine To a mixture of 6-((2S,5R)-4-((4-(difluoromethyl)phenyl)(4-methoxyphenyl)methyl)-2,5-dimethylpiperazin-1-yl)-2-hydrazineyl-8-methyl-9-(((S)-tetrahydrofuran-2-yl)methyl)-9H-purine (Step 2) in AcOH (985 μL, 17.2 mmol) was added triethyl orthoformate (0.287 mL, 1.72 mmol) and the reaction mixture was stirred at 85° C. for 1 h. After cooling to rt, the reaction mixture was diluted with acetonitrile, water, and several drops of TFA, and the mixture was filtered and purified by prep-HPLC (Sunfire C18 column, eluting with a gradient of acetonitrile/water containing 0.1% TFA, at flow rate of 60 mL/min) to afford the desired product as a mixture of diastereomers as its TFA salt. LC-MS calculated for $C_{33}H_{39}F_2N_8O_2(M+H)^+$: m/z=617.3; found 617.4.

Example 93. 4-((2S,5R)-4-(Bis(4-chlorophenyl)methyl)-2,5-dimethylpiperazin-1-yl)-1-(((S)-tetrahydrofuran-2-yl)methyl)-1H-[1,2,4]triazolo[3,4-b]purine

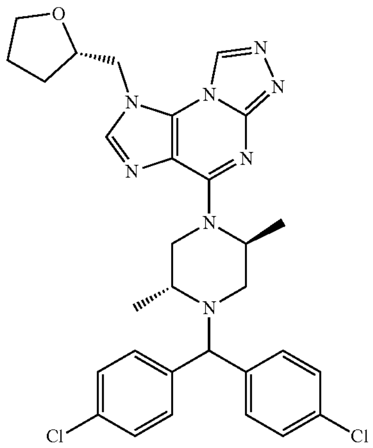 [SMILES: C[C@@H]1CN(c2nc3nncn3c3c2ncn3C[C@@H]2CCCO2)[C@@H](C)CN1C(c1ccc(Cl)cc1)c1ccc(Cl)cc1]

This compound was prepared according to the procedures described in Example 19, with 6-((2S,5R)-4-(bis(4-chlorophenyl)methyl)-2,5-dimethylpiperazin-1-yl)-2-chloro-9H-purine (Intermediate 113) replacing 6-((2S,5R)-4-(bis(4-fluorophenyl)methyl)-2,5-dimethylpiperazin-1-yl)-2-chloro-8-methyl-9H-purine (Intermediate 23) in Step 1. LC-MS calculated for $C_{30}H_{33}Cl_2N_8O$ $(M+H)^+$: m/z=591.2; found 591.2.

Examples 94-99

Examples 94-99 of Table 6 were prepared in accordance with the synthetic protocols set forth in Examples 67 and 68 using the indicated carboxylic acid starting material as described in Intermediate 56.

TABLE 6

| Ex. | Name | Structure | Starting Material | Analytical data |
|---|---|---|---|---|
| 94 and 95 | 4-((2S,5R)-4-((S)-1-(3-Fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(3-fluorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 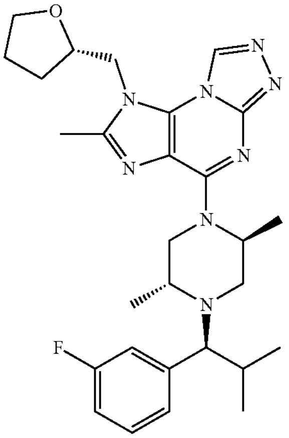 [SMILES: Cc1nc2c(N3C[C@@H](C)N([C@H](c4cccc(F)c4)C(C)C)C[C@@H]3C)nc3nncn3c2n1C[C@@H]1CCCO1] and | 3-Fluorobenzoic acid | Example 94: Retention time on LC-MS $t_r$ = 1.210 min, LC-MS $[M + H]^+$: found 521.3. Example 95: Retention time on LC-MS $t_r$ = 1.271 min, LC-MS $[M + H]^+$: found 521.3. |

TABLE 6-continued

| Ex. | Name | Structure | Starting Material | Analytical data |
|---|---|---|---|---|
| | | 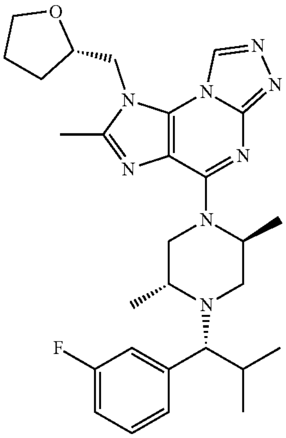 [SMILES: Cc1nc2c(N3C[C@@H](C)N([C@@H](c4cccc(F)c4)C(C)C)C[C@@H]3C)nc3nncn3c2n1C[C@@H]1CCCO1] | | |
| 96 and 97 | 4-((2S,5R)-4-((S)-1-(3-Chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(3-chlorophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 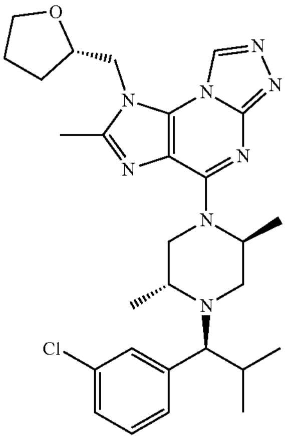 [SMILES: Cc1nc2c(N3C[C@@H](C)N([C@H](c4cccc(Cl)c4)C(C)C)C[C@@H]3C)nc3nncn3c2n1C[C@@H]1CCCO1] and 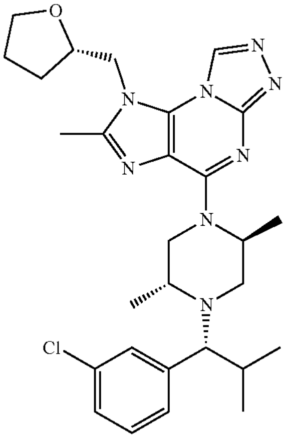 [SMILES: Cc1nc2c(N3C[C@@H](C)N([C@@H](c4cccc(Cl)c4)C(C)C)C[C@@H]3C)nc3nncn3c2n1C[C@@H]1CCCO1] | 3-Chlorobenzoic acid | Example 96: Retention time on LC-MS $t_r$ = 2.028 min, LC-MS [M + H]$^+$: found 537.3. Example 97: Retention time on LC-MS $t_r$ = 2.111 min, LC-MS [M + H]$^+$: found 537.4. |

TABLE 6-continued

| Ex. | Name | Structure | Starting Material | Analytical data |
|---|---|---|---|---|
| 98 and 99 | 4-((2S,5R)-4-((S)-1-(3-Methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(3-methoxyphenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine | 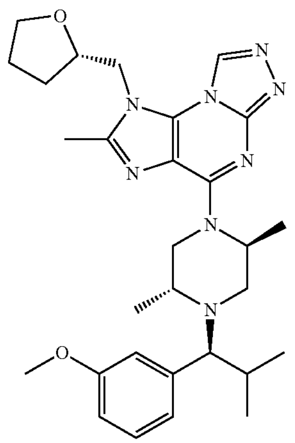 [SMILES: COc1cccc([C@H](C(C)C)N2C[C@H](C)N(c3nc4nncn4c4c3nc(C)n4C[C@@H]3CCCO3)C[C@H]2C)c1] and 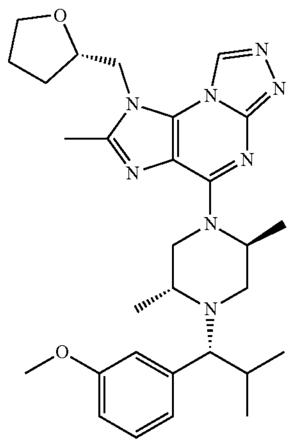 [SMILES: COc1cccc([C@@H](C(C)C)N2C[C@H](C)N(c3nc4nncn4c4c3nc(C)n4C[C@@H]3CCCO3)C[C@H]2C)c1] | 3-Methoxybenzoic acid | Example 98: Retention time on LC-MS $t_r$ = 1.068 min, LC-MS $[M + H]^+$: found 533.4. Example 99: Retention time on LC-MS $t_r$ = 1.109 min, LC-MS $[M + H]^+$: found 533.3. |

Example 100. 2-(4-((2S,5R)-4-(Bis(4-(difluoromethyl)phenyl)methyl)-2,5-dimethylpiperazin-1-yl)-1H-[1,2,4]triazolo[3,4-b]purin-1-yl)-N,N-dimethylethan-1-amine

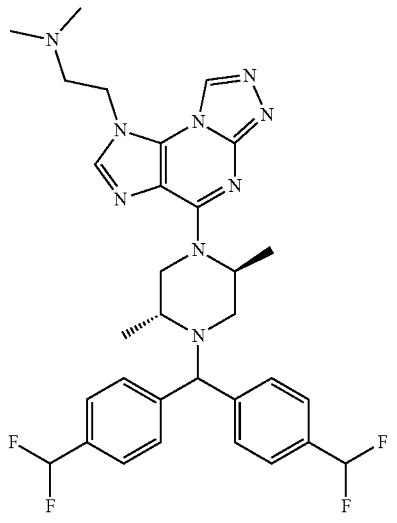 [SMILES: C[C@@H]1CN(c2nc3nncn3c3c2ncn3CCN(C)C)[C@@H](C)CN1C(c1ccc(C(F)F)cc1)c1ccc(C(F)F)cc1]

This compound was prepared according to the procedures described in Example 64, with (2R,5S)-1-(bis(4-(difluoromethyl)phenyl)methyl)-2,5-dimethylpiperazine hydrochloride (Intermediate 72) replacing (2R,5S)-1-((4-chlorophenyl)(3,3-difluorocyclobutyl)methyl)-2,5-dimethylpiperazine hydrochloride in Step 1. LC-MS calculated for $C_{31}H_{36}F_4N_9$ $(M+H)^+$: m/z=610.3; found 610.3.

Examples 101 and 102. 2-(4-((2S,5R)-2,5-Dimethyl-4-((S)-(4-(trifluoromethyl)phenyl)(5-(trifluoromethyl)pyridin-2-yl)methyl)piperazin-1-yl)-1H-[1,2,4]triazolo[3,4-b]purin-1-yl)-N,N-dimethylethan-1-amine and 2-(4-((2S,5R)-2,5-dimethyl-4-((R)-(4-(trifluoromethyl)phenyl)(5-(trifluoromethyl)pyridin-2-yl)methyl)piperazin-1-yl)-1H-[1,2,4]triazolo[3,4-b]purin-1-yl)-N,N-dimethylethan-1-amine

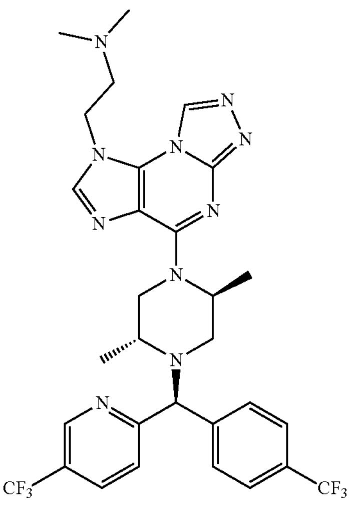

and

-continued

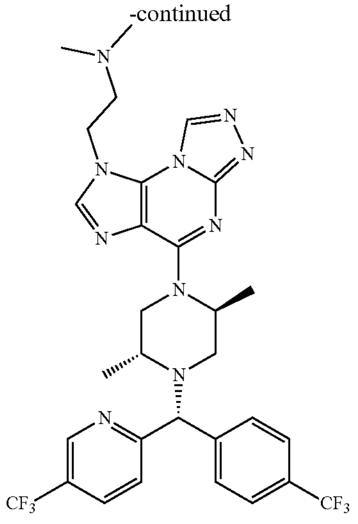

To a mixture of tert-butyl (2-(4-((2S,5R)-2,5-dimethyl-4-((4-(trifluoromethyl)phenyl)(5-(trifluoromethyl)pyridin-2-yl)methyl)piperazin-1-yl)-1H-[1,2,4]triazolo[3,4-b]purin-1-yl)ethyl)(methyl)carbamate (Intermediate 77, 0.262 g, 0.357 mmol) in $CH_2Cl_2$ (2.8 mL) was added TFA (0.70 mL) and the reaction mixture was stirred at rt for 15 min. The mixture was concentrated in vacuo and the crude residue was taken up in THF (1.8 mL). Formaldehyde (37 wt % in water, 0.270 mL, 3.62 mmol) was added and the mixture was stirred at rt for 15 min before sodium triacetoxyborohydride (0.397 g, 1.87 mmol) was added. After 10 min, the mixture was diluted with $CH_2Cl_2$ and quenched with 1 M NaOH. The layers were separated and the aqueous layer was extracted with $CH_2Cl_2$. The combined organic layers were dried over $MgSO_4$ and concentrated in vacuo. The diastereomeric mixture was purified by prep-HPLC (Sunfire C18 column, eluting with a gradient of acetonitrile/water containing 0.1% TFA, at flow rate of 60 mL/min) to afford each diastereomer as its TFA salt.

Example 101: Retention time on LC-MS $t_r$=1.209 min, LC-MS calculated for $C_{30}H_{33}F_6N_{10}$ $(M+H)^+$: m/z=647.3; found 647.3. $^1$H NMR (500 MHz, DMSO-$d_6$) (mixture of rotamers) δ 9.63-9.59 (m, 1H), 8.88 (s, 1H), 8.46 (s, 0.45H), 8.43 (s, 0.55H), 8.31-8.24 (m, 1H), 8.10-8.02 (m, 1H), 7.90-7.83 (m, 2H), 7.77-7.71 (m, 2H), 6.21-6.18 (m, 0.45H), 5.95-5.89 (m, 0.55H), 5.15-5.11 (m, 0.55H), 5.04-4.94 (m, 3H), 4.72-4.66 (m, 0.45H), 3.95 (d, J=13.3 Hz, 0.55H), 3.74-3.64 (m, 2.45H), 3.28-3.15 (m, 1H), 2.95-2.85 (m, 7H), 2.49-2.40 (m, 1H), 1.58 (d, J=6.6 Hz, 1.35H), 1.54-1.50 (m, 1.65H), 0.97-0.92 (m, 3H).

Example 102: Retention time on LC-MS $t_r$=1.225 min, LC-MS calculated for $C_{30}H_{33}F_6N_{10}$ $(M+H)^+$: m/z=647.3; found 647.3. $^1$H NMR (500 MHz, DMSO-$d_6$) (mixture of rotamers) δ 9.61 (s, 1H), 8.94 (s, 1H), 8.46 (s, 0.4H), 8.43 (s, 0.6H), 8.27-8.20 (m, 1H), 8.06-7.98 (m, 1H), 7.88-7.82 (m, 2H), 7.76-7.71 (m, 2H), 6.20-6.16 (m, 0.4H), 5.94-5.88 (m, 0.6H), 5.14-5.10 (m, 0.6H), 5.07 (s, 1H), 5.02-4.94 (m, 2H), 4.71-4.64 (m, 0.4H), 3.95-3.89 (m, 0.6H), 3.72-3.64 (m, 2.4H), 3.23-3.07 (m, 1H), 2.97-2.80 (m, 7H), 2.50-2.43 (m, 1H), 1.55 (d, J=6.6 Hz, 1.2H), 1.49 (d, J=6.7 Hz, 1.8H), 1.00-0.94 (m, 3H).

Examples 103 and 104. 4-((2S,5R)-4-((S)-(5-Fluoro-6-(trifluoromethyl)pyridin-2-yl)(4-fluorophenyl)methyl)-2,5-dimethylpiperazin-1-yl)-1-(((S)-tetrahydrofuran-2-yl)methyl)-1H-[1,2,4]triazolo[3,4-b]purine and 4-((2S,5R)-4-((R)-(5-fluoro-6-(trifluoromethyl)pyridin-2-yl)(4-fluorophenyl) methyl)-2,5-dimethylpiperazin-1-yl)-1-(((S)-tetrahydrofuran-2-yl)methyl)-1H-[1,2,4]triazolo[3,4-b]purine

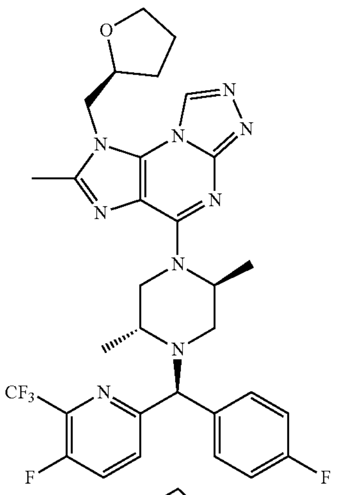

and

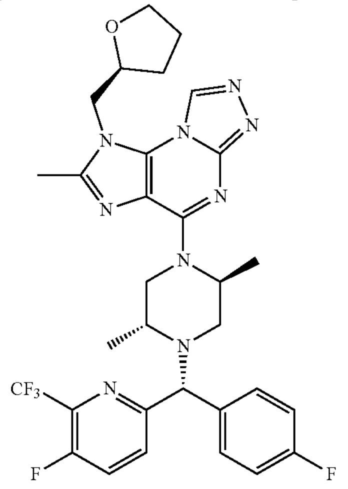

A mixture of 6-((2S,5R)-4-((5-fluoro-6-(trifluoromethyl) pyridin-2-yl)(4-fluorophenyl)methyl)-2,5-dimethylpiperazin-1-yl)-2-hydrazineyl-8-methyl-9-(((S)-tetrahydrofuran-2-yl)methyl)-9H-purine (Intermediate 82, 0.355 g, 0.562 mmol), acetic acid (1.61 mL, 28.1 mmol) and triethyl orthoformate (0.468 mL, 2.81 mmol) was stirred at 95° C. for 1 h. The mixture was cooled to rt, diluted with $CH_2Cl_2$ and slowly transferred to a separatory funnel containing saturated aqueous $NaHCO_3$. Following transfer, the aqueous layer was further basified with 1 M NaOH to pH=10. The layers were separated, and the aqueous layer extracted with $CH_2Cl_2$. The combined organic layers were dried over $MgSO_4$ and concentrated in vacuo. The crude residue was purified by flash column chromatography (24 g $SiO_2$, $MeOH/CH_2Cl_2$) to give the title compound (0.177 g, 49% yield) as a mixture of diastereomers in the form of a light yellow solid. Diastereomer separation was achieved through purification using prep-HPLC (Sunfire C18 column, eluting with a gradient of acetonitrile/water containing 0.1% TFA, at flow rate of 60 mL/min) to afford each diastereomer as its TFA salt.

Example 103: Retention time on LC-MS $t_r$=1.652 min, LC-MS calculated for $C_{31}H_{33}F_5N_9O$ $(M+H)^+$: m/z=642.3; found 642.2. H NMR (500 MHz, DMSO-$d_6$) (mixture of rotamers) δ 9.52-9.48 (m, 1H), 8.27-8.04 (m, 2H), 7.72-7.63 (m, 2H), 7.25-7.17 (m, 2H), 6.25-6.21 (m, 0.4H), 5.98-5.91 (m, 0.6H), 5.09-5.04 (m, 0.6H), 4.86 (s, 1H), 4.77-4.68 (m, 1H), 4.67-4.61 (m, 0.4H), 4.59-4.50 (m, 1H), 4.14-4.06 (m, 1H), 3.91-3.85 (m, 0.6H), 3.73-3.67 (m, 1H), 3.67-3.61 (m, 0.4H), 3.60-3.52 (m, 1H), 3.24-3.10 (m, 1H), 2.93-2.82 (m, 1H), 2.60-2.55 (m, 3H), 2.38-2.28 (m, 1H), 2.18-2.08 (m, 1H), 1.98-1.89 (m, 1H), 1.87-1.78 (m, 1H), 1.77-1.66 (m, 1H), 1.53 (d, J=6.6 Hz, 1.2H), 1.47 (d, J=6.7 Hz, 1.8H), 0.94-0.89 (m, 3H).

Example 104: Retention time on LC-MS $t_r$=1.784 min, LC-MS calculated for $C_{31}H_{33}F_5N_9O$ $(M+H)^+$: m/z=642.3; found 642.2. H NMR (500 MHz, DMSO-$d_6$) (mixture of rotamers) δ 9.50 (s, 1H), 8.24-8.14 (m, 1H), 8.14-8.03 (m, 1H), 7.67-7.58 (m, 2H), 7.24-7.16 (m, 2H), 6.25-6.21 (m, 0.4H), 5.97-5.91 (m, 0.6H), 5.09-5.06 (m, 0.6H), 4.92-4.87 (m, 1H), 4.76-4.68 (m, 1H), 4.67-4.60 (m, 0.4H), 4.59-4.50 (m, 1H), 4.14-4.06 (m, 1H), 3.89-3.82 (m, 0.6H), 3.73-3.67 (m, 1H), 3.67-3.61 (m, 0.4H), 3.60-3.52 (m, 1H), 3.13-3.00 (m, 1H), 2.87-2.73 (m, 1H), 2.64-2.55 (m, 3H), 2.49-2.35 (m, 1H), 2.18-2.08 (m, 1H), 1.98-1.89 (m, 1H), 1.88-1.78 (m, 1H), 1.76-1.67 (m, 1H), 1.52 (d, J=6.6 Hz, 1.2H), 1.46 (d, J=6.7 Hz, 1.8H), 0.98-0.92 (m, 3H).

Example 105. 4-((2S,5R)-4-(Bis(4-chlorophenyl) methyl)-2,5-dimethylpiperazin-1-yl)-2-methyl-1-(((S)-tetrahydrofuran-2-yl)methyl)-1H-[1,2,4]triazolo[3,4-b]purine

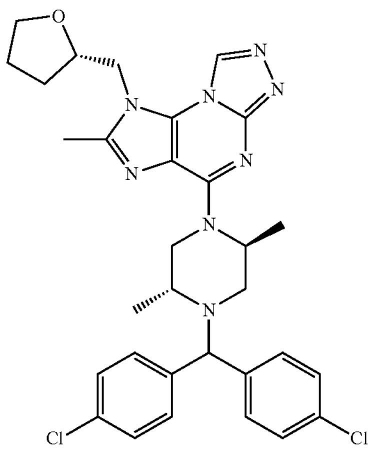

Step 1: 6-((2S,5R)-4-(Bis(4-chlorophenyl)methyl)-2,5-dimethylpiperazin-1-yl)-2-chloro-8-methyl-9-(((S)-tetrahydrofuran-2-yl)methyl)-9H-purine

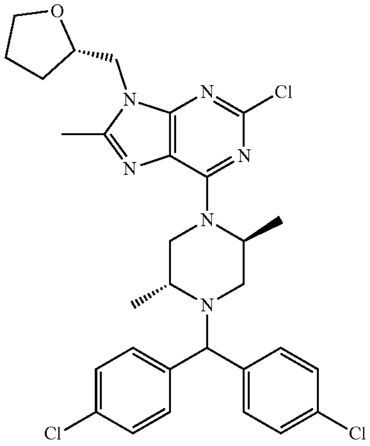 [SMILES: Cc1nc2c(N3C[C@@H](C)N(C(c4ccc(Cl)cc4)c4ccc(Cl)cc4)C[C@@H]3C)nc(Cl)nc2n1C[C@@H]1CCCO1]

A mixture of (2R,5S)-1-(bis(4-chlorophenyl)methyl)-2,5-dimethylpiperazine hydrochloride (Intermediate 83, 0.463 g, 1.20 mmol), (S)-2,6-dichloro-8-methyl-9-((tetrahydrofuran-2-yl)methyl)-9H-purine (Intermediate 41, 0.345 g, 1.20 mmol), and N,N-diisopropylethylamine (0.629 mL, 3.60 mmol) in n-BuOH (3.0 mL) was heated to 85° C. and stirred overnight. After cooling to rt, the mixture was diluted with $CH_2Cl_2$, water, and 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, EtOAc/hexanes) to give the title compound (0.552 g, 77% yield) as an orange solid. LC-MS calculated for $C_{30}H_{34}Cl_3N_6O$ $(M+H)^+$: m/z=599.2; found 599.2.

Step 2: 6-((2S,5R)-4-(Bis(4-chlorophenyl)methyl)-2,5-dimethylpiperazin-1-yl)-2-hydrazineyl-8-methyl-9-(((S)-tetrahydrofuran-2-yl)methyl)-9H-purine

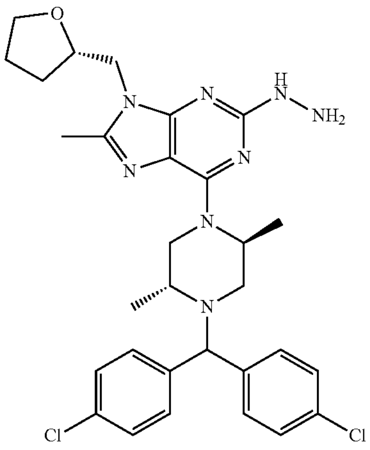 [SMILES: Cc1nc2c(N3C[C@@H](C)N(C(c4ccc(Cl)cc4)c4ccc(Cl)cc4)C[C@@H]3C)nc(NN)nc2n1C[C@@H]1CCCO1]

A mixture of 6-((2S,5R)-4-(bis(4-chlorophenyl)methyl)-2,5-dimethylpiperazin-1-yl)-2-chloro-8-methyl-9-(((S)-tetrahydrofuran-2-yl)methyl)-9H-purine (0.552 g, 0.920 mmol) and hydrazine hydrate (1.15 mL, 18.5 mmol) in n-BuOH (3.45 mL) was heated to 120° C. and stirred for 20 h. After cooling to rt, the mixture was diluted with $CH_2Cl_2$, water, and 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, $MeOH/CH_2Cl_2$) to give the title compound (0.484 g, 88% yield) as a white solid. LC-MS calculated for $C_{30}H_{37}Cl_2N_8O$ $(M+H)^+$: m/z=595.3; found 595.2.

Step 3: 4-((2S,5R)-4-(Bis(4-chlorophenyl)methyl)-2,5-dimethylpiperazin-1-yl)-2-methyl-(((S)-tetrahydrofuran-2-yl)methyl)-1H-[1,2,4]triazolo[3,4-b]purine A mixture of 6-((2S,5R)-4-(bis(4-chlorophenyl)methyl)-2,5-dimethylpiperazin-1-yl)-2-hydrazineyl-8-methyl-9-(((S)-tetrahydrofuran-2-yl)methyl)-9H-purine (0.484 g, 0.813 mmol), acetic acid (2.33 mL, 40.7 mmol) and triethyl orthoformate (0.67 mL, 4.07 mmol) was stirred at 95° C. for 1 h. The mixture was cooled to rt, diluted with $CH_2Cl_2$ and slowly transferred to a separatory funnel containing saturated aqueous $NaHCO_3$. Following transfer, the aqueous layer was further basified with 1 M NaOH to pH=10. The layers were separated, and the aqueous layer extracted with $CH_2Cl_2$. The combined organic layers were dried over $MgSO_4$ and concentrated in vacuo. The crude residue was purified by flash column chromatography (24 g $SiO_2$, $MeOH/CH_2Cl_2$) to give the title compound (0.288 g, 58% yield) as a light orange solid. The material was further purified by prep-HPLC (Sunfire C18 column, eluting with a gradient of acetonitrile/water containing 0.1% TFA, at flow rate of 60 mL/min) to afford the title compound as its TFA salt. LC-MS calculated for $C_{31}H_{35}Cl_2N_8O$ $(M+H)^+$: m/z=605.2; found 605.2. $^1H$ NMR (500 MHz, DMSO-$d_6$) (mixture of rotamers) δ 9.52-9.48 (m, 1H), 7.64-7.55 (m, 4H), 7.43-7.37 (m, 4H), 6.25-6.18 (m, 0.4H), 5.96-5.91 (m, 0.6H), 5.11-5.04 (m, 0.6H), 4.76-4.67 (m, 2H), 4.66-4.61 (m, 0.4H), 4.59-4.51 (m, 1H), 4.14-4.06 (m, 1H), 3.89-3.83 (m, 0.6H), 3.73-3.67 (m, 1H), 3.67-3.61 (m, 0.4H), 3.59-3.52 (m, 1H), 3.24-3.19 (m, 0.4H), 3.18-3.14 (m, 0.6H), 2.83-2.77 (m, 0.4H), 2.76-2.69 (m, 0.6H), 2.59 (s, 1.2H), 2.57 (s, 1.8H), 2.50-2.46 (m, 0.6H), 2.45-2.41 (m, 0.4H), 2.17-2.08 (m, 1H), 1.99-1.89 (m, 1H), 1.88-1.78 (m, 1H), 1.77-1.67 (m, 1H), 1.53 (d, J=6.6 Hz, 1.2H), 1.48 (d, J=6.8 Hz, 1.8H), 0.93-0.88 (m, 3H).

Example 106. 4-((2S,5R)-4-(Bis(4-chlorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine

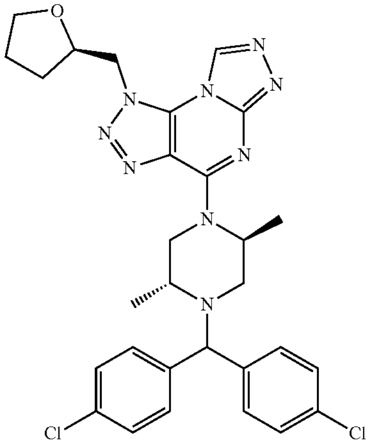

Step 1: 6-((2S,5R)-4-(Bis(4-chlorophenyl)methyl)-2,5-dimethylpiperazin-1-yl)-2-chloro-N4-(((R)-tetrahydrofuran-2-yl)methyl)pyrimidine-4,5-diamine

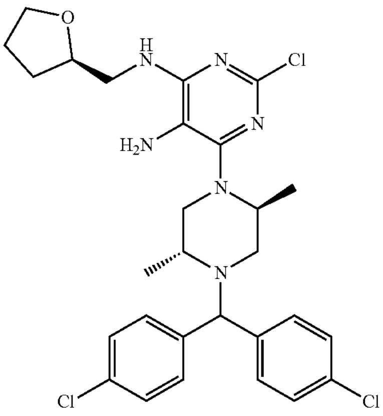 [SMILES: C[C@@H]1CN(c2nc(Cl)nc(NC[C@H]3CCCO3)c2N)[C@@H](C)CN1C(c1ccc(Cl)cc1)c1ccc(Cl)cc1]

A mixture of 6-((2S,5R)-4-(bis(4-chlorophenyl)methyl)-2,5-dimethylpiperazin-1-yl)-2-chloro-5-nitro-N—(((R)-tetrahydrofuran-2-yl)methyl)pyrimidin-4-amine (Intermediate 84, 0.461 g, 0.760 mmol) in DMF (2.9 mL) was stirred in a rt water bath. 4,4'-Dipyridyl (12.0 mg, 76.0 μmol) was added, followed by tetrahydroxydiboron (0.215 g, 2.40 mmol). The mixture was stirred at rt for 5 min, at which point it was diluted with EtOAc and water. The layers were separated and the aqueous layer was extracted with EtOAc. The combined organic extracts were washed with brine, dried over $MgSO_4$, and concentrated in vacuo. The crude material obtained was used directly without further purification. LC-MS calculated for $C_{28}H_{34}Cl_3N_6O$ $(M+H)^+$: m/z=575.2; found 575.3.

Step 2: 7-((2S,5R)-4-(Bis(4-chlorophenyl)methyl)-2,5-dimethylpiperazin-1-yl)-5-chloro-3-(((R)-tetrahydrofuran-2-yl)methyl)-3H-[1,2,3]triazolo[4,5-d]pyrimidine

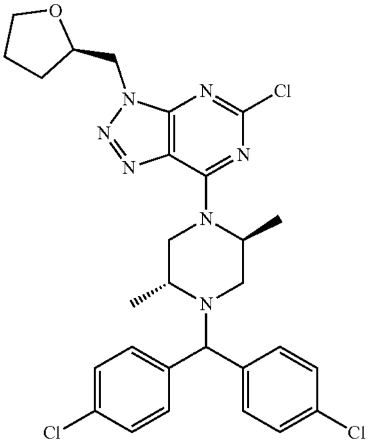 [SMILES: C[C@@H]1CN(c2nc(Cl)nc3c2nnn3C[C@H]2CCCO2)[C@@H](C)CN1C(c1ccc(Cl)cc1)c1ccc(Cl)cc1]

To a mixture of 6-((2S,5R)-4-(bis(4-chlorophenyl)methyl)-2,5-dimethylpiperazin-1-yl)-2-chloro-$N^4$-(((R)-tetrahydrofuran-2-yl)methyl)pyrimidine-4,5-diamine (Step 1) in THF (1.9 mL), water (1.9 mL), and acetic acid (0.206 mL, 3.60 mmol) was added sodium nitrite (0.248 g, 3.60 mmol) and the reaction mixture was stirred at rt for 1 h. The reaction was quenched with saturated aqueous $NaHCO_3$ and diluted with $CH_2Cl_2$. The layers were separated and the aqueous layer was extracted with $CH_2Cl_2$. The combined organic layers were dried over $MgSO_4$ and concentrated in vacuo. The crude material obtained was used directly without further purification. LC-MS calculated for $C_{28}H_{31}Cl_3N_7O$ $(M+H)^+$: m/z=586.2; found 586.2.

Step 3: 7-((2S,5R)-4-(Bis(4-chlorophenyl)methyl)-2,5-dimethylpiperazin-1-yl)-5-hydrazineyl-3-(((R)-tetrahydrofuran-2-yl)methyl)-3H-[1,2,3]triazolo[4,5-d]pyrimidine

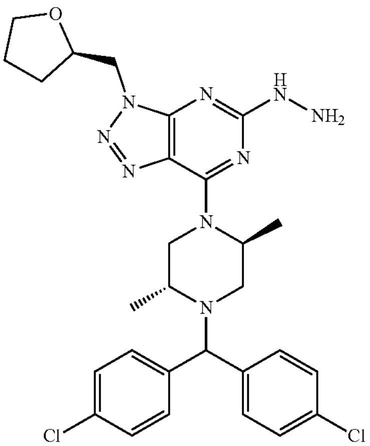 [SMILES: C[C@@H]1CN(c2nc(NN)nc3c2nnn3C[C@H]2CCCO2)[C@@H](C)CN1C(c1ccc(Cl)cc1)c1ccc(Cl)cc1]

A mixture of 7-((2S,5R)-4-(bis(4-chlorophenyl)methyl)-2,5-dimethylpiperazin-1-yl)-5-chloro-3-(((R)-tetrahydrofuran-2-yl)methyl)-3H-[1,2,3]triazolo[4,5-d]pyrimidine (Step 2), hydrazine hydrate (0.942 mL, 15.1 mmol) and ethanol (2.66 mL) was heated to 80° C. and stirred for 1 h. The reaction was cooled to rt, quenched with sat. aq.

$NaHCO_3$, and diluted with $CH_2Cl_2$. The layers were separated and the aqueous layer was extracted with $CH_2Cl_2$. The combined organic layers were dried over $MgSO_4$ and concentrated in vacuo. The crude residue was purified by flash column chromatography (24 g $SiO_2$, $MeOH/CH_2Cl_2$) to give the title compound (0.339 g, 77% yield over three steps) as a white solid. LC-MS calculated for $C_{28}H_{34}Cl_2N_9O$ $(M+H)^+$: m/z=582.2; found 582.3.

Step 4: 4-((2S,5R)-4-(Bis(4-chlorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine A mixture of 7-((2S,5R)-4-(bis(4-chlorophenyl)methyl)-2,5-dimethylpiperazin-1-yl)-5-hydrazineyl-3-(((R)-tetrahydrofuran-2-yl)methyl)-3H-[1,2,3]triazolo[4,5-d]pyrimidine (0.339 g, 0.582 mmol), acetic acid (1.72 mL, 30.0 mmol) and triethyl orthoformate (0.500 mL, 3.00 mmol) was heated to 85° C. and stirred overnight. The mixture was cooled to rt, diluted with $CH_2Cl_2$, and quenched with 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, $MeOH/CH_2Cl_2$) to give the title compound (0.178 g, 52% yield) as a light yellow solid. The material was further purified by prep-HPLC (Sunfire C18 column, eluting with a gradient of acetonitrile/water containing 0.10% TFA, at flow rate of 60 mL/min) to afford the title compound as its TFA salt. LC-MS calculated for $C_{29}H_{32}Cl_2N_9O$ $(M+H)^+$: m/z=592.2; found 592.3. H NMR (500 MHz, DMSO-$d_6$) (mixture of rotamers) δ 9.58 (s, 1H), 7.65-7.57 (m, 4H), 7.43-7.38 (m, 4H), 5.93-5.90 (m, 0.4H), 5.64-5.59 (m, 0.6H), 5.24-5.18 (m, 1H), 5.16-5.10 (m, 0.6H), 5.04-4.96 (m, 1H), 4.71 (s, 1H), 4.69-4.64 (m, 0.4H), 4.32-4.25 (m, 1H), 4.08-4.02 (m, 0.6H), 3.70-3.63 (m, 0.4H), 3.62-3.49 (m, 2H), 3.29-3.16 (m, 1H), 2.89-2.84 (m, 0.4H), 2.79-2.74 (m, 0.6H), 2.55-2.51 (m, 1H), 2.15-2.07 (m, 1H), 1.82-1.63 (m, 3H), 1.58 (d, J=6.6 Hz, 1.2H), 1.52 (d, J=6.7 Hz, 1.8H), 0.96-0.91 (m, 3H).

Example 107. 2-(4-((2S,5R)-4-(Bis(4-chlorophenyl)methyl)-2,5-dimethylpiperazin-1-yl)-1H-[1,2,4]triazolo[3,4-b]purin-1-yl)-N,N-dimethylethan-1-amine

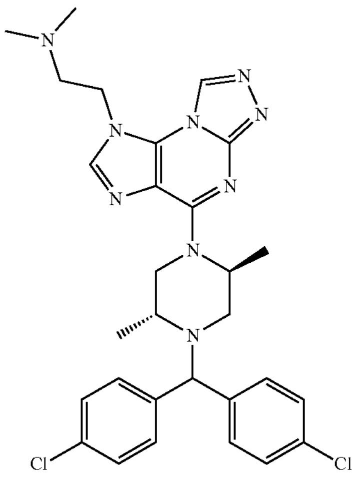 [SMILES: C[C@@H]1CN(c2nc3nncn3c3c2ncn3CCN(C)C)[C@@H](C)CN1C(c1ccc(Cl)cc1)c1ccc(Cl)cc1]

Step 1: tert-Butyl (2-(6-((2S,5R)-4-(bis(4-chlorophenyl)methyl)-2,5-dimethylpiperazin-1-yl)-2-chloro-9H-purin-9-yl)ethyl)(methyl)carbamate

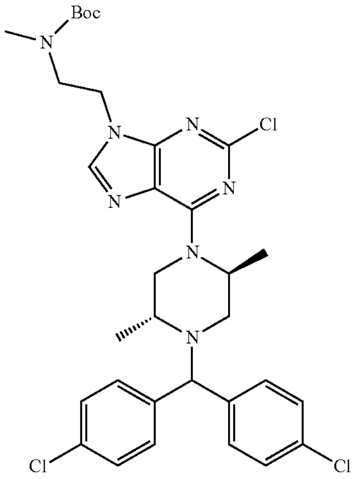 [SMILES: C[C@@H]1CN(c2nc(Cl)nc3c2ncn3CCN(C)C(=O)OC(C)(C)C)[C@@H](C)CN1C(c1ccc(Cl)cc1)c1ccc(Cl)cc1]

A mixture of (2R,5S)-1-(bis(4-chlorophenyl)methyl)-2,5-dimethylpiperazine hydrochloride (Intermediate 83, 0.463 g, 1.20 mmol), tert-butyl (2-(2,6-dichloro-9H-purin-9-yl)ethyl)(methyl)carbamate (Intermediate 51, 0.415 g, 1.20 mmol), and N,N-diisopropylethylamine (0.629 mL, 3.60 mmol) in n-BuOH (3.00 mL) was heated to 85° C. and stirred overnight. After cooling to rt, the reaction mixture was diluted with $CH_2Cl_2$, water, and 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, EtOAc/hexanes) to give the title compound (0.598 g, 76% yield) as a mixture of diastereomers in the form of an orange solid. LC-MS calculated for $C_{32}H_{39}Cl_3N_7O_2$ $(M+H)^+$: m/z=658.2; found 658.2.

Step 2: tert-Butyl (2-(6-((2S,5R)-4-(bis(4-chlorophenyl)methyl)-2,5-dimethylpiperazin-1-yl)-2-hydrazineyl-9H-purin-9-yl)ethyl)(methyl)carbamate

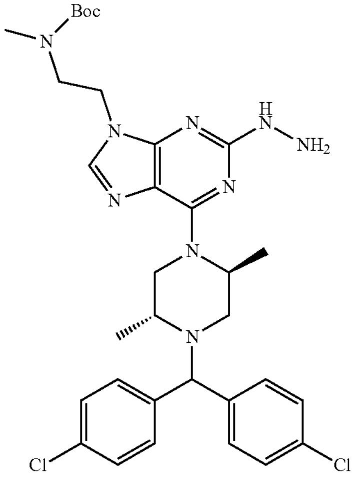 [SMILES: C[C@@H]1CN(c2nc(NN)nc3c2ncn3CCN(C)C(=O)OC(C)(C)C)[C@@H](C)CN1C(c1ccc(Cl)cc1)c1ccc(Cl)cc1]

A mixture of 6 tert-butyl (2-(6-((2S,5R)-4-(bis(4-chlorophenyl)methyl)-2,5-dimethylpiperazin-1-yl)-2-chloro-9H-purin-9-yl)ethyl)(methyl)carbamate (0.598 g, 0.907 mmol) and hydrazine hydrate (1.14 mL, 18.2 mmol) in n-BuOH (3.4 mL) was heated to 120° C. and stirred for 20 h. The mixture was cooled to rt, diluted with $CH_2Cl_2$, and quenched with water and 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, MeOH/$CH_2Cl_2$) to give the title compound (0.446 g, 75% yield) as a white solid. LC-MS calculated for $C_{32}H_{42}Cl_2N_9O_2$ $(M+H)^+$: m/z=654.3; found 654.4.

Step 3: tert-Butyl (2-(4-((2S,5R)-4-(bis(4-chlorophenyl)methyl)-2,5-dimethylpiperazin-1-yl)-1H-[1,2,4]triazolo[3,4-b]purin-1-yl)ethyl)(methyl)carbamate

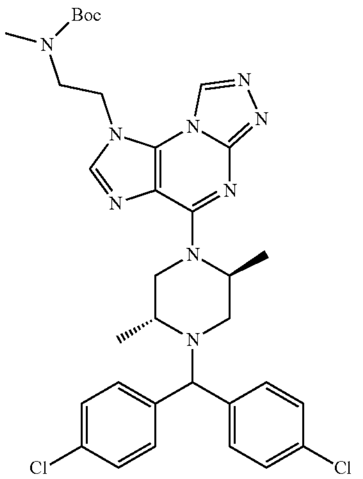 [SMILES: C[C@@H]1CN(c2nc3nncn3c3c2ncn3CCN(C)C(=O)OC(C)(C)C)[C@@H](C)CN1C(c1ccc(Cl)cc1)c1ccc(Cl)cc1]

A mixture of tert-butyl (2-(6-((2S,5R)-4-(bis(4-chlorophenyl)methyl)-2,5-dimethylpiperazin-1-yl)-2-hydrazineyl-9H-purin-9-yl)ethyl)(methyl)carbamate (0.446 g, 0.681 mmol), acetic acid (1.95 mL, 34.1 mmol) and triethyl orthoformate (0.567 mL, 3.41 mmol) was stirred at 95° C. for 1 h. The reaction was cooled to rt, diluted with $CH_2Cl_2$, and quenched with 1 M NaOH. The layers were separated and the aqueous layer was extracted with $CH_2Cl_2$. The combined organic layers were dried over $MgSO_4$, concentrated in vacuo, and the crude residue was purified by flash column chromatography (24 g $SiO_2$, MeOH/$CH_2Cl_2$) to give the title compound (0.350 g, 77% yield) as a light yellow solid. LC-MS calculated for $C_{33}H_{40}Cl_2N_9O_2$ $(M+H)^+$: m/z=664.3; found 664.4.

Step 4: 2-(4-((2S,5R)-4-(Bis(4-chlorophenyl)methyl)-2,5-dimethylpiperazin-1-yl)-1H-[1,2,4]triazolo[3,4-b]purin-1-yl)-N,N-dimethylethan-1-amine To a mixture of tert-butyl (2-(4-((2S,5R)-4-(bis(4-chlorophenyl)methyl)-2,5-dimethylpiperazin-1-yl)-1H-[1,2,4]triazolo[3,4-b]purin-1-yl)ethyl)(methyl)carbamate (0.350 g, 0.527 mmol) in $CH_2Cl_2$ (4 mL) was added TFA (1 mL) and the reaction mixture was stirred at rt for 15 min. The mixture was concentrated in vacuo, and the crude residue was taken up in THF (2.5 mL). Formaldehyde (37 wt % in water, 0.393 mL, 5.28 mmol) was added and the mixture was stirred at rt for 15 min before sodium triacetoxyborohydride (0.560 g, 2.64 mmol) was added. After 10 min, the mixture was diluted with $CH_2Cl_2$ and quenched with 1 M NaOH. The layers were separated and the aqueous layer was extracted with $CH_2Cl_2$. The combined organic layers were dried over $MgSO_4$ and concentrated in vacuo. The mixture was purified by prep-HPLC (Sunfire C18 column, eluting with a gradient of acetonitrile/water containing 0.1% TFA, at flow rate of 60 mL/min) to afford the title compound as its TFA salt. LC-MS calculated for $C_{29}H_{34}Cl_2N_9(M+H)^+$: m/z=578.2; found 578.3. $^1H$ NMR (500 MHz, DMSO-$d_6$) (mixture of rotamers) δ 9.59 (s, 1H), 8.44 (s, 0.4H), 8.42 (s, 0.6H), 7.64-7.55 (m, 4H), 7.44-7.37 (m, 4H), 6.19-6.13 (m, 0.4H), 5.93-5.84 (m, 0.6H), 5.14-5.07 (m, 0.6H), 5.01-4.94 (m, 2H), 4.72-4.63 (m, 1.4H), 3.94-3.84 (m, 0.6H), 3.69-3.63 (m, 2.4H), 3.27-3.13 (m, 1H), 2.89 (s, 6H), 2.81-2.73 (m, 1H), 2.50-2.43 (m, 1H), 1.54 (d, J=6.6 Hz, 1.2H), 1.48 (d, J=6.7 Hz, 1.8H), 0.94-0.88 (m, 3H).

Example 108. 4-((2S,5R)-4-(Bis(4-bromophenyl)methyl)-2,5-dimethylpiperazin-1-yl)-2-methyl-1-(((S)-tetrahydrofuran-2-yl)methyl)-1H-[1,2,4]triazolo[3,4-b]purine

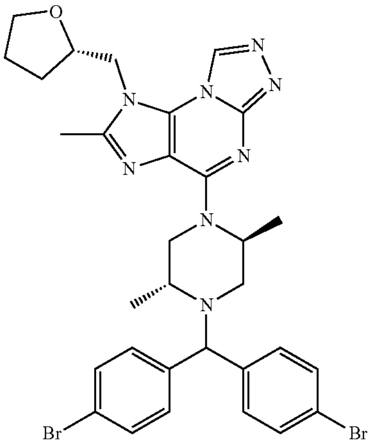 [SMILES: Cc1nc2c(N3C[C@@H](C)N(C(c4ccc(Br)cc4)c4ccc(Br)cc4)C[C@@H]3C)nc3nncn3c2n1C[C@@H]1CCCO1]

This compound was prepared according to the procedures described for Example 105 with (2R,5S)-1-(bis(4-bromophenyl)methyl)-2,5-dimethylpiperazine hydrochloride (Intermediate 86) replacing (2R,5S)-1-(bis(4-chlorophenyl)methyl)-2,5-dimethylpiperazine hydrochloride. LC-MS calculated for $C_{31}H_{35}Br_2N_8O$ $(M+H)^+$: m/z=693.1; found 693.1.

Example 109. 2-(4-((2S,5R)-4-(Bis(4-bromophenyl)methyl)-2,5-dimethylpiperazin-1-yl)-1H-[1,2,4]triazolo[3,4-b]purin-1-yl)-N,N-dimethylethan-1-amine

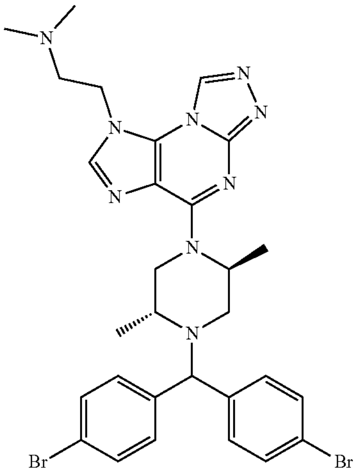 [SMILES: C[C@@H]1CN(c2nc3nncn3c3c2ncn3CCN(C)C)[C@@H](C)CN1C(c1ccc(Br)cc1)c1ccc(Br)cc1]

This compound was prepared according to the procedures described for Example 107, with (2R,5S)-1-(bis(4-bromophenyl)methyl)-2,5-dimethylpiperazine hydrochloride (Intermediate 86) replacing (2R,5S)-1-(bis(4-chlorophenyl)methyl)-2,5-dimethylpiperazine hydrochloride. LC-MS calculated for $C_{29}H_{34}Br_2N_9(M+H)^+$: m/z=666.1; found 666.1.

Example 110. 4-((2S,5R)-4-(Bis(4-bromophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine

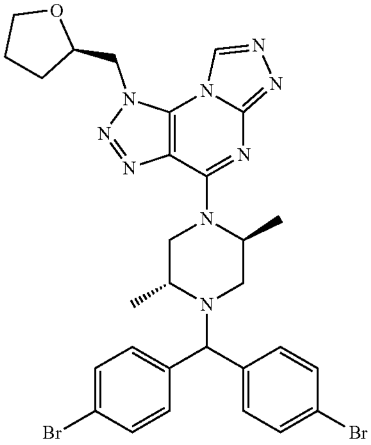

This compound was prepared according to the procedures described for Example 106, with (2R,5S)-1-(bis(4-bromophenyl)methyl)-2,5-dimethylpiperazine hydrochloride (Intermediate 86) replacing (2R,5S)-1-(bis(4-chlorophenyl)methyl)-2,5-dimethylpiperazine hydrochloride. LC-MS calculated for $C_{29}H_{32}Br_2N_9O$ $(M+H)^+$: m/z=680.1; found 680.2.

Example 111: 4-((2S,5R)-4-(Bis(4-bromophenyl)methyl)-2,5-dimethylpiperazin-1-yl)-1-(((S)-tetrahydrofuran-2-yl)methyl)-1H-[1,2,3]triazolo[4,5-e][1,2,4]triazolo[4,3-a]pyrimidine

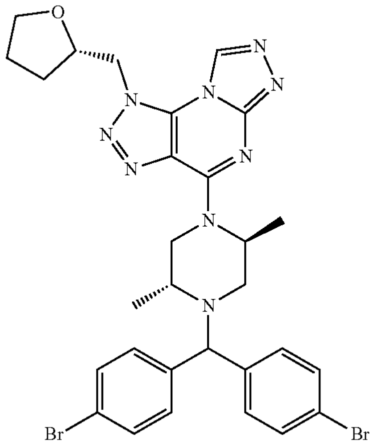 [SMILES: C[C@@H]1CN(c2nc3nncn3c3c2nnn3C[C@@H]2CCCO2)[C@@H](C)CN1C(c1ccc(Br)cc1)c1ccc(Br)cc1]

This compound was prepared according to the procedures described for Example 106, with (2R,5S)-1-(bis(4-bromophenyl)methyl)-2,5-dimethylpiperazine hydrochloride (Intermediate 86) replacing (2R,5S)-1-(bis(4-chlorophenyl)methyl)-2,5-dimethylpiperazine hydrochloride, and (S)-(tetrahydrofuran-2-yl)methanamine replacing of (R)-(tetrahydrofuran-2-yl)methanamine. LC-MS calculated for $C_{29}H_{32}Br_2N_9O$ $(M+H)^+$: m/z=680.1; found 680.1.

Example 112. 2-(4-((2S,5R)-4-(Bis(5-(trifluoromethyl)pyridin-2-yl)methyl)-2,5-dimethylpiperazin-1-yl)-1H-[1,2,4]triazolo[3,4-b]purin-1-yl)-N,N-dimethylethan-1-amine

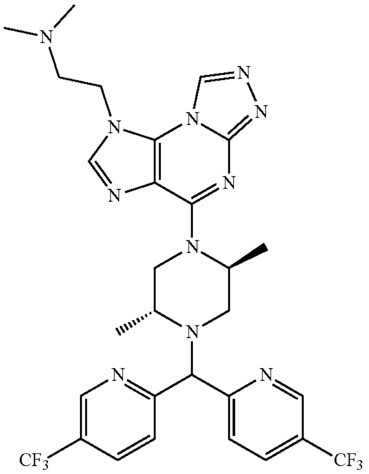 [SMILES: C[C@@H]1CN(c2nc3nncn3c3c2ncn3CCN(C)C)[C@@H](C)CN1C(c1ccc(C(F)(F)F)cn1)c1ccc(C(F)(F)F)cn1]

This compound was prepared according to the procedures described for Examples 101 and 102, with (2R,5S)-1-(bis(5-(trifluoromethyl)pyridin-2-yl)methyl)-2,5-dimethylpiperazine dihydrochloride (Intermediate 88) replacing (2R,5S)-2,5-dimethyl-1-((4-(trifluoromethyl)phenyl)(5-

(trifluoromethyl)pyridin-2-yl)methyl)piperazine hydrochloride. LC-MS calculated for $C_{29}H_{32}F_6N_{11}$ $(M+H)^+$: m/z=648.3; found 648.3.

Example 113. 4-((2S,5R)-4-((3-Chloro-4-fluorophenyl)((trans)-3-(trifluoromethyl)cyclobutyl)methyl)-2,5-dimethylpiperazin-1-yl)-2-methyl-1-(((S)-tetrahydrofuran-2-yl)methyl)-1H-[1,2,4]triazolo[3,4-b]purine

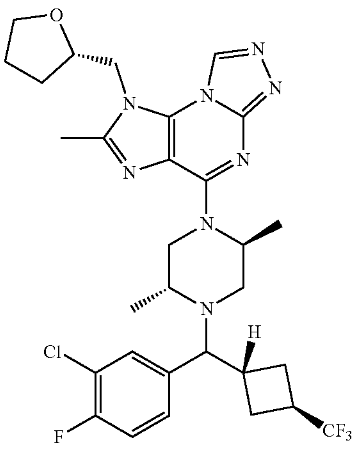 [SMILES: Cc1nc2c(N3C[C@@H](C)N(C(c4ccc(F)c(Cl)c4)[C@H]4C[C@H](C(F)(F)F)C4)C[C@@H]3C)nc3nncn3c2n1C[C@@H]1CCCO1]

This compound was prepared according to the procedures described for Example 44, with (2R,5S)-1-((3-chloro-4-fluorophenyl)((trans)-3-(trifluoromethyl)cyclobutyl)methyl)-2,5-dimethylpiperazine hydrochloride (Intermediate 90) replacing (2R,5S)-1-((3-chloro-4-fluorophenyl)(3,3-difluorocyclobutyl)methyl)-2,5-dimethylpiperazine hydrochloride. LC-MS calculated for $C_{30}H_{36}ClF_4N_8O$ $(M+H)^+$: m/z=635.3; found 635.2.

Example 114: 2-(4-((2S,5R)-4-((3-chloro-4-fluorophenyl)((trans)-3-(trifluoromethyl)cyclobutyl)methyl)-2,5-dimethylpiperazin-1-yl)-1H-[1,2,4]triazolo[3,4-b]purin-1-yl)-N,N-dimethylethan-1-amine

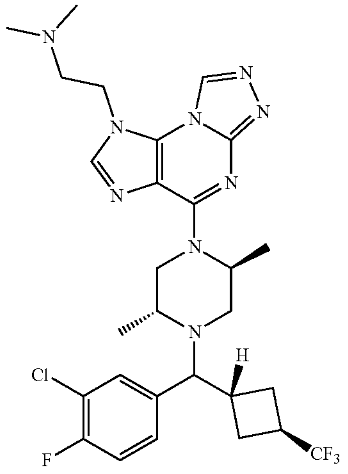 [SMILES: C[C@@H]1CN(c2nc3nncn3c3c2ncn3CCN(C)C)[C@@H](C)CN1C(c1ccc(F)c(Cl)c1)[C@H]1C[C@H](C(F)(F)F)C1]

This compound was prepared according to the procedures described for Example 64, with (2R,5S)-1-((3-chloro-4-fluorophenyl)((trans)-3-(trifluoromethyl)cyclobutyl)methyl)-2,5-dimethylpiperazine hydrochloride (Intermediate 90) replacing (2R,5S)-1-((4-chlorophenyl)(3,3-difluorocyclobutyl)methyl)-2,5-dimethylpiperazine hydrochloride. LC-MS calculated for $C_{28}H_{35}ClF_4N_9$$(M+H)^+$: m/z=608.3; found 608.2.

Example 115. 4-((2S,5R)-2,5-Dimethyl-4-(((trans)-3-(trifluoromethyl)cyclobutyl)(4-(trifluoromethyl)phenyl)methyl)piperazin-1-yl)-2-methyl-1-(((S)-tetrahydrofuran-2-yl)methyl)-1H-[1,2,4]triazolo[3,4-b]purine

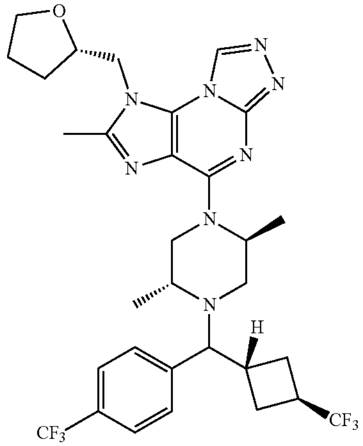 [SMILES: Cc1nc2c(N3C[C@@H](C)N(C(c4ccc(C(F)(F)F)cc4)[C@H]4C[C@H](C(F)(F)F)C4)C[C@@H]3C)nc3nncn3c2n1C[C@@H]1CCCO1]

This compound was prepared according to the procedures described for Example 43, with (2R,5S)-2,5-dimethyl-1-(((trans)-3-(trifluoromethyl)cyclobutyl)(4-(trifluoromethyl)phenyl)methyl)piperazine hydrochloride (Intermediate 91) replacing (2R,5S)-1-((3,3-difluorocyclobutyl)(4-(trifluoromethyl)phenyl)methyl)-2,5-dimethylpiperazine hydrochloride in Step 1. LC-MS calculated for $C_{31}H_{37}F_6N_8O$ $(M+H)^+$: m/z=651.3; found 651.3.

Example 116. 2-(4-((2S,5R)-2,5-Dimethyl-4-(((trans)-3-(trifluoromethyl)cyclobutyl)(4-(trifluoromethyl)phenyl)methyl)piperazin-1-yl)-1H-[1,2,4]triazolo[3,4-b]purin-1-yl)-N,N-dimethylethan-1-amine

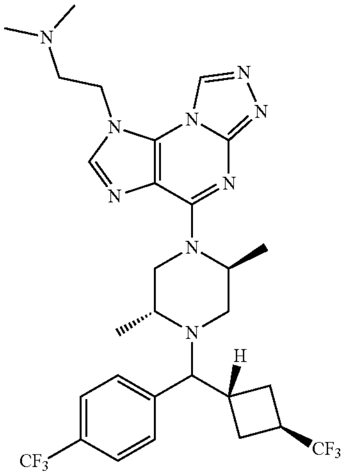 [SMILES: C[C@@H]1CN(c2nc3nncn3c3c2ncn3CCN(C)C)[C@@H](C)CN1C(c1ccc(C(F)(F)F)cc1)[C@H]1C[C@H](C(F)(F)F)C1]

This compound was prepared according to the procedures described for Example 64, with (2R,5S)-2,5-dimethyl-1-(((trans)-3-(trifluoromethyl)cyclobutyl)(4-(trifluoromethyl)phenyl)methyl)piperazine hydrochloride (Intermediate 91)

replacing (2R,5S)-1-((4-chlorophenyl)(3,3-difluorocyclobutyl)methyl)-2,5-dimethylpiperazine hydrochloride. LC-MS calculated for $C_{29}H_{36}F_6N_9$ $(M+H)^+$: m/z=624.3; found 624.3.

Example 117. 4-((2S,5R)-4-((4,4-Difluorocyclohexyl)(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine

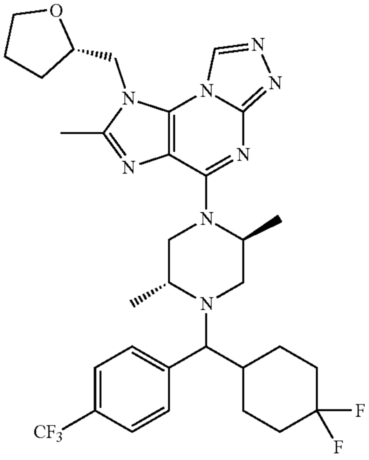 [SMILES: Cc1nc2c(N3C[C@@H](C)N(C(c4ccc(C(F)(F)F)cc4)C4CCC(F)(F)CC4)C[C@@H]3C)nc3nncn3c2n1C[C@@H]1CCCO1]

This compound was prepared according to the procedures described for Example 43, with (2R,5S)-1-((4,4-difluorocyclohexyl)(4-(trifluoromethyl)phenyl)methyl)-2,5-dimethylpiperazine hydrochloride (Intermediate 93) replacing (2R,5S)-1-((3,3-difluorocyclobutyl)(4-(trifluoromethyl)phenyl)methyl)-2,5-dimethylpiperazine hydrochloride in Step 1. LC-MS calculated for $C_{32}H_{40}F_5N_8O$ $(M+H)^+$: m/z=647.3; found 647.4.

Examples 118 and 119. 4-((2S,5R)-2,5-Dimethyl-4-((S)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine and 4-((2S,5R)-2,5-dimethyl-4-((R)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine

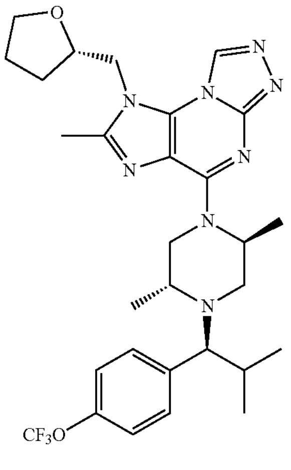

and

-continued

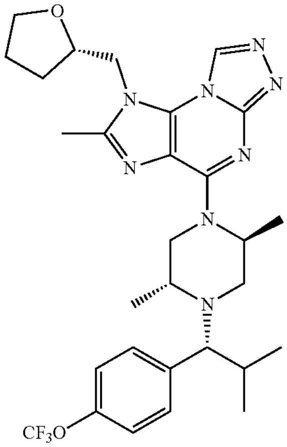

This compound was prepared according to the procedures described for Examples 67 and 68, with 2-chloro-6-((2S,5R)-2,5-dimethyl-4-(2-methyl-1-(4-(trifluoromethoxy)phenyl)propyl)piperazin-1-yl)-8-methyl-9H-purine (Intermediate 96) replacing 2-chloro-6-((2S,5R)-2,5-dimethyl-4-(2-methyl-1-(4-(trifluoromethyl)phenyl)propyl)piperazin-1-yl)-8-methyl-9H-purine in Step 1.

Example 118: Retention time on LC-MS $t_r$=1.148 min, LC-MS calculated for $C_{29}H_{38}F_3N_8O_2$ $(M+H)^+$: m/z=587.3; found 587.4.

Example 119: Retention time on LC-MS $t_r$=1.994 min, LC-MS calculated for $C_{29}H_{38}F_3N_8O_2$ $(M+H)^+$: m/z=587.3; found 587.3.

Example 120. 4-((2S,5R)-4-((3,3-Difluorocyclobutyl)(4-fluorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine

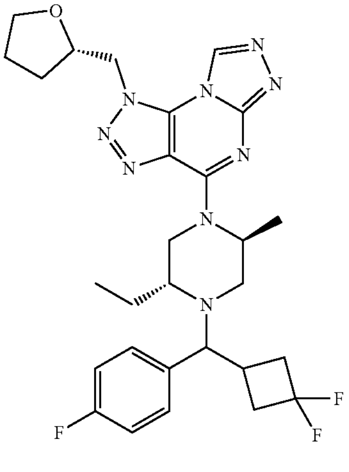 [SMILES: CC[C@@H]1CN(c2nc3nncn3c3c2nnn3C[C@@H]2CCCO2)[C@@H](C)CN1C(c1ccc(F)cc1)C1CC(F)(F)C1]

Step 1: 2-Chloro-6-((2S,5R)-4-((3,3-difluorocyclobutyl)(4-fluorophenyl)methyl)-5-ethyl-2-methylpiperazin-1-yl)-$N^4$—(((S)-tetrahydrofuran-2-yl)methyl)pyrimidine-4,5-diamine

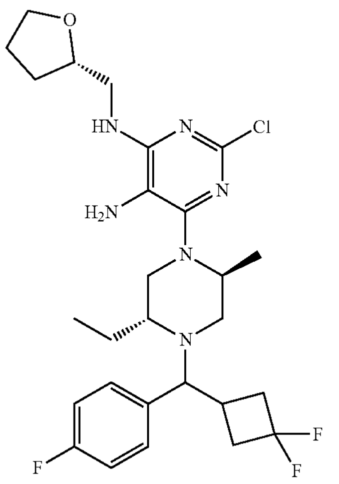 [SMILES: CC[C@@H]1CN(c2nc(Cl)nc(NC[C@@H]3CCCO3)c2N)[C@@H](C)CN1C(c1ccc(F)cc1)C1CC(F)(F)C1]

A mixture of 2,4,6-trichloro-5-nitropyrimidine (50.0 mg, 0.219 mmol, Combi-Blocks, ST-3909) and (2R,5S)-1-((4-fluorophenyl)(3,3-difluorocyclobutyl)methyl)-2-ethyl-5-methylpiperazine hydrochloride (Intermediate 97, 79 mg, 0.219 mmol) in MeCN (5 mL) was cooled to 0° C. in an ice-bath before N-ethyl-N-isopropylpropan-2-amine (191 µL, 1.1 mmol) was added and the reaction mixture was stirred at 0° C. for 30 min. To the mixture was added (S)-(tetrahydrofuran-2-yl)methanamine (22 mg, 0.219 mmol, BLD Pharmatech, BD48352) and the reaction mixture was warmed to rt and stirred for 30 min. The reaction mixture was concentrated in vacuo. To a mixture of the crude residue in saturated aqueous $NH_4Cl$ (2 mL)/MeOH (2 mL)/THF (2 mL) was added iron (24 mg, 0.438 mmol) and the reaction mixture was stirred at 65° C. overnight. After cooling to rt, the reaction mixture was diluted with EtOAc (10 mL) and saturated aqueous $NaHCO_3$ and the resulting mixture was filtered over a pad of Celite. The organic layer was removed, and the aqueous layer was extracted with EtOAc. The combined organic layers were dried over $MgSO_4$, filtered, and concentrated under reduced pressure to afford the desired product as a mixture of diastereomers. The crude material obtained was used directly without further purification. LC-MS calculated for $C_{27}H_{37}ClF_3N_6O$ $(M+H)^+$: m/z=553.3; found 553.4.

Step 2. 5-Chloro-7-((2S,5R)-4-((3,3-difluorocyclobutyl)(4-fluorophenyl)methyl)-5-ethyl-2-methylpiperazin-1-yl)-3-(((S)-tetrahydrofuran-2-yl)methyl)-3H-[1,2,3]triazolo[4,5-d]pyrimidine

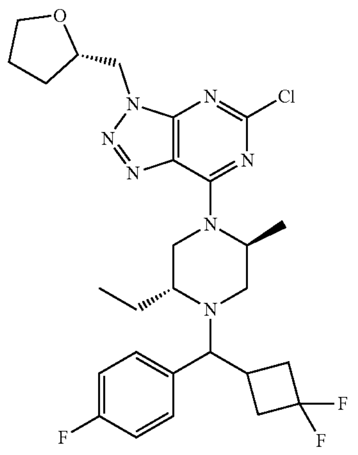 [SMILES: CC[C@@H]1CN(c2nc(Cl)nc3c2nnn3C[C@@H]2CCCO2)[C@@H](C)CN1C(c1ccc(F)cc1)C1CC(F)(F)C1]

To a mixture of 2-chloro-6-((2S,5R)-4-((3,3-difluorocyclobutyl)(4-fluorophenyl)methyl)-5-ethyl-2-methylpiperazin-1-yl)-$N^4$—(((S)-tetrahydrofuran-2-yl)methyl)pyrimidine-4,5-diamine (Step 1) and AcOH (188 µL, 3.28 mmol) in water (2 mL) and THF (2 mL) was added sodium nitrite (60.0 mg, 0.876 mmol) and the reaction mixture was stirred at rt for 30 min. The mixture was diluted with EtOAc (10 mL) and the aqueous layer was adjusted to pH=8 with saturated aqueous $NaHCO_3$. The organic layer was removed, and the aqueous layer was extracted with EtOAc. The organic phases were combined, dried over $MgSO_4$, filtered, and concentrated under reduced pressure. The crude residue was purified by flash column chromatography ($SiO_2$, $MeOH/CH_2Cl_2$) to afford the desired product as a mixture of diastereomers. LC-MS calculated for $C_{27}H_{34}ClF_3N_7O$ $(M+H)^+$: m/z=564.2; found 564.4.

Step 3. 7-((2S,5R)-4-((3,3-Difluorocyclobutyl)(4-fluorophenyl)methyl)-5-ethyl-2-methylpiperazin-1-yl)-5-hydrazineyl-3-(((S)-tetrahydrofuran-2-yl)methyl)-3H-[1,2,3]triazolo[4,5-d]pyrimidine

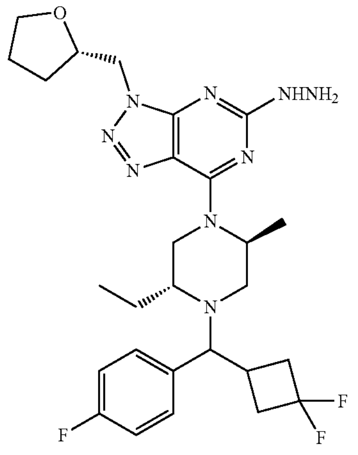 [SMILES: CC[C@@H]1CN(c2nc(NN)nc3c2nnn3C[C@@H]2CCCO2)[C@@H](C)CN1C(c1ccc(F)cc1)C1CC(F)(F)C1]

To a mixture of 5-chloro-7-((2S,5R)-4-((3,3-difluorocyclobutyl)(4-fluorophenyl)methyl)-5-ethyl-2-methylpiperazin-1-yl)-3-(((S)-tetrahydrofuran-2-yl)methyl)-3H-[1,2,3]triazolo[4,5-d]pyrimidine (Step 2) in 1,4-dioxane (5 mL) was added hydrazine (0.25 mL, 7.8 mmol) and the mixture was stirred at 90° C. for 1 h. After cooling to rt, the reaction mixture was diluted with $CH_2Cl_2$ (10 mL) and the mixture was filtered over a pad of Celite. The filtrate was concentrated under reduced pressure, and the crude residue was purified by flash column chromatography ($SiO_2$, 0-5% $MeOH/CH_2Cl_2$) to afford the desired product as a mixture of diastereomers. LC-MS calculated for $C_{27}H_{37}F_3N_9O$ $(M+H)^+$: m/z=560.3; found 560.3.

Step 4. 4-((2S,5R)-4-((3,3-Difluorocyclobutyl)(4-fluorophenyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine To a mixture of 7-((2S,5R)-4-((3,3-difluorocyclobutyl)(4-fluorophenyl)methyl)-5-ethyl-2-methylpiperazin-1-yl)-5-hydrazineyl-3-(((S)-tetrahydrofuran-2-yl)methyl)-3H-[1,2,3]triazolo[4,5-d]pyrimidine (Step 3) in AcOH (2 mL) was added triethyl orthoformate (97.0 mg, 0.657 mmol) and the reaction mixture was stirred at 90° C. for 1 h. After cooling to rt, the reaction mixture was concentrated in vacuo, and the crude residue was taken up in acetonitrile, water, and TFA and purified by prep-HPLC (Sunfire C18 column, eluting with a gradient of acetonitrile/water containing 0.1% TFA, at flow rate of 60 mL/min) to afford the major diastereomer as a single stereoisomer as its TFA salt. LC-MS calculated for $C_{28}H_{35}F_3N_9O(M+H)^+$: m/z=570.3; found 570.4.

Example 121: 4-((2S,5R)-4-((4-Chlorophenyl)(3,3-difluorocyclobutyl)methyl)-5-ethyl-2-methylpiperazin-1-yl)-1-(((S)-tetrahydrofuran-2-yl)methyl)-1H-[1,2,3]triazolo[4,5-e][1,2,4]triazolo[4,3-a]pyrimidine

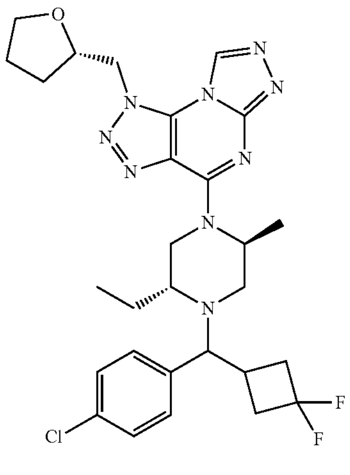 [SMILES: CC[C@@H]1CN(c2nc3nncn3c3c2nnn3C[C@@H]2CCCO2)[C@@H](C)CN1C(c1ccc(Cl)cc1)C1CC(F)(F)C1]

This compound was prepared according to the procedures described in Example 120, with (2R,5S)-1-((4-chlorophenyl)(3,3-difluorocyclobutyl)methyl)-2-ethyl-5-methylpiperazine hydrochloride (Intermediate 55) replacing (2R,5S)-1-((4-fluorophenyl)(3,3-difluorocyclobutyl)methyl)-2-ethyl-5-methylpiperazine hydrochloride in Step 1. LC-MS calculated for $C_{28}H_{35}ClF_2N_9O(M+H)^+$: m/z=586.3; found 586.3.

Example 122. ((2S,5S)-1-((3,3-Difluorocyclobutyl)(4-(trifluoromethyl)phenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)methanol

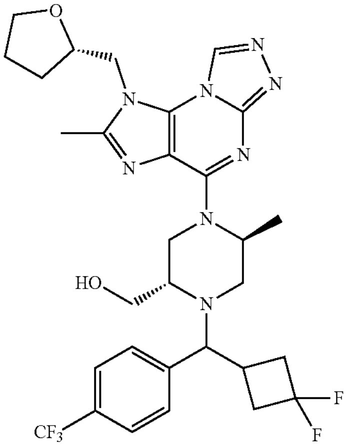 [SMILES: Cc1nc2c(N3C[C@@H](CO)N(C(c4ccc(C(F)(F)F)cc4)C4CC(F)(F)C4)C[C@@H]3C)nc3nncn3c2n1C[C@@H]1CCCO1]

This compound was prepared according to the procedures described in Example 43, with ((2S,5S)-1-((3,3-difluorocyclobutyl)(4-(trifluoromethyl)phenyl)methyl)-5-methylpiperazin-2-yl)methanol hydrochloride (Intermediate 99) replacing (2R,5S)-1-((3,3-difluorocyclobutyl)(4-(trifluoromethyl)phenyl)methyl)-2,5-dimethylpiperazine hydrochloride in Step 1. LC-MS calculated for $C_{30}H_{36}F_5N_8O_2$ $(M+H)^+$: m/z=635.3.3; found 635.3.

Examples 123 and 124: (R)-1-((2S,5S)-1-(Bis(4-fluorophenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)ethan-1-ol and (S)-1-((2S,5S)-1-(bis(4-fluorophenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)ethan-1-ol

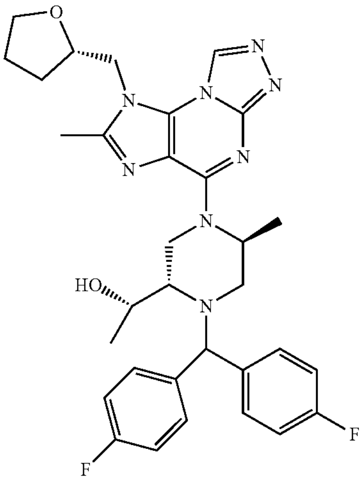

and

-continued

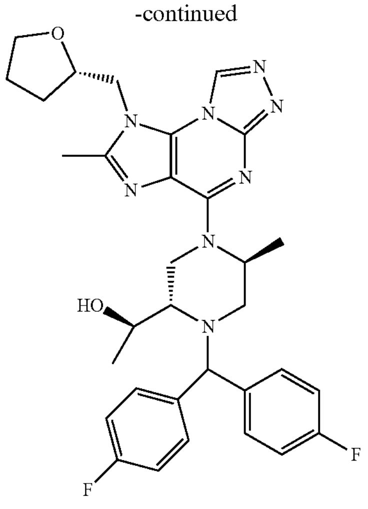

This compound was prepared according to the procedures described in Example 105, with 1-((2S,5S)-1-(bis(4-fluorophenyl)methyl)-5-methylpiperazin-2-yl)ethan-1-ol hydrochloride (Intermediate 100) replacing (2R,5S)-1-(bis(4-chlorophenyl)methyl)-2,5-dimethylpiperazine hydrochloride in Step 1. In Step 3 the diastereomeric mixture was filtered and purified by prep-HPLC (Sunfire C18 column, eluting with a gradient of acetonitrile/water containing 0.10% TFA, at flow rate of 60 mL/min) to afford each diastereomer as its TFA salt.

Example 123: Retention time on LC-MS $t_r$=1.45 min, LC-MS calculated for $C_{32}H_{37}F_2N_8O_2(M+H)^+$: m/z=603.3; found 603.4.

Example 124: Retention time on LC-MS $t_r$=1.51 min, LC-MS calculated for $C_{32}H_{37}F_2N_8O_2(M+H)^+$: m/z=603.3; found 603.4. $^1H$ NMR (600 MHz, DMSO-$d_6$) (mixture of rotamers) δ 9.46 (s, 1H), 7.61-7.50 (m, 4H), 7.22-7.13 (m, 4H), 6.19-6.11 (m, 0.6H), 6.07-6.00 (m, 0.4H), 5.33-5.28 (m, 1H), 5.10-5.02 (m, 0.4H), 4.93-4.85 (m, 0.6H), 4.74-4.66 (m, 1H), 4.59-4.29 (m, 2H), 4.14-4.04 (m, 2H), 3.79-3.73 (m, 0.6H), 3.72-3.65 (m, 1H), 3.59-3.47 (m, 1.4H), 3.29-3.23 (m, 0.4H), 3.23-3.15 (m, 0.6H), 2.67 (s, 1H), 2.57 (s, 3H), 2.53-2.51 (m, 1H), 2.16-2.08 (m, 1H), 1.98-1.87 (m, 1H), 1.87-1.77 (m, 1H), 1.76-1.67 (m, 1H), 1.45 (d, J=6.7 Hz, 1.2H), 1.38 (d, J=6.7 Hz, 1.8H), 1.02 (d, J=6.3 Hz, 1.2H), 0.98 (d, J=6.3 Hz, 1.8H).

Example 125. 2-((2R,5S)-2-Ethyl-5-methyl-4-(2-methyl-1-(((S)-tetrahydrofuran-2-yl)methyl)-1H-[1,2,4]triazolo[3,4-b]purin-4-yl)piperazin-1-yl)-2,2-bis(4-fluorophenyl)ethan-1-ol

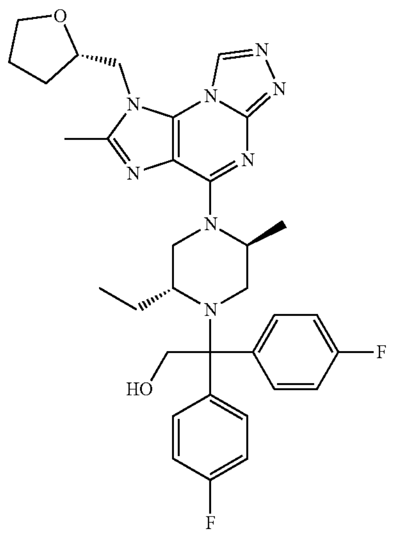 [SMILES: CC[C@@H]1CN(c2nc3nncn3c3c2nc(C)n3C[C@@H]2CCCO2)[C@@H](C)CN1C(CO)(c1ccc(F)cc1)c1ccc(F)cc1]

Step 1. 2,2-Bis(4-fluorophenyl)oxirane

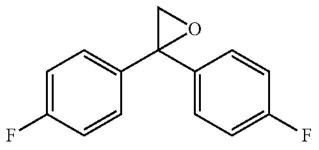 [SMILES: Fc1ccc(C2(c3ccc(F)cc3)CO2)cc1]

Trimethyl sulfonium iodide (1.22 g, 6.0 mmol) was added to a slurry of NaH (60% in mineral oil, 0.240 g, 6.0 mmol) in dry DMSO (10 mL) and THF (7 mL) and the reaction mixture was allowed to stir for 30 min at rt. The reaction mixture was cooled to 0° C. and a solution of bis(4-fluorophenyl)methanone (0.655 g, 3.0 mmol) in dry THF (5 mL) was added dropwise. The reaction mixture was maintained at 0° C. for 2 h and allowed to stir at rt overnight. The reaction mixture was quenched with saturated aqueous $NH_4Cl$, diluted with ethyl acetate, and washed with $H_2O$ and brine. The organic phase was dried over $Na_2SO_4$, filtered, and concentrated and the crude residue was purified using flash column chromatography ($SiO_2$, EtOAc/hexanes) to afford the desired product as a clear oil. LC-MS calculated for $C_{14}H_{11}F_2O(M+H)^+$: m/z=233.1; found 233.2.

Step 2. tert-Butyl (2S,5R)-4-(1,1-bis(4-fluorophenyl)-2-hydroxyethyl)-5-ethyl-2-methylpiperazine-1-carboxylate

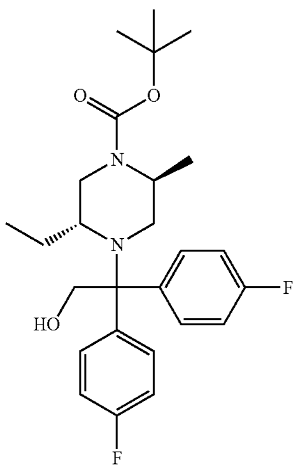 [SMILES: CC[C@@H]1CN(C(=O)OC(C)(C)C)[C@@H](C)CN1C(CO)(c1ccc(F)cc1)c1ccc(F)cc1]

To a mixture of tert-butyl (2S,5R)-5-ethyl-2-methylpiperazine-1-carboxylate (Intermediate 25, 46 mg, 0.20 mmol) in MeOH (1 mL) was added 2,2-bis(4-fluorophenyl)oxirane (140 mg, 0.60 mmol) and LiCl (51 mg, 1.2 mmol) at rt, and the resulting mixture was stirred at 80° C. for 5 h. After cooling to rt, the reaction mixture was quenched with $H_2O$ and the aqueous layer was extracted three times with EtOAc. The combined organic layers were dried over $Na_2SO_4$, filtered, and concentrated in vacuo. The crude material obtained was used directly without further purification. LC-MS calculated for $C_{26}H_{35}F_2N_2O_3(M+H)^+$: m/z=461.3; found 461.3.

Step 3. 2-((2R,5S)-2-Ethyl-5-methylpiperazin-1-yl)-2,2-bis(4-fluorophenyl)ethan-1-ol hydrochloride HCl

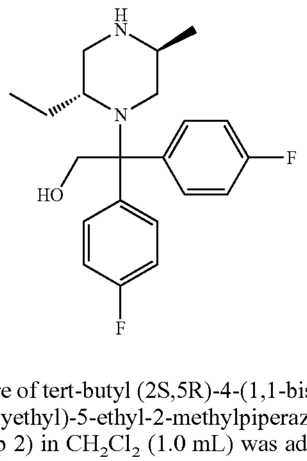

To a mixture of tert-butyl (2S,5R)-4-(1,1-bis(4-fluorophenyl)-2-hydroxyethyl)-5-ethyl-2-methylpiperazine-1-carboxylate (Step 2) in $CH_2Cl_2$ (1.0 mL) was added a 4 molar solution of HCl in 1,4-dioxane (0.5 mL, 2 mmol), and the reaction mixture was allowed to stir at rt for 4 h. The reaction mixture was concentrated in vacuo, and the crude material obtained was used directly without further purification. LC-MS calculated for $C_{21}H_{27}F_2N_2O$ $(M+H)^+$: m/z=361.2; found 361.3.

Step 4. 2-((2R,5S)-4-(2-Chloro-8-methyl-9H-purin-6-yl)-2-ethyl-5-methylpiperazin-1-yl)-2,2-bis(4-fluorophenyl)ethan-1-ol

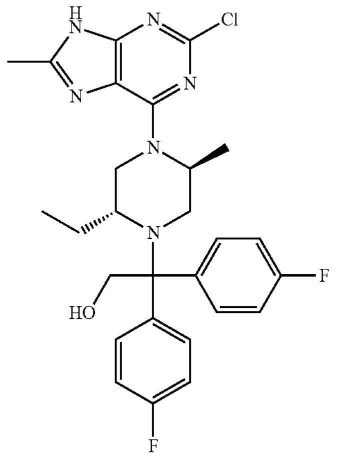 [SMILES: CC[C@@H]1CN(c2nc(Cl)nc3[nH]c(C)nc23)[C@@H](C)CN1C(CO)(c1ccc(F)cc1)c1ccc(F)cc1]

To a mixture of 2,6-dichloro-8-methylpurine (45 mg, 0.22 mmol, PharmaBlock PB02898) and 2-((2R,5S)-2-ethyl-5-methylpiperazin-1-yl)-2,2-bis(4-fluorophenyl)ethan-1-ol hydrochloride (Step 3) in MeCN (2.0 mL) was added N,N-diisopropylethylamine (88 uL, 0.50 mmol) and the reaction mixture was stirred at 80° C. overnight. After cooling to rt, the reaction mixture was concentrated in vacuo, and the crude residue was purified directly by flash column chromatography ($SiO_2$, EtOAc/hexanes) to afford the desired product as a light yellow waxy solid. LC-MS calculated for $C_{27}H_{30}ClF_2N_6O$ $(M+H)^+$: m/z=527.2; found 527.2.

Step 5. 2-((2R,5S)-4-(2-Chloro-8-methyl-9-(((S)-tetrahydrofuran-2-yl)methyl)-9H-purin-6-yl)-2-ethyl-5-methylpiperazin-1-yl)-2,2-bis(4-fluorophenyl)ethan-1-ol

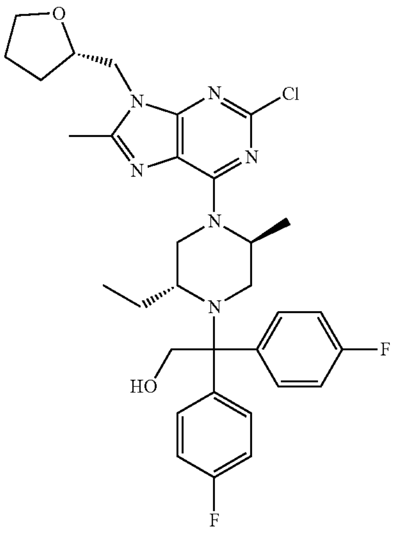 [SMILES: CC[C@@H]1CN(c2nc(Cl)nc3c2nc(C)n3C[C@@H]2CCCO2)[C@@H](C)CN1C(CO)(c1ccc(F)cc1)c1ccc(F)cc1]

To a mixture of 2-((2R,5S)-4-(2-chloro-8-methyl-9H-purin-6-yl)-2-ethyl-5-methylpiperazin-1-yl)-2,2-bis(4-fluorophenyl)ethan-1-ol (Step 4) and cesium carbonate (195 mg, 0.60 mmol) in N,N-dimethylformamide (1.0 mL) was added (S)-(tetrahydrofuran-2-yl)methyl methanesulfonate (Intermediate 22, 72 mg, 0.40 mmol) and the mixture was stirred at 75° C. overnight. After cooling to rt, the reaction mixture was diluted with aqueous LiCl (5% w/v) and extracted with EtOAc. The combined organic phases were washed with three times with water, dried over $Na_2SO_4$, and concentrated in vacuo. The crude residue was used for next step without further purification. LC-MS calculated for $C_{32}H_{38}ClF_2N_6O_2$ $(M+H)^+$: m/z=611.3; found 611.3.

Step 6. 2-((2R,5S)-2-Ethyl-4-(2-hydrazineyl-8-methyl-9-(((S)-tetrahydrofuran-2-yl)methyl)-9H-purin-6-yl)-5-methylpiperazin-1-yl)-2,2-bis(4-fluorophenyl)ethan-1-ol

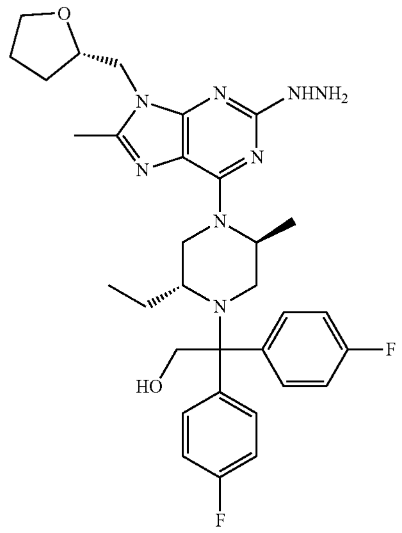 [SMILES: CC[C@@H]1CN(c2nc(NN)nc3c2nc(C)n3C[C@@H]2CCCO2)[C@@H](C)CN1C(CO)(c1ccc(F)cc1)c1ccc(F)cc1]

To a mixture of 2-((2R,5S)-4-(2-chloro-8-methyl-9-(((S)-tetrahydrofuran-2-yl)methyl)-9H-purin-6-yl)-2-ethyl-5-methylpiperazin-1-yl)-2,2-bis(4-fluorophenyl)ethan-1-ol (Step 5), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (6.4 mg, 0.0075 mmol), and cesium carbonate (244 mg, 0.75 mmol) was added a 1 molar solution of hydrazine in THF (0.75 mL, 0.75 mmol) and the mixture was stirred at 60° C. for 30 min. After cooling to rt, the reaction mixture was filtered through a pad of $MgSO_4$ in a SiliaPrep SPE thiol cartridge (SiliCycle SPE-R51030B-06P). The filtrate was concentrated, and the crude material obtained was used directly without further purification. LC-MS calculated for $C_{32}H_{41}F_2N_8O_2$ $(M+H)^+$: m/z=607.3; found 607.4.

Step 7. 2-((2R,5S)-2-Ethyl-5-methyl-4-(2-methyl-1-(((S)-tetrahydrofuran-2-yl)methyl)-1H-[1,2,4]triazolo[3,4-b]purin-4-yl)piperazin-1-yl)-2,2-bis(4-fluorophenyl)ethan-1-ol A mixture of 2-((2R,5S)-2-ethyl-4-(2-hydrazineyl-8-methyl-9-(((S)-tetrahydrofuran-2-yl)methyl)-9H-purin-6-yl)-5-methylpiperazin-1-yl)-2,2-bis(4-fluorophenyl)ethan-1-ol (Step 6), triethyl orthoformate (250 μL, 1.5 mmol), and AcOH (8.6 μL, 0.15 mmol) was stirred at 90° C. for 1 h. After cooling to rt, the reaction mixture was diluted with acetonitrile and water and purified by prep-HPLC (Sunfire C18 column, eluting with a gradient of acetonitrile/water containing 0.1% TFA, at flow rate of 60 mL/min) to afford the desired product as its TFA salt. LC-MS calculated for $C_{33}H_{39}F_2N_8O_2$ $(M+H)^+$: m/z=617.3; found 617.4. $^1H$ NMR (600 MHz, DMSO-$d_6$) (mixture of rotamers) δ 9.48 (s, 1H), 7.64-7.47 (m, 4H), 7.20-7.08 (m, 4H), 6.23-5.57 (m, 2H), 4.98-4.63 (m, 2H), 4.61-4.43 (m, 1H), 4.20-3.91 (m, 1H), 3.75-3.61 (m, 1H), 3.64-3.20 (m, 4H), 3.05-2.88 (m, 1H), 2.88-2.64 (m, 1H), 2.60-2.56 (m, 3H), 2.47-2.21 (m, 1H), 2.20-2.07 (m, 1H), 2.00-1.88 (m, 1H), 1.87-1.77 (m, 1H), 1.75-1.65 (m, 1H), 1.55-1.33 (m, 2H), 1.22-1.02 (m, 3H), 0.90-0.80 (m, 3H).

Examples 126 and 127. 4-((2S,5R)-4-((S)-1-(4-(Difluoromethoxy)phenyl)-2-methylpropyl)-5-ethyl-2-methylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-(difluoromethoxy)phenyl)-2-methylpropyl)-5-ethyl-2-methylpiperazin-1-yl)-2-methyl-1-(((S)-tetrahydrofuran-2-yl)methyl)-1H-[1,2,4]triazolo[3,4-b]purine

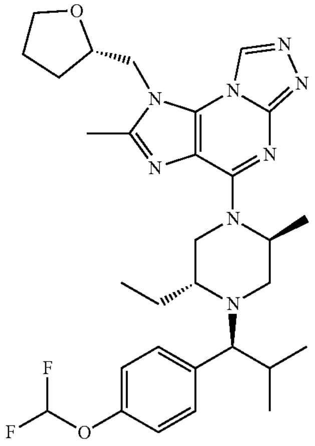

and

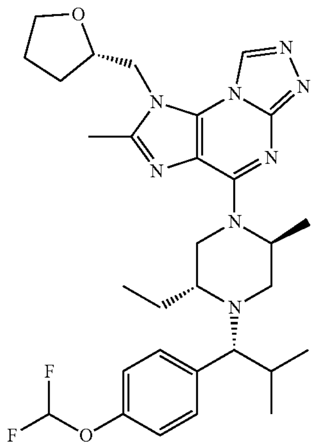

Step 1: 2-Chloro-6-((2S,5R)-4-(1-(4-(difluoromethoxy)phenyl)-2-methylpropyl)-5-ethyl-2-methylpiperazin-1-yl)-8-methyl-9H-purine

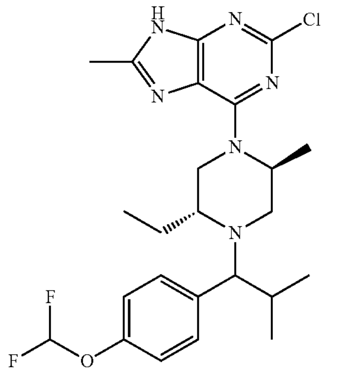 [SMILES: CC[C@@H]1CN(c2nc(Cl)nc3[nH]c(C)nc23)[C@@H](C)CN1C(c1ccc(OC(F)F)cc1)C(C)C]

To a mixture of 2,6-dichloro-8-methyl-9H-purine (36.4 mg, 0.18 mmol, PharmaBlock PB02898) and (2R,5S)-1-(1-(4-(difluoromethoxy)phenyl)-2-methylpropyl)-2-ethyl-5-methylpiperazine hydrochloride (Intermediate 102, 53 mg, 0.16 mmol) in MeCN (2.0 mL) was added NN-diisopropylethylamine (71 uL, 0.41 mmol) and the reaction mixture was stirred at 80° C. overnight. After cooling to rt, the reaction mixture was concentrated in vacuo, and the crude residue obtained was purified by flash column chromatography ($SiO_2$, EtOAc/hexanes) to afford desired product as a mixture of diastereomers. LC-MS calculated for $C_{24}H_{32}ClF_2N_6O$ $(M+H)^+$: m/z=493.2; found 493.2.

Step 2: 2-Chloro-6-((2S,5R)-4-(1-(4-(difluoromethoxy)phenyl)-2-methylpropyl)-5-ethyl-2-methylpiperazin-1-yl)-8-methyl-9-(((S)-tetrahydrofuran-2-yl)methyl)-9H-purine

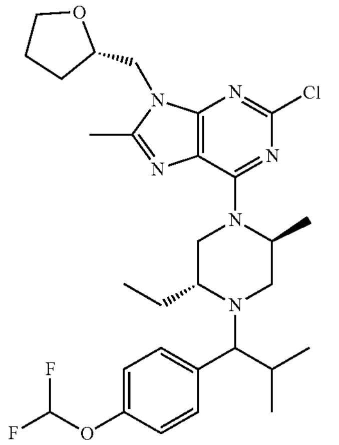 [SMILES: CC[C@@H]1CN(c2nc(Cl)nc3c2nc(C)n3C[C@@H]2CCCO2)[C@@H](C)CN1C(c1ccc(OC(F)F)cc1)C(C)C]

To a mixture of 2-chloro-6-((2S,5R)-4-(1-(4-(difluoromethoxy)phenyl)-2-methylpropyl)-5-ethyl-2-methylpiperazin-1-yl)-8-methyl-9H-purine (Step 1) and cesium carbonate (159 mg, 0.49 mmol) in acetonitrile (2.0 mL) was added (S)-(tetrahydrofuran-2-yl)methyl methanesulfonate (Intermediate 22, 59 mg, 0.33 mmol) and the mixture was stirred at 75° C. overnight. After cooling to rt, the reaction mixture was filtered and the filtrate was concentrated in vacuo. The crude residue was used for next step without further purification. LC-MS calculated for $C_{29}H_{40}ClF_2N_6O_2$ $(M+H)^+$: m/z=577.3; found 577.3.

Step 3: 6-((2S,5R)-4-(1-(4-(Difluoromethoxy)phenyl)-2-methylpropyl)-5-ethyl-2-methylpiperazin-1-yl)-2-hydrazineyl-8-methyl-9-(((S)-tetrahydrofuran-2-yl)methyl)-9H-purine

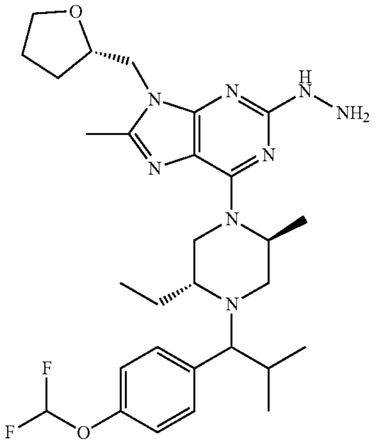 [SMILES: CC[C@@H]1CN(c2nc(NN)nc3c2nc(C)n3C[C@@H]2CCCO2)[C@@H](C)CN1C(c1ccc(OC(F)F)cc1)C(C)C]

To a mixture of 2-chloro-6-((2S,5R)-4-(1-(4-(difluoromethoxy)phenyl)-2-methylpropyl)-5-ethyl-2-methylpiperazin-1-yl)-8-methyl-9-(((S)-tetrahydrofuran-2-yl)methyl)-9H-purine (Step 2), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (7.0 mg, 0.0082 mmol), and cesium carbonate (266 mg, 0.82 mmol) was added a 1 molar solution of hydrazine in THF (0.82 mL, 0.82 mmol) and the mixture was stirred at 60° C. for 30 min. After cooling to rt, the reaction mixture was filtered through a pad of $MgSO_4$ in a SiliaPrep SPE thiol cartridge (SiliCycle SPE-R51030B-06P). The filtrate was concentrated, and the crude material obtained was used directly without further purification. LC-MS calculated for $C_{29}H_{43}F_2N_8O_2$ $(M+H)^+$: m/z=573.4; found 573.4.

Step 4: 4-((2S,5R)-4-((S)-1-(4-(Difluoromethoxy)phenyl)-2-methylpropyl)-5-ethyl-2-methylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-(difluoromethoxy)phenyl)-2-methylpropyl)-5-ethyl-2-methylpiperazin-1-yl)-2-methyl-1-(((S)-tetrahydrofuran-2-yl)methyl)-1H-[1,2,4]triazolo[3,4-b]purine To a mixture of 6-((2S,5R)-4-(1-(4-(difluoromethoxy)phenyl)-2-methylpropyl)-5-ethyl-2-methylpiperazin-1-yl)-2-hydrazineyl-8-methyl-9-(((S)-tetrahydrofuran-2-yl)methyl)-9H-purine (Step 3) in AcOH (0.090 mL, 0.16 mmol) was added triethyl orthoformate (0.27 mL, 1.6 mmol) and the reaction mixture was stirred at 90° C. for 1 h. After cooling to rt, the reaction mixture was diluted with acetonitrile and water and purified by prep-HPLC (Sunfire C18 column, eluting with a gradient of acetonitrile/water containing 0.10% TFA, at flow rate of 60 mL/min) to afford each diastereomer as its TFA salt.

Example 126: Retention time on LCMS $t_r$=1.23 min, LCMS calculated for $C_{30}H_{41}F_2N_8O_2$ $(M+H)^+$: m/z=583.3; found 583.4.

Example 127: Retention time on LCMS $t_r$=1.31 min, LCMS calculated for $C_{30}H_{41}F_2N_8O_2$ $(M+H)^+$: m/z=583.3; found 583.4. $^1H$ NMR (600 MHz, DMSO-$d_6$) (mixture of rotamers) δ 9.51-9.45 (m, 1H), 7.45-7.00 (m, 5H), 6.27-6.04 (m, 1H), 5.03-4.88 (m, 1H), 4.80-4.68 (m, 1H), 4.64-4.44 (m, 1H), 4.18-4.02 (m, 1H), 3.88-3.65 (m, 0.6H), 3.74-3.66 (m, 1H), 3.61-3.51 (m, 1.4H), 3.47-3.41 (m, 1H), 3.19-3.00 (m, 1H), 2.67-2.55 (m, 4H), 2.34-2.26 (m, 1H), 2.22-2.06 (m, 2H), 1.97-1.90 (m, 1H), 1.88-1.79 (m, 1H), 1.77-1.67 (m, 1H), 1.51-1.29 (m, 5H), 1.08-0.92 (m, 3H), 0.83-0.64 (m, 6H).

Examples 128-131

Examples 128-131 of Table 7 were prepared in accordance with the synthetic protocols set forth in Examples 126 and 127 using the indicated carboxylic acid starting material as described in Intermediate 101.

TABLE 7

| Ex. | Name | Structure | Carboxylic Acid Starting Material | Analytical data |
|---|---|---|---|---|
| 128 and 129 | 4-((2S,5R)-5-Ethyl-2-methyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine and 4-((2S,5R)-5-Ethyl-2-methyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine | 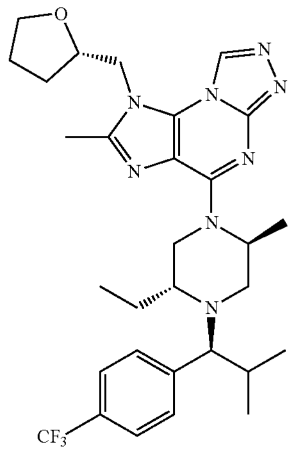 and 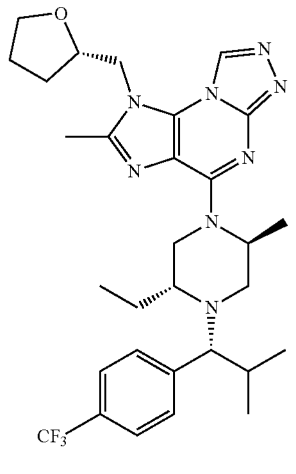 | 4-(Trifluoromethyl) benzoic acid | Example 128: Retention time on LCMS $t_r$ = 1.51 min, LCMS [M+H] +: found 585.4. Example 129: Retention time on LCMS $t_r$ = 1.58 min, LCMS $[M + H]^+$: found 585.3. |

TABLE 7-continued

| Ex. | Name | Structure | Carboxylic Acid Starting Material | Analytical data |
|---|---|---|---|---|
| 130 and 131 | 4-((2S,5R)-5-ethyl-2-methyl-4-((S)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine and 4-((2S,5R)-5-ethyl-2-methyl-4-((R)-2-methyl-1-(4-(trifluoromethoxy)phenyl)propyl)piperazin-1-yl)-2-methyl-1-(((S)-tetrahydrofuran-2-yl)methyl)-1H-[1,2,4]triazolo[3,4-b]purine | 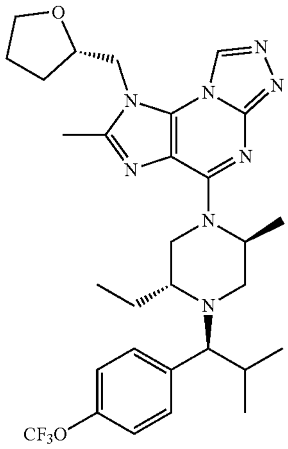 and 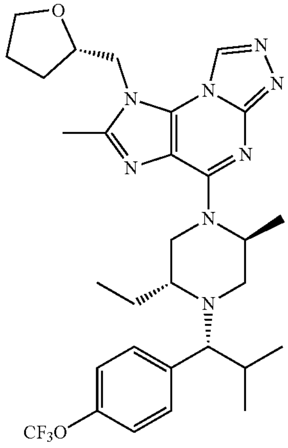 | 4-(Trifluoromethoxy) benzoic acid | Example 130: Retention time on LCMS $t_r$ = 1.47 min, LCMS $[M + H]^+$: found 601.4. Example 131: Retention time on LCMS $t_r$ = 1.55 min, LCMS $[M + H]^+$: found 601.4. |

Example 132. 4-(((2R,5S)-2-Ethyl-5-methyl-4-(2-methyl-1-(((S)-tetrahydrofuran-2-yl)methyl)-1H-[1,2,4]triazolo[3,4-b]purin-4-yl)piperazin-1-yl)(4-fluorophenyl)methyl)benzonitrile

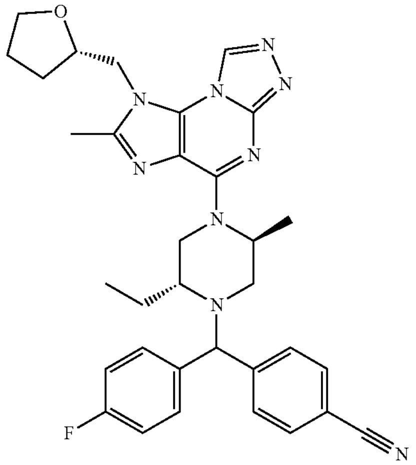 [SMILES: CC[C@@H]1CN(c2nc3nncn3c3c2nc(C)n3C[C@@H]2CCCO2)[C@@H](C)CN1C(c1ccc(F)cc1)c1ccc(C#N)cc1]

Step 1: 4-(((2R,5S)-4-(2-Chloro-8-methyl-9-(((S)-tetrahydrofuran-2-yl)methyl)-9H-purin-6-yl)-2-ethyl-5-methylpiperazin-1-yl)(4-fluorophenyl)methyl)benzonitrile

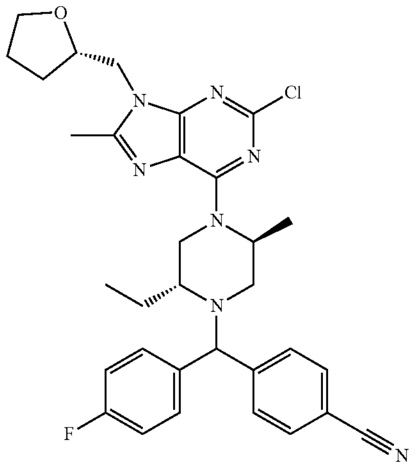 [SMILES: CC[C@@H]1CN(c2nc(Cl)nc3c2nc(C)n3C[C@@H]2CCCO2)[C@@H](C)CN1C(c1ccc(F)cc1)c1ccc(C#N)cc1]

To a mixture of (S)-2,6-dichloro-8-methyl-9-((tetrahydrofuran-2-yl)methyl)-9H-purine (Intermediate 41, 48.6 mg, 0.17 mmol) and 4-(((2R,5S)-2-ethyl-5-methylpiperazin-1-yl)(4-fluorophenyl)methyl)benzonitrile hydrochloride (Intermediate 106, 54.0 mg, 0.16 mmol) in MeCN (1.5 mL) was added potassium carbonate (44.2 mg, 0.32 mmol) and the mixture was stirred at 85° C. overnight. After cooling to rt, the reaction mixture was filtered through a pad of Celite and concentrated in vacuo. The crude material obtained was used directly without further purification. LC-MS calculated for $C_{32}H_{36}ClFN_7O$ $(M+H)^+$: m/z=588.3; found 588.3.

Step 2: 4-(((2R,5S)-2-Ethyl-4-(2-hydrazineyl-8-methyl-9-(((S)-tetrahydrofuran-2-yl)methyl)-9H-purin-6-yl)-5-methylpiperazin-1-yl)(4-fluorophenyl)methyl)benzonitrile

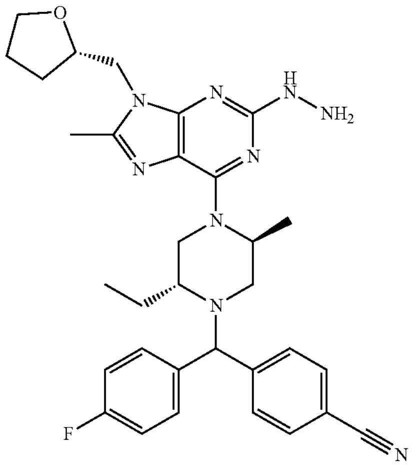 [SMILES: CC[C@@H]1CN(c2nc(NN)nc3c2nc(C)n3C[C@@H]2CCCO2)[C@@H](C)CN1C(c1ccc(F)cc1)c1ccc(C#N)cc1]

To a mixture of 4-(((2R,5S)-4-(2-chloro-8-methyl-9-(((S)-tetrahydrofuran-2-yl)methyl)-9H-purin-6-yl)-2-ethyl-5-methylpiperazin-1-yl)(4-fluorophenyl)methyl)benzonitrile (Step 1), methanesulfonato(2-(di-t-butylphosphino)-3,6-dimethoxy-2',4',6'-tri-1-propyl-1,1'-biphenyl)(2'-amino-1,1'-biphenyl-2-yl)palladium(II) (6.8 mg, 0.008 mmol), and cesium carbonate (293.2 mg, 0.90 mmol) was added a 1 molar solution of hydrazine in THF (0.90 mL, 0.90 mmol) and the mixture was stirred at 60° C. for 30 min. After cooling to rt, the reaction mixture was filtered through a pad of $MgSO_4$ in a SiliaPrep SPE thiol cartridge (SiliCycle SPE-R51030B-06P). The filtrate was concentrated, and the crude material obtained was used directly without further purification. LC-MS calculated for $C_{32}H_{39}FN_9O$ $(M+H)^+$: m/z=584.3; found 584.3.

Step 3: 4-(((2R,5S)-2-Ethyl-5-methyl-4-(2-methyl-1-(((S)-tetrahydrofuran-2-yl)methyl)-1H-[1,2,4]triazolo[3,4-b]purin-4-yl)piperazin-1-yl)(4-fluorophenyl)methyl)benzonitrile To a mixture of 4-(((2R,5S)-2-ethyl-4-(2-hydrazineyl-8-methyl-9-(((S)-tetrahydrofuran-2-yl)methyl)-9H-purin-6-yl)-5-methylpiperazin-1-yl)(4-fluorophenyl)methyl)benzonitrile (Step 2) in AcOH (0.010 mL, 0.16 mmol) was added triethyl orthoformate (0.26 mL, 1.6 mmol) and the reaction mixture was stirred at 90° C. for 1 h. After cooling to rt, the reaction mixture was diluted with acetonitrile and water and purified by prep-HPLC (Sunfire C18 column, eluting with a gradient of acetonitrile/water containing 0.10% TFA, at flow rate of 60 mL/min) to afford the desired product as its TFA salt. LCMS calculated for $C_{33}H_{37}FN_9O$ $(M+H)^+$: m/z=594.3; found 594.4.

Example 133. 4-(((2R,5S)-2-Ethyl-5-methyl-4-(2-methyl-1-(((S)-tetrahydrofuran-2-yl)methyl)-1H-[1,2,4]triazolo[3,4-b]purin-4-yl)piperazin-1-yl)(4-fluorophenyl)methyl)benzonitrile

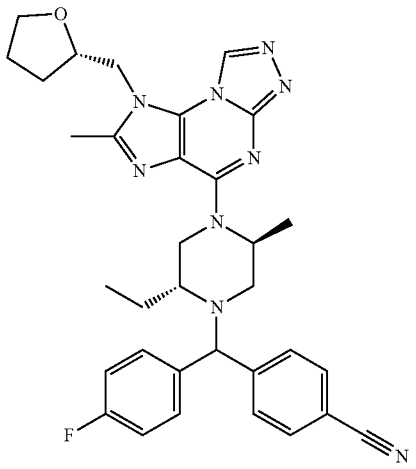 [SMILES: CC[C@@H]1CN(c2nc3nncn3c3c2nc(C)n3C[C@@H]2CCCO2)[C@@H](C)CN1C(c1ccc(F)cc1)c1ccc(C#N)cc1]

This compound was prepared according to the procedures described in Example 132, with 4-(((2R,5S)-2-ethyl-5-methylpiperazin-1-yl)(4-fluorophenyl)methyl)benzonitrile hydrochloride (Intermediate 107) replacing Intermediate 106. LC-MS calculated for $C_{21}H_{25}FN_3$ $(M+H)^+$: m/z=338.2; found 338.2. LCMS calculated for $C_{33}H_{37}FN_9O$ $(M+H)^+$: m/z=594.3; found 594.4.

Example 134: 4-((2S,5R)-4-(Bis(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine

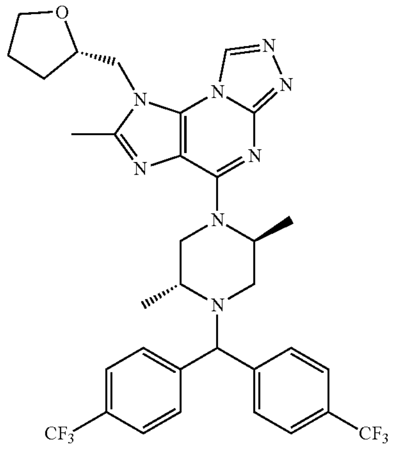 [SMILES: Cc1nc2c(N3C[C@@H](C)N(C(c4ccc(C(F)(F)F)cc4)c4ccc(C(F)(F)F)cc4)C[C@@H]3C)nc3nncn3c2n1C[C@@H]1CCCO1]

This compound was prepared according to the procedures described for Example 19, with 6-((2S,5R)-4-(bis(4-(trifluoromethyl)phenyl)methyl)-2,5-dimethylpiperazin-1-yl)-2-chloro-8-methyl-9H-purine (Intermediate 109) replacing 6-((2S,5R)-4-(bis(4-fluorophenyl)methyl)-2,5-dimethylpiperazin-1-yl)-2-chloro-8-methyl-9H-purine in Step 1. LCMS calculated for $C_{33}H_{35}F_6N_8O$ $(M+H)^+$: m/z=673.3; found 673.3.

Example 135. 4-((2S,5R)-4-((3,3-Difluorocyclobutyl)(4-(difluoromethyl)-3-fluorophenyl)methyl)-2,5-dimethylpiperazin-1-yl)-2-methyl-1-(((S)-tetrahydrofuran-2-yl)methyl)-1H-[1,2,4]triazolo[3,4-b]purine

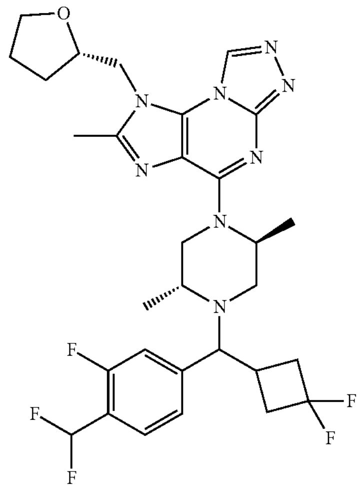 [SMILES: Cc1nc2c(N3C[C@@H](C)N(C(c4ccc(C(F)F)c(F)c4)C4CC(F)(F)C4)C[C@@H]3C)nc3nncn3c2n1C[C@@H]1CCCO1]

This compound was prepared according to the procedures described for Example 81, with (2R,5S)-1-((3,3-difluorocyclobutyl)(4-(difluoromethyl)-3-fluorophenyl)methyl)-2,5-dimethylpiperazine hydrochloride (Intermediate 110) replacing (2R,5S)-1-(1-(4-(difluoromethyl)-3-fluorophenyl)-2-methylpropyl)-2,5-dimethylpiperazine hydrochloride in Step 1. LC-MS calculated for $C_{30}H_{36}F_5N_8O$ $(M+H)^+$: m/z=619.3; found 619.4. $^1H$ NMR (600 MHz, DMSO-$d_6$) (mixture of rotamers) δ 9.49 (s, 1H), 7.68-7.62 (m, 1H), 7.50-7.32 (m, 2H), 7.31-7.09 (m, 1H), 6.17-6.01 (m, 0.5H), 5.87-5.70 (m, 0.5H), 4.99-4.83 (m, 0.5H), 4.78-4.65 (m, 1H), 4.60-4.45 (m, 1.5H), 4.15-4.05 (m, 1H), 3.82-3.30 (m, 4H), 3.16-2.98 (m, 1H), 2.93-2.75 (m, 2H), 2.75-2.51 (m, 5H), 2.47-2.31 (m, 1H), 2.30-2.09 (m, 2H), 2.09-1.99 (m, 1H), 1.98-1.88 (m, 1H), 1.87-1.77 (m, 1H), 1.77-1.66 (m, 1H), 1.54-1.28 (m, 3H), 1.04-0.86 (m, 3H).

Example 136. 2-(4-((2S,5R)-4-((4-Chloro-3-fluorophenyl)(3,3-difluorocyclobutyl)methyl)-2,5-dimethylpiperazin-1-yl)-1H-[1,2,4]triazolo[3,4-b]purin-1-yl)-N,N-dimethylethan-1-amine

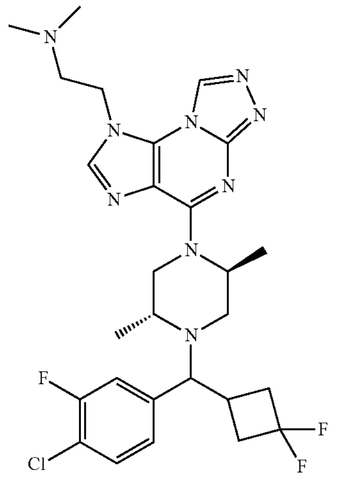 [SMILES: C[C@@H]1CN(c2nc3nncn3c3c2ncn3CCN(C)C)[C@@H](C)CN1C(c1ccc(Cl)c(F)c1)C1CC(F)(F)C1]

This compound was prepared according to the procedures described for Example 64, with (2R,5S)-1-((4-chloro-3-fluorophenyl)(3,3-difluorocyclobutyl)methyl)-2,5-dimethylpiperazine hydrochloride (Intermediate 48) replacing (2R,5S)-1-((4-chlorophenyl)(3,3-difluorocyclobutyl)methyl)-2,5-dimethylpiperazine hydrochloride in Step 1. LC-MS calculated for $C_{27}H_{34}ClF_3N_9(M+H)^+$: m/z=576.3; found 576.3.

Example 137. ((2S,5S)-1-(Bis(4-chlorophenyl)methyl)-5-methyl-4-(2-methyl-1-(((S)-tetrahydrofuran-2-yl)methyl)-1H-[1,2,4]triazolo[3,4-b]purin-4-yl)piperazin-2-yl)methanol

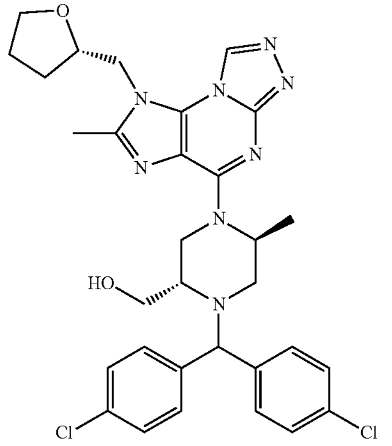 [SMILES: Cc1nc2c(N3C[C@@H](CO)N(C(c4ccc(Cl)cc4)c4ccc(Cl)cc4)C[C@@H]3C)nc3nncn3c2n1C[C@@H]1CCCO1]

This compound was prepared according to the procedures described for Example 105 with ((2S,5S)-1-(bis(4-chlorophenyl)methyl)-5-methylpiperazin-2-yl)methanol hydrochloride (Intermediate 111) replacing (2R,5S)-1-(bis(4-chlorophenyl)methyl)-2,5-dimethylpiperazine hydrochloride in Step 1. LC-MS calculated for $C_{31}H_{35}Cl_2N_8O_2$ $(M+H)^+$: m/z=621.2; found 621.3. $^1H$ NMR (500 MHz, DMSO-$d_6$) (mixture of rotamers) δ 9.49 (s, 1H), 7.63-7.48 (m, 4H), 7.44-7.34 (m, 4H), 6.25-6.15 (m, 0.5H), 6.04-5.96 (m, 0.5H), 5.08-4.96 (m, 2H), 4.76-4.67 (m, 1H), 4.59-4.50 (m, 1H), 4.14-4.05 (m, 1H), 3.81-3.74 (m, 0.5H), 3.74-3.63 (m, 2H), 3.59-3.45 (m, 2.5H), 2.99-2.92 (m, 1H), 2.89-2.79 (m, 1H), 2.60-2.54 (m, 3H), 2.50-2.41 (m, 1H), 2.17-2.07 (m, 1H), 1.99-1.88 (m, 1H), 1.88-1.76 (m, 1H), 1.77-1.67 (m, 1H), 1.49 (d, J=6.6 Hz, 1.5H), 1.43 (d, J=6.6 Hz, 1.5H).

Examples 138 and 139. 4-((2S,5R)-4-((S)-1-(4-Bromophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine and 4-((2S,5R)-4-((R)-1-(4-bromophenyl)-2-methylpropyl)-2,5-dimethylpiperazin-1-yl)-2-methyl-1-(((S)-tetrahydrofuran-2-yl)methyl)-1H-[1,2,4]triazolo[3,4-b]purine

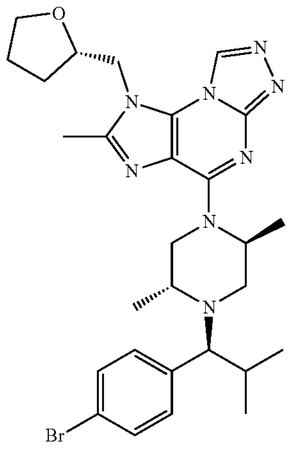

and

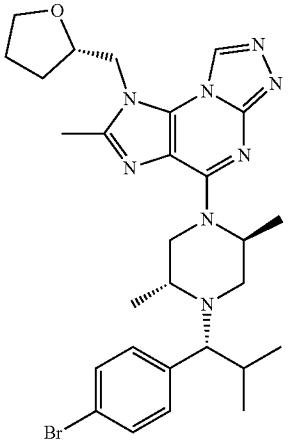

These compounds were prepared according to the procedures described in Examples 46 and 47 with (2R,5S)-1-(1-(4-bromophenyl)-2-methylpropyl)-2,5-dimethylpiperazine hydrochloride (Intermediate 112) replacing (2R,5S)-1-((3,3-difluorocyclobutyl)(3,4-difluorophenyl)methyl)-2,5-dimethylpiperazine hydrochloride in Step 1.

Example 138: Retention time on LC-MS $t_r$=2.034 min, LC-MS calculated for $C_{28}H_{38}BrN_8O$ $(M+H)^+$: m/z=581.2; found 581.3.

Example 139: Retention time on LC-MS $t_r$=2.156 min, LC-MS calculated for $C_{28}H_{38}BrN_8O$ $(M+H)^+$: m/z=581.2; found 581.3.

Example 140. 4-((2S,5R)-4-((3-Chloro-4-fluorophenyl)(4-chlorophenyl)methyl)-2,5-dimethylpiperazin-1-yl)-2-methyl-1-(((S)-tetrahydrofuran-2-yl)methyl)-1H-[1,2,4]triazolo[3,4-b]purine

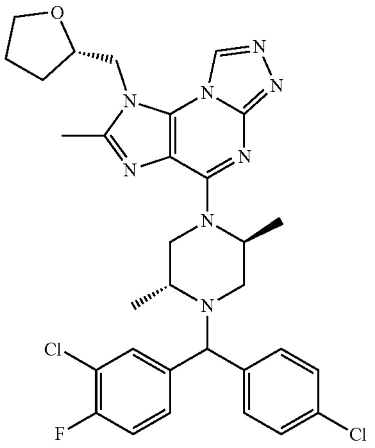 [SMILES: Cc1nc2c(N3C[C@@H](C)N(C(c4ccc(Cl)cc4)c4ccc(F)c(Cl)c4)C[C@@H]3C)nc3nncn3c2n1C[C@@H]1CCCO1]

This compound was prepared according to the procedures described in Example 105, with (2R,5S)-1-((3-chloro-4-fluorophenyl)(4-chlorophenyl)methyl)-2,5-dimethylpiperazine hydrochloride (Intermediate 114) replacing (2R,5S)-1-(bis(4-chlorophenyl)methyl)-2,5-dimethylpiperazine hydrochloride in Step 1. The major diastereomer was isolated as a single stereoisomer as its TFA salt. LC-MS calculated for $C_{31}H_{34}C_{12}FN_8O$ $(M+H)^+$: m/z=623.2; found 623.2.

Example 141. 4-((2S,5R)-4-((3-Chloro-4-fluorophenyl)(4-bromophenyl)methyl)-2,5-dimethylpiperazin-1-yl)-2-methyl-1-(((S)-tetrahydrofuran-2-yl)methyl)-1H-[1,2,4]triazolo[3,4-b]purine

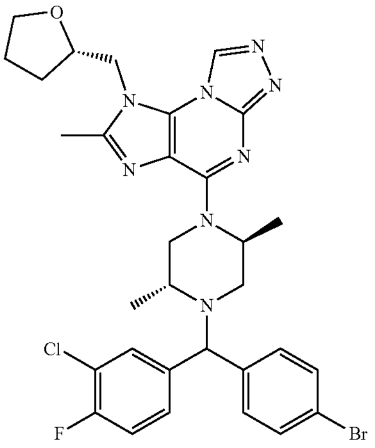 [SMILES: Cc1nc2c(N3C[C@@H](C)N(C(c4ccc(Br)cc4)c4ccc(F)c(Cl)c4)C[C@@H]3C)nc3nncn3c2n1C[C@@H]1CCCO1]

This compound was prepared according to the procedures described in Example 105, with (2R,5S)-1-((3-chloro-4-fluorophenyl)(4-bromophenyl)methyl)-2,5-dimethylpiperazine hydrochloride (Intermediate 115) replacing (2R,5S)-1-(bis(4-chlorophenyl)methyl)-2,5-dimethylpiperazine hydrochloride in Step 1. The major diastereomer was isolated as a single stereoisomer as its TFA salt. LC-MS calculated for $C_{31}H_{34}BrClFN_8O$ $(M+H)^+$: m/z=667.2; found 667.2.

Example A. In Vitro DGKα and DGKξ Inhibition Assays

The DGKα and DGKξ biochemical reactions were performed using His-tagged human recombinant enzymes (Signal Chem, DGKα, #D21-10BH; DGKξ, #D30-10H)) and DLG (Dilauroyl-sn-glycerol) lipid substrate (Signal Chem, #D430-59). ADP-Glo assay was performed using ADP-Glo™ kinase Assay kit (Promega, #V9104). The reactions were carried out in assay buffer containing 40 mM Tris, pH 7.5, 0.1% CHAPS, 0.1% Prionex, 40 mM NaCl, 5 mM $MgCl_2$, 1 mM $CaCl_2$, and 1 mM DTT. DGKα reactions contained 0.1 nM DGKα, 50 μM ATP, and 20 μM DLG. And DGKξ reactions contained 0.4 nM DGK, 30 μM ATP, and 20 μM DLG.

For compound inhibition studies, 40 nL test compound in DMSO was added to wells of white polystyrene plates in 384-well (Greiner, #784075) or 1536-well format (Greiner, #782075). Compounds were added with top concentration of 2 mM with 11 point, 3-fold dilution series. Enzyme solution (contains 2×DGK enzyme concentration in Ix assay buffer) was added to the plate in 2 μL/well volume, followed by 2 μL/well of substrate solution (contains 2× concentration of ATP and DLG substrate in Ix assay buffer). Plates were then centrifuged for 1 min at 1200 RPM and sealed or lidded. For 4 μL reaction volume, test compounds were therefore diluted 100× to final top concentration of 20 μM. After 90 minute incubation, reactions were quenched by addition of 2 μL/well Promega ADP-Glo Reagent, followed by centrifugation and lidding. After 60 min incubation, 2 μL/well Promega Kinase Detection Reagent was added, plates centrifuged, and incubated for 30 min. Plates were then read using Luminescence method on BMG PHERAstar FSX plate reader. Percent inhibition was calculated and IC50s were determined using 4-parameter fit in Genedata Screener. Labcyte Echo acoustic dispenser was used for compound addition, and Formulatrix Tempest liquid handler was used for all reagent dispenses.

TABLE A

| Example | DGKα IC50 (nM) | DGKζ IC50 (nM) |
|---|---|---|
| 1 | + | ++ |
| 2 | + | +++ |
| 3 | + | +++ |
| 4 | + | +++ |
| 5 | + | ++++ |
| 6 | + | ++++ |
| 7 | + | ++++ |
| 8 | + | +++ |
| 9 | + | +++ |
| 10 | + | ++++ |
| 11 | + | ++++ |
| 12 | + | ++++ |
| 13 | + | ++ |
| 14 | + | + |
| 15 | ++ | + |
| 16 | + | + |
| 17 | + | ++ |
| 18 | + | + |
| 19 | + | + |
| 20 | + | + |
| 21 | + | + |
| 22 | + | + |
| 23 | + | + |
| 24 | + | + |

TABLE A-continued

| Example | DGKα IC50 (nM) | DGKζ IC50 (nM) |
|---|---|---|
| 25 | + | ++ |
| 26 | + | + |
| 27 | + | + |
| 28 | + | + |
| 29 | + | + |
| 30 | + | + |
| 31 | + | + |
| 32 | + | + |
| 33 | + | + |
| 34 | + | + |
| 35 | + | + |
| 36 | + | + |
| 37 | + | + |
| 38 | + | + |
| 39 | + | + |
| 40 | + | + |
| 41 | + | + |
| 42 | + | + |
| 43 | + | + |
| 44 | + | + |
| 45 | + | + |
| 46 | + | + |
| 47 | + | + |
| 48 | + | + |
| 49 | + | + |
| 50 | + | + |
| 51 | + | + |
| 52 | + | + |
| 53 | + | + |
| 54 | + | + |
| 55 | + | + |
| 56 | + | + |
| 57 | + | + |
| 58 | + | + |
| 59 | + | + |
| 60 | + | + |
| 61 | + | + |
| 62 | + | + |
| 63 | + | + |
| 64 | + | + |
| 65 | + | + |
| 66 | + | + |
| 67 | + | + |
| 68 | + | + |
| 69 | + | + |
| 70 | + | + |
| 71 | + | + |
| 72 | + | + |
| 73 | + | + |
| 74 | + | + |
| 75 | + | + |
| 76 | + | + |
| 77 | + | + |
| 78 | + | + |
| 79 | + | + |
| 80 | + | ++ |
| 81 | + | + |
| 82 | + | + |
| 83 | + | + |
| 84 | + | + |
| 85 | + | + |
| 86 | + | + |
| 87 | + | + |
| 88 | + | + |
| 89 | + | + |
| 90 | + | + |
| 91 | + | ++ |
| 92 | + | + |
| 93 | + | + |
| 94 | + | + |
| 95 | + | + |
| 96 | + | + |
| 97 | + | + |
| 98 | + | + |
| 99 | + | + |
| 100 | + | + |
| 101 | + | + |
| 102 | + | + |

TABLE A-continued

| Example | DGKα IC50 (nM) | DGKζ IC50 (nM) |
|---|---|---|
| 103 | + | + |
| 104 | + | + |
| 105 | + | + |
| 106 | + | + |
| 107 | + | + |
| 108 | + | + |
| 109 | + | + |
| 110 | + | + |
| 111 | + | + |
| 112 | + | + |
| 113 | + | + |
| 114 | + | + |
| 115 | + | + |
| 116 | + | + |
| 117 | + | + |
| 118 | + | + |
| 119 | + | + |
| 120 | + | + |
| 121 | + | + |
| 122 | + | + |
| 123 | + | + |
| 124 | + | + |
| 125 | + | + |
| 126 | + | + |
| 127 | + | + |
| 128 | + | + |
| 129 | + | + |
| 130 | + | + |
| 131 | + | + |
| 132 | + | + |
| 133 | + | + |
| 134 | + | + |
| 135 | + | + |
| 136 | + | + |
| 137 | + | + |
| 138 | + | + |
| 139 | + | + |
| 140 | + | + |
| 141 | + | + |

+ refers to $IC_{50}$ of ≤20 nM
++ refers to $IC_{50}$ of >20 nM to ≤200 nM
+++ refers to $IC_{50}$ of >200 nM to ≤2000 nM
++++ refers to >2000 nM Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound, which is 4-((2S,5R)-4-(bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine, or a pharmaceutically acceptable salt thereof.

2. A pharmaceutical composition, comprising a compound of claim 1, or a pharmaceutically acceptable salt thereof, and a pharmaceutically acceptable carrier.

3. The compound of claim 1, which is 4-((2S,5R)-4-(bis(4-fluorophenyl)methyl)-2,5-dimethylpiperazin-1-yl)-1-(((R)-tetrahydrofuran-2-yl)methyl)-1H-[1,2,3]triazolo[4,5-e][1,2,4]triazolo[4,3-a]pyrimidine.

4. A compound, which is 4-((2S,5R)-4-((3,3-difluorocyclobutyl)(4-(trifluoromethyl)phenyl)methyl)-2,5-dimethylpiperazin-1-yl)-2-methyl-1-(((S)-tetrahydrofuran-2-yl)methyl)-1H-[1,2,4]triazolo[3,4-b]purine, or a pharmaceutically acceptable salt thereof.

5. The compound of claim 4, which is 4-((2S,5R)-4-((3,3-difluorocyclobutyl)(4-(trifluoromethyl)phenyl)methyl)-2, 5-dimethylpiperazin-1-yl)-2-methyl-1-(((S)-tetrahydrofuran-2-yl)methyl)-1H-[1,2,4]triazolo[3,4-b]purine.

6. A compound, which is 4-((2S,5R)-4-(bis(4-chlorophenyl)methyl)-2,5-dimethylpiperazin-1-yl)-2-methyl-1-(((S)-tetrahydrofuran-2-yl)methyl)-1H-[1,2,4]triazolo[3,4-b]purine, or a pharmaceutically acceptable salt thereof.

7. The compound of claim 6, which is 4-((2S,5R)-4-(bis(4-chlorophenyl)methyl)-2,5-dimethylpiperazin-1-yl)-2-methyl-1-(((S)-tetrahydrofuran-2-yl)methyl)-1H-[1,2,4]triazolo[3,4-b]purine.

8. A compound, which is 4-((2S,5R)-2,5-dimethyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine, or a pharmaceutically acceptable salt thereof.

9. The compound of claim 8, which is 4-((2S,5R)-2,5-dimethyl-4-((S)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine.

10. A compound, which is 4-((2S,5R)-2,5-dimethyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine, or a pharmaceutically acceptable salt thereof.

11. The compound of claim 10, which is 4-((2S,5R)-2,5-dimethyl-4-((R)-2-methyl-1-(4-(trifluoromethyl)phenyl)propyl)piperazin-1-yl)-2-methyl-1-(((S)-tetrahydrofuran-2-yl)methyl)-1H-[1,2,4]triazolo[3,4-b]purine.

12. A pharmaceutical composition, comprising a compound of claim 3, and a pharmaceutically acceptable carrier.

13. A pharmaceutical composition, comprising a compound of claim 4, or a pharmaceutically acceptable salt thereof, and a pharmaceutically acceptable carrier.

14. A pharmaceutical composition, comprising a compound of claim 5, and a pharmaceutically acceptable carrier.

15. A pharmaceutical composition, comprising a compound of claim 6, or a pharmaceutically acceptable salt thereof, and a pharmaceutically acceptable carrier.

16. A pharmaceutical composition, comprising a compound of claim 7, and a pharmaceutically acceptable carrier.

17. A pharmaceutical composition, comprising a compound of claim 8, or a pharmaceutically acceptable salt thereof, and a pharmaceutically acceptable carrier.

18. A pharmaceutical composition, comprising a compound of claim 9, and a pharmaceutically acceptable carrier.

19. A pharmaceutical composition, comprising a compound of claim 10, or a pharmaceutically acceptable salt thereof, and a pharmaceutically acceptable carrier.

20. A pharmaceutical composition, comprising a compound of claim 11, and a pharmaceutically acceptable carrier.

21. A method of treating cancer in a patient in need thereof, the method comprising administering to the patient a therapeutically effective amount of a compound of claim 1, or a pharmaceutically acceptable salt thereof, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

22. A method of treating cancer in a patient in need thereof, the method comprising administering to the patient a therapeutically effective amount of a compound of claim 3, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

23. A method of treating cancer in a patient in need thereof, the method comprising administering to the patient a therapeutically effective amount of a compound of claim 4, or a pharmaceutically acceptable salt thereof, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

24. A method of treating cancer in a patient in need thereof, the method comprising administering to the patient a therapeutically effective amount of a compound of claim 5, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

25. A method of treating cancer in a patient in need thereof, the method comprising administering to the patient a therapeutically effective amount of a compound of claim 6, or a pharmaceutically acceptable salt thereof, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

26. A method of treating cancer in a patient in need thereof, the method comprising administering to the patient a therapeutically effective amount of a compound of claim 7, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

27. A method of treating cancer in a patient in need thereof, the method comprising administering to the patient a therapeutically effective amount of a compound of claim 8, or a pharmaceutically acceptable salt thereof, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

28. A method of treating cancer in a patient in need thereof, the method comprising administering to the patient a therapeutically effective amount of a compound of claim 9, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

29. A method of treating cancer in a patient in need thereof, the method comprising administering to the patient a therapeutically effective amount of a compound of claim 10, or a pharmaceutically acceptable salt thereof, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

30. A method of treating cancer in a patient in need thereof, the method comprising administering to the patient a therapeutically effective amount of a compound of claim 11, wherein the cancer is selected from non-small cell lung cancer, bladder urothelial carcinoma, esophageal carcinoma, stomach adenocarcinoma, mesothelioma, liver hepatocellular carcinoma, diffuse large B cell lymphoma, kidney renal clear cell carcinoma, head and neck squamous cell carcinoma, cholangiocarcinoma, cervical squamous cell carcinoma, endocervical adenocarcinoma, and melanoma.

31. The method of claim 21, wherein the melanoma is metastatic melanoma.

32. The method of claim 22, wherein the melanoma is metastatic melanoma.

33. The method of claim 23, wherein the melanoma is metastatic melanoma.

34. The method of claim 24, wherein the melanoma is metastatic melanoma.

35. The method of claim 25, wherein the melanoma is metastatic melanoma.

36. The method of claim 26, wherein the melanoma is metastatic melanoma.

37. The method of claim 27, wherein the melanoma is metastatic melanoma.

38. The method of claim 28, wherein the melanoma is metastatic melanoma.

39. The method of claim 29, wherein the melanoma is metastatic melanoma.

40. The method of claim 30, wherein the melanoma is metastatic melanoma.

* * * * *